United States Patent
Albaugh et al.

(10) Patent No.: US 8,507,488 B2
(45) Date of Patent: Aug. 13, 2013

(54) FUSED NITROGEN CONTAINING HETEROCYCLES AND COMPOSITIONS THEREOF AS KINASE INHIBITORS

(75) Inventors: Pamela A. Albaugh, Carlsbad, CA (US); Ha-Soon Choi, San Diego, CA (US); Gregory Chopiuk, Vancouver (CA); Yi Fan, Poway, CA (US); Paul Vincent Rucker, Carlsbad, CA (US); Zhicheng Wang, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 12/992,027

(22) PCT Filed: May 7, 2009

(86) PCT No.: PCT/US2009/043073
§ 371 (c)(1),
(2), (4) Date: Feb. 8, 2011

(87) PCT Pub. No.: WO2009/140128
PCT Pub. Date: Nov. 19, 2009

(65) Prior Publication Data
US 2011/0166133 A1    Jul. 7, 2011

Related U.S. Application Data

(60) Provisional application No. 61/052,879, filed on May 13, 2008, provisional application No. 61/152,872, filed on Feb. 16, 2009.

(51) Int. Cl.
*A01N 43/58* (2006.01)
*A61K 31/495* (2006.01)
*C07D 487/00* (2006.01)

(52) U.S. Cl.
USPC .......................................... 514/250; 544/236

(58) Field of Classification Search
USPC ........................................ 544/236; 514/250
See application file for complete search history.

(56) References Cited

U.S. PATENT DOCUMENTS

| 7,306,631 | B2 | 12/2007 | Glenn et al. |
| 7,723,336 | B2 | 5/2010 | Vaccaro et al. |
| 2007/0049591 | A1 | 3/2007 | Pinkerton et al. |
| 2007/0078136 | A1 | 4/2007 | Vaccaro et al. |
| 2007/0093490 | A1* | 4/2007 | Prien et al. ............... 514/248 |
| 2008/0045536 | A1 | 2/2008 | Vaccaro et al. |
| 2008/0153813 | A1 | 6/2008 | Chen et al. |
| 2011/0021513 | A1* | 1/2011 | Durand-Reville et al. 514/230.5 |

FOREIGN PATENT DOCUMENTS

| WO | WO0100213 | 1/2001 |
| WO | WO2005097052 | 10/2005 |
| WO | WO2007025090 | 3/2007 |
| WO | WO2007038314 | 4/2007 |
| WO | WO2008079880 | 7/2008 |
| WO | WO2008138889 | 11/2008 |
| WO | WO2009016286 | 2/2009 |
| WO | WO2010033941 | 3/2010 |

* cited by examiner

*Primary Examiner* — Paul V. Ward
(74) *Attorney, Agent, or Firm* — Daniel E. Raymond; Genomics Institute of the Novartis Research Foundation

(57) ABSTRACT

The invention provides compounds, pharmaceutical compositions comprising such compounds and methods of using such compounds to treat or prevent diseases or disorders associated with abnormal or deregulated kinase activity, particularly Ros, KDR, FMS, C-FMS, FLT3, c-Kit, JAK2, JAK3, Aurora, PDGFR, Lck, TrkA, TrkB, TrkC, IGF-IR, ALK4, ALK5 and ALK or combinations thereof.

15 Claims, No Drawings

FUSED NITROGEN CONTAINING HETEROCYCLES AND COMPOSITIONS THEREOF AS KINASE INHIBITORS

CROSS-REFERENCE TO RELATED APPLICATIONS

This application is a 371 U.S. national phase application of international application number PCT/US2009/043073 filed 7 May 2009, which claims the benefit of priority under 35 U.S.C. §119(e) to U.S. Provisional Patent Application No. 61/052,879, filed May 13, 2008 and U.S. Provisional Patent Application No. 61/152,872, filed Feb. 16, 2009. The disclosure of the priority applications are incorporated herein by reference in their entirety and for all purposes.

FIELD OF THE INVENTION

The invention relates to protein kinase inhibitors, and methods of using such compounds.

BACKGROUND OF THE INVENTION

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (α and β), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, TRKB, TRKC, PYK2, ALK (Anaplastic Lymphoma Kinase), EPHA (1-8), EPHB (1-6), RON, Ros, Fes, Fer or EPHB4 (also EPHB4-1).

Examples of protein-serine/threonine kinases include, but are not limited to, Ark, ATM (1-3), CamK (1-IV), CamKK, Chk1 and 2 (Checkpoint kinases), CK1, CK2, Erk, IKK-I (also IKK-ALPHA or CHUK), IKK-2 (also IKK-BETA), Ilk, Jnk (1-3), LimK (1 and 2), MLK3Raf (A, B and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

SUMMARY OF THE INVENTION

Provide herein are compounds and pharmaceutical compositions thereof, which are useful as protein kinase inhibitors.

In one aspect, the present invention provides compounds having Formula (I), and the pharmaceutically acceptable salts, pharmaceutically acceptable solvates (e.g. hydrates), the N-oxide derivatives, prodrug derivatives, protected derivatives, individual isomers and mixture of isomers thereof:

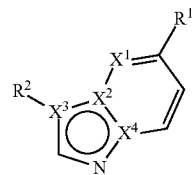

Formula (I)

wherein:
R$^1$ is

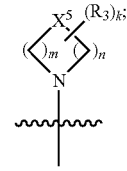

wherein,
X$^1$, X$^2$, X$^3$ and X$^4$ are each independently CR$^9$, C or N, with the proviso that at least one of X$^1$, X$^2$ X$^3$ and X$^4$ is N and at most only two of X$^1$, X$^2$ X$^3$ and X$^4$ are N;
X$^5$ is C(R$^3$)$_2$, O, S, S(O)$_2$, S(O), or NR$^3$;
m is 1, 2, 3 or 4;
n is 0, 1, 2 or 3;
k is 0, 1, 2, 3, 4, 5 or 6;
each R$^3$ is independently selected from halogen, nitro, —N(R$^4$)$_2$, —OR$^9$, —CN, =O, —C(O)N(R$^4$)$_2$, —N(R$^4$)C(O)OR$^4$, —N(R$^4$)C(O)R$^4$, —C(O)R$^9$, —C(O)OR$^9$, —R$^6$, —OR$^6$, -L$^1$R$^5$, -L$^1$R$^6$, —Y$^1$R$^5$, —Y$^1$R$^6$, —S(O)$_2$R$^9$, —S(O)$_2$N(R$^4$)$_2$, —NR$^4$S(O)$_2$, —OC(O)R$^9$, —(CH$_2$)$_p$OR$^9$, -L$^1$C(O)R$^8$, -L$^1$R$^8$, —C(O)R$^9$, —OC(O)R$^9$, —C(O)OR$^9$, —C(O)R$^9$, —N(R$^9$)$_2$, —C(O)N(R$^4$)$_2$, —N(R$^4$)C(O)R$^4$, —N(R$^4$)C(O)OR$^4$, —S(O)$_2$R$^9$, —S(O)$_2$N(R$^4$)$_2$, —NR$^4$S(O)$_2$, C$_1$-C$_8$alkyl, C$_6$-C$_{14}$aryl, C$_3$-C$_8$cycloalkyl, halo-substituted-C$_1$-C$_8$alkyl, C$_1$-C$_8$alkoxy, hydroxyl-C$_1$-C$_8$alkyl, halo-substituted C$_1$-C$_8$alkoxy, C$_2$-C$_{14}$heterocycloalkyl and C$_2$-C$_{13}$heteroaryl, wherein the C$_1$-C$_8$alkyl, C$_6$-C$_{14}$aryl, C$_3$-C$_8$cycloalkyl, C$_2$-C$_{14}$heterocycloalkyl and C$_2$-C$_{13}$heteroaryl of R$^3$ are optionally substituted with 1 to 3 substituents independently selected from halogen, amino, nitro, hydroxyl, cyano, —OR$^9$, —C(O)N(R$^4$)$_2$, —N(R$^4$)C(O)OR$^4$, —N(R$^4$)C(O)R$^4$, —C(O)R$^9$, —C(O)OR$^9$, —R$^6$, —OR$^6$, -L$^1$R$^5$, L$^1$R$^6$, Y$^1$R$^5$, Y$^1$R$^6$, —S(O)$_2$R$^9$, S(O)$_2$N(R$^4$)$_2$, —NR$^4$S(O)$_2$, —OC(O)R$^9$, —(CH$_2$)$_p$OR$^9$, -L$^1$C(O)R$^8$, -L$^1$R$^8$, —C(O)R$^9$, —OC(O)R$^9$, —C(O)OR$^9$, —C(O)R$^9$, —N(R$^9$)$_2$, —C(O)N(R$^4$)$_2$, —N(R$^4$)C(O)R$^4$, —N(R$^4$)C(O)OR$^4$, —S(O)$_2$R$^9$, —S(O)$_2$N(R$^4$)$_2$, —NR$^4$S(O)$_2$, C$_1$-C$_8$alkyl, C$_1$-C$_8$aminoalkyl, C$_1$-C$_8$alkoxy, C$_1$-C$_8$alkylthio, hydroxyl-C$_1$-C$_8$alkyl, halo-substituted-C$_1$-C$_8$alkyl, halo-substituted-C$_1$-C$_8$alkoxy, C$_3$-C$_8$cycloalkyl, C$_2$-C$_{14}$heterocycloalkyl, C$_6$-C$_{14}$aryl and C$_2$-C$_{13}$heteroaryl;

alternatively each R$^3$ is independently a C$_1$-C$_8$alkyl, wherein at least two R$^3$ together form a C$_3$-C$_8$cycloalkyl fused with a heterocycle and wherein each C$_1$-C$_8$alkyl of R$^3$ is optionally substituted with 1 to 3 substituents independently selected from halogen, amino, nitro, hydroxyl, cyano, —OR$^9$, C$_1$-C$_8$alkyl, C$_1$-C$_8$aminoalkyl, C$_1$-C$_8$alkoxy, C$_1$-C$_8$alkylthio, hydroxyl-C$_1$-C$_8$alkyl, halo-substituted-C$_1$-C$_8$alkyl, halo-substituted-C$_1$-C$_8$alkoxy, C$_3$-C$_8$cycloalkyl, C$_2$-C$_{14}$heterocycloalkyl, C$_6$-C$_{14}$aryl and C$_2$-C$_{13}$heteroaryl;

R$^2$ is C$_6$-C$_{14}$aryl, C$_2$-C$_{13}$heteroaryl or C$_2$-C$_{14}$heterocycloalkyl, wherein the C$_6$-C$_{14}$aryl, C$_2$-C$_{13}$heteroaryl or C$_2$-C$_{14}$heterocycloalkyl of R$^2$ are optionally substituted with 1 to 3 substituents independently selected from halogen, C$_2$-C$_{14}$heterocycloalkyl, C$_2$-C$_{13}$heteroaryl, C$_1$-C$_8$alkyl, C$_3$-C$_8$cycloalkyl, —CN, —C(O)N(R$^4$)$_2$, —N(R$^4$)C(O)OR$^4$, —N(R$^4$)C(O)R$^4$, —C(O)R$^9$, —OR$^9$, —C(O)OR$^9$, —N(R$^4$)$_2$, —R$^6$, —OR$^6$, -L$^1$R$^5$, -L$^1$R$^6$, —Y$^1$R$^5$, —Y$^1$R$^6$, —S(O)$_2$R$^9$, —S(O)$_2$N(R$^4$)$_2$, —NR$^4$S(O)$_2$R$^4$, —OC(O)R$^9$, C$_1$-C$_8$alkoxy, hydroxyl-C$_1$-C$_8$alkyl, halo-substituted C$_1$-C$_8$alkyl and halo-substituted C$_1$-C$_8$alkoxy;

each R$^4$ is independently selected from H, C$_1$-C$_8$ alkyl, -L$^1$R$^5$, -L$^1$R$^6$, -L$^1$R$^8$, C$_2$-C$_{13}$heteroaryl, C$_6$-C$_{14}$aryl, C$_2$-C$_{14}$heterocycloalkyl and C$_3$-C$_8$cycloalkyl, wherein the C$_1$-C$_8$alkyl, C$_2$-C$_{13}$heteroaryl and C$_3$-C$_8$cycloalkyl are optionally substituted with 1 to 3 substituents independently selected from halogen, deuterium, —CD$_3$, —S(O)$_2$R$^9$, —CN, C$_1$-C$_8$alkyl, —OR$^9$, —N(R$^9$)$_2$ and —(CH$_2$)$_p$OR$^9$;

L$^1$ is a bond, C$_1$-C$_8$alkylene, C$_2$-C$_8$alkenylene, —O(CH$_2$)$_p$—, —C(O)—, —N(R$^9$)—, (CH$_2$)$_p$C(O)—, —C(O)(CH$_2$)$_p$O(CH$_2$)$_p$— or —C(O)O—;

Y$^1$ is C$_6$-C$_{14}$arylene, C$_2$-C$_{13}$heteroarylene, C$_3$-C$_8$cycloalkylene, C$_2$-C$_{14}$heterocycloalkylene or C$_1$-C$_8$alkoxylene, each of which is optionally substituted with 1 to 3 substituents independently selected from halogen, C$_2$-C$_{14}$heterocycloalkyl, C$_2$-C$_{13}$heteroaryl, C$_1$-C$_8$alkyl, C$_3$-C$_8$cycloalkyl, —CN, —C(O)N(R$^4$)$_2$, —N(R$^4$)C(O)OR$^4$, —N(R$^4$)C(O)R$^4$, —C(O)R$^9$, —OR$^9$, —C(O)OR$^9$, —N(R$^4$)$_2$, —R$^6$, —OR$^6$, L$^1$R$^5$, L$^1$R$^6$, —Y$^1$R$^5$, —Y$^1$R$^6$, —S(O)$_2$R$^9$, —S(O)$_2$N(R$^4$)$_2$, —NR$^4$S(O)$_2$R$^4$, —OC(O)R$^9$, C$_1$-C$_8$alkoxy, hydroxyl-C$_1$-C$_8$alkyl, halo-substituted C$_1$-C$_8$alkyl and halo-substituted C$_1$-C$_8$alkoxy;

R$^5$ is C$_6$-C$_{14}$aryl, C$_2$-C$_{13}$heteroaryl, C$_2$-C$_{14}$heterocycloalkyl, —N(R$^9$)$_2$, —N(R$^9$)C(O)R$^9$, —C(O)N(R$^9$)$_2$, —(CH$_2$)$_p$OR$^9$ or —OR$^9$.

R$^6$ is C$_6$-C$_{14}$aryl, C$_2$-C$_{13}$heteroaryl, C$_2$-C$_{14}$heterocycloalkyl, —OCH(R$^7$)$_2$, —C(O)R$^7$, C$_1$-C$_8$alkyl, or C$_3$-C$_8$cycloalkyl, wherein the C$_1$-C$_8$alkyl, C$_3$-C$_8$cycloalkyl, C$_6$-C$_{14}$aryl, C$_2$-C$_{13}$heteroaryl, and C$_2$-C$_{14}$heterocycloalkyl of R$^6$ are optionally substituted with 1 to 3 substituents independently selected from halogen, —CN, —OR$^9$, —(CH$_2$)$_p$OR$^9$, -L$^1$C(O)R$^8$, L$^1$R$^8$, L$^1$R$^5$, —C(O)R$^9$, —OC(O)R$^9$, —C(O)OR$^9$, —C(O)R$^8$, OC(O)N(R$^4$)$_2$, —N(R$^9$)$_2$, —C(O)C(O)OR$^9$, —(CH$_2$)$_p$N(R$^9$)$_2$, —N(R$^4$)$_2$, —C(O)N(R$^4$)$_2$, —N(R$^4$)C(O)R$^4$, —N(R$^4$)C(O)OR$^4$, —(CH$_2$)$_p$S(O)$_2$R$^9$, —S(O)$_2$R$^9$, —S(O)$_2$N(R$^4$)$_2$, —NR$^4$S(O)$_2$R$^4$, —NR$^4$S(O)$_2$R$^9$, C$_2$-C$_{14}$heterocycloalkyl, C$_2$-C$_{13}$heteroaryl, C$_1$-C$_8$alkyl, C$_2$-C$_8$alkene, C$_1$-C$_8$alkoxy, hydroxyl-substituted C$_1$-C$_8$alkyl, halo-substituted C$_1$-C$_8$alkyl and halo-substituted C$_1$-C$_8$alkoxy;

or R$^6$ is C$_6$-C$_{14}$aryl, C$_2$-C$_{13}$heteroaryl, C$_2$-C$_{14}$heterocycloalkyl or C$_3$-C$_8$cycloalkyl having a C$_1$-C$_4$alkyl bridge;

or R$^6$ is a C$_2$-C$_{14}$heterocycloalkyl optionally substituted with 1 to 3 substituents independently selected from halogen, =O, —CN, —OR$^9$, —(CH$_2$)$_p$OR$^9$, -L$^1$C(O)R$^8$, -L$^1$R$^8$, -L$^1$R$^5$, —C(O)R$^9$, —OC(O)R$^9$, —C(O)OR$^9$, —C(O)R$^8$, OC(O)N(R$^4$)$_2$, —N(R$^9$)$_2$, —C(O)C(O)OR$^9$, —(CH$_2$)$_p$N(R$^9$)$_2$, —N(R$^4$)$_2$, —C(O)N(R$^4$)$_2$, —N(R$^4$)C(O)R$^4$, —N(R$^4$)C(O)OR$^4$, —(CH$_2$)$_p$S(O)$_2$R$^9$, —S(O)$_2$R$^9$, —S(O)$_2$N(R$^4$)$_2$, —NR$^4$S(O)$_2$R$^4$, —NR$^4$S(O)$_2$R$^9$, C$_2$-C$_{14}$heterocycloalkyl, C$_2$-C$_{13}$heteroaryl, C$_1$-C$_8$alkyl, C$_2$-C$_8$alkene, C$_1$-C$_8$alkoxy, hydroxyl-substituted C$_1$-C$_8$alkyl, halo-substituted C$_1$-C$_8$alkyl and halo-substituted C$_1$-C$_8$alkoxy;

each R$^7$ is independently selected from H, C$_1$-C$_8$alkyl and -L$^1$R$^8$;

R$^8$ is H, —N(R$^9$)$_2$, —N(R$^4$)$_2$, —SR$^9$, —CN, C$_1$-C$_8$alkyl, C$_3$-C$_8$cycloalkyl and C$_2$-C$_{14}$heterocycloalkyl, wherein the C$_1$-C$_8$alkyl, C$_3$-C$_8$cycloalkyl and C$_2$-C$_{14}$heterocycloalkyl of R$^8$ are optionally substituted with 1 to 3 substituents independently selected from halogen, C$_1$-C$_6$alkyl, —(CH$_2$)$_p$OR$^9$, -L$^1$C(O)R$^8$, —C(O)R$^9$, —OC(O)R$^9$, —C(O)OR$^9$, —N(R$^9$)$_2$, —N(R$^4$)$_2$, —C(O)N(R$^4$)$_2$, —N(R$^4$)C(O)R$^4$, —N(R$^4$)C(O)OR$^4$, —S(O)$_2$R$^9$, —S(O)$_2$N(R$^4$)$_2$, and —NR$^4$S(O)$_2$;

each R$^9$ is independently selected from H, C$_3$-C$_8$cycloalkyl and C$_1$-C$_8$alkyl, and each p is independently 1, 2, 3, 4, 5 or 6.

In certain embodiments of the aforementioned compounds of Formula (I), R$^1$ is

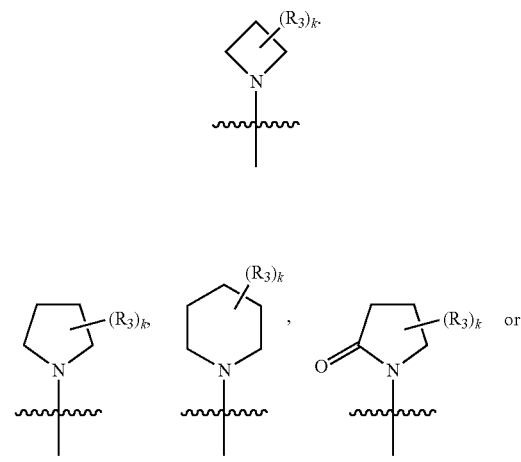

-continued

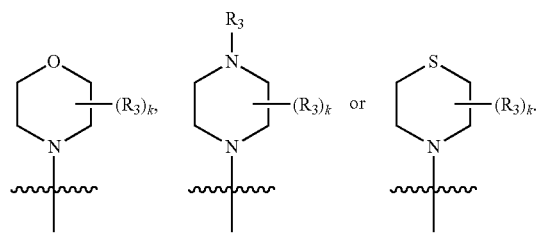

while in other embodiments R¹ is

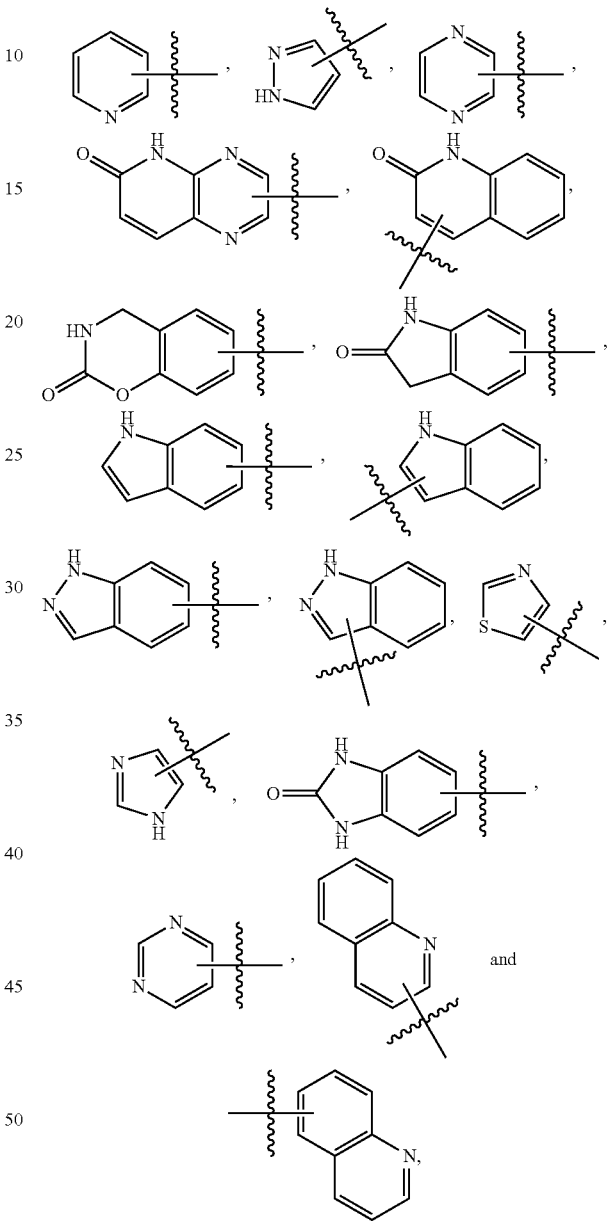

In certain embodiments of the aforementioned compounds of Formula (I), each $R^3$ is independently selected from halogen, —$OR^9$, $C_1$-$C_8$alkyl, $C_6$-$C_{14}$aryl, $C_3$-$C_8$cycloalkyl, halo-substituted-$C_1$-$C_8$alkyl, $C_2$-$C_{14}$heterocycloalkyl and $C_2$-$C_{13}$heteroaryl, wherein the $C_1$-$C_8$alkyl, $C_6$-$C_{14}$aryl, $C_3$-$C_8$cycloalkyl, $C_2$-$C_{14}$heterocycloalkyl and $C_2$-$C_{13}$heteroaryl of $R^3$ are optionally substituted with 1 to 3 substituents independently selected from halogen, hydroxyl, —$OR^9$, $C_1$-$C_8$alkyl, $C_1$-$C_8$alkoxy, hydroxyl-$C_1$-$C_8$alkyl, halo-substituted-$C_1$-$C_8$alkyl, halo-substituted-$C_1$-$C_8$alkoxy and $C_3$-$C_8$cycloalkyl.

In certain embodiments of the aforementioned compounds of Formula (I), the $C_6$-$C_{14}$aryl of $R^3$ is phenyl optionally substituted with 1 to 3 substituents independently selected from halogen, $C_1$-$C_8$alkyl, and halo-substituted-$C_1$-$C_8$alkyl.

In certain embodiments of the aforementioned compounds of Formula (I), the $C_6$-$C_{14}$aryl of $R^3$ is phenyl optionally substituted with 1 to 3 substituents independently selected from fluoro and $C_1$-$C_8$alkyl.

In certain embodiments of the aforementioned compounds of Formula (I), $R^2$ is $C_6$-$C_{14}$aryl or $C_2$-$C_{13}$heteroaryl, wherein the $C_6$-$C_{14}$aryl and $C_2$-$C_{13}$heteroaryl of $R^2$ are optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N($R^4$)$_2$, —N($R^4$)C(O)O$R^4$, —N($R^4$)C(O)$R^4$, —C(O)$R^9$, —O$R^9$, —C(O)O$R^9$, —N($R^4$)$_2$, —$R^6$, —O$R^6$, $L^1R^5$, $L^1R^6$, —$Y^1R^5$, —$Y^1R^6$, —S(O)$_2R^9$, —S(O)$_2$N($R^4$)$_2$, —N$R^4$S(O)$_2R^4$, —OC(O)$R^9$, $C_1$-$C_8$alkoxy, hydroxyl-$C_1$-$C_8$alkyl, halo-substituted $C_1$-$C_8$alkyl and halo-substituted $C_1$-$C_8$alkoxy.

In certain embodiments of the aforementioned compounds of Formula (I), $R^2$ is $C_6$-$C_{14}$aryl or $C_2$-$C_{13}$heteroaryl, wherein the $C_6$-$C_{14}$aryl and $C_2$-$C_{13}$heteroaryl of $R^2$ are optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N($R^4$)$_2$, —N($R^4$)C(O)O$R^4$, —N($R^4$)C(O)$R^4$, —C(O)$R^9$, —O$R^9$, —C(O)O$R^9$, —N($R^4$)$_2$, —$R^6$, —O$R^6$, $L^1R^5$, $L^1R^6$, —$Y^1R^5$, —$Y^1R^6$ and —S(O)$_2R^9$.

In certain embodiments of the aforementioned compounds of Formula (I), the $C_6$-$C_{14}$aryl of $R^2$ is phenyl optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N($R^4$)$_2$, —N($R^4$)C(O)O$R^4$, —N($R^4$)C(O)$R^4$, —C(O)$R^9$, —O$R^9$, —C(O)O$R^9$, —N($R^4$)$_2$, —$R^6$, —O$R^6$, $L^1R^5$, $L^1R^6$, —$Y^1R^5$, —$Y^1R^6$ and —S(O)$_2R^9$.

In certain embodiments of the aforementioned compounds of Formula (I), the $C_2$-$C_{13}$heteroaryl of $R^2$ is selected from

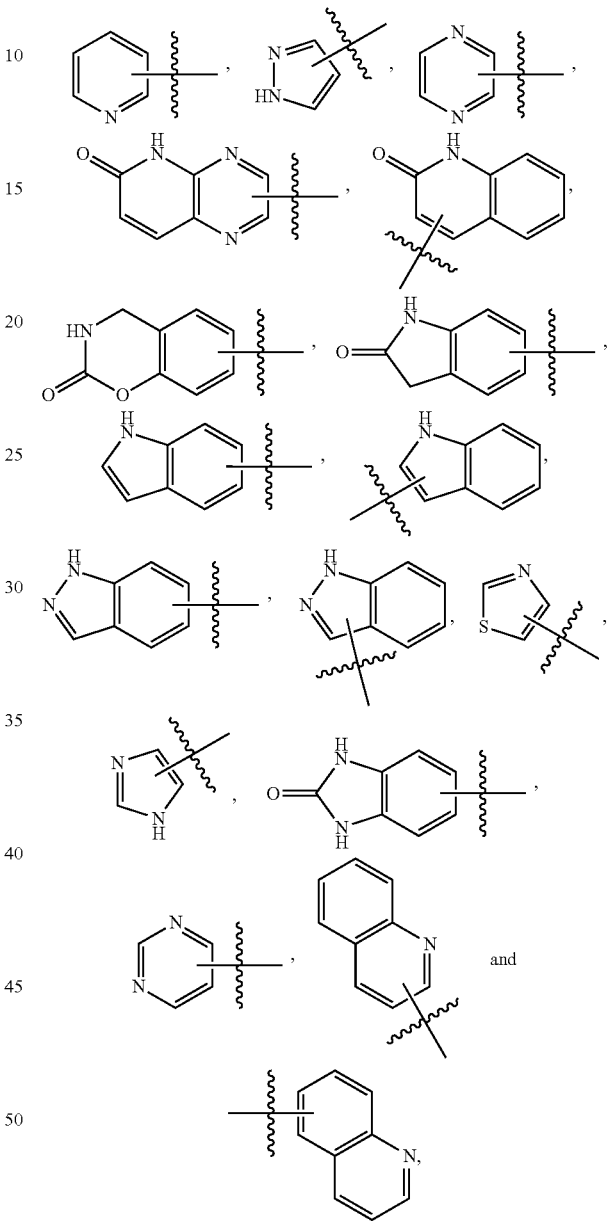

wherein each is optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N($R^4$)$_2$, —N($R^4$)C(O)O$R^4$, —N($R^4$)C(O)$R^4$, —C(O)$R^9$, —O$R^9$, —C(O)O$R^9$, —N($R^4$)$_2$, —$R^6$, —O$R^6$, $L^1R^5$, $L^1R^6$, —$Y^1R^5$, —$Y^1R^6$ and —S(O)$_2R^9$.

In certain embodiments of the aforementioned compounds of Formula (I), the $C_2$-$C_{13}$heteroaryl of $R^2$ is selected from

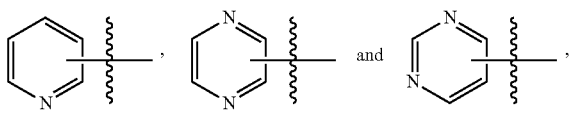

wherein each is optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N($R^4$)$_2$, —N($R^4$)C(O)O$R^4$, —N($R^4$)C(O)$R^4$, —C(O)$R^9$, —O$R^9$, —C(O)O$R^9$, —N($R^4$)$_2$, —$R^6$, —O$R^6$, $L^1R^5$, $L^1R^6$, —$Y^1R^5$, —$Y^1R^6$ and —S(O)$_2R^9$.

In certain embodiments of the aforementioned compounds of Formula (I), $R^6$ is $C_2$-$C_{13}$heteroaryl, $C_2$-$C_{14}$heterocycloalkyl, —OCH($R^7$)$_2$, $C_1$-$C_8$alkyl, or $C_3$-$C_8$cycloalkyl, wherein the $C_1$-$C_8$alkyl, $C_3$-$C_8$cycloalkyl, $C_2$-$C_{13}$heteroaryl, and $C_2$-$C_{14}$heterocycloalkyl of $R^6$ are optionally substituted with 1 to 3 substituents independently selected from halogen, —CN, —O$R^9$, —(CH$_2$)$_p$O$R^9$, -$L^1$C(O)$R^8$, $L^1R^8$, $L^1R^5$, —C(O)O$R^9$, —C(O)$R^9$, —N($R^9$)$_2$, —C(O)N($R^4$)$_2$, —N($R^4$)C(O)O$R^4$, —N($R^4$)C(O)$R^4$, —N($R^4$)$_2$, —S(O)$_2R^9$, $C_2$-$C_{14}$heterocycloalkyl, $C_2$-$C_{13}$heteroaryl, $C_1$-$C_8$alkyl, $C_2$-$C_8$alkene, and hydroxyl-substituted $C_1$-$C_8$alkyl.

In certain embodiments of the aforementioned compounds of Formula (I), $R^6$ is selected from

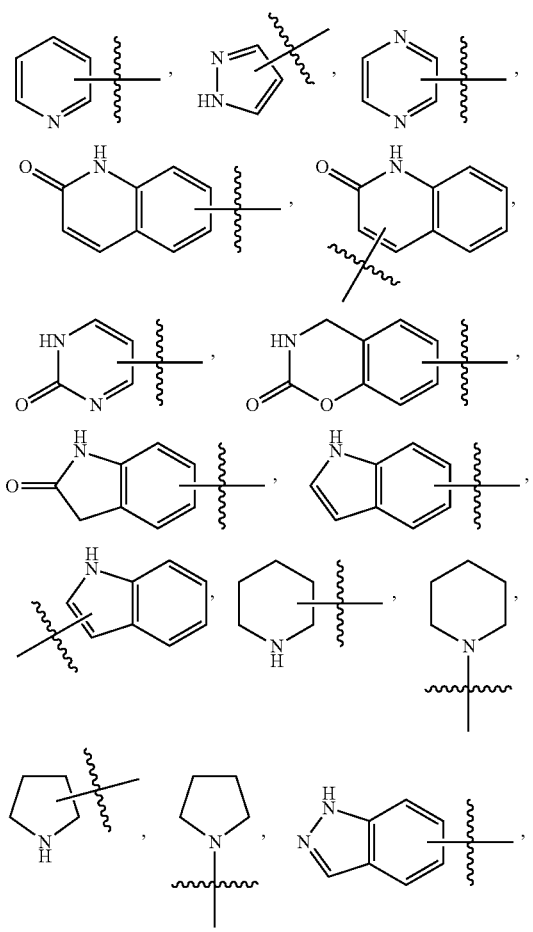

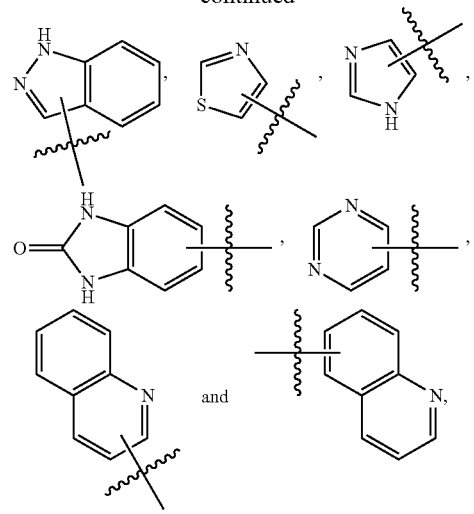

wherein each is optionally substituted with 1 to 3 substituents independently selected from halogen, —CN, —O$R^9$, —(CH$_2$)$_p$O$R^9$, -$L^1$C(O)$R^8$, -$L^1R^8$, -$L^1R^5$, —C(O)O$R^9$, —C(O)$R^9$, —N($R^9$)$_2$, —C(O)N($R^4$)$_2$, —N($R^4$)C(O)O$R^4$, —N($R^4$)C(O)$R^4$, —N($R^4$)$_2$, —S(O)$_2R^9$, $C_2$-$C_{14}$heterocycloalkyl, $C_2$-$C_{13}$heteroaryl, $C_1$-$C_8$alkyl, $C_2$-$C_8$alkene, and hydroxyl-substituted $C_1$-$C_8$alkyl.

In certain embodiments of the aforementioned compounds of Formula (I), $Y^1$ is $C_6$-$C_{14}$arylene or $C_2$-$C_{13}$heteroarylene, while in other embodiments $Y^1$ is selected from

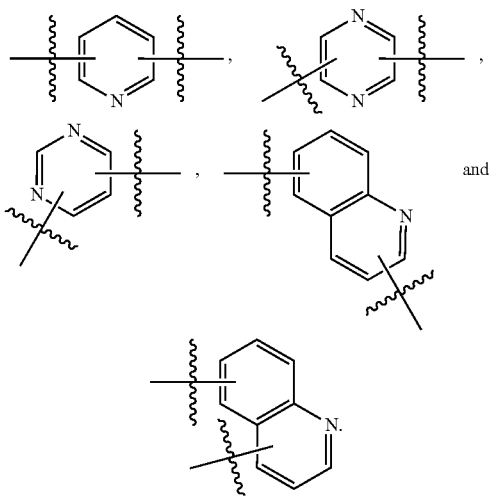

In certain embodiments of the aforementioned compounds of Formula (I), each $R^4$ is independently selected from H, $C_1$-$C_8$ alkyl, $C_6$-$C_{14}$aryl, $C_2$-$C_{14}$heterocycloalkyl, -$L^1R^5$, -$L^1R^6$ and $C_3$-$C_8$cycloalkyl, wherein the $C_1$-$C_8$alkyl, $C_6$-$C_{14}$aryl, $C_2$-$C_{14}$heterocycloalkyl, and $C_3$-$C_8$cycloalkyl are optionally substituted with —(CH$_2$)$_p$O$R^9$.

In certain embodiments of the aforementioned compounds of Formula (I), $R^5$ is $C_6$-$C_{14}$aryl, $C_2$-$C_{13}$heteroaryl, $C_2$-$C_{14}$heterocycloalkyl, —N($R^9$)$_2$, —N($R^9$)C(O)$R^9$, —(CH$_2$)$_p$O$R^9$, or —O$R^9$.

In certain embodiments of the aforementioned compounds of Formula (I), $R^7$ is -$L^1R^8$. In certain embodiments of the aforementioned compounds of Formula (I), $R^8$ is —N($R^9$)$_2$ or —CN.

In certain embodiments compounds of Formula (I) are selected from: (R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol; (R)-1-(6-(6-(2-(3-fluorophenyl)pyrrolidin-1-yl)imidazo[1,2-b]pyridazin-3-yl)-2,4'-bipyridin-2'-yl)piperidin-4-ol; 6-(6-(3-(3-fluorophenyl)morpholino)imidazo[1,2-b]pyridazin-3-yl)indolin-2-one; 3-(6-((3S)-2-(3-fluorophenyl)-3-hydroxypyrrolidin-1-yl)imidazo[1,2-b]pyridazin-3-yl)benzonitrile; 5-(6-(2-(2,5-dimethylphenyl)pyrrolidin-1-yl)imidazo[1,2-b]pyridazin-3-yl)-2-fluorobenzonitrile; (R)-4-(6-(2-(2,5-difluorophenyl)pyrrolidin-1-yl)imidazo[1,2-b]pyridazin-3-yl)benzonitrile; 4-(5-(6-(2-(3-fluorophenyl)piperidin-1-yl)imidazo[1,2-b]pyridazin-3-yl)pyridin-2-yl)morpholine; 4-(5-(6-(2-(3-fluorophenyl)pyrrolidin-1-yl)imidazo[1,2-b]pyridazin-3-yl)pyridin-2-yl)morpholine; 5-(6-(2-(3-fluorophenyl)pyrrolidin-1-yl)imidazo[1,2-b]pyridazin-3-yl)-N-methylpicolinamide; 4-(6-(2-(3-fluorophenyl)pyrrolidin-1-yl)imidazo[1,2-b]pyridazin-3-yl)benzonitrile; 5-(6-(2-(3-fluorophenyl)piperidin-1-yl)imidazo[1,2-b]pyridazin-3-yl)-N-methylpicolinamide; (S)-4-(6-(2-(3-fluorophenyl)pyrrolidin-1-yl)imidazo[1,2-b]pyridazin-3-yl)benzonitrile; (R)-4-(6-(2-(3-fluorophenyl)pyrrolidin-1-yl)imidazo[1,2-b]pyridazin-3-yl)benzonitrile; 4-(6-(2-(2,5-difluorophenyl)pyrrolidin-1-yl)imidazo[1,2-b]pyridazin-3-yl)benzonitrile; 4-(5-(6-(2-(2,5-difluorophenyl)pyrrolidin-1-yl)imidazo[1,2-b]pyridazin-3-yl)pyridin-2-yl)morpholine; 4-(6-(2-phenylazetidin-1-yl)imidazo[1,2-b]pyridazin-3-yl)benzonitrile; (R)-4-(6-(2-(2,5-difluorophenyl)pyrrolidin-1-yl)imidazo[1,2-b]pyridazin-3-yl)benzonitrile; (S)-4-(6-(2-(2,5-difluorophenyl)pyrrolidin-1-yl)imidazo[1,2-b]pyridazin-3-yl)benzonitrile; 4-(6-(2-(3-fluorophenyl)-2-methylpyrrolidin-1-yl)imidazo[1,2-b]pyridazin-3-yl)benzonitrile; 6-(6-(2-(3-fluorophenyl)pyrrolidin-1-yl)imidazo[1,2-b]pyridazin-3-yl)-3,4-dihydro-2H-benzo[e][1,3]oxazin-2-one; 6-(6-(2-(2,5-difluorophenyl)pyrrolidin-1-yl)imidazo[1,2-b]pyridazin-3-yl)-3,4-dihydro-2H-benzo[e][1,3]oxazin-2-one; 5-(6-(2-(3-fluorophenyl)pyrrolidin-1-yl)imidazo[1,2-b]pyridazin-3-yl)indolin-2-one; 6464243-fluorophenyl)pyrrolidin-1-yl)imidazo[1,2-b]pyridazin-3-yl)indolin-2-one; 4-(6-(2-(2,5-difluorophenyl)-5-methylpyrrolidin-1-yl)imidazo[1,2-b]pyridazin-3-yl)benzonitrile; 4-(2-(4-(6-(2-(2,5-difluorophenyl)pyrrolidin-1-yl)imidazo[1,2-b]pyridazin-3-yl)-1H-pyrazol-1-yl)ethyl)morpholine; N-(2-(4-(6-(2-(2,5-difluorophenyl)pyrrolidin-1-yl)imidazo[1,2-b]pyridazin-3-yl)-1H-pyrazol-1-yl)ethyl)acetamide; (Z)-3-((1H-pyrrol-2-yl)methylene)-6-(6-(2-(3-fluorophenyl)pyrrolidin-1-yl)imidazo[1,2-b]pyridazin-3-yl)indolin-2-one; 5-(6-(2-(2,5-difluorophenyl)pyrrolidin-1-yl)imidazo[1,2-b]pyridazin-3-yl)-2-fluorobenzonitrile; 5-(6-(2-(2,5-difluorophenyl)pyrrolidin-1-yl)imidazo[1,2-b]pyridazin-3-yl)-2-morpholinobenzonitrile; 4-(6-(2-(2,5-difluorophenyl)pyrrolidin-1-yl)imidazo[1,2-b]pyridazin-3-yl)-2-fluorobenzonitrile; 5-(6-(2-(2,5-difluorophenyl)pyrrolidin-1-yl)imidazo[1,2-b]pyridazin-3-yl)-2-(dimethylamino)benzonitrile; 5-(6-(2-(2,5-difluorophenyl)pyrrolidin-1-yl)imidazo[1,2-b]pyridazin-3-yl)-2-(4-methylpiperazin-1-yl)benzonitrile; 5-(6-(2-(2,5-difluorophenyl)pyrrolidin-1-yl)imidazo[1,2-b]pyridazin-3-yl)-2-(4-(2-methoxyethyl)piperazin-1-yl)benzonitrile; 5-(6-(2-(2,5-difluorophenyl)pyrrolidin-1-yl)imidazo[1,2-b]pyridazin-3-yl)-2-(2-morpholinoethylamino)benzonitrile; 4-(6-(2-(2,5-difluorophenyl)pyrrolidin-1-yl)imidazo[1,2-b]pyridazin-3-yl)-2-(dimethylamino)benzonitrile; 4-(6-(2-(2,5-difluorophenyl)pyrrolidin-1-yl)imidazo[1,2-b]pyridazin-3-yl)-2-(4-methylpiperazin-1-yl)benzonitrile; 4-(6-(2-(2,5-difluorophenyl)pyrrolidin-1-yl)imidazo[1,2-b]pyridazin-3-yl)-2-(4-(2-methoxyethyl)piperazin-1-yl)benzonitrile; 4-(6-(2-(2,5-difluorophenyl)pyrrolidin-1-yl)imidazo[1,2-b]pyridazin-3-yl)-2-(2-morpholinoethylamino)benzonitrile; 4-(6-(2-(2,5-difluorophenyl)pyrrolidin-1-yl)imidazo[1,2-b]pyridazin-3-yl)-2-morpholinobenzonitrile; 3-(6-(2-(2,5-difluorophenyl)pyrrolidin-1-yl)imidazo[1,2-b]pyridazin-3-yl)benzonitrile; 4-(6-(2-(2,5-difluorophenyl)pyrrolidin-1-yl)imidazo[1,2-b]pyridazin-3-yl)-2-(4-morpholinopiperidin-1-yl)benzonitrile; 4-(6-(2-(2,5-difluorophenyl)pyrrolidin-1-yl)imidazo[1,2-b]pyridazin-3-yl)-2-(pyrrolidin-1-yl)benzonitrile; 4-(6-(2-(2,5-difluorophenyl)pyrrolidin-1-yl)imidazo[1,2-b]pyridazin-3-yl)-2-(3-(dimethylamino)pyrrolidin-1-yl)benzonitrile; 4-(6-(2-(2,5-difluorophenyl)pyrrolidin-1-yl)imidazo[1,2-b]pyridazin-3-yl)-2-(2,6-dimethylmorpholino)benzonitrile; 4-(6-(2-(2,5-difluorophenyl)pyrrolidin-1-yl)imidazo[1,2-b]pyridazin-3-yl)-2-(2-(pyrrolidin-1-yl)ethoxy)benzonitrile; 5-(6-(2-(2,5-difluorophenyl)pyrrolidin-1-yl)imidazo[1,2-b]pyridazin-3-yl)nicotinonitrile; 6-(6-(2-(2,5-difluorophenyl)pyrrolidin-1-yl)imidazo[1,2-b]pyridazin-3-yl)picolinonitrile; 4-(4-(6-(2-(2,5-difluorophenyl)pyrrolidin-1-yl)imidazo[1,2-b]pyridazin-3-yl)thiazol-2-yl)morpholine; 4-(6-(2-(2,5-difluorophenyl)pyrrolidin-1-yl)imidazo[1,2-b]pyridazin-3-yl)-2-(3-morpholinopropylamino)benzonitrile; 4-(6-(2-(2,5-difluorophenyl)pyrrolidin-1-yl)imidazo[1,2-b]pyridazin-3-yl)-2-(3-morpholinopyrrolidin-1-yl)benzonitrile; 4-(6-(2-(2,5-difluorophenyl)pyrrolidin-1-yl)imidazo[1,2-b]pyridazin-3-yl)-2-(1-methylpyrrolidin-3-yloxy)benzonitrile; 4-(6-(2-(2,5-difluorophenyl)pyrrolidin-1-yl)imidazo[1,2-b]pyridazin-3-yl)-2-((2-(dimethylamino)ethyl)(methyl)amino)benzonitrile; 4-(6-(2-(2,5-difluorophenyl)pyrrolidin-1-yl)imidazo[1,2-b]pyridazin-3-yl)-2-((1-methylpyrrolidin-3-yl)methoxy)benzonitrile; 4-(6-(2-(2,5-difluorophenyl)pyrrolidin-1-yl)imidazo[1,2-b]pyridazin-3-yl)-2-(3-morpholinopropoxy)benzonitrile; 3-(5-(2-(3-fluorophenyl)pyrrolidin-1-yl)-3H-imidazo[4,5-b]pyridin-3-yl)benzonitrile; 4-(5-(2-(3-fluorophenyl)pyrrolidin-1-yl)-3H-imidazo[4,5-b]pyridin-3-yl)benzonitrile; 3-(5-(2-(2,5-difluorophenyl)thiazolidin-3-yl)-3H-imidazo[4,5-b]pyridin-3-yl)benzonitrile; 3-(5-(2-(2,5-difluorophenyl)thiazolidin-3-yl)-3H-imidazo[4,5-b]pyridin-3-yl)benzonitrile; 3-(3-(1H-imidazol-2-yl)phenyl)-5-(2-(2,5-difluorophenyl)pyrrolidin-1-yl)-3H-imidazo[4,5-b]pyridine; 3-(5-(2-(2,5-difluorophenyl)-4-oxothiazolidin-3-yl)-3H-imidazo[4,5-b]pyridin-3-yl)benzonitrile; 3-(5-(2-(2,5-difluorophenyl)pyrrolidin-1-yl)-3H-imidazo[4,5-b]pyridin-3-yl)benzonitrile; 4-(5-(2-(2,5-difluorophenyl)pyrrolidin-1-yl)-3H-imidazo[4,5-b]pyridin-3-yl)benzonitrile; 3-(6-(2-(3-fluorophenyl)-3-oxopyrazolidin-1-yl)imidazo[1,2-b]pyridazin-3-yl)benzonitrile; 5-(6-(3-(3-fluorophenyl)morpholino)imidazo[1,2-b]pyridazin-3-yl)-2-(4-hydroxypiperidin-1-yl)benzonitrile; 2-(1,3-bis(dimethylamino)propan-2-yloxy)-4-(6-(2-(2,5-difluorophenyl)pyrrolidin-1-yl)imidazo[1,2-b]pyridazin-3-yl)benzonitrile; 4-(6-(2-(2,5-difluorophenyl)pyrrolidin-1-yl)imidazo[1,2-b]pyridazin-3-yl)-2-(1-(dimethylamino)propan-2-yloxy)benzonitrile; 4-(6-(2-(2,5-difluorophenyl)pyrrolidin-1-yl)imidazo[1,2-b]pyridazin-3-yl)-2-(2-(1-methylpyrrolidin-2-yl)ethoxy)benzonitrile; 4-(6-(2-(2,5-difluorophenyl)pyrrolidin-1-yl)imidazo[1,2-b]pyridazin-3-yl)-2-(3-(dimethylamino)-2-hydroxypropoxy)benzonitrile; 4-(6-(2-(2,5-difluorophenyl)pyrrolidin-1-yl)imidazo[1,2-b]pyridazin-3-yl)-2-((1-methylpyrrolidin-2-yl)methoxy)benzonitrile; 4-(6-(2-(3-fluorophenyl)piperidin-1-yl)imidazo[1,2-b]pyridazin-3-yl)benzonitrile; 3-(6-(2-(3-fluorophenyl)piperidin-1-yl)imidazo[1,2-b]pyridazin-3-yl)benzonitrile; 2-(2-(diethylamino)ethylamino)-4-(6-(2-(2,5-difluorophenyl)pyrrolidin-1-yl)imidazo[1,2-b]pyridazin-3-yl)benzonitrile; 7-(6-(2-(2,5-difluorophenyl)pyrrolidin-1-yl)imidazo[1,2-b]pyridazin-3-yl)-2-oxo-1,2-dihydroquinoline-3-carbonitrile; 5-(6-(2-(3-fluorophenyl)pyrrolidin-1-yl)imidazo[1,2-b]pyridazin-3-yl)-2-morpholinobenzonitrile; 5-(6-(2-(3-fluorophenyl)pyrrolidin-1-yl)imidazo[1,2-b]pyridazin-3-yl)-2-(4-methylpiperazin-1-yl)benzonitrile; 5-(6-(2-(3-fluorophenyl)pyrrolidin-1-yl)imidazo[1,2-b]pyridazin-3-yl)-2-(4-(2-methoxyethyl)piperazin-1-yl)benzonitrile; 5-(6-(2-(3-fluorophenyl)pyrrolidin-1-yl)imidazo[1,2-b]pyridazin-3-yl)-2-(2-morpholinoethylamino)benzonitrile; 5-(6-(2-(3-fluorophenyl)pyrrolidin-1-yl)imidazo[1,2-b]pyridazin-3-yl)-2-(4-morpholinopiperidin-1-yl)benzonitrile; 5-(6-(2-(3-fluorophenyl)pyrrolidin-1-yl)imidazo[1,2-b]pyridazin-3-yl)-2-(2-(pyrrolidin-1-yl)ethoxy)benzonitrile; 5-(6-(2-(3-fluorophenyl)pyrrolidin-1-yl)imidazo[1,2-b]pyridazin-3-yl)-2-(1-methylpyrrolidin-2-yl)ethoxy)benzonitrile; 4-(6-(2-(3-fluorophenyl)pyrrolidin-1-yl)imidazo[1,2-b]pyridazin-3-yl)-2-(4-methylpiperazin-1-yl)benzonitrile; 4-(6-(2-(3-fluorophenyl)pyrrolidin-1-yl)imidazo[1,2-b]pyridazin-3-yl)-2-(pyrrolidin-1-yl)ethoxy)benzonitrile; 4-(6-(2-(3-fluorophenyl)pyrrolidin-1-yl)imidazo[1,2-b]pyridazin-3-yl)-2-(2-morpholinoethoxy)benzonitrile; (R)-3-(6-(2-(3-fluorophenyl)piperidin-1-yl)imidazo[1,2-b]pyridazin-3-yl)benzonitrile; (S)-3-(6-(2-(3-fluorophenyl)piperidin-1-yl)imidazo[1,2-b]pyridazin-3-yl)benzonitrile; 4-(6-(3-(3-fluorophenyl)morpholino)imidazo[1,2-b]pyridazin-3-yl)benzonitrile; (R)-4-(6-(2-(3-fluorophenyl)piperidin-1-yl)imidazo[1,2-b]pyridazin-3-yl)benzonitrile; (S)-4-(6-(2-(3-fluorophenyl)piperidin-1-yl)imidazo[1,2-b]pyridazin-3-yl)benzonitrile; 6-(6-(2-(2,5-dimethylphenyl)pyrrolidin-1-yl)imidazo[1,2-b]pyridazin-3-yl)picolinic acid; 3-(6-((2R,4S)-3,3-difluoro-4-methyl-2-phenylpyrrolidin-1-yl)imidazo[1,2-b]pyridazin-3-yl)benzonitrile; 3-(6-(2-phenylpyrrolidin-1-yl)imidazo[1,2-b]pyridazin-3-yl)benzonitrile; 6-(6-(2-phenylpyrrolidin-1-yl)imidazo[1,2-b]pyridazin-3-yl)-3,4-dihydro-2H-benzo[e][1,3]oxazin-2-one; 4-(6-(2-(2,5-difluorophenyl)pyrrolidin-1-yl)imidazo[1,2-b]pyridazin-3-yl)-2-((R)-pyrrolidin-2-ylmethoxy)benzonitrile; 4-(6-(2-(2,5-difluorophenyl)pyrrolidin-1-yl)imidazo[1,2-b]pyridazin-3-yl)-2-((S)-pyrrolidin-2-ylmethoxy)benzonitrile; 5-(6-(2-(3-fluorophenyl)pyrrolidin-1-yl)imidazo[1,2-b]pyridazin-3-yl)-2-(4-(2-morpholino-2-oxoethyl)piperazin-1-yl)benzonitrile; 2-(4-(2-cyano-4-(6-(2-(3-fluorophenyl)pyrrolidin-1-yl)imidazo[1,2-b]pyridazin-3-yl)phenyl)piperazin-1-yl)-N,N-dimethylacetamide; 2-(4-(3-(dimethylamino)propyl)piperazin-1-yl)-5-(6-(2-(3-fluorophenyl)pyrrolidin-1-yl)imidazo[1,2-b]pyridazin-3-yl)benzonitrile; 5-(6-(2-(3-fluorophenyl)pyrrolidin-1-yl)imidazo[1,2-b]pyridazin-3-yl)-2-(4-hydroxypiperidin-1-yl)benzonitrile; 5-(6-(2-(3-fluorophenyl)pyrrolidin-1-yl)imidazo[1,2-b]pyridazin-3-yl)-2-(2-(4-isopropylpiperazin-1-yl)ethoxy)benzonitrile; 5-(6-(2-(3-fluorophenyl)pyrrolidin-1-yl)imidazo[1,2-b]pyridazin-3-yl)-2-(2-(4-(2-hydroxyethyl)piperazin-1-yl)ethoxy)benzonitrile; 5-(6-(2-(3-fluorophenyl)pyrrolidin-1-yl)imidazo[1,2-b]pyridazin-3-yl)-2-(((R)-5-oxopyrrolidin-2-yl)methoxy)benzonitrile; 3-(6-((2R,4S)-3,3-difluoro-2-(3-fluorophenyl)-4-methylpyrrolidin-1-yl)imidazo[1,2-b]pyridazin-3-yl)benzonitrile; 6-(2-(3-fluorophenyl)pyrrolidin-1-yl)-3-(1H-indol-4-yl)imidazo[1,2-b]pyridazine; 6-(2-(3-fluorophenyl)pyrrolidin-1-yl)-3-(1-methyl-1H-indol-2-yl)imidazo[1,2-b]pyridazine; 6-(2-(3-fluorophenyl)pyrrolidin-1-yl)-3-(1H-indol-5-yl)imidazo[1,2-b]pyridazine; 6-(2-(3-fluorophenyl)pyrrolidin-1-yl)-3-(5-(4-methylpiperazin-1-yl)pyrazin-1-yl)imidazo[1,2-b]pyridazine; 4-(6-(2-(3-fluorophenyl)pyrrolidin-1-yl)imidazo[1,2-b]pyridazin-3-yl)-2-(piperidin-1-yl)thiazole; 6-(2-(3-fluorophenyl)pyrrolidin-1-yl)-3-(5-(pyrrolidin-1-yl)pyrazin-2-yl)imidazo[1,2-b]pyridazine; tert-butyl 4-(6-(6-(2-(3-fluorophenyl)pyrrolidin-1-yl)imidazo[1,2-b]pyridazin-3-yl)pyridin-2-yl)piperazine-1-carboxylate; 3-(6-(2-(3-fluorophenyl)pyrrolidin-1-yl)imidazo[1,2-b]pyridazin-3-yl)benzonitrile; tert-butyl 5-(6-(2-(3-fluorophenyl)pyrrolidin-1-yl)imidazo[1,2-b]pyridazin-3-yl)-2-methylphenylcarbamate; 6-(2-(3-fluorophenyl)pyrrolidin-1-yl)-3-(pyridin-2-yl)imidazo[1,2-b]pyridazine; 3-(6-chloropyrazin-2-yl)-6-(2-(3-fluorophenyl)pyrrolidin-1-yl)imidazo[1,2-b]pyridazine; 3-(6-(1H-imidazol-1-yl)pyrazin-2-yl)-6-(2-(3-fluorophenyl)pyrrolidin-1-yl)imidazo[1,2-b]pyridazine; 2-chloro-5-(6-(2-(3-fluorophenyl)pyrrolidin-1-yl)imidazo[1,2-b]pyridazin-3-yl)thiazole; 5-(6-(2-(3-fluorophenyl)pyrrolidin-1-yl)imidazo[1,2-b]pyridazin-3-yl)-N,N-dimethylpyrazin-2-amine; 6-(2-(3-fluorophenyl)pyrrolidin-1-yl)-3-(6-(piperazin-1-yl)pyridin-2-yl)imidazo[1,2-b]pyridazine; 4-(6-(6-(2-(3-fluorophenyl)pyrrolidin-1-yl)imidazo[1,2-b]pyridazin-3-yl)pyridin-2-yl)morpholine; (S)-6-(6-(2-(2,5-difluorophenyl)pyrrolidin-1-yl)imidazo[1,2-b]pyridazin-3-yl)picolinonitrile; (R)-6-(6-(2-(2,5-difluorophenyl)pyrrolidin-1-yl)imidazo[1,2-b]pyridazin-3-yl)picolinonitrile; 3-(6-(3-(3-fluorophenyl)morpholino)imidazo[1,2-b]pyridazin-3-yl)-benzonitrile; 6-(6-(3-(3-fluorophenyl)morpholino)imidazo[1,2-b]pyridazin-3-yl)indolin-2-one; 6-(2-(2,5-difluorophenyl)pyrrolidin-1-yl)-3-(1H-indol-4-yl)imidazo[1,2-b]pyridazine; 4-(6-(6-(2-(2,5-difluorophenyl)pyrrolidin-1-yl)imidazo[1,2-b]pyridazin-3-yl)pyridin-2-yl)morpholine; 6-(2-(2,5-difluorophenyl)pyrrolidin-1-yl)-3-(1H-indol-5-yl)imidazo[1,2-b]pyridazine; (R)-4-(6-(3-(3-fluorophenyl)morpholino)imidazo[1,2-b]pyridazin-3-yl)benzonitrile; (S)-4-(6-(3-(3-fluorophenyl)morpholino)imidazo[1,2-b]pyridazin-3-yl)benzonitrile; 6-(2-(3-fluorophenyl)pyrrolidin-1-yl)-3-(1H-indazol-5-yl)imidazo[1,2-b]pyridazine; 3-(5-fluoro-6-methylpyridin-2-yl)-6-(2-(3-fluorophenyl)pyrrolidin-1-yl)imidazo[1,2-b]pyridazine; 3-(3-fluorophenyl)-4-(3-(pyridin-2-yl)imidazo[1,2-b]pyridazin-6-yl)morpholine; 6-(6-(3-(3-fluorophenyl)morpholino)imidazo[1,2-b]pyridazin-3-yl)nicotinonitrile; 2-fluoro-5-(6-(3-(3-fluorophenyl)morpholino)imidazo[1,2-b]pyridazin-3-yl)benzonitrile; 6-(2-(3-fluorophenyl)pyrrolidin-1-yl)-3-(6-methoxypyridin-2-yl)imidazo[1,2-b]pyridazine; 6-(2-(3-fluorophenyl)pyrrolidin-1-yl)-3-(6-fluoropyridin-2-yl)imidazo[1,2-b]pyridazine; 5-(6-(2-(3-fluorophenyl)pyrrolidin-1-yl)imidazo[1,2-b]pyridazin-3-yl)-N-(2-hydroxyethyl)picolinamide; 5-(6-(2-(3-fluorophenyl)pyrrolidin-1-yl)imidazo[1,2-b]pyridazin-3-yl)picolinamide; 6-(2-(3-fluorophenyl)pyrrolidin-1-yl)-3-(1H-indazol-6-yl)imidazo[1,2-b]pyridazine; 6-(4-(2,5-difluorophenyl)pyrrolidin-1-yl)-3-(1H-indazol-6-yl)imidazo[1,2-b]pyridazine; 6-(2-(3-fluorophenyl)pyrrolidin-1-yl)-3-(6-(piperazin-1-yl)pyridin-3-yl)imidazo[1,2-b]pyridazine; 2-(4-(2-cyano-4-(6-(3-(3-fluorophenyl)morpholino)imidazo[1,2-b]pyridazin-3-yl)phenyl)piperazin-1-yl)-N,N-dimethylacetamide; 2-(6-(6-(2-(3-fluorophenyl)pyrrolidin-1-yl)imidazo[1,2-b]pyridazin-3-yl)pyridin-2-ylamino)ethanol; 1-(6-(6-(2-(3-fluorophenyl)pyrrolidin-1-yl)imidazo[1,2-b]pyridazin-3-yl)pyridin-2-yl)piperidin-4-ol; 6-(2-(2,5-difluorophenyl)pyrrolidin-1-yl)-3-(6-fluoropyridin-2-yl)imidazo[1,2-b]pyridazine; 4-(6-(6-(2-(3-fluorophenyl)pyrrolidin-1-yl)imidazo[1,2-b]pyridazin-3-yl)pyridin-2-yl)piperazin-2-one; 7-(6-(2-(3-fluorophenyl)pyrrolidin-1-yl)imidazo[1,2-b]pyridazin-3-yl)-2-oxo-1,2-dihydroquinoline-3-carbonitrile; 4-(6-(2-(3-fluorophenyl)pyrrolidin-1-yl)imidazo[1,2-b]pyridazin-3-yl)-2-(piperazin-1-ylmethyl)benzonitrile; N1,N1-diethyl-N2-(6-(6-(2-(3- fluorophenyl)pyrrolidin-1-yl)imidazo[1,2-b]pyridazin-3-yl)pyridin-2-yl)ethane-1,2-diamine; 6-(2-(3-fluorophenyl)pyrrolidin-1-yl)-3-(6-(4-methylpiperazin-1-yl)pyridin-2-yl)imidazo[1,2-b]pyridazine; (2S)-3-(6-(6-(2-(3-fluorophenyl)pyrrolidin-1-yl)imidazo[1,2-b]pyridazin-3-yl)pyridin-2-ylamino)propane-1,2-diol; 6-(2-(2,5-difluorophenyl)pyrrolidin-1-yl)-3-(6-(piperazin-1-yl)pyridin-3-yl)imidazo[1,2-b]pyridazine; 6-(2-(2,5-difluorophenyl)pyrrolidin-1-yl)-3-(6-(piperazin-1-yl)pyridin-2-yl)imidazo[1,2-b]pyridazine; 6-(2-(2,5-difluorophenyl)pyrrolidin-1-yl)-3-(6-(4-methylpiperazin-1-yl)pyridin-2-yl)imidazo[1,2-b]pyridazine; 4-(6-(6-(2-(2,5-difluorophenyl)pyrrolidin-1-yl)imidazo[1,2-b]pyridazin-3-yl)pyridin-2-yl)piperazin-2-one; (3S)-1-(6-(6-(2-(3-fluorophenyl)pyrrolidin-1-yl)imidazo[1,2-b]pyridazin-3-yl)pyridin-2-yl)pyrrolidin-3-ol; (3R)-1-(6-(6-(2-(3-fluorophenyl)pyrrolidin-1-yl)imidazo[1,2-b]pyridazin-3-yl)pyridin-2-yl)pyrrolidin-3-ol; (3S,4S)-1-(6-(6-(2-(3-fluorophenyl)pyrrolidin-1-yl)imidazo[1,2-b]pyridazin-3-yl)pyridin-2-yl)pyrrolidine-3,4-diol; 3-(3-fluorophenyl)-4-(3-(5-(morpholinomethyl)pyridin-2-yl)imidazo[1,2-b]pyridazin-6-yl)morpholine; 4-((6-(6-(2-(3-fluorophenyl)pyrrolidin-1-yl)imidazo[1,2-b]pyridazin-3-yl)pyridin-3-yl)methyl)morpholine; 4-(6-(3-(3-fluorophenyl)morpholino)imidazo[1,2-b]pyridazin-3-yl)-2-((4-methylpiperazin-1-yl)methyl)benzonitrile; 1-(6-(6-(2-(2,5-difluorophenyl)pyrrolidin-1-yl)imidazo[1,2-b]pyridazin-3-yl)pyridin-2-yl)piperidin-4-ol; 3-(3-fluorophenyl)-4-(3-(6-fluoropyridin-2-yl)imidazo[1,2-b]pyridazin-6-yl)morpholine; (5-(6-(2-(3-fluorophenyl)pyrrolidin-1-yl)imidazo[1,2-b]pyridazin-3-yl)pyridin-2-yl)(4-hydroxypiperidin-1-yl)methanone; 3-(3-fluorophenyl)-4-(3-(6-morpholinopyridin-2-yl)imidazo[1,2-b]pyridazin-6-yl)morpholine; 3-(3-fluorophenyl)-4-(3-(6-(piperazin-1-yl)pyridin-2-yl)imidazo[1,2-b]pyridazin-6-yl)morpholine; 4-(6-(2-(2-fluorophenyl)pyrrolidin-1-yl)imidazo[1,2-b]pyridazin-3-yl)benzonitrile; 3-(6-(2-(2-fluorophenyl)pyrrolidin-1-yl)imidazo[1,2-b]pyridazin-3-yl)benzonitrile; 4-(4-(6-(2-(2-fluorophenyl)pyrrolidin-1-yl)imidazo[1,2-b]pyridazin-3-yl)thiazol-2-yl)morpholine; 5-(6-(3-(3-fluorophenyl)morpholino)imidazo[1,2-b]pyridazin-3-yl)-2-(4-methylpiperazin-1-yl)benzonitrile; 2-(4-acetylpiperazin-1-yl)-5-(6-(3-(3-fluorophenyl)morpholino)imidazo[1,2-b]pyridazin-3-yl)benzonitrile; 5-(6-(2-(2-fluorophenyl)pyrrolidin-1-yl)imidazo[1,2-b]pyridazin-3-yl)-2-(4-hydroxypiperidin-1-yl)benzonitrile; 1-(6-(6-(3-(3-fluorophenyl)morpholino)imidazo[1,2-b]pyridazin-3-yl)pyridin-2-yl)piperidin-4-ol; N-(5-(6-(2-(3-fluorophenyl)pyrrolidin-1-yl)imidazo[1,2-b]pyridazin-3-yl)pyrazin-2-yl)cyclopropanecarboxamide; 4-(6-(2-(3-fluorophenyl)pyrrolidin-1-yl)imidazo[1,2-b]pyridazin-3-yl)-2-((4-methylpiperazin-1-yl)methyl)benzonitrile; (2S)-4-(6-(6-(2-(3-fluorophenyl)pyrrolidin-1-yl)imidazo[1,2-b]pyridazin-3-yl)pyridin-2-yl)-2-methylmorpholine; 1-(6-(6-(2-(3-fluorophenyl)pyrrolidin-1-yl)imidazo[1,2-b]pyridazin-3-yl)pyridin-2-yl)piperidine-4-carboxylic acid; 5-(6-(2-(3-fluorophenyl)pyrrolidin-1-yl)imidazo[1,2-b]pyridazin-3-yl)-2-methoxythiazole; 4-(6-(2-(3-fluorophenyl)pyrrolidin-1-yl)imidazo[1,2-b]pyridazin-3-yl)thiazole-2-carboxylic acid; (4-(6-(2-(3-fluorophenyl)pyrrolidin-1-yl)imidazo[1,2-b]pyridazin-3-yl)thiazol-2-yl)methanol; 1-(6-(6-(2-(3-fluorophenyl)pyrrolidin-1-yl)imidazo[1,2-b]pyridazin-3-yl)pyridin-2-yl)piperidin-3-ol; (3R)-1-(6-(6-(2-(3-fluorophenyl)pyrrolidin-1-yl)imidazo[1,2-b]pyridazin-3-yl)pyridin-2-yl)-N,N-dimethylpyrrolidin-3-amine; 6-(2-(3-fluorophenyl)pyrrolidin-1-yl)-3-(1-methyl-1H-imidazol-2-yl)imidazo[1,2-b]pyridazine; 5-(6-(3-(3-fluorophenyl)morpholino)imidazo[1,2-b]pyridazin-3-yl)-2-(piperazin-1-yl)benzonitrile; tert-butyl 4-(6-(6-(3-(3-fluorophenyl)morpholino)imidazo[1,2-b]pyridazin-3-yl)pyridin-2-yl)piperazine-1-carboxylate; 3-(3-fluorophenyl)-4-(3-(6-(4-methylpiperazin-1-yl)pyridin-2-yl)imidazo[1,2-b]pyridazin-6-yl)morpholine; 4-(6-(6-(3-(3-fluorophenyl)morpholino)imidazo[1,2-b]pyridazin-3-yl)pyridin-2-yl)-2,6-dimethylmorpholine; 3-(3-fluorophenyl)-4-(3-(6-(piperidin-4-yloxy)pyridin-2-yl)imidazo[1,2-b]pyridazin-6-yl)morpholine; 4-(6-(2-(3-fluorophenyl)pyrrolidin-1-yl)imidazo[1,2-b]pyridazin-3-yl)-2-(piperazin-1-ylmethyl)thiazole; 2,2'-(6-(6-(2-(3-fluorophenyl)pyrrolidin-1-yl)imidazo[1,2-b]pyridazin-3-yl)pyridin-2-ylazanediyl)diethanol; 4-(2-(6-(6-(2-(3-fluorophenyl)pyrrolidin-1-yl)imidazo[1,2-b]pyridazin-3-yl)pyridin-2-yloxy)ethyl)morpholine; 6-(2-(3-fluorophenyl)pyrrolidin-1-yl)-3-(6-(2-(pyrrolidin-1-yl)ethoxy)pyridin-2-yl)imidazo[1,2-b]pyridazine; 4-((6-(6-(2-(3-fluorophenyl)pyrrolidin-1-yl)imidazo[1,2-b]pyridazin-3-yl)pyridin-2-yl)methyl)morpholine; 4-((6-(6-(2-(3-fluorophenyl)pyrrolidin-1-yl)imidazo[1,2-b]pyridazin-3-yl)pyridin-2-yl)methyl)-2,6-dimethylmorpholine; 1-((6-(6-(2-(3-fluorophenyl)pyrrolidin-1-yl)imidazo[1,2-b]pyridazin-3-yl)pyridin-2-yl)methyl)pyrrolidin-3-ol; 4-(6-(2-(3-fluorophenyl)pyrrolidin-1-yl)imidazo[1,2-b]pyridazin-3-yl)-2-methoxythiazole; ethyl 4-(5-(6-(3-(3-fluorophenyl)morpholino)imidazo[1,2-b]pyridazin-3-yl)-2-oxo-2,3-dihydro-1H-benzo[d]imidazol-1-yl)piperidine-1-carboxylate; 6-(6-(2-(2,5-difluorophenyl)pyrrolidin-1-yl)imidazo[1,2-b]pyridazin-3-yl)nicotinonitrile; 5-(6-(3-(3-fluorophenyl)morpholino)imidazo[1,2-b]pyridazin-3-yl)-1-(piperidin-4-yl)-1H-benzo[d]imidazol-2(3H)-one; 2-(4-(6-(6-(2-(3-fluorophenyl)pyrrolidin-1-yl)imidazo[1,2-b]pyridazin-3-yl)pyridin-2-yl)piperazin-1-yl)-N,N-dimethylacetamide; 6-(2-(3-fluorophenyl)pyrrolidin-1-yl)-3-(6-(4-isopropylpiperazin-1-yl)pyridin-2-yl)imidazo[1,2-b]pyridazine; 2-(1-(6-(6-(2-(3-fluorophenyl)pyrrolidin-1-yl)imidazo[1,2-b]pyridazin-3-yl)pyridin-2-yl)piperidin-4-yl)propan-2-ol; 4-(1-(6-(6-(2-(3-fluorophenyl)pyrrolidin-1-yl)imidazo[1,2-b]pyridazin-3-yl)pyridin-2-yl)piperidin-4-yl)morpholine; 3-(4-(6-(6-(2-(3-fluorophenyl)pyrrolidin-1-yl)imidazo[1,2-b]pyridazin-3-yl)pyridin-2-yl)piperazin-1-yl)propanenitrile; 1-(6-(6-(2-(3-fluorophenyl)piperidin-1-yl)imidazo[1,2-b]pyridazin-3-yl)pyridin-2-yl)piperidin-4-ol; 2-(4-(6-(6-(2-(3-fluorophenyl)pyrrolidin-1-yl)imidazo[1,2-b]pyridazin-3-yl)pyridin-2-yl)piperazin-1-yl)-N-isopropylacetamide; (1-(6-(6-(2-(3-fluorophenyl)pyrrolidin-1-yl)imidazo[1,2-b]pyridazin-3-yl)pyridin-2-yl)piperidin-4-yl)methanol; (1-(6-(6-(2-(3-fluorophenyl)pyrrolidin-1-yl)imidazo[1,2-b]pyridazin-3-yl)pyridin-2-yl)piperidin-3-yl)methanol; 1-(6-(6-(2-(3-fluorophenyl)pyrrolidin-1-yl)imidazo[1,2-b]pyridazin-3-yl)pyridin-2-yl)piperidine-4-carbonitrile; 2-(4-(6-(6-(2-(3-fluorophenyl)pyrrolidin-1-yl)imidazo[1,2-b]pyridazin-3-yl)pyridin-2-yl)piperazin-1-yl)ethanol; (6-(6-(2-(3-fluorophenyl)pyrrolidin-1-yl)imidazo[1,2-b]pyridazin-3-yl)pyridin-2-yl)methanol; 6-(2-(3-fluorophenyl)pyrrolidin-1-yl)-3-(6-(5-methyl-1H-imidazol-2-yl)pyridin-2-yl)imidazo[1,2-b]pyridazine; 6-(6-(2-(3-fluorophenyl)pyrrolidin-1-yl)imidazo[1,2-b]pyridazin-3-yl)picolinamide; (R)-6-(2-(3-fluorophenyl)pyrrolidin-1-yl)-3-(6-fluoropyridin-2-yl)imidazo[1,2-b]pyridazine; (R)-1-(6-(6-(2-(3-fluorophenyl)pyrrolidin-1-yl)imidazo[1,2-b]pyridazin-3-yl)pyridin-2-yl)piperidin-4-ol; (1-(6-(6-(3-(3-fluorophenyl)morpholino)imidazo[1,2-b]pyridazin-3-yl)pyridin-2-yl)piperidin-4-yl)methanol; 2-(1-(6-(6-(3-(3-fluorophenyl)morpholino)imidazo[1,2-b]pyridazin-3-yl)pyridin-2-yl)piperidin-4-yl)ethanol; 1-(6-(6-(3-(3-fluorophenyl)morpholino)imidazo[1,2-b]pyridazin-3-yl)pyridin-2-yl)piperidine-3-carboxamide;

1-(6-(6-(3-(3-fluorophenyl)morpholino)imidazo[1,2-b]pyridazin-3-yl)pyridin-2-yl)piperidine-4-carboxamide; 6-(6-(2-(3-fluorophenyl)pyrrolidin-1-yl)imidazo[1,2-b]pyridazin-3-yl)pyridin-2-ol; 6-(6-(2-(3-fluorophenyl)pyrrolidin-1-yl)imidazo[1,2-b]pyridazin-3-yl)picolinic acid; 2-fluoro-3-(6-(2-(3-fluorophenyl)pyrrolidin-1-yl)imidazo[1,2-b]pyridazin-3-yl)quinoline; 3-(6-(2-(3-fluorophenyl)pyrrolidin-1-yl)imidazo[1,2-b]pyridazin-3-yl)quinolin-2(1H)-one; 5-(6-(2-(3-fluorophenyl)pyrrolidin-1-yl)imidazo[1,2-b]pyridazin-3-yl)quinoline; 6-(2-(3-fluorophenyl)pyrrolidin-1-yl)-3-(4-(methylsulfonyl)phenyl)imidazo[1,2-b]pyridazine; 6-(2-(3-fluorophenyl)pyrrolidin-1-yl)-3-(6-(piperidin-4-yloxy)pyridin-2-yl)imidazo[1,2-b]pyridazine; (1-(6-(6-(2-(3-fluorophenyl)pyrrolidin-1-yl)imidazo[1,2-b]pyridazin-3-yl)pyridin-2-ylamino)cyclopentyl)methanol; 3-(3-fluorophenyl)-4-(3-(6-(4-(1-methylpiperidin-4-yl)piperazin-1-yl)pyridin-2-yl)imidazo[1,2-b]pyridazin-6-yl)morpholine; 3-(6-(2-(3-fluorophenyl)pyrrolidin-1-yl)imidazo[1,2-b]pyridazin-3-yl)quinoline; (6-(6-(2-(3-fluorophenyl)pyrrolidin-1-yl)imidazo[1,2-b]pyridazin-3-yl)pyridin-2-yl)(4-hydroxypiperidin-1-yl)methanone; 6-(2-(3-fluorophenyl)pyrrolidin-1-yl)-3-(2-fluoropyridin-4-yl)imidazo[1,2-b]pyridazine; 1-(4-(6-(2-(3-fluorophenyl)pyrrolidin-1-yl)imidazo[1,2-b]pyridazin-3-yl)pyridin-2-yl)piperidin-4-ol; N1,N1-diethyl-N2-(6-(6-(2-(3-fluorophenyl)piperidin-1-yl)imidazo[1,2-b]pyridazin-3-yl)pyridin-2-yl)ethane-1,2-diamine; 6-(2-(3-fluorophenyl)piperidin-1-yl)-3-(6-(4-isopropylpiperazin-1-yl)pyridin-2-yl)imidazo[1,2-b]pyridazine; (3S)-1-(6-(6-(2-(3-fluorophenyl)piperidin-1-yl)imidazo[1,2-b]pyridazin-3-yl)pyridin-2-yl)-N,N-dimethylpyrrolidin-3-amine; 4-(3-(6-(2,5-diazabicyclo[2.2.1]heptan-2-yl)pyridin-2-yl)imidazo[1,2-b]pyridazin-6-yl)-3-(3-fluorophenyl)morpholine; 6-(6-(3-(3-fluorophenyl)morpholino)imidazo[1,2-b]pyridazin-3-yl)-N-(2-(piperazin-1-yl)ethyl)pyridin-2-amine; 6-(2-(3-fluorophenyl)pyrrolidin-1-yl)-3-(6-(1-(methylsulfonyl)piperidin-4-yloxy)pyridin-2-yl)imidazo[1,2-b]pyridazine; 4-(6-(2-(2,5-difluorophenyl)pyrrolidin-1-yl)imidazo pyridin-3-yl)-2-fluorobenzonitrile; 2-ethoxy-4-(6-(2-(3-fluorophenyl)pyrrolidin-1-yl)imidazo[1,2-a]pyridin-3-yl)thiazole; 5-(6-(2-(2,5-difluorophenyl)pyrrolidin-1-yl)imidazo[1,2-a]pyridin-3-yl)-2-fluorobenzonitrile; 4-(6-(2-(3-fluorophenyl)pyrrolidin-1-yl)imidazo[1,2-b]pyridazin-3-yl)picolinic acid; 5-(6-(2-(3-fluorophenyl)pyrrolidin-1-yl)imidazo[1,2-b]pyridazin-3-yl)picolinic acid; (2S,6R)-4-(6-(6-(2-(3-fluorophenyl)pyrrolidin-1-yl)imidazo[1,2-b]pyridazin-3-yl)pyridin-2-yl)-2,6-dimethylmorpholine; 4-(6-(6-(2-(pyridin-2-yl)pyrrolidin-1-yl)imidazo[1,2-b]pyridazin-3-yl)pyridin-2-yl)morpholine; 1-(6-(6-(2-(pyridin-2-yl)pyrrolidin-1-yl)imidazo[1,2-b]pyridazin-3-yl)pyridin-2-yl)piperidin-4-ol; 1-(6-(6-(2-(pyridin-3-yl)pyrrolidin-1-yl)imidazo[1,2-b]pyridazin-3-yl)pyridin-2-yl)piperidin-4-ol; 6-(6-(2-(3-fluorophenyl)piperidin-1-yl)imidazo[1,2-b]pyridazin-3-yl)-N-methylpyridin-2-amine; 6-(6-(2-(3-fluorophenyl)piperidin-1-yl)imidazo[1,2-b]pyridazin-3-yl)-N-isopropylpyridin-2-amine; N-(6-(6-(2-(3-fluorophenyl)piperidin-1-yl)imidazo[1,2-b]pyridazin-3-yl)pyridin-2-yl)methanesulfonamide; 6-(6-(2-(3-fluorophenyl)piperidin-1-yl)imidazo[1,2-b]pyridazin-3-yl)-N,N-dimethylpyridin-2-amine; 6-(2-(3-fluorophenyl)piperidin-1-yl)-3-(6-(piperidin-4-yloxy)pyridin-2-yl)imidazo[1,2-b]pyridazine; 1-(6-(6-(2-(3-fluorophenyl)pyrrolidin-1-yl)imidazo[1,2-b]pyridazin-3-yl)pyridin-2-yl)azetidine-3-carboxylic acid; 1-(6-(6-(2-(3-fluorophenyl)pyrrolidin-1-yl)imidazo[1,2-b]pyridazin-3-yl)pyridin-2-yl)azetidin-3-ol; 4-(6-(2-(2,5-difluorophenyl)pyrrolidin-1-yl)imidazo pyridin-3-yl)-2-ethoxythiazole; 1-(6-(6-(3-(3-fluorophenyl)morpholino)imidazo[1,2-b]pyridazin-3-yl)pyridin-2-yl)piperidin-4-ol; (6-(6-(2-(3-fluorophenyl)pyrrolidin-1-yl)imidazo[1,2-b]pyridazin-3-yl)pyridin-2-yl)methanol; 6-(2-(3-fluorophenyl)pyrrolidin-1-yl)-3-(6-(5-methyl-1H-imidazol-2-yl)pyridin-2-yl)imidazo[1,2-b]pyridazine; (1-(6-(6-(3-(3-fluorophenyl)morpholino)imidazo[1,2-b]pyridazin-3-yl)pyridin-2-yl)piperidin-4-yl)methanol; 2-(4-(6-(6-(3-(3-fluorophenyl)morpholino)imidazo[1,2-b]pyridazin-3-yl)pyridin-2-yl)piperazin-1-yl)ethanol; 1-(6-(6-(3-(3-fluorophenyl)morpholino)imidazo[1,2-b]pyridazin-3-yl)pyridin-2-yl)piperidine-3-carboxamide; 1-(6-(6-(3-(3-fluorophenyl)morpholino)imidazo[1,2-b]pyridazin-3-yl)pyridin-2-yl)piperidine-4-carboxamide; 3-(3-fluorophenyl)-4-(3-(6-(4-(1-methylpiperidin-4-yl)piperazin-1-yl)pyridin-2-yl)imidazo[1,2-b]pyridazin-6-yl)morpholine; 4-(3-(6-(2,5-diazabicyclo[2.2.1]heptan-2-yl)pyridin-2-yl)imidazo[1,2-b]pyridazin-6-yl)-3-(3-fluorophenyl)morpholine; 6-(6-(3-(3-fluorophenyl)morpholino)imidazo[1,2-b]pyridazin-3-yl)-N-(2-(piperazin-1-yl)ethyl)pyridin-2-amine; 1-(6-(6-(3-(3-fluorophenyl)morpholino)imidazo[1,2-b]pyridazin-3-yl)pyridin-2-yl)-N-methylpiperidine-4-carboxamide; 1-(6-(6-(3-(3-fluorophenyl)morpholino)imidazo[1,2-b]pyridazin-3-yl)pyridin-2-yl)-N-(2-hydroxyethyl)piperidine-4-carboxamide; (S)-6-(6-(3-(3-fluorophenyl)morpholino)imidazo[1,2-b]pyridazin-3-yl)indolin-2-one; (R)-6-(6-(3-(3-fluorophenyl)morpholino)imidazo[1,2-b]pyridazin-3-yl)indolin-2-one; (S)-1-(6-(6-(3-(3-fluorophenyl)morpholino)imidazo[1,2-b]pyridazin-3-yl)pyridin-2-yl)piperidin-4-ol; (R)-1-(6-(6-(3-(3-fluorophenyl)morpholino)imidazo[1,2-b]pyridazin-3-yl)pyridin-2-yl)piperidin-4-ol; ethyl 1-(6-(6-(3-(3-fluorophenyl)morpholino)imidazo[1,2-b]pyridazin-3-yl)pyridin-2-yl)piperidine-4-carboxylate; 3-(6-(1,3-dioxolan-2-yl)pyridin-2-yl)-6-(2-(3-fluorophenyl)pyrrolidin-1-yl)imidazo[1,2-b]pyridazine; 1-(6-(6-(3-(3-fluorophenyl)morpholino)imidazo[1,2-b]pyridazin-3-yl)pyridin-2-yl)piperidine-4-carboxylic acid; 5-(6-(6-(2-(3-fluorophenyl)pyrrolidin-1-yl)imidazo[1,2-b]pyridazin-3-yl)pyridin-2-yl)oxazole; 3-(3-fluorophenyl)-4-(3-(6-(4-(3-isopropyl-1,2,4-oxadiazol-5-yl)piperidin-1-yl)pyridin-2-yl)imidazo[1,2-b]pyridazin-6-yl)morpholine; N-(cyclopropylmethoxy)-1-(6-(6-(3-(3-fluorophenyl)morpholino)imidazo[1,2-b]pyridazin-3-yl)pyridin-2-yl)piperidine-4-carboxamide; 1-(6-(6-(3-(3-fluorophenyl)morpholino)imidazo[1,2-b]pyridazin-3-yl)pyridin-2-yl)-N-isopropylpiperidine-4-carboxamide; N-cyclopropyl-1-(6-(6-(3-(3-fluorophenyl)morpholino)imidazo[1,2-b]pyridazin-3-yl)pyridin-2-yl)piperidine-4-carboxamide; 1-(6-(6-(3-(3-fluorophenyl)morpholino)imidazo[1,2-b]pyridazin-3-yl)pyridin-2-yl)-N-(isoxazol-3-yl)piperidine-4-carboxamide; (1-(6-(6-(3-(3-fluorophenyl)morpholino)imidazo[1,2-b]pyridazin-3-yl)pyridin-2-yl)piperidin-4-yl)(3-hydroxypyrrolidin-1-yl)methanone; N-(cyanomethyl)-1-(6-(6-(3-(3-fluorophenyl)morpholino)imidazo[1,2-b]pyridazin-3-yl)pyridin-2-yl)piperidine-4-carboxamide; 2-(1-(6-(6-(3-(3-fluorophenyl)morpholino)imidazo[1,2-b]pyridazin-3-yl)pyridin-2-yl)piperidin-4-yl)ethanol; 3-(6-(1H-pyrazol-5-yl)pyridin-2-yl)-6-(2-(3-fluorophenyl)pyrrolidin-1-yl)imidazo[1,2-b]pyridazine; 5-(6-(6-(2-(3-fluorophenyl)pyrrolidin-1-yl)imidazo[1,2-b]pyridazin-3-yl)pyridin-2-yl)pyrazolo[1,5-a]pyrimidine-2-carbonitrile; 6-(2-(3-fluorophenyl)pyrrolidin-1-yl)-3-(6-(2-methylpyrimidin-4-yl)pyridin-2-yl)imidazo[1,2-b]pyridazine; 4-(6-(6-(2-(3-fluorophenyl)pyrrolidin-1-yl)imidazo[1,2-b]pyridazin-3-yl)pyridin-2-yl)pyrimidin-2-amine; 3-(6-((2R,5S)-2,5-dimethylpiperazin-1-yl)pyridin-2-yl)-6-(2-(3-fluorophenyl)pyrrolidin-1-yl)imidazo[1,2-b]pyridazine; 3-(6-((3S,5R)-3,5-dimethylpiperazin-1-yl)pyridin-2-yl)-6-(2-(3-fluorophenyl)pyrrolidin-1-yl)imidazo[1,2-b]pyridazine; 6-(6-(6-(2-(3-fluorophenyl)pyrrolidin-1- yl)imidazo[1,2-b]pyridazin-3-yl)pyridin-2-yl)pyrimidin-2 (1H)-one; 6-(2-(3-fluorophenyl)pyrrolidin-1-yl)-3-(6-(4-(pyrazin-2-yl)piperazin-1-yl)pyridin-2-yl)imidazo[1,2-b] pyridazine; 6-(2-(3-fluorophenyl)pyrrolidin-1-yl)-3-(6-(4-(pyrimidin-2-yl)piperazin-1-yl)pyridin-2-yl)imidazo[1,2-b] pyridazine; 6-(2-(3-fluorophenyl)pyrrolidin-1-yl)-3-(6-(3-(piperidin-4-yl)-1H-pyrazol-5-yl)pyridin-2-yl)imidazo[1,2-b]pyridazine; 4-(4-(6-(6-(2-(3-fluorophenyl)pyrrolidin-1-yl)imidazo[1,2-b]pyridazin-3-yl)pyridin-2-yl)pyrimidin-2-yl)morpholine; 6-(2-(3-fluorophenyl)pyrrolidin-1-yl)-3-(6-(4-(2-(methylsulfonyl)ethyl)piperazin-1-yl)pyridin-2-yl)imidazo[1,2-b]pyridazine; 2-(4-(6-(6-(2-(3-fluorophenyl)pyrrolidin-1-yl)imidazo[1,2-b]pyridazin-3-yl)pyridin-2-yl)pyrimidin-2-ylamino)ethanol; 6-(2-(3-fluorophenyl)pyrrolidin-1-yl)-3-(6-(6-(piperidin-4-yl)pyrimidin-4-yl)pyridin-2-yl)imidazo[1,2-b]pyridazine; 2-(4-(6-(6-(2-(3-fluorophenyl)pyrrolidin-1-yl)imidazo[1,2-b]pyridazin-3-yl)pyridin-2-yl)piperazin-1-yl)-N,N-dimethylethanamine; 6-(2-(3-fluorophenyl)pyrrolidin-1-yl)-3-(6-(pyrimidin-4-yl)pyridin-2-yl)imidazo[1,2-b]pyridazine; 4-(1-(6-(6-(2-(3-fluorophenyl)pyrrolidin-1-yl)imidazo[1,2-b]pyridazin-3-yl)pyridin-2-yl)pyrrolidin-3-yl)morpholine; 3-(6-(4-(cyclopropylsulfonyl)piperazin-1-yl)pyridin-2-yl)-6-(2-(3-fluorophenyl)pyrrolidin-1-yl)imidazo[1,2-b]pyridazine; 1-(4-(6-(6-(2-(3-fluorophenyl)pyrrolidin-1-yl)imidazo[1,2-b]pyridazin-3-yl)pyridin-2-yl)piperazin-1-yl)-2-hydroxyethanone; (4-(6-(6-(2-(3-fluorophenyl)pyrrolidin-1-yl)imidazo[1,2-b]pyridazin-3-yl)pyridin-2-yl)piperazin-1-yl)(1-hydroxycyclopropyl)methanone; (R)-6-(2-(3-fluorophenyl)pyrrolidin-1-yl)-3-(6-(2-methylpyrimidin-4-yl)pyridin-2-yl)imidazo[1,2-b]pyridazine; (4-(6-(6-(2-(3-fluorophenyl)pyrrolidin-1-yl)imidazo[1,2-b]pyridazin-3-yl)pyridin-2-yl)piperazin-1-yl)(tetrahydro-2H-pyran-4-yl)methanone; (4-(6-(6-(2-(3-fluorophenyl)pyrrolidin-1-yl)imidazo[1,2-b]pyridazin-3-yl)pyridin-2-yl)piperazin-1-yl)(tetrahydrofuran-2-yl)methanone; 4-(6-(6-(2-(3-fluorophenyl)pyrrolidin-1-yl)imidazo[1,2-b]pyridazin-3-yl)-2,3'-bipyridin-6'-yl)morpholine; 6-(2-(3-fluorophenyl)pyrrolidin-1-yl)-3-(6-(5-(pyrrolidin-1-yl)pyrazin-2-yl)pyridin-2-yl)imidazo[1,2-b]pyridazine; 4-(5-(6-(6-(2-(3-fluorophenyl)pyrrolidin-1-yl)imidazo[1,2-b]pyridazin-3-yl)pyridin-2-yl)pyrimidin-2-yl)morpholine; 1-(6-(6-(2-(3-fluorophenyl)pyrrolidin-1-yl)imidazo[1,2-b]pyridazin-3-yl)-2,4'-bipyridin-2'-yl)piperidin-4-ol; N1-(4-(6-(6-(2-(3-fluorophenyl)pyrrolidin-1-yl)imidazo[1,2-b]pyridazin-3-yl)pyridin-2-yl)pyrimidin-2-yl)-N2,N2-dimethylethane-1,2-diamine; 1-(4-(6-(6-(2-(3-fluorophenyl)pyrrolidin-1-yl)imidazo[1,2-b]pyridazin-3-yl)pyridin-2-yl)pyrimidin-2-yl)piperidin-4-ol; 4-(6-(6-(2-(3-fluorophenyl)pyrrolidin-1-yl)imidazo[1,2-b]pyridazin-3-yl)pyridin-2-yl)-N,N-dimethylpyrimidin-2-amine; 3-(6-(1H-indazol-5-yl)pyridin-2-yl)-6-(2-(3-fluorophenyl)pyrrolidin-1-yl)imidazo[1,2-b]pyridazine; 2-(6-(6-(2-(3-fluorophenyl)pyrrolidin-1-yl)imidazo[1,2-b]pyridazin-3-yl)-2,3'-bipyridin-6'-ylamino)ethanol; 1-(6-(6-(2-(3-fluorophenyl)pyrrolidin-1-yl)imidazo[1,2-b]pyridazin-3-yl)-2,3'-bipyridin-6'-yl)piperidin-4-ol; (R)-2-(4-(6-(6-(2-(3-fluorophenyl)pyrrolidin-1-yl)imidazo[1,2-b]pyridazin-3-yl)pyridin-2-yl)pyrimidin-2-ylamino)ethanol; 4-((S)-1-(6-(6-((R)-2-(3-fluorophenyl)pyrrolidin-1-yl)imidazo[1,2-b]pyridazin-3-yl)pyridin-2-yl)pyrrolidin-3-yl)morpholine; (2S,6R)-4-((S)-1-(6-(6-((R)-2-(3-fluorophenyl)pyrrolidin-1-yl)imidazo[1,2-b]pyridazin-3-yl)pyridin-2-yl)pyrrolidin-3-yl)-2,6-dimethylmorpholine; (R)-1-(4-(6-(6-(2-(3-fluorophenyl)pyrrolidin-1-yl)imidazo[1,2-b]pyridazin-3-yl)pyridin-2-yl)pyrimidin-2-yl)azetidin-3-ol; (R)—N-(4-(6-(6-(2-(3-fluorophenyl)pyrrolidin-1-yl)imidazo[1,2-b]pyridazin-3-yl)pyridin-2-yl)pyrimidin-2-yl)methanesulfonamide; (R)-4-((S)-1-(6-(6-((R)-2-(3-fluorophenyl)pyrrolidin-1-yl)imidazo[1,2-b]pyridazin-3-yl)pyridin-2-yl)pyrrolidin-3-yl)-2-methylmorpholine; (R)-2-(6-(6-(2-(3-fluorophenyl)pyrrolidin-1-yl)imidazo[1,2-b]pyridazin-3-yl)-2,4'-bipyridin-2'-ylamino)ethanol; (R)-1-(6-(6-(2-(3-fluorophenyl)pyrrolidin-1-yl)imidazo[1,2-b]pyridazin-3-yl)-2,4'-bipyridin-2'-yl)azetidin-3-ol; (R)-1-(6-(6-((R)-2-(3-fluorophenyl)pyrrolidin-1-yl)imidazo[1,2-b]pyridazin-3-yl)-2,4'-bipyridin-2'-yl)pyrrolidin-3-ol; (R)—N-(6-(6-(2-(3-fluorophenyl)pyrrolidin-1-yl)imidazo[1,2-b]pyridazin-3-yl)-2,4'-bipyridin-2'-yl)methanesulfon amide; (R)-4-(6-(6-(2-(3-fluorophenyl)pyrrolidin-1-yl)imidazo[1,2-b]pyridazin-3-yl)pyridin-2-yl)-N-(pyridin-3-ylmethyl)pyrimidin-2-amine; (S)-1-(6-(6-((R)-2-(3-fluorophenyl)pyrrolidin-1-yl)imidazo[1,2-b]pyridazin-3-yl)-2,4'-bipyridin-2'-yl)-N-methylpyrrolidin-3-amine; (R)-4-(6-(6-(2-(3-fluorophenyl)pyrrolidin-1-yl)imidazo[1,2-b]pyridazin-3-yl)pyridin-2-yl)-N-(2-(methylsulfonyl)ethyl)pyrimidin-2-amine; (R)—N-(6-(6-(2-(3-fluorophenyl)pyrrolidin-1-yl)imidazo[1,2-b]pyridazin-3-yl)-2,3'-bipyridin-6'-yl)methanesulfonamide; (R)-3-(6-(1H-indazol-6-yl)pyridin-2-yl)-6-(2-(3-fluorophenyl)pyrrolidin-1-yl)imidazo[1,2-b]pyridazine; (R)-1-(6-(6-((R)-2-(3-fluorophenyl)pyrrolidin-1-yl)imidazo[1,2-b]pyridazin-3-yl)-2,4'-bipyridin-2'-yl)-N-methylpyrrolidin-3-amine; (R)-1-(6'-(6-(2-(3-fluorophenyl)pyrrolidin-1-yl)imidazo[1,2-b]pyridazin-3-yl)-2,2'-bipyridin-6-yl)piperidin-4-ol; (R)-2-(6'-(6-(2-(3-fluorophenyl)pyrrolidin-1-yl)imidazo[1,2-b]pyridazin-3-yl)-2,2'-bipyridin-6-ylamino)ethanol; (R)-1-(6'-(6-((R)-2-(3-fluorophenyl)pyrrolidin-1-yl)imidazo[1,2-b]pyridazin-3-yl)-2,2'-bipyridin-6-yl)-N-methylpyrrolidin-3-amine; (R)-1-(4-(6-(6-((R)-2-(3-fluorophenyl)pyrrolidin-1-yl)imidazo[1,2-b]pyridazin-3-yl)pyridin-2-yl)pyrimidin-2-yl)-N-methylpyrrolidin-3-amine; (R)-2-(4-(4-(6-(6-(2-(3-fluorophenyl)pyrrolidin-1-yl)imidazo[1,2-b]pyridazin-3-yl)pyridin-2-yl)pyrimidin-2-yl)piperazin-1-yl)ethanol; (R)-2-(4-(6-(6-(2-(3-fluorophenyl)pyrrolidin-1-yl)imidazo[1,2-b]pyridazin-3-yl)-2,4'-bipyridin-2'-yl)piperazin-1-yl)ethanol; 1-((2S,6R)-4-(6-(6-((R)-2-(3-fluorophenyl)pyrrolidin-1-yl)imidazo[1,2-b]pyridazin-3-yl)pyridin-2-yl)-2,6-dimethylpiperazin-1-yl)-2-hydroxyethanone; (R)-1-(6'-(6-((R)-2-(3-fluorophenyl)pyrrolidin-1-yl)imidazo[1,2-b]pyridazin-3-yl)-2,2'-bipyridin-6-yl)pyrrolidin-3-ol; (R)-2-(4-(6'-(6-(2-(3-fluorophenyl)pyrrolidin-1-yl)imidazo[1,2-b]pyridazin-3-yl)-2,2'-bipyridin-6-yl)piperazin-1-yl)ethanol; (R)-4-(6-(6-(2-(3-fluorophenyl)pyrrolidin-1-yl)imidazo[1,2-b]pyridazin-3-yl)pyridin-2-yl)benzenesulfonamide; (R)-3-(6-(6-(2-(3-fluorophenyl)pyrrolidin-1-yl)imidazo[1,2-b]pyridazin-3-yl)pyridin-2-yl)benzenesulfonamide; (R)—N-(6'-(6-(2-(3-fluorophenyl)pyrrolidin-1-yl)imidazo[1,2-b]pyridazin-3-yl)-2,2'-bipyridin-6-yl)methanesulfonamide; (R)-6-(2-(3-fluorophenyl)pyrrolidin-1-yl)-3-(2'-(piperazin-1-yl)-2,4'-bipyridin-6-yl)imidazo[1,2-b]pyridazine; (R)-6-(2-(3-fluorophenyl)pyrrolidin-1-yl)-3-(6-(4-(methylsulfonyl)phenyl)pyridin-2-yl)imidazo[1,2-b]pyridazine; (R)-4-(2-(4-(6-(6-(2-(3-fluorophenyl)pyrrolidin-1-yl)imidazo[1,2-b]pyridazin-3-yl)pyridin-2-yl)-1H-pyrazol-1-yl)ethyl)morpholine; (R)-6-(2-(3-fluorophenyl)pyrrolidin-1-yl)-3-(2'-(4-isopropylpiperazin-1-yl)-2,4'-bipyridin-6-yl)imidazo[1,2-b]pyridazine; (R)-4-(6-(6-(2-(3-fluorophenyl)pyrrolidin-1-yl)imidazo[1,2-b]pyridazin-3-yl)pyridin-2-yl)-N-methylbenzenesulfonamide; (S)-1-(6-(6-((R)-2-(3-fluorophenyl)pyrrolidin-1-yl)imidazo[1,2-b]pyridazin-3-yl)-2,4'-bipyridin-2'-yl)pyrrolidin-3-ol; 2-{6-[2-(3-fluorophenyl)pyrrolidin-1-yl]imidazo[1,2-b]pyridazin-3-yl}-6-(piperidin-4-yloxy)pyridine; {1-[(6-{6-[2-(3-fluorophenyl)pyrrolidin-1-yl]imidazo[1,2-b]pyridazin-3- yl}pyridin-2-yl)amino]cyclopentyl}methanol; (3S,4S)-1-(6-{6-[2-(3-fluorophenyl)pyrrolidin-1-yl]imidazo[1,2-b]pyridazin-3-yl}pyridin-2-yl)pyrrolidine-3,4-diol; 1-{6-[6-(3-phenylthiomorpholin-4-yl)imidazo[1,2-b]pyridazin-3-yl]pyridin-2-yl}piperidin-4-ol; 2-{6-[2-(3-fluorophenyl)pyrrolidin-1-yl]imidazo[1,2-b]pyridazin-3-yl}-6-[(1-methanesulfonylpiperidin-4-yl)oxy]pyridine; (3S,4S)-1-(6-{6-[(2S)-2-(3-fluorophenyl)pyrrolidin-1-yl]imidazo[1,2-b]pyridazin-3-yl}pyridin-2-yl)pyrrolidine-3,4-diol; (3S,4S)-1-(6-{6-[(2R)-2-(3-fluorophenyl)pyrrolidin-1-yl]imidazo[1,2-b]pyridazin-3-yl}pyridin-2-yl)pyrrolidine-3,4-diol; 4-(4-{6-[2-(3-fluorophenyl)pyrrolidin-1-yl]imidazo[1,2-b]pyridazin-3-yl}-1H-pyrazol-1-yl)piperidine; N-[(3R)-1-(6-{6-[2-(3-fluorophenyl)pyrrolidin-1-yl]imidazo[1,2-b]pyridazin-3-yl}pyridin-2-yl)pyrrolidin-3-yl]-N-methylmethanesulfonamide; 2-{6-[2-(3-fluorophenyl)pyrrolidin-1-yl]imidazo[1,2-b]pyridazin-3-yl}-6-(3-fluoropiperidin-1-yl)pyridine; N-[(3R)-1-(6-{6-[2-(3-fluorophenyl)pyrrolidin-1-yl]imidazo[1,2-b]pyridazin-3-yl}pyridin-2-yl)pyrrolidin-3-yl]-N-methylacetamide; N-[(3R)-1-(6-{6-[2-(3-fluorophenyl)pyrrolidin-1-yl]imidazo[1,2-b]pyridazin-3-yl}pyridin-2-yl)pyrrolidin-3-yl]-2-hydroxy-N-methylacetamide; 2-(3,3-difluoropiperidin-1-yl)-6-{6-[2-(3-fluorophenyl)pyrrolidin-1-yl]imidazo[1,2-b]pyridazin-3-yl}pyridine; N-ethyl-N-[(3R)-1-(6-{6-[2-(3-fluorophenyl)pyrrolidin-1-yl]imidazo[1,2-b]pyridazin-3-yl}pyridin-2-yl)pyrrolidin-3-yl]acetamide; N-ethyl-N-[(3R)-1-(6-{6-[2-(3-fluorophenyl)pyrrolidin-1-yl]imidazo[1,2-b]pyridazin-3-yl}pyridin-2-yl)pyrrolidin-3-yl]-2-hydroxyacetamide; N-[(3R)-1-(6-{6-[2-(3-fluorophenyl)pyrrolidin-1-yl]imidazo[1,2-b]pyridazin-3-yl}pyridin-2-yl)pyrrolidin-3-yl]methanesulfonamide; N-[1-(6-{6-[2-(3-fluorophenyl)pyrrolidin-1-yl]imidazo[1,2-b]pyridazin-3-yl}pyridin-2-yl)piperidin-4-yl]-N-methylmethanesulfonamide; N-[1-(6-{6-[2-(3-fluorophenyl)pyrrolidin-1-yl]imidazo[1,2-b]pyridazin-3-yl}pyridin-2-yl)piperidin-4-yl]acetamide; 1-(6-{6-[2-(3-fluorophenyl)pyrrolidin-1-yl]imidazo[1,2-b]pyridazin-3-yl}pyridin-2-yl)-3-methylpiperidin-4-ol; 1-(6-{6-[2-(3-fluorophenyl)pyrrolidin-1-yl]imidazo[1,2-b]pyridazin-3-yl}pyridin-2-yl)pyrrolidin-3-amine; 2,2,2-trifluoro-N-[(3S)-1-(6-{6-[2-(3-fluorophenyl)pyrrolidin-1-yl]imidazo[1,2-b]pyridazin-3-yl}pyridin-2-yl)pyrrolidin-3-yl]acetamide; N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]methanesulfonamide; N-ethyl-N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]acetamide; N-[1-(6-{6-[(2R)-2-(3-fluorophenyl)pyrrolidin-1-yl]imidazo[1,2-b]pyridazin-3-yl}pyridin-2-yl)azetidin-3-yl]-N-methylmethanesulfonamide; (3S)-1-(6-{6-[(2R)-2-(3-fluorophenyl)pyrrolidin-1-yl]imidazo[1,2-b]pyridazin-3-yl}pyridin-2-yl)pyrrolidin-3-amine; 2-(dimethylamino)-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one; (3R)-1-(6-{6-[(2R)-2-(3-fluorophenyl)pyrrolidin-1-yl]imidazo[1,2-b]pyridazin-3-yl}pyridin-2-yl)-3-methylpiperazine; 2-[(2R)-4-(6-{6-[(2R)-2-(3-fluorophenyl)pyrrolidin-1-yl]imidazo[1,2-b]pyridazin-3-yl}pyridin-2-yl)-2-methylpiperazin-1-yl]-2-oxoethyl acetate; 1-[(2R)-4-(6-{6-[(2R)-2-(3-fluorophenyl)pyrrolidin-1-yl]imidazo[1,2-b]pyridazin-3-yl}pyridin-2-yl)-2-methylpiperazin-1-yl]-2-hydroxyethan-1-one; 2-amino-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one; 1-[4-(6-{6-[(2R)-2-(3-fluorophenyl)pyrrolidin-1-yl]imidazo[1,2-b]pyridazin-3-yl}pyridin-2-yl)piperazin-1-yl]-2-(methylamino)ethan-1-one; 2-(dimethylamino)-1-[(2R)-4-(6-{6-[(2R)-2-(3-fluorophenyl)pyrrolidin-1-yl]imidazo[1,2-b]pyridazin-3-yl}pyridin-2-yl)-2-methylpiperazin-1-yl]ethan-1-one; (3R)-3-{[4-(6-{6-[(2R)-2-(3-fluorophenyl)pyrrolidin-1-yl]imidazo[1,2-b]pyridazin-3-yl}pyridin-2-yl)piperazin-1-yl]carbonyl}morpholine; (3R)-3-{[(2R)-4-(6-{6-[(2R)-2-(3-fluorophenyl)pyrrolidin-1-yl]imidazo[1,2-b]pyridazin-3-yl}pyridin-2-yl)-2-methylpiperazin-1-yl]carbonyl}morpholine; 8-(6-{6-[(2R)-2-(3-fluorophenyl)pyrrolidin-1-yl]imidazo[1,2-b]pyridazin-3-yl}pyridin-2-yl)-octahydropiperazino[2,1-c]morpholin-4-one; (3R,4R)-1-[4-(6-{6-[(2R)-2-(3-fluorophenyl)pyrrolidin-1-yl]imidazo[1,2-b]pyridazin-3-yl}pyridin-2-yl]pyrrolidine-3,4-diol; 1-(6-{6-[2-(3-fluorophenyl)piperidin-1-yl]imidazo[1,2-b]pyridazin-3-yl}pyridin-2-yl)piperidin-4-ol; 6-{6-[2-(3-fluorophenyl)pyrrolidin-1-yl]imidazo[1,2-b]pyridazin-3-yl}pyridine-2-carboxamide; 6-{6-[2-(3-fluorophenyl)pyrrolidin-1-yl]imidazo[1,2-b]pyridazin-3-yl}pyridin-2-ol; 6-{6-[2-(3-fluorophenyl)pyrrolidin-1-yl]imidazo[1,2-b]pyridazin-3-yl}pyridine-2-carboxylic acid; 2-fluoro-3-{6-[2-(3-fluorophenyl)pyrrolidin-1-yl]imidazo[1,2-b]pyridazin-3-yl}quinoline; 3-{6-[2-(3-fluorophenyl)pyrrolidin-1-yl]imidazo[1,2-b]pyridazin-3-yl}-1,2-dihydroquinolin-2-one; 5-{6-[2-(3-fluorophenyl)pyrrolidin-1-yl]imidazo[1,2-b]pyridazin-3-yl}quinoline; 2-(3-fluorophenyl)-1-[3-(4-methanesulfonylphenyl)imidazo[1,2-b]pyridazin-6-yl]pyrrolidine; 3-{6-[2-(3-fluorophenyl)pyrrolidin-1-yl]imidazo[1,2-b]pyridazin-3-yl}quinoline; 1-[(6-{6-[2-(3-fluorophenyl)pyrrolidin-1-yl]imidazo[1,2-b]pyridazin-3-yl}pyridin-2-yl)carbonyl]piperidin-4-ol; 2-fluoro-4-{6-[2-(3-fluorophenyl)pyrrolidin-1-yl]imidazo[1,2-b]pyridazin-3-yl}pyridine; 1-(4-{6-[2-(3-fluorophenyl)pyrrolidin-1-yl]imidazo[1,2-b]pyridazin-3-yl}pyridin-2-yl)piperidin-4-ol; 1-(4-{6-[2-(3-fluorophenyl)pyrrolidin-1-yl]imidazo[1,2-b]pyridazin-3-yl}pyridin-2-yl)-4-methylpiperazine; 2-[(4-{6-[2-(3-fluorophenyl)pyrrolidin-1-yl]imidazo[1,2-b]pyridazin-3-yl}pyridin-2-yl)amino]ethan-1-ol; (3R)-1-[(6-{6-[2-(3-fluorophenyl)pyrrolidin-1-yl]imidazo[1,2-b]pyridazin-3-yl}pyridin-2-yl)carbonyl]-N,N-dimethylpyrrolidin-3-amine; 1-(5-{6-[2-(3-fluorophenyl)pyrrolidin-1-yl]imidazo[1,2-b]pyridazin-3-yl}pyrimidin-2-yl)piperidin-4-ol; 6-{6-[2-(3-fluorophenyl)pyrrolidin-1-yl]imidazo[1,2-b]pyridazin-3-yl}-N-methylpyridine-2-carboxamide; 4-[(6-{6-[2-(3-fluorophenyl)pyrrolidin-1-yl]imidazo[1,2-b]pyridazin-3-yl}pyridin-2-yl)carbonyl]morpholine; (3R)-1-(4-{6-[2-(3-fluorophenyl)pyrrolidin-1-yl]imidazo[1,2-b]pyridazin-3-yl}pyridin-2-yl)pyrrolidin-3-ol; (3S)-1-(4-{6-[2-(3-fluorophenyl)pyrrolidin-1-yl]imidazo[1,2-b]pyridazin-3-yl}pyridin-2-yl)pyrrolidin-3-ol; (3R,4R)-1-(4-{6-[2-(3-fluorophenyl)pyrrolidin-1-yl]imidazo[1,2-b]pyridazin-3-yl}pyridin-2-yl)pyrrolidine-3,4-diol; 1-(6-{6-[2-(3-fluorophenyl)pyrrolidin-1-yl]imidazo[1,2-b]pyridazin-3-yl}pyridin-2-yl)-N,N-dimethylpiperidin-4-amine; 2-[(5-{6-[2-(3-fluorophenyl)pyrrolidin-1-yl]imidazo[1,2-b]pyridazin-3-yl}pyrimidin-2-yl)amino]ethan-1-ol; 5-{6-[2-(3-fluorophenyl)pyrrolidin-1-yl]imidazo[1,2-b]pyridazin-3-yl}-N-methylpyrimidin-2-amine; 5-{6-[2-(3-fluorophenyl)pyrrolidin-1-yl]imidazo[1,2-b]pyridazin-3-yl}-N,N-dimethylpyrimidin-2-amine; 1-(4-{6-[2-(3-fluorophenyl)pyrrolidin-1-yl]imidazo[1,2-b]pyridazin-3-yl}pyridin-2-yl)-N,N-dimethylpiperidin-4-amine; 2-chloro-5-{6-[2-(3-fluorophenyl)pyrrolidin-1-yl]imidazo[1,2-b]pyridazin-3-yl}pyrimidine; tert-butyl 4-[(5-{6-[2-(3-fluorophenyl)pyrrolidin-1-yl]imidazo[1,2-b]pyridazin-3-yl}pyrimidin-2-yl)oxy]piperidine-1-carboxylate; 5-{6-[2-(3-fluorophenyl)pyrrolidin-1-yl]imidazo[1,2-b]pyridazin-3-yl}-2-(piperidin-4-yloxy)pyrimidine; 1-(6-{6-[(2R)-2-(3-fluorophenyl)

pyrrolidin-1-yl]imidazo[1,2-b]pyridazin-3-yl}pyridin-2-yl)-N,N-dimethylpiperidin-4-amine; 5-{6-[2-(3-fluorophenyl)pyrrolidin-1-yl]imidazo[1,2-b]pyridazin-3-yl}pyrimidine; 5-{6-[2-(3-fluorophenyl)pyrrolidin-1-yl]imidazo[1,2-b]pyridazin-3-yl}-1,2-dihydropyrimidine; 1-(6-{6-[(2R)-2-(3-fluorophenyl)pyrrolidin-1-yl]imidazo[1,2-b]pyridazin-3-yl}pyridin-2-yl)piperidin-4-one; 1-(6-{6-[(2R)-2-(3-fluorophenyl)pyrrolidin-1-yl]imidazo[1,2-b]pyridazin-3-yl}pyridin-2-yl)piperazine; 6-{6-[2-(3-fluorophenyl)pyrrolidin-1-yl]imidazo[1,2-b]pyridazin-3-yl}-N-[1-(propan-2-yl)piperidin-4-yl]pyridin-2-amine; [1-(6-{6-[(2R)-2-(3-fluorophenyl)pyrrolidin-1-yl]imidazo[1,2-b]pyridazin-3-yl}pyridin-2-yl)piperidin-4-yl]carbamate; 1-(6-{6-[(2R)-2-(3-fluorophenyl)pyrrolidin-1-yl]imidazo[1,2-b]pyridazin-3-yl}pyridin-2-yl)piperidin-4-yl N-methylcarbamate; 1-(6-{6-[(2R)-2-(3-fluorophenyl)pyrrolidin-1-yl]imidazo[1,2-b]pyridazin-3-yl}pyridin-2-yl)piperidin-4-yl N-tert-butylcarbamate; 1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one; N,N-diethyl-1-(6-{6-[(2R)-2-(3-fluorophenyl)pyrrolidin-1-yl]imidazo[1,2-b]pyridazin-3-yl}pyridin-2-yl)piperidin-4-amine; 2,2,2-trifluoro-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one; 1-(6-{6-[(2R)-2-(3-fluorophenyl)pyrrolidin-1-yl]imidazo[1,2-b]pyridazin-3-yl}pyridin-2-yl)-4-methanesulfonylpiperazine; 2-(benzyloxy)-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one; 1-[4-(6-{6-[(2R)-2-(3-fluorophenyl)pyrrolidin-1-yl]imidazo[1,2-b]pyridazin-3-yl}pyridin-2-yl)piperazin-1-yl]-2-hydroxyethan-1-one; 2-{[1-(6-{6-[(2R)-2-(3-fluorophenyl)pyrrolidin-1-yl]imidazo[1,2-b]pyridazin-3-yl}pyridin-2-yl)piperidin-4-yl]amino}ethan-1-ol; 2-{6-[(2R)-2-(3-fluorophenyl)pyrrolidin-1-yl]imidazo[1,2-b]pyridazin-3-yl}-6-(1,2,3,6-tetrahydropyridin-1-yl)pyridine; N,N-diethyl-1-(6-{6-[2-(3-fluorophenyl)pyrrolidin-1-yl]imidazo[1,2-b]pyridazin-3-yl}pyridin-2-yl)pyrrolidin-3-amine; N-cyclopropyl-1-(6-{6-[(2R)-2-(3-fluorophenyl)pyrrolidin-1-yl]imidazo[1,2-b]pyridazin-3-yl}pyridin-2-yl)piperidin-4-amine; (3R)-1-(6-{6-[2-(3-fluorophenyl)pyrrolidin-1-yl]imidazo[1,2-b]pyridazin-3-yl}pyridin-2-yl)-N-methylpyrrolidin-3-amine; (3R)-1-(6-{6-[(2R)-2-(3-fluorophenyl)pyrrolidin-1-yl]imidazo[1,2-b]pyridazin-3-yl}pyridin-2-yl)-N-methylpyrrolidin-3-amine; 1-(6-{6-[(2R)-2-(3-fluorophenyl)pyrrolidin-1-yl]imidazo[1,2-b]pyridazin-3-yl}pyridin-2-yl)-N-methylpiperidin-4-amine; 2-fluoro-N-[1-(6-{6-[2-(3-fluorophenyl)pyrrolidin-1-yl]imidazo[1,2-b]pyridazin-3-yl}pyridin-2-yl)pyrrolidin-3-yl]-N,2-dimethylpropanamide; 2-fluoro-N-[1-(6-{6-[2-(3-fluorophenyl)pyrrolidin-1-yl]imidazo[1,2-b]pyridazin-3-yl}pyridin-2-yl)pyrrolidin-3-yl]-N-methylpropanamide; 1-tert-butyl-4-(6-{6-[(2R)-2-(3-fluorophenyl)pyrrolidin-1-yl]imidazo[1,2-b]pyridazin-3-yl}pyridin-2-yl)piperazine; 1-(6-{6-[(2R)-2-(3-fluorophenyl)pyrrolidin-1-yl]imidazo[1,2-b]pyridazin-3-yl}pyridin-2-yl)azetidine-3-carboxylic acid; 2-{6-[(2R)-2-(3-fluorophenyl)pyrrolidin-1-yl]imidazo[1,2-b]pyridazin-3-yl}-6-[4-(pyrrolidin-1-yl)piperidin-1-yl]pyridine; 2-fluoro-N-[1-(6-{6-[(2R)-2-(3-fluorophenyl)pyrrolidin-1-yl]imidazo[1,2-b]pyridazin-3-yl}pyridin-2-yl)piperidin-4-yl]-N,2-dimethylpropanamide; 2,2,2-trifluoro-N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-N-methylacetamide; 6-{6-[(2R)-2-(3-fluorophenyl)pyrrolidin-1-yl]imidazo[1,2-b]pyridazin-3-yl}-N-methyl-N-(piperidin-4-yl)pyridin-2-amine; 2-fluoro-N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-N,2-dimethylpropanamide; [146-{6-[(2R)-2-(3-fluorophenyl)pyrrolidin-1-yl]imidazo[1,2-b]pyridazin-3-yl}pyridin-2-yl)azetidin-3-yl]methanol; (3R)—N-(2-fluoro-2-methylpropyl)-1-(6-{6-[(2R)-2-(3-fluorophenyl)pyrrolidin-1-yl]imidazo[1,2-b]pyridazin-3-yl}pyridin-2-yl)-N-methylpyrrolidin-3-amine; 1-(6-{6-[(2R)-2-(3-fluorophenyl)pyrrolidin-1-yl]imidazo[1,2-b]pyridazin-3-yl}pyridin-2-yl)-4-(propane-2-sulfonyl)piperazine; 1-(6-{6-[(2R)-2-(3-fluorophenyl)pyrrolidin-1-yl]imidazo[1,2-b]pyridazin-3-yl}pyridin-2-yl)-4-[(2-methylpropane)sulfonyl]piperazine; 1-(butane-2-sulfonyl)-4-(6-{6-[(2R)-2-(3-fluorophenyl)pyrrolidin-1-yl]imidazo[1,2-b]pyridazin-3-yl}pyridin-2-yl)piperazine; 1-(ethanesulfonyl)-4-(6-{6-[(2R)-2-(3-fluorophenyl)pyrrolidin-1-yl]imidazo[1,2-b]pyridazin-3-yl}pyridin-2-yl)piperazine; (3S)-1-(6-{6-[(2R)-2-(3-fluorophenyl)pyrrolidin-1-yl]imidazo[1,2-b]pyridazin-3-yl}pyridin-2-yl)-N-methylpyrrolidin-3-amine; (3S)—N-ethyl-1-(6-{6-[(2R)-2-(3-fluorophenyl)pyrrolidin-1-yl]imidazo[1,2-b]pyridazin-3-yl}pyridin-2-yl)pyrrolidin-3-amine; (3R)-1-(6-{6-[(2R)-2-(3-fluorophenyl)pyrrolidin-1-yl]imidazo[1,2-b]pyridazin-3-yl}pyridin-2-yl)-N-(2,2,2-trifluoroethyl)pyrrolidin-3-amine; 2-[4-(6-{6-[(2R)-2-(3-fluorophenyl)pyrrolidin-1-yl]imidazo[1,2-b]pyridazin-3-yl}pyridin-2-yl)piperazin-1-yl]-2-oxoethyl acetate; {[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]carbamoyl}methyl acetate; N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-2-hydroxyacetamide; 4-(6-{6-[(2R)-2-(3-fluorophenyl)pyrrolidin-1-yl]imidazo[1,2-b]pyridazin-3-yl}pyridin-2-yl)-1-methylpiperazin-2-one; 4-(6-{6-[(2R)-2-(3-fluorophenyl)pyrrolidin-1-yl]imidazo[1,2-b]pyridazin-3-yl}pyridin-2-yl)-1-(2-hydroxyethyl)piperazin-2-one; 2-{6-[(2R)-2-(3-fluorophenyl)pyrrolidin-1-yl]imidazo[1,2-b]pyridazin-3-yl}-6-[4-(piperidin-1-yl)piperidin-1-yl]pyridine; {[1-(6-{6-[(2R)-2-(3-fluorophenyl)pyrrolidin-1-yl]imidazo[1,2-b]pyridazin-3-yl}pyridin-2-yl)piperidin-4-yl]methyl}dimethylamine; 2-(4,4-dimethylpiperidin-1-yl)-6-{6-[(2R)-2-(3-fluorophenyl)pyrrolidin-1-yl]imidazo[1,2-b]pyridazin-3-yl}pyridine; 2-(3,3-dimethylpiperidin-1-yl)-6-{6-[(2R)-2-(3-fluorophenyl)pyrrolidin-1-yl]imidazo[1,2-b]pyridazin-3-yl}pyridine; 4-[4-(6-{6-[(2R)-2-(3-fluorophenyl)pyrrolidin-1-yl]imidazo[1,2-b]pyridazin-3-yl}pyridin-2-yl)piperazin-1-yl]benzoic acid; 1-[4-(6-{6-[(2R)-2-(3-fluorophenyl)pyrrolidin-1-yl]imidazo[1,2-b]pyridazin-3-yl}pyridin-2-yl)piperazin-1-yl]-2-methyl-1-oxopropan-2-yl acetate; (2S)-1-[4-(6-{6-[(2R)-2-(3-fluorophenyl)pyrrolidin-1-yl]imidazo[1,2-b]pyridazin-3-yl}pyridin-2-yl)piperazin-1-yl]-1-oxopropan-2-yl acetate; 1-(6-{6-[(2R)-2-(3-fluorophenyl)pyrrolidin-1-yl]imidazo[1,2-b]pyridazin-3-yl}pyridin-2-yl)-N,N-dimethylpiperidin-4-amine; N,N-diethyl-4-(6-{6-[(2R)-2-(3-fluorophenyl)pyrrolidin-1-yl]imidazo[1,2-b]pyridazin-3-yl}pyridin-2-yl)piperazine-1-sulfonamide; N-ethyl-1-(6-{6-[(2R)-2-(3-fluorophenyl)pyrrolidin-1-yl]imidazo[1,2-b]pyridazin-3-yl}pyridin-2-yl)-N-methylpiperidin-4-amine; (2S)-1-[4-(6-{6-[(2R)-2-(3-fluorophenyl)pyrrolidin-1-yl]imidazo[1,2-b]pyridazin-3-yl}pyridin-2-yl)piperazin-1-yl]-2-hydroxypropan-1-one; 1-[4-(6-{6-[(2R)-2-(3-fluorophenyl)pyrrolidin-1-yl]imidazo[1,2-b]pyridazin-3-yl}pyridin-2-yl)piperazin-1-yl]-2-hydroxy-2-methylpropan-1-one; 8-(6-{6-[(2R)-2-(3-fluorophenyl)pyrrolidin-1-yl]imidazo[1,2-b]pyridazin-3-yl}pyridin-2-yl)-1,4-dioxa-8-azaspiro[4.5]decane; 4-ethyl-1-(6-{6-[(2R)-2-(3-fluorophenyl)pyrrolidin-1-yl]imidazo[1,2-b]pyridazin-3-yl}pyridin-2-yl)piperidin-4-ol; 1-(6-{6-[(2R)-2-(3-fluorophenyl)pyrrolidin-1-yl]

imidazo[1,2-b]pyridazin-3-yl}pyridin-2-yl)-4-(propan-2-yl)piperidin-4-ol; 4-ethenyl-1-(6-{6-[(2R)-2-(3-fluorophenyl)pyrrolidin-1-yl]imidazo[1,2-b]pyridazin-3-yl}pyridin-2-yl)piperidin-4-01; 1-(6-{6-[(2R)-2-(3-fluorophenyl)pyrrolidin-1-yl]imidazo[1,2-b]pyridazin-3-yl}pyridin-2-yl)-4-methylpiperidin-4-ol; 2-{6-[(2R)-2-(3-fluorophenyl)pyrrolidin-1-yl]imidazo[1,2-b]pyridazin-3-yl}-6-{octahydropyrrolo[1,2-b]piperazin-2-yl}pyridine; 8-(6-{6-[(2R)-2-(3-fluorophenyl)pyrrolidin-1-yl]imidazo[1,2-b]pyridazin-3-yl}pyridin-2-yl)-3-methyl-1,3,8-triazaspiro[4.5]decane-2,4-dione; (1S)-1-{[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]carbamoyl}ethyl acetate; (2S)—N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-2-hydroxypropanamide; 1-(6-{6-[(2R)-2-(3-fluorophenyl)pyrrolidin-1-yl]imidazo[1,2-b]pyridazin-3-yl}pyridin-2-yl)-3-(trifluoromethyl)piperazine; 1-(6-{6-[(2R)-2-(3-fluorophenyl)pyrrolidin-1-yl]imidazo[1,2-b]pyridazin-3-yl}pyridin-2-yl)-N-methylpiperidin-3-amine; 1-[4-(6-{6-[(2R)-2-(3-fluorophenyl)pyrrolidin-1-yl]imidazo[1,2-b]pyridazin-3-yl}pyridin-2-yl)pyridin-2-yl]-N,N-dimethylpiperidin-4-amine; 2-[4-(6-{6-[(2R)-2-(3-fluorophenyl)pyrrolidin-1-yl]imidazo[1,2-b]pyridazin-3-yl}pyridin-2-yl)-2-(trifluoromethyl)piperazin-1-yl]-2-oxoethyl acetate; 1-[4-(6-{6-[(2R)-2-(3-fluorophenyl)pyrrolidin-1-yl]imidazo[1,2-b]pyridazin-3-yl}pyridin-2-yl)-2-(trifluoromethyl)piperazin-1-yl]-2-hydroxyethan-1-one; 1-[4-(6-{6-[(2R)-2-(3-fluorophenyl)pyrrolidin-1-yl]imidazo[1,2-b]pyridazin-3-yl}pyridin-2-yl)pyridin-2-yl]-N-methylpiperidin-4-amine; 4-(6-{6-[(2R)-2-(3-fluorophenyl)pyrrolidin-1-yl]imidazo[1,2-b]pyridazin-3-yl}pyridin-2-yl)pyridin-2-ol; N-cyclobutyl-6-{6-[(2R)-2-(3-fluorophenyl)pyrrolidin-1-yl]imidazo[1,2-b]pyridazin-3-yl}pyridin-2-amine; N-cyclopropyl-6-{6-[(2R)-2-(3-fluorophenyl)pyrrolidin-1-yl]imidazo[1,2-b]pyridazin-3-yl}pyridin-2-amine; N-cyclopropyl-1-[4-(6-{6-[(2R)-2-(3-fluorophenyl)pyrrolidin-1-yl]imidazo[1,2-b]pyridazin-3-yl}pyridin-2-yl)pyridin-2-yl]piperidin-4-amine; 1-[4-(6-{6-[(2R)-2-(3-fluorophenyl)pyrrolidin-1-yl]imidazo[1,2-b]pyridazin-3-yl}pyridin-2-yl)pyridin-2-yl]piperidin-4-one; 1-(6-{6-[(2R)-2-(3-fluorophenyl)pyrrolidin-1-yl]imidazo[1,2-b]pyridazin-3-yl}pyridin-2-yl)-4-(pyridin-3-yl)piperazine; 1-(6-{6-[(2R)-2-(3-fluorophenyl)pyrrolidin-1-yl]imidazo[1,2-b]pyridazin-3-yl}pyridin-2-yl)-4-(pyridin-2-yl)piperazine; 1-(4-(6-{6-[(2R)-2-(3-fluorophenyl)pyrrolidin-1-yl]imidazo[1,2-b]pyridazin-3-yl}pyridin-2-yl)piperazine; 1-(6-{6-[(2R)-2-(3-fluorophenyl)pyrrolidin-1-yl]imidazo[1,2-b]pyridazin-3-yl}pyridin-2-yl)-4-(6-methylpyridin-2-yl)piperazine; 1-(6-{6-[(2R)-2-(3-fluorophenyl)pyrrolidin-1-yl]imidazo[1,2-b]pyridazin-3-yl}pyridin-2-yl)-4-[5-(trifluoromethyl)pyridin-2-yl]piperazine; 2-[4-(6-{6-[(2R)-2-(3-fluorophenyl)pyrrolidin-1-yl]imidazo[1,2-b]pyridazin-3-yl}pyridin-2-yl)piperazin-1-yl]-N-methyl-N-phenylacetamide; 2-[4-(6-{6-[(2R)-2-(3-fluorophenyl)pyrrolidin-1-yl]imidazo[1,2-b]pyridazin-3-yl}pyridin-2-yl)piperazin-1-yl]-2-oxoacetic acid; 6-{6-[(2R)-2-(3-fluorophenyl)pyrrolidin-1-yl]imidazo[1,2-b]pyridazin-3-yl}pyridine-2-carboxamide; 6-{6-[(2S)-2-(3-fluorophenyl)pyrrolidin-1-yl]imidazo[1,2-b]pyridazin-3-yl}pyridine-2-carboxamide; 2-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-ol; 2-[4-(6-{6-[2-(3-fluorophenyl)pyrrolidin-1-yl]imidazo[1,2-b]pyridazin-3-yl}pyridin-2-yl)piperazin-1-yl]-N-(propan-2-yl)acetamide; [1-(6-{6-[2-(3-fluorophenyl)pyrrolidin-1-yl]imidazo[1,2-b]pyridazin-3-yl}pyridin-2-yl)piperidin-4-yl]methanol; [1-(6-{6-[2-(3-fluorophenyl)pyrrolidin-1-yl]imidazo[1,2-b]pyridazin-3-yl}pyridin-2-yl)piperidin-3-yl]methanol; 1-(6-{6-[2-(3-fluorophenyl)pyrrolidin-1-yl]imidazo[1,2-b]pyridazin-3-yl}pyridin-2-yl)piperidine-4-carbonitrile; 2-[4-(6-{6-[2-(3-fluorophenyl)pyrrolidin-1-yl]imidazo[1,2-b]pyridazin-3-yl}pyridin-2-yl)piperazin-1-yl]ethan-1-ol; 1-(6-{6-[(2R)-2-(3-fluorophenyl)pyrrolidin-1-yl]imidazo[1,2-b]pyridazin-3-yl}pyridin-2-yl)piperidin-4-ol; 2-fluoro-6-{6-[(2S)-2-(3-fluorophenyl)pyrrolidin-1-yl]imidazo[1,2-b]pyridazin-3-yl}pyridine; 2-fluoro-6-{6-[(2R)-2-(3-fluorophenyl)pyrrolidin-1-yl]imidazo[1,2-b]pyridazin-3-yl}pyridine; diethyl({2-[(6-{6-[2-(3-fluorophenyl)piperidin-1-yl]imidazo[1,2-b]pyridazin-3-yl}pyridin-2-yl)amino]ethyl})amine; 1-(6-{6-[2-(3-fluorophenyl)piperidin-1-yl]imidazo[1,2-b]pyridazin-3-yl}pyridin-2-yl)-4-(propan-2-yl)piperazine; (3S)-1-(6-{6-[2-(3-fluorophenyl)piperidin-1-yl]imidazo[1,2-b]pyridazin-3-yl}pyridin-2-yl)-N,N-dimethylpyrrolidin-3-amine; 6-{6-[2-(3-fluorophenyl)piperidin-1-yl]imidazo[1,2-b]pyridazin-3-yl}-N-methylpyridin-2-amine; 6-{6-[2-(3-fluorophenyl)piperidin-1-yl]imidazo[1,2-b]pyridazin-3-yl}-N-(propan-2-yl)pyridin-2-amine; N-(6-{6-[2-(3-fluorophenyl)piperidin-1-yl]imidazo[1,2-b]pyridazin-3-yl}pyridin-2-yl)methanesulfonamide; 6-{6-[2-(3-fluorophenyl)piperidin-1-yl]imidazo[1,2-b]pyridazin-3-yl}-N,N-dimethylpyridin-2-amine; 2-{6-[2-(3-fluorophenyl)piperidin-1-yl]imidazo[1,2-b]pyridazin-3-yl}-6-(piperidin-4-yloxy)pyridine; 1-(6-{6-[2-(3-fluorophenyl)pyrrolidin-1-yl]imidazo[1,2-b]pyridazin-3-yl}pyridin-2-yl)azetidin-3-ol; (3R)-1-(6-{6-[(2R)-2-(3-fluorophenyl)pyrrolidin-1-yl]imidazo[1,2-b]pyridazin-3-yl}pyridin-2-yl)-N,N-dimethylpyrrolidin-3-amine; 1-(6-{6-[2-(3-fluorophenyl)pyrrolidin-1-yl]imidazo[1,2-b]pyridazin-3-yl}pyridin-2-yl)-N-(2-hydroxyethyl)piperidine-4-carboxamide; N-[2-(dimethylamino)ethyl]-1-(6-{6-[2-(3-fluorophenyl)pyrrolidin-1-yl]imidazo[1,2-b]pyridazin-3-yl}pyridin-2-yl)piperidine-4-carboxamide; 1-(6-{6-[2-(3-fluorophenyl)pyrrolidin-1-yl]imidazo[1,2-b]pyridazin-3-yl}pyridin-2-yl)azetidine-3-carboxylic acid; N-(cyanomethyl)-1-(6-{6-[2-(3-fluorophenyl)pyrrolidin-1-yl]imidazo[1,2-b]pyridazin-3-yl}pyridin-2-yl)piperidine-4-carboxamide; 2-{6-[2-(3-fluorophenyl)pyrrolidin-1-yl]imidazo[1,2-b]pyridazin-3-yl}pyrazine; N-[(3R)-1-(6-{6-[2-(3-fluorophenyl)pyrrolidin-1-yl]imidazo[1,2-b]pyridazin-3-yl}pyridin-2-yl)pyrrolidin-3-yl]acetamide; 1-{6-[2-(3-fluorophenyl)pyrrolidin-1-yl]imidazo[1,2-b]pyridazin-3-yl}-1H-pyrazole; 1-(6-{6-[2-(3-fluorophenyl)pyrrolidin-1-yl]imidazo[1,2-b]pyridazin-3-yl}pyrazin-2-yl)piperidin-4-ol; (3S)-1-(6-{6-[2-(3-fluorophenyl)pyrrolidin-1-yl]imidazo[1,2-b]pyridazin-3-yl}pyrazin-2-yl)-N,N-dimethylpyrrolidin-3-amine; 2-{6-[2-(3-fluorophenyl)pyrrolidin-1-yl]imidazo[1,2-b]pyridazin-3-yl}-6-(piperazin-1-yl)pyrazine; 2-[4-(6-{6-[2-(3-fluorophenyl)pyrrolidin-1-yl]imidazo[1,2-b]pyridazin-3-yl}pyrazin-2-yl)piperazin-1-yl]ethan-1-ol; (3R)-1-(6-{6-[2-(3-fluorophenyl)pyrrolidin-1-yl]imidazo[1,2-b]pyridazin-3-yl}pyrazin-2-yl)-N,N-dimethylpyrrolidin-3-amine; N-[1-(6-{6-[(2R)-2-(3-fluorophenyl)pyrrolidin-1-yl]imidazo[1,2-b]pyridazin-3-yl}pyridin-2-yl)azetidin-3-yl]acetamide; 1-(6-{6-[(2R)-2-(3-fluorophenyl)pyrrolidin-1-yl]imidazo[1,2-b]pyridazin-3-yl}pyridin-2-yl)azetidin-3-amine; N-[1-(6-{6-[(2R)-2-(3-fluorophenyl)pyrrolidin-1-yl]imidazo[1,2-b]pyridazin-3-yl}pyridin-2-yl)azetidin-3-yl]methanesulfonamide; N-ethyl-1-(6-{6-[(2R)-2-(3-fluorophenyl)pyrrolidin-1-yl]imidazo[1,2-b]pyridazin-3-yl}pyridin-2-yl)azetidin-3-amine; N,N-diethyl-1-(6-{6-[(2R)-2-(3-fluorophenyl)pyrrolidin-1-yl]imidazo[1,2-b]pyridazin-3-yl}pyridin-2-yl)azetidin-3-amine; 3-{6-[(2R)-2-(3-fluorophenyl)pyrrolidin-1-yl]imidazo[1,2-b]pyridazin-3-yl}-1H-pyrrole; N-[1-(6-{6-

[(2R)-2-(3-fluorophenyl)pyrrolidin-1-yl]imidazo[1,2-b] pyridazin-3-yl}pyridin-2-yl)azetidin-3-yl]-2-hydroxyacetamide; N-ethyl-N-[1-(6-{6-[(2R)-2-(3-fluorophenyl)pyrrolidin-1-yl]imidazo[1,2-b]pyridazin-3-yl}pyridin-2-yl)azetidin-3-yl]methanesulfonamide; 1-[6-(6-{6-[(2R)-2-(3-fluorophenyl)pyrrolidin-1-yl]imidazo[1,2-b] pyridazin-3-yl}pyridin-2-yl)pyridin-2-yl]piperidin-4-ol; 6-(6-{6-[(2R)-2-(3-fluorophenyl)pyrrolidin-1-yl]imidazo[1,2-b]pyridazin-3-yl}pyridin-2-yl)-2-oxa-6-azaspiro[3.3]heptane; 6-[4-(6-{6-[(2R)-2-(3-fluorophenyl)pyrrolidin-1-yl] imidazo[1,2-b]pyridazin-3-yl}pyridin-2-yl)pyrimidin-2-yl]-2-oxa-6-azaspiro[3.3]heptane; 6-{6-[2-(3-fluorophenyl) pyrrolidin-1-yl]imidazo[1,2-b]pyridazin-3-yl}-2,3-dihydro-1H-indol-2-one; 6-{6-[3-(3-fluorophenyl)morpholin-4-yl] imidazo[1,2-b]pyridazin-3-yl}-2,3-dihydro-1H-indol-2-one; 3-(3-fluorophenyl)-4-{3-[6-(piperazin-1-yl)pyridin-2-yl]imidazo[1,2-b]pyridazin-6-yl}morpholine; (3S)-4-[3-(6-fluoropyridin-2-yl)imidazo[1,2-b]pyridazin-6-yl]-3-phenylmorpholine; 1-(6-{6-[(3S)-3-phenylmorpholin-4-yl] imidazo[1,2-b]pyridazin-3-yl}pyridin-2-yl)piperidin-4-ol; 1-(6-{6-[3-(3-fluorophenyl)morpholin-4-yl]imidazo[1,2-b] pyridazin-3-yl}pyridin-2-yl)piperidine-4-carb aldehyde; 3-(3-fluorophenyl)-4-(3-{6-[4-(4-methyl-1H-imidazol-2-yl) piperidin-1-yl]imidazo[1,2-b]pyridazin-6-yl}) morpholine; 6-{6-[3-(3-fluorophenyl)morpholin-4-yl]imidazo[1,2-b]pyridazin-3-yl}-N,N-dimethylpyridin-2-amine; 3-(3-fluorophenyl)-4-[3-(6-{4-[2-(methylsulfanyl)ethyl] piperazin-1-yl}pyridin-2-yl)imidazo[1,2-b]pyridazin-6-yl] morpholine; 3-(3-fluorophenyl)-4-(3-{6-[4-(2-methanesulfonylethyl)piperazin-1-yl]pyridin-2-yl}imidazo[1,2-b] pyridazin-6-yl)morpholine; (N-cyclopropyl-1-(6-(6-(2-(3-fluorophenyl)pyrrolidin-1-yl)imidazo[1,2-b]pyridazin-3-yl)-2,4'-bipyridin-2'-yl)piperidin-4-amine); 3-(3-fluorophenyl)-4-(3-{6-[4-(1H-1,2,4-triazol-5-yl)piperidin-1-yl]pyridin-2-yl}imidazo[1,2-b]pyridazin-6-yl) morpholine, and 3-(3-fluorophenyl)-4-(3-{6-[4-(1,2,4-oxadiazol-5-yl)piperidin-1-yl]pyridin-2-yl}imidazo[1,2-b] pyridazin-6-yl)morpholine.

Another aspect provided herein are pharmaceutical compositions comprising a therapeutically effective amount of a compound of Formula (I) and a pharmaceutically acceptable carrier.

In certain embodiments of such pharmaceutical compositions, the pharmaceutical compositions are formulated for intravenous, oral administration, rectal administration inhalation, nasal administration, topical administration, ophthalmic administration or otic administration. In certain embodiments of such pharmaceutical compositions, the pharmaceutical composition is a tablet, a pill, a capsule, a liquid, an inhalant, a nasal spray solution, a suppository, a solution, an emulsion, an ointment, eye drop or ear drop.

Another aspect provided herein are medicaments for treating a kinase-mediated disease or condition in a patient wherein the medicament comprises a therapeutically effective amount of a compound of Formula (I), wherein the kinase is selected from Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK.

Another aspect provided herein is the use of a compound of Formula (I) in the manufacture of a medicament for treating a kinase-mediated disease or condition, wherein the kinase is selected from Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK.

Another aspect provided herein is a method of making any of the aforementioned compounds of Formula (I), in which $X^1$ is N; $X^2$ is N; $X^3$ is C and $X^4$ is C. Such a method comprises: admixing a compound of structure:

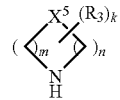

with a compound having the structure:

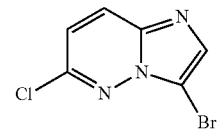 [SMILES: Clc1ccc2ncc(Br)n2n1]

in the presence of KF a to yield a compound having the structure:

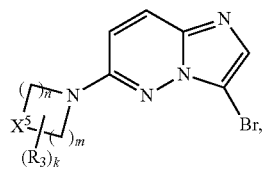

and admixing, in the presence of a palladium catalyst, the compound having the structure:

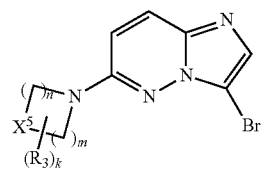

with a compound having either the structure: $R^2$—B(OH)$_2$,

to yield a compound having the structure:

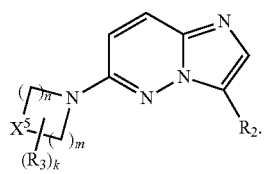

Another aspect provided herein is a method of making any of the aforementioned compounds of Formula (I), in which $X^1$ is CR$^9$; $X^2$ is N; $X^3$ is C and $X^4$ is C. Such a method comprises: admixing a compound of structure:

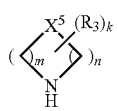

with a compound having the structure:

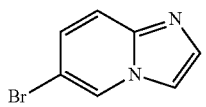

in the presence of a palladium catalyst to yield a compound having the structure:

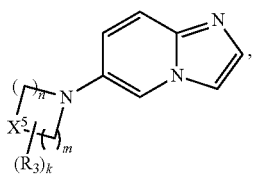

and admixing, in the presence of a palladium catalyst, the compound having the structure:

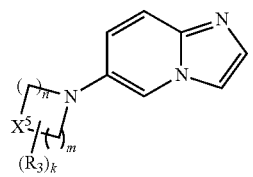

with a compound having the structure: $R^2$—Br, to yield a compound having the structure:

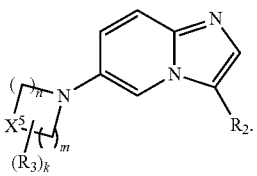

Another aspect provided herein is a method of making any of the aforementioned compounds of Formula (I), in which $X^1$ is N; $X^2$ is C; $X^3$ is N and $X^4$ is C. Such a method comprises: admixing a compound of structure:

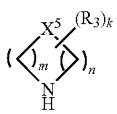

with a compound having the structure:

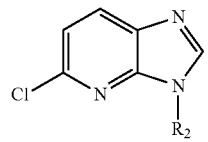

in the presence of a palladium catalyst a to yield a compound having the structure:

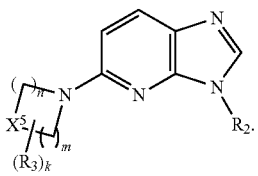

Another aspect provided herein are methods for inhibiting a kinase, comprising administering to a system or a subject in need thereof, a therapeutically effective amount of a compound any of Formula (I), or pharmaceutically acceptable salts or pharmaceutical compositions thereof, thereby inhibiting the kinase. In certain embodiments of such methods, the kinase is selected from Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK or a combination thereof. In certain embodiments of such methods the kinase is TrkA, TrkB, TrkC or ALK. In certain embodiments of such methods, the method comprises administering the compound to a cell or tissue system or to a human or animal subject.

Another aspect provided herein are methods for treating a kinase-mediated disease or condition, comprising administering to a system or subject in need of such treatment an effective amount of a compound of Formula (I), or pharmaceutically acceptable salts or pharmaceutical compositions thereof, thereby treating the condition, and wherein the kinase is selected from Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK or a combination thereof. In certain embodiments of such methods, the method comprises administering the compound to a cell or tissue system; or to a human or animal subject. In certain embodiments of such methods, the disease or condition is cancer, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease. In certain embodiments of such methods, the disease or condition is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV or lupus.

Another aspect provided herein are methods for treating a cell-proliferative condition, comprising administering to a system or subject in need of such treatment an effective amount of a compound of Formula (I), or pharmaceutically acceptable salts or pharmaceutical compositions thereof; wherein the cell-proliferative condition is lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer or gastrointestinal cancer. In certain embodiments of such methods, the cell-proliferative condition is anaplastic large-cell lymphoma, pancreatic cancer, ovarian cancer and lung cancer.

Another aspect provided herein are compounds for use in a method of medical treatment, wherein the method of medical treatment is for treating a disease selected from cancer, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease, and wherein the compound is a compound of Formula (I). In certain embodiments of the disease is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV or lupus.

DETAILED DESCRIPTION OF THE INVENTION

Definitions

The terms "alkenyl" and "alkene," as used herein, refers to a partially unsaturated branched or straight chain hydrocarbon having at least one carbon-carbon double bond. Atoms oriented about the double bond are in either the cis (Z) or trans (E) conformation. An alkenyl or alkene group can be optionally substituted. As used herein, the terms "$C_2$-$C_3$alkyenyl", "$C_2$-$C_4$alkyenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. Non-limiting examples of alkenyl groups, as used herein, include ethenyl, propenyl, butenyl, pentenyl, hexenyl, heptenyl, octenyl, nonenyl, decenyl and the like. As used herein, the terms "$C_2$-$C_3$alkyene", "$C_2$-$C_4$alkyene", "$C_2$-$C_5$alkene", "$C_2$-$C_6$alkene", "$C_2$-$C_7$alkene", and "$C_2$-$C_8$alkene" refer to an alkene group containing at least 2, and at most 3, 4, 5, 6, 7 or 8 carbon atoms, respectively. Non-limiting examples of alkene groups, as used herein, include ethene, propene, butene, pentene, hexene, heptene, octene, nonene, decene and the like.

The term "alkenylene," as used herein, refers to a partially unsaturated branched or straight chain divalent hydrocarbon radical derived from an alkenyl group. An alkenylene group can be optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. An alkyl group can be optionally substituted. As used herein, the terms "$C_1$-$C_3$alkyl", "$C_1$-$C_4$alkyl", "$C_r$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. An alkylene group can be optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl," as used herein, refers to a partially unsaturated branched or straight chain hydrocarbon having at least one carbon-carbon triple bond. An alkynyl group can be optionally substituted. As used herein, the terms "$C_2$-$C_3$alkynyl", "$C_2$-$C_4$alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 3, 4, 5, 6, 7 or 8 carbon atoms, respectively. Non-limiting examples of alkynyl groups, as used herein, include ethynyl, propynyl, butynyl, pentynyl, hexynyl, heptynyl, octynyl, nonynyl, decynyl and the like.

The term "alkynylene," as used herein, refers to a partially unsaturated branched or straight chain divalent hydrocarbon radical derived from an alkynyl group. An alkynylene group can be optionally substituted. As used herein, the terms "$C_2$-$C_3$alkynylene", "$C_2$-$C_4$alkynylene", "$C_2$-$C_5$alkynylene", "$C_2$-$C_6$alkynylene", "$C_2$-$C_7$alkynylene", and "$C_2$-$C_8$alkynylene" refer to an alkynylene group containing at least 2, and at most 3, 4, 5, 6, 7 or 8 carbon atoms respectively. Non-limiting examples of alkynylene groups as used herein include, ethynylene, propynylene, butynylene, pentynylene, hexynylene, heptynylene, octynylene, nonynylene, decynylene and the like.

The term "alkoxy," as used herein, refers to the group —OR$_a$, where R$_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. An aryl group can be optionally substituted with one or more substituents. Non-limiting examples of aryl groups, as used herein, include phenyl, naphthyl, fluorenyl, indenyl, azulenyl, anthracenyl and the like.

The term "arylene," as used means a divalent radical derived from an aryl group. An arylene group can be optionally substituted.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. A cycloalkyl group can be optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "cycloalkylene," as used means a divalent radical derived from a cycloalkyl group. A cycloalkylene group can be optionally substituted.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. A haloalkenyl group can be optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The terms "haloalkynyl" or "halo-substituted alkynyl," as used herein, refers to an alkynyl group as defined above, substituted with one or more halogen groups, wherein the halogen groups are the same or different. A haloalkynyl group can be optionally substituted. Non-limiting examples of such branched or straight chained haloalkynyl groups, as used herein, include ethynyl, propynyl, butynyl, pentynyl, hexynyl, heptynyl, octynyl, nonynyl, decynyl, and the like substituted with one or more halogen groups, wherein the halogen groups are the same or different.

The term "haloalkoxy," as used herein, refers to an alkoxy group as defined herein, substituted with one or more halogen groups, wherein the halogen groups are the same or different. A haloalkoxy group can be optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. A heteroaryl group can be optionally substituted with one or more substituents. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, 1H-benzo[d]imidazol-2(3H)-one, benzo[e][1,3]oxazin-2-one, cinnolinyl, furazanyl, furyl, furopyridinyl, imidazolyl, indolyl, indolizinyl, indolin-2-one, indazolyl, indolin-2-one, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, quinolin-2(1H)-one, thiazolyl, thiadiazolyl, thienyl, triazinyl, triazolyl and tetrazolyl.

The term "heteroarylene," as used means a divalent radical derived from a heteroaryl group. A heteroarylene group can be optionally substituted.

The term "heterocycloalkyl," as used herein, refers to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen, $C_1$-$C_4$alkyl or a nitrogen protecting group, with the proviso that the ring of said group does not contain two adjacent O or S atoms. A heterocycloalkyl group can be optionally substituted. Non-limiting examples of heterocycloalkyl groups, as used herein, include morpholino, pyrrolidinyl, pyrrolidinyl-2-one, piperazinyl, piperazinyl-2-one, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, 2,5-diazabicyclo[2.2.1]heptane and 3-azabicyclo[4.1.0]heptanyl.

The term "heterocycloalkylene," as used means a divalent radical derived from a heterocycloalkyl group. A heterocycloalkylene group can be optionally substituted.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "isocyanato," as used herein, refers to a —N═C═O group.

The term "isothiocyanato," as used herein, refers to a —N═C═S group.

The term "mercaptyl," as used herein, refers to an (alkyl)S— group.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, ═O, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$, —NRS(O)$_2$, —NHS(O)$_2$R, —NRS(O)$_2$R, C$_1$-C$_8$alkyl, C$_1$-C$_8$alkoxy, aryl, heteroaryl, cycloalkyl, heterocycloalkyl, halo-substituted C$_1$-C$_8$alkyl, halo-substituted C$_1$-C$_8$alkoxy, where each R is independently selected from H, halo, C$_1$-C$_8$alkyl, C$_1$-C$_8$alkoxy, aryl, heteroaryl, cycloalkyl, heterocycloalkyl, halo-substituted C$_1$-C$_8$alkyl, and halo-substituted C$_1$-C$_8$alkoxy. The placement and number of such substituent groups is done in accordance with the well-understood valence limitations of each group, for example ═O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of the invention and prodrugs thereof to a subject in need of treatment.

The term "bone disease," as used herein, refers to a disease or condition of the bone, including, but not limited to, inappropriate bone remodeling, loss or gain, osteopenia, osteomalacia, osteofibrosis, and Paget's disease.

The term "cardiovascular disease," as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

The term "diluent" as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic", as used herein, means a condition, disorder, or disease created or worsened by medical or surgical therapy.

The term "inflammatory disorders", as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract (Disease); skin (dermatitis); or multiple organs and tissues (systemic lupus erythematosus).

The term "Kinase Panel", as used herein, refers to is a list of kinases including but not limited to Abl(human), Abl (T315I), JAK2, JAK3, ALK, JNK1α1, ALK4, KDR, Aurora-A, Lck, Blk, MAPK1, Bmx, MAPKAP-K2, BRK, MEK1, CaMKII(rat), Met, CDK1/cyclinB, p70S6K, CHK2, PAK2, CK1, PDGFRα, CK2, PDK1, c-Kit, Pim-2, C-Raf, PKA(h), CSK, PKBα, Src, PKCα, DYRK2, Plk3, EGFR, ROCK-I, Fes, Ron, FGFR-3, Ros, Flt3, SAPK2α, Fms, SGK, Fyn, SIK, GSK3β, Syk, IGFR, Tie-2, IKKβ, IR, WNK3, IRAK4, ZAP-70, ITK, AMPK(rat), LIMK1, Rsk2, Ax1, LKB1, SAPK2β, BrSK2, Lyn (h), SAPK3, BTK, MAPKAP-K3, SAPK4, CaMKIV, MARK1, Snk, CDK2/cyclinA, MINK, SRPK1, CDK3/cyclinE, MKK4(m), TAK1, CDK5/p25, MKK6(h), TBK1, CDK6/cyclinD3, MLCK, TrkA, TrkB, TrkC, CDK7/cyclinH/MAT1, MRCKβ, TSSK1, CHK1, MSK1, Yes, CK1d, MST2, ZIPK, c-Kit (D816V), MuSK, DAPK2, NEK2, DDR2, NEK6, DMPK, PAK4, DRAK1, PAR-1Bα, EphA1, PDGFRβ, EphA2, Pim-1, EphA5, PKBfβ, EphB2, PKCβI, EphB4, PKCδ, FGFR1, PKCη, FGFR2, PKCθ, FGFR4, PKD2, Fgr, PKG1β, Flt1, PRK2, Hck, PYK2, HIPK2, Ret, IKKα, RIPK2, IRR, ROCK-II(human), JNK2α2, Rse, JNK3, Rsk1(h), PI3 Kγ, PI3 Kδ and PI3-Kβ.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system (brain and spinal cord).

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjuctivitis, vernal conjunctivitis, pappillary conjunctivitis.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt", as used herein, refers to a formulation of a compound that does not cause significant irritation to an organism to which it is administered and does not abrogate the biological activity and properties of the compounds described herein.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a coagent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The term "pharmaceutical composition", as used herein, refers to a mixture of a compound described herein with other chemical components, such as carriers, stabilizers, diluents, dispersing agents, suspending agents, thickening agents, and/or excipients.

The term "prodrug", as used herein, refers to an agent that is converted into the parent drug in vivo. Prodrugs are often useful because, in some situations, they may be easier to administer than the parent drug. Prodrugs are bioavailable by oral administration whereas the parent is not. Prodrugs improve solubility in pharmaceutical compositions over the parent drug. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient", as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

The term "therapeutically effective amount", as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat", "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The terms "use" or "used," as used herein, are intended to include a compound of Formula (I) provided herein for use in the prophylactic and/or therapeutic treatment of one or more diseases provided herein, a method of use or a method of treatment comprising administering a compound of the Formula (I) to a person in need of such treatment in an effective amount for the prophylactic and/or therapeutic treatment of one or more diseases provided herein, the preparation or a method or preparation of a pharmaceutical formulation/preparation for use in the prophylactic and therapeutic treatment of one or more diseases provided herein, especially involving mixing a compound of the Formula (I) (as therapeutically active ingredient) with at least one pharmaceutically acceptable carrier material, including making it ready for use in such treatment (e.g. adding an instruction insert (e.g. package leaflet or the like), formulation, appropriate preparation, adaptation for specific uses, customizing and the like), and the use of a compound of the Formula (I) for such preparation, and/or all other prophylactic or therapeutic uses mentioned herein.

Other objects, features and advantages of the methods and compositions described herein will become apparent from the following detailed description. It should be understood, however, that the detailed description and the specific examples, while indicating specific embodiments, are given by way of illustration only.

Compounds

Provided herein are compounds, pharmaceutically acceptable salts, solvates, N-oxides, prodrugs and isomers thereof, which are modulators of kinase activity. Provided herein are compounds, pharmaceutically acceptable salts, solvates, N-oxides, prodrugs and isomers thereof, which are modulators of protein kinases. Also provided herein are compounds, pharmaceutically acceptable salts, solvates, N-oxides, prodrugs and isomers thereof, pharmaceutical compositions, pharmaceutical combinations and methods for the treatment and/or prevention of protein kinase related diseases or conditions/disorders, including disease or conditions/disorders associated with abnormal or deregulated protein kinase activity. In certain embodiments, compounds, pharmaceutically acceptable salts, solvates, N-oxides, prodrugs and isomers thereof, provided herein are modulators of Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinases. In certain embodiments, compounds, pharmaceutically acceptable salts, solvates, N-oxides, prodrugs and isomers thereof, provided herein are inhibitors of Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinases. In certain embodiments, compounds, pharmaceutically acceptable salts, solvates, N-oxides, prodrugs and isomers thereof, provided herein are inhibitors of TrkA, TrkB, TrkC, IGF-1R, and/or ALK protein kinases. In other embodiments, the compounds, pharmaceutically acceptable salts, solvates, N-oxides, prodrugs and isomers thereof, provided herein are used to treat and/or prevent diseases and conditions related to, or mediated by, Ros, KDR, FMS, c-FMS, FLT3, c-Kit, JAK2, JAK3, Aurora, PDGFR, Lck, TrkA, TrkB, TrkC, IGR-1R, ALK4, ALK5, ALK or a combination thereof. In other embodiments, the compounds, pharmaceutically acceptable salts, solvates, N-oxides, prodrugs and isomers thereof, provided herein are used to treat and/or prevent diseases and conditions related to, or mediated by, TrkA, TrkB, TrkC, IGR-1R, ALK protein kinases or a combination thereof.

Further provided herein are compounds, pharmaceutically acceptable salts, solvates, N-oxides, prodrugs and isomers thereof, and pharmaceutical compositions containing such pharmaceutically acceptable salts, solvates, N-oxides, prodrugs and isomers thereof, for the treatment and/or prevention of diseases and/or disorders in which aberrant, abnormal or deregulated activity of Ros, KDR, FMS, c-FMS, FLT3, c-Kit, JAK2, JAK3, Aurora, PDGFR, Lck, TrkA, TrkB, TrkC, IGR-1R, ALK4, ALK5, or ALK protein kinase contributes to the pathology and/or symptomology of such diseases and/or disorders. Also provided herein are compounds, pharmaceutically acceptable salts, solvates, N-oxides, prodrugs and isomers thereof, and pharmaceutical compositions containing such pharmaceutically acceptable salts, solvates, N-oxides, prodrugs and isomers thereof, for the treatment and/or prevention of diseases and/or disorders in which aberrant, abnormal or deregulated activity of TrkA, TrkB, TrkC, IGR-1R, or ALK protein kinase contributes to the pathology and/or symptomology of such diseases and/or disorders.

In certain embodiments, such diseases and/or disorders include, but are not limited to, cancer, proliferative diseases, pain, dermatological diseases and/or disorders, metabolic diseases and/or disorders, muscle diseases and/or disorders, neurodegenerative diseases and/or disorders, neurological diseases and/or disorders, immunodeficiency diseases and/or disorders, immunologically-mediated diseases and/or disorders, autoimmune diseases, autoimmune mediated diseases, bone diseases and/or disorders, inflammatory diseases, fibrosis, ophthalmic/occular diseases and/or disorders, infectious diseases, viral diseases, wound repair, respiratory diseases and/or disorders, pulmonary diseases and/or disorders, renal disease, kidney disease, liver disease, cardiovascular diseases and/or disorders, vascular diseases and/or disorders heart disease, cell death and hyperplasia.

Such cancer and proliferative diseases include, but are not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes.

Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Such pain disorders include, but are not limited to, cancer-related pain, skeletal pain caused by tumor metastasis, osteoarthritis, visceral pain, inflammatory pain and neurogenic pain.

Such dermatological diseases and/or disorders include, but are not limited to, inflammatory or allergic conditions of the skin, dermatitis, eczema, psoriasis, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis, pityriasis alba, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, peritoneal and sub dermal adhesion and photoaging of the skin.

Such metabolic diseases and/or disorders and eating disorder include, but are not limited to, obesity, diabetes and anoerexia.

Such muscle diseases and/or disorders include, but are not limited to, muscular atrophies (e.g. disuse), muscular dystrophies (e.g. Duchenne's muscle dystrophy, Becker's muscle dystrophy, Limb-Girdle muscle dystrophy), sarcopenia, cachexia, wasting and Facioscapulohumeral dystrophy.

Such neurological diseases and/or disorders and neurodegenerative disorders include, but are not limited to, impaired neurological function and Alzheimer's disease.

Such immunodeficiency diseases and/or disorders and immunologically-mediated diseases and/or disorders include, but are not limited to, pathologic immune conditions involving T cell activation, anaphylaxis, allergy and psoriasis. Such allergy disorders include, but are not limited to, respiratory diseases and dermatolgical disorders.

Such autoimmune diseases and/or disorders and autoimmune-mediated diseases and/or disorders include, but are not limited to, destructive arthritis, rheumatoid arthritis, systemic lupus erythematosus, Sjogren's syndrome, multiple sclerosis, dermatomyositis, progressive systemic sclerosis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), primary binary cirrhosis (PBC), lupus, systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Such bone diseases and/or disorders include, but are not limited to, osteoporosis, osteitis deformans, Paget's disease, osteoarthritis, prosthesis failure, osteopenia, and fractures and other disorders in which low bone mineral density are a hallmark of the disease.

Such inflammatory diseases and/or disorders include, but are not limited to, uveitis, atherosclerosis, atherogenesis, glomerulonephritis, Kawasaki disease, inflammatory responses, polymyositis, arthritis, neurological inflammation, chronic arthritis inflammation and osteoarthritis.

Such fibrosis diseases and/or disorders include, but are not limited to, extracellular matrix accumulation and fibrosis, scleroderma, fibrosclerosis, radiation-induced fibrosis, kidney fibrosis, lung fibrosis and liver fibrosis, haemochromatosis, primary biliary cirrhosis, restenosis, retroperitoneal fibrosis, mesenteric fibrosis, endometriosis and keloids.

Such ophthalmic/ocular diseases and/or disorders include, but are not limited to, proliferative vitreoretinopathy, ocular scarring, corneal scarring, ocular disorders, corneal wounds, conjunctivitis, keratoconjunctivitis sicca, and vernal conjunctivitis.

Such infectious and viral diseases and/or disorders include, but are not limited to, HIV-1 infection, for example, hepatitis B virus (HBV), hepatitis C virus (HCV), alcohol-induced hepatitis.

Wound repair includes, but are not limited to, excessive or hypertrophic scar or keloid formation in the dermis occurring during wound healing resulting from trauma or surgical wounds, ulcers (including diabetic ulcers, chronic ulcers, gastric ulcers, and duodenal ulcers).

Such respiratory diseases and/or disorders and pulmonary disorders include, but are not limited to, asthma, bronchial asthma, allergic asthma, intrinsic (non-allergic) asthma, extrinsic (allergic) asthma, exercise-induced asthma, drug-induced asthma (including aspirin and NSAID-induced) and dust-induced asthma, chronic obstructive pulmonary disease (COPD); chronic obstructive airways disease (COAD), chronic obstructive lung disease (COLD), bronchitis, chronic bronchitis, acute bronchitis, dyspnea, arachidic bronchitis, catarrhal bronchitis, croupus bronchitis, phthinoid bronchitis, rhinitis, acute rhinitis, chronic rhinitis, rhinitis medicamentosa, vasomotor rhinitis, perennial and seasonal allergic rhinitis, rhinitis nervosa (hay fever), inflammatory or obstructive airways diseases, pulmonary hypertension, acute lung injury, adult/acute respiratory distress syndrome (ARDS), pulmonary fibrosis, idiopathic pulmonary fibrosis, chronic obstructive pulmonary disease, pulmonary disease due to infectious or toxic agents, emphysema, pneumoconiosis, aluminosis, anthracosis, asbestosis, chalicosis, ptilosis, siderosis, silicosis, tabacosis, byssinosis, acute lung injury (ALI), hypereosinophilia, Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, pulmonary hypertension, primary pulmonary hypertension (PPH), secondary pulmonary hypertension (SPH), familial PPH, sporadic PPH, pre-capillary pulmonary hypertension, pulmonary arterial hypertension (PAH), pulmonary artery hypertension, idiopathic pulmonary hypertension, thrombotic pulmonary arteriopathy (TPA), plexogenic pulmonary arteriopathy, functional classes I to IV pulmonary hypertension, and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, hypoxemia, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Such renal diseases and/or disorders include, but are not limited to, glomerulonephritis, renal interstitial fibrosis, renal fibrosis, chronic renal disease and acute renal disease. Such kidneey diseases and/or disorders include, but are not limited to, diabetic nephropathy, lupus nephritis, hypertension-induced nephropathy, HIV-associated nephropathy and transplant necropathy. Such liver diseases and/or disorders include, but are not limited to, hepatic dysfunction attributable to infections, alcohol-induced hepatitis, disorders of the biliary tree and hepatic ischemia.

Such cardiovascular, vascular or heart diseases and/or disorders include, but are not limited to, congestive heart failure, post-infarction cardiac fibrosis, congestive heart failure, reperfusion/ischemia in stroke, heart attacks, and organ hypoxia, ischemia, dilated cardiomyopathy, myocarditis, myocardial infarction vascular stenosis, restenosis, atherosclerosis, male erectile dysfunction, Raynaud's syndrome, thrombosis and thrombin-induced platelet aggregation.

In other embodiments the compounds of Formula (I) provided herein are immunosuppressive agents and are used to treat organ transplant rejection, chronic transplant rejection, lupus, multiple sclerosis, rheumatoid arthritis, psoriasis, dermatitis, Crohn's disease, type-1 diabetes and complications from type-1 diabetes.

In certain embodiments, the compounds, pharmaceutically acceptable salts, solvates, N-oxides, prodrugs and isomers thereof, and pharmaceutical compositions and pharmaceutical combinations provided herein are inhibitors of Ros, KDR, FMS, c-FMS, FLT3, c-Kit, JAK2, JAK3, Aurora, PDGFR, Lck, TrkA, TrkB, TrkC, IGR-1R, ALK4, ALK5, and/or ALK protein kinase activity.

The aforementioned compounds and pharmaceutically acceptable salts, solvates, N-oxides, prodrugs and isomers thereof, are compounds having structures according to Formula (I),

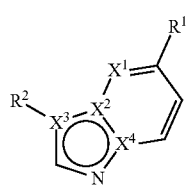

Formula (I)

wherein:
$R^1$ is

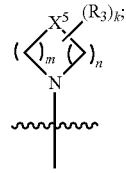

wherein,
$X^1$, $X^2$ $X^3$ and $X^4$ are each independently $CR^9$, C or N, with the proviso that at least one of $X^1$, $X^2$ $X^3$ and $X^4$ is N and at most only two of $X^1$, $X^2$ $X^3$ and $X^4$ are N;
$X^5$ is $C(R^3)_2$, O, S, $S(O)_2$, S(O), or N;
m is 1, 2, 3 or 4;
n is 0, 1, 2 or 3;
k is 0, 1, 2, 3, 4, 5 or 6;
each $R^3$ is independently selected from halogen, nitro, $-N(R^4)_2$, $-OR^9$, $-CN$, $=O$, $-C(O)N(R^4)_2$, $-N(R^4)C(O)OR^4$, $-N(R^4)C(O)R^4$, $-C(O)R^9$, $-C(O)OR^9$, $-R^6$, $-OR^6$, $L^1R^5$, $L^1R^6$, $-Y^1R^5$, $-Y^1R^6$, $-S(O)_2R^9$, $-S(O)_2N(R^4)_2$, $-NR^4S(O)_2$, $-OC(O)R^9$, $-(CH_2)_pOR^9$, $-L^1C(O)R^8$, $-L^1R^8$, $-C(O)R^9$, $-OC(O)R^9$, $-C(O)OR^9$, $-C(O)R^9$, $-N(R^9)_2$, $-C(O)N(R^4)_2$, $-N(R^4)C(O)R^4$, $-N(R^4)C(O)OR^4$, $-S(O)_2R^9$, $-S(O)_2N(R^4)_2$, $-NR^4S(O)_2$, $C_1$-$C_8$alkyl, $C_6$-$C_{14}$aryl, $C_3$-$C_8$cycloalkyl, halo-substituted-$C_1$-$C_8$alkyl, $C_1$-$C_8$alkoxy, hydroxyl-$C_1$-$C_8$alkyl, halo-substituted $C_1$-$C_8$alkoxy, $C_2$-$C_{14}$heterocycloalkyl and $C_2$-$C_{13}$heteroaryl, wherein the $C_1$-$C_8$alkyl, $C_6$-$C_{14}$aryl, $C_3$-$C_8$cycloalkyl, $C_2$-$C_{14}$heterocycloalkyl and $C_2$-$C_{13}$heteroaryl of $R^3$ are optionally substituted with 1 to 3 substituents independently selected from halogen, amino, nitro, hydroxyl, cyano, $-OR^9$, $-C(O)N(R^4)_2$, $-N(R^4)C(O)OR^4$, $-N(R^4)C(O)R^4$, $-C(O)R^9$, $-C(O)OR^9$, $-R^6$, $-OR^6$, $L^1R^5$, $L^1R^6$, $-Y^1R^5$, $-Y^1R^6$, $-S(O)_2R^9$, $-S(O)_2N(R^4)_2$, $-NR^4S(O)_2$, $-OC(O)R^9$, $-(CH_2)_pOR^9$, $-L^1C(O)R^8$, $-C(O)R^9$, $-OC(O)R^9$, $-C(O)OR^9$, $-C(O)R^9$, $-N(R^9)_2$, $-C(O)_N(R^4)_2$, $-N(R^4)C(O)R^4$, $-N(R^4)C(O)OR^4$, $-S(O)_2R^9$, $-S(O)_2N(R^4)_2$, $-NR^4S(O)_2$, $C_1$-$C_8$alkyl, $C_1$-$C_8$aminoalkyl, $C_1$-$C_8$alkoxy, $C_1$-$C_8$alkylthio, hydroxyl-$C_1$-$C_8$alkyl, halo-substituted-$C_1$-$C_8$alkyl, halo-substituted-$C_1$-$C_8$alkoxy, $C_3$-$C_8$cycloalkyl, $C_2$-$C_{14}$heterocycloalkyl, $C_6$-$C_{14}$aryl and $C_2$-$C_{13}$heteroaryl;
alternatively each $R^3$ is independently a $C_1$-$C_8$alkyl, wherein at least two $R^3$ together form a $C_3$-$C_8$cycloalkyl fused with a heterocycle and wherein each $C_1$-$C_8$alkyl of $R^3$ is optionally substituted with 1 to 3 substituents independently selected from halogen, amino, nitro, hydroxyl, cyano, $-OR^9$, $C_1$-$C_8$alkyl, $C_1$-$C_8$aminoalkyl, $C_1$-$C_8$alkoxy, $C_1$-$C_8$alkylthio, hydroxyl-$C_1$-$C_8$alkyl, halo-substituted-$C_1$-$C_8$alkyl, halo-substituted-$C_1$-$C_8$alkoxy, $C_3$-$C_8$cycloalkyl, $C_2$-$C_{14}$heterocycloalkyl, $C_6$-$C_{14}$aryl and $C_2$-$C_{13}$heteroaryl;
$R^2$ is $C_6$-$C_{14}$aryl, $C_2$-$C_{13}$heteroaryl or $C_2$-$C_{14}$heterocycloalkyl, wherein the $C_6$-$C_{14}$aryl, $C_2$-$C_{13}$heteroaryl or $C_2$-$C_{14}$heterocycloalkyl of $R^2$ are optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R^4)_2, —N(R^4)C(O)OR^4, —N(R^4)C(O)R^4, —C(O)R^9, —OR^9, —C(O)OR^9, —N(R^4)_2, —R^6, —OR^6, L^1R^5, L^1R^6, —Y^1R^5, —Y^1R^6, —S(O)_2R^9, —S(O)_2N(R^4)_2, —NR^4S(O)_2R^4, —OC(O)R^9, $C_1$-$C_8$alkoxy, hydroxyl-$C_1$-$C_8$alkyl, halo-substituted $C_1$-$C_8$alkyl and halo-substituted $C_1$-$C_8$alkoxy;

each $R^4$ is independently selected from H, $C_1$-$C_8$ alkyl, -L^1R^5, -L^1R^6, -L^1R^8, $C_2$-$C_{13}$heteroaryl, $C_6$-$C_{14}$aryl, $C_2$-$C_{14}$heterocycloalkyl and $C_3$-$C_8$cycloalkyl, wherein the $C_1$-$C_8$alkyl, $C_2$-$C_{13}$heteroaryl and $C_3$-$C_8$cycloalkyl are optionally substituted with 1 to 3 substituents independently selected from halogen, deuterium, —CD_3, —S(O)_2R^9, —CN, $C_1$-$C_8$alkyl, —OR^9, —N(R^9)_2 and —(CH_2)_pOR^9;

$L^1$ is a bond, $C_1$-$C_8$alkylene, $C_2$-$C_8$alkenylene, —O(CH_2)_p—, —C(O)—, —N(R^9)—, —(CH_2)_pC(O)—, —C(O)(CH_2)_pO(CH_2)_p— or —C(O)O—;

$Y^1$ is $C_6$-$C_{14}$arylene, $C_2$-$C_{13}$heteroarylene, $C_3$-$C_8$cycloalkylene, $C_2$-$C_{14}$heterocycloalkylene or $C_1$-$C_8$alkoxylene, each of which is optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R^4)_2, —N(R^4)C(O)OR^4, —N(R^4)C(O)R^4, —C(O)R^9, —OR^9, —C(O)OR^9, —N(R^4)_2, —R^6, —OR^6, -L^1R^5, -L^1R^6, —Y^1R^5, —Y^1R^6, —S(O)_2R^9, —S(O)_2N(R^4)_2, —NR^4S(O)_2R^4, —OC(O)R^9, $C_1$-$C_8$alkoxy, hydroxyl-$C_1$-$C_8$alkyl, halo-substituted $C_1$-$C_8$alkyl and halo-substituted $C_1$-$C_8$alkoxy;

$R^5$ is $C_6$-$C_{14}$aryl, $C_2$-$C_{13}$heteroaryl, $C_2$-$C_{14}$heterocycloalkyl, —N(R^9)_2, —N(R^9)C(O)R^9, —C(O)N(R^9)_2, —(CH_2)_pOR^9 or —OR^9.

$R^6$ is $C_6$-$C_{14}$aryl, $C_2$-$C_{13}$heteroaryl, $C_2$-$C_{14}$heterocycloalkyl, —OCH(R^7)_2, —C(O)R^7, $C_2$-$C_8$alkyl, or $C_3$-$C_8$cycloalkyl, wherein the $C_1$-$C_8$alkyl, $C_3$-$C_8$cycloalkyl, $C_6$-$C_{14}$aryl, $C_2$-$C_{13}$heteroaryl, and $C_2$-$C_{14}$heterocycloalkyl of $R^6$ are optionally substituted with 1 to 3 substituents independently selected from halogen, —CN, —OR^9, —(CH_2)_pOR^9, -L^1C(O)R^8, L^1R^8, L^1R^5, —C(O)R^9, —OC(O)R^9, —C(O)OR^9, —C(O)R^8, OC(O)N(R^4)_2, —N(R^9)_2, —C(O)C(O)OR^9, —(CH_2)_pN(R^9)_2, —N(R^4)_2, —C(O)N(R^4)_2, —N(R^4)C(O)R^4, —N(R^4)C(O)OR^4, —(CH_2)_pS(O)_2R^9, —S(O)_2R^9, —S(O)_2N(R^4)_2, —NR^4S(O)_2R^4, —NR^4S(O)_2R^9, $C_2$-$C_{14}$heterocycloalkyl, $C_2$-$C_{13}$heteroaryl, $C_1$-$C_8$alkyl, $C_2$-$C_8$alkene, $C_1$-$C_8$alkoxy, hydroxyl-substituted $C_1$-$C_8$alkyl, halo-substituted $C_1$-$C_8$alkyl and halo-substituted $C_1$-$C_8$alkoxy;

or $R^6$ is $C_6$-$C_{14}$aryl, $C_2$-$C_{13}$heteroaryl, $C_2$-$C_{14}$heterocycloalkyl or $C_3$-$C_8$cycloalkyl having a $C_1$-$C_4$alkyl bridge;

or $R^6$ is a $C_2$-$C_{14}$heterocycloalkyl optionally substituted with 1 to 3 substituents selected from halogen, =O, —CN, —OR^9, —(CH_2)_pOR^9, -L^1C(O)R^8, -L^1R^5, —C(O)R^9, —OC(O)R^9, —C(O)OR^9, —C(O)R^8, OC(O)N(R^4)_2, —N(R^9)_2, —C(O)C(O)OR^9, —(CH_2)_pN(R^9)_2, —N(R^4)_2, —C(O)N(R^4)_2, —N(R^4)C(O)R^4, —N(R^4)C(O)OR^4, —(CH_2)_pS(O)_2R^9, —S(O)_2R^9, —S(O)_2N(R^4)_2, —NR^4S(O)_2R^4, —NR^4S(O)_2R^9, $C_2$-$C_{14}$heterocyclo alkyl, $C_2$-$C_{13}$heteroaryl, $C_1$-$C_8$alkyl, $C_2$-$C_8$alkene, $C_1$-$C_8$alkoxy, hydroxyl-substituted $C_1$-$C_8$alkyl, halo-substituted $C_1$-$C_8$alkyl and halo-substituted $C_1$-$C_8$alkoxy;

each $R^7$ is independently selected from H, $C_1$-$C_8$alkyl and -L^1R^8;

$R^8$ is H, —N(R^9)_2, —N(R^4)_2, —SR^9, —CN, $C_1$-$C_8$alkyl, $C_3$-$C_8$cycloalkyl and $C_2$-$C_{14}$heterocyclo alkyl, wherein the $C_1$-$C_8$alkyl, $C_3$-$C_8$cycloalkyl and $C_2$-$C_{14}$heterocycloalkyl of $R^8$ are optionally substituted with 1 to 3 substituents independently selected from halogen, $C_1$-$C_6$alkyl, —CN, —OR^9, —(CH_2)_pOR^9, -L^1C(O)R^8, —C(O)R^9, —OC(O)R^9, —C(O)OR^9, —N(R^9)_2, —N(R^4)_2, —C(O)N(R^4)_2, —N(R^4)C(O)R^4, —N(R^4)C(O)OR^4, —S(O)_2R^9, —S(O)_2N(R^4)_2, and —NR^4S(O)_2;

each $R^9$ is independently selected from H, $C_3$-$C_8$cycloalkyl and $C_1$-$C_8$alkyl, and each p is independently 1, 2, 3, 4, 5 or 6.

In certain embodiments $R^1$ is

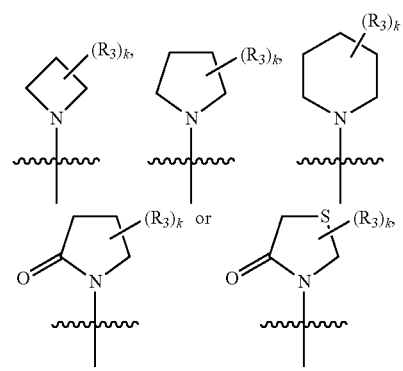

while in other embodiments $R^1$ is

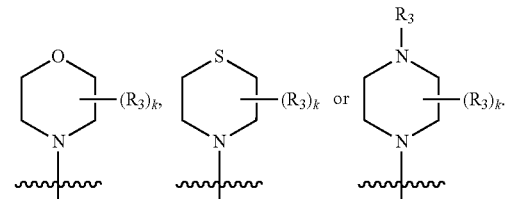

In certain embodiments each $R^3$ is independently selected from halo, —OR^9, $C_1$-$C_8$alkyl, $C_6$-$C_{18}$aryl, $C_3$-$C_8$cycloalkyl, halo-substituted-$C_1$-$C_8$alkyl, $C_2$-$C_{14}$heterocycloalkyl and $C_2$-$C_{13}$heteroaryl, wherein the $C_1$-$C_8$alkyl, $C_6$-$C_{14}$aryl, $C_3$-$C_8$cycloalkyl, $C_2$-$C_{14}$heterocycloalkyl and $C_2$-$C_{13}$heteroaryl of $R^3$ are optionally substituted with 1 to 3 substituents independently selected from halo, hydroxyl, —OR^9, $C_1$-$C_8$alkyl, $C_1$-$C_8$alkoxy, hydroxyl-$C_1$-$C_8$alkyl, halo-substituted-$C_1$-$C_8$alkyl, halo-substituted-$C_1$-$C_8$alkoxy and $C_3$-$C_8$cycloalkyl.

In certain embodiments the $C_6$-$C_{14}$aryl of $R^3$ is phenyl optionally substituted with 1 to 3 substituents independently selected from halo, $C_1$-$C_8$alkyl, and halo-substituted-$C_1$-$C_8$alkyl.

In certain embodiments the $C_6$-$C_{14}$aryl of $R^3$ is phenyl optionally substituted with 1 to 3 substituents independently selected from fluoro and $C_1$-$C_8$alkyl.

In certain embodiments $R^2$ is $C_6$-$C_{14}$aryl or $C_2$-$C_{13}$heteroaryl, wherein the $C_6$-$C_{14}$aryl and $C_2$-$C_{13}$heteroaryl of $R^2$ are optionally substituted with 1 to 3 substituents independently selected from halo, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R$^4$)$_2$, —N(R$^4$)C(O)OR$^4$, —N(R$^4$)C(O)R$^4$, —C(O)R$^9$, —OR$^9$, —C(O)OR$^9$, —N(R$^4$)$_2$, —R$^6$, —OR$^6$, -L$^1$R$^5$, -L$^1$R$^6$, —Y$^1$R$^5$, —Y$^1$R$^6$, —S(O)$_2$R$^9$, —S(O)$_2$N(R$^4$)$_2$, —NR$^4$S(O)$_2$R$^4$, —OC(O)R$^9$, $C_1$-$C_8$alkoxy, hydroxyl-$C_1$-$C_8$alkyl, halo-substituted $C_1$-$C_8$alkyl and halo-substituted $C_1$-$C_8$alkoxy.

In certain embodiments $R^2$ is $C_6$-$C_{14}$aryl or $C_2$-$C_{13}$heteroaryl, wherein the $C_6$-$C_{14}$aryl and $C_2$-$C_{13}$heteroaryl of $R^2$ are optionally substituted with 1 to 3 substituents independently selected from halo, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R$^4$)$_2$, —N(R$^4$)C(O)OR$^4$, —N(R$^4$)C(O)R$^4$, —C(O)R$^9$, —OR$^9$, —C(O)OR$^9$, —N(R$^4$)$_2$, —R$^6$, —OR$^6$, -L$^1$R$^5$, -L$^1$R$^6$, —Y$^1$R$^5$, —Y$^1$R$^6$ and —S(O)$_2$R$^9$.

In certain embodiments the $C_6$-$C_{14}$aryl of $R^2$ is phenyl optionally substituted with 1 to 3 substituents independently selected from halo, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R$^4$)$_2$, —N(R$^4$)C(O)OR$^4$, —N(R$^4$)C(O)R$^4$, —C(O)R$^9$, —OR$^9$, —C(O)OR$^9$, —N(R$^4$)$_2$, —R$^6$, —OR$^6$, -L$^1$R$^5$, -L$^1$R$^6$, —Y$^1$R$^5$, —Y$^1$R$^6$ and —S(O)$_2$R$^9$.

In certain embodiments the $C_2$-$C_{13}$heteroaryl of $R^2$ is selected from

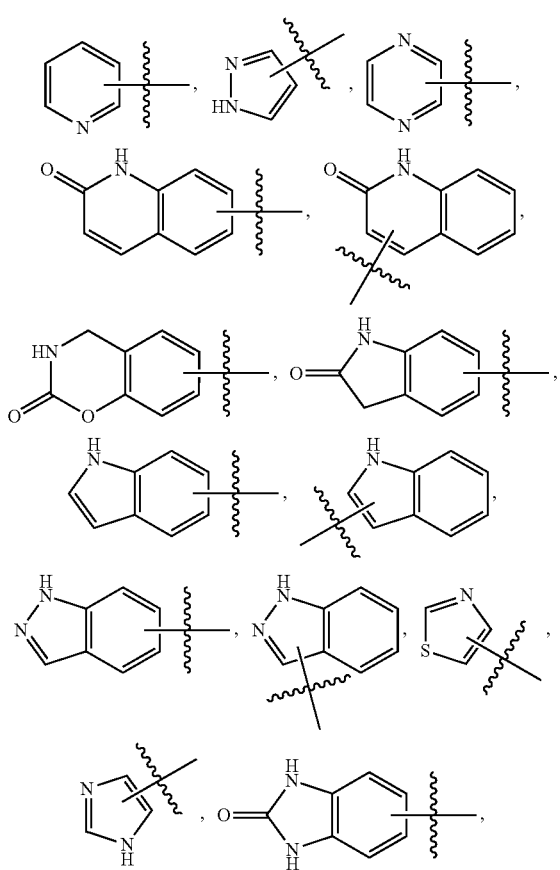

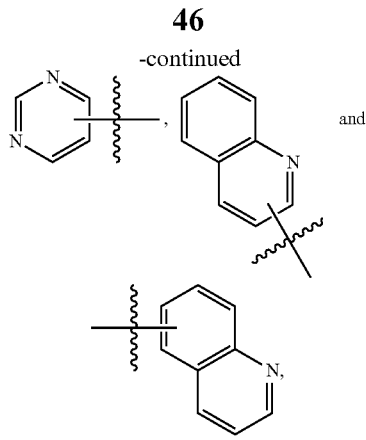

-continued wherein each is optionally substituted with 1 to 3 substituents independently selected from halo, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R$^4$)$_2$, —N(R$^4$)C(O)OR$^4$, —N(R$^4$)C(O)R$^4$, —C(O)R$^9$, —OR$^9$, —C(O)OR$^9$, —N(R$^4$)$_2$, —R$^6$, —OR$^6$, -L$^1$R$^5$, -L$^1$R$^6$, —Y$^1$R$^5$, —Y$^1$R$^6$ and —S(O)$_2$R$^9$.

In certain embodiments of the aforementioned compounds of Formula (I), the $C_2$-$C_{13}$heteroaryl of $R^2$ is selected from

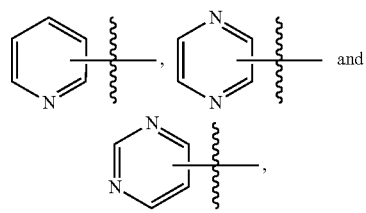

wherein each is optionally substituted with 1 to 3 substituents independently selected from halogen, $C_2$-$C_{14}$heterocycloalkyl, $C_2$-$C_{13}$heteroaryl, $C_1$-$C_8$alkyl, $C_3$-$C_8$cycloalkyl, —CN, —C(O)N(R$^4$)$_2$, —N(R$^4$)C(O)OR$^4$, —N(R$^4$)C(O)R$^4$, —C(O)OR$^9$, —OR$^9$, —C(O)OR$^9$, —N(R$^4$)$_2$, —R$^6$, OR$^6$, L$^1$R$^5$, L$^1$R$^6$, —Y$^1$R$^5$, Y$^1$R$^6$ and —S(O)$_2$R$^9$.

In certain embodiments of the aforementioned compounds of Formula (I), $R^6$ is $C_2$-$C_{13}$heteroaryl, $C_2$-$C_{14}$heterocycloalkyl, —OCH(R$^7$)$_2$, $C_1$-$C_8$alkyl, or $C_3$-$C_8$cycloalkyl, wherein the $C_1$-$C_8$alkyl, $C_3$-$C_8$cycloalkyl, $C_2$-$C_{13}$heteroaryl, and $C_2$-$C_{14}$heterocycloalkyl of $R^6$ are optionally substituted with 1 to 3 substituents independently selected from halogen, —CN, —OR$^9$, —(CH$_2$)$_p$OR$^9$, -L$^1$C(O)R$^8$, L$^1$R$^8$, L$^1$R$^5$, —C(O)OR$^9$, —C(O)R$^9$, —N(R$^9$)$_2$, —C(O)N(R$^4$)$_2$, —N(R$^4$)C(O)OR$^4$, N(R$^4$)C(O)R$^4$, —N(R$^4$)$_2$, —S(O)—S(O)$_2$R$^9$, $C_2$, —$C_{14}$heterocycloalkyl, $C_2$-$C_{13}$heteroaryl, $C_1$-$C_8$alkyl, $C_2$-$C_8$alkene, and hydroxyl-substituted $C_1$-$C_8$alkyl.

In certain embodiments of the aforementioned compounds of Formula (I), $R^6$ is selected from

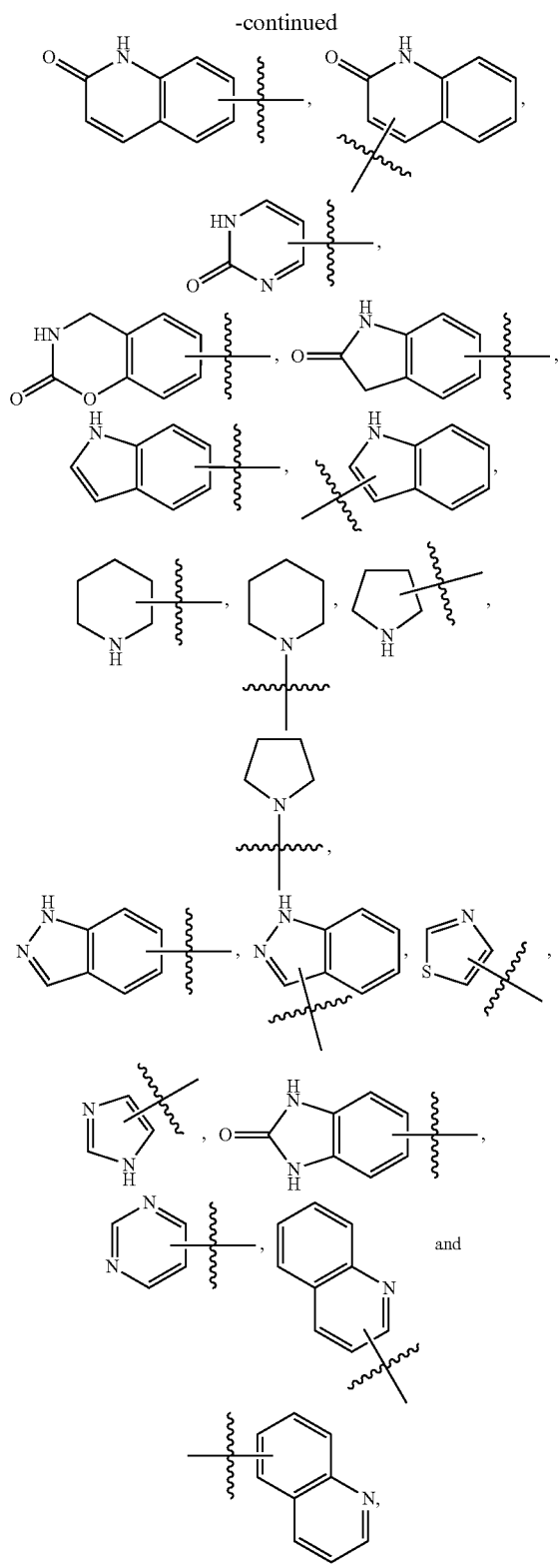

wherein each is optionally substituted with 1 to 3 substituents independently selected from halogen, —CN, —OR$^9$, —(CH$_2$)$_p$OR$^9$, -L$^1$C(O)R$^8$, -L$^1$R$^8$, -L$^1$R$^5$, —C(O)OR$^9$, —C(O)R$^9$, —N(R$^9$)$_2$, —C(O)N(R$^4$)$_2$, —N(R$^4$)C(O)OR$^4$, —N(R$^4$)C(O)R$^4$, —N(R$^4$)$_2$, —S(O)$_2$R$^9$, C$_2$-C$_{14}$heterocycloalkyl, C$_2$-C$_{13}$heteroaryl, C$_1$-C$_8$alkyl, C$_2$-C$_8$alkene, and hydroxyl-substituted C$_1$-C$_8$alkyl.

In certain embodiments of the aforementioned compounds of Formula (I), Y$^1$ is C$_6$-C$_{14}$arylene or C$_2$-C$_{13}$heteroarylene, while in other embodiments Y$^1$ is selected from

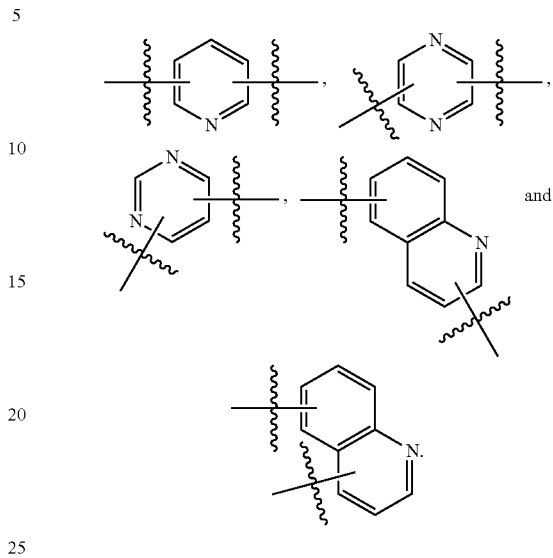

In certain embodiments of the aforementioned compounds of Formula (I), each R$^4$ is independently selected from H, C$_1$-C$_8$ alkyl, C$_6$-C$_{14}$aryl, C$_2$-C$_{14}$heterocycloalkyl, -L$^1$R$^6$ and C$_3$-C$_8$cycloalkyl, wherein the C$_1$-C$_8$alkyl, C$_6$-C$_{14}$aryl, C$_2$-C$_{14}$heterocycloalkyl, and C$_3$-C$_8$cycloalkyl are optionally substituted with —(CH$_2$)$_p$OR$^9$.

In certain embodiments of the aforementioned compounds of Formula (I), R$^5$ is C$_6$-C$_{14}$aryl, C$_2$-C$_{13}$heteroaryl, C$_2$-C$_{14}$heterocycloalkyl, —N(R$^9$)$_2$, —N(R$^9$)C(O)R$^9$, —(CH$_2$)$_p$OR$^9$, or —OR$^9$.

In certain embodiments of the aforementioned compounds of Formula (I), R$^7$ is -L$^1$R$^8$. In certain embodiments of the aforementioned compounds of Formula (I), R$^8$ is —N(R$^9$)$_2$ or —CN.

The compounds, pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

Processes for Making Compounds of Formula (I)

General procedures for preparing compounds of Formula (I) are described in the Examples, infra. In the reactions described, reactive functional groups, for example hydroxyl, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) described herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) described herein is prepared by reacting the free acid form of the compound of Formula (I) with a pharmaceutically acceptable organic base or inorganic base. Alternatively, the salt forms of the compounds of Formula (I) described herein are prepared using salts of the starting materials or intermediates. In certain embodiments, the compounds of Formula (I) described herein are in the form of other salts including, but not limited to, oxalates and trifluoroacetates. In certain embodiments, hemisalts of acids and bases are formed, for example, hemisulphate and hemicalcium salts.

The pharmaceutically acceptable organic acid or inorganic acids used to form pharmaceutically acceptable acid addition salts of compounds of Formula (I) include, but are not limited to, hydrofluoric acid, hydrochloric acid, hydrobromic acid, hydroiodic acid, nitric acid, sulfuric acid, phosphoric acid, formic acid, acetic acid, trifluoroacetic acid, propionic acid, butyric acid, caprylic acid, dichloroacetic acid, hippuric acid, lactic acid, citric acid, tartaric acid, malic acid, gluconic acid, mandelic acid, maleic acid, succinic acid, adipic acid, aspartic acid, fumaric acid, glutamic acid, malonic acid, sebacic acid, salicylic acid, hexanoic acid, benzoic acid, p-chlorobenzoic acid, nicotinic acid, diphenylacetic acid, triphenylacetic acid, o-hydroxybenzoic acid, p-hydroxybenzoic acid, 1-hydroxynaphthalene-2-carboxylic acid or 3-hydroxynaphthalene-2-carboxylic acid, sulfonic acids, methanesulfonic acid, benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid and p-toluenesulfonic acid. Pharmaceutically acceptable solvates are generally hydrates.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

Such pharmaceutically acceptable base addition salt of a compound of Formula (I) include, but are not limited to, aluminium, ammonium, arginine, benzathine, calcium, choline, diethylamine, diolamine, glycine, lysine, magnesium, meglumine, olamine, potassium, sodium, tromethamine, ethanolamines, benzylamines, pyridine, benethamine, diethanolamine, 4-(2-hydroxy-ethyl)morpholine, 1-(2-hydroxyethyl)pyrrolidine, N-methyl glutamine, piperazine, triethanol-amine and zinc salts.

In certain embodiments, the free acid or free base forms of the compounds of Formula (I) described herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, the compounds of Formula (I) described herein in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) described herein are prepared using methods known to those of ordinary skill in the art (e.g., for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxyalkylcarbanochloridate, para-nitrophenyl carbonate, or the like).

In certain embodiments, the compounds of Formula (I) described herein are prepared as protected derivatives using methods known to those of ordinary skill in the art. A detailed description of the techniques applicable to the creation of protecting groups and their removal can be found in T. W. Greene, "Protecting Groups in Organic Chemistry," $3^{rd}$ edition, John Wiley and Sons, Inc., 1999.

In certain embodiments, the compounds of Formula (I) described herein are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, the compounds of Formula (I) provided herein are prepared as a racemic mixture. In certain embodiments, the compounds of Formula (I) described herein are prepared as their individual stereoisomers. In certain embodiments, the compounds of Formula (I) provided herein are prepared as a racemic mixture and their individual stereoisomers are aobtained using chiral chromatography, including, but not limited to, chiral liquid chromatogtaphy. In other embodiments, the compounds of Formula (I) described herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are provided in substantially pure form. In certain embodiments compounds of Formula (I) are at least 60% pure. In certain embodiments compounds of Formula (I) are at least 75% pure. In certain embodiments compounds of Formula (I) are at 85% pure. In certain embodiments compounds of Formula (I) are at least 98% pure (% are on a weight for weight basis).

Compounds of Formula (I) are made by processes described herein and as illustrated in the Examples. In certain embodiments, compounds of Formula (I) are made by (a) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Non-limiting examples of synthetic schemes used to make compounds of Formula (I) described herein are illustrated in reaction schemes (I)-(V), wherein n, m, k, $X^5$, $R^2$ and $R^3$ are as defined herein.

Reaction Scheme (I)

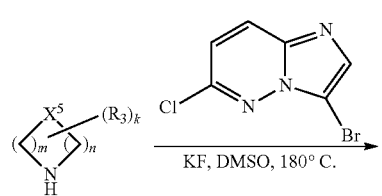

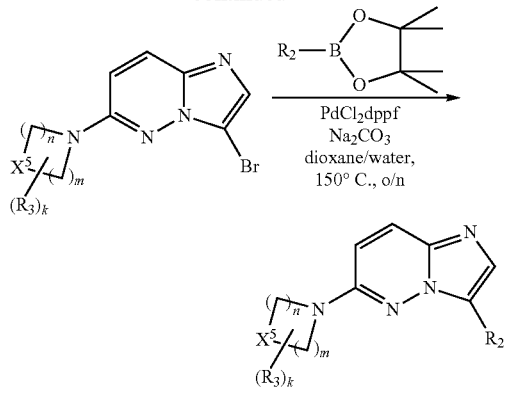

$X^5$ is $CH_2$, O, S or N
m is 1, 2, 3 or 4
n is 0, 1, 2 or 3

Reaction Scheme (II)

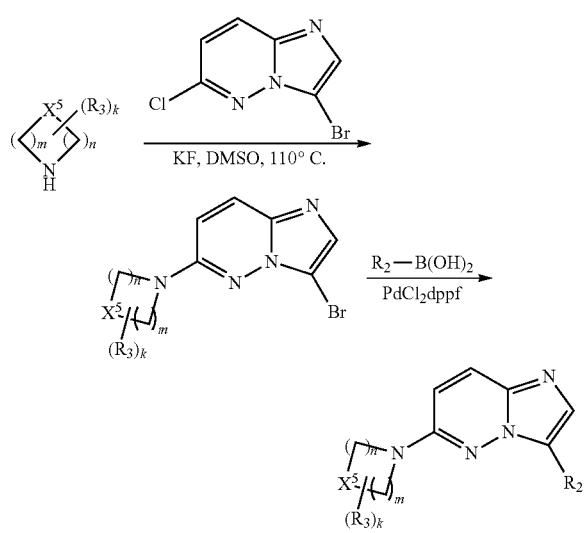

$X^5$ is $CH_2$, O, or N
m is 1, 2, 3 or 4
n is 0, 1, 2 or 3

Reaction Scheme (III)

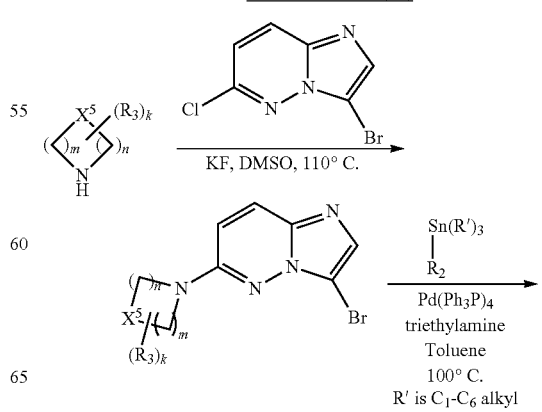

$R'$ is $C_1$-$C_6$ alkyl

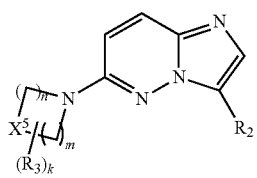

$X^5$ is CH$_2$, O, or N
m is 1, 2, 3 or 4
n is 0, 1, 2 or 3

Reaction Scheme (IV)

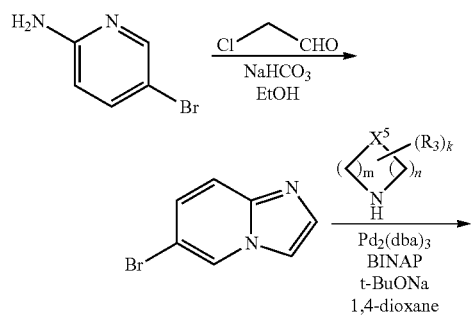

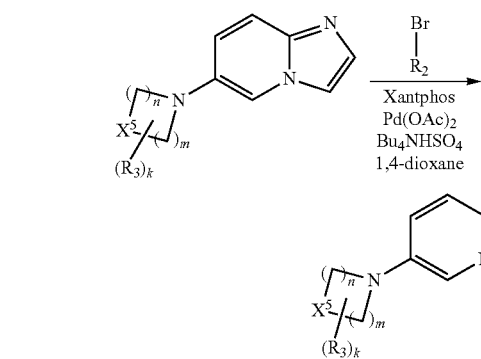

$X^5$ is CH$_2$, O, S or N
m is 1, 2, 3 or 4
n is 0, 1, 2 or 3

Reaction Scheme (V)

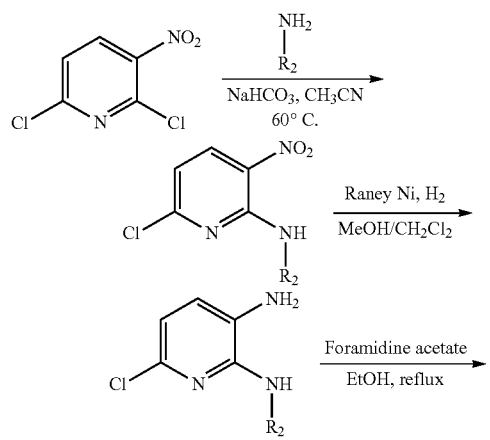

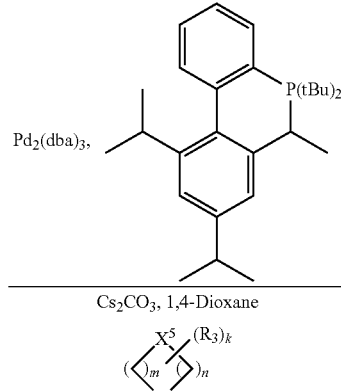

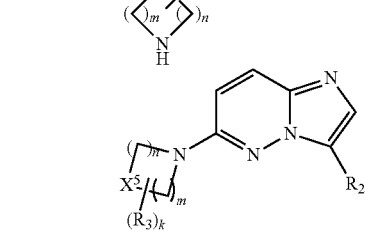

$X^5$ is CH$_2$, O, or N
m is 1, 2, 3 or 4
n is 0, 1, 2 or 3

A non-limiting example of the synthesis of the intermediate

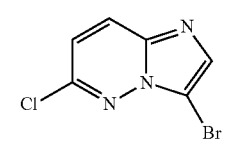 [SMILES: Clc1ccc2ncc(Br)n2n1]

is shown below:

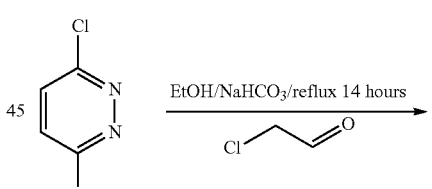

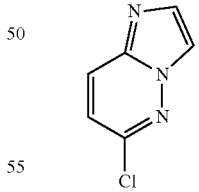

Pharmacology and Utility

Protein kinases (PTK) play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone-related diseases.

Examples of protein-tyrosine kinases include, but are not limited to, (a) tyrosine kinases such as Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR ($\alpha$ and $\beta$), Tie-1, Tie-2 (also Tek-1 or Tek), VEGFR1 (also FLT-1), c-FMS, VEGFR2 (also KDR), FLT-3, FLT-4, c-KIT, JAKE JAK2, JAK3, TYK2, LOK, RET, Ros, TRKA, TRKB, TRKC, PYK2, ALK (Anaplastic Lymphoma Kinase), EPHA (1-8), EPHB (1-6), RON, Fes, Fer or EPHB4 (also EPHB4-1), and (b) and serine/threonine kinases such as Aurora, c-RAF, SGK, MAP kinases (e.g., MKK4, MKK6, etc.), SAPK2$\alpha$, SAPK2$\beta$, Ark, ATM (1-3), CamK (1-IV), CamKK, Chk1 and 2 (Checkpoint kinases), CK1, CK2, Erk, IKK-I (also IKK-ALPHA or CHUK), IKK-2 (also IKK-BETA), Ilk, Jnk (1-3), LimK (1 and 2), MLK3Raf (A, B and C), CDK (1-10), PKC (including all PKC subtypes), Plk (1-3), NIK, Pak (1-3), PDK1, PKR, RhoK, RIP, RIP-2, GSK3 ($\alpha$ and $\beta$), PKA, P38, Erk (1-3), PKB (including all PKB subtypes) (also AKT-1, AKT-2, AKT-3 or AKT3-1), IRAK1, FRK, SGK, TAK1 and Tp1-2 (also COT).

Phosphorylation modulates or regulates a variety of cellular processes such as proliferation, growth, differentiation, metabolism, apoptosis, motility, transcription, translation and other signaling processes. Aberrant or excessive PTK activity has been observed in many disease states including, but not limited to, benign and malignant proliferative disorders, diseases resulting from inappropriate activation of the immune system and diseases resulting from inappropriate activation of the nervous systems. Specific diseases and disease conditions include, but are not limited to, autoimmune disorders, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, obesity, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, auto-immune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Tyrosine kinases can be broadly classified as receptor-type (having extracellular, transmembrane and intracellular domains) or the non-receptor type (being wholly intracellular) protein tyrosine kinases. Inappropriate or uncontrolled activation of many of these kinase (aberrant protein tyrosine kinase activity), for example by over-expression or mutation, results in uncontrolled cell growth. Many of the protein tyrosine kinases, whether a receptor or non-receptor tyrosine kinase have been found to be involved in cellular signaling pathways involved in numerous pathogenic conditions, including, but not limited to, immunomodulation, inflammation, or proliferative disorders such as cancer.

Compounds of the invention are screened against a kinase panel (wild type and/or mutation thereof) and modulate the activity of at least one kinase panel member. Examples of kinases that are inhibited by the compounds and pharmaceutical compositions provided herein, and against which the methods described herein are useful, include, but are not limited to Ros, KDR, c-FMS, FLT3, c-Kit, JAK2, JAK3, Aurora, PDGFR, Lck, TrkA, TrkB, TrkC, IGF-1R, and/or Alk protein kinases, and mutant forms thereof. As such, the compounds and pharmaceutical compositions provided herein are useful for treating diseases or disorders in which such kinases contribute to the pathology and/or symptomology of a disease or disorder associated with such kinases. Such diseases or disorders include, but are not limited to, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, psoriasis, metastasis, cancer-related pain and neuroblastoma.

Receptor Tyrosine Kinases (RTKs).

The Receptor Tyrosine Kinases (RTKs) comprise a large family of transmembrane receptors with diverse biological activities. A number of distinct RTK subfamilies have been identified including, but not limited to, ALK receptor family, EGF receptor family, the Insulin receptor family, the PDGF receptor family, the FGF receptor family, the VEGF receptor family, the HGF receptor family, the Trk receptor family, the EPH receptor family, the AXL receptor family, the LTK receptor family, the TIE receptor family, the ROR receptor family, the DDR receptor family, the RET receptor family, the KLG receptor family, the RYK receptor family and the MuSK receptor family.

Receptor tyrosine kinases have been shown to be not only key regulators of normal cellular processes but also to have a critical role in the development and progression of many types of cancer. The receptor tyrosine kinase (RTK) family includes receptors that are crucial for the growth and differentiation of a variety of cell types. The intrinsic function of RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response such as, by way of example only, cell division, differentiation, metabolic effects, and changes in the extracellular microenvironment.

Tropomyosin-Receptor-Kinase (Trk) Family

The Trk family receptor tyrosine kinases (NTRK genes), TrkA (NTRK1), TrkB (NTRK2), and TrkC (NTRK3), are the signaling receptors that mediate the biological actions of the peptide hormones of the neurotrophin family. Trk receptors are membrane-bound receptors that, through several signal cascades, control neuronal growth and survival, and differentiation, migration and metastasis of tumor cells. The neurotrophin family of growth factors includes nerve growth factor (NGF), brain-derived neurotrophic factor (BDNF), and two neurotrophins (NT), NT-3, and NT-4. Neurotrophins are critical to the functioning of the nervous system, and the activation of Trk receptors by neurotrophin binding leads to activation of signal cascades resulting in promoting survival and other functional regulation of cells. Each type of neurotrophin has a different binding affinity toward its corresponding Trk receptor, and upon neurotrophin binding, the Trk receptors phosphorylates themselves and members of the MAPK pathway. The differences in the signaling initiated by these distinct types of receptors are important for generating diverse biological responses.

The Trk family kinase receptors promote tumorigenesis and are able to control tumor cell growth and survival as well as differentiation, migration and metastasis. The Trk receptors are implicated in the development and progression of cancer, through upregulation of either, the receptor, their ligand (NGF, BDNF, NT-3, and NT-4), or both. In many cases high Trk expression is associated with aggressive tumor behavior, poor prognosis and metastasis. Thus, diseases and disorders related to Trk receptors result from 1) expression of a Trk receptor(s) in cells which normally do not express such a receptor(s); 2) expression of a Trk receptor(s) by cells which normally do not express such a receptor(s); 3) increased expression of Trk receptor(s) leading to unwanted cell proliferation; 4) increased expression of Trk receptor(s) leading to adhesion independent cell survival; 5) mutations leading to constitutive activation of Trk receptor(s); 6) over stimulation of Trk receptor(s) due to abnormally high amount of, or mutations in, Trk receptor(s), and/or 7) abnormally high amount of Trk receptor(s) activity due to abnormally high amount of, or mutations in, Trk receptor(s).

Genetic abnormalities, i.e. point mutations and chromosomal rearrangements involving both the genes expressing TrkB and TrkC have been found in a variety of cancer types. In a kinome-wide approach to identify point mutants in tyrosine kinases, mutations in the genes expressing TrkB and TrkC were found in cell lines and primary samples from patients with colorectal cancer. In addition, chromosomal translocations involving the genes expressing TrkA and TrkB have been found in several different types of tumors. Gene rearrangements involving the genes expressing TrkA and a set of different fusion partners (TPM3, TPR, TFG) are a hallmark of a subset of papillary thyroid cancers. Moreover, secretary breast cancer, infant fibrosarcoma and congenital mesoblastic nephroma have been shown to be associated with a chromosomal rearrangement t(12;15) generating a ETV6-NTRK3 fusion gene that was shown to have constitutive kinase activity and transforming potential in several different cell lines including fibroblasts, hematopoietic cells and breast epithelial cells.

TrkA has the highest affinity to the binding nerve growth factor (NGF). NGF is important in both local and nuclear actions, regulating growth cones, motility, and expression of genes encoding the biosynthesis enzymes for neurotransmitters. Nocireceptive sensory neurons express mostly TrkA and not TrkB or TrkC.

TrkB serves as a receptor for both BDNF and NT-4, and is expressed in neuroendocrine-type cells in the small intestine and the colon, in the alpha cells of the pancreas, in the monocytes and macrophages of the lymph nodes and of the spleen, and in the granular layers of the epidermis. TrkB is also expressed in cancerous prostate cells but not in normal cells. The binding of BDNF to TrkB receptor causes activation of intercellular cascades which regulate neuronal development and plasticity, long-term potentiation, and apoptosis. BDNF promotes the proliferation, differentiation and growth and survival of normal neural components such as retinal cells and glial cells. In addition, TrkB activation is a potent and specific suppressor of anchorage independent cell death (anoikis), which is apoptosis induced by loss of attachment of a cell to its matrix. By way of example, activation of the Phosphatidylinositol-3-kinase/Protein Kinase B signaling axis by TrkB promotes the survival of non-transformed epithelial cells in 3-dimensional cultures and induces tumor formation and metastasis of those cells in immunocompromised mice. Anchorage independent cell survival is a metastatic process allowing tumor cells to migrate through the systemic circulation and grow at distant organs. Agonism of TrkB results in the failure of induced cell death by cancer treatments. Thus, TrkB modulation is a target for treatment of benign and malignant proliferative diseases, especially tumor diseases.

Diseases and disorders related to the TrkB receptor include, but are not limited to, cancers, such as, by way of example only, neuroblastoma progression, Wilm's tumor progression, breast cancer, pancreatic cancer, colon cancer, prostate cancer, and lung cancer. The TrkB receptor has been shown to be associated with Alzheimer's disease.

Additional research has discovered mutations in TrkB in humans that result in a partial loss of enzymatic activity of the receptor. This genetic legion results in an increase in apetite and obesity (hyperphagic obesity). Similar results have been obtained in mouse models, thus strengthening the hypothesis that lowering TrkB activity could serve to modulate feeding behavior, and would be useful in the treatment of disorders such as anorexia.

Other non-oncology indications for a Trk inhibitor include atopic dermatitis and psoriasis.

TrkC is activated by binding with NT-3 and is expressed by proprioceptive sensory neurons. The axons of these proprioceptive sensory neurons are much thicker than those of nocireceptive sensory neurons, which express TrkA. Signalling through TrkC leads to cell differentiation and development of proprioceptive neurons that sense body position. Mutations in this gene expressing TrkC is associated with medulloblastomas, secretory breast carcinomas and other cancers. In addition, high expression of TrkC is a hallmark of melanoma, especially in cases with brain metastasis.

Trk family members, especially NTRK1 and NTRK2, play a role in pancreatic cancer wherein: i) high expression of various members of the Trk family and their cognate ligands have been shown in tissue samples from patients with pancreatic cancer; ii) NTRK2 overexpression has been linked to a malignant, highly metastatic phenotype of pancreatic cancer; iii) high expression of NTRK1/NGF, has been correlated with enhanced proliferation, invasive behavior and pain in PC patients; and iv) nerve growth factor has been shown to increase the invasive potential of pancreatic cancer cell lines. Overexpression of TrkA in pancreatic cancer might be caused by methylation of negative regulatory AP-1 sites in the promoter region of TrkA.

Gene rearrangements involving NTRK1 are a hallmark of a subset of papillary thyroid cancers. Thyroid-specific TRK oncogenes are generated by rearrangements of the NTRK1 gene with three different activating genes, namely TPR, TPM3, and TFG.

Several loss of function mutations in thr TrkA are responsible for congenital insensitivity to pain with anhidrosis (CIPA), a disorder characterized by a lack of pain sensation and anhidrosis. More recently, an antagonistic TrkA antibody has been shown to be efficacious in inflammatory and neupathic pain animal models. In addition, TrkA and NGF have been implicated in eliciting cancer related pain. It was shown that NGF secreted by tumor cell and tumor invading macrophages secret NGF which directly stimulates TrkA located on peripheral pain fibers. Using various tumor models in both mouse and rats it was demonstrated that neutralizing NGF with a monoclonal antibody inhibits cancer related pain to a degree similar or superior to the highest tolerated dose of morphine. Therefore, a selective inhibitor of TrkA can be used in the treatment of pain associated with cancer.

High expression of Trk's are found in Wilm's tumor, prostate carcinoma and pancreatic cancers. High expression of TrkC is a hallmark of carcinoma. In neuroblastoma, high TRKB expression is correlated with an aggressive untreatable tumors and resistance to standard cytotoxic therapies. In mouse models of cancer metastasis, the NTRK2 gene (TrkB protein) can induce metastasis and removal of the gene reverses this metastatic potential. The bulk of evidence suggests that inhibition of Trk enzymes would block the growth and spread of various cancers where Trk is involved. Furthermore, activating mutations in Trk's are present in 7% of cancers.

Certain compounds, pharmaceutical compositions and pharmaceutical combination provided herein are inhibitors of Trk receptor tyrosine kinases (TrkA, TrkB, and TrkC), thus such compounds, pharmaceutical compositions and pharmaceutical combination are useful for the treatment of diseases and/or disorders that respond to inhibition of Trk receptor tyrosine kinases (TrkA, TrkB, and TrkC). In certain embodiments, such compounds, pharmaceutical compositions and pharmaceutical combination are useful in the treatment of cancer by inhibiting the development and/or progression of the cancer. In certain embodiments, such compounds, pharmaceutical compositions and pharmaceutical combination are useful in the treatment of diseases and/or disorders including, but are not limited to, neuroblastoma, Wilm's tumor, breast cancer, pancreatic cancer, colon cancer, prostate cancer, lung cancer, melanoma, anoerexia, atopic dermatitis, psoriasis and Alzheimer's disease.

Platelet-Derived Growth Factor (PDGF) Receptor Family

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. The PDGF growth factor family consists of PDGF-A, PDGF-B, PDGF-C and PDGF-D, which form either homo- or heterodimers (AA, AB, BB, CC, DD) that bind to the protein tyrosine kinase receptors PDGFR-α and PDGFR-β. Dimerization of the growth factors is a prerequisite for activation of the kinase, as the monomeric forms are inactive. The two receptor isoforms dimerize upon binding resulting in three possible receptor combinations, PDGFR-αα, PDGFR-ββ and PDGFR-αβ. Growth factor AA binds only to -αα, growth factor BB can bind with -αα, -ββ and -αβ, growth factors CC and AB specifically interact with -αα and -αβ, and growth factor DD binds to -ββ.

Key downstream mediators of PDGFR signaling are Ras/mitogen-activated protein kinase (MAPK), PI-3 kinase and phospholipase-γ (PLCγ) pathways. MAPK family members regulate various biological functions by phosphorylation of target molecules (transcription factors and other kinases) and thus contribute to regulation of cellular processes such as proliferation, differentiation, apoptosis and immunoresponses. PI-3 kinase activation generated PIP3 which functions as a second messenger to activate downstream tyrosine kinases Btk and Itk, the Ser/Thr kinases PDK1 and Akt (PKB). Akt activation is involved in survival, proliferation and cell growth. After activation PLCγ hydrolyses its substrate, PtdIns(4,5)P2, and forms two secondary messengers, diacylglycerol and Ins(1,4,5)P3 which stimulates intracellular processes such as proliferation, angiogenesis and cell motility. The PDGF-receptor plays an important role in the maintenance, growth and development of hematopoietic and non-hematopoietic cells.

PDGFR is expressed on early stem cells, mast cells, myeloid cells, mesenchymal cells and smooth muscle cells. Only PDGFR-β is implicated in myeloid leukemias-usually as a translocation partner with Tel, Huntingtin interacting protein (HIP1) or Rabaptin5. Activation mutations in PDGFR-α kinase domain are associated with gastrointestinal stromal tumors (GIST).

Certain compounds, pharmaceutical compositions and pharmaceutical combination provided herein are inhibitors of PDGFR receptor tyrosine kinases, thus such compounds, pharmaceutical compositions and pharmaceutical combination are useful for the treatment of diseases and/or disorders that respond to inhibition of PDGFR receptor tyrosine kinases. In certain embodiments, such compounds, pharmaceutical compositions and pharmaceutical combination are useful in the treatment of hematopoietic and non-hematopoietic cells cancer. In certain embodiments, such compounds, pharmaceutical compositions and pharmaceutical combination are useful in the treatment of diseases and/or disorders including, but are not limited to, myeloid leukemias, and gastrointestinal stromal tumors (GIST).

Vascular Endothelial Growth Factor (VEGF) Receptor Family

VEGF, also known as fms-related tyrosine kinase-1 (FLT1), is an important signaling protein involved in both vasculogenesis (formation of embryonic circulatory system) and angiogenesis (growth of blood vessels from pre-existing vasculature). Structurally VEGF belongs to the PDGF family of cytokine-knot growth factors. The VEGF sub-family of growth factors includes VEGF-A, VEGF-B, VEGF-C and VEGF-D. VEGF-A binds to receptor VEGFR-1 (Flt-1) and to VEGFR-2 (KDR/Flk-1). VEGF-C and VEGF-D bind to receptor VEGFR-3 and mediate lymphangiogenesis. The VGFR receptors mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Certain compounds, pharmaceutical compositions and pharmaceutical combination provided herein are inhibitors of VEGFR-2 (KDR) receptor tyrosine kinases, thus such compounds, pharmaceutical compositions and pharmaceutical combination are useful for the treatment of diseases and/or disorders that respond to inhibition of VEGFR-2 (KDR) receptor tyrosine kinases. In certain embodiments, such compounds, pharmaceutical compositions and pharmaceutical combination are useful in the treatment of cancer by inhibiting the development and/or progression of the cancer.

Fms-Like Tyrosine Kinase

The fms-like tyrosine kinase-3 (FLT3) ligand (FLT3L) is one of the cytokines that affects the development of multiple hematopoietic lineages. These effects occur through the binding of FLT3L to the FLT3 receptor, also referred to as fetal liver kinase-2 (flk-2) and STK-1, a receptor tyrosine kinase (RTK) expressed on hematopoietic stem and progenitor cells. FLT3 is a member of the type III receptor tyrosine kinase (RTK) family. The ligand for FLT3 is expressed by the marrow stromal cells and other cells and synergizes with other growth factors to stimulate proliferation of stem cells, progenitor cells, dendritic cells, and natural killer cells. Flt3 plays an important role in the maintenance, growth and development of hematopoietic and non-hematopoietic cells.

The FLT3 gene encodes a membrane-bound RTK that plays an important role in proliferation, differentiation and apoptosis of cells during normal hematopoiesis. The FLT3 gene is mainly expressed by early myeloid and lymphoid progenitor cells. Hematopoietic disorders are pre-malignant disorders and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma— for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma.

Aberrant expression of the Flt3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). Activating mutations of the Flt3 receptor have been found in about 35% of patients with acute myeloblastic leukemia (AML), and are associated with a poor prognosis. The most common mutation involves in-frame duplication within the juxtamembrane domain, with an additional 5-10% of patients having a point mutation at asparagine 835. Both of these mutations are associated with constitutive activation of the tyrosine kinase activity of Flt3, and result in proliferation and viability signals in the absence of ligand. Patients expressing the mutant form of the receptor have been shown to have a decreased chance for cure. Thus, there is accumulating evidence for a role for hyper-activated (mutated) Flt3 kinase activity in human leukemias and myelodysplastic syndrome.

FLT-3 and c-Kit regulate maintenance of stem cell/early progenitor pools as well the development of mature lymphoid and myeloid cells. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propagate the activation signal leading to growth, differentiation and survival. Some of the downstream regulators of FLT-3 and c-Kit receptor signaling include, PLCγ, PI3-kinase, Grb-2, SHIP and Src related kinases. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype.

Certain compounds, pharmaceutical compositions and pharmaceutical combination provided herein are inhibitors of FLT-3 receptor tyrosine kinases, thus such compounds, pharmaceutical compositions and pharmaceutical combination are useful for the treatment of diseases and/or disorders that respond to inhibition of FLT-3 receptor tyrosine kinases. In certain embodiments, such compounds, pharmaceutical compositions and pharmaceutical combination are useful in the treatment of hematopoietic disorders. Such hematopoietic disorders include, but are not limited to, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma— for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma.

Macrophage Colony-Stimulating Factor Receptor (c-FMS)

Macrophage colony stimulating factor (M-CSF) is a member of the family of proteins referred to as colony stimulating factors (CSFs). M-CSF is a secreted cytokine or a cell surface glycoprotein, comprised of two subunits that are joined by a disulfide bond with a total molecular mass varying from 40 to 90 kD. Similar to other CSFs, M-CSF is produced by macrophages, monocytes, and human joint tissue cells, such as chondrocytes and synovial fibroblasts, in response to proteins such as interleukin-1 or tumor necrosis factor-α. M-CSF stimulates the formation of macrophage colonies from pluripotent hematopoietic progenitor stem cells. Eukaryotic cells also produce M-CSF in order to combat intercellular viral infection.

M-CSF typically bind to its receptor, c-FMS, in order to exert a biological effect. c-FMS contains five extracellular Ig domains, one transmembrane domain, and an intracellular domain with two kinase domains. Upon M-CSF binding to c-FMS, the receptor homo-dimerizes and initiates a cascade of signal transduction pathways including the JAK/STAT, PI3K, and ERK pathways.

M-CSF is an important regulator of the function, activation, and survival of monocytes/macrophages. M-CSF is involved in various diseases, including rheumatoid arthritis (RA) and cancer. Macrophages comprise key effector cells in RA. The degree of synovial macrophage infiltration in RA has been shown to closely correlate with the extent of underlying joint destruction. M-CSF, endogenously produced in the rheumatoid joint by monocytes/macrophages, fibroblasts, and endothelial cells, acts on cells of the monocyte/macrophage lineage to promote their survival and differentiation into bone destroying osteoclasts, and enhance pro-inflammatory cellular functions such as cytotoxicity, superoxide production, phagocytosis, chemotaxis and secondary cytokine production. For example, treatment with M-CSF in the rat *streptococcus agalactiae* sonicate-induced experimental arthritis model lead to enhanced pathology Similarly, subcutaneous injections of M-CSF in a murine model of collagen-induced arthritis, which is a model for RA, results in a significant exacerbation of the RA disease symptoms. Furthermore, MRL/lpr mice that are highly susceptible to RA and other autoimmune diseases have elevated basal M-CSF serum concentrations.

M-CSF binding to c-FMS and its subsequent activation of monocyte/macrophages is important in a number of disease states. In addition to RA and cancer, the other examples of M-CSF-related disease states include osteoporosis, destructive arthritis, atherogenesis, glomerulonephritis, Kawasaki disease, and HIV-1 infection, in which monocytes/macrophages and related cell types play a role. For instance, osteoclasts are similar to macrophages and are regulated in part by M-CSF. Growth and differentiation signals induced by M-CSF in the initial stages of osteoclast maturation are essential for their subsequent osteoclastic activity in bone. M-CSF is uniquely essential for osteoclastogenesis.

M-CSF has a central role in atherogenesis, and in proliferative intimal hyperplasia after mechanical trauma to the arterial wall. All the major cell types in atherosclerotic lesions have been shown to express M-CSF, and this is further up-regulated by exposure to oxidized lipoprotein.

Kawasaki disease (KD) is an acute, febrile, pediatric vasculitis of unknown cause. Its most common and serious complications involve the coronary vasculature in the form of aneurismal dilatation. Serum M-CSF levels are significantly elevated in acute phase Kawasaki's disease, and normalize following treatment with intravenous immunoglobulin. Giant cell arthritis (GCA) is an inflammatory vasculopathy mainly occurring in the elderly in which T cells and macrophages infiltrate the walls of medium and large arteries leading to clinical consequences that include blindness and stroke secondary to arterial occlusion. The active involvement of macrophages in GCA is evidenced by the presence of elevated levels of macrophage derived inflammatory mediators within vascular lesions.

M-CSF has been reported to render human monocyte derived macrophages more susceptible to HIV-1 infection in vitro. In a recent study, M-CSF increased the frequency with which monocyte-derived macrophages became infected, the amount of HIV mRNA expressed per infected cell, and the level of proviral DNA expressed per infected culture.

Certain compounds, pharmaceutical compositions and pharmaceutical combination provided herein are inhibitors of c-FMS receptor tyrosine kinases, thus such compounds, pharmaceutical compositions and pharmaceutical combination are useful for the treatment of diseases and/or disorders that respond to inhibition of c-FMS receptor tyrosine kinases. In certain embodiments, such compounds, pharmaceutical compositions and pharmaceutical combination are useful in the treatment of autoimmune diseases, inflammatory diseases and cancer. In certain embodiments, such compounds, pharmaceutical compositions and pharmaceutical combination are useful in the treatment of diseases and/or disorders includind, but are not limited to, rheumatoid arthritis, ovarian cancer, uterine cancer, breast cancer, prostate cancer, lung cancer, colon cancer, stomach cancer, hairy cell leukemia, skeletal pain caused by tumor metastasis or osteoarthritis, visceral pain, inflammatory pain, neurogenic pain, osteoporosis, Paget's disease, osteoarthritis, prosthesis failure, osteolytic sarcoma, myeloma, tumor metastasis to bone, systemic lupus erythematosus, psoriasis, Sjogren's syndrome, multiple sclerosis, uveitis, atherosclerosis, fibrosis and proliferative vitreoretinopathy.

Insulin-Like Growth Factor 1 (IGF-1) Receptor

The Insulin-like Growth Factor 1 (IGF-1) Receptor is a transmembrane receptor that is activated by IGF-1 and by the related growth factor IGF-2. IGF-1R mediates the effects of IGF-1, which is a polypeptide protein hormone similar in molecular structure to insulin. IGF-1 plays an important role in survival and proliferation in mitosis-competent cells, and growth (hypertrophy) in tissues such as skeletal muscle and cardiac muscle. The IGFR signalling pathway is of critical importance during normal development of mammary gland tissue during pregnancy and lactation. During pregnancy, there is intense proliferation of epithelial cells which form the duct and gland tissue. Following weaning, the cells undergo apoptosis and all the tissue is destroyed. Several growth factors and hormones are involved in this overall process, and IGF-1R is believed to have roles in the differentiation of the cells and a key role in inhibiting apoptosis until weaning is complete.

The IGF-1R is implicated in several cancers including, but not limited to, breast cancer. In some instances its anti-apoptotic properties allow cancerous cells to resist the cytotoxic properties of chemotheraputic drugs or radiotherapy. It is further implicated in breast cancer by increasing the metastatic potential of the original tumour by inferring the ability to promote vascularisation.

c-Kit Receptor

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation.

c-Kit has a substantial homology to the PDGF receptor and to the CSF-1 receptor (c-Fms). Investigations on various erythroid and myeloid cell lines indicate an expression of the c-Kit gene in early stages of differentiation. Certain tumors such as glioblastoma cells likewise exhibit a pronounced expression of the c-Kit gene.

Anaplastic Lymphoma Kinase (Ki-1 or ALK)

Anaplastic lymphoma kinase (ALK) is a 200-kDa receptor tyrosine kinase (RTK) encoded by the ALK gene on chromosome 2p23. ALK was first identified as part of the NPM-ALK oncogenic fusion protein in which the N-terminal portion of the phosphoprotein nucleophosmin (NPM) linked to the cytoplasmic portion of ALK. This ocogenic fusion protein results from the (2;5)(p23;q35) translocation that is frequently associated with anaplastic large-cell lymphoma (ALCL). This translocation produces a fusion gene that encodes a soluble chimeric transforming protein comprising the NPM-ALK oncogenic fusion protein. The NPM portion is responsible for the dimerization of the fusion protein, leading to constitutive activation of the kinase and to oncogenicity. ALK is highly homologous to leukocyte tyrosine kinase and belongs to the insulin receptor superfamily of receptor tyrosine kinases. Full-length ALK has the typical structure of an RTK, with a large extracellular domain, a lipophilic transmembrane segment, and a cytoplasmic tyrosine kinase domain. The ALK fusion proteins maintain the intracytoplasmic tail of the ALK receptor at their C terminus. This region contains a catalytic domain, whereas the N-terminal region of all fusion proteins has dimerization domains. As a consequence of dimerization, ALK chimeras undergo autophosphorylation and become constitutively active.

The ALK gene encodes a tyrosine kinase receptor, whose physiologic expression in mammals is largely limited to specific regions of the central and the peripheral nervous system. The normal ALK gene is dominantly expressed in the neural system, and the ALK mRNA is essentially and transiently expressed in specific regions of the central and peripheral nervous systems, such as the thalamus, mid-brain, olfactory bulb, and peripheral ganglia, and it is mainly localized in neuronal cells. ALK plays an important role in the development of the brain and in the normal development and function of the nervous system by exerting its effects on specific neurons in the nervous system.

Expression of the ALK protein has also been detected in tumors derived from the nervous system, such as neuroblastomas. Pleiotrophin (PTN) and midkine, two heparin-binding growth factors with pleiotrophic activities involved in normal development and tumor growth, may serve as possible ligands for ALK in mammals, although it is still unclear whether these molecules are the physiological ligands of ALK.

Anaplastic lymphoma kinase (ALK) has been implicated in oncogenesis in hematopoietic and non-hematopoietic tumors. The aberrant expression of full-length ALK receptor proteins has been reported in a subset of nonlymphoid tumors, including sarcomas, neuroblastomas, and gliomas and glioblastomas, and ALK fusion proteins have occurred in anaplastic large cell lymphoma (ALCL). Anaplastic large cell lymphomas (ALCLs) represent a subset of non-Hodgkin lymphomas in which the anaplastic lymphoma kinase (ALK) gene is frequently fused to the nucleophosmin (NPM) gene, and is characterized by unique cell morphology and expression of CD30. ALK activity is required for the survival of ALCL cells in vitro and in vivo. ALK kinase activity is essential for an antiapoptotic effect, as kinase-dead NPM-ALK-expressing cells are not protected against doxorubicin-induced apoptosis. ALK is also involved in different variant chromosomal translocations, all leading to the expression of fusion proteins with a constitutively active kinase.

Phospholipase C-γ, PI3K, STATs, and Src are important downstream targets of NPM-ALK that contribute to its mitogenic and antiapoptotic activities. Activated ALK chimeras bind multiple adaptor proteins capable of firing different pathways regulating cell proliferation, survival, and transformation. The known adaptors include Grb2, Shc, IRS-1, phospholipase Cγ (PLC-γ) PI3K, and JAK3, which activate numerous downstream molecules, including cyclin D, ERK1/2, STAT, and AKT. The genetic ablation of STAT3 in ALK-positive cells leads to cell death and prevents the generation of B cell neoplasms. PLC-γ and AKT play an essential role in ALK-mediated transformation in vitro. Ras/ERK and PLC-γ pathways may contribute to the enhancement of cell growth and Stat3 and PI3K/AKT may play a major role in inhibiting apoptosis.

V-ros UR2 Sarcoma Virus Oncogene Homolog 1 (Avian), (ROS1 Gene)

The transmembrane tyrosine kinase Ros, encoded by the proto-oncogene c-ros, is an orphan tyrosine kinase receptor usually classified as a member of the subfamily of insulin receptors, and is expressed in specific epithelia. The temporal and tissue expression profile of c-Ros in chicken and rats suggests that it plays a role in epithelial cell differentiation during embryogenesis, particularly in the tubules of the kidney and testis. The c-ros oncogene is has been found to be constitutively active in glioblastomas.

The oncogenic potential of the Ros tyrosine kinase has also been demonstrated by ligand-dependent transformation of NIH3T3 fibroblasts, which were stably transfected with a chimeric receptor consisting of the TrkA/nerve growth factor (NGF) receptor extracellular domain and the Ros transmembrane and cytoplasmic domains. The physiological function of Ros has been characterized in mice with a targeted mutation of c-ros. Male $Ros^{-/-}$ mice exhibit defects in differentiation and regionalization of the epididymal epithelium and, because of this defect, are sterile.

Receptor Serine/Threonine Kinases (RTKs).

Activin-Like Kinase-4 (ALK-4) and Activin-Like Kinase-5 (ALK-5)

Transforming Growth Factor-β1 (TGF-β1) is the prototypic member of a family of cytokines including the Transforming Growth Factors-β (TGF-βs), activins, inhibins, bone morphogenetic proteins and Mullerian-inhibiting substance, that signal through a family of single transmembrane serine/threonine kinase receptors. These receptors can be divided into two classes, the type I or activin-like kinase receptors and type II receptors. The activin-like kinase receptors are distinguished from the type II receptors in that the activin-like kinase receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the activin-like kinase receptors and type II receptors. Specifically, the type II receptor phosphorylates the GS domain of the type I receptor for TGF-β, activin-like kinase-5 receptor (ALK5), in the presence of TGF-β. The ALK5, in turn, phosphorylates the cytoplasmic proteins smad2 and smad3 at two carboxy terminal serines. The phosphorylated smad proteins translocate into the nucleus and activate genes that contribute to the production of extracellular matrix.

Activins transduce signals in a manner similar to TGF-β. Activins bind to serine/threonine kinase, the activin type II receptor (ActRIIB), and the activated type II receptor hyperphosphorylates serine/threonine residues in the GS region of the activin-like kinase-4 receptor (ALK4). The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Further, TGF-β1 plays a role in the formation of fibronectin and plasminogen activator inhibitor-1, components of sclerotic deposits, through the action of smad3 phosphorylation by the TGF-β1 receptor ALK5.

Progressive fibrosis in the kidney and cardiovascular system is a major cause of suffering and death and an important contributor to the cost of health care. TGF-β1 has been implicated in many renal fibrotic disorders. TGF-β1 is elevated in acute and chronic glomerulonephritis, diabetic nephropathy, allograft rejection, HIV nephropathy and angiotensin-induced nephropathy. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing anti-bodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Thus, inhibition of TGF-β1 activity is indicated as a therapeutic intervention in chronic renal disease.

TGF-β1 and its receptors are increased in injured blood vessels and are indicated in neointima formation following balloon angioplasty. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β receptor ALK5 correlated with total cholesterol ($P<0.001$). Furthermore, SMC derived from human atherosclerotic lesions have an increased ALK5/TGF-β type II receptor ratio. Because TGF-β1 is over-expressed in fibroproliferative vascular lesions, receptor-I variant cells would be allowed to grow in a slow, but uncontrolled fashion, while overproducing extracellular matrix components. TGF-β1 is immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer. Several cellular signaling pathways are known to be altered upon chronic liver injury.

TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. Elevated TGFβ signaling is involved in all types of fibrotic diseases including liver fibrosis. TGFβ mediates it signal by binding to two ser/thr kinase receptors, TGFβRII and ALK5. Expressing a dominant negative TGFβRII showed beneficial effects in a rat model of dimethylnitrosamine induced liver fibrosis Inhibiting TGFβ expression using an antisense approach also reduced liver fibrosis induced by bile duct ligation. Thus, inhibiting TGFβ signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats. Moreover, TGF-β antibodies also improve healing of corneal wounds in rabbits, and accelerate wound healing of gastric ulcers in the rat. Thus, limiting the activity of TGF-β would be beneficial in many tissues and any disease with chronic elevation of TGF-β would benefit by inhibiting smad2 and smad3 signalling pathways. TGF-β is also implicated in peritoneal adhesions. Therefore, inhibitors of ALK5 would be beneficial in preventing peritoneal and sub-dermal fibrotic adhesions following surgical procedures. TGF-β is also implicated in photoaging of the skin.

TGF-β signalling is also implicated in the development of pulmonary disorders, in particular pulmonary hypertension and pulmonary fibrosis. TGF-β1 levels are increased in animal models of pulmonary hypertension. Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension. Apoptosis of pulmonary microvascular endothelial cells stimulates vascular smooth muscle cell growth. Therefore, inhibiting the action of TGF-β1 on ALK5 is indicated as a therapeutic intervention in pulmonary hypertension.

Additionally, dys-regulated TGF-β signalling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis and in animal models of idiopathic pulmonary fibrosis. Transient over-expression of active TGF-β1 in murine lungs, using adenoviral vector-mediated gene transfer, resulted in progressive pulmonary fibrosis in wild-type mice, whereas no fibrosis was seen in the lungs of Smad3 knockout mice up to 28 days following TGF-β1 challenge. Thus, inhibition of TGF-β1 activation of ALK5 is also indicated for pulmonary fibrosis.

Activin signalling and overexpression of activin is linked to pathological disorders that involve extracellular matrix accumulation and fibrosis, inflammatory responses, cachexia or wasting, diseases or pathological responses in the central nervous system and hypertension. Studies have shown that TGF-β and activin can act synergistically to induce extracellular matrix production. Activin signalling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodelling associated with interstitial pulmonary fibrosis and pulmonary hypertension. An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodelling observed in pulmonary fibrosis and hypertension. The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis.

Reduction in TGF-β signalling, through its effector Smad3, enhances the mechanical properties and mineral concentration of the bone matrix, as well as the bone mass, enabling the bone to better resist fracture. Thus, inhibition of TGF-β1 activation of ALK5 is also indicated for increasing mineral density strength and content of bone and may be utilized to treat a wide variety of bone disorders including, but not limited to, osteopenia, osteoporosis, fractures and other disorders in which low bone mineral density are a hallmark of the disease.

Osteoporosis is a systemic skeletal disorder characterized by low bone mass and micro-architectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture. Thus, in certain embodiments, compounds, pharmaceutical compositions and pharmaceutical combination provided herein are used in preventing or treating bone conditions which are associated with increased calcium depletion or resorption or in which stimulation of bone formation and calcium fixation in the bone is desirable.

Diseases or condition mediated by ALK-5 inhibition or ALK-4 inhibition include, but are not limited to, glomerulonephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include, but are not limited to, chronic renal disease, acute renal disease, wound healing, arthritis, osteoporosis, kidney disease, congestive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neuro-logical function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photagging of the skin.

Certain compounds, pharmaceutical compositions and pharmaceutical combination provided herein are inhibitors of ALK-4 receptors, thus such compounds, pharmaceutical compositions and pharmaceutical combination are useful for the treatment of the diseases and/or disorders presented herein that are mediated by with ALK-4 receptors. Certain compounds, pharmaceutical compositions and pharmaceutical combination provided herein are inhibitors of ALK-5 receptors, thus such compounds, pharmaceutical compositions and pharmaceutical combination are useful for the treatment of the diseases and/or disorders presented herein that are mediated by ALK-5 receptors. Certain compounds, pharmaceutical compositions and pharmaceutical combination provided herein are inhibitors of ALK-4 receptors and ALK-5 receptors, thus such compounds, pharmaceutical compositions and pharmaceutical combination are useful for the treatment of the diseases and/or disorders presented herein that are mediated by ALK-4 receptors and ALK-5 receptors.

In certain embodiments, the compounds, pharmaceutical compositions and pharmaceutical combination provided herein are used to treat and/or prevent inflammatory or obstructive airways diseases including, but not limited to, asthma (both intrinsic (non-allergic) asthma and extrinsic (allergic) asthma), adult/acute respiratory distress syndrome (ARDS), chronic obstructive pulmonary or airways disease (COPD or COAD), including chronic bronchitis, or dyspnea associated therewith, acute bronchitis, arachidic bronchitis, catarrhal bronchitis, croupus bronchitis, phthinoid bronchitis, emphysema, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, as well as exacerbation of airways hyperreactivity consequent to other drug therapy, in particular other inhaled drug therapy.

Prophylactic efficacy in the treatment of asthma is evidenced by reduced frequency or severity of symptomatic attack, e.g. of acute asthmatic or bronchoconstrictor attack, improvement in lung function or improved airways hyperreactivity. Further evidence is reduced requirement for other, symptomatic therapy, i.e. therapy for or intended to restrict or abort symptomatic attack when it occurs, for example antiinflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

In certain embodiments, the compounds, pharmaceutical compositions and pharmaceutical combination provided herein are used to treat and/or prevent pulmonary hypertension including, but not limited to, primary pulmonary hypertension (PPH); secondary pulmonary hypertension (SPH);

familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

In certain embodiments, the pulmonary hypertension treated with compounds, pharmaceutical compositions and pharmaceutical combination provided herein is pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease.

In certain embodiments, the compounds, pharmaceutical compositions and pharmaceutical combination provided herein are used to treat diseases or disorders mediated by ALK-5 inhibition or ALK-4 inhibition including, but not limited to, pulmonary hypertension, pulmonary fibrosis, liver fibrosis or osteoporosis. In certain embodiments, the compounds, pharmaceutical compositions and pharmaceutical combination provided herein are used to treat lung fibrosis including, but not limted to, idiopathic pulmonary fibrosis.

Myostatin, a member of the transforming growth factor β (TGFβ) family, is a key negative regulator of skeletal muscle mass. In double-muscle cattle and in a human body with skeletal muscle hypertrophy, different mutations in the myostatin gene were detected. The important role of myostatin for skeletal muscle growth and disorders was confirmed in a wide variety of in vivo and in vitro studies. For example, muscle-specific overexpression of myostatin in mice causes loss of muscle mass, whereas myostatin null mice have increased skeletal muscle mass and reduced body fat. In accordance systemic administration of myostatin induces cachexia, whereas inhibition of myostatin by, for example, the myostatin neutralizing antibody JA16 increases muscle mass and strength in wildtype and dystrophic mdx mice. In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment. These findings show the high potential of myostatin inhibitors as treatments for muscular atrophies and dystrophies.

Myostatin signals through Smad2/3, moreover, mature myostatin has been shown to act via activin type IIb and activin receptor like kinase receptors in adipocytes. Myostatin is believed to inhibit differentiation and cause atrophy via activin receptor like kinase receptor signaling. Moreover, inhibition of activin receptor like kinase receptor signaling promotes skMC differentiation and causes skMC hypertrophy.

The compounds, pharmaceutical compositions and pharmaceutical combination provided herein are also used to treat muscle diseases including muscular atrophies (e.g. disuse), muscular dystrophies (e.g. Duchenne's Muscle Dystrophy, Becker's Muscle Dystrophy, Limb-Girdle Muscle Dystrophy, Facioscapulohumeral Dystrophy), sarcopenia and cachexia.

Aurora Kinase Family

Aurora kinases are serine/threonine protein kinases that regulate many processes during cell division and are essential for cell proliferation. Aurora kinases play an essential role in the orchestration of chromosome separation and cytokinesis during mitosis. The correct ploidy of cells requires accurate mitotic chromosome separation. Aurora kinase controls chromatid segregation and helps the dividing cell share its genetic materials with its daughter cells. Defects in this segregation can cause genetic instability, a condition which is highly associated with tumorigenesis. Besides being implicated as mitotic regulators, these three members of the mammalian family have generated significant interest in the cancer research field due to their elevated expression profiles in many human cancers.

Three Aurora kinases have been identified in mammalian cells: Aurora Kinase A; Aurora Kinase B; and Aurora Kinase C (Aie1). The human Aurora kinases present a similar domain organization, with a N-terminal domain of 39 to 129 residues in length, a protein kinase domain and a short C-terminal domain containing 15 to 20 residues. All have a highly conserved kinase domain but differ in their N-terminal regions, which vary in length and share low sequence conservation, which determines selectivity during protein-protein interactions. The Aurora kinases have an ATP-binding site with an adjacent cleft which is not present in other kinases.

The Aurora A (also known as Aurora 2, AIK, BTAK and IAK1) family functions during prophase of mitosis and is required for correct function of the centrosomes (the microtubule organizing centres in eukaryotic cells). Aurora kinase A functions in centosome separation and localizes at the centrosomes, spindle poles and spindle microtubules, in prophase to telophase. Aurora kinase A protein levels and kinase activity are both increased in the late $G_2$-M phase. Aurora-A kinase is oncogenic and is frequently overexpressed/activated in many human cancer cell lines and tissues, including human ovarian and breast cancers.

Aurora B (also known as Aurora 1, AIK2, ARK2, and AIM-1) is cell-cycle regulated and plays a role in events that occur during anaphase and/or telophase. Aurora B functions in the attachment of the mitotic spindle to the centromere. Aurora kinase B is a chromosomal passenger protein localizing first to centromeres and then to the midzone of mitotic cells during telophase. Histone H3 phosphorylation is important for chromosome condensation and entry into mitosis. Phosphorylaation of histone H3 is controlled by Aurora A and Aurora B.

Aurora C (Mouse Aie1 and human AIE2, also known as STK-13, and AIK3 AURKC) exhibit a testis-specific expression pattern. Aurora-C kinase may, like Aurora-B kinase, function as a chromosomal passenger protein localizing first to centromeres and then to the midzone of mitotic cells. Aurora-C was first detected at clusters of chromocenters in diplotene spermatocytes and was concentrated at centromeres in metaphase I and II. Interestingly, Aurora-C was also found along the chromosome axes, including both the regions of centromeres and the chromosome arms in diakinesis. During the anaphase I/telophase I and anaphase II/telophase II transitions, Aurora-C was relocalized to the spindle midzone and midbody. The level of Aurora-C transcript is elevated in several human cancer cell types.

Non-Receptor Tyrosine Kinases.

Non-receptor tyrosine kinases represent a collection of cellular enzymes that lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis and immune responses.

The Src family of kinases is implicated in cancer, immune system dysfunction osteopetrosis, and bone remodeling diseases, and therefore Src kinases are considered as potential therapeutic targets for various human diseases. Src expression is linked to cancers such as colon, breast, hepatic and pancreatic cancer, certain B-cell leukemias and lymphomas. In addition, antisense Src expressed in ovarian and colon tumor cells inhibits tumor growth.

Csk, or C-terminal Src kinase, phosphorylates and thereby inhibits Src catalytic activity. Suppression of arthritic bone destruction has been achieved by the overexpression of Csk in rheumatoid synoviocytes and osteoclasts. This implies that Src inhibition may prevent joint destruction that is characteristic in patients suffering from rheumatoid arthritis. Src also plays a role in the replication of hepatitis B virus. The virally encoded transcription factor HBx activates Src in a step required for propagation of the virus.

Other Src family kinases are also potential therapeutic targets. Lck plays a role in T-cell signaling, and mice that lack the Lck gene have a poor ability to develop thymocytes. The function of Lck as a positive activator of T-cell signaling suggests that Lck inhibitors may be useful for treating autoimmune disease such as rheumatoid arthritis. Hck, Fgr and Lyn are important mediators of integrin signaling in myeloid leukocytes Inhibition of these kinase mediators may therefore be useful for treating inflammation.

Janus Kinase Family (JAK)

Janus kinase (JAK) is a family of intracellular non-receptor tyrosine kinases, ranging from 120-140 kDa in size that transduce cytokine-mediated signals via the JAK-STAT pathway. The JAK family includes four members: JAK1, JAK2, JAK3 and TYK2. Type I and type II cytokine receptor families possess no catalytic kinase activity, and therefore rely on the JAK family of tyrosine kinases to phosphorylate and activate downstream proteins involved in their signal transduction pathways.

The receptors exist as paired polypeptides thus exhibiting two intracellular signal-transducing domains. JAKs possess two near-identical phosphate-transferring domains, with one domain exhibiting the kinase activity while the other plays a role in downstream signaling. JAKs associate with a proline-rich region in each intracellular domain, which is adjacent to the cell membrane and called a box1/box2 region. After the receptor associates with its respective cytokine/ligand it goes through a conformational change, bringing the two JAKs close enough to phosphorylate each other. The JAK autophosphorylation induces a conformational change within itself enabling it to transduce the intracellular signal by further phosphorylating and activating transcription factors called STATs. The activated STATs dissociate from the receptor and form dimers before translocating to the cell nucleus where they regulate transcription of selected genes.

JAK1 is essential for signaling for certain type I and type II cytokines. It interacts with the common gamma chain (γc) of type I cytokine receptors, to elicit signals from the IL-2 receptor family (e.g. IL-2R, IL-7R, IL-9R and IL-15R), the IL-4 receptor family (e.g. IL-4R and IL-13R), the gp130 receptor family (e.g. IL-6R, IL-11R, LIF-R, OSM-R, cardiotrophin-1 receptor (CT-1R), ciliary neurotrophic factor receptor (CNTF-R), neurotrophin-1 receptor (NNT-1R) and Leptin-R). JAK1 is also important for transducing a signal by type I (IFN-α/β) and type II (IFN-γ) interferons, and members of the IL-10 family via type II cytokine receptors. JAK1 plays a critical role in initiating responses to multiple major cytokine receptor families.

JAK2 has been implicated in signaling by members of the type II cytokine receptor family (e.g. interferon receptors), the GM-CSF receptor family (IL-3R, IL-5R and GM-CSF-R), the gp130 receptor family (e.g IL-6R), and the single chain receptors (e.g. Epo-R, Tpo-R, GH-R, PRL-R). JAK2 signaling is activated downstream from the prolactin receptor. JAK2 gene fusions with the TEL(ETV6) (TEL-JAK2) and PCM1 genes have been found in leukemia patients. Further, mutations in JAK2 have been implicated in polycythemia vera, essential thrombocythemia, and other myeloproliferative disorders. This mutation, a change of valine to phenylalanine at the 617 position, appears to render hematopoietic cells more sensitive to growth factors such as erythropoietin and thrombopoietin.

JAK3 functions in signal transduction and interacts with members of the STAT (signal transduction and activators of transcription) family. JAK3 is predominantly expressed in immune cells and transduces a signal in response to its activation via tyrosine phosphorylation by interleukin receptors. Mutations that abrogate JAK3 function cause an autosomal SCID (severe combined immunodeficiency disease). JAK3 expression is restricted mostly to hematopoietic cells. It is most commonly expressed in T cells and NK cells, but has been induced in other leukocytes, including monocytes. JAK3 is involved in signal transduction by receptors that employ the common gamma chain (γC) of the type I cytokine receptor family (e.g. IL-2R, IL-4R, IL-7R, IL-9R, IL-15R, and IL-21R) [2]. Mutations of JAK3 result in severe combined immunodeficiency (SCID).

Tyrosine kinase 2 (TYK2) is implicated in IFN-α, IL-6, IL-10 and IL-12 signaling.

Leukocyte-Specific Protein Tyrosine Kinase (Lck)

Lck (or leukocyte-specific protein tyrosine kinase) is a protein located in lymphocytes. Lck is a member of the Src family of tyrosine kinases and it phosphorylates tyrosine residues of certain proteins involved in the intracellular signaling pathways of lymphocytes.

Lck is most commonly found in T cells. It associates with the cytoplasmic tails of the CD4 and CD8 co-receptors on T helper cells and cytotoxic T cells, respectively, to assist signaling from the T cell receptor (TCR) complex. When the T cell receptor is engaged by the specific antigen presented by MHC, Lck acts to phosphorylate the intracellular chains of the CD3 and ζ-chains of the TCR complex, allowing another cytoplasmic tyrosine kinase called ZAP-70 to bind to them. Lck then phosphorylates and activates ZAP-70, which in turn phosphorylates another molecule in the signaling cascade called LAT (short for Linker of Activated T cells), a transmembrane protein that serves as a docking site for a number of other proteins, the most important of which are Shc-Grb2-SOS, PI3K, and phospholipase C (PLC).

The tyrosine phosphorylation cascade initiated by Lck culminates in the intracellular mobilization of a calcium (Ca2+) ions and activation of important signaling cascades within the lymphocyte. These include the Ras-MEK-ERK pathway, which goes on to activate certain transcription factors such as NFAT, NFκB, and AP-1. These transcription factors regulate the production of a large number of gene products, most notable, cytokines such as Interleukin-2 that promote long-term proliferation and differentiation of the activated lymphocytes.

Lck tyrosine phosphorylates a number of proteins, the most important of which are the CD3 receptor, ZAP-70, SLP-76, the IL-2 receptor, Protein kinase C, ITK, PLC, SHC, Ras-GAP, Cbl, Vav1, and PI3K.

Lipid Kinases.

PI3-Kinase(PIKK)

The phosphatidylinositol-3'-OH kinase (PI3K) pathway is one of the central signaling pathways that exerts its effect on numerous cellular functions including cell cycle progression, proliferation, motility, metabolism and survival. An activation of receptor tyrosine kinases causes PI3K to phosphorylate phosphatidylinositol-(4,5)-diphosphate, resulting in membrane-bound phosphatidylinositol-(3,4,5)-triphosphate. The latter promotes the transfer of a variety of protein kinases from the cytoplasm to the plasma membrane by binding of phosphatidylinositol-(3,4,5)-triphosphate to the pleckstrin-homology (PH) domain of the kinase. Kinases that are key downstream targets of PI3K include phosphoinositide-dependent kinase 1 (PDK1) and AKT (also known as Protein Kinase B). Phosphorylation of such kinases then allows for the activation or deactivation of numerous other pathways, involving mediators such as GSK3, mTOR, PRAS40, FKHD, NF-κB, BAD, Caspase-9, and the like. An important negative feedback mechanism for the PI3K pathway is PTEN, a phosphatase that catalyses the dephosphorylation of phosphatidylinositol-(3,4,5)-triphosphate to phosphorylate phosphatidylinositol-(4,5)-diphosphate. In more than 60% of all solid tumors, PTEN is mutated into an inactive form, permitting a constitutive activation of the PI3K pathway. As most cancers are solid tumors, such an observation provides evidence that a targeting of PI3k itself or individual downstream kinases in the PI3K pathway provide a promising approach to mitigate or even abolish the dysregulation in many cancers and thus restore normal cell function and behaviour. This, however, does not exclude that other mechanisms may be responsible for the beneficial effects of PI3K activity modifying agents such as those compounds provided herein.

In certain embodiments, the compounds and pharmaceutically acceptable salts and solvates thereof, provided herein and inhibit the activity of the lipid kinases, such as the PI3-kinase and/or members of the PI3-kinase-related protein kinase family (also called PIKK and include DNA-PK, ATM, ATR, hSMG-1 and mTOR), such as the DNA protein-kinase. Such compounds and pharmaceutically acceptable salts and solvates thereof, are useful in the treatment of conditions which are mediated by the activation (including normal activity or especially overactivity) of one or more of the members of the PI3 kinase family, especially PI3 kinase enzyme, such as proliferative, inflammatory or allergic conditions, obstructive airways diseases and/or disorders commonly occurring in connection with transplantation.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Routes of Administration and Pharmaceutical Compositions

For the therapeutic uses of compounds of Formula (I), or pharmaceutically acceptable salts, solvates, N-oxides, prodrugs and isomers thereof, described herein, such compounds are administered in therapeutically effective amounts either alone or as part of a pharmaceutical composition. Accordingly, provided herein are pharmaceutical compositions, which comprise at least one compound of Formulas (I) described herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The routes of administration of compounds of Formula (I) and pharmaceutical compositions include, but are not limited to, oral administration, intravitreal administration, rectal administration, parenteral, intravenous administration, intraperitoneal administration, intramuscular administration, inhalation, transmucosal administration, pulmonary administration, intestinal administration, subcutaneous administration, intramedullary administration, intrathecal administration, direct intraventricular, intranasal administration, topical administration, ophthalmic administration or otic administration.

In certain embodiments, compounds of Formula (I) or pharmaceutical compositions described herein are administered locally, while in other embodiments compounds of Formula (I) or pharmaceutical composite described herein are administered systemically. Local administration includes, but is not limited to, injection into an organ, optionally in a depot or sustained release formulation. Systemic administration includes, but is not limited to, oral administration or intravenous administration. In other embodiments, compounds of Formula (I) or pharmaceutical compositions described herein are administered in a targeted drug delivery system, such as, by way of example only, in a liposome coated with organ-specific antibody. The liposome is targeted to and taken up selectively by the organ. In other embodiments, compounds of Formula (I) or pharmaceutical compositions described herein are administered in the form of a rapid release formulation, while in other embodiments, compounds of Formula (I) or pharmaceutical compositions described herein are administered in the form of an extended release formulation. In other embodiments, compounds of Formula (I) or pharmaceutical compositions described herein are administered in the form of an intermediate release formulation.

The therapeutically effective amount will vary depending on, among others, the disease indicated, the severity of the disease, the age and relative health of the subject, the potency of the compound administered, the route of administration and the treatment desired. In certain embodiments, satisfactory results are indicated to be obtained at daily dosages daily dosage of a compound of Formula (I) from about 0.03 to 2.5 mg/kg per body weight. In certain embodiments, the daily dosage of a compound of Formula (I), administered orally, is in the range from 0.05 micrograms per kilogram body weight (μg/kg) to 100 micrograms per kilogram body weight (μg/kg). In certain embodiments, the daily dosage of a compound of Formula (I), administered topically, is in the range from 0.05 micrograms per kilogram body weight (μg/kg) to 100 micrograms per kilogram body weight (μg/kg). In other embodiments, the daily dosage of a compound of Formula (I), administered parenterally, is in the range from 0.05 micrograms per kilogram body weight (μg/kg) to 100 milligrams per kilogram body weight (mg/kg). In certain embodiments, the daily dosage of a compound of Formula (I), administered intrermuscularlly, is in the range from 0.05 micrograms per kilogram body weight (µg/kg) to 100 micrograms per kilogram body weight (µg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

Other aspects provided herein are processes for the preparation of pharmaceutical composition which comprise at least one compound of Formula (I) described herein. In certain embodiments, such processes include admixing a compound of Formula (I) described herein with one or more pharmaceutically acceptable carriers, diluents or excipients. In certain embodiments, the pharmaceutical compositions comprise a compound of Formula (I) in free form or in a pharmaceutically acceptable salt or solvate form. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, dissolving, granulating dragee-making, levigating, emulsifying, encapsulating, entrapping or compression processes and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, pills, dragees, granules, liquids, gels, syrups, flavored syrups, elixirs, slurries, solutions or suspensions in aqueous or non-aqueous liquids, edible foams or whips, and oil-in-water liquid emulsions or water-in-oil liquid emulsions. The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compound of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, physiological saline buffer, Ringer's Injection solution, Dextrose Injection, Dextrose and Sodium Chloride Injection, and Lactated Ringer's Injection solution; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments, a compound of Formula (I) or composition containing one or more compounds of Formula (I) is parenteral administration by bolus injection. In other embodiments, a compound of Formula (I) or composition containing one or more compounds of Formula (I) is parenteral administration by continuous infusion. Formulations for injection are presented in unit dosage form, by way of example only, in ampoules or formulations for injection are presented in multi-dose containers, with an added preservative. The compositions may take such forms as suspensions, solutions or emulsions in oily or aqueous vehicles, and may contain formulatory agents such as suspending, stabilizing and/or dispersing agents.

Transdermal Administration

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used. In certain embodiments transdermal administration is used to provide continuous, while in other embodiments transdermal administration is used to provide discontinuous infusion of a compound of Formula (I) in controlled amounts.

In certain embodiments, the rate of absorption is slowed by using rate-controlling membranes or by trapping the compound within a polymer matrix or gel. In certain embodiments, transdermal delivery is via a transdermal patch.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compound of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compound of Formula (I) are used to further adjust the properties of the resulting composition.

In other embodiments, transdermal delivery of the compound of Formula (I) is accomplished by means of iontophoretic patches and the like Topical Dosage Forms In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Pulmonary Administration

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compound of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compound of Formula (I) are delivered to the lung using a liquid spray device, wherein such devices use extremely small nozzle holes to aerosolize liquid drug formulations that can then be directly inhaled into the lung. In other embodiments, compound of Formula (I) are delivered to the lung using a nebulizer device, wherein a nebulizers creates an aerosols of liquid drug formulations by using ultrasonic energy to form fine particles that can be readily inhaled. In other embodiments, compound of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

Rectal Administration

In certain embodiments pharmaceutical compositions containing at least one compound of Formula (I) are administered rectally in the form of suppositories, enemas, retention enemas ointment, creams rectal foams or rectal gels. In certain embodiments such suppositories are prepared from fatty emulsions or suspensions, cocoa butter or other glycerides.

Depot Administration

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In certain embodiments injectable depot forms are made by forming microencapsulated matrices of the compound of Formula (I) in biodegradable polymers. The rate of compound of Formula (I) release is controlled by varying the ratio of compound of Formula (I) to polymer and the nature of the particular polymer employed. In other embodiments, depot injectable formulations are prepared by entrapping the compound of Formula (I) in liposomes or microemulsions.

Ophthalmic Administration

In certain embodiments, a compound of Formula (I) or pharmaceutical composition described herein are ophthalmically administered to the eye. Administration to the eye generally results in direct contact of the agents with the cornea, through which at least a portion of the administered agents pass. In certain embodiments, such compounds of Formula (I) or pharmaceutical compositions have an effective residence time in the eye of about 2 to about 24 hours. In certain embodiments, such compounds of Formula (I) or pharmaceutical compositions have an effective residence time in the eye of about 4 to about 24 hours. In certain embodiments, such compounds of Formula (I) or pharmaceutical compositions have an effective residence time in the eye of about 6 to about 24 hours.

Ophthalmic administration, as used herein, includes, but is not limited to, topical administration, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the formix). In certain embodiments, the compounds of Formula (I) or pharmaceutical composition described herein are formulated as an ophthalmic composition and are administered topically to the eye. Such topically administered ophthalmic compositions include, but are not limited to, solutions, suspensions, gels or ointments.

In certain embodiments the pharmaceutical compositions, comprising at least one compound of Formula (I) described herein, used for ophthalmic administration take the form of a liquid where the compositions are present in solution, in suspension or both. In some embodiments, a liquid composition includes a gel formulation. In other embodiments, the liquid composition is aqueous. In other embodiments, such liquid compositions take the form of an ointment. In certain embodiments pharmaceutical compositions containing at least one compound of Formula (I) are administered ophthamically as eye drops formulated as aqueous solutions that optionally contain solubilizers, stabilizers, tonicity enhancing agents, buffers and preservatives. A desired dosage is administered via a known number of drops into the eye. By way of example only, for a drop volume of 25 µl, administration of 1-6 drops delivers 25-150 µl of the composition. In certain embodiments, the aqueous compositions contain from about 0.01% to about 50% weight/volume of a compound of Formula (I). In other embodiments, the aqueous compositions contain from about 0.1% to about 20% weight/volume of a compound of Formula (I). In still other embodiments, the aqueous compositions contain from about 0.2% to about 10% weight/volume of a compound of Formula (I). In certain embodiments, the aqueous compositions contain from about 0.5% to about 5%, weight/volume of a compound of Formula (I).

In certain embodiments the aqueous compositions have an ophthalmically acceptable pH and osmolality. In certain embodiments the aqueous compositions include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

In certain embodiments the compositions also include also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments the aqueous compositions also contain one or more polymers as suspending agents. Such polymers include, but are not limited to, water-soluble polymers such as cellulosic polymers described herein, (for example only, hydroxypropyl methylcellulose), and water-insoluble polymers described herein (for example only, cross-linked carboxyl-containing polymers). In certain embodiments, the aqueous compositions also include an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In certain embodiments the compositions also include ophthalmically acceptable solubilizing agents to aid in the solubility of a compound of Formula (I). The term "solubilizing agent" generally includes agents that result in formation of a micellar solution or a true solution of the agent. In certain embodiments, ophthalmically acceptable nonionic surfactants including, but not limited to, polysorbate 80 are used as solubilizing agents. In other embodiments, ophthalmically acceptable glycols including, but not limited to, polyglycols, polyethylene glycol 400, and glycol ethers are used as solubilizing agents.

In certain embodiments the compositions also include one or more ophthalmically acceptable surfactants to enhance physical stability or for other purposes. Such nonionic surfactants include, but are not limited to, polyoxyethylene fatty acid glycerides and vegetable oils (by way of example only, polyoxyethylene (60) hydrogenated castor oil) and polyoxyethylene alkylethers and alkylphenyl ethers (by way of example only, octoxynol 10 and octoxynol 40).

In certain embodiments the compositions also include one or more ophthalmically acceptable preservatives to inhibit microbial activity. Such preservatives include, but are not limited to mercury-containing substances such as merfen and thiomersal; stabilized chlorine dioxide; and quaternary ammonium compounds such as benzalkonium chloride, cetyltrimethylammonium bromide and cetylpyridinium chloride.

In certain embodiments the compositions also include one or more antioxidants to enhance chemical stability where required. Such antioxidants include, but are not limited to, ascorbic acid and sodium metabisulfite.

In certain embodiments, the aqueous compositions provided herein are packaged in single-dose non-reclosable containers, while in other embodiments the aqueous compositions provided herein are packaged in multiple-dose reclosable containers wherein a preservative is included in the composition.

Otic Administration

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

Combination Therapies

In certain embodiments, a compound of Formula (I) provided herein, or a pharmaceutically acceptable salt or solvate thereof, or a pharmaceutical composition containing at least one compound of Formula (I), is administered alone (without an additional therapeutic agent) for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In certain embodiments, a compound of Formula (I) provided herein, or a pharmaceutically acceptable salt or solvate thereof, or a pharmaceutical composition containing at least one compound of Formula (I), is administered alone (without an additional therapeutic agent) for the treatment of one or more of the disease and/or disorders associated with TrkA, TrkB, TrkC, IGF-1R, and/or ALK protein kinase activity described herein.

In other embodiments, a compound of Formula (I) provided herein, or a pharmaceutically acceptable salt or solvate thereof, or a pharmaceutical composition containing at least one compound of Formula (I) provided herein, is administered in combination with one or more additional therapeutic agents, for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In other embodiments, a compound of Formula (I) provided herein, or a pharmaceutically acceptable salt or solvate thereof, or a pharmaceutical composition containing at least one compound of Formula (I) provided herein, is administered in combination with one or more additional therapeutic agents, for the treatment of one or more of the disease and/or disorders associated with TrkA, TrkB, TrkC, IGF-1R and/or ALK protein kinase activity described herein.

In other embodiments, a compound of Formula (I) provided herein, or a pharmaceutically acceptable salt or solvate thereof, or a pharmaceutical composition containing at least one compound of Formula (I) provided herein, is formulated in combination with one or more additional therapeutic agents and administered for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In other embodiments, a compound of Formula (I) provided herein, or a pharmaceutically acceptable salt or solvate thereof, or a pharmaceutical composition containing at least one compound of Formula (I) provided herein, is formulated in combination with one or more additional therapeutic agents and administered for the treatment of one or more of the disease and/or disorders associated with TrkA, TrkB, TrkC, IGF-1R and/or ALK protein kinase activity described herein.

In another embodiment, a compound of Formula (I) provided herein, or a pharmaceutically acceptable salt or solvate thereof, or a pharmaceutical composition containing at least one compound of Formula (I) provided herein, is administered sequentially with one or more additional therapeutic agents, for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In another embodiment, a compound of Formula (I) provided herein, or a pharmaceutically acceptable salt or solvate thereof, or a pharmaceutical composition containing at least one compound of Formula (I) provided herein, is administered sequentially with one or more additional therapeutic agents, for the treatment of one or more of the disease and/or disorders associated with TrkA, TrkB, TrkC, IGF-1R and/or ALK protein kinase activity described herein.

In other embodiments, the combination treatments provided herein include administration of a compound of Formula (I) provided herein, or a pharmaceutically acceptable salt or solvate thereof, or a pharmaceutical composition containing a compound of Formula (I) prior to administration of one or more additional therapeutic agents, for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In other embodiments, the combination treatments provided herein include administration of a compound of Formula (I) provided herein, or a pharmaceutically acceptable salt or solvate thereof, or a pharmaceutical composition containing a compound of Formula (I) prior to administration of one or more additional therapeutic agents, for the treatment of one or more of the disease and/or disorders associated with TrkA, TrkB, TrkC, IGF-1R and/or ALK protein kinase activity described herein.

In other embodiments, the combination treatments provided herein include administration of a compound of Formula (I) provided herein, or a pharmaceutically acceptable salt or solvate thereof, or a pharmaceutical composition containing a compound of Formula (I), subsequent to administration of one or more additional therapeutic agents, for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In other embodiments, the combination treatments provided herein include administration of a compound of Formula (I) provided herein, or a pharmaceutically acceptable salt or solvate thereof, or a pharmaceutical composition containing a compound of Formula (I), subsequent to administration of one or more additional therapeutic agents, for the treatment of one or more of the disease and/or disorders associated with TrkA, TrkB, TrkC, IGF-1R and/or ALK protein kinase activity described herein.

In other embodiments, the combination treatments provided herein include administration of a compound of Formula (I) provided herein, or a pharmaceutically acceptable salt or solvate thereof, or a pharmaceutical composition containing a compound of Formula (I), concurrently with administration of one or more additional therapeutic agents, for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In other embodiments, the combination treatments provided herein include administration of a compound of Formula (I) provided herein, or a pharmaceutically acceptable salt or solvate thereof, or a pharmaceutical composition containing a compound of Formula (I), concurrently with administration of one or more additional therapeutic agents, for the treatment of one or more of the disease and/or disorders associated with TrkA, TrkB, TrkC, IGF-1R and/or ALK protein kinase activity described herein.

In certain embodiments, the combination treatments provided herein include administration of a compound of Formula (I) provided herein, or a pharmaceutically acceptable salt or solvate thereof, or a pharmaceutical composition containing a compound of Formula (I)-(XIX) formulated with one or more additional therapeutic agents, for the treatment of one or more of the disease and/or disorders associated with Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity described herein.

In certain embodiments, the combination treatments provided herein include administration of a compound of Formula (I) provided herein, or a pharmaceutically acceptable salt or solvate thereof, or a pharmaceutical composition containing a compound of Formula (I)-(XIX) formulated with one or more additional therapeutic agents, for the treatment of one or more of the disease and/or disorders associated with TrkA, TrkB, TrkC, IGF-1R and/or ALK protein kinase activity described herein.

In certain embodiments of the combination treatments described herein the compounds of Formula (I), or a pharmaceutically acceptable salts or solvates thereof, are modulators of Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinase activity. In certain embodiments of the combination treatments described herein the compounds of Formula (I), or a pharmaceutically acceptable salts or solvates thereof, are inhibitors of TrkA, TrkB, TrkC, IGF-1R and/or ALK protein kinase activity.

In certain embodiments of the combination therapies described herein, the compounds of Formula (I) provided herein, or a pharmaceutically acceptable salts or solvates thereof, and the additional therapeutics agent(s) act additively. In certain embodiments of the combination therapies described herein, the compounds of Formula (I) provided herein, or a pharmaceutically acceptable salts or solvates thereof, and the additional therapeutics agent(s) act synergistically.

In other embodiments, a compound of Formula (I) provided herein, or a pharmaceutically acceptable salts or solvates thereof, or a pharmaceutical composition containing a compound of Formula (I), is administered to a patient who has not previously undergone or is not currently undergoing treatment with another therapeutic agent.

The additional therapeutic agents used in combination with at least one compound of Formula (I) provided herein, or a pharmaceutically acceptable salt or solvate thereof, include, but are not limited to chemotherapeutic agents, anti-inflammatory agents, bronchodilatory agents, antihistamine agents, decongestant agents, anti-tussive agents, immunomodulatory agents antiproliferative agents, cytostatic agents, cytotoxic agents,
inhibitors of polyamine biosynthesis, inhibitors of a protein kinase, inhibitors of a serine/threonine protein kinase, inhibitors of protein kinase C, inhibitors of a tyrosine protein kinase, inhibitors of EGF receptor tyrosine kinase, (e.g. Iressa®),
inhibitors of VEGF receptor tyrosine kinase, (e.g. PTK787 or Avastin®), inhibitors of PDGF receptor tyrosine kinase, (e.g. STI571 (Glivec®)), a cytokine, a negative growth regulator, such as TGF-β or IFN-β, an aromatase inhibitor (e.g. letrozole (Femara®) or anastrozole), an inhibitor of the interaction of an SH2 domain with a phosphorylated protein, antiestrogens, bisphosphonates (e.g. AREDIA® or ZOMETA®) and monoclonal antibodies (e.g. against HER2, such as trastuzumab).

The anti-inflammatory agents used in combination with at least one compound of Formula (I) described herein, or a pharmaceutically acceptable salt or solvate thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone diproprionate, amcinonide, beclomethasone dipropionate, betametasone, betamethasone benzoate, betamethasone diproprionate, betamethasone sodium phosphate, betamethasone valerate, budesonide, ciclesonide, clobetasol proprionate, clocortolone pivalate, hydrocortisone, hydrocortisone derivatives, desonide, desoximatasone, dexamethasone, flunisolide, flucoxinolide, flurandrenolide, fluticasone propionate, glucocorticosteroids, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

Other anti-inflammatory agents used in combination with at least one compound of Formula (I) described herein, or a pharmaceutically acceptable salt or solvate thereof, include, but are not limited to, steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BILL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being Viozan®—AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544; A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

The bronchodilatory agents used in combination with at least one compound of Formula (I) described herein, or a pharmaceutically acceptable salt or solvate thereof, include, but are not limited to, beta-2 adrenoceptor agonists, anticholinergic agents, antimuscarinic agents, ipratropium bromide, oxitropium bromide, tiotropium salts, glycopyrrolate, CHF 4226 (Chiesi), SVT-40776, albuterol (salbutamol), metaproterenol, terbutaline, salmeterol, fenoterol, procaterol, formoterol, carmoterol, and GSK159797 and pharmaceutically acceptable salts thereof.

Other bronchodilatory agents used in combination with at least one compound of Formula (I) described herein, or a pharmaceutically acceptable salt or solvate thereof, include, but are not limited to, compounds (in free or salt or solvate form) of formula I of WO 0075114, preferably compounds of the Examples thereof, compounds (in free or salt or solvate form) of formula I of WO 04/16601 or of formula I of WO 04/087142, compounds, such as those described in EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897, WO 06/8173, EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Dual anti-inflammatory and bronchodilatory agents used in combination with at least one compound of Formula (I)

described herein, or a pharmaceutically acceptable salt or solvate thereof, include, but are not limited to, dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

The antihistamine drug substances agents used in combination with at least one compound of Formula (I) described herein, or a pharmaceutically acceptable salt or solvate thereof, include, but are not limited to, cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

The immunomodulatory agents used in combination with at least one compound of Formula (I) described herein, or a pharmaceutically acceptable salt or solvate thereof, include, but are not limited to, azathioprine, tacrolimus, cyclosporin, antimalarials, methothrexate, leflunomide, corticosteroids, cyclophosphamide, cyclosporin A, cyclosporin G, mycophenolate mofetil, ascomycin, rapamycin (sirolimus), FK-506, mizoribine, 15-deoxyspergualin, brequinar, mycophenolic acid, malononitriloamindes (such as, by way of example only, leflunamide), CTLA41g, T cell receptor modulators, and cytokine receptor modulators, peptide mimetics, and antibodies (such as, by way of example only, human, humanized, chimeric, monoclonal, polyclonal, Fvs, ScFvs, Fab or F(ab)2 fragments or epitope binding fragments), nucleic acid molecules (such as, by way of example only, antisense nucleic acid molecules and triple helices), small molecules, organic compounds, and inorganic compounds. Examples of monoclonal antibodies include, but are not limited to, monoclonal antibodies for leukocyte receptors such as, by way of example only MHC, CD2, CD3, CD4, CD7, CD25, CD28, B7, CD45, CD58 or their ligands. Examples of T cell receptor modulators include, but are not limited to, anti-T cell receptor antibodies (such as, by way of example only, anti-CD4 antibodies (such as, by way of example only, cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (such as, by way of example only, an anti-CD5 ricin-linked immunoconjugate), anti-CD7 antibodies (such as, by way of example only, CHH-380 (Novartis)), anti-CD8 antibodies, anti-CD40 ligand monoclonal antibodies (such as, by way of example only, IDEC-131 (IDEC)), anti-CD52 antibodies (such as, by way of example only, CAMPATH 1H (Ilex)), anti-CD2 antibodies, anti-CD11a antibodies (such as, by way of example only, Xanelim (Genentech)), anti-B7 antibodies (such as, by way of example only, IDEC-114 (IDEC)), CTLA4-immunoglobulin, toll-like receptor (TLR) modulators. Examples of cytokine receptor modulators include, but are not limited to, soluble cytokine receptors (such as, by way of example only, the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (such as, by way of example only, interleukin (IL)-2, IL-3, IL-4, IL-5, IL-6, IL-7, IL-8, IL-9, IL-10, IL-11, IL-12, IL-15, TNF-.alpha., interferon (IFN)-α, IFN-β, IFN-γ, and GM-CSF), anti-cytokine receptor antibodies (such as, by way of example only, anti-IFN receptor antibodies, anti-IL-2 receptor antibodies (such as, by way of example only, Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (such as, by way of example only, anti-IFN antibodies, anti-TNF-α antibodies, anti-IL-1β antibodies, anti-IL-6 antibodies, anti-IL-8 antibodies (such as, by way of example only, ABX-IL-8 (Abgenix)), and anti-IL-12 antibodies).

In certain embodiments, the additional thereapeutic agent(s) used in the combination therapies described herein include, but are not limited to, agents such as tumour necrosis factor alpha (TNF-α) inhibitors (such as anti-TNF monoclonal antibodies (by way of example only, Remicade, CDP-870 and adalimumab) and TNF receptor immunoglobulin molecules (by way of example only, Enbrel, Remicade, and Humira)); non-selective cyclo-oxygenase COX-1/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocortico steroids; methotrexate, lefunomide; hydroxychloroquine, d-penicillamine, auranofin or other parenteral or oral gold preparations.

Chemotherapeutic agents or other anti-proliferative agents used in combination with the compounds provided herein to treat proliferative diseases and cancer include, but are not limited to, surgery, radiotherapy (γ-radiation, neutron beam radiotherapy, electron beam radiotherapy, proton therapy, brachytherapy, and systemic radioactive isotopes), endocrine therapy, biologic response modifiers (interferons, interleukins, and tumor necrosis factor (TNF)), hyperthermia and cryotherapy, agents to attenuate any adverse effects (e.g., antiemetics), and other chemotherapeutic drugs, including, but not limited to, anthracyclines, alkyl sulfonates, aziridines, ethylenimines, methylmelamines, nitrogen mustards, nitrosoureas, folic acid analogs, dihydrofolate reductase inhibitor, purine analogs, pyrimidine analogs, podophyllotoxins, platinum-containing agents, interferons, interleukins, alkylating agents (mechlorethamine, chlorambucil, Cyclophosphamide, Melphalan, Ifosfamide), antimetabolites (Methotrexate, gemcitabine or capecitabine), purine antagonists and pyrimidine antagonists (6-Mercaptopurine, 5-Fluorouracil, Cytarabile, Gemcitabine), spindle poisons/microtubule active agents (Vinblastine, Vincristine, Vinorelbine, Paclitaxel, epothilone), topoisomerase I inhibitors, topoisomerase II inhibitors, podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), GLEEVEC™ adriamycin, dexamethasone, cyclophosphamide, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, methotrexate, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, diaziquone or combinations thereof.

Other agents used in combination with the compounds provided herein include, but are not limited to: treatments for Alzheimer's Disease such as ARRICEPT™ and EXCELON™; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., AVONEX™ and REBIF™), COPAXONE™, and mitoxantrone; treatments for asthma such as albuterol and SINGULAIR™; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In other embodiments the compounds of Formula (I) provided herein are used adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31)NH2 or PTS 893.

Treatment of Diseases Mediated by Kinase Activity

Compounds of Formula (I), pharmaceutically acceptable salts, solvates, N-oxides, prodrugs and isomers thereof, pharmaceutical compositions, and combination therapies provided herein are modulators of Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK kinase activity, and are used in the treatment and/or prevention of diseases and/or disorders in which aberrant, abnormal or deregulated activity of Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK contributes to the pathology and/or symptomology of such diseases and/or disorders. Such diseases and/or disorders mediated by Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinases are provided herein.

In certain embodiments, compounds of Formula (I), pharmaceutically acceptable salts, solvates, N-oxides, prodrugs and isomers thereof, pharmaceutical compositions, and combination therapies provided herein are inhibitors of Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK kinase activity, and are used in the treatment and/or prevention of diseases and/or disorders in which aberrant, abnormal or deregulated activity of Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK contributes to the pathology and/or symptomology of such diseases and/or disorders. Such diseases and/or disorders mediated by Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinases are provided herein.

In certain embodiments, such diseases and/or disorders associated with aberrant, abnormal or deregulated activity of Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinases include, but are not limited to, cancer, proliferative diseases, pain, dermatological diseases and/or disorders, metabolic diseases and/or disorders, muscle diseases and/or disorders, neurodegenerative diseases and/or disorders, neurological diseases and/or disorders, immunodeficiency diseases and/or disorders, immunologically-mediated diseases and/or disorders, autoimmune diseases, autoimmune mediated diseases, bone diseases and/or disorders, inflammatory diseases, fibrosis, ophthalmic/occular diseases and/or disorders, infectious diseases, viral diseases, wound repair, respiratory diseases and/or disorders, pulmonary diseases and/or disorders, renal disease, kidney disease, liver disease, cardiovascular diseases and/or disorders, vascular diseases and/or disorders heart disease, cell death and hyperplasia.

Such cancer and proliferative diseases include, but are not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes.

Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Such pain disorders include, but are not limited to, cancer-related pain, skeletal pain caused by tumor metastasis, osteoarthritis, visceral pain, inflammatory pain and neurogenic pain.

Such dermatological diseases and/or disorders include, but are not limited to, inflammatory or allergic conditions of the skin, dermatitis, eczema, psoriasis, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis, pityriasis alba, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, peritoneal and sub dermal adhesion and photoaging of the skin.

Such metabolic diseases and/or disorders and eating disorder include, but are not limited to, obesity, diabetes and anoerexia.

Such muscle diseases and/or disorders include, but are not limited to, muscular atrophies (e.g. disuse), muscular dystrophies (e.g. Duchenne's muscle dystrophy, Becker's muscle dystrophy, Limb-Girdle muscle dystrophy), sarcopenia, cachexia, wasting and Facioscapulohumeral dystrophy.

Such neurological diseases and/or disorders and neurodegenerative disorders include, but are not limited to, impaired neurological function and Alzheimer's disease.

Such immunodeficiency diseases and/or disorders and immunologically-mediated diseases and/or disorders include, but are not limited to, pathologic immune conditions involving T cell activation, anaphylaxis, allergy and psoriasis. Such allergy disorders include, but are not limited to, respiratory diseases and dermatolgical disorders.

Such immunological-mediated disorders include, but are not limited to, allergy and psoriasis. Such allergy disorders include, but are not limited to, respiratory diseases and dermatolgical disorders.

Such autoimmune diseases and/or disorders and autoimmune-mediated diseases and/or disorders include, but are not limited to, destructive arthritis, rheumatoid arthritis, systemic lupus erythematosus, Sjogren's syndrome, multiple sclerosis, dermatomyositis, progressive systemic sclerosis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia, idiopathic thrombocytopenic purpura and idiopathic thrombocytopenia), primary binary cirrhosis (PBC), lupus, systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Such bone diseases and/or disorders include, but are not limited to, osteoporosis, osteitis deformans, Paget's disease, osteoarthritis, prosthesis failure, osteopenia, and fractures and other disorders in which low bone mineral density are a hallmark of the disease.

Such inflammatory diseases and/or disorders include, but are not limited to, uveitis, atherosclerosis, atherogenesis, glomerulonephritis, Kawasaki disease, inflammatory responses, polymyositis, arthritis, neurological inflammation, chronic arthritis inflammation and osteoarthritis.

Such fibrosis diseases and/or disorders include, but are not limited to, extracellular matrix accumulation and fibrosis, scleroderma, fibrosclerosis, radiation-induced fibrosis, kidney fibrosis, lung fibrosis and liver fibrosis, haemochromatosis, primary biliary cirrhosis, restenosis, retroperitoneal fibrosis, mesenteric fibrosis, endometriosis and keloids.

Such ophthalmic/ocular diseases and/or disorders include, but are not limited to, proliferative vitreoretinopathy, ocular scarring, corneal scarring, ocular disorders, corneal wounds, conjunctivitis, keratoconjunctivitis sicca, and vernal conjunctivitis.

Such infectious and viral diseases and/or disorders include, but are not limited to, HIV-1 infection, for example, hepatitis B virus (HBV), hepatitis C virus (HCV), alcohol-induced hepatitis.

Wound repair includes, but are not limited to, excessive or hypertrophic scar or keloid formation in the dermis occurring during wound healing resulting from trauma or surgical wounds, ulcers (including diabetic ulcers, chronic ulcers, gastric ulcers, and duodenal ulcers).

Such respiratory diseases and/or disorders and pulmonary disorders include, but are not limited to, asthma, bronchial asthma, allergic asthma, intrinsic (non-allergic) asthma, extrinsic (allergic) asthma, exercise-induced asthma, drug-induced asthma (including aspirin and NSAID-induced) and dust-induced asthma, chronic obstructive pulmonary disease (COPD); chronic obstructive airways disease (COAD), chronic obstructive lung disease (COLD), bronchitis, chronic bronchitis, acute bronchitis, dyspnea, arachidic bronchitis, catarrhal bronchitis, croupus bronchitis, phthinoid bronchitis, rhinitis, acute rhinitis, chronic rhinitis, rhinitis medicamentosa, vasomotor rhinitis, perennial and seasonal allergic rhinitis, rhinitis nervosa (hay fever), inflammatory or obstructive airways diseases, pulmonary hypertension, acute lung injury, adult/acute respiratory distress syndrome (ARDS), pulmonary fibrosis, idiopathic pulmonary fibrosis, chronic obstructive pulmonary disease, pulmonary disease due to infectious or toxic agents, emphysema, pneumoconiosis, aluminosis, anthracosis, asbestosis, chalicosis, ptilosis, siderosis, silicosis, tabacosis, byssinosis, acute lung injury (ALI), hypereosinophilia, Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, pulmonary hypertension, primary pulmonary hypertension (PPH), secondary pulmonary hypertension (SPH), familial PPH, sporadic PPH, precapillary pulmonary hypertension, pulmonary arterial hypertension (PAH), pulmonary artery hypertension, idiopathic pulmonary hypertension, thrombotic pulmonary arteriopathy (TPA), plexogenic pulmonary arteriopathy, functional classes I to IV pulmonary hypertension, and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, hypoxemia, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Such renal diseases and/or disorders include, but are not limited to, glomerulonephritis, renal interstitial fibrosis, renal fibrosis, chronic renal disease and acute renal disease. Such kidneey diseases and/or disorders include, but are not limited to, diabetic nephropathy, lupus nephritis, hypertension-induced nephropathy, HIV-associated nephropathy and transplant necropathy. Such liver diseases and/or disorders include, but are not limited to, hepatic dysfunction attributable to infections, alcohol-induced hepatitis, disorders of the biliary tree and hepatic ischemia.

Such cardiovascular, vascular or heart diseases and/or disorders include, but are not limited to, congestive heart failure, post-infarction cardiac fibrosis, congestive heart failure, reperfusion/ischemia in stroke, heart attacks, and organ hypoxia, ischemia, dilated cardiomyopathy, myocarditis, myocardial infarction vascular stenosis, restenosis, atherosclerosis, male erectile dysfunction, Raynaud's syndrome, thrombosis and thrombin-induced platelet aggregation.

In other embodiments the compounds of Formula (I) provided herein are immunosuppressive agents and are used to treat organ transplant rejection, chronic transplant rejection, lupus, multiple sclerosis, rheumatoid arthritis, psoriasis, dermatitis, Crohn's disease, type-1 diabetes and complications from type-1 diabetes.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, acute and chronic rhinitis including rhinitis medicamentosa, and vasomotor rhinitis; perennial and seasonal allergic rhinitis including rhinitis nervosa (hay fever).

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of dermatological disorders including, but not limited to, psoriasis, dermatitis, eczema, atopic dermatitis, contact dermatitis, urushiol-induced contact dermatitis, eczematous dermatoses, and delayed-type hypersensitivity reactions; phyto- and photodermatitis; seborrhoeic dermatitis, dermatitis herpetiformis, lichen simplex chronicus, lichen planus, lichen sclerosus et atrophica, discoid lupus erythematosus, diaper rash, erythroderma, prurigo nodularis, itch, pruritus ani, nummular dermatitis, dyshidrosis and pityriasis alba.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of cancer including, but not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of cancer including, but not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome. Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes. Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

In certain embodiments, the compounds of Formula (I), pharmaceutically acceptable salts, solvates, N-oxides, prodrugs and isomers thereof, and pharmaceutical compositions and combination therapies provided herein are used as immunosuppressant agents to treat and/or prevent rheumatoid arthritis (RA), multiple sclerosis (MS), systemic lupus erythematosus (SLE), immune thrombocytopenic purpura (ITP), hemolytic anemia and transplant rejection.

Compounds of Formula (I), pharmaceutically acceptable salts, solvates, N-oxides, prodrugs and isomers thereof, pharmaceutical compositions, and combination therapies provided herein are used in methods for modulating Ros, KDR, FMS, c-FMS, FLT3, c-Kit, JAK2, JAK3, Aurora, PDGFR, Lck, TrkA, TrkB, TrkC, IGF-1R, ALK4, ALK5 and ALK kinase activity in a subject (human or other mammal) for the treatment and/or prevention of diseases and/or disorders associated with or mediated by aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity. In certain embodiments, such methods include administering to a subject an effective amount of a compound of Formula (I), or a pharmaceutical composition containing a compound of Formula (I).

In certain embodiments, the methods for the treatment of a subject suffering from a disease and/or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity include administering to the subject an effective amount of a compound of Formula (I), or a pharmaceutically acceptable salt, solvate thereof, either alone or as part of a pharmaceutical composition as described herein.

In certain embodiments, a compound of Formula (I), or a pharmaceutically acceptable salt or solvate thereof, is used in the preparation of a medicament for the treatment of a disease or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity. In other embodiments, a compound of Formula (I), or a pharmaceutically acceptable salt or solvate thereof, is used in the treatment of a disease or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity.

In a further embodiment, pharmaceutical compositions comprising at least one compound of Formula (I) are adapted for oral administration for the treatment of a disease or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity. In a further embodiment, pharmaceutical compositions comprising at least one compound of Formula (I) are adapted for topical administration for the treatment of a disease or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity. In a further embodiment, pharmaceutical compositions comprising at least one compound of Formula (I) are adapted for parenteral administration for the treatment of a disease or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity. In a further embodiment, pharmaceutical compositions comprising at least one compound of Formula (I) are adapted for pulmonary/inhalation administration for the treatment of a disease or disorder associated with aberrant, abnormal or deregulated Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinase activity.

In certain embodiments, the system or subject used in the methods provided herein are cell or tissue systems. In certain embodiments, the system or subject used in the methods provided herein are human or animal subjects.

In accordance with the foregoing, provided herein are methods for preventing, treating and/or ameliorating the condition of any of the diseases or disorders described above in a subject in need of such treatment, which method comprises administering to said subject a therapeutically effective amount of a compound of Formula (I), or a pharmaceutically acceptable salt thereof. For any of the methods and uses provided herein, the required dosage will vary depending on the mode of administration, the particular condition to be treated and the effect desired.

Kits

Also provided herein are pharmaceutical packs or kits that include one or more containers containing a compound of Formula (I) useful for the treatment or prevention of a disease or disorder mediated by Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinases. In other embodiments, such pharmaceutical packs or kits include one or more containers containing a compound of Formula (I) useful for the treatment or prevention of a disease or disorder mediated by Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinases and one or more containers containing an additional therapeutic agent, including but not

99 limited to those listed above. In certain embodiments, such pharmaceutical packs or kits optionally include instructions for its administration of a compound of Formula (I).

EXAMPLES

The following examples are offered to illustrate, but not to limit, the compounds of Formula (I) provided herein, and the preparation of such compounds.

Scheme 1

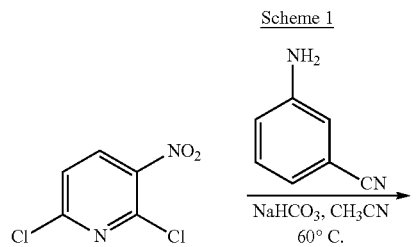

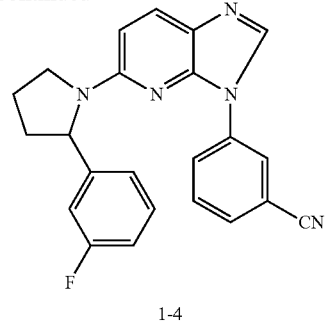

100

-continued

Example 1

Preparation of 3-(5-(2-(3-Fluorophenyl)pyrrolidin-1-yl)-3H-imidazo[4,5-b]pyridin-3-yl)benzonitrile 3-(5-(2-(3-fluorophenyl)pyrrolidin-1-yl)-3H-imidazo[4,5-b]pyridin-3-yl)benzonitrile (1-4) was synthesized in four steps as shown in scheme 1.

In step 1-1, sodium bicarbonate (1.68 g, 20 mmol) was added into a solution of 2,6-dichloro-3-nitropyridine (1.93 g, 10 mmol) and 3-amino benzonitrile (1.18 g, 10 mmol) in acetonitrile and the suspension was heated for 24 hours at 60° C. The mixture was filtered and washed twice with water to give 3-(6-chloro-3-nitropyridin-2-ylamino)benzonitrile (1-1) as a pale yellow solid. $^1$H NMR DMSO-d6 δ (ppm) 10.24 (s, 1H), 8.57 (d, 1H), 8.09 (m, 1H), 7.93 (m, 1H), 7.62 (m, 2H), 7.08 (d, 1H); m/z 357 M+1.

In step 1-2, Raney nickel was added to a suspension of 3-(6-chloro-3-nitropyridin-2-ylamino)benzonitrile in methanol/dichloromethane (1:1) and the resulting suspension was set up in Parr shaker under a hydrogen atmosphere (40 psi) for 18 hours. The remaining catalyst was removed through a Celite pad, and the reaction mixture was concentrated to afford the crude product 3-(3-amino-6-chloropyridin-2-ylamino)benzonitrile (1-2) which was used in the next step without further purification.

In step 1-3, a solution of 3-(3-amino-6-chloropyridin-2-ylamino)benzonitrile (1.07 g, 4.38 mmol) and foramidine acetate (1.37 g, 13.1 mmol) in ethanol was refluxed for 3 hours. The reaction mixture was concentrated and purified to afford 3-(5-chloro-3H-imidazo[4,5-b]pyridin-3-yl)benzonitrile (1-3) as a yellow solid.

In step 1-4, tris(dibenzylideneacetone) dipalladium (0) (10.8 mg, 0.012 mmol), dicyclohexyl(2',4',6'-triisopropylbiphenyl-2-yl)phosphine (22 mg, 0.047 mmol) and cesium carbonate (77 mg, 0.24 mmol) were added consecutively into a solution of 3-(5-chloro-3H-imidazo[4,5-b]pyridin-3-yl)benzonitrile (30 mg, 0.12 mmol) and 2-(3-fluorophenyl)pyrrolidine (29 mg, 0.18 mmol) in 1,4-dioxane. The mixture was degased under house vacuum, and charged with nitrogen and heated for 18 hours at 100° C. The reaction mixtures was purified using HPLC to afford 3-(5-(2-(3-fluorophenyl)pyrrolidin-1-yl)-3H-imidazo[4,5-b]pyridin-3-yl)benzonitrile (1-4) as a white solid. $^1$H NMR methanol-d4 δ (ppm) 8.86 (s, 1H), 8.28 (s, 1H), 7.98 (m, 1H), 7.89 (d, 1H), 7.78 (d, 1H), 7.63 (t, 1H), 7.33 (m, 1H), 7.09 (dm, 1H), 6.93 (m, 2H), 6.70 (d, 1H), 5.18 (d, 1H), 3.94 (m, 1H), 3.68 (m, 1H), 2.48 (m, 1H), 2.11 (m, 2), 1.97 (m, 1H); m/z 384 (M+1).

By repeating the procedures described in the above examples, using appropriate starting materials, the following compounds of Formula I, as identified in Table 1, were obtained.

TABLE 1

| Compound Number | Structure | Physical Data<br>¹H NMR 400 MHz (DMSO-$d_6$)<br>and/or MS (m/z) |
|---|---|---|
| 1 | 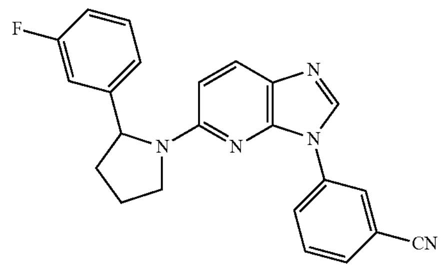 [SMILES: N#Cc1cccc(-n2cnc3ccc(N4CCCC4c4cccc(F)c4)nc32)c1] | ¹H NMR methanol-d4 δ (ppm) 8.86 (s, 1H), 8.28 (s, 1H), 7.98 (m, 1H), 7.89 (d, 1H), 7.78 (d, 1H), 7.63 (t, 1H), 7.33 (m, 1H), 7.09 (dm, 1H), 6.93 (m, 2H), 6.70 (d, 1H), 5.18 (d, 1H), 3.94 (m, 1H), 3.68 (m, 1H), 2.48 (m, 1H), 2.11 (m, 2H), 1.97 (m, 1H); m/z 384 (M + 1) |
| 2 | 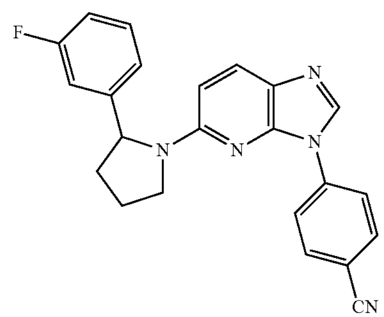 [SMILES: N#Cc1ccc(-n2cnc3ccc(N4CCCC4c4cccc(F)c4)nc32)cc1] | ¹H NMR methanol-d4 δ (ppm) 8.79 (s, 1H), 7.89 (m, 3H), 7.80 (m, 2H), 7.36 (m, 1H), 7.09 (d, 1H), 6.99 (m, 2H), 6.70 (d, 1H), 5.13 (dd, 1H), 3.94 (m, 1H), 3.69 (m, 1H), 2.49 (m, 1H), 2.11 (m, 2H), 1.97 (m, 1H); m/z 384 (M + 1) |
| 3 | 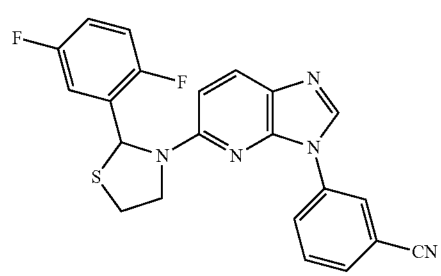 [SMILES: N#Cc1cccc(-n2cnc3ccc(N4CCSC4c4cc(F)ccc4F)nc32)c1] | m/z 420 (M + 1) |
| 4 | 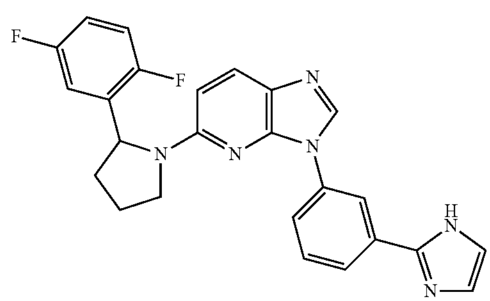 [SMILES: Fc1ccc(F)c(C2CCCN2c2ccc3ncn(-c4cccc(-c5ncc[nH]5)c4)c3n2)c1] | m/z 443 (M + 1) |
| 5 | 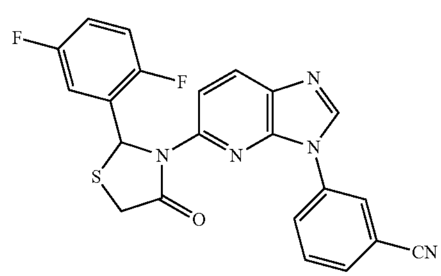 [SMILES: N#Cc1cccc(-n2cnc3ccc(N4C(=O)CSC4c4cc(F)ccc4F)nc32)c1] | m/z 443 (M + 1) |

TABLE 1-continued
| Compound Number | Structure | Physical Data $^1$H NMR 400 MHz (DMSO-$d_6$) and/or MS (m/z) |
|---|---|---|
| 6 | 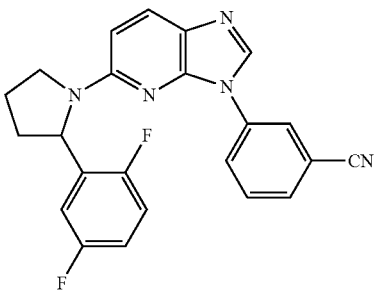 [SMILES: N#Cc1cccc(-n2cnc3ccc(N4CCCC4c4cc(F)ccc4F)nc32)c1] | MS m/z 402 (M + 1) |
| 7 | 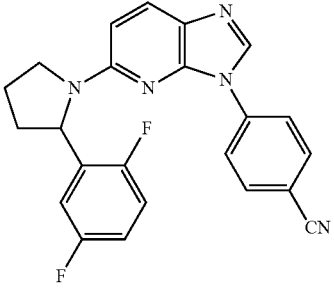 [SMILES: N#Cc1ccc(-n2cnc3ccc(N4CCCC4c4cc(F)ccc4F)nc32)cc1] | MS m/z 402 (M + 1) |
| 8 | 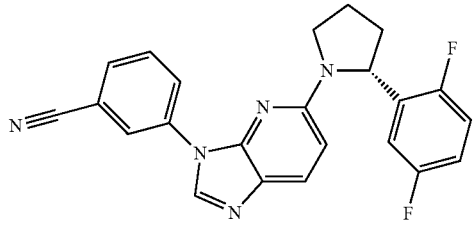 [SMILES: N#Cc1cccc(-n2cnc3ccc(N4CCC[C@@H]4c4cc(F)ccc4F)nc32)c1] | MS m/z 402 (M + 1) |
| 9 | 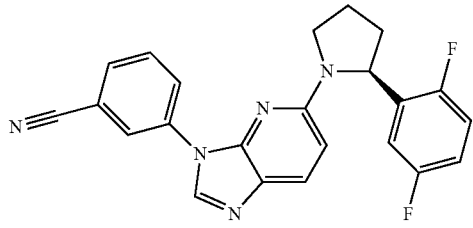 [SMILES: N#Cc1cccc(-n2cnc3ccc(N4CCC[C@H]4c4cc(F)ccc4F)nc32)c1] | MS m/z 402 (M + 1) |
| 10 | 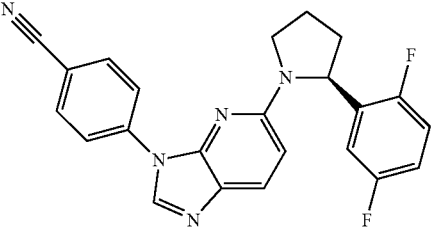 [SMILES: N#Cc1ccc(-n2cnc3ccc(N4CCC[C@H]4c4cc(F)ccc4F)nc32)cc1] | MS m/z 402 (M + 1) |
| 11 | 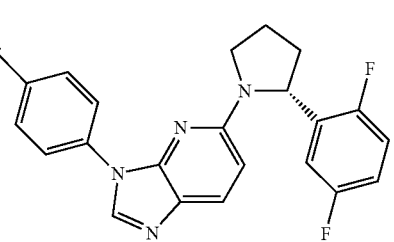 | MS m/z 402 (M + 1) |

TABLE 1-continued

| Compound Number | Structure | Physical Data $^1$H NMR 400 MHz (DMSO-$d_6$) and/or MS (m/z) |
|---|---|---|
| 12 | 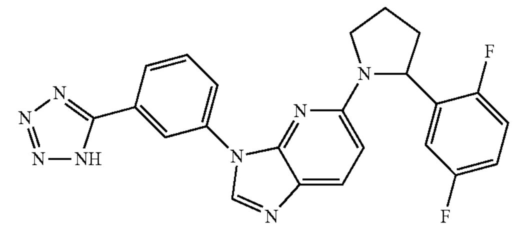 [SMILES: Fc1ccc(F)c(C2CCCN2c2ccc3ncn(-c4cccc(-c5nnn[nH]5)c4)c3n2)c1] | MS m/z 402 (M + 1) |

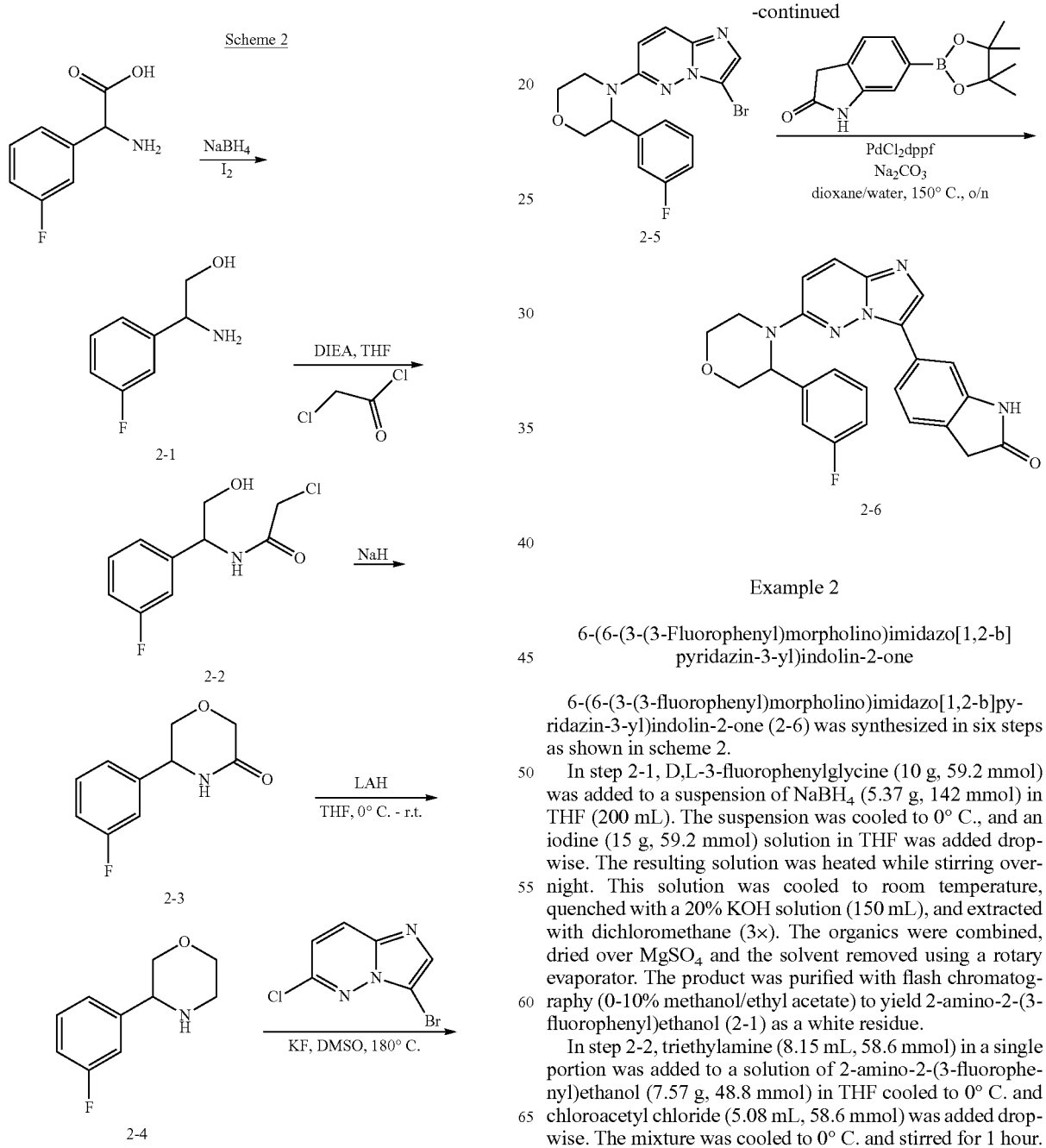

Example 2

6-(6-(3-(3-Fluorophenyl)morpholino)imidazo[1,2-b]pyridazin-3-yl)indolin-2-one 6-(6-(3-(3-fluorophenyl)morpholino)imidazo[1,2-b]pyridazin-3-yl)indolin-2-one (2-6) was synthesized in six steps as shown in scheme 2.

In step 2-1, D,L-3-fluorophenylglycine (10 g, 59.2 mmol) was added to a suspension of NaBH$_4$ (5.37 g, 142 mmol) in THF (200 mL). The suspension was cooled to 0° C., and an iodine (15 g, 59.2 mmol) solution in THF was added dropwise. The resulting solution was heated while stirring overnight. This solution was cooled to room temperature, quenched with a 20% KOH solution (150 mL), and extracted with dichloromethane (3×). The organics were combined, dried over MgSO$_4$ and the solvent removed using a rotary evaporator. The product was purified with flash chromatography (0-10% methanol/ethyl acetate) to yield 2-amino-2-(3-fluorophenyl)ethanol (2-1) as a white residue.

In step 2-2, triethylamine (8.15 mL, 58.6 mmol) in a single portion was added to a solution of 2-amino-2-(3-fluorophenyl)ethanol (7.57 g, 48.8 mmol) in THF cooled to 0° C. and chloroacetyl chloride (5.08 mL, 58.6 mmol) was added dropwise. The mixture was cooled to 0° C. and stirred for 1 hour. The reaction mixture was quenched with water and the organic phase was washed with 0.5 N HCl, saturated NaHCO$_3$, brine, and dried over MgSO$_4$. The organic phase was concentrated and purified with flash chromatography (50% EtOAc/hexanes) to yield 2-chloro-N-(1-(3-fluorophenyl)-2-hydroxyethyl)acetamide (2-2) as a yellow solid.

In step 2-3, a solution of 2-chloro-N-(1-(3-fluorophenyl)-2-hydroxyethyl)acetamide (5.5 g, 24 mmol) in THF (150 mL) was slowly added to a suspension of NaH (1.05 g, 26 mmol) in THF (600 mL) at 0° C. The heterogeneous solution was warmed to room temperature and stirred overnight. The reaction mixtures was quenched, concentrated and ethyl acetate was added to the residue. This solution was washed with water and brine and the organic phase was dried over MgSO$_4$, filtered and concentrated to yield 5-(3-fluorophenyl)morpholin-3-one (2-3).

In step 2-4, a solution of 5-(3-fluorophenyl)morpholin-3-one (4.56 g, 23.4 mmol) in THF at 0° C. was treated with lithium aluminum hydride (4.3 g, 107 mmol) in a single portion. The suspension was warmed to room temperature and stirred overnight. The reaction mixture was quenched with Na$_2$SO$_4$ 10 H$_2$O and stirred for 4 hours. The heterogeneous solution was filtered through a celite pad, and the filtrate was concentrated and purified with flash chromatography (5-10% methanol/EtOAc) to obtain 3-(3-fluorophenyl)morpholine (2-4) as a clear oil. $^1$H NMR CDCl$_3$ (δ) ppm 7.28 (m, 1H), 7.13 (m, 2H), 6.97 (m, 1H), 3.93 (dd, 1H), 3.89 (m, 1H), 3.81 (dd, 1H), 3.64 (td, 1H), 3.35 (m, 1H), 3.12 (td, 1H), 3.02 (m, 1H).

In step 2-5, a suspension of 3-(3-fluorophenyl)morpholine (1.59 g, 6.9 mmol), 3-bromo-6-chloroimidazo[1,2-b]pyridazine (12-1) (1.5 g, 8.29 mmol) and potassium fluoride (1.6 g, 27.6 mmol) in DMSO (6 mL) was heated at 180° C. for 18 hours while stirring. The resulting solution was cooled to room temperature and purified with HPLC to yield 4-(3-Bromoimidazo[1,2-b]pyridazin-6-yl)-3-(3-fluorophenyl) morpholine (2-5) as a yellow foam.

In step 2-6, a suspension of 4-(3-bromoimidazo[1,2-b]pyridazin-6-yl)-3-(3-fluorophenyl)morpholine (25 mg, 0.067 mmol), 6-(4,4,5,5-tetramethyl-1,3,2-dioxaborolan-2-yl)indolin-2-one (34 mg, 0.13 mmol) and [1,1'-bis(diphenylphosphino)ferrocene]dichloropalladium(II) (2.7 mg, 0.0033 mmol) in 3 mL of 1,4-dioxane and 0.5 mL of 2.0M sodium carbonate was bubbled with nitrogen and heated to 150° C. and stirred for 20 hours. The solution was cooled to room temperature and purified with HPLC to afford 6-(6-(3-(3-fluorophenyl)morpholino)imidazo[1,2-b]pyridazin-3-yl)indolin-2-one (2-6) as a white solid.

By repeating the procedures described in the above examples, using appropriate starting materials, the following compounds of Formula I, as identified in Table 2, were obtained.

TABLE 2

| Compound Number | Structure | Physical Data $^1$H NMR 400 MHz, (DMSO-d$_6$) and/or MS (m/z) |
|---|---|---|
| 1 | 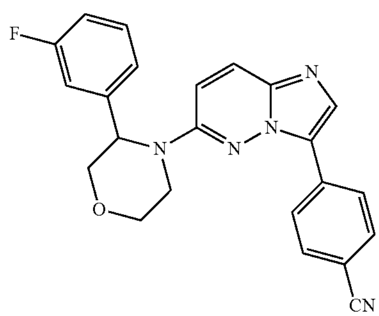 [SMILES: N#Cc1ccc(-c2cnc3ccc(N4CCOCC4c4cccc(F)c4)nn23)cc1] | $^1$H NMR methanol-d4 δ (ppm) 7.97 (m, 3H), 7.72 (d, 2H), 7.66 (b, 1H), 7.45 (s, 1H), 2.24 (q, 1H), 7.11 (d, 1H), 7.07 (m, 1H), 6.89 (m, 1H), 5.17 (m, 1H), 1.46 (dd, 1H), 4.00 (m, 3H), 3.76 (m, 1H), 3.66 (m, 1H); m/z 400 (M + 1) |
| 2 | 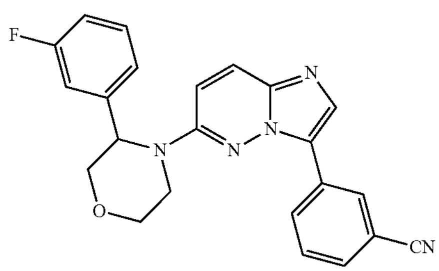 [SMILES: N#Cc1cccc(-c2cnc3ccc(N4CCOCC4c4cccc(F)c4)nn23)c1] | m/z 400 (M + 1) |
| 3 | 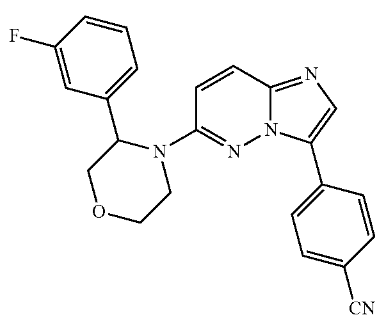 [SMILES: N#Cc1ccc(-c2cnc3ccc(N4CCOCC4c4cccc(F)c4)nn23)cc1] | $^1$H NMR methanol-d4 δ (ppm) 7.97 (m, 3H), 7.72 (d, 2H), 7.66 (b, 1H), 7.45 (s, 1H), 2.24 (q, 1H), 7.11 (d, 1H), 7.07 (m, 1H), 6.89 (m, 1H), 5.17 (m, 1H), 1.46 (dd, 1H), 4.00 (m, 3H), 3.76 (m, 1H), 3.66 (m, 1H); m/z 400 (M + 1) |

TABLE 2-continued

| Compound Number | Structure | Physical Data<br>¹H NMR 400 MHz, (DMSO-d₆)<br>and/or MS (m/z) |
|---|---|---|
| 4 | 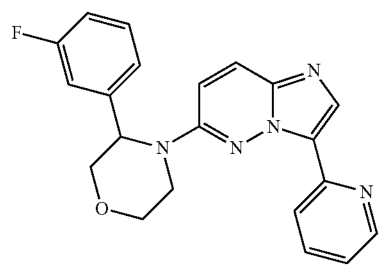 [SMILES: Fc1cccc(C2COCCN2c2ccc3ncc(-c4ccccn4)n3n2)c1] | ¹H NMR CDCl₃ δ (ppm) 8.72 (s, 1H), 8.49 (d, 1H), 8.30 (s, 1H), 8.08 (d, 1H), 7.84 (t, 1H), 7.39 (m, 1H), 7.26 (m, 2H), 7.03 (m, 2H), 6.91 (m, 1H), 5.08 (s, 1H), 4.22 (dd, 1H), 4.06 (m, 2H), 3.92 (m, 1H), 3.81 (m, 1H), 3.67 (m, 1H); m/z 376 (M + 1) |
| 5 | 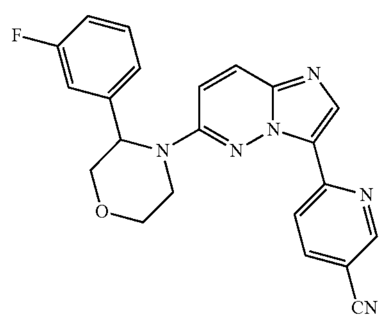 [SMILES: N#Cc1ccc(-c2cnc3ccc(N4CCOCC4c4cccc(F)c4)nn23)nc1] | m/z 401 (M + 1) |
| 6 | 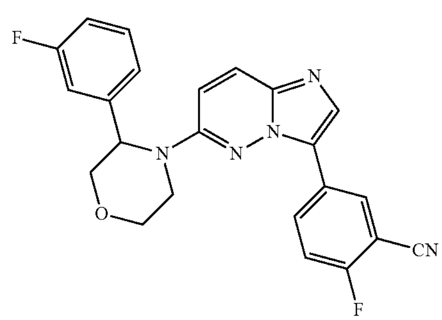 [SMILES: N#Cc1cc(-c2cnc3ccc(N4CCOCC4c4cccc(F)c4)nn23)ccc1F] | m/z 418 (M + 1) |
| 7 | 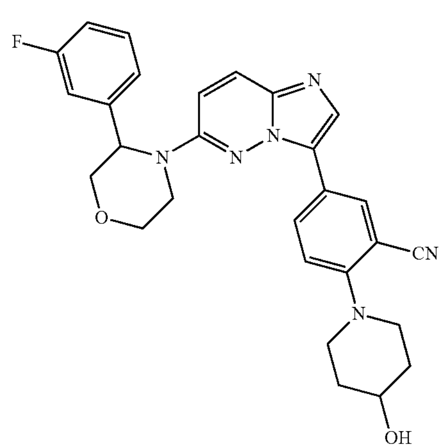 [SMILES: N#Cc1cc(-c2cnc3ccc(N4CCOCC4c4cccc(F)c4)nn23)ccc1N1CCC(O)CC1] | m/z 499 (M + 1) |

TABLE 2-continued
| Compound Number | Structure | Physical Data<br>¹H NMR 400 MHz, (DMSO-d₆)<br>and/or MS (m/z) |
|---|---|---|
| 8 | 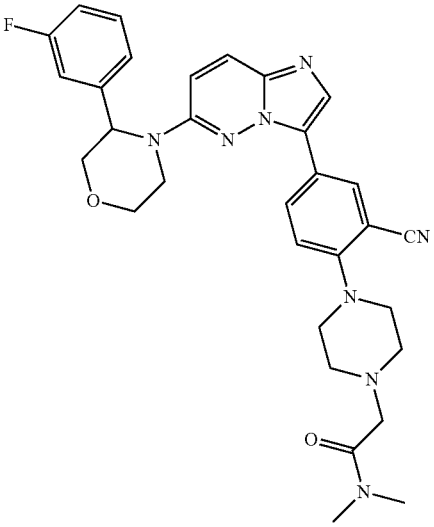 [SMILES: CN(C)C(=O)CN1CCN(c2ccc(-c3cnc4ccc(N5CCOCC5c5cccc(F)c5)nn34)cc2C#N)CC1] | m/z 569 (M + 1) |
| 9 | 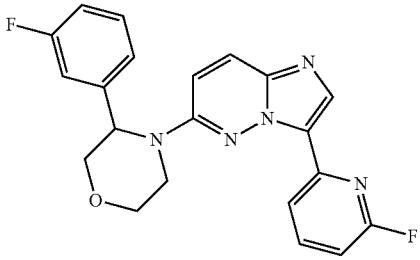 [SMILES: Fc1cccc(C2COCCN2c2ccc3ncc(-c4cccc(F)n4)n3n2)c1] | m/z 394 (M + 1) |
| 10 | 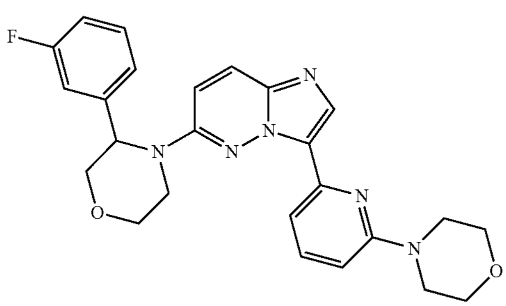 [SMILES: Fc1cccc(C2COCCN2c2ccc3ncc(-c4cccc(N5CCOCC5)n4)n3n2)c1] | ¹H NMR methanol-d4 δ (ppm) 8.43 (s, 1H), 8.12 (d, 1H), 7.69 (m, 3H), 7.34 (m, 1H), 7.25 (m, 2H), 7.00 (m, 1H), 6.88 (dd, 1H), 5.39 (m, 1H), 4.33 (dd, 1H), 4.15 (m, 3H), 3.82 (m, 6H), 3.58 (m, 4H); m/z 461 (M + 1) |
| 11 | 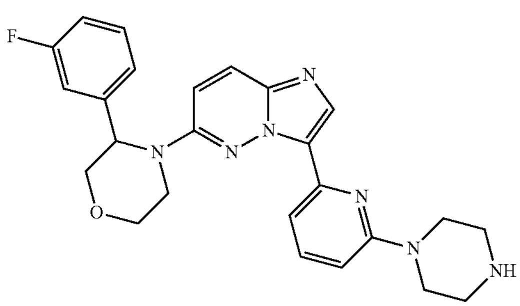 [SMILES: Fc1cccc(C2COCCN2c2ccc3ncc(-c4cccc(N5CCNCC5)n4)n3n2)c1] | ¹H NMR methanol-d4 δ (ppm) 8.50 (s, 1H), 8.14 (d, 1H), 7.77 (m, 3H), 7.36 (m, 1H), 7.36 (m, 2H), 7.01 (m, H), 5.40 (m, 1H), 4.34 (dd, 1H), 4.14 (m, 3H), 3.91 (m, 6H), 3.77 (m, 1H), 3.34 (m, 5H); m/z 460 (M + 1) |

TABLE 2-continued

| Compound Number | Structure | Physical Data<br>¹H NMR 400 MHz, (DMSO-d₆) and/or MS (m/z) |
|---|---|---|
| 12 | 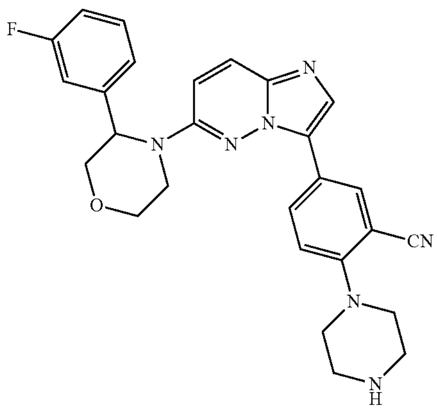 [SMILES: N#Cc1cc(-c2cnc3ccc(N4CCOCC4c4cccc(F)c4)nn23)ccc1N1CCNCC1] | m/z 484 (M + 1) |
| 13 | 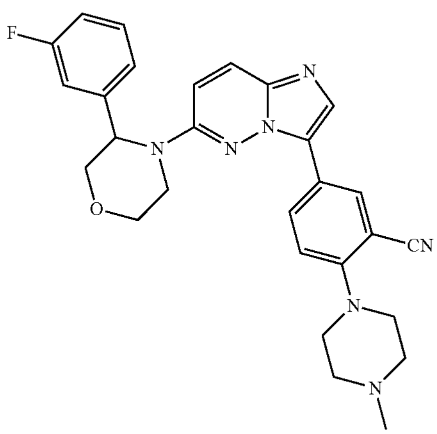 [SMILES: CN1CCN(c2ccc(-c3cnc4ccc(N5CCOCC5c5cccc(F)c5)nn34)cc2C#N)CC1] | ¹H NMR methanol-d4 δ (ppm) 8.31 (d, 1H), 8.22 (s, 1H), 8.12 (m, 2H), 7.72 (d, 1H), 7.34 (m, 2H), 7.23 (d, 1H), 7.16 (m, 1H), 6.97 (m, 1H), 5.29 (m, 1H), 4.27 (dd, 1H), 4.05 (m, 3H), 3.86 (m, 3H), 3.72 (m, 3H), 3.45 (m, 4H), 3.03 (s, 3H); m/z 498 (M + 1) |
| 14 | 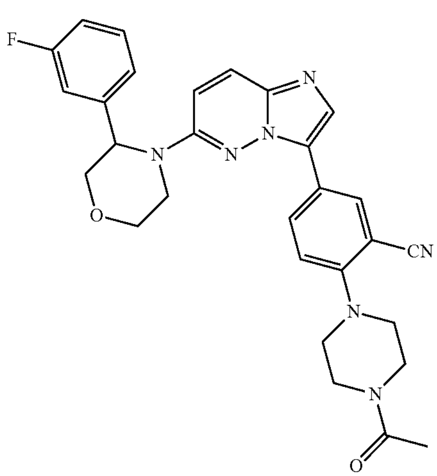 [SMILES: CC(=O)N1CCN(c2ccc(-c3cnc4ccc(N5CCOCC5c5cccc(F)c5)nn34)cc2C#N)CC1] | m/z 526 (M + 1) |

TABLE 2-continued

| Compound Number | Structure | Physical Data<br>¹H NMR 400 MHz, (DMSO-d₆)<br>and/or MS (m/z) |
|---|---|---|
| 15 | 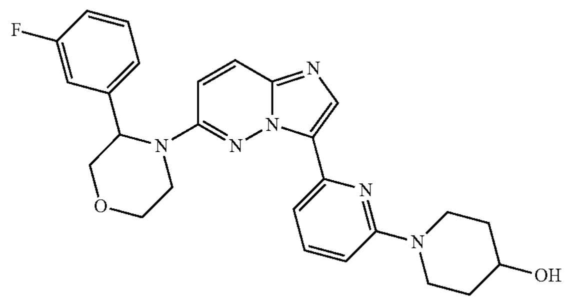 [SMILES: OC1CCN(c2cccc(-c3cnc4ccc(N5CCOCC5c5cccc(F)c5)nn34)n2)CC1] | m/z 475 (M + 1) |
| 16 | 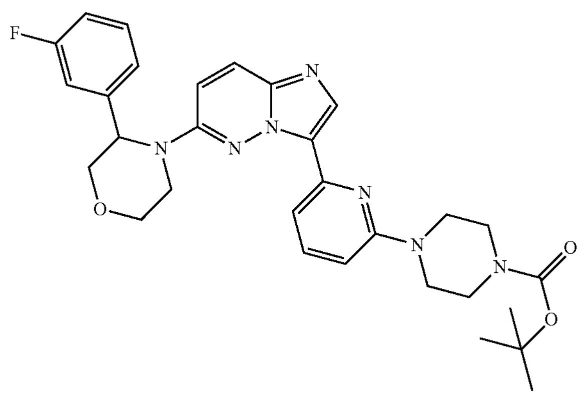 [SMILES: CC(C)(C)OC(=O)N1CCN(c2cccc(-c3cnc4ccc(N5CCOCC5c5cccc(F)c5)nn34)n2)CC1] | m/z 560 (M + 1) |
| 17 | 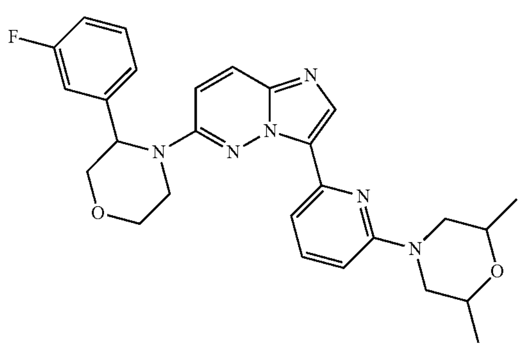 [SMILES: CC1CN(c2cccc(-c3cnc4ccc(N5CCOCC5c5cccc(F)c5)nn34)n2)CC(C)O1] | ¹H NMR DMSO-d6 δ (ppm) 8.12 (m, 1H), 7.95 (m, 1H), 7.59 (d, 1H), 7.51 (t, 1H), 7.20 (m, 4H), 6.97 (td, 1H), 6.71 (d, 1H), 5.23 (m, 1H), 4.16 (m, 3H), 3.97 (m, 3H), 3.71 (td, 1H), 3.56 (m, 3H), 2.33 (m, 2H), 1.12 (s, 3H), 1.10 (s, 3H); m/z 489 (M + 1) |
| 18 | 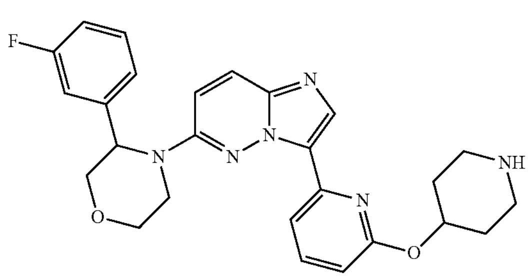 [SMILES: Fc1cccc(C2COCCN2c2ccc3ncc(-c4cccc(OC5CCNCC5)n4)n3n2)c1] | m/z 475 (M + 1) |

TABLE 2-continued

| Compound Number | Structure | Physical Data<br>¹H NMR 400 MHz, (DMSO-d₆) and/or MS (m/z) |
|---|---|---|
| 19 | 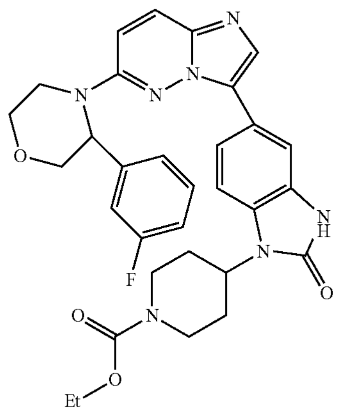 [SMILES: CCOC(=O)N1CCC(n2c(=O)[nH]c3cc(-c4cnc5ccc(N6CCOCC6c6cccc(F)c6)nn45)ccc32)CC1] | ¹H NMR methanol-d4 δ (ppm) 8.18 (s, 1H), 8.12 (d, 1H), 7.73 (m, 2H), 7.56 (dd, 1H), 7.34 (d, 1H), 7.28 (m, 1H), 7.20 (m, 2H), 6.96 (m, 1H), 5.29 (m, 1H), 4.51 (m, 1H), 4.36 (m, H), 4.18 (q, 2H), 4.09 (m, 3H), 3.87 (td, 1H), 3.74 (m, 1H), 3.00 (m, 2H), 2.41 (m, 2H), 1.85 (m, 2H), 1.31 (t, 3H); m/z 586 (M + 1) |
| 20 | 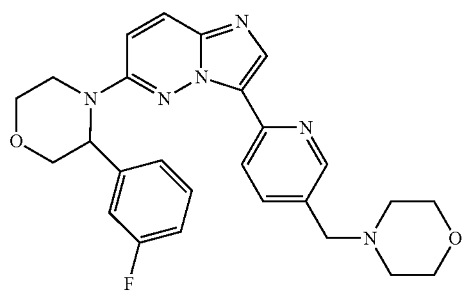 [SMILES: Fc1cccc(C2COCCN2c2ccc3ncc(-c4ccc(CN5CCOCC5)cn4)n3n2)c1] | MS m/z 475 (M + 1) |
| 21 | 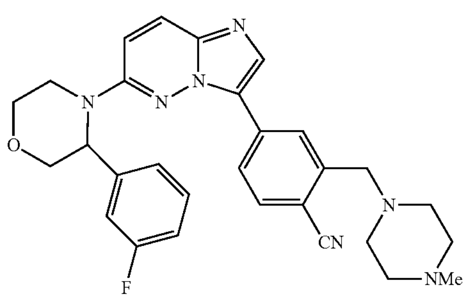 [SMILES: CN1CCN(Cc2cc(-c3cnc4ccc(N5CCOCC5c5cccc(F)c5)nn34)ccc2C#N)CC1] | MS m/z 512 (M + 1) |
| 22 | 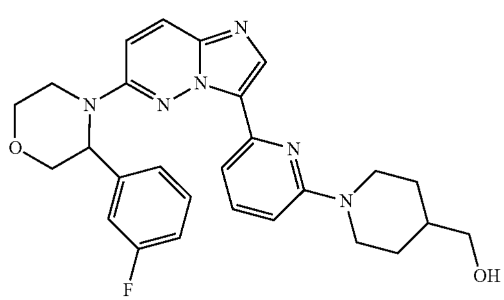 [SMILES: OCC1CCN(c2cccc(-c3cnc4ccc(N5CCOCC5c5cccc(F)c5)nn34)n2)CC1] | MS m/z 489 (M + 1) |

TABLE 2-continued
| Compound Number | Structure | Physical Data $^1$H NMR 400 MHz, (DMSO-$d_6$) and/or MS (m/z) |
|---|---|---|
| 23 | 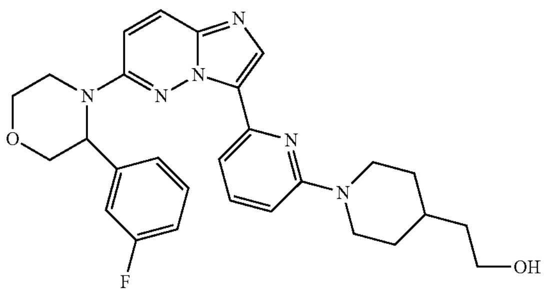 [SMILES: OCCC1CCN(c2cccc(-c3cnc4ccc(N5CCOCC5c5cccc(F)c5)nn34)n2)CC1] | MS m/z 503 (M + 1) |
| 24 | 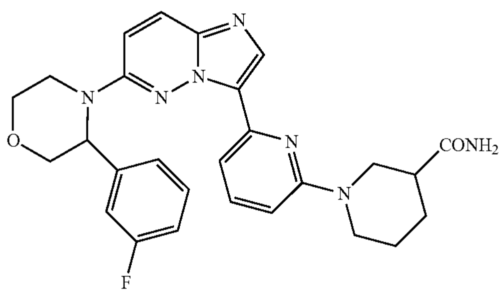 [SMILES: NC(=O)C1CCCN(c2cccc(-c3cnc4ccc(N5CCOCC5c5cccc(F)c5)nn34)n2)C1] | MS m/z 502 (M + 1) |
| 25 | 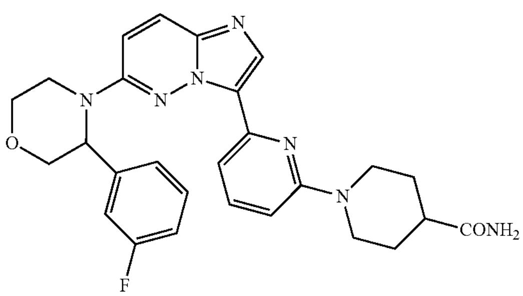 [SMILES: NC(=O)C1CCN(c2cccc(-c3cnc4ccc(N5CCOCC5c5cccc(F)c5)nn34)n2)CC1] | MS m/z 502 (M + 1) |
Scheme 3
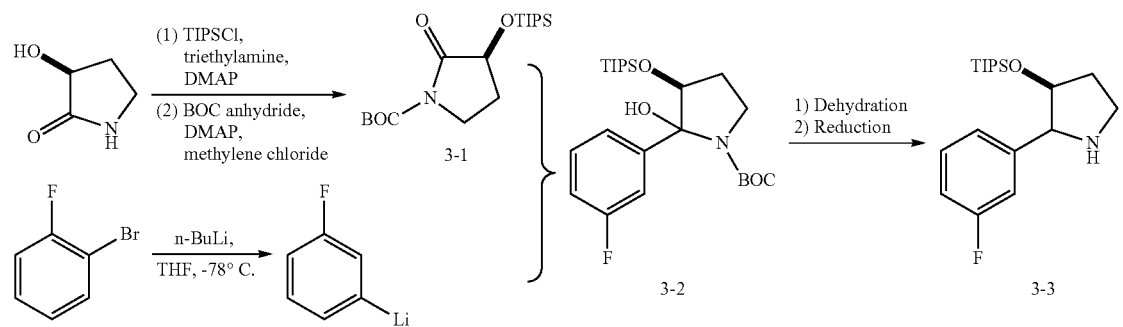

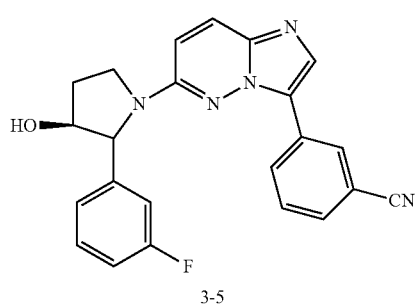 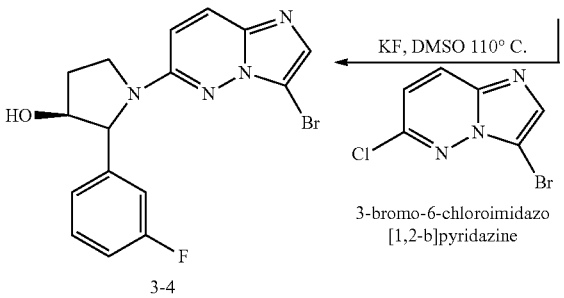

3-bromo-6-chloroimidazo
[1,2-b]pyridazine

Example 3

3-(6-((3S)-2-(3-fluorophenyl)-3-hydroxypyrrolidin-1-yl)imidazo[1,2-b]pyridazin-3-yl)benzonitrile 3-(6-((3S)-2-(3-fluorophenyl)-3-hydroxypyrrolidin-1-yl) imidazo[1,2-b]pyridazin-3-yl)benzonitrile (3-5) was synthesized in five steps as shown in scheme 3.

In step 3-1, triethylamine (20 ml, 139 mmol), p-N,N-dimethylaminopyridine (150 mg, 1 mmol) and then triisopropylsilyl chloride (22.6 grams, 118 mmol) were added dropwise over 4 minutes to a solution of S-3-hydroxy-2-pyrrolidinone (4.00 grams, 39.6 mmol) in 40 mL of methylene chloride. The reaction mixture was stirred for 3 days and was then quenched with 200 mL of brine. The solution was extracted with of ethyl acetate (3×300 mL) and the organic extracts were concentrated using a rotary evaporator. The product was then used directly without any purification. The residue was dissolved in 100 mL of methylene chloride and 50 mL of triethylamine (co-solvent) and treated with p-N,N-dimethylaminopyridine (100 mg, 0.8 mmol) followed by BOC anhydride (22.9 grams, 104 mmoles). The reaction mixture was stirred vigorously for 6 hours, quenched with 100 mL of brine, and extracted with 200 mL of ethyl acetate. The organic extracts were concentrated and then purified using flash chromatography (10% ethyl acetate to hexanes isocratic solvent system) affording (S)-tert-butyl 2-oxo-3-(triisopropylsilyloxy)pyrrolidine-1-carboxylate (3-1) as an oil. $^1$H NMR (400 MHz, $D_3$ acetonitrle) δ ppm 4.50 (t, J=8.0 Hz, 1H), 3.70 (t, J=8.2, 1H), 3.44-3.39 (m, 1H), 2.40-2.30 (m, 1H), 1.96-1.80 (m, 1H), 1.52 (s, 9H), 1.21-1.05 (m, 21H). LCMS observed m/z 737.5 major ion (calcd for 2M+Na, 737.5).

In step 3-2, a solution of 3-fluoro-1-bromo benzene (4.0 g, 22.9 mmol) in THF (10 mL) was cooled to −60° C. To this solution n-BuLi in hexanes solution (1.6 M hexanes, 14.3 ml, 22.9 mmol) was added over 12 minutes allowing for a gradual temperature ramp (2° C./minute) until a net internal temperature of −40° C. was obtained and all the n-BuLi was added. The reaction mixture was then allowed to warm over a 30 minute period until an internal temperature of −22° C. was reached, then the resulting solution (dark in color) was cooled to −45° C. and then a solution of (S)-tert-butyl 2-oxo-3-(triisopropylsilyloxy)pyrrolidine-1-carboxylate (2.0 grams, 5.6 mmoles) in THF (10 mL) was added over 6 minutes (do not allow the internal temperature to exceed −40° C. during this addition event). The mixture was then allowed to warm to −20° C. over a 35 minute period and the temperature was then held at −20° C. for 2 hours. The reaction mixture was then quenched with cold saturated ammonium chloride aqueous solution (150 mL), warmed to room temperature and extracted with ethyl acetate (3×150 mL). The organic extracts were combined, concentrated using a rotary evaporator and purified using flash chromatography (5% ethyl acetate in hexanes to 10% ethyl acetate in hexanes over a 30 minute gradient) yielding the racemate of (3S)-tert-butyl 2-(3-fluorophenyl)-2-hydroxy-3-(triisopropylsilyloxy)pyrrolidine-1-carboxylate (3-2) as an oil. $^1$H NMR (400 MHz, $D_6$ acetone) δ ppm 7.92-7.23 (m, 4H), 5.80 (br s, 1H), 5.10 (app t, J=8.2, 1H), 3.20-2.95 (m, 2H), 2.05-1.95 (m, 2H), 1.35 (s, 9H), 1.21-0.99 (m, 21H). LCMS observed m/z 737.5 major ion.

In step 3-3, a 4 N HCl dioxane (3 mL) solution was added to a solution of (3S)-tert-butyl 2-(3-fluorophenyl)-2-hydroxy-3-(triisopropylsilyloxy)pyrrolidine-1-carboxylate (1.1 g, 2.4 mmol) in methanol (30 mL) and stirred for 6 hours at room temperature. The reaction mixture was quenched with sodium bicarbonate (4 grams, 48 mmol) and the resulting slurry was treated with solid sodium borohydride (3 g, 79 mmol) and stirred for 4 hours. 200 mL of brine was added to the reaction mixture and the solution was extracted with ethyl acetate (2×200 mL) and purified with reverse phase C-18 chromatography (water/acetonitrile 90:10 to 10:90 gradient) to afford (3S)-2-(3-fluorophenyl)-3-(triisopropylsilyloxy) pyrrolidine (3-3) as a dark red oil (mixture of diastereomers). $^1$H NMR (400 MHz, $D_3$ acetonitrle) δ ppm 7.62-7.57 (m, 1H), 7.56-7.43 (m, 3H), 4.90-4.80 (m, 1H), 3.85-3.53 (m, 2H), 2.60-2.50 (m, 2H), 1.96-1.80 (m, 1H), 1.52 (s, 9H), 1.21-1.05 (m, 21H). LCMS observed m/z 338.2 major ion.

In step 3-4, KF (100 mg, 1.72 mmol) and 3-bromo-6-chloroimidazo[1,2-b]pyridazine (12-1) (700 mg, 3.0 mmol) were added to a solution of (3S)-2-(3-fluorophenyl)-3-(triisopropylsilyloxy)pyrrolidine (4-3) (700 g, 2.0 mmol) in 3 mL of DMSO. The resulting slurry was heated to 110° C. for 6 hours and then cooled, diluted with 8 mL of MeOH and purified using reverse phase C-18 chromatography (water/acetonitrile 90:10 to 10:90 gradient) to furnish (3S)-1-(3-bromoimidazo [1,2-b]pyridazin-6-yl)-2-(3-fluorophenyl)pyrrolidin-3-ol (3-4) as a solid (as a mixture of diastereomers). $^1$H NMR (400 MHz, $D_6$ acetone) δ ppm 8.20 (app t, J=6.5 Hz, 1H), 7.85-6.70 (m, 6H), 5.05 (app d, J=5.5 Hz, 1H), 4.68 (app q, J=7.5 Hz, 1H), 4.30 (br s, 1H), 4.01-3.92 (m, 1H), 3.82-3.70 (m, 1H), 2.35-1.87 (m, 2H). LCMS observed m/z 377.1, 379.1 major ion.

In step 3-5, in a microwave vessel sodium carbonate (105 mg, 1.0 mmol), 3-cyano phenylboronic acid (200 mg, 1.36 mmol) and Pd(DPPF)-dichloride catalyst (1,1' bis(diphenyl-sphosphino-ferrocene)-dichloropalladium (II) adduct with dichloromethane) (100 mg, 0.12 mmol) were added to a solution (3S)-1-(3-bromoimidazo[1,2-b]pyridazin-6-yl)-2-(3-fluorophenyl)pyrrolidin-3-ol (1.40 g, 0.36 mmol) and 4 mL of 1,4-dioxane/water (3:1). This solution was then subjected to the following microwave conditions using a laboratory microwave instrument (conditions: 150° C., 200 W max threshold, 20 atm. max pressure, 20 minute reaction time). The reaction mixture was purified directly with reverse phase C-18 HPLC (water/acetonitrile 90:10 to 10:90 gradient) to yield 3-(6-((3S)-2-(3-fluorophenyl)-3-hydroxypyrrolidin-1-yl)imidazo[1,2-b]pyridazin-3-yl)benzonitrile (3-5) as a mixture of diastereomers. $^1$H NMR (400 MHz, D$_6$ acetone) δ ppm 8.85 (br s, 1H), 8.40-8.03 (m, 3H), 7.90-7.22 (m, 5H), 7.10 (app d, J=5.5 Hz, 1H), 6.98 (app t, J=4.5 Hz, 1H), 5.25 (app d, J=4.5 Hz, 1H), 4.80 (app q, J=7.5 Hz, 1H), 4.30 (br s, 1H), 3.82-3.75 (m, 1H), 3.3-3.55 (m, 1H), 2.42-2.34 (m, 1H), 2.25-2.12 (m, 1H). LCMS observed m/z 400.2.

Example 4

5-(6-(3-(3-Fluorophenyl)morpholino)imidazo[1,2-b]pyridazin-3-yl)-1-(piperidin-4-yl)-1H-benzo[d]imidazol-2(3H)-one 5-(6-(2-(2,5-dimethylphenyl)pyrrolidin-1-yl)imidazo[1,2-b]pyridazin-3-yl)-2-fluorobenzonitrile (5-2) was synthesized in two steps as shown in scheme 4.

In step 4-1, potassium fluoride (58 mg, 1.0 mmol), and (3-bromo-6-chloroimidazo[1,2-b]pyridazine (12-1) (100 mg, 0.43 mmol) was added to a solution of 2-(2,5-dimethylphenyl)pyrrolidine (100 mg, 0.57 mmol) in 3 mL of DMSO. The reaction mixture was heated to 130° C. and stirred for 6 hours at 130° C. The reaction mixture was cooled to room temperature and purified using normal phase flash chromatography with ethyl acetate and hexanes (1:1) as a mobile phase to yield 3-bromo-6-(2-(2,5-dimethylphenyl)pyrrolidin-1-yl)imidazo[1,2-b]pyridazine (4-1) as its racemic mixture. $^1$H NMR (400 MHz, D$_3$ acetonitrile) δ ppm 7.50 (app d, J=9.5 Hz, 1H), 7.40 (br s, 1H), 7.08 (d, J=6.5 Hz, 1H), 6.92 (d, J=6.6 Hz, 1H), 6.82 (br s, 1H), 6.58 (br d, J=9.5 Hz, 1H), 5.28 (br d, J=5.0 Hz, 1H), 4.08-3.95 (m, 1H), 3.62 (app q, J=6.4 Hz, 1H), 3.30 (s, 1H), 2.51-2.42 (m, 1H), 2.24 (br s, 6H), 2.17-2.04 (m, 2H). LCMS observed m/z 371.1, 373.1 major ion.

In step 4-2, sodium carbonate (30 mg, 0.30 mmol), 3-cyano-4-fluoro phenylboronic acid (30 mg, 0.24 mmol) and Pd(DPPF)-dichloride catalyst (1,1' bis(diphenylsphosphino-ferrocene)-dichloropalladium (II) adduct with dichloromethane) (10 mg, 0.012 mmol) was added into in a microwave vessel containing a solution of 3-bromo-6-(2-(2,5-dimethylphenyl)pyrrolidin-1-yl)imidazo[1,2-b]pyridazine (50 mg, 0.13 mmol) and 2.5 mL of 1,4-dioxane/water (3:1). The reaction mixture was subjected to the following microwave conditions using a laboratory microwave instrument (conditions: 150° C., 200 W max threshold, 20 atm. Max pressure, 20 minute reaction time). The resulting solution was purified using preparatory LC/MS (reverse phase C-18 chromatography) to yield 5-(6-(2-(2,5-dimethylphenyl)pyrrolidin-1-yl)imidazo[1,2-b]pyridazin-3-yl)-2-fluorobenzonitrile (4-2). $^1$H NMR (400 MHz, D$_3$ acetonitrile) δ ppm 8.50-8.10 (m, 2H), 7.80 (br s, 1H), 7.50 (app d, J=8.5 Hz, 1H), 7.20 (app t, J=6.5 Hz, 1H), 7.06 (d, J=6.5 Hz, 1H), 6.93 (d, J=6.6 Hz, 1H), 6.81 (br s, 1H), 6.60 (br s, 1H), 5.22 (app dd, J=6.2, 2.1 Hz, 1H), 4.05-4.00 (m, 1H), 3.76 (app q, J=6.4 Hz, 1H), 3.36 (app d, J=2.2 Hz, 1H), 2.58-2.43 (m, 1H), 2.24 (br s, 6H), 2.19-2.08 (m, 2H). LCMS observed m/z 412.2.

By repeating the procedures described in the above examples, using appropriate starting materials, the following compounds of Formula I, as identified in Table 3, were obtained.

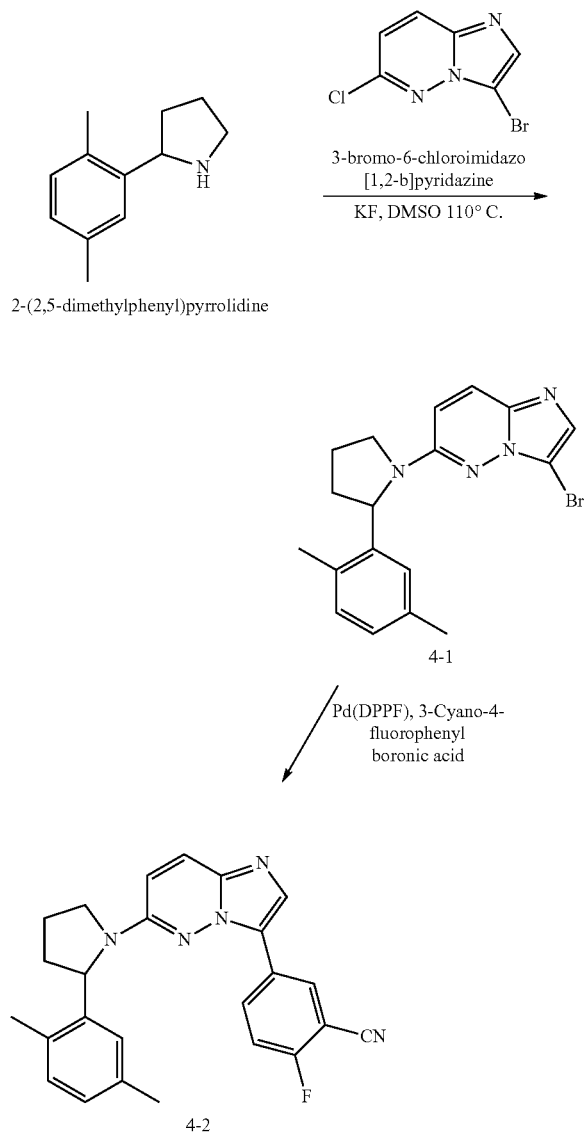

Scheme 4

TABLE 3
| Compound Number | Structure | Physical Data ¹H NMR 400 MHz (DMSO-$d_6$) and/or MS (m/z) |
|---|---|---|
| 1 | 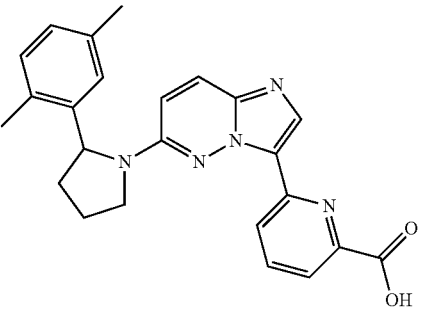 [SMILES: Cc1ccc(C)c(C2CCCN2c2ccc3ncc(-c4cccc(C(=O)O)n4)n3n2)c1] | m/z 414.2 (M + 1) |
| 2 | 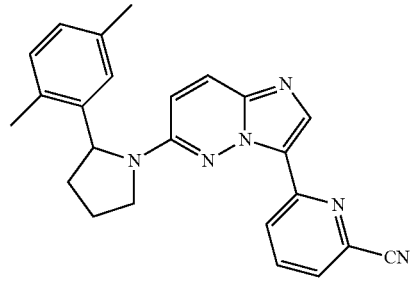 [SMILES: Cc1ccc(C)c(C2CCCN2c2ccc3ncc(-c4cccc(C#N)n4)n3n2)c1] | m/z 395.2 (M + 1) |
| 3 | 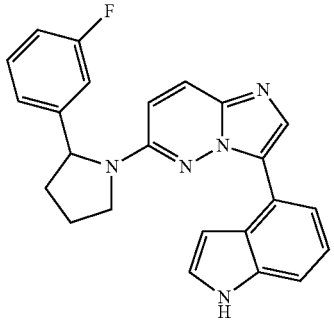 [SMILES: Fc1cccc(C2CCCN2c2ccc3ncc(-c4cccc5[nH]ccc45)n3n2)c1] | m/z 398.2 (M + 1) |
| 4 | 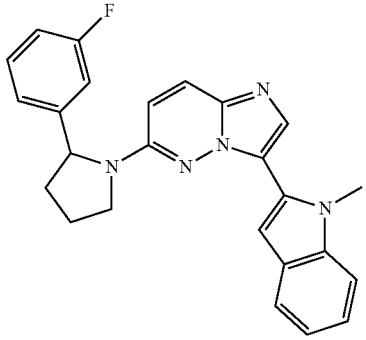 [SMILES: Cn1c(-c2cnc3ccc(N4CCCC4c4cccc(F)c4)nn23)cc2ccccc21] | m/z 412.2 (M + 1) |

TABLE 3-continued
| Compound Number | Structure | Physical Data<br>¹H NMR 400 MHz<br>(DMSO-$d_6$) and/or MS (m/z) |
|---|---|---|
| 5 | 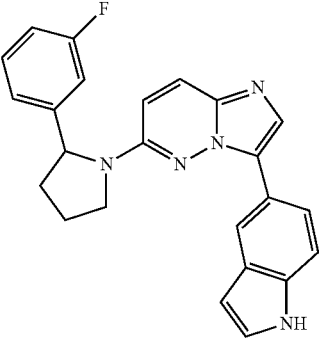 [SMILES: Fc1cccc(C2CCCN2c2ccc3ncc(-c4ccc5[nH]ccc5c4)n3n2)c1] | m/z 398.2 (M + 1) |
| 6 | 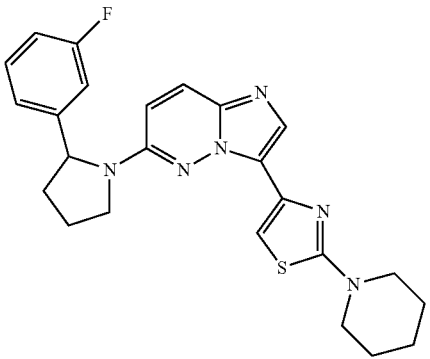 [SMILES: Fc1cccc(C2CCCN2c2ccc3ncc(-c4csc(N5CCCCC5)n4)n3n2)c1] | m/z 449.2 (M + 1) |
| 7 | 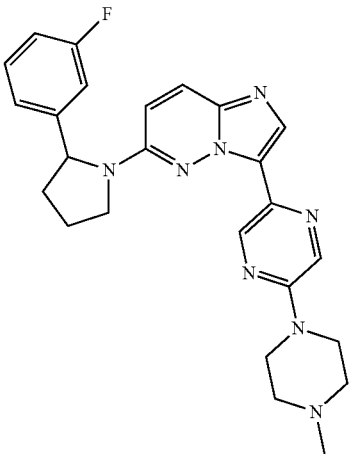 [SMILES: CN1CCN(c2cnc(-c3cnc4ccc(N5CCCC5c5cccc(F)c5)nn34)cn2)CC1] | m/z 459.2 (M + 1) |
| 8 | 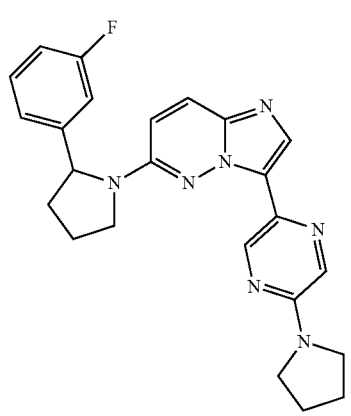 [SMILES: Fc1cccc(C2CCCN2c2ccc3ncc(-c4cnc(N5CCCC5)cn4)n3n2)c1] | m/z 430.2 (M + 1) |

TABLE 3-continued
| Compound Number | Structure | Physical Data<br>¹H NMR 400 MHz<br>(DMSO-d₆) and/or MS (m/z) |
|---|---|---|
| 9 | 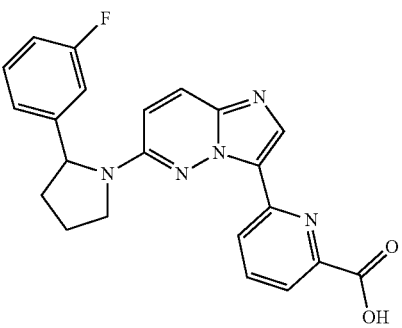 [SMILES: O=C(O)c1cccc(-c2cnc3ccc(N4CCCC4c4cccc(F)c4)nn23)n1] | m/z 404.2 (M + 1) |
| 10 | 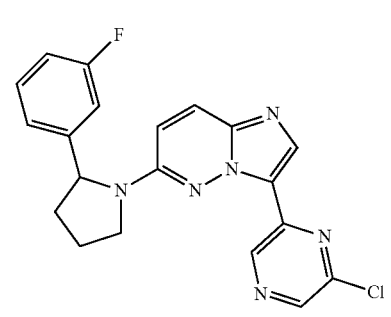 [SMILES: Fc1cccc(C2CCCN2c2ccc3ncc(-c4cncc(Cl)n4)n3n2)c1] | m/z 395.2 (M + 1) |
| 11 | 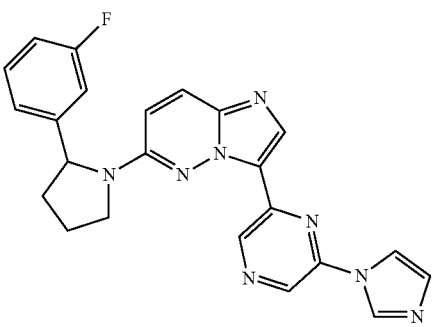 [SMILES: Fc1cccc(C2CCCN2c2ccc3ncc(-c4cncc(-n5ccnc5)n4)n3n2)c1] | m/z 427.2 (M + 1) |
| 12 | 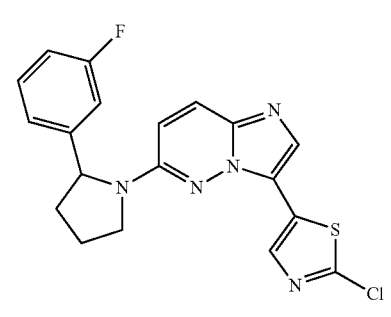 [SMILES: Fc1cccc(C2CCCN2c2ccc3ncc(-c4cnc(Cl)s4)n3n2)c1] | m/z 400.6 (M + 1) |

TABLE 3-continued
| Compound Number | Structure | Physical Data<br>¹H NMR 400 MHz<br>(DMSO-d₆) and/or MS (m/z) |
|---|---|---|
| 13 | 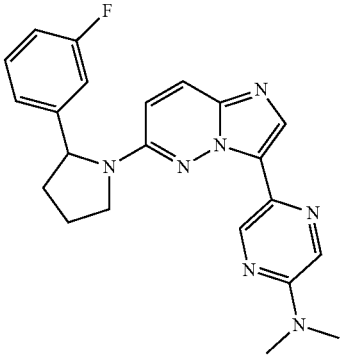 [SMILES: CN(C)c1cnc(-c2cnc3ccc(N4CCCC4c4cccc(F)c4)nn23)cn1] | m/z 404.2 (M + 1) |
| 14 | 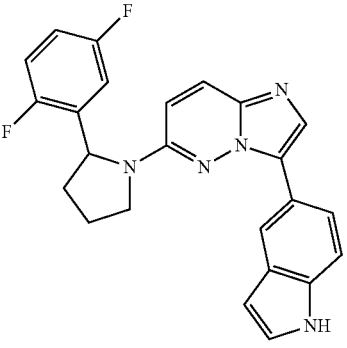 [SMILES: Fc1ccc(F)c(C2CCCN2c2ccc3ncc(-c4ccc5[nH]ccc5c4)n3n2)c1] | m/z 416.2 (M + 1) |
| 15 | 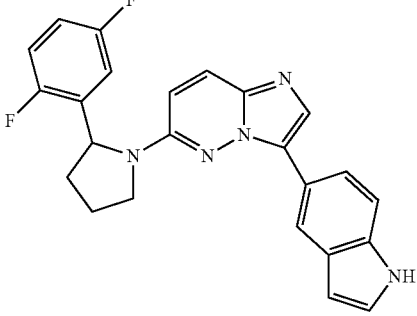 | m/z 416.2 (M + 1) |
| 16 | 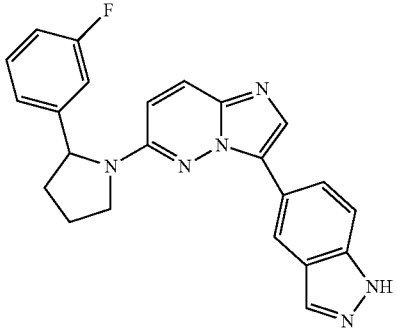 [SMILES: Fc1cccc(C2CCCN2c2ccc3ncc(-c4ccc5[nH]ncc5c4)n3n2)c1] | m/z 399.2 (M + 1) |

TABLE 3-continued
| Compound Number | Structure | Physical Data $^1$H NMR 400 MHz (DMSO-$d_6$) and/or MS (m/z) |
|---|---|---|
| 17 | 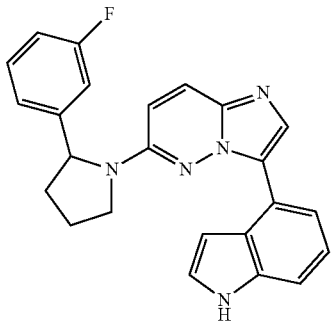 [SMILES: Fc1cccc(C2CCCN2c2ccc3ncc(-c4cccc5[nH]ccc45)n3n2)c1] | m/z 398.2 (M + 1) |
| 18 | 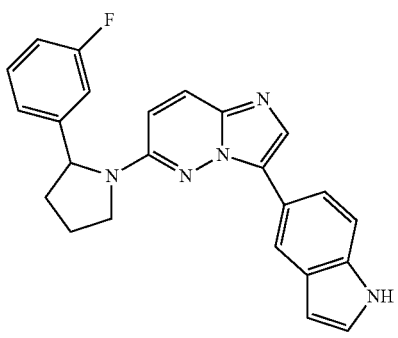 [SMILES: Fc1cccc(C2CCCN2c2ccc3ncc(-c4ccc5[nH]ccc5c4)n3n2)c1] | m/z 398.2 (M + 1) |
| 19 | 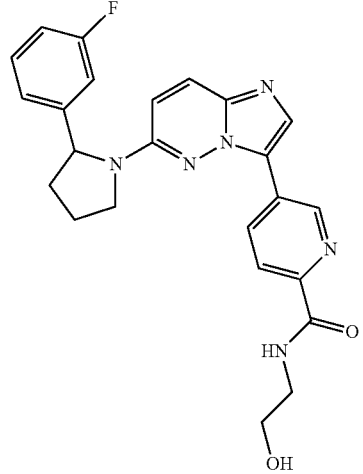 [SMILES: O=C(NCCO)c1ccc(-c2cnc3ccc(N4CCCC4c4cccc(F)c4)nn23)cn1] | m/z 447.2 (M + 1) |
| 20 | 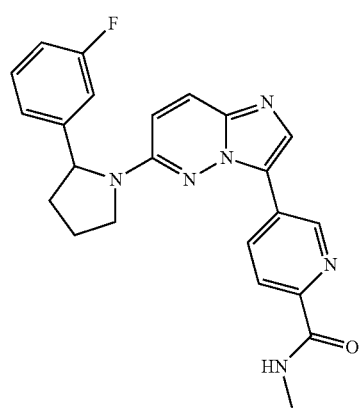 [SMILES: CNC(=O)c1ccc(-c2cnc3ccc(N4CCCC4c4cccc(F)c4)nn23)cn1] | m/z 417.2 (M + 1) |

TABLE 3-continued

| Compound Number | Structure | Physical Data ¹H NMR 400 MHz (DMSO-d₆) and/or MS (m/z) |
|---|---|---|
| 21 | 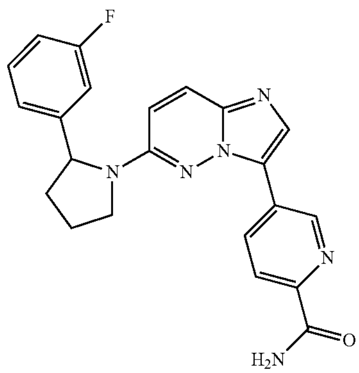 [SMILES: NC(=O)c1ccc(-c2cnc3ccc(N4CCCC4c4cccc(F)c4)nn23)cn1] | m/z 404.2 (M + 1) |
| 22 | 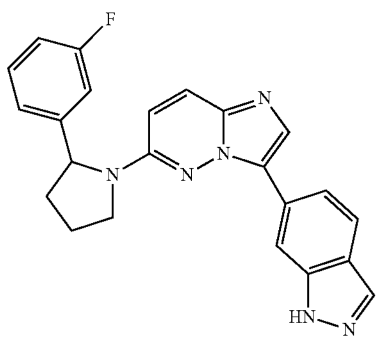 [SMILES: Fc1cccc(C2CCCN2c2ccc3ncc(-c4ccc5cn[nH]c5c4)n3n2)c1] | m/z 399.2 (M + 1) |
| 23 | 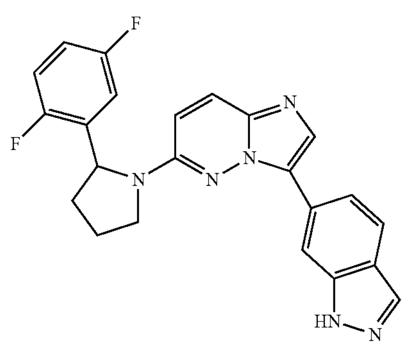 [SMILES: Fc1ccc(F)c(C2CCCN2c2ccc3ncc(-c4ccc5cn[nH]c5c4)n3n2)c1] | m/z 417.2 (M + 1) |
| 24 | 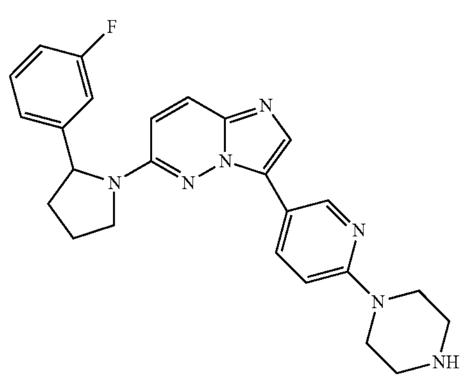 [SMILES: Fc1cccc(C2CCCN2c2ccc3ncc(-c4ccc(N5CCNCC5)nc4)n3n2)c1] | m/z 444.5 (M + 1) |

TABLE 3-continued
| Compound Number | Structure | Physical Data<br>¹H NMR 400 MHz<br>(DMSO-d₆) and/or MS (m/z) |
|---|---|---|
| 25 | 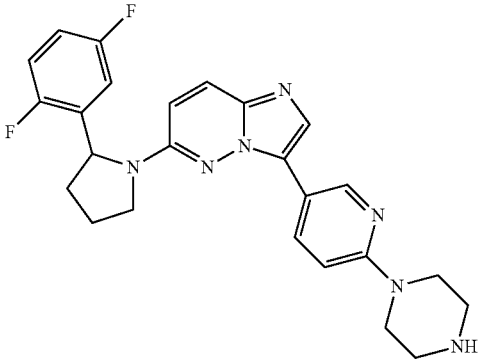 [SMILES: Fc1ccc(F)c(C2CCCN2c2ccc3ncc(-c4ccc(N5CCNCC5)nc4)n3n2)c1] | m/z 462.2 (M + 1) |
| 26 | 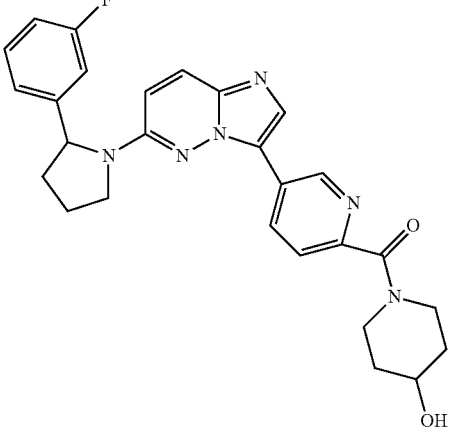 | m/z 487.3 (M + 1) |
| 27 | 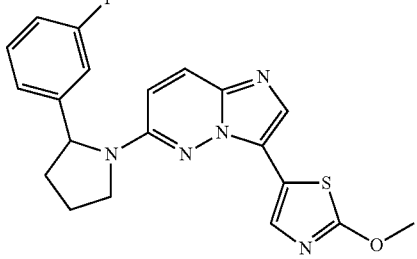 | m/z 396.2 (M + 1) |
| 28 | 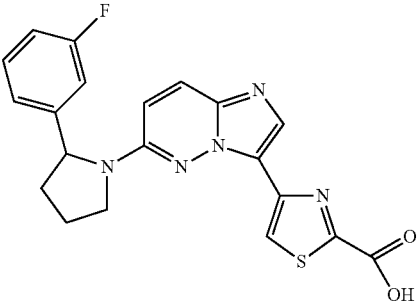 [SMILES: O=C(O)c1nc(-c2cnc3ccc(N4CCCC4c4cccc(F)c4)nn23)cs1] | m/z 410.2 (M + 1) |

TABLE 3-continued
| Compound Number | Structure | Physical Data ¹H NMR 400 MHz (DMSO-d$_6$) and/or MS (m/z) |
|---|---|---|
| 29 | 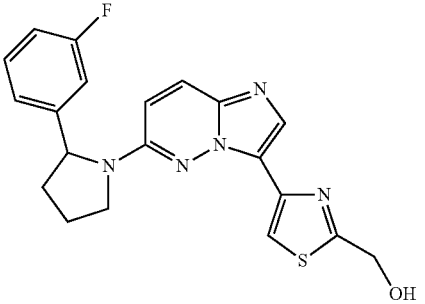 [SMILES: OCc1nc(-c2cnc3ccc(N4CCCC4c4cccc(F)c4)nn23)cs1] | m/z 396.2 (M + 1) |
| 30 | 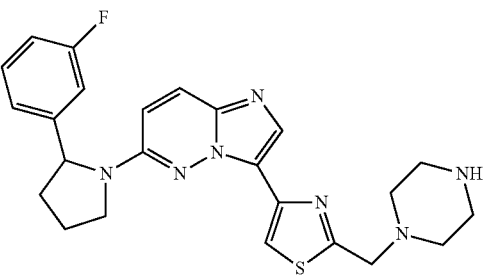 [SMILES: Fc1cccc(C2CCCN2c2ccc3ncc(-c4csc(CN5CCNCC5)n4)n3n2)c1] | m/z 464.2 (M + 1) |
| 31 | 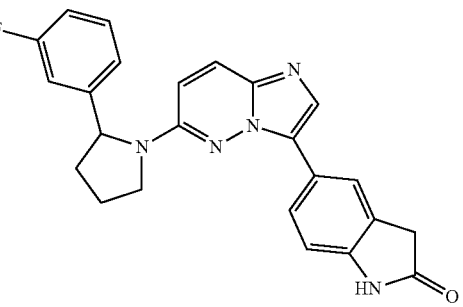 | m/z 414 (M + 1) |
| 32 | 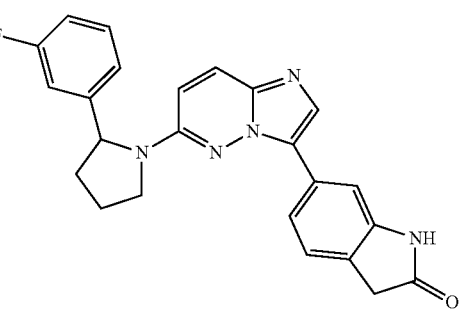 | ¹H NMR DMSO-d6 (ppm) 10.64 (s, 1H), 8.31 (m, 1H), 8.05 (m, 1H), 7.64 (m, 1H), 7.35 (m, 2H), 7.13 (m, 5H), 5.23 (m, 1H), 4.01 (m, 2H), 3.69 (m, 1H), 3.56 (s, 2H), 2.05 (m, 2H), 1.91 (m, 1H); m/z 414 (M + 1) |

TABLE 3-continued

| Compound Number | Structure | Physical Data<br>$^1$H NMR 400 MHz<br>(DMSO-$d_6$) and/or MS (m/z) |
| --- | --- | --- |
| 33 | 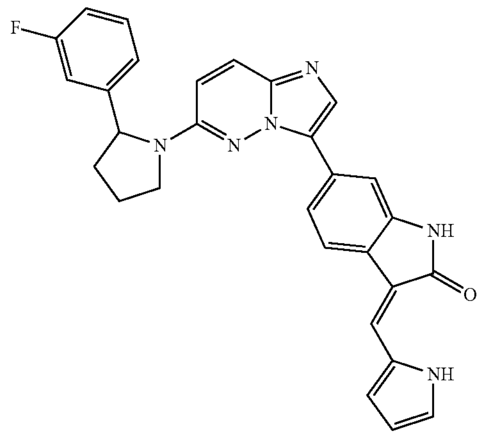 [SMILES: O=C1Nc2cc(-c3cnc4ccc(N5CCCC5c5cccc(F)c5)nn34)ccc2/C1=C/c1ccc[nH]1] | m/z 491 (M + 1) |
| 34 | 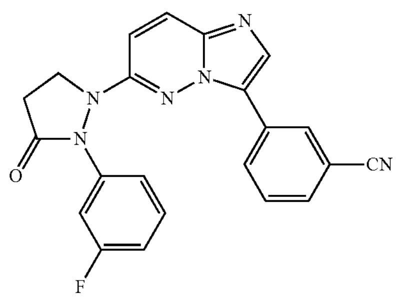 [SMILES: N#Cc1cccc(-c2cnc3ccc(N4CCC(=O)N4c4cccc(F)c4)nn23)c1] | MS m/z 399 (M + 1) |
| 35 | 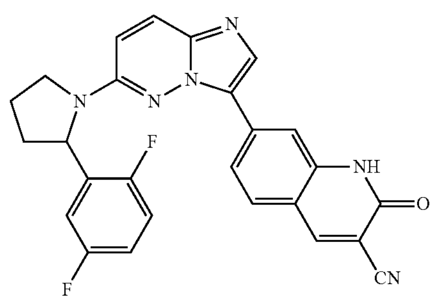 [SMILES: N#Cc1cc2ccc(-c3cnc4ccc(N5CCCC5c5cc(F)ccc5F)nn34)cc2[nH]c1=O] | MS m/z 469 (M + 1) |
| 36 | 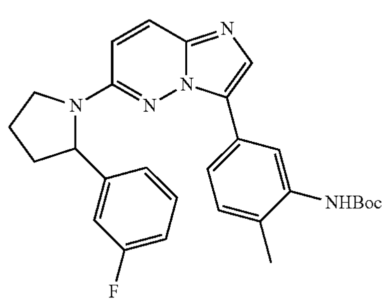 [SMILES: Cc1ccc(-c2cnc3ccc(N4CCCC4c4cccc(F)c4)nn23)cc1NC(=O)OC(C)(C)C] | MS m/z 488 (M + 1) |

TABLE 3-continued
| Compound Number | Structure | Physical Data $^1$H NMR 400 MHz (DMSO-$d_6$) and/or MS (m/z) |
|---|---|---|
| 37 | 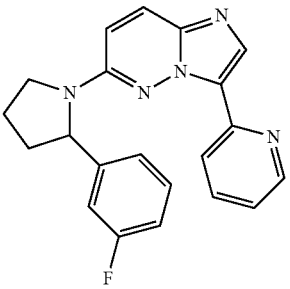 [SMILES: Fc1cccc(C2CCCN2c2ccc3ncc(-c4ccccn4)n3n2)c1] | MS m/z 360 (M + 1) |
| 38 | 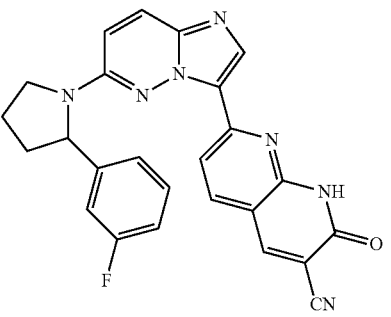 [SMILES: N#Cc1cc2ccc(-c3cnc4ccc(N5CCCC5c5cccc(F)c5)nn34)nc2[nH]c1=O] | MS m/z 451 (M + 1) |
| 39 | 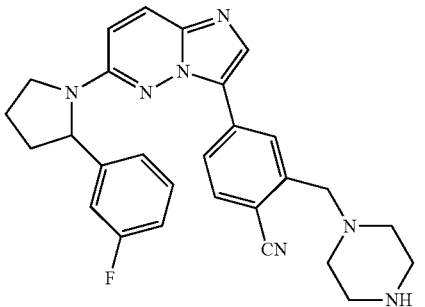 [SMILES: N#Cc1ccc(-c2cnc3ccc(N4CCCC4c4cccc(F)c4)nn23)cc1CN1CCNCC1] | MS m/z 482 (M + 1) |
| 40 | 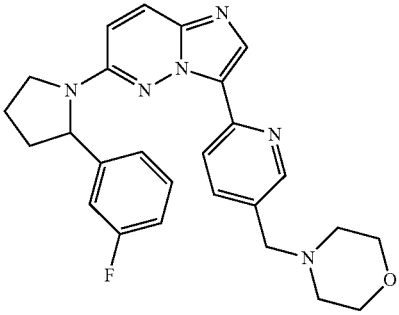 [SMILES: Fc1cccc(C2CCCN2c2ccc3ncc(-c4ccc(CN5CCOCC5)cn4)n3n2)c1] | MS m/z 459 (M + 1) |

TABLE 3-continued

| Compound Number | Structure | Physical Data<br>¹H NMR 400 MHz<br>(DMSO-d$_6$) and/or MS (m/z) |
|---|---|---|
| 41 | 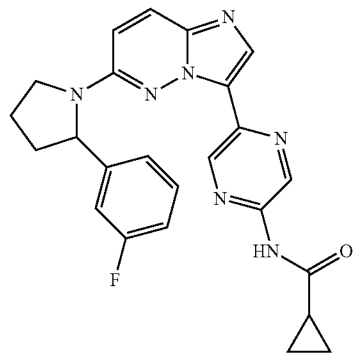 [SMILES: O=C(Nc1cnc(-c2cnc3ccc(N4CCCC4c4cccc(F)c4)nn23)cn1)C1CC1] | MS m/z 444 (M + 1) |
| 42 | 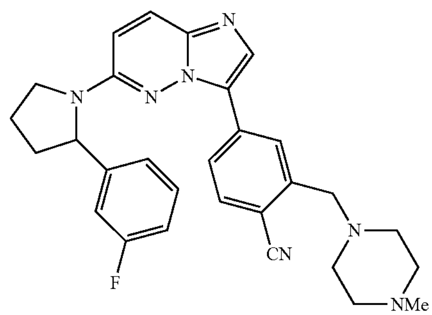 [SMILES: CN1CCN(Cc2cc(-c3cnc4ccc(N5CCCC5c5cccc(F)c5)nn34)ccc2C#N)CC1] | MS m/z 496 (M + 1) |
| 43 | 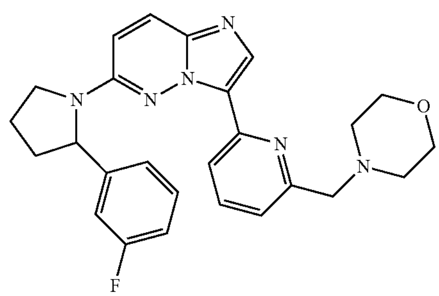 [SMILES: Fc1cccc(C2CCCN2c2ccc3ncc(-c4cccc(CN5CCOCC5)n4)n3n2)c1] | MS m/z 459 (M + 1) |
| 44 | 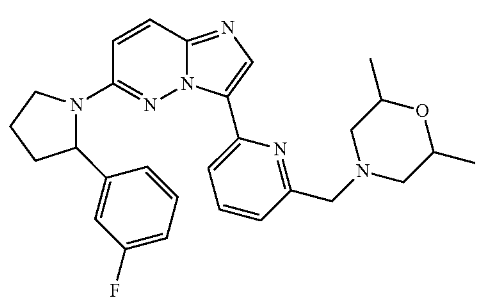 [SMILES: CC1CN(Cc2cccc(-c3cnc4ccc(N5CCCC5c5cccc(F)c5)nn34)n2)CC(C)O1] | MS m/z 487 (M + 1) |

TABLE 3-continued

| Compound Number | Structure | Physical Data $^1$H NMR 400 MHz (DMSO-d$_6$) and/or MS (m/z) |
|---|---|---|
| 45 | 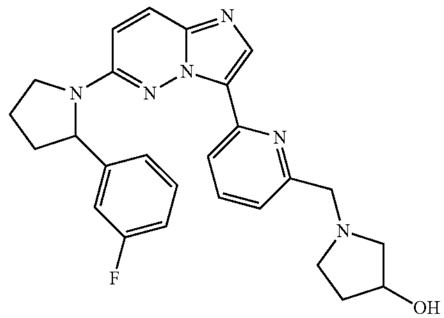 [SMILES: OC1CCN(Cc2cccc(-c3cnc4ccc(N5CCCC5c5cccc(F)c5)nn34)n2)C1] | MS m/z 459 (M + 1) |
| 46 | 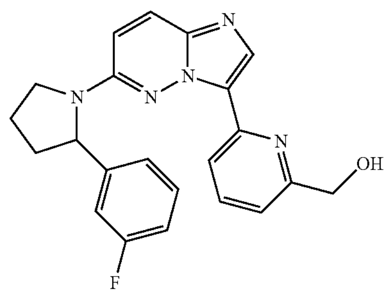 [SMILES: OCc1cccc(-c2cnc3ccc(N4CCCC4c4cccc(F)c4)nn23)n1] | MS m/z 389 (M + 1) |
| 47 | 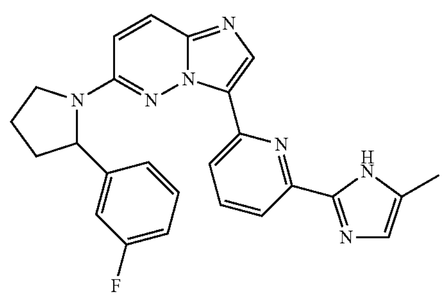 [SMILES: Cc1cnc(-c2cccc(-c3cnc4ccc(N5CCCC5c5cccc(F)c5)nn34)n2)[nH]1] | MS m/z 440 (M + 1) |
| 48 | 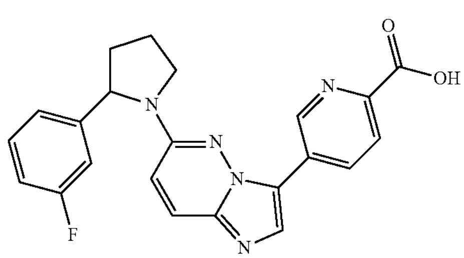 [SMILES: O=C(O)c1ccc(-c2cnc3ccc(N4CCCC4c4cccc(F)c4)nn23)cn1] | m/z 404.2 (M + 1) |
| 49 | 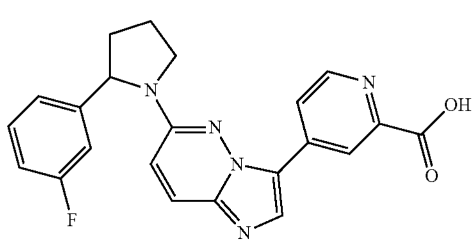 [SMILES: O=C(O)c1cc(-c2cnc3ccc(N4CCCC4c4cccc(F)c4)nn23)ccn1] | m/z 404.2 (M + 1) |

TABLE 3-continued

| Compound Number | Structure | Physical Data<br>¹H NMR 400 MHz<br>(DMSO-d₆) and/or MS (m/z) |
|---|---|---|
| 50 | 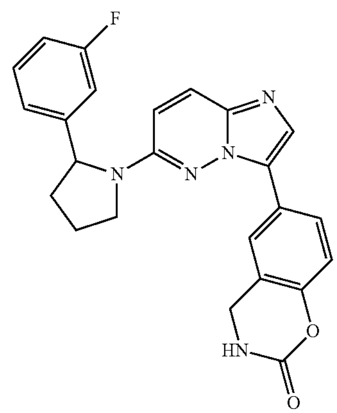 [SMILES: O=C1NCc2cc(-c3cnc4ccc(N5CCCC5c5cccc(F)c5)nn34)ccc2O1] | 1H NMR (DMSO-d6): δ 8.02 (s, 1H), 7.90 (s, 1H), 7.88 (s, 1H), 7.86 (s, 1H), 7.37-7.40 (m, 1H), 7.14 (d, 2H), 7.05 (t, 1H), 6.95 (d, 1H), 6.81 (d, 1H), 5.18 (d, 1H), 4.40-4.45 (m, 1H), 4.30-4.40 (m, 1H), 3.95-3.99 (m, 1H), 3.62-3.66 (m, 1H), ; 2.43-2.49 (m, 1H), 1.95-2.05 (m, 2H), 1.85-1.90 (m, 1H)<br>m/z 430.4 (M + 1) |
| 51 | 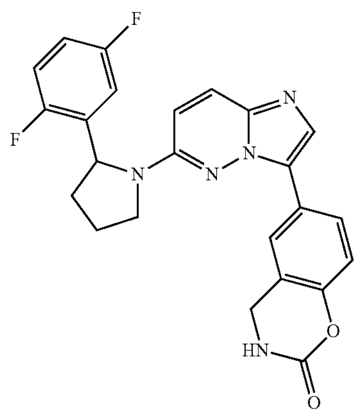 [SMILES: O=C1NCc2cc(-c3cnc4ccc(N5CCCC5c5cc(F)ccc5F)nn34)ccc2O1] | m/z 448.4 (M + 1) |
| 52 | 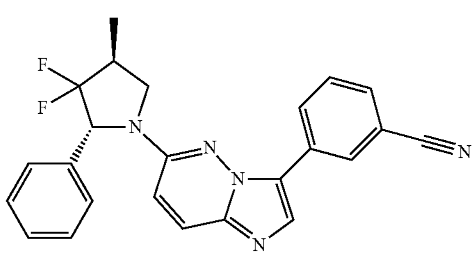 [SMILES: C[C@H]1CN(c2ccc3ncc(-c4cccc(C#N)c4)n3n2)[C@H](c2ccccc2)C1(F)F] | 1H NMR (DMSO-d6): d 8.49 (s, 1H), 8.18-8.24 (m, 1H), 8.16 (s, 1H), 8.00 (d, 1H), 7.73 (d, 1H), 7.56 (t, 1H), 7.49 (d, 2H), 7.40 (t, 2H), 7.32 (t, 1H), 6.88-6.96 (m, 1H), 5.43 (d, 1H), 4.37 (t, 1H), 3.40 (t, 1H), 2.76-2.94 (m, 1H), 1.17 (d, 3H)<br>m/z 416.4 (M + 1) |
| 53 | 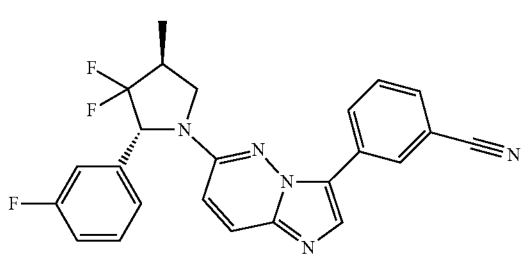 [SMILES: C[C@H]1CN(c2ccc3ncc(-c4cccc(C#N)c4)n3n2)[C@H](c2cccc(F)c2)C1(F)F] | 1H NMR (DMSO-d6): 8.55 (s, 1H), 8.18-8.25 (m, 1H), 8.16 (s, 1H), 8.00 (d, 1H), 7.74 (d, 1H), 7.55 (t, 1H), 7.42-7.49 (m, 1H), 7.33-7.39 (m, 2H), 7.11-7.19 (m, 1H), 6.88-6.98 (m, 1H), 5.47 (d, 1H), 4.38 (t, 1H), 3.86 (t, 1H), 2.78-2.94 (m, 1H), 1.17 (d, 3H)<br>m/z 434.4 (M + 1) |

TABLE 3-continued

| Compound Number | Structure | Physical Data ¹H NMR 400 MHz (DMSO-d$_6$) and/or MS (m/z) |
|---|---|---|
| 54 | 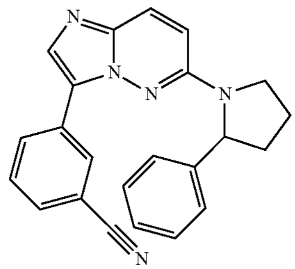 [SMILES: N#Cc1cccc(-c2cnc3ccc(N4CCCC4c4ccccc4)nn23)c1] | H NMR (DMSO-d6) d 855 (s, 1H), 8.20-8.32 (bs, 1H), 8.12 (s, 1H), 7.89 (d, 1H), 7.71 (d, 1H), 7.54 (t, 1H), 7.26-7.36 (m, 4H), 7.18-7.24 (m, 1H), 6.76-6.91 (bs, 1H), 5.15-5.21 (m, 1H), 3.94-4.02 (m, 1H), 3.66-3.72 (m, 1H), 2.45-2.50 (m, 1H), 2.01-2.08 (m, 2H), 1.82-1.90 (m, 1H) m/z 366.4 (M + 1) |
| 55 | 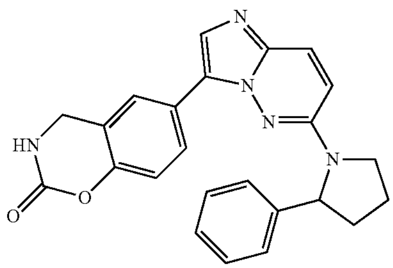 [SMILES: O=C1NCc2cc(-c3cnc4ccc(N5CCCC5c5ccccc5)nn34)ccc2O1] | m/z 412.5 (M + 1) |
| 56 | 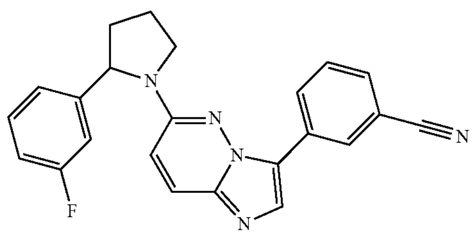 [SMILES: N#Cc1cccc(-c2cnc3ccc(N4CCCC4c4cccc(F)c4)nn23)c1] | m/z 384.4 (M + 1) |
| 57 | 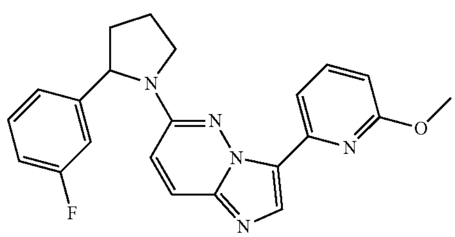 [SMILES: COc1cccc(-c2cnc3ccc(N4CCCC4c4cccc(F)c4)nn23)n1] | 1H NMR (DMSO-d6) 8.14 (s, 1H), 7.91 (s, 1H), 7.58-7.64 (m, 2 H), 7.53-7.57 (m, 1H), 7.35-7.41 (m, 1H), 7.15-7.17 (m, 2H), 7.01-7.05 (m, 1H), 6.68 (d, 1H), 5.16-5.19 (q, 1H), 3.98-4.02 (m, 1H), 3.91 (s, 3H), 3.65-3.71 (m, 1H), 2.44-2.49 (m, 1H), 2.01-2.07 (m, 2H), 1.85-1.90 (m, 1H) m/z 390.4 (M + 1) |
| 58 | 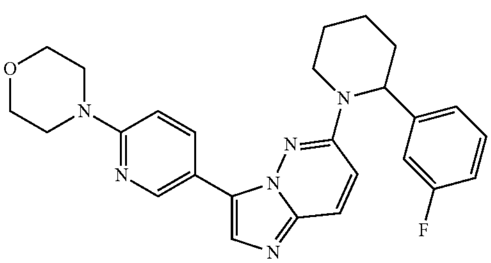 [SMILES: Fc1cccc(C2CCCCN2c2ccc3ncc(-c4ccc(N5CCOCC5)nc4)n3n2)c1] | HNMR (DMSO-d6, 400 MHz) 8.725 (d, J = 0.005, 1H), 8.374 (s, 1H), 8.195 (d, J = 0.025, 1H) 8.074 (dd, J = 0.023, 0.006, 1H) 7.705 (d, J = 0.026, 1H) 7.406 (q, J = 0.02, 1H) 7.149 (s, 1H) 7.129 (s, 1H) 7.082 (dt, J = 0.015, 0.005, 1H) 6.973 (d, J = 0.023, 1H) 5.561 (t, J = 0.01, 1H) 4.270 (d, J = 0.033, 1H) 3.725 (t, J = 0.011, 4H) 3.561 (t, J = 0.013, 4H) 3.317 (dt, J = 0.035, 0.01, 1H) 2.265 (m, 1H) 20.39 (m, 1H) 1.782 (m, 1H) 1.649 (m, 2H) 1.455 (m, 1H) m/z 459.2 (M + 1) |
| 59 | 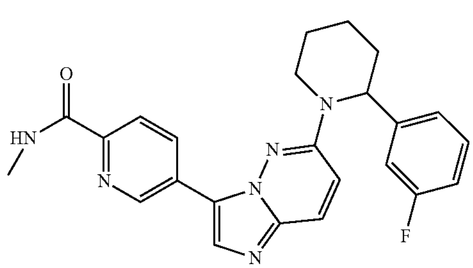 [SMILES: CNC(=O)c1ccc(-c2cnc3ccc(N4CCCCC4c4cccc(F)c4)nn23)cn1] | m/z 431.2 (M + 1) |

TABLE 3-continued

| Compound Number | Structure | Physical Data $^1$H NMR 400 MHz (DMSO-d$_6$) and/or MS (m/z) |
|---|---|---|
| 60 | 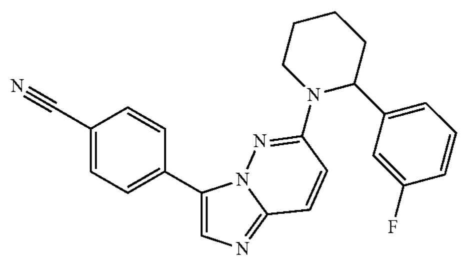 [SMILES: N#Cc1ccc(-c2cnc3ccc(N4CCCCC4c4cccc(F)c4)nn23)cc1] | m/z 398.2 (M + 1) |
| 61 | 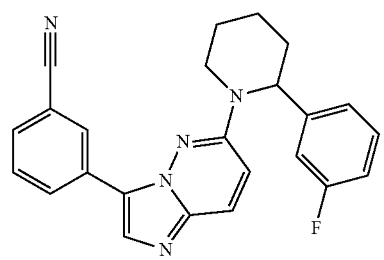 [SMILES: N#Cc1cccc(-c2cnc3ccc(N4CCCCC4c4cccc(F)c4)nn23)c1] | m/z 398.2 (M + 1) |
| 62 | 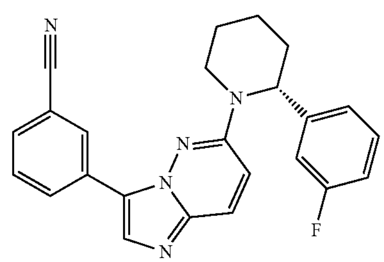 [SMILES: N#Cc1cccc(-c2cnc3ccc(N4CCCC[C@@H]4c4cccc(F)c4)nn23)c1] | m/z 398.2 (M + 1) |
| 63 | 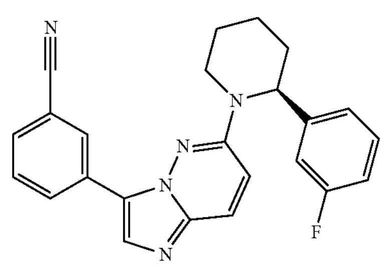 [SMILES: N#Cc1cccc(-c2cnc3ccc(N4CCCC[C@H]4c4cccc(F)c4)nn23)c1] | m/z 398.2 (M + 1) |
| 64 | 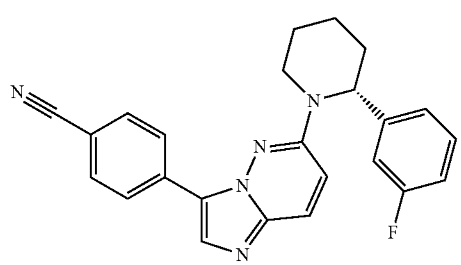 [SMILES: N#Cc1ccc(-c2cnc3ccc(N4CCCC[C@@H]4c4cccc(F)c4)nn23)cc1] | m/z 398.2 (M + 1) |

TABLE 3-continued

| Compound Number | Structure | Physical Data<br>¹H NMR 400 MHz<br>(DMSO-d₆) and/or MS (m/z) |
|---|---|---|
| 65 | 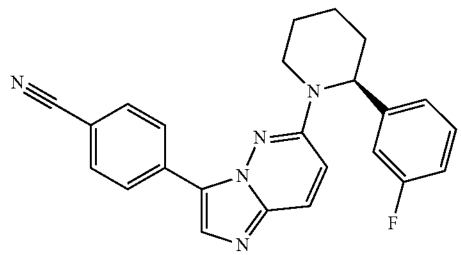 [SMILES: N#Cc1ccc(-c2cnc3ccc(N4CCCC[C@H]4c4cccc(F)c4)nn23)cc1] | m/z 398.2 (M + 1) |
| 66 | 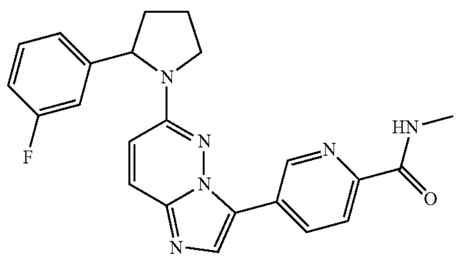 [SMILES: CNC(=O)c1ccc(-c2cnc3ccc(N4CCCC4c4cccc(F)c4)nn23)cn1] | HNMR (DMSO-d6, 400 MHz)<br>9.198 (br.s, 1H) 8.790 (ds, J = 0.011,<br>1H) 8.504 (s, 1H) 8.102 (d, J = 0.025,<br>1H) 8.008 (br.s, 1H) 7.377 (q, J = 0.019,<br>1H) 7.166 (d, J = 0.019) 7.166 (m, 3H)<br>7.083 (dt, J = 0.019, 0.004, 1H) 5.192<br>(d, J = 0.017, 1H) 4.011 (m, 1H)<br>3.695 (q, J = 0.025, 1H) 2.868 (d,<br>J = 0.102, 3H) 2.451 (m, 1H)<br>2.056 (m, 2H), 1.898 (m, 1H)<br>m/z 417.5 (M + 1) |
| 67 | 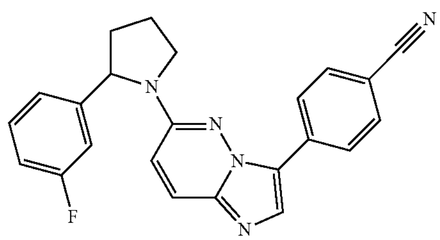 [SMILES: N#Cc1ccc(-c2cnc3ccc(N4CCCC4c4cccc(F)c4)nn23)cc1] | m/z 384.4 (M + 1) |
| 68 | 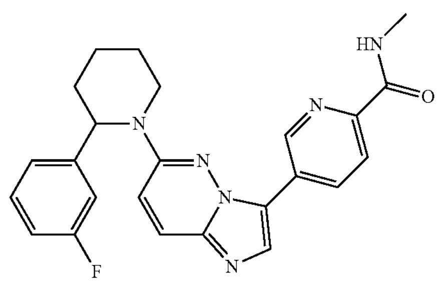 [SMILES: CNC(=O)c1ccc(-c2cnc3ccc(N4CCCCC4c4cccc(F)c4)nn23)cn1] | m/z 431.5 (M + 1) |
| 69 | 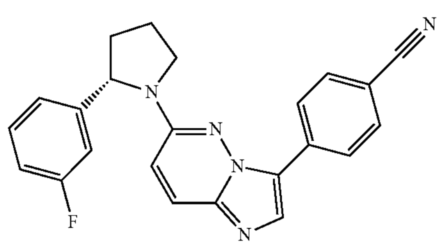 | HNMR (DMSO-d6, 400 MHz)<br>8.205 (br.s 2H) 7.994 (d, J = 0.025,<br>1H) 7.815 (d, J = 0.019, 2H) 7.486<br>(q, J = 0.021, 1H) 7.222 (m, 2H)<br>7.108 (dt, J = 0.023, 0.006, 1H) 6.959<br>(br.s, 1H) 5.209 (dd, J = 0.021, 0.007,<br>1H) 4.048 (p, J = 0.014, 1H) 3.719 (q,<br>J = 0.02, 1H) 2.513 (m, 1H),<br>2.092 (m, 2H) 1.919 (m, 1H)<br>m/z 384.4 (M + 1) |
| 70 | 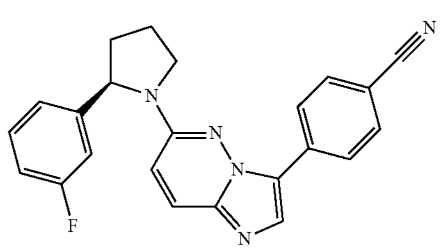 [SMILES: N#Cc1ccc(-c2cnc3ccc(N4CCC[C@@H]4c4cccc(F)c4)nn23)cc1] | HNMR (DMSO-d6, 400 MHz)<br>8.084 (br.s, 2H) 7.875 (d, J =<br>0.024, 1H) 7.697 (d, J = 0.02, 2H)<br>7.364 (q, J = 0.02, 1H) 7.100 (m,<br>2H) 6.985 (dt, J = 0.023, 0.006,<br>2H) 6.841 (br.s, 1H) 5.091 (dd, J = 0.02,<br>0.006, 1H) 3.928 (p, J = 0.014 1H)<br>3.600 (q, J = 0.021, 1H) 2.370 (m, 1H)<br>1.971 (m, 2H) 1.797 (m, 1H)<br>m/z 384.4 (M + 1) |

TABLE 3-continued

| Compound Number | Structure | Physical Data<br>¹H NMR 400 MHz<br>(DMSO-d₆) and/or MS (m/z) |
|---|---|---|
| 71 | 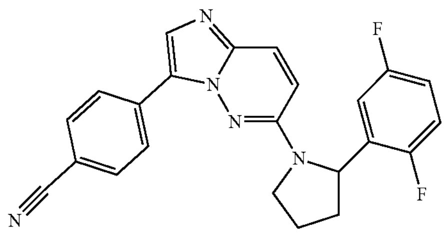 [SMILES: N#Cc1ccc(-c2cnc3ccc(N4CCCC4c4cc(F)ccc4F)nn23)cc1] | m/z 402.4 (M + 1) |
| 72 | 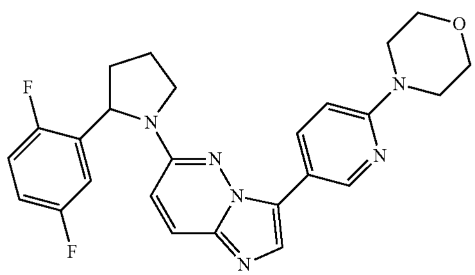 [SMILES: Fc1ccc(F)c(C2CCCN2c2ccc3ncc(-c4ccc(N5CCOCC5)nc4)n3n2)c1] | HNMR (DMSO-d6, 400 MHz)<br>8.572 (br.s, 1H) 7.739 (m, 3H)<br>7.306 (m, 1H) 7.056 (m,<br>1H) 7.056 (m, 1H) 6.954 (m, 1H)<br>6.739 (s, 1H) 6.638 (m, 1H) 5.203<br>(d, J = 0.016, 1H) 3.916 (m, 1H)<br>3.837 (m, 1H) 3.667 (m, 4H)<br>3.540 (m, 1H) 3.425 (m, 4H)<br>2.391 (m, 1H) 2.009 (m, 2H)<br>1.830 (m, 1H)<br>m/z 463.5 (M + 1) |
| 73 | 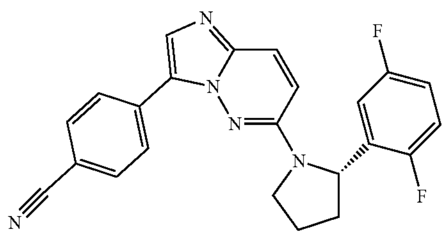 [SMILES: N#Cc1ccc(-c2cnc3ccc(N4CCC[C@H]4c4cc(F)ccc4F)nn23)cc1] | HNMR (DMSO-d6, 400 MHz)<br>8.094 (s, 1H) 7.998 (br.s, 2H)<br>7.917 (d, J = 0.024, 1H) 7.660 (d,<br>J = 0.021 2H) 7.423 (dq, J =<br>0.024, 0.011, 1H) 7.061 (m, 1H)<br>6.992 (m, 1H) 6.925 (br.s, 1H) 5.248<br>(d, J = 0.019, 1H) 3.962 (m, 1H) 3.561<br>(q, J = 0.018, 1H) 2.382 (m, 1H)<br>1.998 (m, 2H) 1.830 (m, 1H)<br>m/z 402.4 (M + 1) |
| 74 | 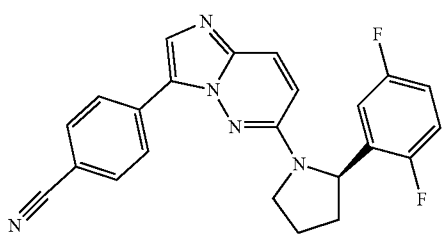 [SMILES: N#Cc1ccc(-c2cnc3ccc(N4CCC[C@@H]4c4cc(F)ccc4F)nn23)cc1] | HNMR (DMSO-d6, 400 MHz)<br>8.091 (s, (1H) 7.994 (br.s, 2H)<br>7.913 (d, J = 0.025, 1H) 7.655 (d,<br>J = 0.02, 1H) 7.421 (dq, J =<br>0.021, 0.011, 1H) 7.059 (m, 1H)<br>6.989 (m, 1H) 6.925 (br.s, 1H)<br>5.242 (d, J = 0.019, 1H) 3.959 (m, 1H)<br>3.556 (q, J = 0.018, 1H) 2.390 (m, 1H)<br>1.997 (m, 2H) 1.819 (m, 1H)<br>m/z 402.4 (M + 1) |
| 75 | 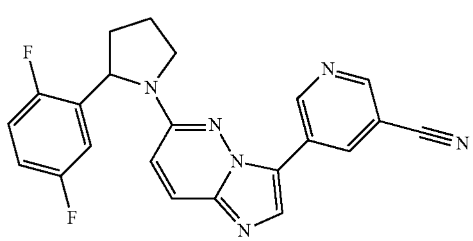 [SMILES: N#Cc1cncc(-c2cnc3ccc(N4CCCC4c4cc(F)ccc4F)nn23)c1] | m/z 403.4 (M + 1) |
| 76 | 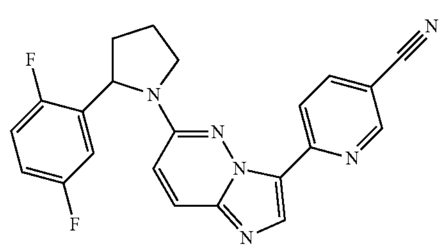 [SMILES: N#Cc1ccc(-c2cnc3ccc(N4CCCC4c4cc(F)ccc4F)nn23)nc1] | m/z 403.4 (M + 1) |

TABLE 3-continued

| Compound Number | Structure | Physical Data<br>¹H NMR 400 MHz<br>(DMSO-d₆) and/or MS (m/z) |
|---|---|---|
| 77 | 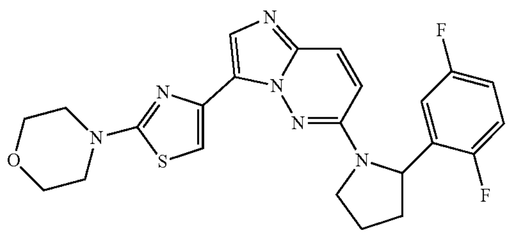 [SMILES: Fc1ccc(F)c(C2CCCN2c2ccc3ncc(-c4csc(N5CCOCC5)n4)n3n2)c1] | HNMR (DMSO-d6, 400 MHz) 7.854 (d, J = 0.024, 1H) 7.710 (s, 1H) 7.248 (m, 1H) 7.072 (m, 1H) 6.979 (m, 1H) 6.801 (m, 1H), 6.694 (m, 1H) 5.274 (d, J = 0.019, 1H) 3.948 (dt, J = 0.025, 0.007, 1H) 3.658 (t, 0.011, 4H), 3.572 (q, J = 0.024, 1H) 3.359 (t, J = 0.012, 3H) 2.007 (m, 3H) 1.285 (s, 1H) 1.164 (s, 1H) m/z 469.5 (M + 1) |
| 78 | 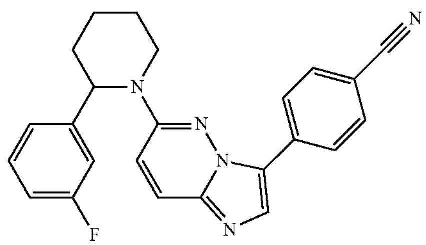 [SMILES: N#Cc1ccc(-c2cnc3ccc(N4CCCCC4c4cccc(F)c4)nn23)cc1] | m/z 398.4 (M + 1) |
| 79 | 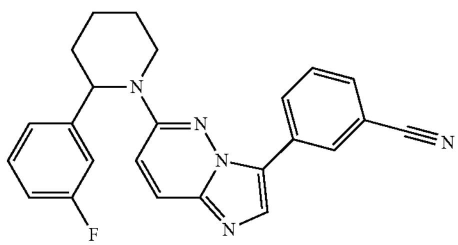 [SMILES: N#Cc1cccc(-c2cnc3ccc(N4CCCCC4c4cccc(F)c4)nn23)c1] | m/z 398.4 (M + 1) |
| 80 | 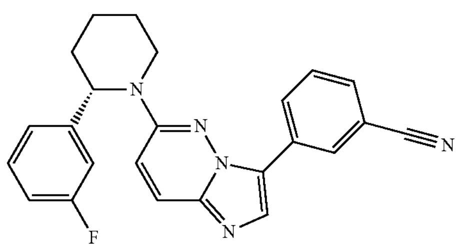 [SMILES: N#Cc1cccc(-c2cnc3ccc(N4CCCC[C@H]4c4cccc(F)c4)nn23)c1] | m/z 398.4 (M + 1) |
| 81 | 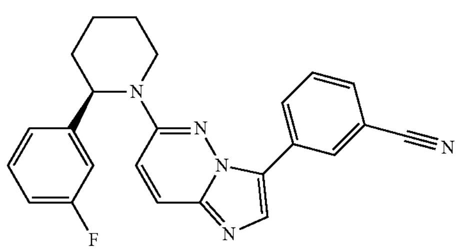 [SMILES: N#Cc1cccc(-c2cnc3ccc(N4CCCC[C@@H]4c4cccc(F)c4)nn23)c1] | m/z 398.4 (M + 1) |
| 82 | 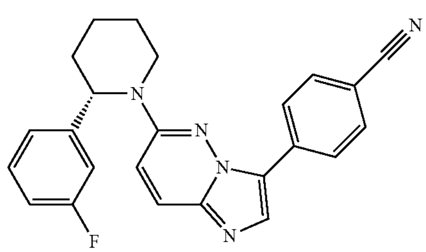 [SMILES: N#Cc1ccc(-c2cnc3ccc(N4CCCC[C@H]4c4cccc(F)c4)nn23)cc1] | m/z 398.4 (M + 1) |

TABLE 3-continued

| Compound Number | Structure | Physical Data<br>¹H NMR 400 MHz<br>(DMSO-d₆) and/or MS (m/z) |
|---|---|---|
| 83 | 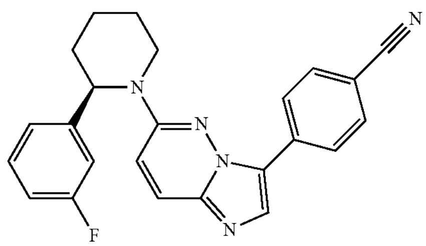 [SMILES: N#Cc1ccc(-c2cnc3ccc(N4CCCC[C@@H]4c4cccc(F)c4)nn23)cc1] | m/z 398.4 (M + 1) |
| 84 | 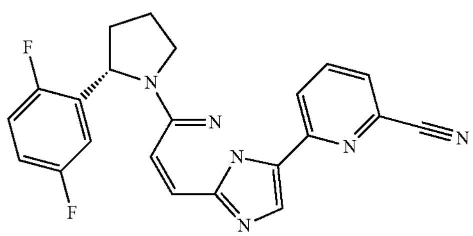 [SMILES: N#Cc1cccc(-c2cnc(/C=C\C(=N)N3CCC[C@H]3c3cc(F)ccc3F)[nH]2)n1] | m/z 403.4 (M + 1) |
| 85 | 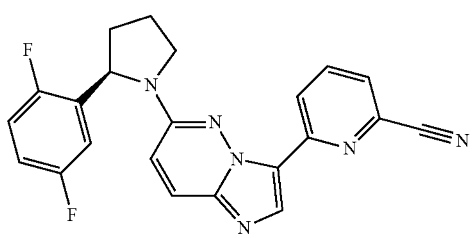 [SMILES: N#Cc1cccc(-c2cnc3ccc(N4CCC[C@@H]4c4cc(F)ccc4F)nn23)n1] | m/z 403.4 (M + 1) |
| 86 | 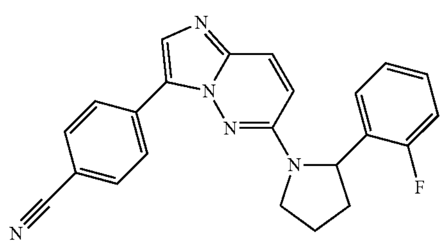 [SMILES: N#Cc1ccc(-c2cnc3ccc(N4CCCC4c4ccccc4F)nn23)cc1] | m/z 384.4 (M + 1) |
| 87 | 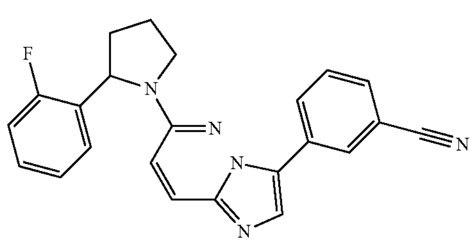 [SMILES: N#Cc1cccc(-c2cnc(/C=C\C(=N)N3CCCC3c3ccccc3F)[nH]2)c1] | m/z 384.4 (M + 1) |
| 88 | 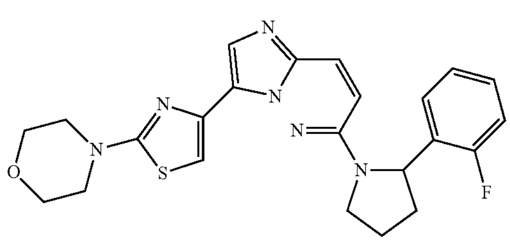 [SMILES: N=C(/C=C\c1ncc(-c2csc(N3CCOCC3)n2)[nH]1)N1CCCC1c1ccccc1F] | m/z 451.5 (M + 1) |

TABLE 3-continued

| Compound Number | Structure | Physical Data $^1$H NMR 400 MHz (DMSO-d$_6$) and/or MS (m/z) |
|---|---|---|
| 89 | 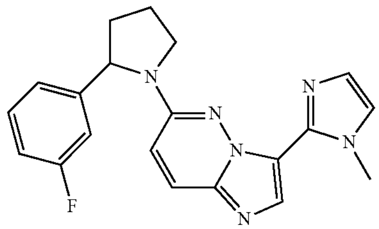 [SMILES: Cn1ccnc1-c1cnc2ccc(N3CCCC3c3cccc(F)c3)nn12] | m/z 363.4 (M + 1) |
| 90 | 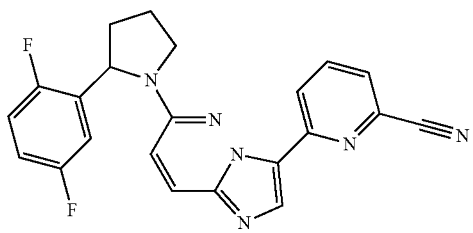 [SMILES: N#Cc1cccc(-c2cnc(/C=C\C(=N)N3CCCC3c3cc(F)ccc3F)[nH]2)n1] | m/z 403.4 (M + 1) |
| 91 | 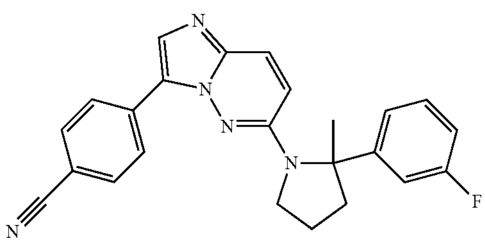 [SMILES: CC1(c2cccc(F)c2)CCCN1c1ccc2ncc(-c3ccc(C#N)cc3)n2n1] | m/z 398.4 (M + 1) |
| 92 | 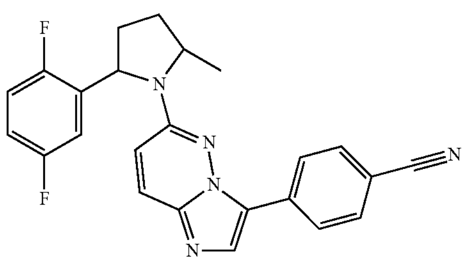 [SMILES: CC1CCC(c2cc(F)ccc2F)N1c1ccc2ncc(-c3ccc(C#N)cc3)n2n1] | 8.166 (s, 1H) 8.019 (s, 1H) 7.998 (d, J = 0.01, 1H) 7.963 (s, 1H) 7.719 (d, J = 0.021, 2H) 7.514 (dq, J = 0.024, 0.011, 1H) 7.143 (m, 1H) 6.990 (m, 2H) 5.199 (t, J = 0.02, 1H) 4.338 (d, sextet, J = 0.017, 0.006 1H) 2.550 (m, 1H) 2.223 (m, 1H) 1.944 (m, 1H) 1.768 (m, 1H) 1.497 (d, J = 0.016, 3H)<br>m/z 416.4 (M + 1) |
| 93 | 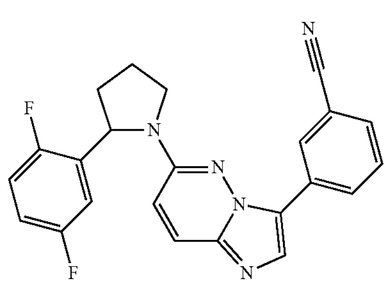 [SMILES: N#Cc1cccc(-c2cnc3ccc(N4CCCC4c4cc(F)ccc4F)nn23)c1] | 8.327 (br s, 1H) 8.123 (s, 2H) 7.938 (d, J = 0.025, 1H) 7.678 (d, J = 0.020, 1H) 7.423 (t, J = 0.020, 1H) 7.272 (m, 1H) 7.045 (m, 1H) 6.964 (m, 2H) 5.275 (d, J = 0.019, 1H) 3.967 (dt, J = 0.024, 0.006, 1H) 3.564 (q, J = 0.023, 2H) 1.998 (m, 3H)<br>m/z 402.4 (M + 1) |

165

Scheme 5

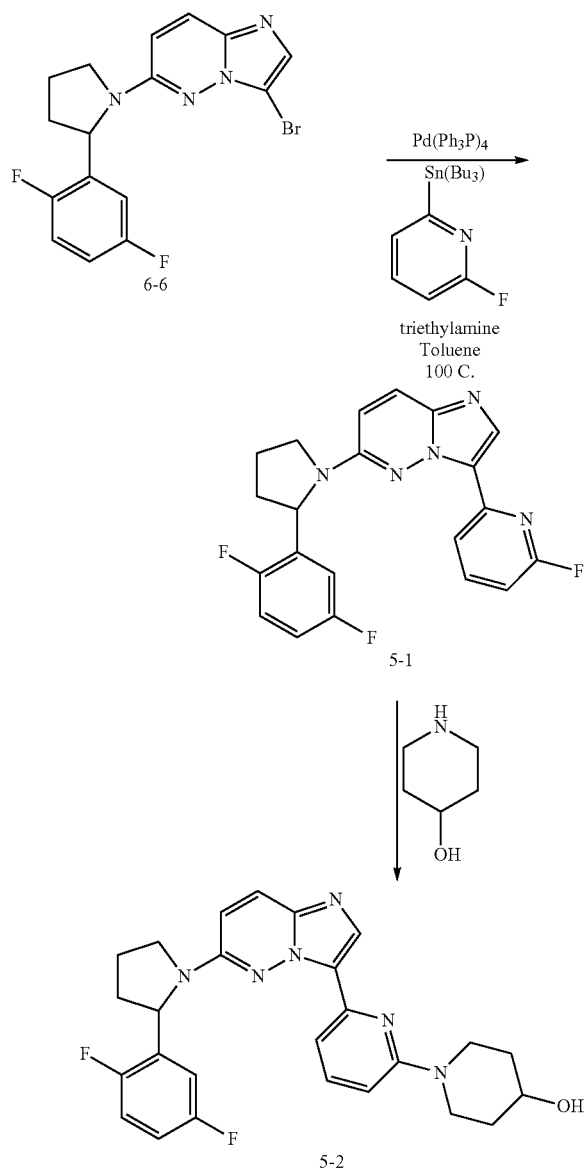

166

Example 5

1-(6-(6-(2-(2,5-difluorophenyl)pyrrolidin-1-yl)imidazo[1,2-b]pyridazin-3-yl)pyridin-2-yl)piperidin-4-ol 1-(6-(6-(2-(2,5-difluorophenyl)pyrrolidin-1-yl)imidazo[1,2-b]pyridazin-3-yl)pyridin-2-yl)piperidin-4-ol (5-2) was synthesized in two steps as shown in scheme 5.

In step 5-1, triethylamine (0.045 mL, 0.29 mmol), tetrakis(triphenylphospine)palladium (0) (12 mg, 0.01 mmol), and 6-fluoro-2(tributylstannyl)pyridine (80 mg, 0.201 mmol) were added to a solution of 3-bromo-6-(2-(2,5-difluorophenyl)pyrrolidin-1-yl)imidazo[1,2-b]pyridazine (6-6) (53 mg, 0.13 mmol) in 3 mL of toluene. The reaction mixture was heated to 100° C. and stirred for 6 hours at 100° C. The reaction mixture was then cooled to room temperature and purified using flash chromatography (ethyl acetate and hexanes (1:1)) giving 6-(2-(2,5-difluorophenyl)pyrrolidin-1-yl)-3-(6-fluoropyridin-2-yl)imidazo[1,2-b]pyridazine (5-1). $^1$H NMR (400 MHz, $D_3$ acetonitrile) δ ppm 8.35-8.17 (m, 2H), 8.02-7.83 (m, 1H), 7.48-7.22 (m, 3H), 7.15-6.92 (m, 3H), 5.42 (br d, J=5.8 Hz, 1H), 4.12-3.99 (m, 1H), 3.81-3.72 (m, 1H), 2.70-2.56 (m, 1H), 2.30-2.06 (m, 3H). LCMS observed m/z 396.1

In step 5-2, 4-hydroxy-piperidine (30 mg, 0.30 mmol) was added to a mixture of 6-(2-(2,5-difluorophenyl)pyrrolidin-1-O-3-(6-fluoropyridin-2-yl)imidazo[1,2-b]pyridazine (40 mg, 0.13 mmol), 12 mg KF (0.30 mmol) in 1.5 mL of DMSO. The resulting mixture was heated to 110° C. and stirred for 8 hours at 110° C. The product was then purified using mass triggered preparatory LC/MS giving 1-(6-(6-(2-(2,5-difluorophenyl)pyrrolidin-1-yl)imidazo[1,2-b]pyridazin-3-yl)pyridin-2-yl)piperidin-4-ol (5-2). $^1$H NMR (400 MHz, $D_3$ acetonitrile) δ ppm 8.35 (br s, 1H), 8.22 (app q, J=6.1 Hz, 2H), 7.58 (br s, 1H), 7.42-7.02 (m, 4H), 6.82 (app d, J=6.5 Hz, 1H), 5.42 (dd, J=5.2, 1.4 Hz, 1H), 4.25-4.00 (m, 3H), 3.88-3.82 (m, 1H), 3.76 (app q, J=6.4 Hz, 1H), 3.15 (app dd, J=4.7, 2.2 Hz, 2H), 2.49-2.42 (m, 2H), 2.09-2.01 (m, 3H), 1.88-1.80 (m, 2H), 1.44 (app q, J=7.4 Hz, 2H). LCMS observed m/z 477.2

By repeating the procedures described in the above examples, using appropriate starting materials, the following compounds of Formula (I), as identified in Table 4, were obtained.

TABLE 4

| Compound Number | Structure | Physical Data $^1$H NMR 400 MHz (DMSO-$d_6$) and/or MS (m/z) |
|---|---|---|
| 1 | 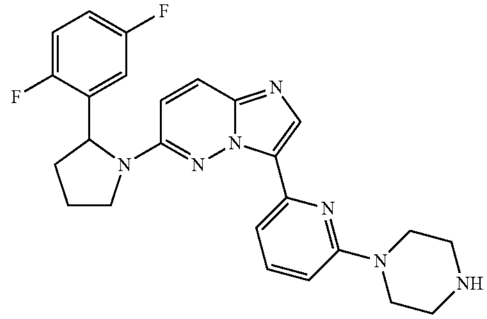 [SMILES: Fc1ccc(F)c(C2CCCN2c2ccc3ncc(-c4cccc(N5CCNCC5)n4)n3n2)c1] | m/z 462.2 (M + 1) |

TABLE 4-continued

| Compound Number | Structure | Physical Data<br>¹H NMR 400 MHz (DMSO-d₆)<br>and/or MS (m/z) |
|---|---|---|
| 2 | 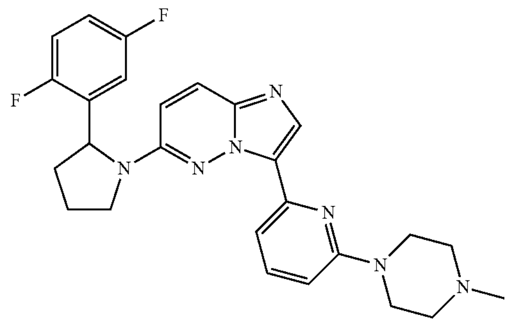 [SMILES: CN1CCN(c2cccc(-c3cnc4ccc(N5CCCC5c5cc(F)ccc5F)nn34)n2)CC1] | m/z 476.3 (M + 1) |
| 3 | 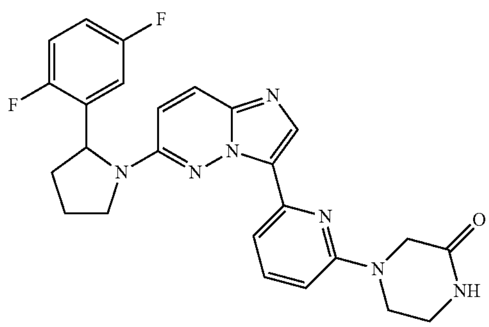 [SMILES: O=C1CN(c2cccc(-c3cnc4ccc(N5CCCC5c5cc(F)ccc5F)nn34)n2)CCN1] | m/z 476.3 (M + 1) |
| 4 | 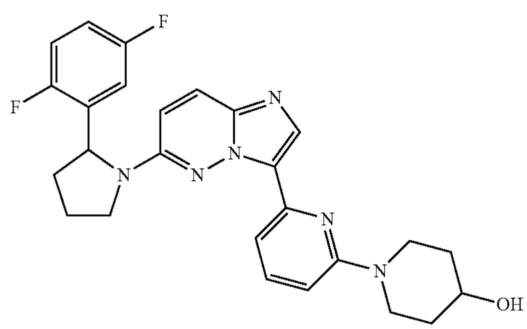 [SMILES: OC1CCN(c2cccc(-c3cnc4ccc(N5CCCC5c5cc(F)ccc5F)nn34)n2)CC1] | m/z 477.3 (M + 1) |
| 5 | 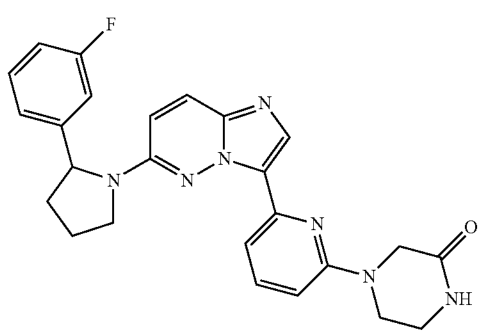 [SMILES: O=C1CN(c2cccc(-c3cnc4ccc(N5CCCC5c5cccc(F)c5)nn34)n2)CCN1] | m/z 458.2 (M + 1) |

TABLE 4-continued
| Compound Number | Structure | Physical Data<br>¹H NMR 400 MHz (DMSO-d$_6$)<br>and/or MS (m/z) |
|---|---|---|
| 6 | 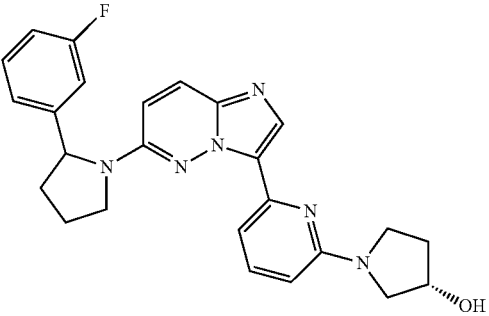 [SMILES: O[C@H]1CCN(c2cccc(-c3cnc4ccc(N5CCCC5c5cccc(F)c5)nn34)n2)C1] | m/z 445.2 (M + 1) |
| 7 | 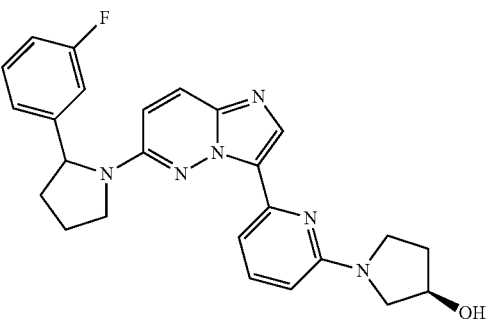 [SMILES: O[C@@H]1CCN(c2cccc(-c3cnc4ccc(N5CCCC5c5cccc(F)c5)nn34)n2)C1] | m/z 445.2 (M + 1) |
| 8 | 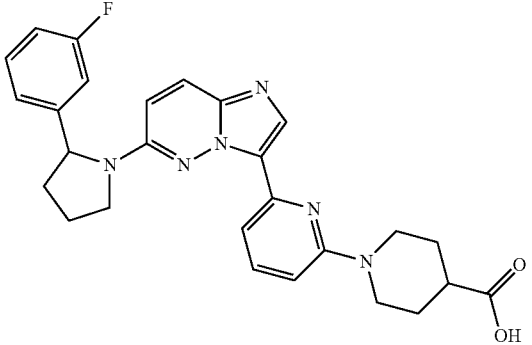 [SMILES: O=C(O)C1CCN(c2cccc(-c3cnc4ccc(N5CCCC5c5cccc(F)c5)nn34)n2)CC1] | m/z 487.2 (M + 1) |
| 9 | 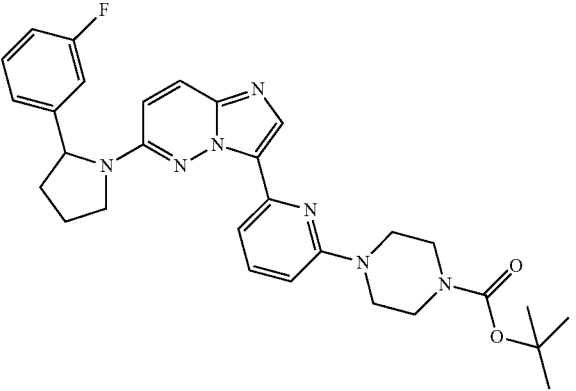 [SMILES: CC(C)(C)OC(=O)N1CCN(c2cccc(-c3cnc4ccc(N5CCCC5c5cccc(F)c5)nn34)n2)CC1] | m/z 544.3 (M + 1) |

TABLE 4-continued
| Compound Number | Structure | Physical Data<br>$^1$H NMR 400 MHz (DMSO-d$_6$)<br>and/or MS (m/z) |
|---|---|---|
| 10 | 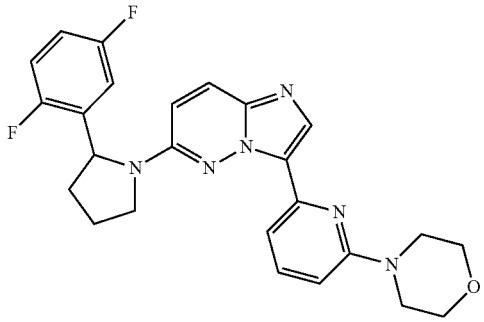 [SMILES: Fc1ccc(F)c(C2CCCN2c2ccc3ncc(-c4cccc(N5CCOCC5)n4)n3n2)c1] | m/z 463.2 (M + 1) |
| 11 | 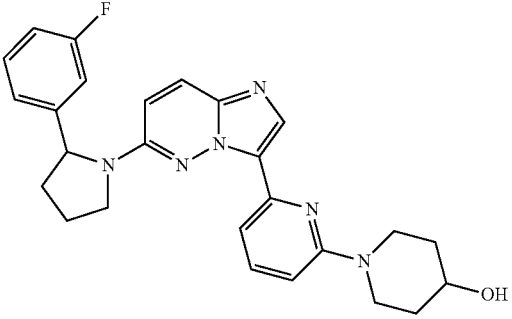 [SMILES: OC1CCN(c2cccc(-c3cnc4ccc(N5CCCC5c5cccc(F)c5)nn34)n2)CC1] | 1H NMR (DMSO-d6) 8.04 (s, 1H), 7.88 (d, 1H), 7.40-7.60 (m, 2H), 7.37 (q, 1H), 7.13-7.17 (m, 2H), 7.00-7.05 (m, 1H), 6.75-6.85 (bs, 1H), 6.73 (d, 1H), 5.15-5.17 (m, 1H), 4.67 (d, 1H), 4.40-4.10 (m, 2H), 3.96-4.01 (m, 1H), 3.64-3.71 (m, 2H), 3.05-3.11 (m, 2H), 2.00-2.06 (m, 2H), 1.84-1.89 (m, 1H), 1.77-1.82 (m, 2H), 1.33-1.40 (m, 2H)<br>m/z 473.2 (M + 1) |
| 12 | 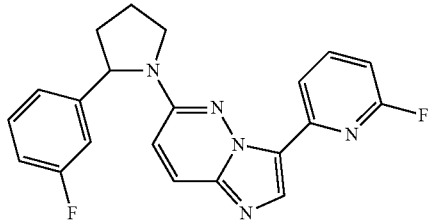 [SMILES: Fc1cccc(C2CCCN2c2ccc3ncc(-c4cccc(F)n4)n3n2)c1] | m/z 378.4 (M + 1) |
| 13 | 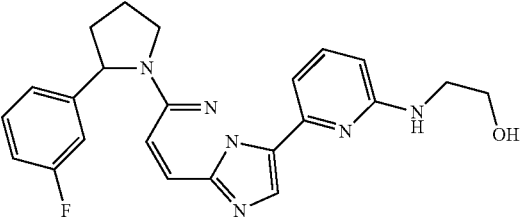 [SMILES: N=C(/C=C\c1ncc(-c2cccc(NCCO)n2)[nH]1)N1CCCC1c1cccc(F)c1] | m/z 419.5 (M + 1) |
| 14 | 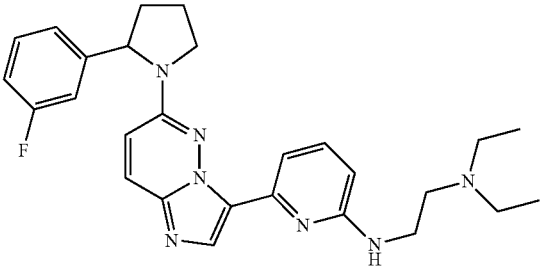 [SMILES: CCN(CC)CCNc1cccc(-c2cnc3ccc(N4CCCC4c4cccc(F)c4)nn23)n1] | m/z 474.6 (M + 1) |

TABLE 4-continued

| Compound Number | Structure | Physical Data<br>¹H NMR 400 MHz (DMSO-d₆)<br>and/or MS (m/z) |
|---|---|---|
| 15 | 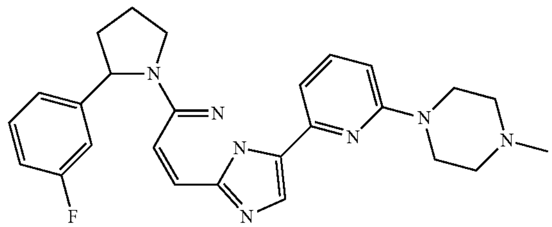 [SMILES: CN1CCN(c2cccc(-c3cnc(/C=C\C(=N)N4CCCC4c4cccc(F)c4)[nH]3)n2)CC1] | 1H NMR (DMSO-d6) 8.10 (s, 1H), 7.88 (d, 1H), 7.46-7.66 (m, 2H), 7.36-7.40 (m, 1H), 7.12-7.18 (m, 2H), 7.00-7.06 (m, 1H), 6.80-6.90 (m, 1H), 6.78 (d, 1H), 5.14-5.18 (m, 1H), 4.20 (d, 1H), 4.11 (d, 1H), 3.96-4.02 (m, 1H), 3.50-3.90 (m, 4H), 3.64-3.70 (m, 1H), 3.32 (s, 3H), 2.70-3.00 (m, 4H), 2.45-2.50 (m, 1H), 2.00-2.08 (m, 2H), 1.84-1.91 (m, 1H)<br>m/z 458.5 (M + 1) |
| 16 | 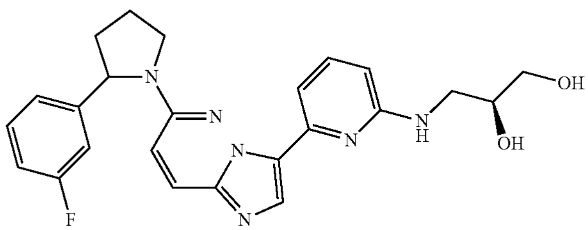 [SMILES: N=C(/C=C\c1ncc(-c2cccc(NC[C@H](O)CO)n2)[nH]1)N1CCCC1c1cccc(F)c1] | 1H NMR (DMSO-d6) 8.03 (s, 1H), 7.88 (d, 1H), 7.26-7.44 (m, 3H), 7.12-7.18 (m, 2H), 7.01-7.06 (m, 1H), 6.75-6.85 (m, 1H), 6.50-6.56 (m, 1H), 6.43 (d, 1H), 5.14-5.18 (m, 1H), 5.00-5.06 (bs, 1H), 4.58-4.68 (m, 1H), 3.95-4.05 (m, 1H), 3.62-3.70 (m, 2H), 3.42-3.50 (m, 1H), 3.36-3.38 (m, 2H), 3.18-3.26 (m, 1H), 2.45-2.50 (m, 1H), 2.00-2.08 (m, 2H), 1.82-1.90 (m, 1H)<br>m/z 449.5 (M + 1) |
| 17 | 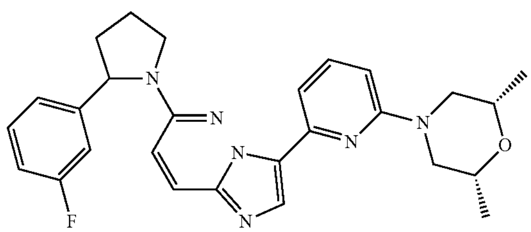 [SMILES: C[C@@H]1CN(c2cccc(-c3cnc(/C=C\C(=N)N4CCCC4c4cccc(F)c4)[nH]3)n2)C[C@H](C)O1] | 1H NMR (DMSO-d6) 8.10 (s, 1H), 7.89 (d, 1H), 7.42-7.60 (m, 2H), 7.34-7.42 (m, 1H), 7.12-7.18 (m, 2H), 6.98-7.06 (m, 1H), 6.76-6.86 (m, 1H), 6.74 (d, 1H), 5.14-5.19 (m, 1H), 4.21 (d, 2H), 3.96-4.02 (m, 1H), 3.64-3.70 (m, 3H), 2.45-2.50 (m, 1H), 2.35-2.43 (m, 2H), 1.98-2.08 (m, 2H), 1.82-1.90 (m, 1H), 1.18 (m, 6H)<br>m/z 473.6 (M + 1) |
| 18 | 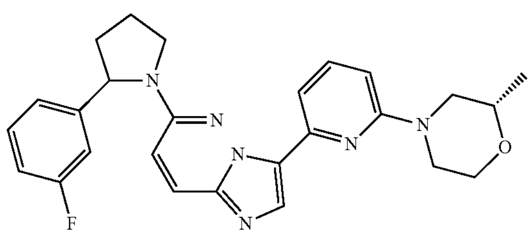 [SMILES: C[C@H]1CN(c2cccc(-c3cnc(/C=C\C(=N)N4CCCC4c4cccc(F)c4)[nH]3)n2)CCO1] | 1H NMR (DMSO-d6) 8.09 (s, 1H), 7.89 (d, 1H), 7.42-7.64 (m, 2H), 7.33-7.42 (m, 1H), 7.12-7.18 (m, 2H), 6.98-7.06 (m, 1H), 6.76-6.86 (m, 1H), 6.73 (d, 1H), 5.14-5.18 (m, 1H), 4.20 (d, 1H), 4.11 (d, 1H), 3.95-4.05 (m, 1H), 3.62-3.70 (m, 1H), 3.50-3.62 (m, 2H), 3.36-3.38 (m, 2H), 2.74-2.84 (m, 1H), 2.45-2.50 (m, 1H), 1.98-2.07 (m, 2H), 1.82-1.91 (m, 1H), 1.18 (m, 3H)<br>m/z 459.5 (M + 1) |
| 19 | 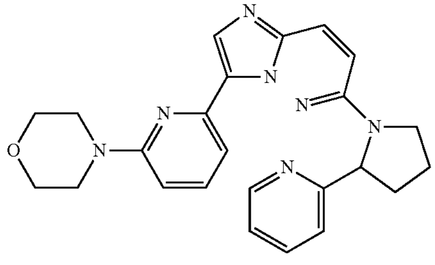 [SMILES: N=C(/C=C\c1ncc(-c2cccc(N3CCOCC3)n2)[nH]1)N1CCCC1c1ccccn1] | m/z 428.5 (M + 1) |

TABLE 4-continued

| Compound Number | Structure | Physical Data<br>$^1$H NMR 400 MHz (DMSO-$d_6$)<br>and/or MS (m/z) |
|---|---|---|
| 20 | 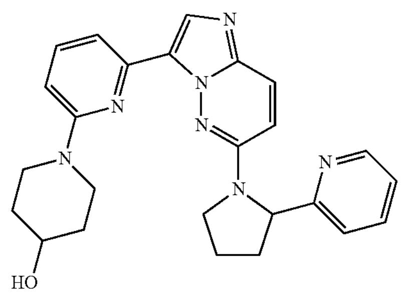 [SMILES: OC1CCN(c2cccc(-c3cnc4ccc(N5CCCC5c5ccccn5)nn34)n2)CC1] | 1H NMR (DMSO-d6) 8.57 (d, 1H), 8.03 (s, 1H), 7.87 (d, 1H), 7.67-7.71 (m, 1H), 7.36-7.48 (bs, 2H), 7.29 (d, 1H), 7.20-7.23 (m, 1H), 6.78-6.88 (bs, 1H), 6.71 (d, 1H), 5.16-5.19 (q, 1H), 4.65-4.68 (d, 1H), 4.-04-4.09 (m, 2H), 3.94-3.98 (m, 1H), 3.65-3.73 (m, 2H), 3.04-3.11 (m, 2H), 2.45-2.48 (m, 1H), 2.03-2.08 (m, 2H), 1.95-2.01 (m, 1H), 1.76-1.82 (m, 2H), 1.33-1.40 (m, 2H)<br>m/z 442.5 (M + 1) |
| 21 | 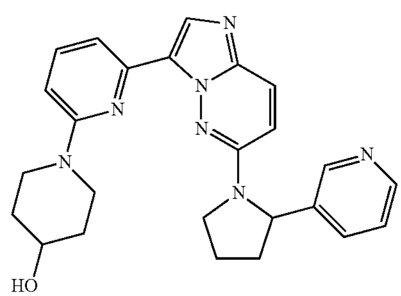 [SMILES: OC1CCN(c2cccc(-c3cnc4ccc(N5CCCC5c5cccnc5)nn34)n2)CC1] | m/z 442.5 (M + 1) |
| 22 | 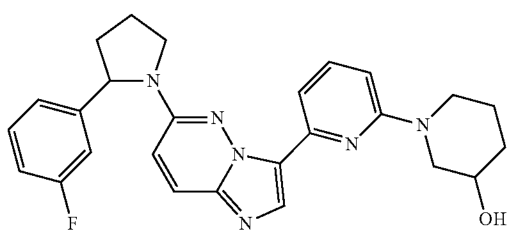 [SMILES: OC1CCCN(c2cccc(-c3cnc4ccc(N5CCCC5c5cccc(F)c5)nn34)n2)C1] | 1H NMR (DMSO-d6) 8.06 (s, 1H), 7.88 (d, 1H), 7.40-7.50 (m, 2H), 7.35-7.40 (m, 1H), 7.13-7.17 (m, 2H), 7.01-7.05 (m, 1H), 6.75-6.85 (bs, 1H), 6.69 (d, 1H), 5.14-5.18 (q, 1H), 4.83 (t, 1H), 4.24-4.29 (m, 1H), 3.95-4.05 (m, 2H), 3.63-3.70 (m, 1H), 3.44-3.53 (m, 1H), 2.87-2.93 (m, 1H), 2.67-2.73 (q, 1H), 2.45-2.50 (m, 1H), 2.00-2.06 (m, 2H), 1.84-1.94 (m, 2H), 1.70-1.76 (m, 1H), 1.33-1.40 (m, 2H)<br>m/z 459.5 (M + 1) |
| 23 | 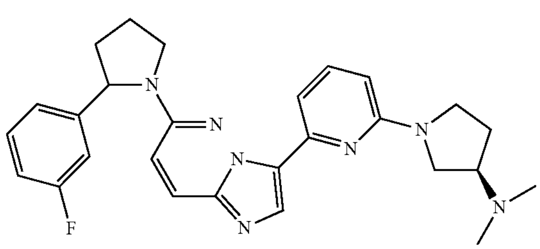 [SMILES: CN(C)[C@@H]1CCN(c2cccc(-c3cnc(/C=C\C(=N)N4CCCC4c4cccc(F)c4)[nH]3)n2)C1] | 1H NMR (DMSO-d6) 8.07 (s, 1H), 7.87 (d, 1H), 7.32-7.60 (m, 3H), 7.11-7.19 (m, 2H), 7.00-7.05 (m, 1H), 6.75-6.85 (bs, 1H), 6.36 (d, 1H), 5.15-5.18 (m, 1H), 3.96-4.01 (m, 1H), 3.60-3.75 (m, 3H), 3.33-3.37 (m, 1H), 3.10-3.15 (m, 1H), 2.73-2.80 (m, 1H), 2.45-2.50 (m, 1H), 2.11-2.18 (m, 1H), 2.00-2.06 (m, 2H), 1.84-1.90 (m, 1H), 1.76-1.82 (m, 1H)<br>m/z 472.6 (M + 1) |
| 24 | 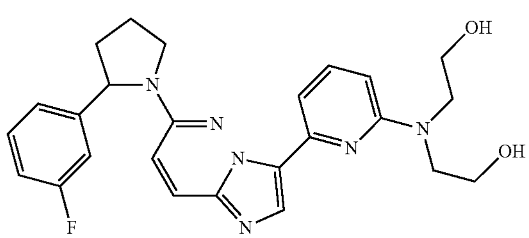 [SMILES: N=C(/C=C\c1ncc(-c2cccc(N(CCO)CCO)n2)[nH]1)N1CCCC1c1cccc(F)c1] | 1H NMR (DMSO-d6) 8.58 (d, 1H), 8.41-8.43 (q, 1H), 8.02 (s, 1H), 7.89 (d, 1H), 7.68-7.71 (m, 1H), 7.39-7.45 (m, 2H), 7.32-7.35 (q, 1H), 6.82-6.90 (bs, 1H), 6.72 (d, 1H), 5.19-5.23 (q, 1H), 4.67 (d, 1H), 4.03-4.09 (m, 2H), 3.97-4.02 (m, 1H), 3.65-3.71 (m, 2H), 3.05-3.10 (m, 2H), 2.51-2.53 (m, 1H), 2.01-2.09 (m, 2H), 1.85-1.91 (m, 1H), 1.76-1.82 (m, 2H), 1.31-1.40 (m, 2H)<br>m/z 463.5 (M + 1) |

TABLE 4-continued

| Compound Number | Structure | Physical Data<br>¹H NMR 400 MHz (DMSO-d₆)<br>and/or MS (m/z) |
|---|---|---|
| 25 | 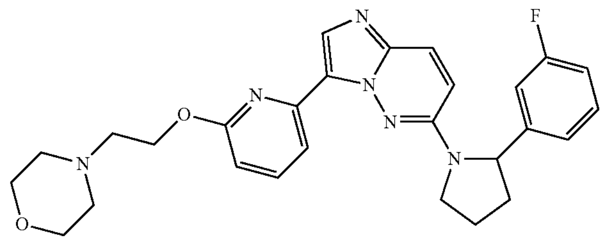 [SMILES: Fc1cccc(C2CCCN2c2ccc3ncc(-c4cccc(OCCN5CCOCC5)n4)n3n2)c1] | 1H NMR (DMSO-d6) 8.58 (d, 1H), 8.41-8.43 (q, 1H), 8.02 (s, 1H), 7.89 (d, 1H), 7.68-7.71 (m, 1H), 7.39-7.45 (m, 2H), 7.32-7.35 (q, 1H), 6.82-6.90 (bs, 1H), 6.72 (d, 1H), 5.19-5.23 (q, 1H), 4.67 (d, 1H), 4.03-4.09 (m, 2H), 3.97-4.02 (m, 1H), 3.65-3.71 (m, 2H), 3.05-3.10 (m, 2H), 2.51-2.53 (m, 1H), 2.01-2.09 (m, 2H), 1.85-1.91 (m, 1H), 1.76-1.82 (m, 2H), 1.31-1.40 (m, 2H)<br>m/z 489.6 (M + 1) |
| 26 | 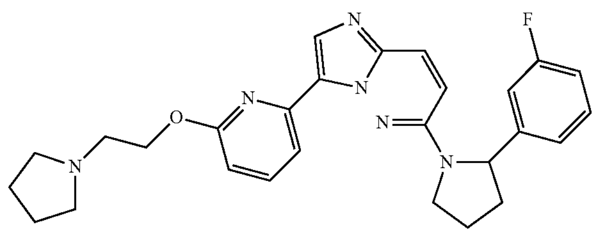 [SMILES: N=C(/C=C\c1ncc(-c2cccc(OCCN3CCCC3)n2)[nH]1)N1CCCC1c1cccc(F)c1] | 1H NMR (DMSO-d6) 8.13 (s, 1H), 7.92 (d, 1H), 7.74-7.98 (bs, 1H), 7.68-7.66 (bs, 1H), 7.36-7.40 (m, 1H), 7.14-7.20 (m, 2H), 7.00-7.06 (m, 1H), 6.80-6.92 (bs, 1H), 6.70 (d, 1H), 5.16-5.20 (q, 1H), 4.47-4.56 (m, 2H), 3.98-4.03 (m, 1H), 3.65-3.71 (m, 1H), 3.03-3.20 (m, 2H), 2.70-2.95 (m, 4H), 2.45-2.50 (m, 1H), 2.00-2.08 (m, 2H), 1.85-1.90 (m, 1H), 1.71-1.83 (m, 4H)<br>m/z 473.6 (M + 1) |
| 27 | 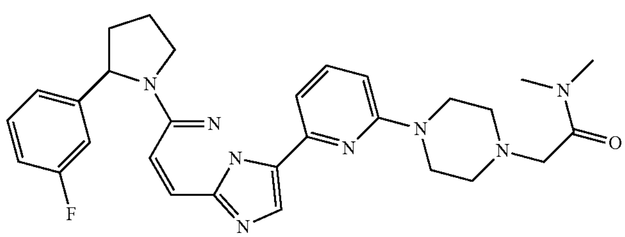 [SMILES: CN(C)C(=O)CN1CCN(c2cccc(-c3cnc(/C=C\C(=N)N4CCCC4c4cccc(F)c4)[nH]3)n2)CC1] | 1H NMR (DMSO-d6) 8.06 (s, 1H), 7.88 (d, 1H), 7.42-7.60 (m, 2H), 7.34-7.40 (m, 1H), 7.13-7.17 (m, 2H), 7.00-7.05 (m, 1H), 6.75-6.85 (bs, 1H), 6.73 (d, 1H), 5.14-5.19 (q, 1H), 3.96-4.01 (m, 1H), 3.64-3.70 (q, 1H), 3.48-3.58 (bs, 4H), 3.15-3.24 (bs, 2H), 3.04 (s, 3H), 2.82 (s, 3H), 2.50-2.60 (bs, 4H), 2.45-2.50 (m, 1H), 2.01-2.06 (m, 2H), 1.84-1.89 (m, 1H)<br>m/z 529.6 (M + 1) |
| 28 | 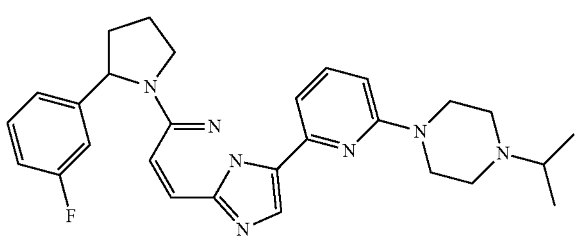 [SMILES: CC(C)N1CCN(c2cccc(-c3cnc(/C=C\C(=N)N4CCCC4c4cccc(F)c4)[nH]3)n2)CC1] | 1H NMR (DMSO-d6) 8.05 (s, 1H), 7.88 (d, 1H), 7.42-7.60 (m, 2H), 7.35-7.40 (m, 1H), 7.13-7.17 (m, 2H), 7.00-7.05 (m, 1H), 6.76-6.86 (bs, 1H), 6.71 (d, 1H), 5.15-5.17 (q, 1H), 3.96-4.01 (m, 1H), 3.64-3.70 (q, 1H), 3.46-3.54 (bs, 4H), 2.64-2.71 (m, 1H), 2.50-2.56 (bs, 4H), 2.45-2.50 (m, 1H), 2.00-2.06 (m, 2H), 1.84-1.90 (m, 1H), 1.00 (d, 6H)<br>m/z 486.6 (M + 1) |
| 29 | 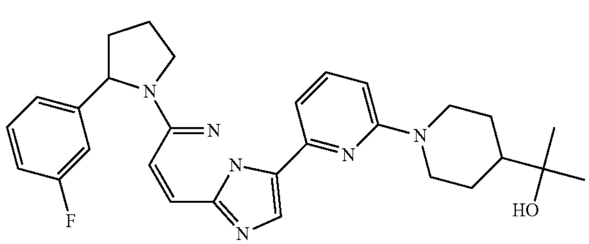 [SMILES: CC(C)(O)C1CCN(c2cccc(-c3cnc(/C=C\C(=N)N4CCCC4c4cccc(F)c4)[nH]3)n2)CC1] | 1H NMR (DMSO-d6) 8.04 (s, 1H), 7.88 (d, 1H), 7.34-7.50 (m, 3H), 7.12-7.37 (m, 2H), 7.00-7.16 (m, 1H), 6.76-6.83 (bs, 1H), 6.72 (d, 1H), 5.15-5.18 (q, 1H), 4.45 (d, 1H), 4.01 (s, 1H), 3.96-4.01 (m, 1H), 3.64-3.68 (m, 1H), 2.65-2.71 (m, 2H), 2.44-2.48 (m, 1H), 2.00-2.06 (m, 2H), 1.84-1.89 (m, 1H), 1.74-1.79 (m, 2H), 1.38-1.45 (m, 1H), 1.18-1.28 (m, 2H), 1.04 (s, 6H), 0.82-.088 (m, 1H)<br>m/z 501.6 (M + 1) |

TABLE 4-continued

| Compound Number | Structure | Physical Data<br>¹H NMR 400 MHz (DMSO-d₆)<br>and/or MS (m/z) |
|---|---|---|
| 30 | 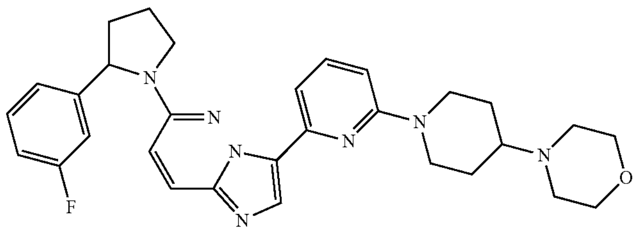 [SMILES: N=C(/C=C\c1ncc(-c2cccc(N3CCC(N4CCOCC4)CC3)n2)[nH]1)N1CCCC1c1cccc(F)c1] | 1H NMR (DMSO-d6) 8.04 (s, 1H), 7.87 (d, 1H), 7.40-7.52 (m, 2H), 7.34-7.40 (m, 1H), 7.13-7.17 (m, 2H), 7.00-7.05 (m, 1H), 6.77-6.85 (bs, 1H), 6.74 (d, 1H), 5.14-5.18 (q, 1H), 4.36 (d, 2H), 3.96-4.01 (m, 1H), 3.63-3.69 (q, 1H), 3.55 (t, 4H), 2.80 (t, 2H), 2.42-2.50 (m, 5H), 2.34-2.40 (m, 1H), 2.00-2.05 (m, 2H), 1.82-1.89 (m, 3H), 1.33-1.41 (m, 2H)<br>m/z 528.6 (M + 1) |
| 31 | 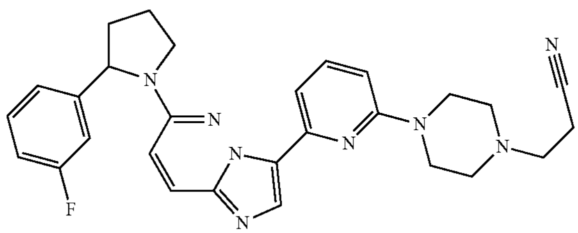 [SMILES: N#CCCN1CCN(c2cccc(-c3cnc(/C=C\C(=N)N4CCCC4c4cccc(F)c4)[nH]3)n2)CC1] | 1H NMR (DMSO-d6) 8.06 (s, 1H), 7.88 (d, 1H), 7.41-7.60 (m, 2H), 7.34-7.40 (m, 1H), 7.12-7.18 (m, 2H), 7.00-7.15 (m, 1H), 6.77-6.85 (bs, 1H), 6.74 (d, 1H), 5.15-5.18 (q, 1H), 3.96-4.01 (m, 1H), 3.64-3.70 (q, 1H), 3.54 (t, 4H), 2.72 (t, 2H), 2.62 (t, 2H), 2.51-2.55 (m, 4H), 2.45-2.50 (m, 1H), 2.00-2.06 (m, 2H), 1.84-1.90 (m, 1H)<br>m/z 497.6 (M + 1) |
| 32 | 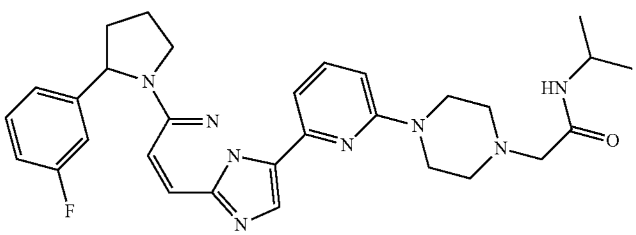 [SMILES: CC(C)NC(=O)CN1CCN(c2cccc(-c3cnc(/C=C\C(=N)N4CCCC4c4cccc(F)c4)[nH]3)n2)CC1] | 1H NMR (DMSO-d6) 8.07 (s, 1H), 7.88 (d, 1H), 7.50-7.58 (bs, 1H), 7.42-7.48 (bs, 1H), 7.35-7.40 (m, 1H), 7.13-7.17 (m, 2H), 7.01-7.05 (m, 1H), 6.78-6.85 (bs, 1H), 6.73 (d, 1H), 5.15-5.18 (q, 1H), 3.96-4.01 (m, 1H), 3.87-3.94 (m, 1H), 3.64-3.70 (m, 1H), 3.54-360 (bs, 4H), 2.91-2.96 (bs, 2H), 2.50-2.60 (bs, 4H), 2.45-2.50 (m, 1H), 2.00-2.06 (m, 2H), 1.84-1.90 (m, 1H), 1.08 (d, 6H)<br>m/z 543.7 (M + 1) |
| 33 | 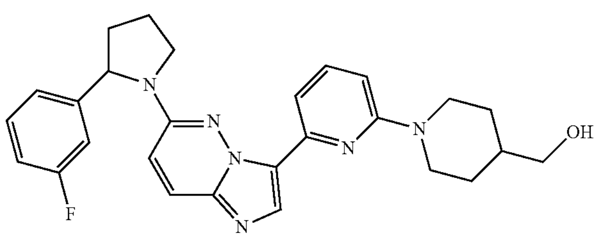 [SMILES: OCC1CCN(c2cccc(-c3cnc4ccc(N5CCCC5c5cccc(F)c5)nn34)n2)CC1] | 1H NMR (DMSO-d6) 8.04 (s, 1H), 7.87 (d, 1H), 7.04-7.50 (m, 2H), 7.35-7.40 (m, 1H), 7.13-7.17 (m, 2H), 7.01-7.05 (m, 1H), 6.76-6.85 (bs, 1H), 6.72 (d, 1H), 5.14-5.17 (q, 1H), 4.46 (t, 1H), 4.37 (d, 2H), 3.96-4.01 (m, 1H), 3.64-3.69 (q, 1H), 3.27 (t, 2H), 2.74-2.81 (m, 2H), 2.45-2.50 (m, 1H), 2.00-2.06 (m, 2H), 1.84-1.89 (m, 1H), 1.58-1.64 (m, 1H), 1.08-1.17 (m, 2H)<br>m/z 473.6 (M + 1) |
| 34 | 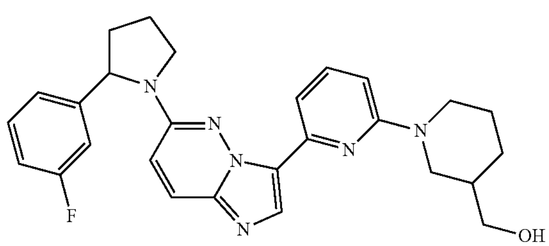 [SMILES: OCC1CCCN(c2cccc(-c3cnc4ccc(N5CCCC5c5cccc(F)c5)nn34)n2)C1] | 1H NMR (DMSO-d6) 8.05 (s, 1H), 7.88 (d, 1H), 7.40-7.50 (m, 2H), 7.34-7.40 (m, 1H), 7.13-7.17 (m, 2H), 7.00-7.05 (m, 1H), 6.76-6.85 (bs, 1H), 6.69 (t, 1H), 5.15-5.18 (q, 1H), 4.54-4.57 (m, 1H), 4.34 (d, 1H), 4.22 (d, 1H), 3.96-4.02 (m, 1H), 3.64-3.70 (q, 1H), 3.28-3.37 (m, 2H), 2.81-2.88 (m, 1H), 2.59 (t, 1H), 2.45-2.50 (m, 1H), 2.00-2.08 (m, 2H), 1.84-1.90 (m, 1H), 1.72-1.77 (m, 1H), 1.66-1.72 (m, 1H), 1.58-1.65 (m, 1H), 1.40-1.59 (m, 1H), 1.14-1.22 (m, 1H)<br>m/z 473.6 (M + 1) |

TABLE 4-continued
| Compound Number | Structure | Physical Data <sup>1</sup>H NMR 400 MHz (DMSO-d<sub>6</sub>) and/or MS (m/z) |
|---|---|---|
| 35 | 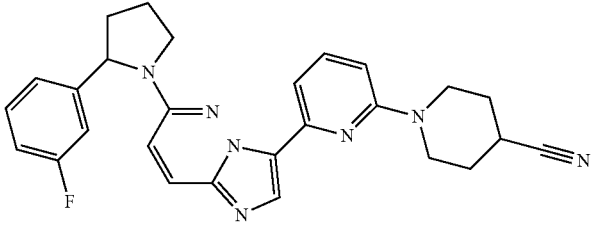 [SMILES: N#CC1CCN(c2cccc(-c3cnc(/C=C\C(=N)N4CCCC4c4cccc(F)c4)[nH]3)n2)CC1] | 1H NMR (DMSO-d6) 8.07 (s, 1H), 7.88 (d, 1H), 7.41-7.60 (m, 2H), 7.34-7.40 (m, 1H), 7.12-7.18 (m, 2H), 7.00-7.15 (m, 1H), 6.78-6.85 (bs, 1H), 6.77 (d, 1H), 5.15-5.18 (q, 1H), 3.96-4.01 (m, 1H), 3.83-3.89 (m, 2H), 3.64-3.70 (q, 1H), 3.09-3.14 (m, 1H), 2.45-2.50 (m, 1H), 2.00-2.06 (m, 2H), 1.94-1.97 (m, 2H), 1.84-1.89 (m, 1H), 1.71-1.77 (m, 2H) m/z 468.5 (M + 1) |
| 36 | 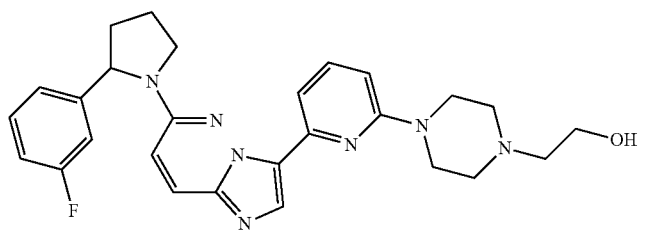 [SMILES: N=C(/C=C\c1ncc(-c2cccc(N3CCN(CCO)CC3)n2)[nH]1)N1CCCC1c1cccc(F)c1] | 1H NMR (DMSO-d6) 8.05 (s, 1H), 7.88 (d, 1H), 7.42-7.60 (m, 2H), 7.35-7.40 (m, 1H), 7.13-7.17 (m, 2H), 7.00-7.05 (m, 1H), 6.75-6.85 (bs, 1H), 6.72 (d, 1H), 5.14-5.18 (q, 1H), 4.43 (t, 1H), 3.96-4.01 (m, 1H), 3.63-3.70 (q, 1H), 3.47-3.57 (m ,6H), 2.50-2.55 (m, 4H), 2.40-2.50 (m, 3 H), 2.00-2.06 (m ,2H), 1.84-1.89 (m, 1H) m/z 488.6 (M + 1) |
| 37 | 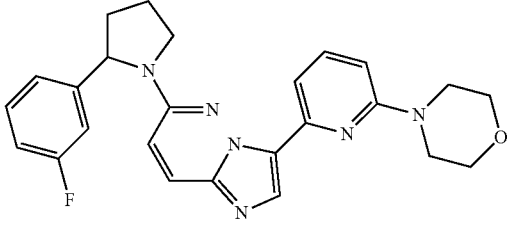 [SMILES: N=C(/C=C\c1ncc(-c2cccc(N3CCOCC3)n2)[nH]1)N1CCCC1c1cccc(F)c1] | 1H NMR (DMSO-d6) 8.07 (s, 1H), 7.88 (d, 1H), 7.46-7.68 (m, 2H), 7.36-7.40 (q, 1H), 7.12-7.18 (m, 2H), 7.00-7.06 (m, 1H), 6.78-6.88 (bs, 1H), 6.73 (d, 1H), 5.15-5.18 (q, 1H), 3.96-4.01 (m, 1H), 3.70-3.73 (m, 4H), 3.64-3.69 (q, 1H), 3.46-3.51 (m, 4H), 2.45-2.50 (m, 1H), 2.01-2.06 (m, 2H), 1.84-1.89 (m, 1H) m/z 445.5 (M + 1) |
| 38 | 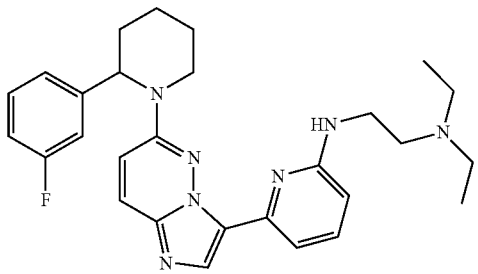 [SMILES: CCN(CC)CCNc1cccc(-c2cnc3ccc(N4CCCCC4c4cccc(F)c4)nn23)n1] | m/z 488.3 (M + 1) |
| 39 | 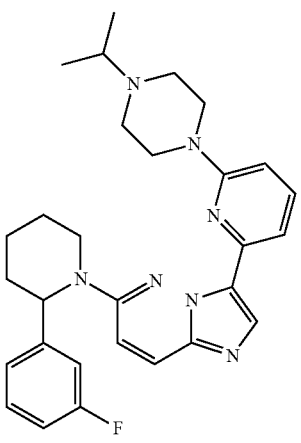 [SMILES: CC(C)N1CCN(c2cccc(-c3cnc(/C=C\C(=N)N4CCCCC4c4cccc(F)c4)[nH]3)n2)CC1] | m/z 500.3 (M + 1) |

TABLE 4-continued

| Compound Number | Structure | Physical Data<br>¹H NMR 400 MHz (DMSO-d₆)<br>and/or MS (m/z) |
|---|---|---|
| 40 | 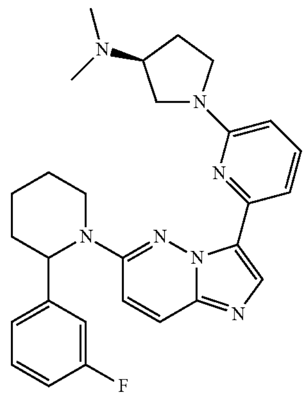 [SMILES: CN(C)[C@H]1CCN(c2cccc(-c3cnc4ccc(N5CCCCC5c5cccc(F)c5)nn34)n2)C1] | m/z 486.3 (M + 1) |
| 41 | 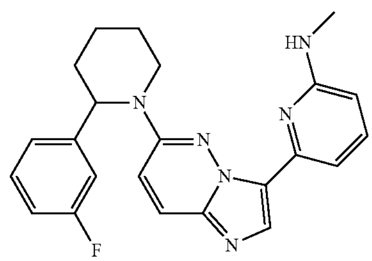 [SMILES: CNc1cccc(-c2cnc3ccc(N4CCCCC4c4cccc(F)c4)nn23)n1] | 1H NMR (DMSO-d6): d 8.06 (s, 1H), 7.75 (s, 1H), 7.51 (d, 1H), 7.32-7.40 (m, 2H), 7.22 (d, 1H), 7.14 (d, 2H), 6.99-7.05 (m, 1H), 6.45-6.50 (m, 1H), 6.35 9d, 1H), 4.14-4.21 (m, 1H), 3.30-3.39 (m, 2H), 2.82 (d, 3H), 2.17-2.26 (m, 1H), 2.00-2.10 (m, 1H), 1.56-1.83 (m, 3H), 1.35-1.50 (m, 1H)<br>m/z 403.2 (M + 1) |
| 42 | 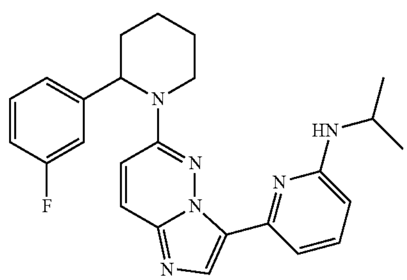 [SMILES: CC(C)Nc1cccc(-c2cnc3ccc(N4CCCCC4c4cccc(F)c4)nn23)n1] | 1H NMR (DMSO-d6): d 8.02 (s, 1H), 7.90 (d, 1H), 7.46 (d, 1H), 7.30-7.40 (m, 2H), 7.21 (d, 1H), 7.13 (d, 2H), 6.98-7.06 (m, 1H), 6.30-6.36 (m, 2H), 4.12-4.20 (m, 1H), 4.02-4.10 (m, 1H), 3.30-3.38 (m, 2H), 2.18-2.26 (m, 1H), 2.00-2.10 (m, 1H), 1.56-1.84 (m, 3H), 1.36-1.48 (m, 1H), 1.17 (d, 6H)<br>m/z 431.2 (M + 1) |
| 43 | 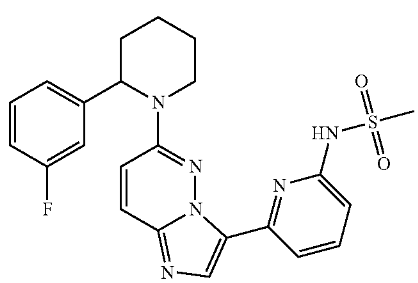 [SMILES: CS(=O)(=O)Nc1cccc(-c2cnc3ccc(N4CCCCC4c4cccc(F)c4)nn23)n1] | 1H NMR (DMSO-d6): d 10.63 (s, 1H), 8.06 (s, 1H), 7.97 (s, 1H), 7.94 (d, 1H), 7.72 (t, 1H), 7.33-7.40 (m, 1H), 7.25 (d, 1H), 7.12-7.18 (m, 2H), 6.99-7.05 (m, 1H), 6.80 (d, 1H), 4.15-4.22 (m, 1H), 3.42 (s, 3H), 3.35-3.42 (m, 2H), 2.17-2.26 (m, 1H), 2.01-2.14 (m, 1H), 1.57-1.85 (m, 3H), 1.36-1.49 (m, 1H)<br>m/z 467.2 (M + 1) |
| 44 | 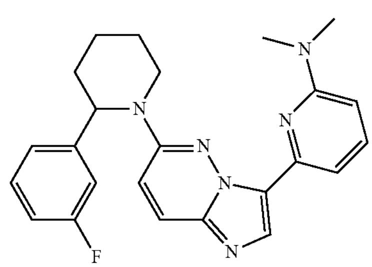 [SMILES: CN(C)c1cccc(-c2cnc3ccc(N4CCCCC4c4cccc(F)c4)nn23)n1] | m/z 417.3 (M + 1) |

TABLE 4-continued
| Compound Number | Structure | Physical Data<br>¹H NMR 400 MHz (DMSO-d₆)<br>and/or MS (m/z) |
|---|---|---|
| 45 | 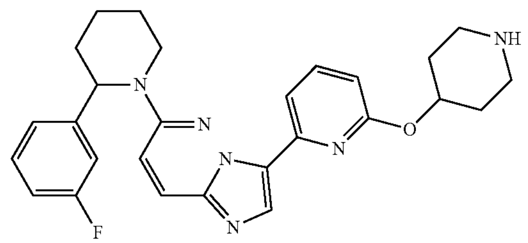 [SMILES: N=C(/C=C\c1ncc(-c2cccc(OC3CCNCC3)n2)[nH]1)N1CCCCC1c1cccc(F)c1] | m/z 473.3 (M + 1) |
| 46 | 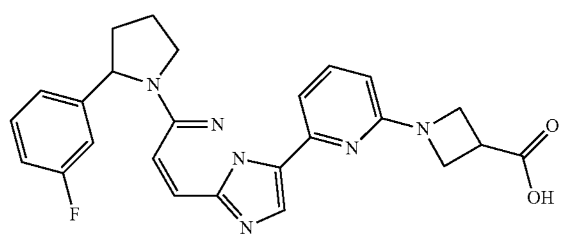 [SMILES: N=C(/C=C\c1ncc(-c2cccc(N3CC(C(=O)O)C3)n2)[nH]1)N1CCCC1c1cccc(F)c1] | m/z 459.2 (M + 1) |
| 47 | 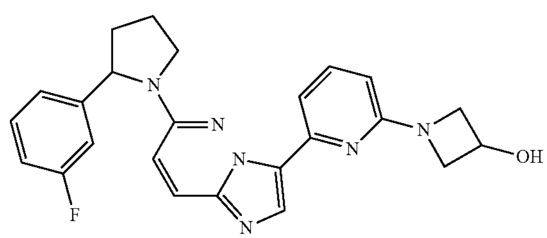 [SMILES: N=C(/C=C\c1ncc(-c2cccc(N3CC(O)C3)n2)[nH]1)N1CCCC1c1cccc(F)c1] | m/z 431.1 (M + 1) |
| 48 | 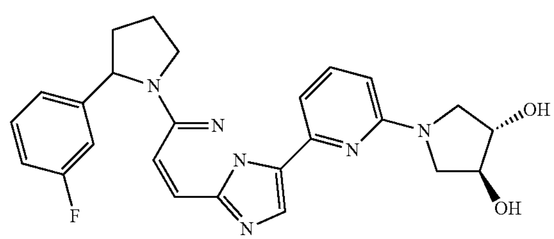 [SMILES: N=C(/C=C\c1ncc(-c2cccc(N3C[C@H](O)[C@@H](O)C3)n2)[nH]1)N1CCCC1c1cccc(F)c1] | m/z 461.5 (M + 1) |
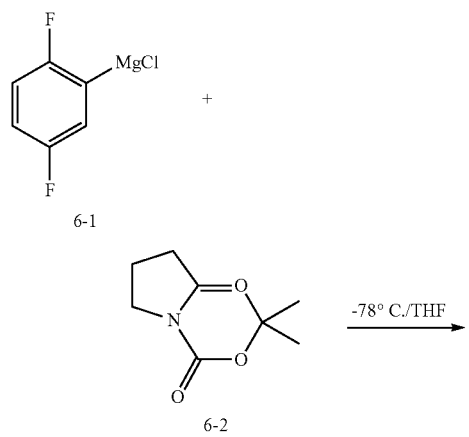
Scheme 6A
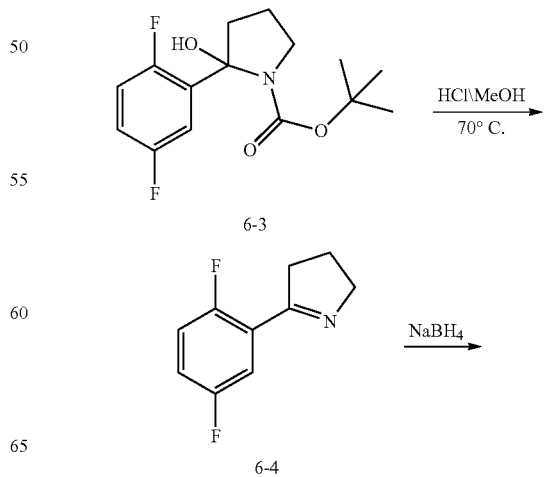

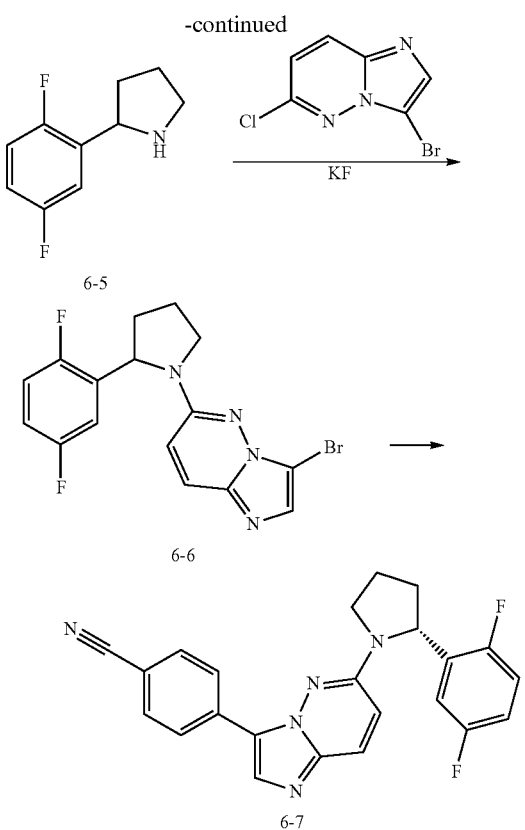

Scheme 6B

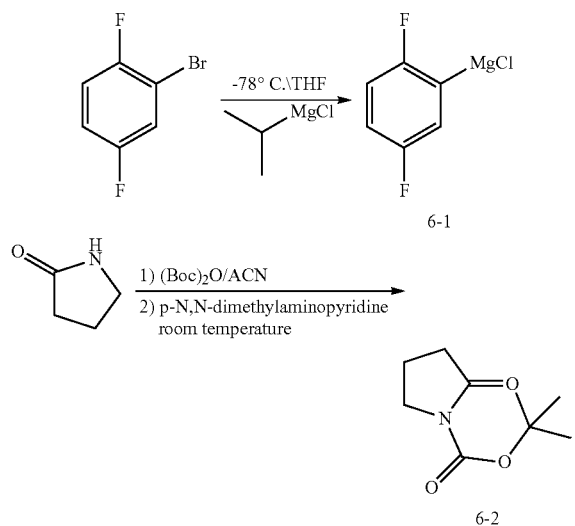

Example 6

(R)-4-(6-(2-(2,5-difluorophenyl)pyrrolidin-1-yl)imidazo[1,2-b]pyridazin-3-yl)benzonitrile (R)-4-(6-(2-(2,5-difluorophenyl)pyrrolidin-1-yl)imidazo[1,2-b]pyridazin-3-yl)benzonitrile (6-7) was synthesized from (2,5-difluorophenyl)magnesium chloride (6-1) and tert-butyl 2-oxopyrrolidine-1-carboxylate (6-2) in five steps as shown in scheme 6A. (2,5-difluorophenyl)magnesium chloride (6-1) and tert-butyl 2-oxopyrrolidine-1-carboxylate (6-2) were synthesized as shown in reaction scheme 6B.

To synthesize (2,5-difluorophenyl)magnesium chloride (6-1), a solution of 2-bromo-1,4-difluorobenzene (10 g, 52 mmol) in 30 mL of anhydrous THF was cooled to −78° C. under argon and then 27 mL of isopropylmagnesium chloride in THF (2.0 M, 54 mmol) was added drop-wise. The reaction mixture was warmed to between −20° C. and −30° C. for 30 minutes, and then cooled to −78° C. until used in the synthesis of tert-butyl 2-(2,5-difluorophenyl)-2-hydroxypyrrolidine-1-carboxylate (6-3) without further purification.

To synthesize tert-butyl 2-oxopyrrolidine-1-carboxylate (7-2), p-N,N-dimethylaminopyridine (0.7 g, 5.9 mmol) was added at room temperature to a solution of 2-pyrrolidone (5 g, 59 mmol) and di-tert-butyl dicarbonate (26 g, 118 mmol) in 100 mL of acetonitrile. The reaction mixture was stirred for 3 hours and the acetonitrile was removed using a rotary evaporator resulting in a light orange residue. The residue was reconstituted in ethyl acetate (300 mL) and the organic layer washed with brine (3×150 mL). The organic layer was dried with sodium sulfate and the ethyl acetate was removed using a rotary evaporator resulting in tert-butyl 2-oxopyrrolidine-1-carboxylate (6-2) as a light orange residue.

In step 6A-1, (2,5-difluorophenyl)magnesium chloride (6-1) was added drop-wise to a solution of tert-butyl 2-oxopyrrolidine-1-carboxylate (6-2) (9.6 g, 52 mmol) in THF under argon at −78° C. A maximum of 5 mL aliquots was used to minimize the temperature increase of the magnesium chloride reagent. The resulting solution was then stirred at −78° C. for one hour. The solution was then warmed to room temperature and quenched with concentrated HCl (4 mL). The solvent was then removed using a rotary evaporator resulting in a light yellow residue. The residue was then reconstituted in ethyl acetate and extracted with brine (3×150 mL). The organic layer was then dried using sodium sulfate. The ethyl acetate was removed yielding tert-butyl 2-(2,5-difluorophenyl)-2-hydroxypyrrolidine-1-carboxylate (6-3) as a light yellow oil. m/z=300 [M+1] The product was used without further purification.

In step 6A-2, concentrated hydrochloric acid (23 mL, 260 mmol) was added to a solution of tert-butyl 2-(2,5-difluorophenyl)-2-hydroxypyrrolidine-1-carboxylate (6-3) (15.6 g, 52 mmol) in methanol. The reaction mixture was heated to 70° C. while stirring and was then stirred at 70° C. for 6 hours. The reaction mixture was cooled to room temperature and neutralized with a 7.5 M solution of sodium hydroxide (35 mL, 263 mmol). The methanol was removed and the resulting slurry was reconstituted with ethyl acetate (250 mL). The organic layer was washed with brine (3×150 mL), and then dried with sodium sulfate. The ethyl acetate was then removed to yield 5-(2,5-difluorophenyl)-3,4-dihydro-2H-pyrrole (6-4) as a light yellow oil. m/z=182.2 [M+1].

In step 6A-3, sodium borohydride (2.1 g, 55.2 mmol) was added at room temperature to a solution of 5-(2,5-difluorophenyl)-3,4-dihydro-2H-pyrrole (6-4) (5.0 g, 28 mmol) in anhydrous ethanol (150 mL). The reaction mixture was stirred over-night at room temperature. The ethanol was removed using a rotary evaporator and the resulting orange solid was reconstituted with ethyl acetate. The organic layer was washed with brine (3×150 mL), dried with sodium sulfate and the. ethyl acetate was removed to yield 2-(2,5-difluorophenyl)pyrrolidine (6-5) as a light yellow oil. m/z=184.2 [M+1].

In step 6A-4, 2-(2,5-difluorophenyl)pyrrolidine (6-5) (1.7 g, 9.3 mmol) was added to a solution of 3-bromo-6-chloroimidazo[1,2-b]pyridazine (11-1) (1.1 g, 230.92) and potassium fluoride (2.7 g, 46 mmol) in DMSO (10 mL). The resulting solution was heated to 130° C. and stirred overnight. The resulting dark orange slurry was cooled to room temperature, poured into 50 mL of DI water and extracted with ethyl acetate (3×150 mL). The ethyl acetate was dried with sodium sulfate and then removed to yield an orange solid. This solid was reconstituted with minimal amounts of dichloromethane (DCM) and purified using a silica gel column (40 g, ISCO) and a 0-5% gradient of methanol:DCM over a 20 minute period followed by 5% methanol for an additional 10 minutes. The solvent was removed from the desired fractions to yield 3-bromo-6-(2-(2,5-difluorophenyl) pyrrolidin-1-yl)imidazo[1,2-b]pyridazine (6-6) as a light yellow solid. m/z=379.2 [M+1].

In step 6A-5, palladium tetrakis (25 mg, 0.02 mmol) was added to a solution of 3-bromo-6-(2-(2,5-difluorophenyl)pyrrolidin-1-yl)imidazo[1,2-b]pyridazine (6-6) (77 mg, 0.23 mmol), sodium carbonate (85 mg, 0.81 mmol), and 4-cyanophenylboronic acid (60 mg, 0.41 mmol) in 2 mL of dioxane and 0.5 mL of water contained in a microwave reaction tube. The resulting solution was heated in a microwave for 25 minutes at 150° C. and the yellow slurry was cooled to room temperature and filtered through a 0.2 µm nylon frit. The solvent was removed from the mother liquor and the remaining residue was reconstituted in methanol and further purified by preparative LC/MS. The desired fractions were dried to yield the desired product as a racemic mixture, which was then purified by chiral LC to yield (R)-4-(6-(2-(2,5-difluorophenyl)pyrrolidin-1-yl)imidazo[1,2-b]pyridazin-3-yl)benzonitrile (6-7) as a chiral pure white solid along with (S)-4-(6-(2-(2,5-difluorophenyl)pyrrolidin-1-yl)imidazo[1,2-b]pyridazin-3-yl)benzonitrile as a chiral pure white solid.

Scheme 7

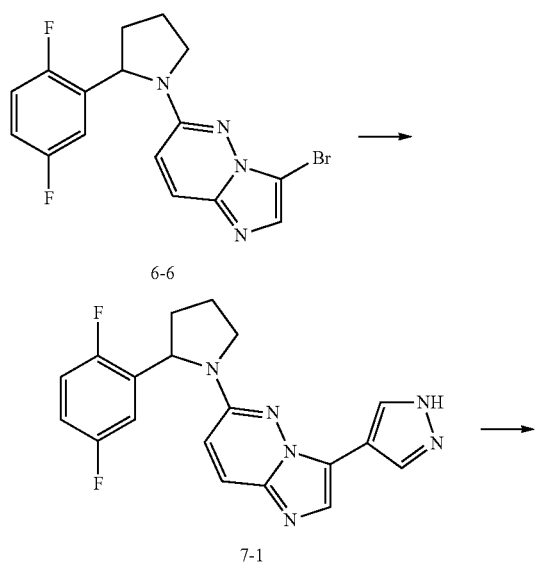

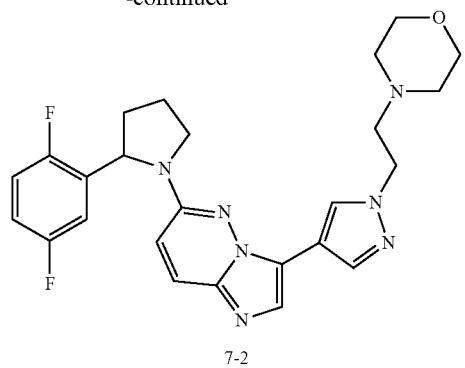

Example 7

4-(2-(4-(6-(2-(2,5-difluorophenyl)pyrrolidin-1-yl) imidazo[1,2-b]pyridazin-3-yl)-1H-pyrazol-1-yl) ethyl)morpholine 4-(2-(4-(6-(2-(2,5-difluorophenyl)pyrrolidin-1-yl)imidazo[1,2-b]pyridazin-3-yl)-1H-pyrazol-1-yl)ethyl)morpholine (7-2) was synthesized in two steps as shown in scheme 7.

In step 7-1, [Pd(dppf)$_2$]Cl$_2$ (54 mg, 0.07 mmol) in 2.5 mL of 1,4-dioxane and 0.5 mL of water was added to a solution of 3-bromo-6-(2-(2,5-difluorophenyl)pyrrolidin-1-yl)imidazo [1,2-b]pyridazine (6-6) (0.25 g, 0.7 mmol), sodium carbonate (0.25 g, 2.5 mmol), and 4-(4,4,5,5-tetramethyl-1,3,2-dioxaborolan-2-yl)-1H-pyrazole (0.27 g, 1.4 mmol) contained in a microwave reaction tube. The reaction mixture was heated in the microwave for twenty minutes at 150° C., and the yellow slurry was then cooled to room temperature and filtered through a 0.2 µM nylon fit. The solvent was removed from the mother liquor and the remaining residue was reconstituted in dichloromethane (DCM). This solution was loaded onto a 12 g silica gel column and eluted using a 0-5% methanol in DCM gradient over 30 minutes. The solvent was removed from the desired fractions to yield 6-(2-(2,5-difluorophenyl)pyrrolidin-1-yl)-3-(1H-pyrazol-4-yl)imidazo[1,2-b]pyridazine(7-1) as an off-white solid. m/z=367.4 [M+1].

In step 7-2, 4-(2-chloroethyl)morpholine hydrochloride (40 mg, 0.2 mmol) was added to a solution of 6-(2-(2,5-difluorophenyl)pyrrolidin-1-yl)-3-(1H-pyrazol-4-yl)imidazo[1,2-b]pyridazine (7-1) (35 mg, 0.1 mmol) and cesium carbonate (100 mg, 0.35 mmol) in DMF (5 mL). The reaction mixture was stirred at room temperature over-night and the DMF was then removed using a rotary evaporator. The resulting residue was reconstituted in ethyl acetate (30 mL) and the organic layer extracted with brine and then dried using sodium sulfate. The ethyl acetate was removed and the product was further purify by preparative LC/MS to yield 4-(2-(4-(6-(2-(2,5-difluorophenyl)pyrrolidin-1-yl)imidazo[1,2-b] pyridazin-3-yl)-1H-pyrazol-1-yl)ethyl)morpholine (7-2) as a white solid. m/z=480.2 [M+1].

Scheme 8

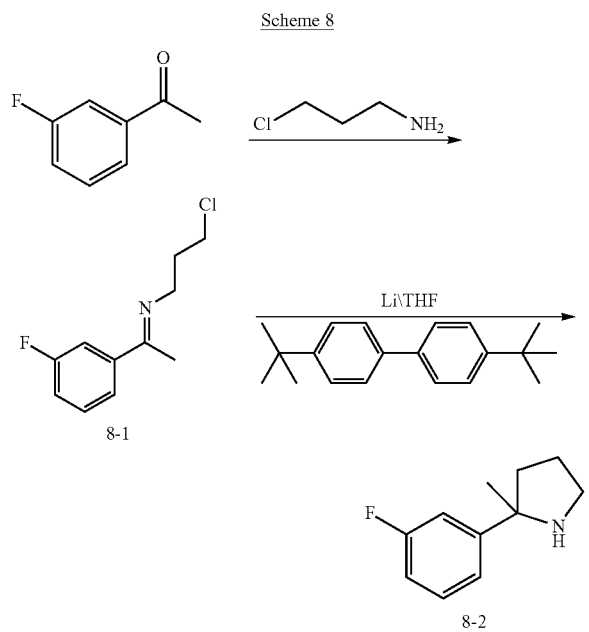

Scheme 9

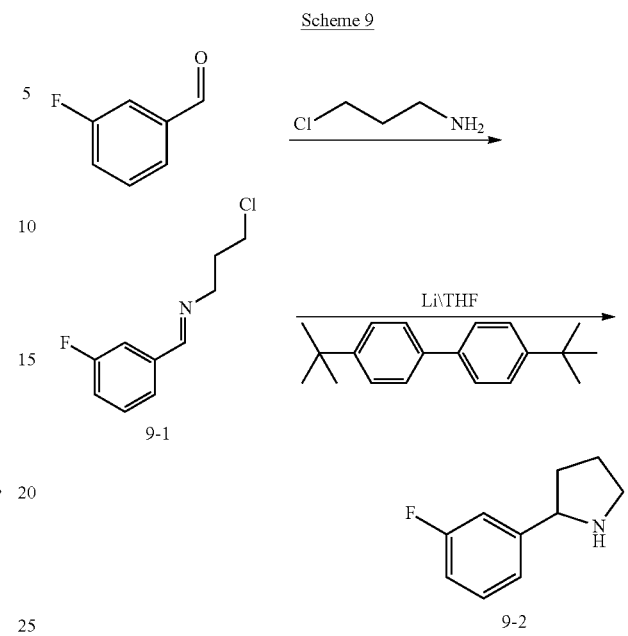

Example 8

2-(3-fluorophenyl)-2-methylpyrrolidine 2-(3-fluorophenyl)-2-methylpyrrolidine (8-2) was synthesized in two steps as shown in scheme 8.

In step 8-1, 3-chloropropan-1-amine hydrochloride (4.1 g, 32 mmol) was added to a suspension of 1-(3-fluorophenyl) ethanone (4.4 g, 32 mmol) and sodium carbonate (3.7 g, 35 mmol) in water (15 mL). The reaction mixture was stirred overnight and the resulting solution was then extracted with ethyl acetate (3×150 mL). The organic layer was dried with sodium sulfate, and the ethyl acetate removed to yield 3-chloro-N-(1-(3-fluorophenyl)ethylidene)propan-1-amine (8-1) as a light yellow oil. m/z=214.0 [M+1].

In step 8-2, 3-chloro-N-(1-(3-fluorophenyl)ethylidene) propan-1-amine (8-1) (4.7 g, 22 mmol) was added at −78° C. to a solution of lithium granules (0.8 g, 110 mmol) and 4,4'-di-tert-butylbiphenyl (0.6 g, 2.2 mmol) in THF (40 mL) cooled to −78° C. The resulting solution was stirred at −78° C. for 2 hours then quenched with water and the temperature was allowed to increase to 20° C. Solids were then removed by filtration, the mother liquor was reduced using a rotary evaporator and the resulting residue was reconstituted in ethyl acetate. The organic was washed with 1N HCl (3×25 mL) and the aqueous layer extracted with ethyl acetate. The aqueous layer was neutralized with 1N NaOH solution and extracted with ethyl acetate (3×100 mL). The organic layer was dried with sodium sulfate and the solvent removed to yield 2-(3-fluorophenyl)-2-methylpyrrolidine (8-2) as a light yellow oil. m/z=180.3 [M+1].

Example 9

2-(3-fluorophenyl)pyrrolidine 2-(3-fluorophenyl)pyrrolidine (9-2) was synthesized in two steps as shown in scheme 9.

In step 9-1, 3-chloropropan-1-amine hydrochloride (43 g, 331 mmol) was added to a suspension of 3-fluorobenzaldehyde (41 g, 331 mmol) and sodium carbonate (39 g, 364 mmol) in water (100 mL) and the resulting slurry was stirred over-night. The resulting solution was extracted with ethyl acetate (3×150 mL) and the organic layer dried with sodium sulfate. The ethyl acetate was removed to yield 3-chloro-N-(3-fluorobenzylidene)propan-1-amine (9-1) as a light yellow oil m/z=200.0 [M+1].

In step 9-2, 3-chloro-N-(3-fluorobenzylidene)propan-1-amine (9-1) (53 g, 266 mmol) was added at −78° C. to a solution of lithium granules (5.5 g, 800 mmol) and 4,4'-di-tert-butylbiphenyl (5.7 g, 21 mmol) in THF (50 mL) cooled to −78° C. The resulting solution was stirred at −78° C. for 2 hours then quenched with water and the temperature was allowed to rise up to 20° C. The solids were removed by filtration and the mother liquor was reduced using a rotary evaporator. The resulting residue was reconstituted in ethyl acetate, the organic washed with 1N HCl (3×25 mL) and the aqueous layer was extracted with ethyl acetate. The aqueous layer was then neutralized with 1N NaOH solution and the aqueous layer was extracted with ethyl acetate (3×100 mL). The organic layer was dried with sodium sulfate and the solvent was removed to yield 2-(3-fluorophenyl)pyrrolidine (9-2) as a light yellow oil. m/z=165.2 [M+1].

Scheme 10

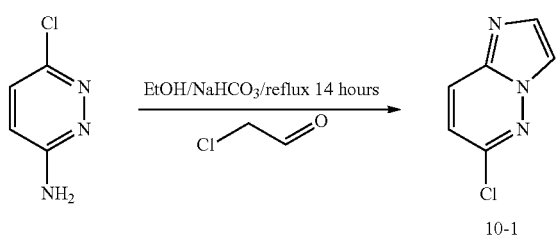

10-1

Example 10

Chloro-imidazo[1,2-b]pyridazine

Chloro-imidazo[1,2-b]pyridazine (10-1) was synthesized as shown in scheme 10, wherein chloracetaldehyde (55% in water, 126 ml, 880 mmol) was added to a solution of 6-chloropyridazin-3-ylamine (25.43 g, 196 mmol) and NaHCO$_3$ (28 g, 334 mmol) in EtOH (600 ml) and then the reaction mixture was heated to reflux while stirring for 14 hours. The resulting dark brown reaction mixture was then concentrated under vacuum and the resulting residue reconstituted with dichloromethane (DCM). This solution was filtered through a celite pad and the solid washed with DCM and the solvent was then removed to yield a dark brown oil. 2M HCl (290 ml) and water (300 ml) was added to the residue and the resulting slurry was stirred at room temperature for 15 minutes. The solution was filtered through a celite pad and the filter cake was washed with water. The filtrate was extracted with diethyl ether (3×200 ml). The aqueous layer was cooled to 0° C. (ice bath) and neutralized using NaOH (24 g). The resulting slurry was extracted with diethyl ether (6×300 ml), dried using sodium sulfate and the diethyl ether was removed using a rotary evaporator to yield chloro-imidazo[1,2-b]pyridazine (10-1) as a light orange solid. MS: 155.1 [M+1]$^+$.

Scheme 11

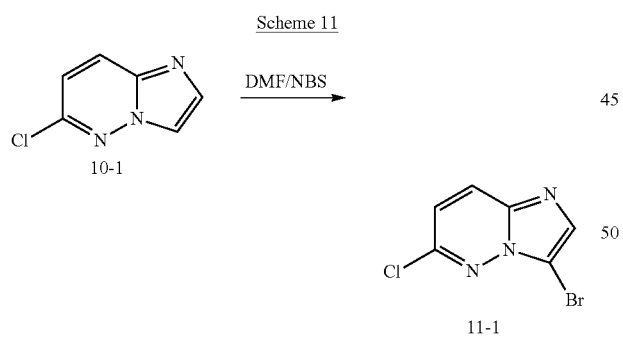

11-1

Example 11

3-bromo-6-chloroimidazo[1,2-b]pyridazine 3-bromo-6-chloroimidazo[1,2-b]pyridazine (11-1) was synthesized as shown in scheme 11, wherein N-bromosuccinamide (19.2 g, 108 mmol) was added to a solution of chloro-imidazo[1,2-b]pyridazine (10-1) (15 g, 98 mmol) in DMF cooled to 0° C. The resulting solution was stirred at 0° C. for 1 hour and the reaction mixture was then poured into 1.4 L of stirring water at room temperature. The resulting yellow heterogeneous solution was then stirred at room temperature for one hour and the solids were then filtered and washed with hexanes. The solid was dried under vacuum over-night to yield 3-bromo-6-chloroimidazo[1,2-b]pyridazine (11-1) as a yellow solid.

Scheme 12

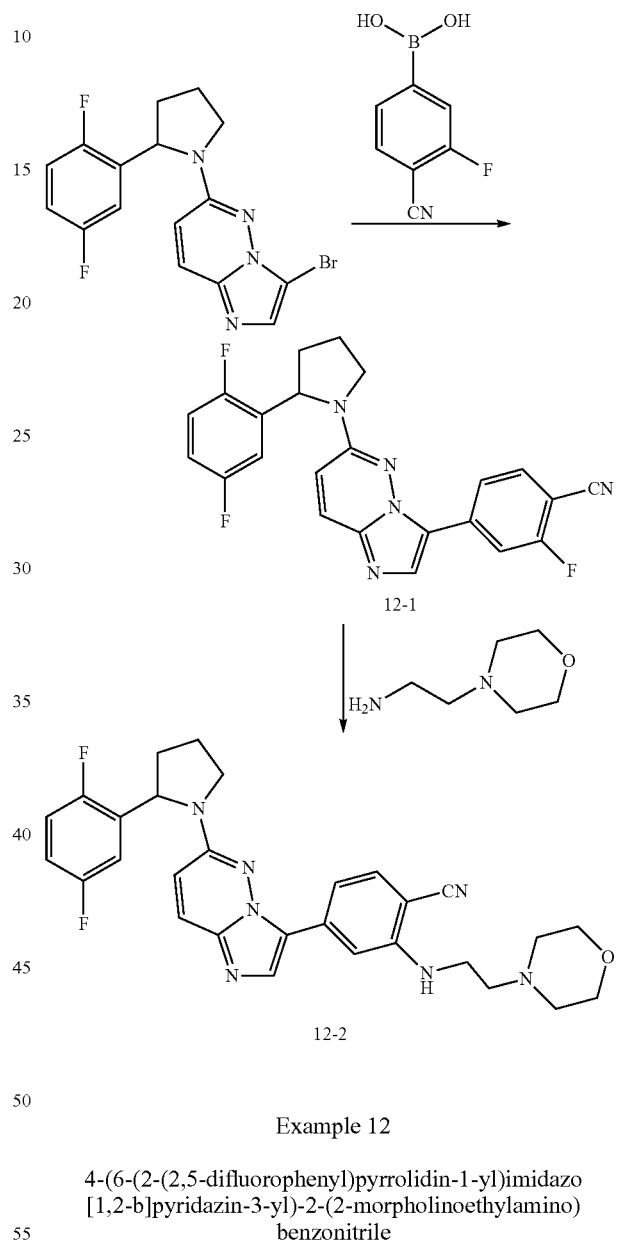

Example 12

4-(6-(2-(2,5-difluorophenyl)pyrrolidin-1-yl)imidazo[1,2-b]pyridazin-3-yl)-2-(2-morpholinoethylamino)benzonitrile 4-(6-(2-(2,5-difluorophenyl)pyrrolidin-1-yl)imidazo[1,2-b]pyridazin-3-yl)-2-(2-morpholinoethylamino)benzonitrile (12-2) was synthesized in two steps as shown in scheme 12.

In step 12-1, [Pd(Dppf)$_2$]Cl$_2$ (90 mg, 0.11 mmol), sodium carbonate (0.41 g, 3.9 mmol), and 4-cyano-3-fluorophenylboronic acid (0.36 g, 2.2 mmol) were added to a solution of 3-bromo-6-(2-(2,5-difluorophenyl)pyrrolidin-1-yl)imidazo[1,2-b]pyridazine (6-6) (0.42 g, 1.1 mmol) in 3 mL of dioxane and 1 mL of DI water. The reaction mixture was heated in a microwave for twenty minutes at 150° C., and the slurry was then cooled to room temperature and filtered through a 0.2

μM nylon fit. The solvent was removed from the mother liquor and the remaining residue was reconstituted in dichloromethane (DCM). This solution was loaded onto a 12 g silica gel column and eluted using a 0-10% methanol in DCM gradient over 30 minutes. The solvent was removed from the desired fractions to yield 4-(6-(2-(2,5-difluorophenyl)pyrrolidin-1-yl)imidazo[1,2-b]pyridazin-3-yl)-2-fluorobenzonitrile. m/z=420.2 [M+1].

In step 12-2, 2-morpholinoethanamine (30 mg, 0.30 mmol) was added to 4-(6-(2-(2,5-difluorophenyl)pyrrolidin-1-yl)imidazo[1,2-b]pyridazin-3-yl)-2-fluorobenzonitrile (40 mg, 0.13 mmol) in 1 mL of DMF. The resulting mixture was heated to 110° C. and stirred for 12 hours at 110° C. The product was then purified using mass triggered preparatory LC/MS giving 1-(6-(6-(2-(2,5-difluorophenyl)pyrrolidin-1-yl)imidazo[1,2-b]pyridazin-3-yl)pyridin-2-yl)piperidin-4-ol (13-2). $^1$H NMR (400 MHz, D$_6$ Dimethylsulfoxide) 8.050 (s, 1H) 7.854 (d, 0.025, 1H) 7.434 (br s, 1H) 7.327 (dt, J=0.023, 0.011, 1H) 7.262 (m, 1H) 7.173 (m, 1H) 7.070 (m, 1H) 6.937 (m, 1H) 6.747 (br s, 1H) 5.770 (t, J=0.012, 1H) 5.244 (d, J=0.019, 1H) 3.949 (dt, J=0.017, 0.006, 1H) 3.575 (q, J=0.023, 1H) 3.522 (t, J=0.011, 4H) 3.268 (m, 4H) 2.536 (t, J=0.016, 2H) 1.985 (m, 3H) LCMS m/z 530.2 [M+1]

By repeating the procedures described in the above examples, using appropriate starting materials, the following compounds of Formula (I), as identified in Table 5, were obtained.

TABLE 5

| Compound Number | Structure | Physical Data $^1$H NMR 400 MHz (DMSO-d$_6$) and/or MS (m/z) |
|---|---|---|
| 1 | 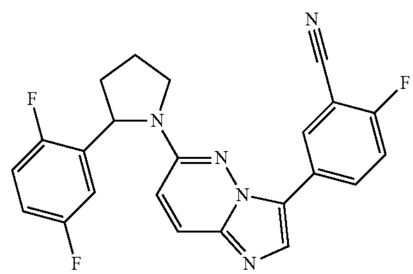 [SMILES: N#Cc1cc(-c2cnc3ccc(N4CCCC4c4cc(F)ccc4F)nn23)ccc1F] | 420.4 (M + H) |
| 2 | 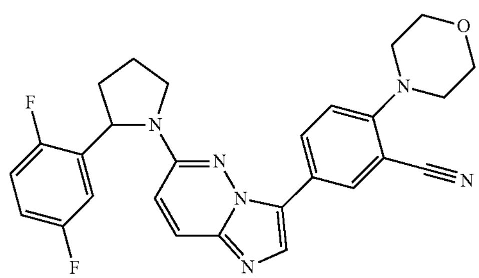 [SMILES: N#Cc1cc(-c2cnc3ccc(N4CCCC4c4cc(F)ccc4F)nn23)ccc1N1CCOCC1] | 487.5 (M + H) |
| 3 | 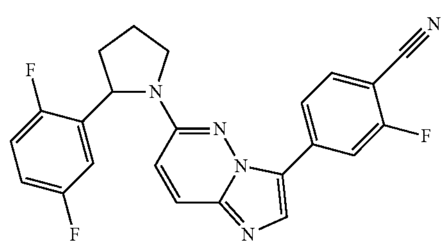 [SMILES: N#Cc1ccc(-c2cnc3ccc(N4CCCC4c4cc(F)ccc4F)nn23)cc1F] | 487.5 (M + H) |
| 4 | 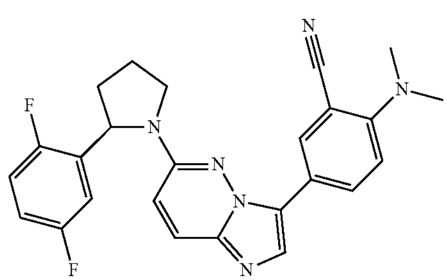 [SMILES: CN(C)c1ccc(-c2cnc3ccc(N4CCCC4c4cc(F)ccc4F)nn23)cc1C#N] | 8.247 (s, 1H) 8.192 (br s, 1H) 8.071 (d, J = 0.024, 1H) 7.926 (br s, 1H) 7.341 (dt, J = 0.024, 0.011, 1H) 7.139 (m, 2H) 7.037 (m, 1H) 6.929 (m, 1H) 5.332 (d, J = 0.018, 1H) 4.033 (m, 1H) 3.652 (q, J = 0.023, 2H) 3.090 (s, 6H) 2.122 (m, 3H) 445.5 (M + H) |

TABLE 5-continued

| Compound Number | Structure | Physical Data $^1$H NMR 400 MHz (DMSO-$d_6$) and/or MS (m/z) |
|---|---|---|
| 5 | 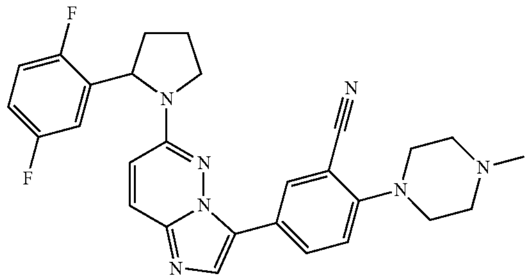 [SMILES: CN1CCN(c2ccc(-c3cnc4ccc(N5CCCC5c5cc(F)ccc5F)nn34)cc2C#N)CC1] | 8.212 (br s, 1H) 8.019 (br s, 1H) 7.927 (s, 1H) 7.849 (d, J = 0.024, 1H) 7.274 (dt, J = 0.024, 0.012, 1H) 7.046 (m, 1H) 6.950 (m, 2H) 6.782 (m, 1H) 5.250 (d, J = 0.019, 1H) 3.933 (dt, J = 0.024, 0.006, 1H) 3.553 (q, 0.022, 1H) 3.132 (t, J = 0.012, 3H) 2.473 (m, 6H) 2.197 (s, 3H) 1.986 (m, 3H) 500.6 (M + H) |
| 6 | 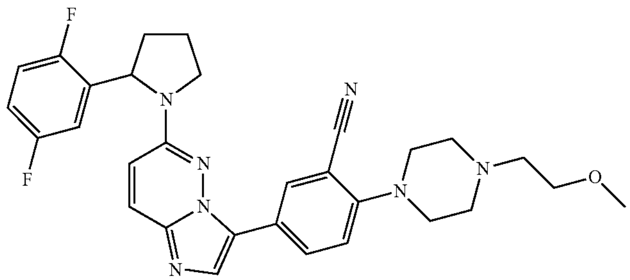 [SMILES: COCCN1CCN(c2ccc(-c3cnc4ccc(N5CCCC5c5cc(F)ccc5F)nn34)cc2C#N)CC1] | 544.6 (M + H) |
| 7 | 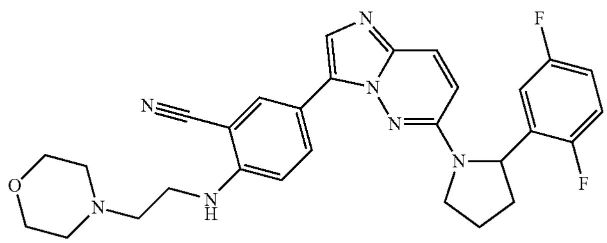 [SMILES: N#Cc1cc(-c2cnc3ccc(N4CCCC4c4cc(F)ccc4F)nn23)ccc1NCCN1CCOCC1] | 530.6 (M + H) |
| 8 | 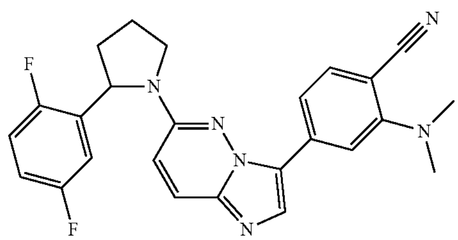 [SMILES: CN(C)c1cc(-c2cnc3ccc(N4CCCC4c4cc(F)ccc4F)nn23)ccc1C#N] | 445.5 (M + H) |
| 9 | 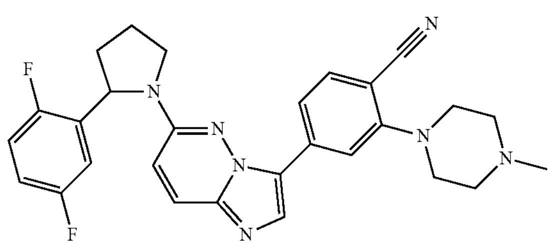 [SMILES: CN1CCN(c2cc(-c3cnc4ccc(N5CCCC5c5cc(F)ccc5F)nn34)ccc2C#N)CC1] | 9.935 (br s, 1H) 8.364 (s, 1H) 8.019 (d, J = 0.024, 1H) 7.626 (m, 2H) 7.430 (dt, J = 0.024, 0.011, 1H) 7.153 (m, 1H) 7.033 (m, 2H) 5.325 (d, J = 0.019, 1H) 4.035 (dt, J = 0.019, 0.006, 1H) 3.727 (d, J = 0.028, 2H) 3.603 (m, 3H) 3.241 (m, 4H) 2.926 (s, 3H) 2.090 (m, 4H) 500.6 (M + H) |
| 10 | 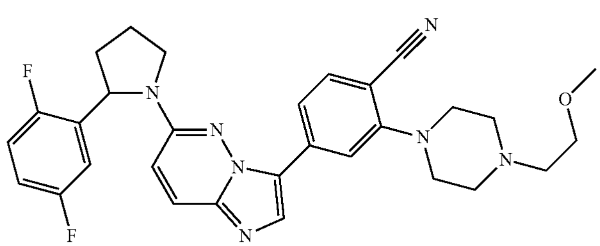 [SMILES: COCCN1CCN(c2cc(-c3cnc4ccc(N5CCCC5c5cc(F)ccc5F)nn34)ccc2C#N)CC1] | 9.840 (br s, 1H) 8.335 (s, 1H) 8.007 (d, J = 0.025, 1H) 7.622 (m, 2H) 7.429 (m, 1H) 7.153 (m, 1H) 7.033 (m, 2H) 5.324 (d, J = 0.019, 1H) 4.035 (dt, J = 0.019, 0.007, 1H) 3.724 (m, 9H) 3.357 (s, 3H) 3.305 (m, 4H) 2.122 (m, 4H) 544.6 (M + H) |

TABLE 5-continued

| Compound Number | Structure | Physical Data <sup>1</sup>H NMR 400 MHz (DMSO-d<sub>6</sub>) and/or MS (m/z) |
|---|---|---|
| 11 | 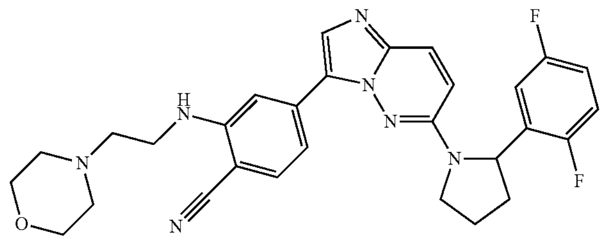 [SMILES: N#Cc1ccc(-c2cnc3ccc(N4CCCC4c4cc(F)ccc4F)nn23)cc1NCCN1CCOCC1] | 8.050 (s, 1H) 7.854 (d, 0.025, 1H) 7.434 (br s, 1H) 7.327 (dt, J = 0.023, 0.011, 1H) 7.262 (m, 1H) 7.173 (m, 1H) 7.070 (m, 1H) 6.937 (m, 1H) 6.747 (br s, 1H) 5.770 (t, J = 0.012, 1H) 5.244 (d, J = 0.019, 1H) 3.949 (dt, J = 0.017, 0.006, 1H) 3.575 (q, J = 0.023, 1H) 3.522 (t, J = 0.011, 4H) 3.268 (m, 4H) 2.536 (t, J = 0.016, 2H) 1.985 (m, 3H) 530.6 (M + H) |
| 12 | 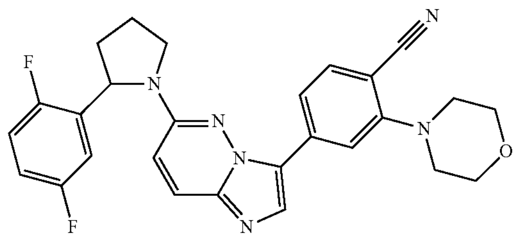 [SMILES: N#Cc1ccc(-c2cnc3ccc(N4CCCC4c4cc(F)ccc4F)nn23)cc1N1CCOCC1] | 487.5 (M + H) |
| 13 | 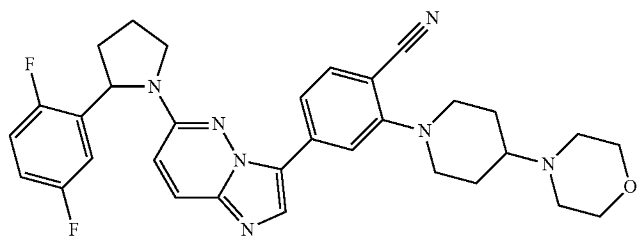 [SMILES: N#Cc1ccc(-c2cnc3ccc(N4CCCC4c4cc(F)ccc4F)nn23)cc1N1CCC(N2CCOCC2)CC1] | 9.908 (br s, 1H) 8.362 (s, 1H) 8.046 (d, J = 0.025, 1H) 7.600 (br s, 2H) 7.437 (dt, J = 0.024, 0.011, 1H) 7.155 (m, 1H) 7.032 (m, 2H) 5.330 (d, J = 0.019, 1H) 4.035 (d, J = 0.024, 3H) 3.698 (m, 5H) 3.543 (d, J = 0.030, 2H) 3.409 (m, 2H) 3.182 (m, 2H) 2.898 (t, J = 0.030, 2H) 2.277 (d, J = 0.026, 2H) 1.950 (m, 5H) 570.6 (M + H) |
| 14 | 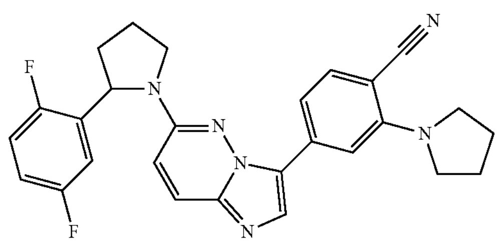 [SMILES: N#Cc1ccc(-c2cnc3ccc(N4CCCC4c4cc(F)ccc4F)nn23)cc1N1CCCC1] | 8.230 (s, 1H) 7.910 (d, J = 0.025, 1H) 7.239 (m, 2H) 7.008 (m, 3H) 6.867 (m, 2H) 5.178 (d, J = 0.020, 1H) 3.883 (t, J = 0.019, 2H) 3.441 (m, 5H) 1.829 (m, 7H) 471.5 (M + H) |
| 15 | 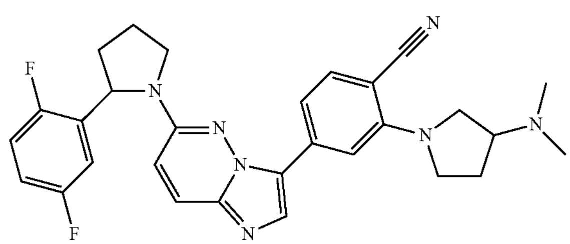 [SMILES: CN(C)C1CCN(c2cc(-c3cnc4ccc(N5CCCC5c5cc(F)ccc5F)nn34)ccc2C#N)C1] | 9.934 (br s, 1H) 8.264 (s, 1H) 7.994 (d, J = 0.025, 1H) 7.419 (m, 3H) 7.154 (m, 1H) 7.024 (m, 2H) 5.310 (m, 1H) 3.799 (m, 12H) 2.904 (d, J = 0.019, 4H) 2.228 (m, 1H) 2.0677 (m, 2H) 514.6 (M + H) |
| 16 | 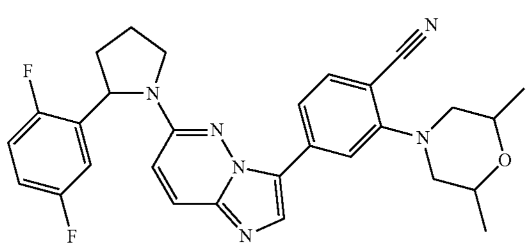 [SMILES: CC1CN(c2cc(-c3cnc4ccc(N5CCCC5c5cc(F)ccc5F)nn34)ccc2C#N)CC(C)O1] | 515.6 (M + H) |

TABLE 5-continued

| Compound Number | Structure | Physical Data $^1$H NMR 400 MHz (DMSO-$d_6$) and/or MS (m/z) |
|---|---|---|
| 17 | 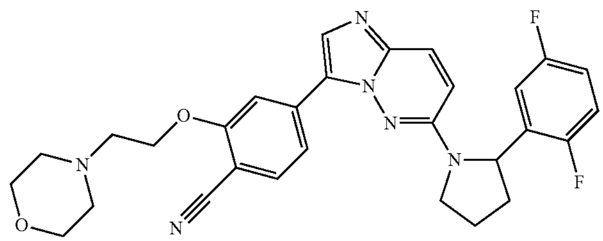 [SMILES: N#Cc1ccc(-c2cnc3ccc(N4CCCC4c4cc(F)ccc4F)nn23)cc1OCCN1CCOCC1] | 531.6 (M + H) |
| 18 | 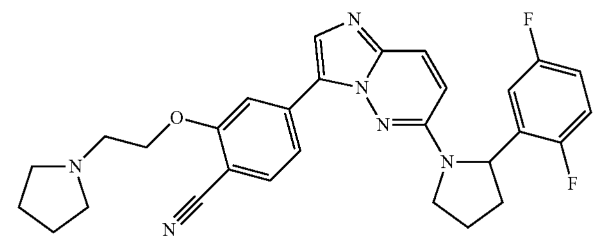 [SMILES: N#Cc1ccc(-c2cnc3ccc(N4CCCC4c4cc(F)ccc4F)nn23)cc1OCCN1CCCC1] | 515.6 (M + H) |
| 19 | 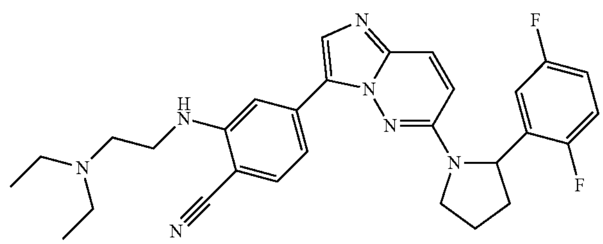 [SMILES: CCN(CC)CCNc1cc(-c2cnc3ccc(N4CCCC4c4cc(F)ccc4F)nn23)ccc1C#N] | 515.6 (M + H) |
| 20 | 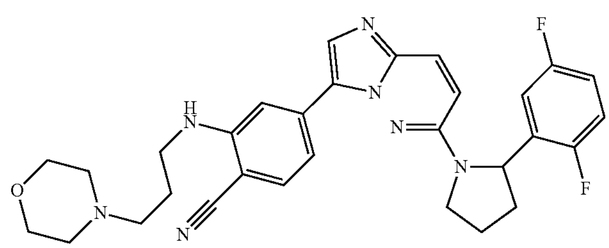 [SMILES: N#Cc1ccc(-c2cnc(/C=C\C(=N)N3CCCC3c3cc(F)ccc3F)[nH]2)cc1NCCCN1CCOCC1] | 9.747 (br s, 1H) 8.280 (d, J = 0.009, 1H) 7.999 (m, 1H) 7.419 (m, 3H) 7.132 (m, 3H) 6.297 (br s, 1H) 5.313 (d, J = 0.019, 1H) 4.001 (m, 4H) 3.625 (m, 3H) 3.433 (m, 4H) 3.197 (m, 4H) 1.994 (m, 5H) 544.6 (M + H) |
| 21 | 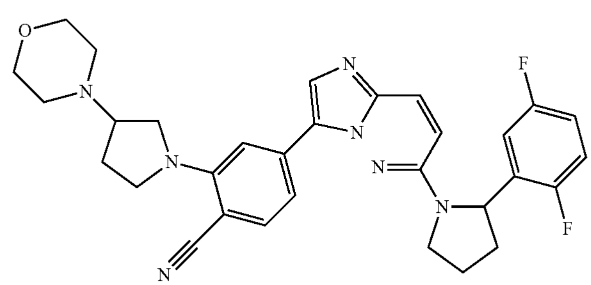 [SMILES: N#Cc1ccc(-c2cnc(/C=C\C(=N)N3CCCC3c3cc(F)ccc3F)[nH]2)cc1N1CCC(N2CCOCC2)C1] | 556.6 (M + H) |
| 22 | 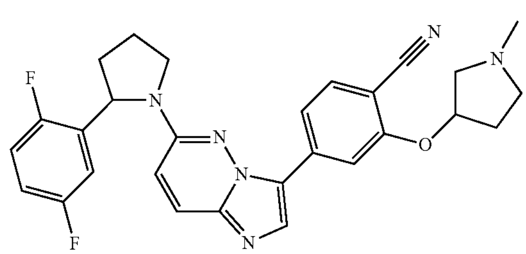 [SMILES: CN1CCC(Oc2cc(-c3cnc4ccc(N5CCCC5c5cc(F)ccc5F)nn34)ccc2C#N)C1] | 501.5 (M + H) |

TABLE 5-continued

| Compound Number | Structure | Physical Data<br>¹H NMR 400 MHz (DMSO-d₆)<br>and/or MS (m/z) |
|---|---|---|
| 23 | 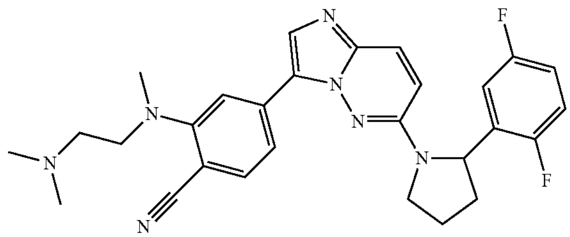 [SMILES: CN(C)CCN(C)c1cc(-c2cnc3ccc(N4CCCC4c4cc(F)ccc4F)nn23)ccc1C#N] | 502.6 (M + H) |
| 24 | 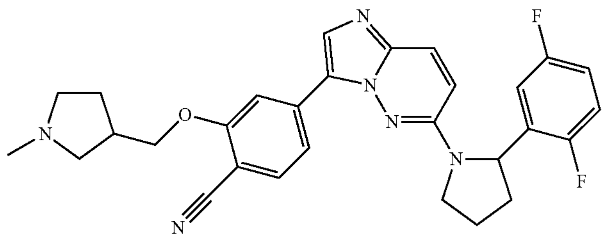 [SMILES: CN1CCC(COc2cc(-c3cnc4ccc(N5CCCC5c5cc(F)ccc5F)nn34)ccc2C#N)C1] | 515.6 (M + H) |
| 25 | 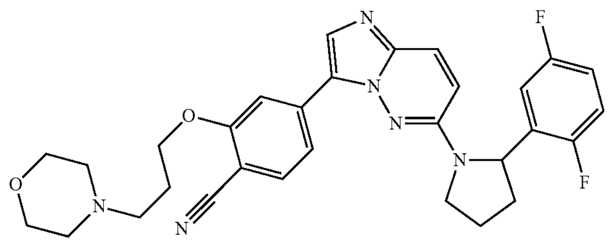 [SMILES: N#Cc1ccc(-c2cnc3ccc(N4CCCC4c4cc(F)ccc4F)nn23)cc1OCCCN1CCOCC1] | 545.6 (M + H) |
| 26 | 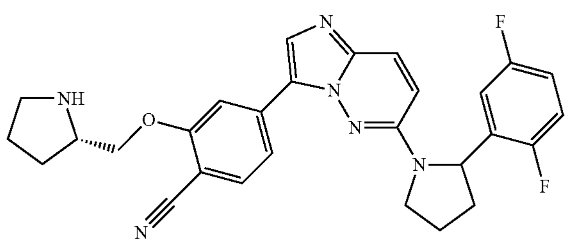 [SMILES: N#Cc1ccc(-c2cnc3ccc(N4CCCC4c4cc(F)ccc4F)nn23)cc1OC[C@@H]1CCCN1] | 9..321 (m, 1H) 8.935 (m, 1H)<br>8.365 (m,1H) 7.998 (m, 1H)<br>7.743 (m, 2H) 7.408 (m, 1H)<br>7.147 (m, 1H) 7.034 (m, 1H)<br>5.321 (d, J = 0.019, 1H) 4.530 (m, 2H) 4.371 (m, 2H) 4.048 (m, 2H)<br>3.674 (m, 1H) 3.281 (m, 2H)<br>2.216 (m, 1H) 2.072 (m, 3H)<br>1.947 (m, 3H)<br>501.5 (M + H) |
| 27 | 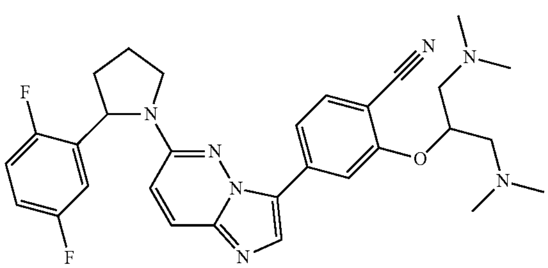 [SMILES: CN(C)CC(CN(C)C)Oc1cc(-c2cnc3ccc(N4CCCC4c4cc(F)ccc4F)nn23)ccc1C#N] | 546.6 (M + H) |
| 28 | 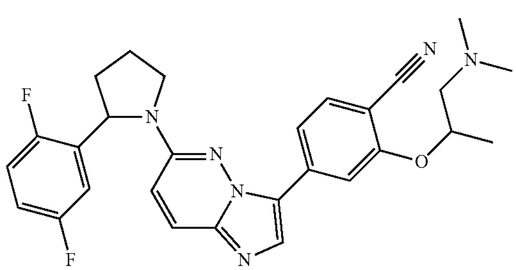 [SMILES: CC(CN(C)C)Oc1cc(-c2cnc3ccc(N4CCCC4c4cc(F)ccc4F)nn23)ccc1C#N] | 9.774 (br s, 1H) 8.374 (s, 1H)<br>8.014 (m, 1H) 7.863 (m, 1H)<br>7.726 (m, 1H) 7.632 (m, 1H) 7.453 (m, 1H) 7.152 (m, 1H)<br>7.047 (m, 1H) 5.327 (m, 2H)<br>5.203 (d, J = 0.02, 1H) 4.533 (m, 1H) 4.038 (m, 1H) 3.653 (m, 1H)<br>3.543 (m, 2H) 2.920 (m, 4H)<br>2.046 (m, 2H) 1.914 (m, 1H)<br>1.349 (d, J = 0.015, 2H)<br>503.6 (M + H) |

TABLE 5-continued

| Compound Number | Structure | Physical Data $^1$H NMR 400 MHz (DMSO-$d_6$) and/or MS (m/z) |
|---|---|---|
| 29 | 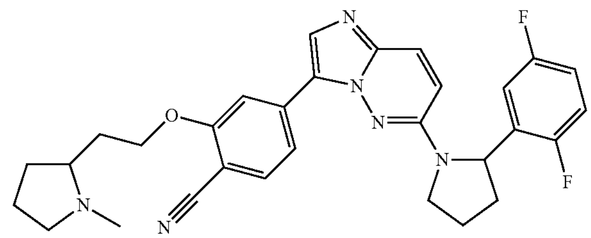 [SMILES: CN1CCCC1CCOc1cc(-c2cnc3ccc(N4CCCC4c4cc(F)ccc4F)nn23)ccc1C#N] | 9.584 (br s, 1H) 8.324 (s, 1H) 7.988 (m, 1H) 7.697 (m, 1H) 7.608 (m, 1H) 7.428 (m, 2H) 7.145 (m, 1H) 7.033 (m, 1H) 5.337 (d, J = 0.019, 1H) 4.342 (m, 3H) 4.041 (m, 2H) 3.644 (m, 3H) 3.415 (m, 1H) 3.132 (m, 1H) 2.922 (d, J = 0.013,, 2H) 2.334 (m, 1H) 2.036 (m, 6H) 1.829 (m, 1H) 529.6 (M + H) |
| 30 | 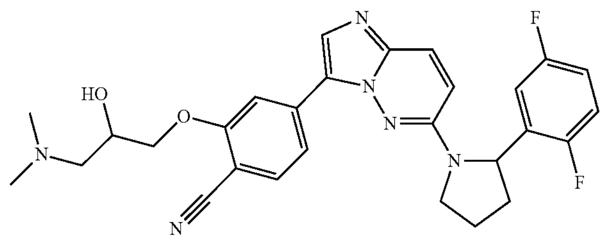 [SMILES: CN(C)CC(O)COc1cc(-c2cnc3ccc(N4CCCC4c4cc(F)ccc4F)nn23)ccc1C#N] | 519.6 (M + H) |
| 31 | 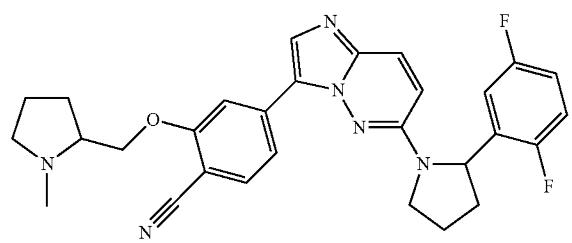 [SMILES: CN1CCCC1COc1cc(-c2cnc3ccc(N4CCCC4c4cc(F)ccc4F)nn23)ccc1C#N] | 9.973 (br s, 1H) 8.358 (m, 1H) 7.994 (m, 2H) 7.764 (m, 1H), 7.667 (m, 1H) 7.410 (m, 1H) 7.147 (m, 1H) 7.034 (m, 2H) 5.343 (d, J = 0.02, 1H) 4.655 (m, 2H) 4.390 (m, 2H) 4.038 (m, 2H) 3.657 (m, 2H) 3.191 (m, 1H) 2.334 (m, 1H) 2.122 (m, 5H) 515.6 (M + H) |
| 32 | 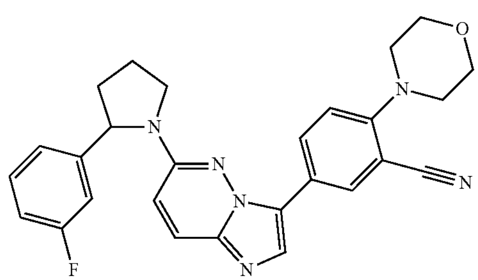 [SMILES: N#Cc1cc(-c2cnc3ccc(N4CCCC4c4cccc(F)c4)nn23)ccc1N1CCOCC1] | 8.367 (br d, 1H) 8.221 (d, J = 0.013, 1H) 7.952 (t, J = 0.024, 1H) 7.142 (m, 7H) 5.151 (dd, J = 0.016, 0.004, 1H) 3.930 (m, 2H) 3.738 (t, J = 0.011, 4H) 3.614 (t, J = 0.021, 2H) 3.174 (m, 3H) 1.977 (m, 2H) 1.826 (m, 1H) 469.5 (M + H) |
| 33 | 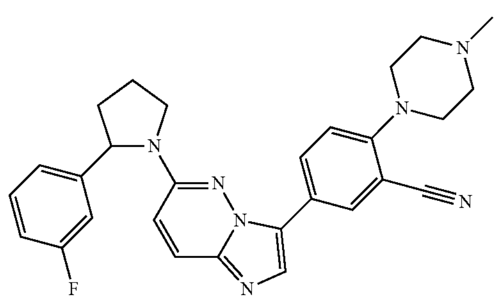 [SMILES: CN1CCN(c2ccc(-c3cnc4ccc(N5CCCC5c5cccc(F)c5)nn34)cc2C#N)CC1] | 482.6 (M + H) |

| Compound Number | Structure | Physical Data ¹H NMR 400 MHz (DMSO-d$_6$) and/or MS (m/z) |
|---|---|---|
| 34 | 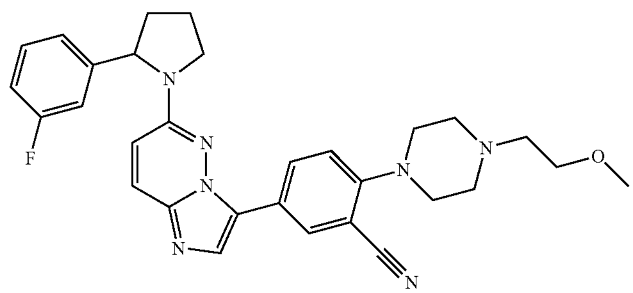 [SMILES: COCCN1CCN(c2ccc(-c3cnc4ccc(N5CCCC5c5cccc(F)c5)nn34)cc2C#N)CC1] | 526.6 (M + H) |
| 35 | 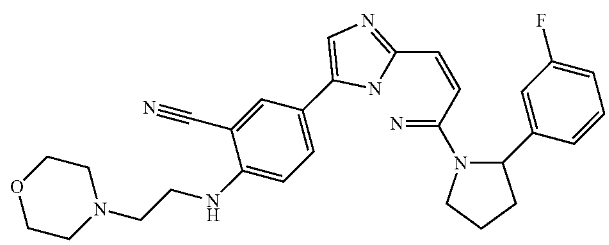 [SMILES: N#Cc1cc(-c2cnc(/C=C\C(=N)N3CCCC3c3cccc(F)c3)[nH]2)ccc1NCCN1CCOCC1] | 512.6 (M + H) |
| 36 | 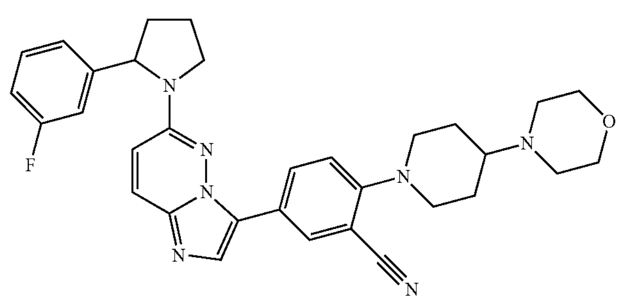 [SMILES: N#Cc1cc(-c2cnc3ccc(N4CCCC4c4cccc(F)c4)nn23)ccc1N1CCC(N2CCOCC2)CC1] | 552.7 (M + H) |
| 37 | 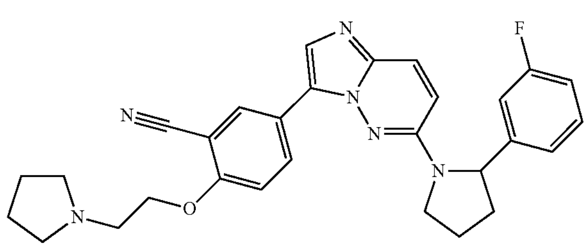 [SMILES: N#Cc1cc(-c2cnc3ccc(N4CCCC4c4cccc(F)c4)nn23)ccc1OCCN1CCCC1] | 497.6 (M + H) |
| 38 | 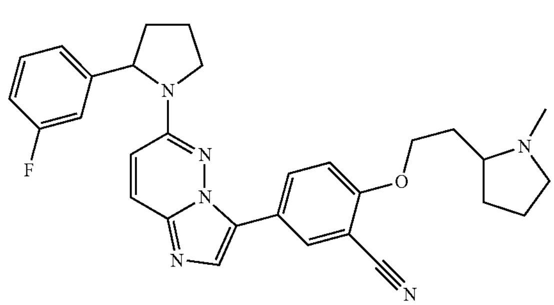 [SMILES: CN1CCCC1CCOc1ccc(-c2cnc3ccc(N4CCCC4c4cccc(F)c4)nn23)cc1C#N] | 511.6 (M + H) |

TABLE 5-continued

| Compound Number | Structure | Physical Data<br>¹H NMR 400 MHz (DMSO-d₆) and/or MS (m/z) |
|---|---|---|
| 39 | 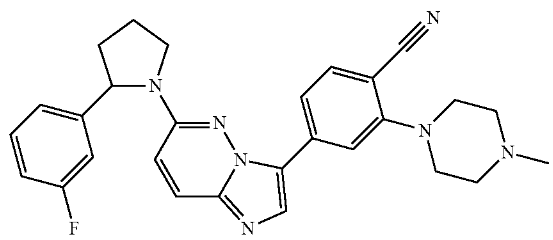 [SMILES: CN1CCN(c2cc(-c3cnc4ccc(N5CCCC5c5cccc(F)c5)nn34)ccc2C#N)CC1] | 482.6 (M + H) |
| 40 | 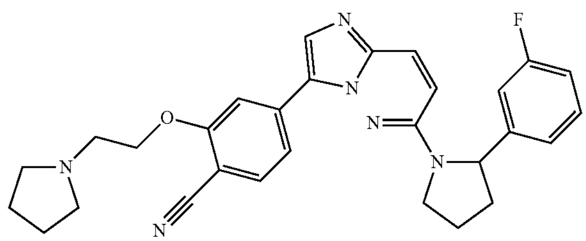 [SMILES: N#Cc1ccc(-c2cnc(/C=C\C(=N)N3CCCC3c3cccc(F)c3)[nH]2)cc1OCCN1CCCC1] | 497.6 (M + H) |
| 41 | 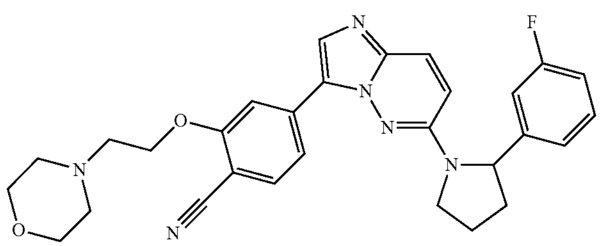 [SMILES: N#Cc1ccc(-c2cnc3ccc(N4CCCC4c4cccc(F)c4)nn23)cc1OCCN1CCOCC1] | 513.6 (M + H) |
| 42 | 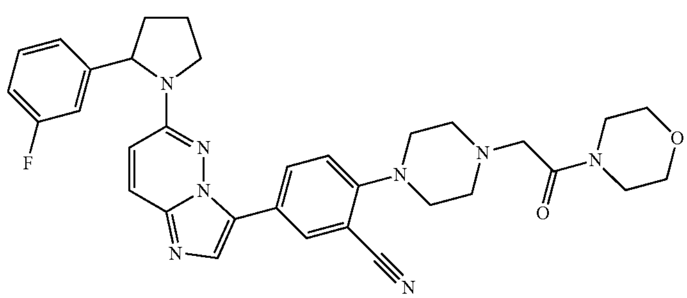 [SMILES: N#Cc1cc(-c2cnc3ccc(N4CCCC4c4cccc(F)c4)nn23)ccc1N1CCN(CC(=O)N2CCOCC2)CC1] | 595.7 (M + H) |
| 43 | 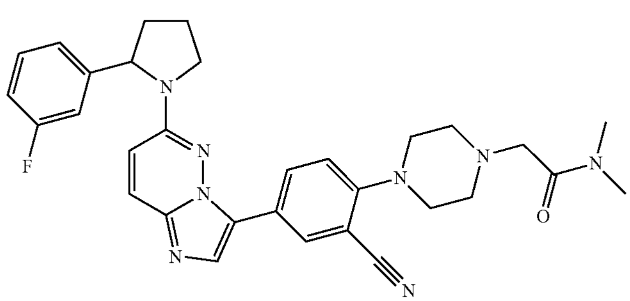 [SMILES: CN(C)C(=O)CN1CCN(c2ccc(-c3cnc4ccc(N5CCCC5c5cccc(F)c5)nn34)cc2C#N)CC1] | 553.6 (M + H) |

TABLE 5-continued

| Compound Number | Structure | Physical Data $^1$H NMR 400 MHz (DMSO-d$_6$) and/or MS (m/z) |
|---|---|---|
| 44 | 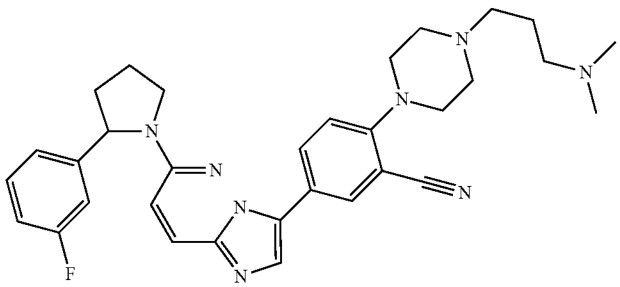 [SMILES: CN(C)CCCN1CCN(c2ccc(-c3cnc(/C=C\C(=N)N4CCCC4c4cccc(F)c4)[nH]3)cc2C#N)CC1] | 553.7 (M + H) |
| 45 | 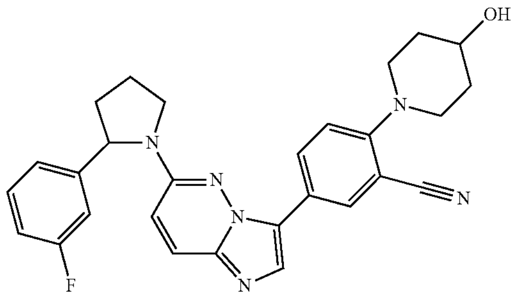 [SMILES: N#Cc1cc(-c2cnc3ccc(N4CCCC4c4cccc(F)c4)nn23)ccc1N1CCC(O)CC1] | 483.6 (M + H) |
| 46 | 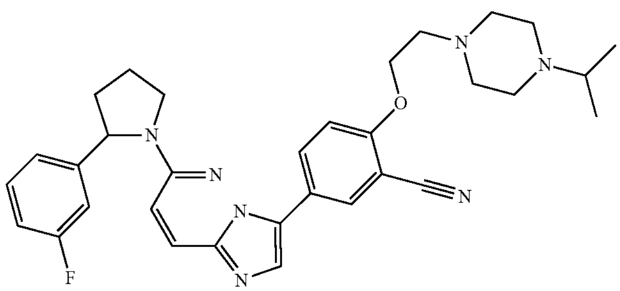 [SMILES: CC(C)N1CCN(CCOc2ccc(-c3cnc(/C=C\C(=N)N4CCCC4c4cccc(F)c4)[nH]3)cc2C#N)CC1] | 554.7 (M + H) |
| 47 | 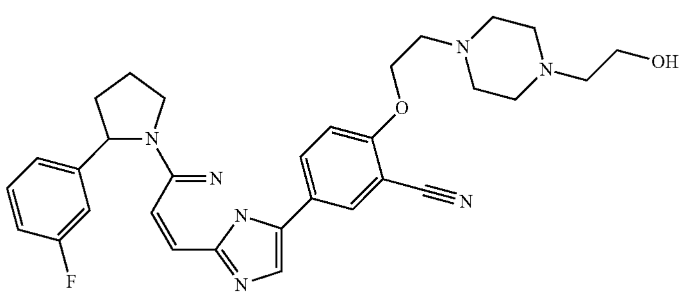 [SMILES: N#Cc1cc(-c2cnc(/C=C\C(=N)N3CCCC3c3cccc(F)c3)[nH]2)ccc1OCCN1CCN(CCO)CC1] | 556.6 (M + H) |
| 48 | 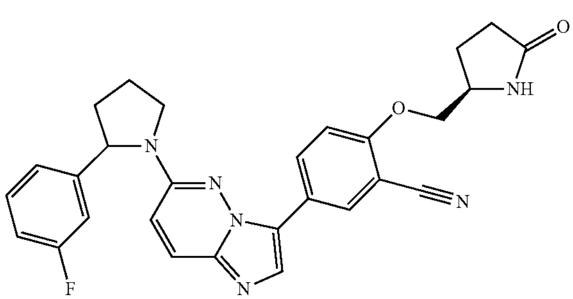 [SMILES: N#Cc1cc(-c2cnc3ccc(N4CCCC4c4cccc(F)c4)nn23)ccc1OC[C@H]1CCC(=O)N1] | 497.5 (M + H) |

TABLE 5-continued

| Compound Number | Structure | Physical Data $^1$H NMR 400 MHz (DMSO-d$_6$) and/or MS (m/z) |
| --- | --- | --- |
| 49 | 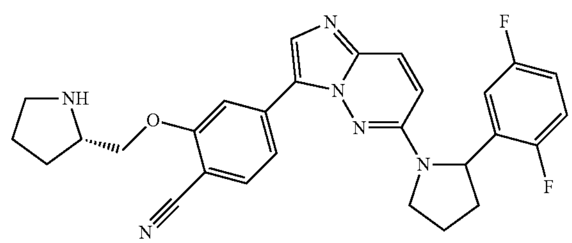 [SMILES: N#Cc1ccc(-c2cnc3ccc(N4CCCC4c4cc(F)ccc4F)nn23)cc1OC[C@@H]1CCCN1] | 501.5 (M + H) |
| 50 | 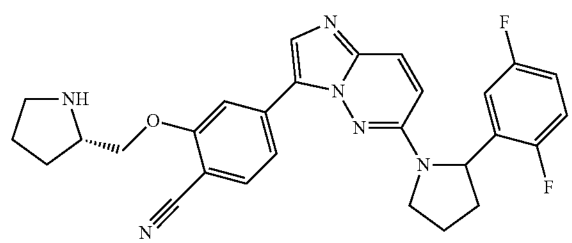 [SMILES: N#Cc1ccc(-c2cnc3ccc(N4CCCC4c4cc(F)ccc4F)nn23)cc1OC[C@@H]1CCCN1] | 501.5 (M + H) |
| 51 | 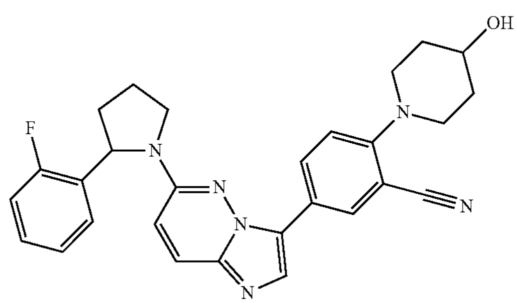 [SMILES: N#Cc1cc(-c2cnc3ccc(N4CCCC4c4ccccc4F)nn23)ccc1N1CCC(O)CC1] | 483.6 (M + H) |
| 52 | 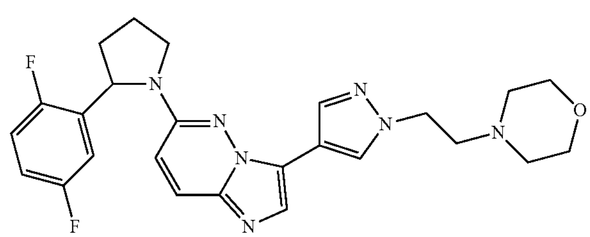 [SMILES: Fc1ccc(F)c(C2CCCN2c2ccc3ncc(-c4cnn(CCN5CCOCC5)c4)n3n2)c1] | 480.5 (M + H) |
| 53 | 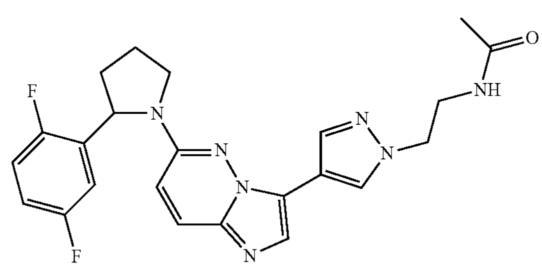 [SMILES: CC(=O)NCCn1cc(-c2cnc3ccc(N4CCCC4c4cc(F)ccc4F)nn23)cn1] | 452.5 (M + H) |

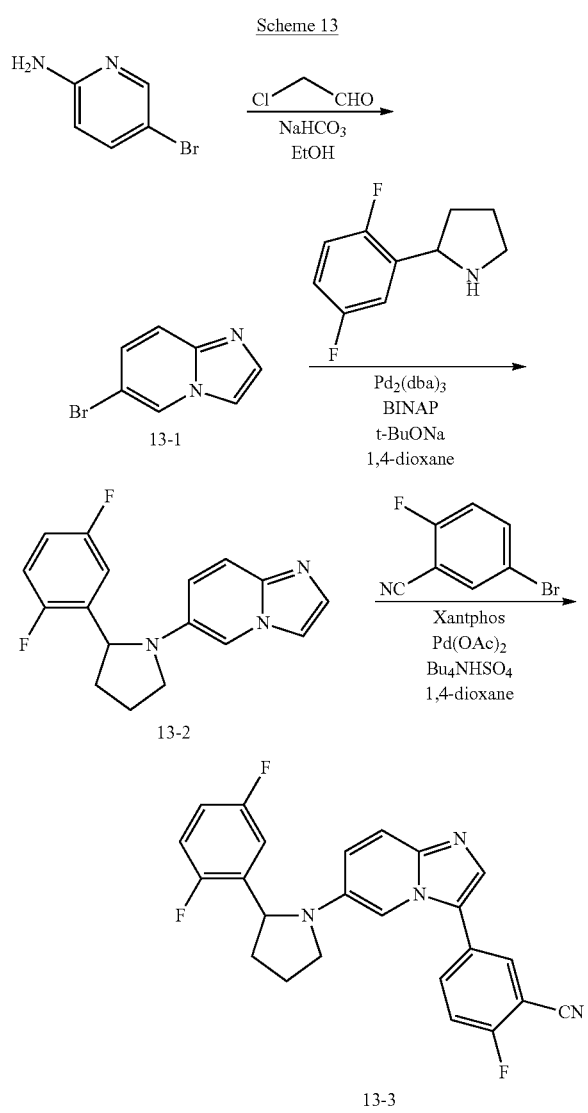

Example 13

5-(6-(2-(2,5-difluorophenyl)pyrrolidin-1-yl)imidazo[1,2-a]pyridin-3-yl)-2-fluorobenzonitrile 5-(6-(2-(2,5-difluorophenyl)pyrrolidin-1-yl)imidazo[1,2-a]pyridin-3-yl)-2-fluorobenzonitrile (13-3) was synthesized in three steps as shown in scheme 13.

In step 13-1, chloracetaldehyde (55% in water, 0.27 mL, 4.5 mmol) and NaHCO$_3$ (143 mg, 1.7 mmol) were added to a solution of 5-bromopyridin-2-amine (173 mg, 1 mmol) in EtOH (7 mL). The mixture was heated to reflux and continued overnight. The reaction mixture was cooled to room temperature and concentrated under vacuum. Dichloromethane was added to extract the residue. The organic layer was washed with water, brine, dried over Na$_2$SO$_4$, filtered, and evaporated to give the crude product. The crude was purified column chromatography (Silica gel, EtOAc/Hexane, gradient) to give 6-bromoimidazo[1,2-a]pyridine (13-1).

In step 13-2, a microwaveable vial was charged with 6-bromoimidazo[1,2-a]pyridine (197 mg, 1 mmol), 2-(2,5-difluorophenyl)pyrrolidine (238 mg, 1.3 mmol), Pd$_2$(dba)$_3$ (18 mg, 0.02 mmol), BINAP (50 mg, 0.08 mmol), t-BuONa (135 mg, 1.4 mmol) and 1,4-dioxane (5 ml), and the mixture was heated to 120° C. for 30 minutes using microwave irridiation. The mixture was filtered through celite. The filtrate was concentrated and purified by column chromatography (Silica gel, EtOAc/hexane, gradient) to give 6-(2-(2,5-difluorophenyl)pyrrolidin-1-yl)imidazo[1,2-a]pyridine (13-2).

In step 13-3, a sealed vial was charged with 6-(2-(2,5-difluorophenyl)pyrrolidin-1-yl)imidazo[1,2-a]pyridine (30 mg, 0.1 mmol), 5-bromo-2-fluorobenzonitrile (20 mg, 0.1 mmol), Pd(OAc)$_2$ (1 mg, 0.005 mmol), Xantphos (6 mg, 0.01 mmol), Cs$_2$CO$_3$ (49 mg, 0.15 mmol), Bu$_4$NHSO$_4$ (3 mg, 0.01 mmol) and 1,4-dioxane (0.5 ml), and the mixture was heated to 90° C. overnight. The mixture was filtered through celite. The filtrate was concentrated and purified by preparative LC-MS to give 5-(6-(2-(2,5-difluorophenyl)pyrrolidin-1-yl)imidazo[1,2-a]pyridin-3-yl)-2-fluorobenzonitrile (12-3). LC-MS: 419.2 (MH$^+$).

By repeating the procedures described in example 13, using appropriate starting materials, the following compounds of Formula I, as identified in Table 6, were obtained.

TABLE 6

| Compound Number | Structure | Physical Data $^1$H NMR 400 MHz (DMSO-d$_6$) and/or MS (m/z) |
|---|---|---|
| 1 | 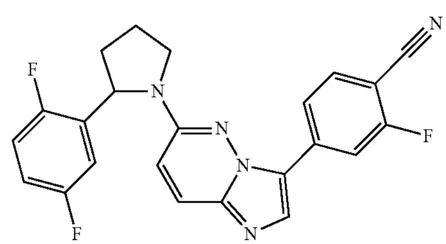 [SMILES: N#Cc1ccc(-c2cnc3ccc(N4CCCC4c4cc(F)ccc4F)nn23)cc1F] | 419.1 (M + H) |

TABLE 6-continued

| Compound Number | Structure | Physical Data $^1$H NMR 400 MHz (DMSO-$d_6$) and/or MS (m/z) |
|---|---|---|
| 2 | 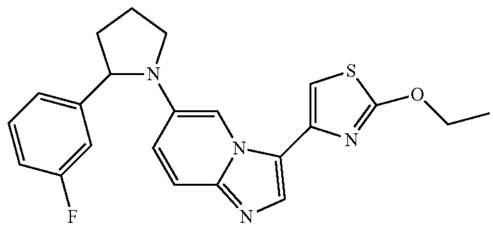 | 427.2 (M + H) |
| 3 | 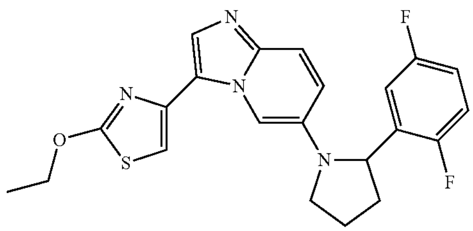 [SMILES: CCOc1nc(-c2cnc3ccc(N4CCCC4c4cc(F)ccc4F)cn23)cs1] | 409.2 (M + H) |

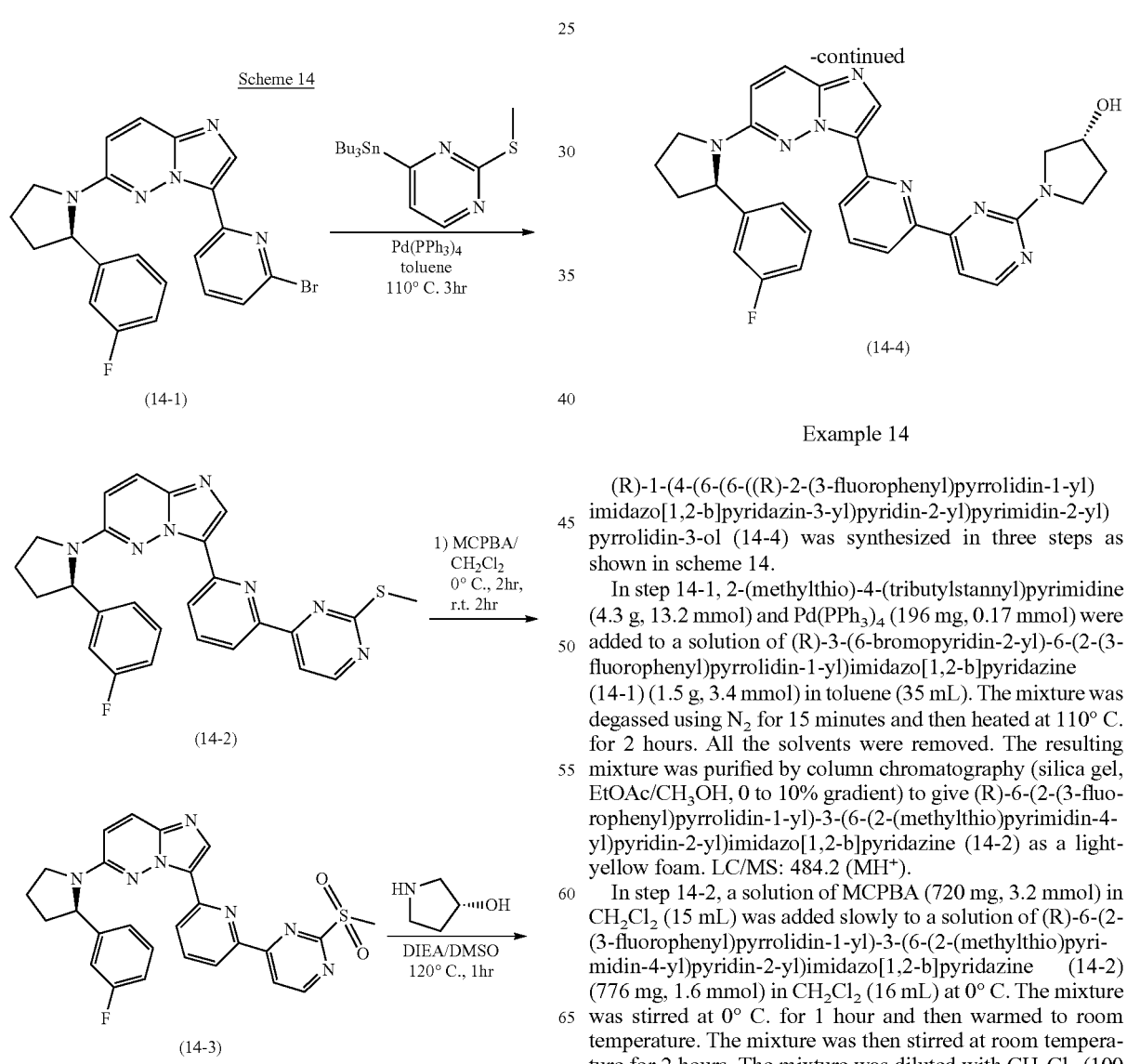

Example 14

(R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol (14-4) was synthesized in three steps as shown in scheme 14.

In step 14-1, 2-(methylthio)-4-(tributylstannyl)pyrimidine (4.3 g, 13.2 mmol) and Pd(PPh$_3$)$_4$ (196 mg, 0.17 mmol) were added to a solution of (R)-3-(6-bromopyridin-2-yl)-6-(2-(3-fluorophenyl)pyrrolidin-1-yl)imidazo[1,2-b]pyridazine (14-1) (1.5 g, 3.4 mmol) in toluene (35 mL). The mixture was degassed using N$_2$ for 15 minutes and then heated at 110° C. for 2 hours. All the solvents were removed. The resulting mixture was purified by column chromatography (silica gel, EtOAc/CH$_3$OH, 0 to 10% gradient) to give (R)-6-(2-(3-fluorophenyl)pyrrolidin-1-yl)-3-(6-(2-(methylthio)pyrimidin-4-yl)pyridin-2-yl)imidazo[1,2-b]pyridazine (14-2) as a light-yellow foam. LC/MS: 484.2 (MH$^+$).

In step 14-2, a solution of MCPBA (720 mg, 3.2 mmol) in CH$_2$Cl$_2$ (15 mL) was added slowly to a solution of (R)-6-(2-(3-fluorophenyl)pyrrolidin-1-yl)-3-(6-(2-(methylthio)pyrimidin-4-yl)pyridin-2-yl)imidazo[1,2-b]pyridazine (14-2) (776 mg, 1.6 mmol) in CH$_2$Cl$_2$ (16 mL) at 0° C. The mixture was stirred at 0° C. for 1 hour and then warmed to room temperature. The mixture was then stirred at room temperature for 2 hours. The mixture was diluted with CH$_2$Cl$_2$ (100 mL) and washed with 1N NaOH (75 mL×2) and brine (75 mL×2). The organic layer was separated, dried over Na₂SO₄ and concentrated. The mixture was purified by column chromatography (silica gel, CH₂Cl₂/CH₃OH, 2 to 5% gradient). (R)-6-(2-(3-fluorophenyl)pyrrolidin-1-yl)-3-(6-(2-(methylsulfonyl)pyrimidin-4-yl)pyridin-2-yl)imidazo[1,2-b]pyridazine (14-3) was obtained as a light yellow solid. LC/MS: 516.2 (MH⁺). Also obtained was 6-((R)-2-(3-fluorophenyl)pyrrolidin-1-yl)-3-(6-(2-(methylsulfinyl)pyrimidin-4-yl)pyridin-2-yl)imidazo[1,2-b]pyridazine.

In step 14-3, (R)-pyrrolidin-3-ol (136 mg, 1.56 mmol) and DIEA (453 uL, 2.6 mmol) were added to a solution of (R)-6-(2-(3-fluorophenyl)pyrrolidin-1-yl)-3-(6-(2-(methylsulfonyl)pyrimidin-4-yl)pyridin-2-yl)imidazo[1,2-b]pyridazine (14-3) (268 mg, 0.52 mmol) in DMSO (3 mL). The mixture was heated to 120° C. for 1 hour. The mixture was diluted with CH₂Cl₂, washed with H₂O and brine, dried over Na₂SO₄, filtered and concentrated. The mixture was purified by column chromatography (silica gel, CH₂Cl₂/CH₃OH, 5% gradient) to give (R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol (14-4). LC/MS: 523.2 (MH⁺).

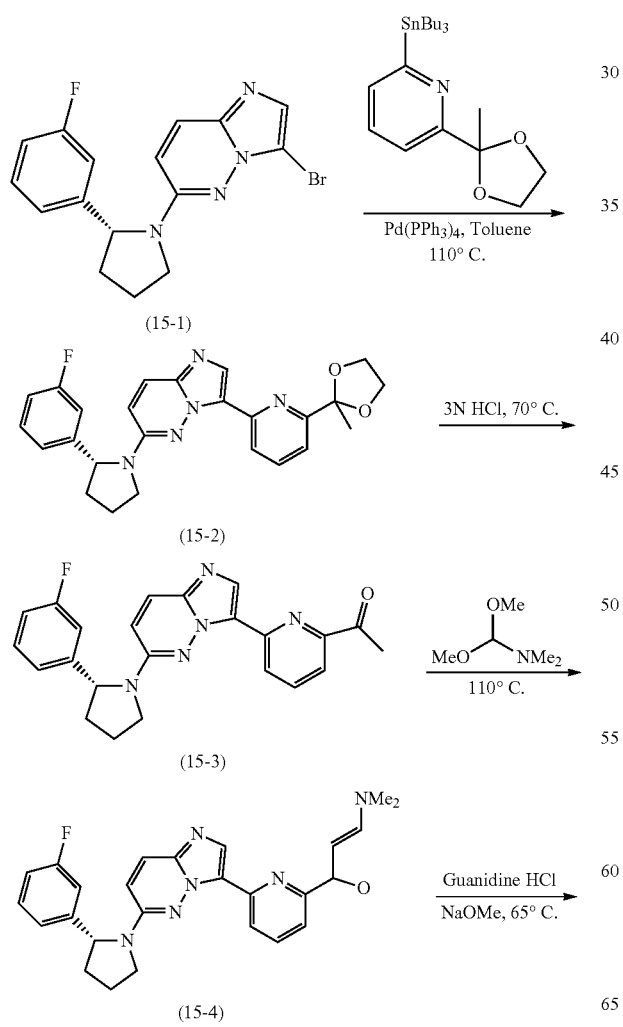

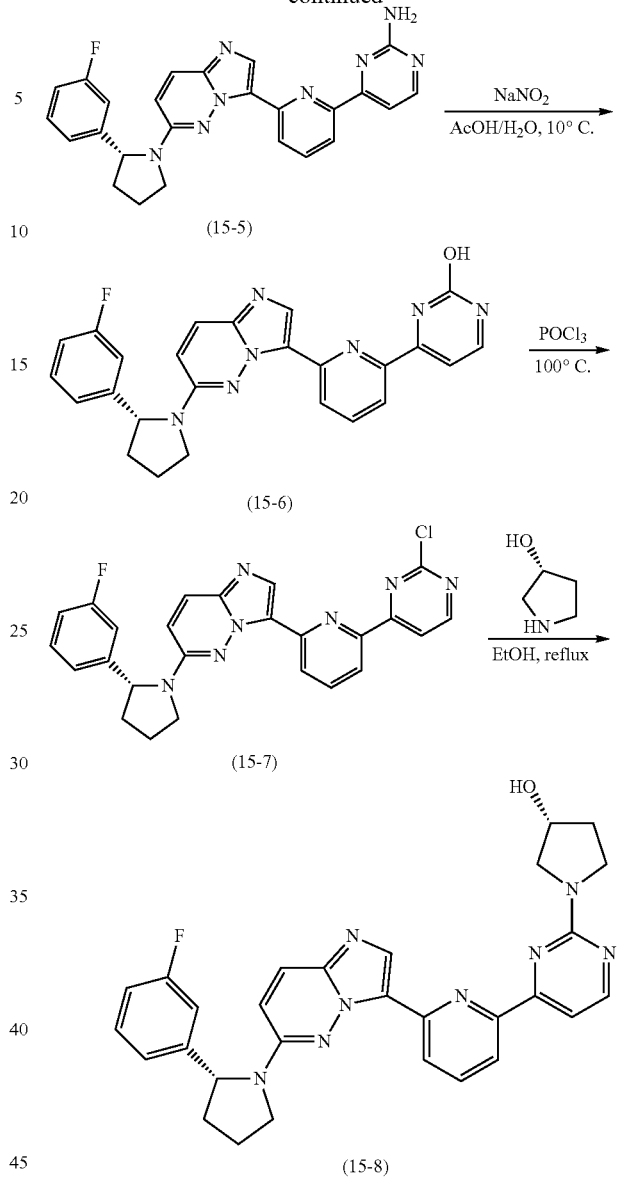

Example 15

(R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol was also synthesized in seven steps as shown in scheme 15.

In step 15-1, 2-(2-methyl-1,3-dioxolan-2-yl)-6-(tributylstannyl)pyridine (57 g, 124 mmol) in 100 mL of toluene was cannula transferred under the argon atmosphere to a suspension of 3-bromo-6-(2-(2,5-difluorophenyl)pyrrolidin-1-yl)imidazo[1,2-b]pyridazine (15-1) (30 g, 83 mmol) and tetrakis (triphenylphospine)palladium (4.8 mg, 4.15 mmol) in 500 mL of toluene. The resulting reaction mixture was heated to 110° C. for overnight. The reaction progress was monitored by LC/Mass. After the reaction was complete, the reaction vessel was cooled to room temperature and the solvent reduced to ⅓ of the original volume. The purification was performed by flash chromatography using pure ethyl acetate to afford (R)-6-(2-(3-fluorophenyl)pyrrolidin-1-yl)-3-(6-(2-methyl-1,3-dioxolan-2-yl)pyridine-2-yl)imidazo[1,2-b]pyridazine (15-2). $^1$H NMR (400 MHz, DMSO-d6) δ 8.10 (s, 1H), 8.09 (s br, 1H), 7.93 (d, 1H, J=9.6 Hz), 7.72 (m, 1H), 7.39 (m, 2H), 7.18 (m, 2H), 7.04 (m, 1H), 6.89 (br s, 1H), 5.16 (d, 1H, J=8.0 Hz), 4.02 (m, 3H), 3.91 (m, 2H), 3.68 (m, 2H), 2.48 (m, 1H), 2.05 (m, 2H), 1.88 (m, 1H), 1.69 (s, 3H). LCMS: m/z 446.2 (M+1).

In step 15-2, (R)-6-(2-(3-fluorophenyl)pyrrolidin-1-yl)-3-(6-(2-methyl-1,3-dioxolan-2-yl)pyridine-2-yl)imidazo[1,2-b]pyridazine (15-2) (30 g, 67.4 mmol) was charged with mixture of THF (150 mL) and 2N HCl (450 mL) and the resulting solution was heated to 70° C. overnight. LC/MS was used to confirm the reaction was complete. The reaction mixture was then neutralized using 10N NaOH resulting in the formation of (R)-1-(6-(6-(2-(3-fluorophenyl)pyrrolidin-1-yl)imidazole[1,2-b]pyridazin-3-yl)pyridine-2-yl)ethanone (15-3) as a pale yellow precipitate which was filtered and dried (Note: that the product needs to be dry for step 15-3 as any amount of water makes the reaction sluggish). $^1$H NMR: ppm 8.52 (s, 1H), 8.32 (br s, 1H), 8.10 (d, 1H, J=10 Hz), 7.96 (br s, 1H), 7.87 (d, 1H, J=7.6 Hz), 7.41 (m, 1H), 7.20 (m, 3H), 7.05 (m, 1H), 5.23 (dd, 1H, J=8.2 Hz, 2 Hz), 4.06 (m, 1H), 3.72 (q, 1H, J=8.0 Hz), 2.71 (s, 3H), 2.51 (m, 1H), 2.07 (m, 2H), 1.91 (m, 1H). LCMS: m/z 446.2 (M+1)

In step 15-3, a mixture of (R)-1-(6-(6-(2-(3-fluorophenyl)pyrrolidin-1-yl)imidazole[1,2-b]pyridazin-3-yl)pyridine-2-yl)ethanone (15-3) (25 g, 62.3 mmol) and dimethylforamide dimethylacetal (300 mL) was heated overnight at reflux and then cooled to room temperature. The volatiles were removed by rotary evaporation under reduced pressure and the residual solids were triturated with 200 mL of the mixture of EtOAc/Hexane (1:5) and filtered to give (R,E)-3-(dimethylamino)1-(6-(6-(2-(3-fluorophenyl)pyrrolidin-1-yl)imidazole[1,2-b]pyridazin-3-yl)pyridine-2-yl)prop-2-en-1-one (15-4) as a yellow solid which was used in the next step without further purification.

In step 15-4, freshly prepared sodium methoxide in methanol (400 mL) was cannula transferred to a solution of (R,E)-3-(dimethylamino)1-(6-(6-(2-(3-fluorophenyl)pyrrolidin-1-yl)imidazole[1,2-b]pyridazin-3-yl)pyridine-2-yl)prop-2-en-1-one (15-4) and guanidine HCl in methanol (200 mL). The resulting suspension was heated overnight at 65° C. The reaction progress was monitored by LC/Mass. After the reaction was complete, the reaction mixture was neutralized with 4N aqueous HCl and then stirred for 1 hour at room temperature. The reaction mixture was filtered to give (R)-4-(6-(6-(2-(3-fluorophenyl)pyrrolidin-1-yl)imidazo[1,2-b]pyridazin-3-yl)pyridin-2-yl)pyrimidin-2-amine (15-5) as a yellow solid. $^1$H NMR: ppm 8.42 (d, 1H, J=4.8 Hz), 8.31 (s, 1H), 8.16 (d, 1H, J=8.0 Hz), 7.96 (d, 1H, J=10 Hz), 7.89 (m, 1H), 7.64 (d, 1H, J=4.8 Hz), 7.42 (ddd, 1H, J=8.0, 8.0, 6.0 Hz), 7.20 (m, 2H), 7.05 (ddd, 1H, J=8.4, 8.4, 2.0 Hz), 6.91 (br s, 1H), 6.76 (s, 2H), 5.22 (dd, 1H, J=8.2 Hz, 2.4 Hz), 4.03 (m, 1H), 3.70 (q, 1H, J=8.4 Hz), 2.51 (s, 1H), 2.06 (m, 2H), 1.90 (m, 1H), 1.18 (d, 1H, J=6.4 Hz). LCMS: m/z 453.2 (M+1).

In step 15-5, an aqueous solution of sodium nitrite (NaNO$_2$) was added dropwise to a solution of (R)-4-(6-(6-(2-(3-fluorophenyl)pyrrolidin-1-yl)imidazo[1,2-b]pyridazin-3-yl)pyridin-2-yl)pyrimidin-2-amine (15-5) (20 g, 44.2 mmol) in AcOH (250 mL) and H$_2$O (250 mL) while maintaining the temperature between 5° C. and 10° C. The reaction progress was monitored by LC/MS. After the reaction was complete, the solvents were concentrated to dryness and the residue was then treated with K$_2$CO$_3$ in methanol. The resulting mixture was then neutralized with 3N HCl, the solvent concentrated and the mixture then extracted with dichloromethane (X3). The extract was dried over Na$_2$SO$_4$, filtered and concentrated under reduced pressure to give the crude product which was purified by column chromatography (10% MeOH in CH$_2$Cl$_2$ with increasing amounts of methanol to 15%) to afford (R)-4-(6-(6-(2-(3-fluorophenyl)pyrrolidin-1-yl)imidazole[1,2-b]pyridazin-3-yl)pyridine-2-yl)pyrimidin-2-ol (15-6) as a yellow solid. $^1$H NMR: ppm 12.1 (s, 1H), 8.32 (s, 1H), 8.16 (d, 1H, J=8.0 Hz), 7.95 (d, 1H, J=10 Hz), 7.90 (m, 1H), 7.49 (d, 1H, J=6.4 Hz), 7.42 (ddd, 1H, J=8.0, 8.0, 6.4 Hz), 7.20 (m, 2H), 7.05 (ddd, 1H, J=8.4, 8.4, 2.4 Hz), 6.91 (br s, 1H), 5.2 (dd, 1H, J=8.2 Hz, 2.4 Hz), 4.02 (m, 1H), 3.69 (q, 1H, J=8.0 Hz), 2.49 (m, 2H), 2.05 (m, 2H), 1.89 (m, 1H). LCMS: 454.2 (M+1).

In step 15-6, (R)-4-(6-(6-(2-(3-fluorophenyl)pyrrolidin-1-yl)imidazole[1,2-b]pyridazin-3-yl)pyridine-2-yl)pyrimidin-2-ol (15-6) (15 g, 33.2 mmol) was charged with POCl$_3$ (200 mL) and then heated overnight at 100° C. The reaction progress was monitored by LC/MS. After the reaction was complete, the volatile residuals were removed by distillation under reduced pressure. After the removal of most of the POCl$_3$, the resultant solids were dissolved with dichloromethane and neutralized with aqueous K$_2$CO$_3$. The organic solvents were dried over Na$_2$SO$_4$, filtered and concentrated with rotary evaporator under reduced pressure to give crude yellow solids which were purified by column chromatography (5% MeOH in CH$_2$Cl$_2$) to give (R)-3-(6-(2-chloropyrimidin-4-yl)pyrimidin-2-yl)-6-(2-(3-fluorophenyl)pyrrolidin-1-yl)imidazole[1,2-b]pyridazine (15-7) as a yellow solid. $^1$H NMR: ppm 8.93 (d, 1H, J=4.8 Hz), 8.58 (d, 1H, J=2.8 Hz), 8.41 (s, 1H), 8.34 (ba s, 1H), 8.22 (d, 1H, J=8.0 Hz), 7.95 (m, 2H), 7.41 (ddd, 1H, J=8.0, 8.0, 6.4 Hz), 7.20 (m, 2H), 7.05 (ddd, 1H, J=8.4, 8.4, 2.4 Hz), 6.92 (br s, 1H), 5.21 (dd, 1H, J=8.2 Hz, 2.4 Hz), 4.03 (m, 1H), 3.70 (q, 1H, J=8.0 Hz), 2.47 (m, 2H), 2.06 (m, 2H), 1.90 (m, 1H). LCMS: 472.2 (M+1).

In step 15-7, (R)-3-hydroxy pyrrolidine was added to a solution of the (R)-3-(6-(2-chloropyrimidin-4-yl)pyrimidin-2-yl)-6-(2-(3-fluorophenyl)pyrrolidin-1-yl)imidazole[1,2-b]pyridazine (15-7) (10 g, 21.2 mmol) in ethanol (100 mL) and the resulting mixture was heated at reflux for 7 hours. The volatile residuals were removed by rotary evaporator under reduced pressure followed by column chromatography to give (R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol as a pale yellow solid. $^1$H NMR: ppm 8.51 (d, 1H, J=5.2 Hz), 8.32 (s, 1H), 8.30 (br s, 1H), 8.24 (d, 1H, J=7.6 Hz), 7.93 (d, 1H, J=10 Hz), 7.86 (m, 1H), 7.65 (d, 1H, J=4.8 Hz), 7.40 (ddd, 1H, J=8.0, 8.0, 6.4 Hz), 7.20 (s, 1H), 7.17 (m, 1H), 7.04 (ddd, 1H, J=8.4, 8.4, 2.4 Hz), 6.85 (br s, 1H), 5.17 (dd, 1H, J=8.2 Hz, 2.4 Hz), 5.01 (d, 1H, J=3.2 Hz), 4.43 (br s, 1H), 4.02 (m, 1H), 3.65 (m, 5H), 2.45 (m, 1H), 2.05 (m, 3H), 1.89 (m, 2H). 13C NMR: ppm 163.58, 162.17, 161.16, 160.15, 159.14, 153.65, 151.80, 147.53, 147.13 (d, J=25.6 Hz), 137.66, 133.20, 130.39 (d, J=30.4 Hz), 126.44, 126.06, 121.64, 120.67, 118.52, 113.45 (d, J=83.2 Hz), 112.40 (d, J=87.6 Hz), 110.31, 104.90, 69.10, 61.26, 54.82, 48.39, 44.42, 35.27, 33.47, 22.66. LCMS: 523.2 (M+1).

Scheme 6

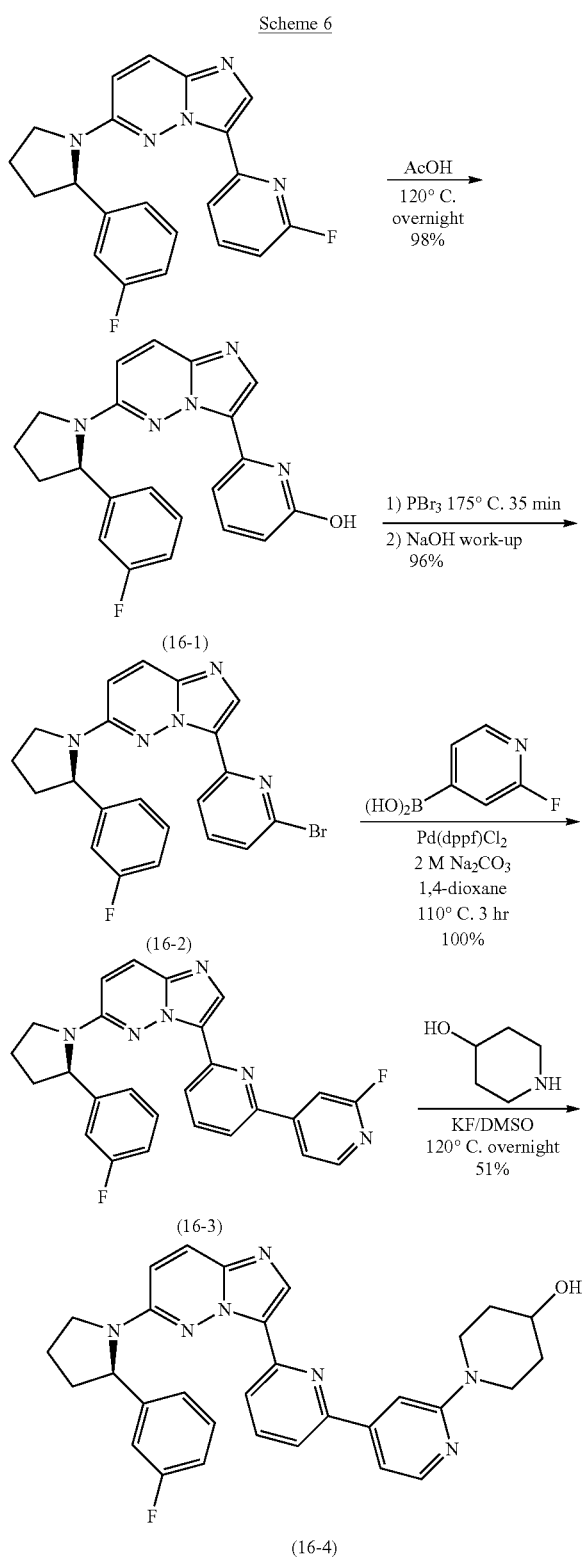

Example 16

(R)-1-(6-(6-(2-(3-fluorophenyl)pyrrolidin-1-yl)imidazo[1,2-b]pyridazin-3-yl)-2,4'-bipyridin-2'-yl)piperidin-4-ol was synthesized in four steps as shown in scheme 16.

In step 16-1, a suspension of (R)-6-(2-(3-fluorophenyl)pyrrolidin-1-yl)-3-(6-fluoropyridin-2-yl)imidazo[1,2-b]pyridazine (16 g, 42 mmol) in acetic acid (150 mL) was heated overnight at 120° C. (approx. 20 hours). The suspension turned clear after heating. The mixture was concentrated under vacuum to give a brown oil. The oil was dissolved in $CH_2Cl_2$ (750 mL) and washed with saturated $NaHCO_3$ (300 mL×3), brine (300 mL×2). The organic layer was separated, dried over ($Na_2SO_4$) and concentrated to give 15.5 g of the crude (R)-6-(6-(2-(3-fluorophenyl)pyrrolidin-1-yl)imidazo[1,2-b]pyridazin-3-yl)pyridin-2-ol (16-1) which was used in the next step without further purification. LC/MS: 376.2 (M+H$^+$).

In step 16-2, a suspension of crude (R)-6-(6-(2-(3-fluorophenyl)pyrrolidin-1-yl)imidazo[1,2-b]pyridazin-3-yl)pyridin-2-ol (16-1) (13.3 g, 35.4 mmol) in PBr$_3$ (25 mL) was heated to 175° C. for 35 minutes. While the mixture was hot, it was poured into ice-cold 2N NaOH (1.2 L). The solid was collected by filtration and washed with $H_2O$. The final product was dried under high vacuum overnight to give (R)-3-(6-bromopyridin-2-yl)-6-(2-(3-fluorophenyl)pyrrolidin-1-yl)imidazo[1,2-b]pyridazine (16-2) as a light-yellow solid which was used in the next step without further purification. LC/MS: 438.2 (M+H$^+$).

In step 16-3, 2-fluoropyridin-4-ylboronic acid (97%) (9.6 g, 66 mmol), Pd(dppf)Cl$_2$ (1.3 g, 1.65 mmol) and 2N $Na_2CO_3$ (50 mL, 99 mmol) were added to a suspension of (R)-3-(6-bromopyridin-2-yl)-6-(2-(3-fluorophenyl)pyrrolidin-1-yl)imidazo[1,2-b]pyridazine (16-2) (14.5 g, 33 mmol) in 1,4-dioane (250 mL). The mixture was degassed for 15 minute using N$_2$ and then heated at 110° C. for 3 hours. The mixture was filtered through a celite pad and rinsed with ethyl acetate (EtOAc). The filtrate was washed with brine, dried over $Na_2SO_4$, and concentrated to give (R)-3-(2'-fluoro-2,4'-bipyridin-6-yl)-6-(2-(3-fluorophenyl)pyrrolidin-1-yl)imidazo[1,2-b]pyridazine (16-3) as a dark oil, which was used in the next step without further purification. LC/MS: 455.2 (M+H$^+$).

In step 16-4, potassium fluoride (10 g, 175 mmol) and 4-hydroxypiperidine (10.6 g, 105 mmol) were added to a solution of crude (R)-3-(2'-fluoro-2,4'-bipyridin-6-yl)-6-(2-(3-fluorophenyl)pyrrolidin-1-yl)imidazo[1,2-b]pyridazine (16-3) (16.1 g, 35 mmol) in DMSO (100 mL). The mixture was heated overnight to 120° C. (approx. 14 hours). The mixture was filtered through a celite pad and rinsed with EtOAc (1 L). The filtrate was washed with brine, dried over $Na_2SO_4$, filtered and concentrated to give a dark oil. The mixture was purified by column chromatography (silica gel, $CH_2Cl_2/CH_3OH$, gradient 5% to 15%) to yield (R)-1-(6-(6-(2-(3-fluorophenyl)pyrrolidin-1-yl)imidazo[1,2-b]pyridazin-3-yl)-2,4'-bipyridin-2'-yl)piperidin-4-ol (16-4) which was crashed out from $CH_2Cl_2$, filtered and dried under high vacuum. $^1$H NMR (400 MHz, DMSO, ppm): δ 8.30 (s, 1H), 8.22 (d, 1H, J=5.2 Hz), 8.10-8.24 (bs, 1H), 7.90-7.98 (m, 2H), 7.76-7.86 (bs, 1H), 7.52 (s, 1H), 7.40 (q, 1H, J=7.4 Hz), 7.34 (d, 1H, J=5.2 Hz), 7.04 (t, 1H, J=8 Hz), 6.80-6.94 (bs, 1H), 5.19 (d, 1H, J=8 Hz), 4.71 (d, 1H, J=4 Hz), 4.10-4.18 (m, 2H), 3.93-4.06 (m, 1H), 3.65-3.75 (m, 2H), 3.10-3.20 (m, 2H), 1.98-2.10 (m, 2H), 1.78-1.92 (m, 3H), LC/MS: 536.2 (M+H$^+$), 1.34-1.45 (m, 2H). $^{13}$C NMR (400 MHz, DMSO, ppm): 163.53, 161.11, 159.53, 153.95, 151.76, 148.27 (d, J=34.7 Hz), 147.69, 147.10 (d, J=25.6 Hz), 146.92, 137.61, 133.14 (d, J=23.2 Hz), 130.34 (d, J=32.4 Hz), 126.54, 126.04, 121.56, 119.26, 118.75, 113.40 (d, J=83.6 Hz), 112.41 (d, J=86.0), 110.26, 109.86, 103.75, 66.34, 61.24, 48.37, 42.72, 35.12, 33.71, 22.65.

Scheme 17

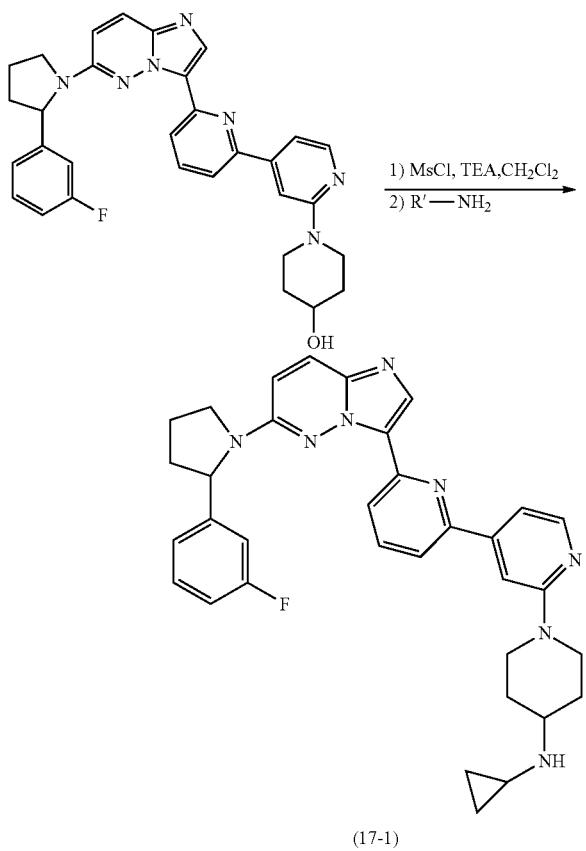

Example 17

(N-cyclopropyl-1-(6-(6-(2-(3-fluorophenyl)pyrrolidin-1-yl)imidazo[1,2-b]pyridazin-3-yl)-2,4'-bipyridin-2'-yl)piperidin-4-amine) (17-1) was synthesized as shown in scheme 17.

(N-cyclopropyl-1-(6-(6-(2-(3-fluorophenyl)pyrrolidin-1-yl)imidazo[1,2-b]pyridazin-3-yl)-2,4'-bipyridin-2'-yl)piperidin-4-amine) was prepared in the following manner. To a 20 mL reaction flask was added 1-(6-(6-(2-(3-fluorophenyl)pyrrolidin-1-yl)imidazo[1,2-b]pyridazin-3-yl)-2,4'-bipyridin-2'-yl)piperidin-4-ol (30 mg, 0.056 mmol) and 0.8 mL of methylene chloride. This solution was charged with triethylamine (0.10 mL, 0.69 mmol) and dropwise addition of methane sulfonyl chloride (MsCl, approx. 20 mg, 0.18 mmol). The resulting solution was stirred for 2 hours, followed by quenching with water, ethyl acetate extraction (3×30 mL), and the organic extracts were transferred to a 10 mL volume resealable vessel. The residue in the vessel was charged with 2 mL cyclopropylamine (excess, co-solvent) and 0.5 mL of THF. The vessel was sealed and heated for 6 hours at 90° C. Upon cooling, the contents of the vessel were concentrated to a volume of 1 mL and directly subjected to reverse phase separation (gradient, C-18 support, 10 to 70%, acetonitrile:water) to give (N-cyclopropyl-1-(6-(6-(2-(3-fluorophenyl)pyrrolidin-1-yl)imidazo[1,2-b]pyridazin-3-yl)-2,4'-bipyridin-2'-yl)piperidin-4-amine). $^1$H NMR (400 MHz, D$_3$ acetonitrile) δ ppm 8.71 (br s, 1H), 8.41 (s, 1H) 8.26 (d, J=7.2 Hz, 1H), 7.99 (app d, J=6.7 Hz, 2H), 7.85 (d, J=6.2 Hz, 1H), 7.73 (br s, 1H), 7.63 (s, 1H), 7.42 (d, J=6.4 Hz, 1H), 7.39 (app q, J=6.8 Hz, 1H), 7.20 (d, J=7.2 Hz, 1H), 7.05 (dt, J=8.6, 1.9 Hz, 1H), 6.99-6.82 (m, 1H), 5.27 (d, J=6.4 Hz, 1H), 4.54 (app d, J=10 Hz, 2H), 4.00 (app q, J=3.9 Hz, 1H), 3.69-3.62 (m, 1H), 3.46 (app d, J=5.8 Hz, 1H), 2.98 (app q, J=4.2 Hz, 2H), 2.73 (br s, 2H), 2.47-2.35 (m, 1H), 2.13 (app dd, J=5.6 Hz, 2H), 2.08-2.03 (m, 2H), 1.89-1.86 (m, 1H), 0.82-0.66 (m, 5H). LRMS observed m/z 575.3 major ion (calcd for M+H, 575.3).

Additional representative compounds of Formula (I), prepared following the procedures described above, were set forth in Table 7.

TABLE 7

| Compound Number | Structure | Physical Data $^1$H NMR 400 MHz (DMSO-d$_6$) and/or MS (m/z) |
|---|---|---|
| 1 | 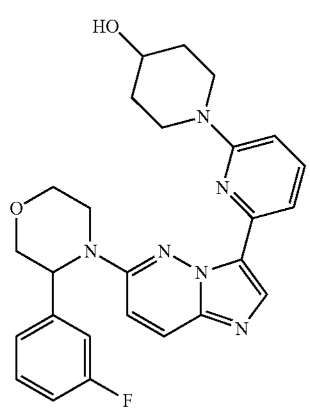 [SMILES: OC1CCN(c2cccc(-c3cnc4ccc(N5CCOCC5c5cccc(F)c5)nn34)n2)CC1] | $^1$H NMR (400 MHz, MeOH-d4) d 7.99 (s, 1H), 7.71 (d, 1H, J = 10.0 Hz), 7.46 (m, 2H), 7.19 (m, 1H), 7.11 (m, 3H), 6.83 (m, 1H), 6.65 (d, 1H, J = 8.0 Hz), 5.01 (t, 1H, J = 3.6 Hz), 4.10 (m, 3H), 4.00 (m, 2H), 3.77 (m, 3H), 3.59 (m, 1H), 3.03 (m, 1H), 1.91 (s, 1H), 1.84 (m, 2H), 1.44 (m, 2H) MS (m/z): 474.53 |

TABLE 7-continued

| Compound Number | Structure | Physical Data<br>¹H NMR 400 MHz (DMSO-d₆) and/or MS (m/z) |
|---|---|---|
| 2 | 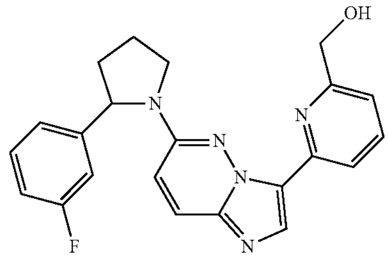 [SMILES: OCc1cccc(-c2cnc3ccc(N4CCCC4c4cccc(F)c4)nn23)n1] | MS (m/z): 389.42 |
| 3 | 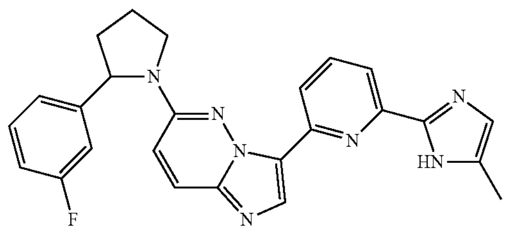 [SMILES: Cc1cnc(-c2cccc(-c3cnc4ccc(N5CCCC5c5cccc(F)c5)nn34)n2)[nH]1] | MS (m/z): 439.49 |
| 4 | 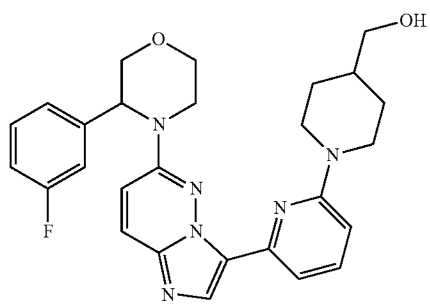 [SMILES: OCC1CCN(c2cccc(-c3cnc4ccc(N5CCOCC5c5cccc(F)c5)nn34)n2)CC1] | ¹H NMR (400 MHz, CHCl3-d3) d 8.54 (d, 1H, J = 10.0 Hz), 8.23 (s, 1H), 7.46 (m, 2H), 7.23 (m, 1H), 7.12 (d, 1H, J = 10.4 Hz), 7.05 (m, 2H), 6.91 (m, 1H), 6.65 (m, 1H), 5.09 (t, 1H, J = 2.8 Hz), 4.34 (m, 2H), 4.24 (dd, 1H, J = 12.0, 2.0 Hz), 4.12 (dt, 1H, J = 11.2, 2.8 Hz), 4.05 (dd, 1H, J = 12.8, 3.6 Hz), 3.92 (dt, 1H, J = 12.8, 2.8 Hz), 3.82 (ddd, 1H, J = 11.2, 11.2, 3.2 Hz), 3.65 (m, 2H), 3.48 (d, 2H, J = 6.0 Hz), 3.30 (brs, 1H), 2.82 (ddd, 1H, J = 12.4, 12.4, 1.6 Hz), 1.73 (m, 1H), 1.24 (m, 3H), 0.80 (m, 1H)<br>MS (m/z): 488.56 |
| 5 | 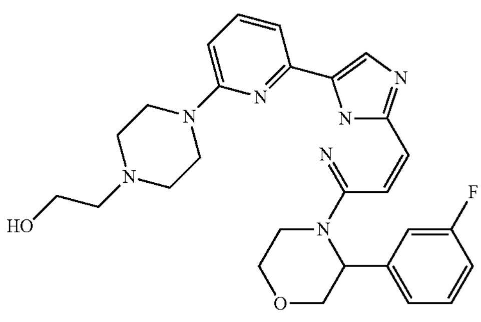 [SMILES: N=C(/C=C\c1ncc(-c2cccc(N3CCN(CCO)CC3)n2)[nH]1)N1CCOCC1c1cccc(F)c1] | ¹H NMR (400 MHz, CHCl3-d3) d 8.41 (d, 1H, J = 10.0 Hz), 8.20 (s, 1H), 7.64 (d, 1H, J = 7.6 Hz), 7.58 (t, 1H, J = 8.0 Hz), 7.24 (m, 1H), 7.13 (d, 1H, J = 10.0 Hz), 7.05 (m, 1H), 6.91 (m, 1H), 6.67 (d, 1H, J = 8.4 Hz), 5.09 (t, 1H, J = 2.8 Hz), 4.23 (dd, 2H, J = 12.0, 2.4 Hz), 4.12 (dt, 2H, J = 12.8, 3.2 Hz), 4.05 (dd, 2H, J = 12.0, 4.0 Hz), 3.99 (m, 3H), 3.90 (dt, 2H, J = 13.2, 2.8 Hz), 3.82 (ddd, 2H, J = 10.4, 10.4, 3.2 Hz), 3.66 (m, 3H), 3.17 (m, 3H)<br>MS (m/z): 503.57 |
| 6 | 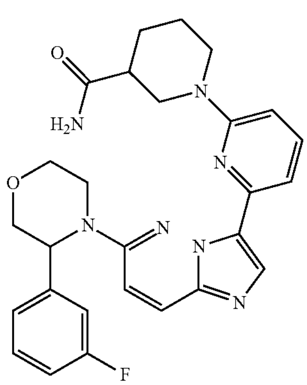 [SMILES: N=C(/C=C\c1ncc(-c2cccc(N3CCCC(C(N)=O)C3)n2)[nH]1)N1CCOCC1c1cccc(F)c1] | MS (m/z): 501.55 |

TABLE 7-continued

| Compound Number | Structure | Physical Data<br>¹H NMR 400 MHz (DMSO-d₆)<br>and/or MS (m/z) |
|---|---|---|
| 7 | 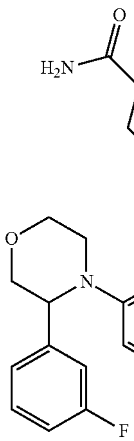 | MS (m/z): 501.55 |
| 8 | 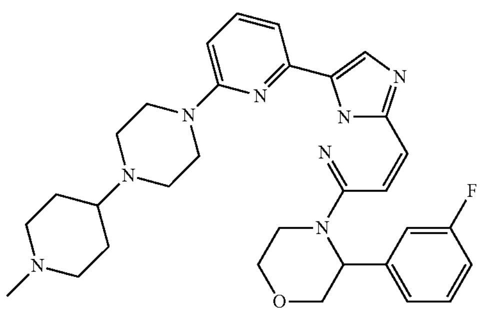 [SMILES: CN1CCC(N2CCN(c3cccc(-c4cnc(/C=C\C(=N)N5CCOCC5c5cccc(F)c5)[nH]4)n3)CC2)CC1] | MS (m/z): 556.68 |
| 9 | 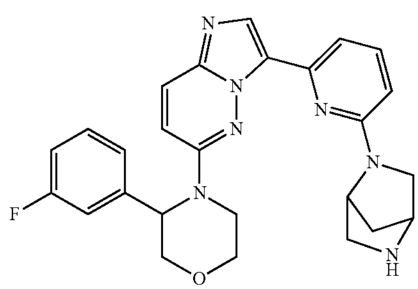 [SMILES: Fc1cccc(C2COCCN2c2ccc3ncc(-c4cccc(N5CC6CC5CN6)n4)n3n2)c1] | ¹H NMR (400 MHz, MeOH-d4) d 8.19 (s, 1H), 7.74 (d, 1H, J = 10.0 Hz), 7.51 (t, 1H, J = 8.8 Hz), 7.42 (ddd, 1H, J = 8.0, 8.0, 2.8 Hz), 7.17 (m, 1H), 7.08 (m, 2H), 6.84 (ddd, 1H, J = 8.4, 8.4, 2.0 Hz), 6.76 (d, 1H, J = 9.6 Hz), 6.23 (d, 1H, J = 8.0 Hz), 5.00 (m, 1H), 4.11 (dd, 1H, J = 13.2, 3.2 Hz), 4.03 (m, 2H), 3.80 (m, 3H), 3.59 (m, 2H), 3.28 (d, 1H, J = 9.6 Hz), 3.08 (s, 2H), 1.85 (m, 1H)<br>MS (m/z): 471.53 |
| 10 | 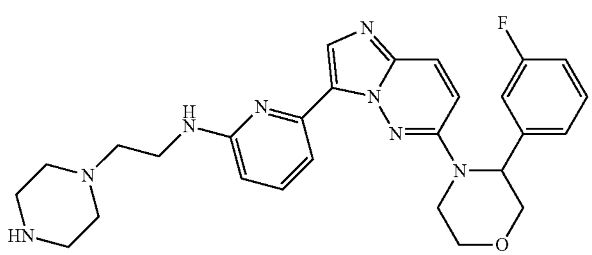 [SMILES: Fc1cccc(C2COCCN2c2ccc3ncc(-c4cccc(NCCN5CCNCC5)n4)n3n2)c1] | MS (m/z): 502.59 |

TABLE 7-continued

| Compound Number | Structure | Physical Data<br>¹H NMR 400 MHz (DMSO-d₆)<br>and/or MS (m/z) |
|---|---|---|
| 11 | 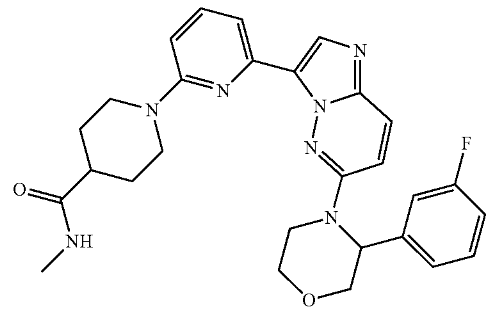 [SMILES: CNC(=O)C1CCN(c2cccc(-c3cnc4ccc(N5CCOCC5c5cccc(F)c5)nn34)n2)CC1] | ¹H NMR (400 MHz, MeOH-d4) d 8.10 (s, 1H), 7.82 (d, 1H, J = 10.0 Hz), 7.57 (m, 2H), 7.32 (m, 1H), 7.20 (m, 3H), 6.91(m, 1H), 6.76 (d, 1H, J = 8.40 Hz), 5.22 (t, 1H, J = 3.2 Hz), 4.49 (d, 2H, J = 13.2 Hz), 4.20 (dd, 1H, J = 12.0, 3.2 Hz), 4.11 (m, 2H), 3.90 (m, 2H), 3.70 (m, 1H), 2.88 (ddd, 2H, J = 12.4, 12.4, 2.4 Hz), 2.72 (s, 3H), 2.72 (s, 1H), 1.84 (m, 2H), 1.74 (m, 2H)<br>MS (m/z): 515.58 |
| 12 | 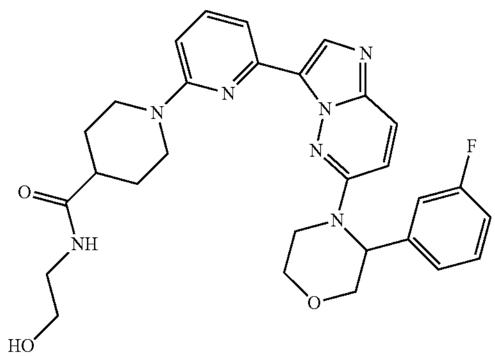 [SMILES: O=C(NCCO)C1CCN(c2cccc(-c3cnc4ccc(N5CCOCC5c5cccc(F)c5)nn34)n2)CC1] | ¹H NMR (400 MHz, MeOH-d4) d 8.18 (s, 1H), 7.73 (d, 1H, J = 10.0 Hz), 7.53 (d, 1H, J = 7.6 Hz), 7.45 (t, 1H, J = 8.0 Hz), 7.17 (m, 1H), 7.07 (m, 2H), 6.84 (m, 1H), 6.76 (d, 1H, J = 8.0 Hz), 6.54 (d, 1H, J = 8.4 Hz), 6.16 (t, 1H, J = 4.2 Hz), 5.00 (t, 1H, J = 3.6 Hz), 4.38 (d, 2H, J = 12.4 Hz), 4.11 (dd, 1H, J = 12.0, 3.6 Hz), 4.03 (m, 2H), 3.80 (m, 2H), 3.66 (t, 2H, J = 4.8), 3.60 (m, 1H), 3.37 (m, 1H), 2.83 (m, 2H), 2.31 (m, 1H), 1.80 (m, 2H), 1.74 (m, 2H), 1.18 (m, 1H)<br>MS (m/z): 545.61 |
| 13 | 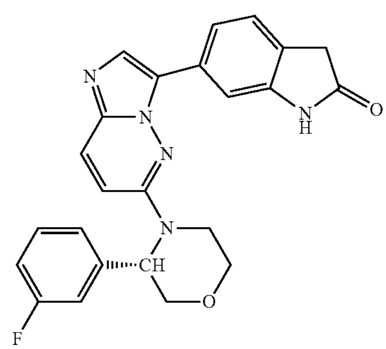 [SMILES: O=C1Cc2ccc(-c3cnc4ccc(N5CCOC[C@@H]5c5cccc(F)c5)nn34)cc2N1] | MS (m/z): 429.45 |
| 14 | 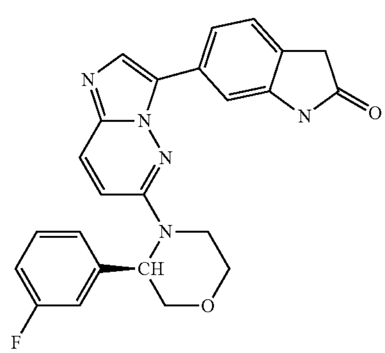 [SMILES: O=C1Cc2ccc(-c3cnc4ccc(N5CCOC[C@H]5c5cccc(F)c5)nn34)cc2N1] | MS (m/z): 429.45 |

TABLE 7-continued

| Compound Number | Structure | Physical Data ¹H NMR 400 MHz (DMSO-d$_6$) and/or MS (m/z) |
|---|---|---|
| 15 | 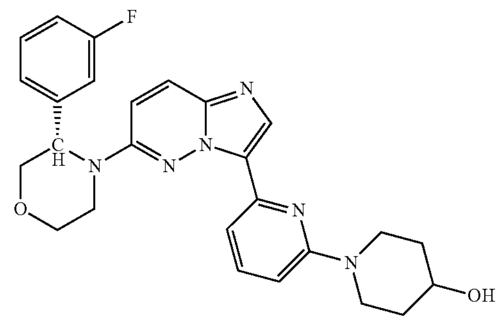 [SMILES: OC1CCN(c2cccc(-c3cnc4ccc(N5CCOC[C@@H]5c5cccc(F)c5)nn34)n2)CC1] | MS (m/z): 474.53 |
| 16 | 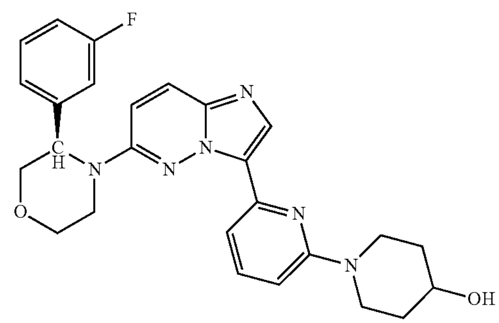 [SMILES: OC1CCN(c2cccc(-c3cnc4ccc(N5CCOC[C@H]5c5cccc(F)c5)nn34)n2)CC1] | MS (m/z): 474.53 |
| 17 | 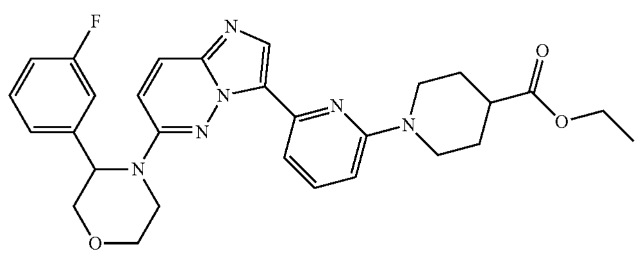 [SMILES: CCOC(=O)C1CCN(c2cccc(-c3cnc4ccc(N5CCOCC5c5cccc(F)c5)nn34)n2)CC1] | MS (m/z): 530.59 |
| 18 | 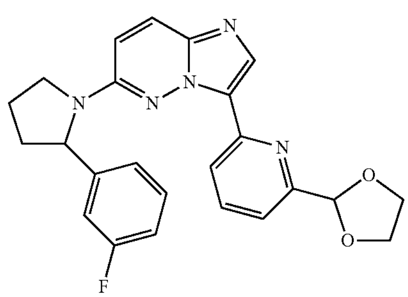 [SMILES: Fc1cccc(C2CCCN2c2ccc3ncc(-c4cccc(C5OCCO5)n4)n3n2)c1] | MS (m/z): 431.46 |
| 19 | 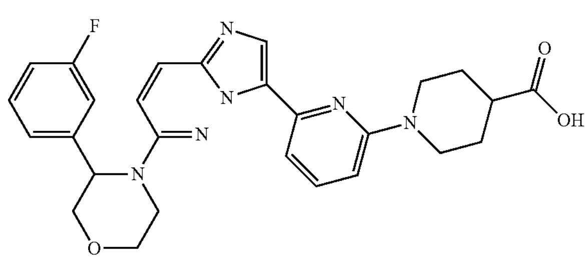 [SMILES: N=C(/C=C\c1ncc(-c2cccc(N3CCC(C(=O)O)CC3)n2)[nH]1)N1CCOCC1c1cccc(F)c1] | MS (m/z): 502.54 |

TABLE 7-continued

| Compound Number | Structure | Physical Data<br>¹H NMR 400 MHz (DMSO-d₆) and/or MS (m/z) |
|---|---|---|
| 20 | 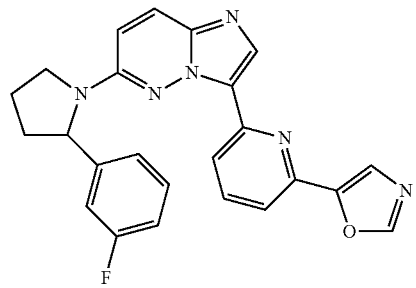 [SMILES: Fc1cccc(C2CCCN2c2ccc3ncc(-c4cccc(-c5cnco5)n4)n3n2)c1] | MS (m/z): 426.45 |
| 21 | 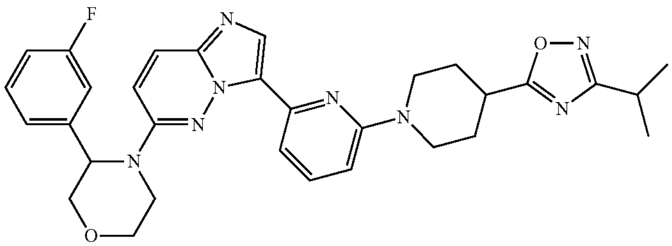 [SMILES: CC(C)c1noc(C2CCN(c3cccc(-c4cnc5ccc(N6CCOCC6c6cccc(F)c6)nn45)n3)CC2)n1] | MS (m/z): 568.64 |
| 22 | 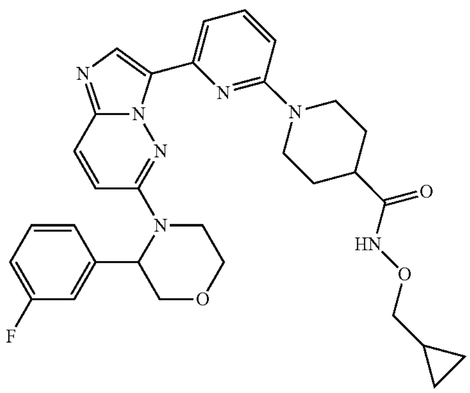 [SMILES: O=C(NOCC1CC1)C1CCN(c2cccc(-c3cnc4ccc(N5CCOCC5c5cccc(F)c5)nn34)n2)CC1] | MS (m/z): 571.65 |
| 23 | 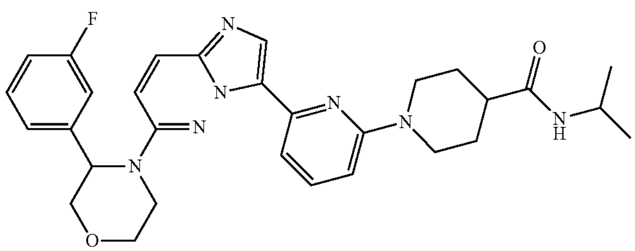 [SMILES: CC(C)NC(=O)C1CCN(c2cccc(-c3cnc(/C=C\C(=N)N4CCOCC4c4cccc(F)c4)[nH]3)n2)CC1] | ¹H NMR (400 MHz, DMSO-d6) d 8.12 (s, 1H), 8.09 (d, 1H, J = 6.0 Hz), 7.67 (d, 1H, J = 7.6 Hz), 7.56 (m, 2H), 7.09 (m, 4H), 7.04 (ddd, 1H, J = 8.4, 8.4, 2.4 Hz), 6.78 (d, 1H, J = 8.0 Hz), 5.30 (s, 1H), 4.40 (d, 2H, J = 11.6 Hz), 4.19 (dd, 1H, J = 12.0, 2.0 Hz), 4.02 (m, 3H), 3.80 (m, 2H), 3.60 (m, 1H), 2.82 (t, 2H, J = 12.0 Hz), 2.34 (m, 1H), 1.70 (m, 2H), 1.56 (m, 2H), 1.03 (d, 6H, J = 6.4 Hz)<br>MS (m/z): 543.64 |
| 24 | 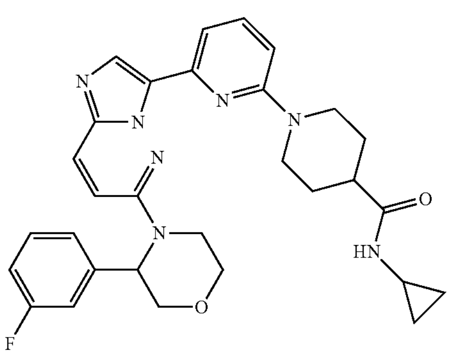 [SMILES: N=C(/C=C\c1ncc(-c2cccc(N3CCC(C(=O)NC4CC4)CC3)n2)[nH]1)N1CCOCC1c1cccc(F)c1] | MS (m/z): 541.62 |

TABLE 7-continued

| Compound Number | Structure | Physical Data<br>¹H NMR 400 MHz (DMSO-d₆)<br>and/or MS (m/z) |
|---|---|---|
| 25 | 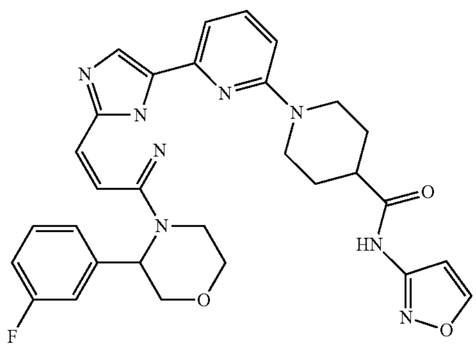 [SMILES: N=C(/C=C\c1ncc(-c2cccc(N3CCC(C(=O)Nc4ccon4)CC3)n2)[nH]1)N1CCOCC1c1cccc(F)c1] | MS (m/z): 568.60 |
| 26 | 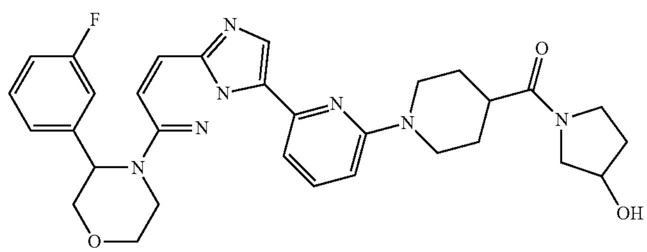 [SMILES: N=C(/C=C\c1ncc(-c2cccc(N3CCC(C(=O)N4CCC(O)C4)CC3)n2)[nH]1)N1CCOCC1c1cccc(F)c1] | MS (m/z): 571.65 |
| 27 | 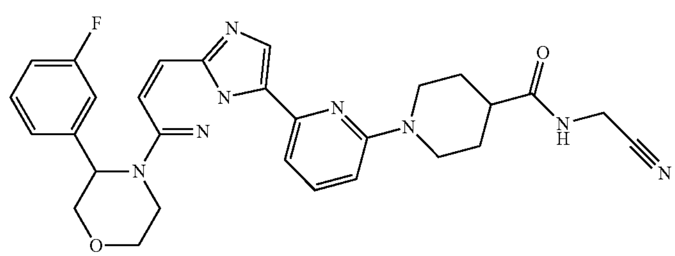 [SMILES: N#CCNC(=O)C1CCN(c2cccc(-c3cnc(/C=C\C(=N)N4CCOCC4c4cccc(F)c4)[nH]3)n2)CC1] | MS (m/z): 540.59 |
| 28 | 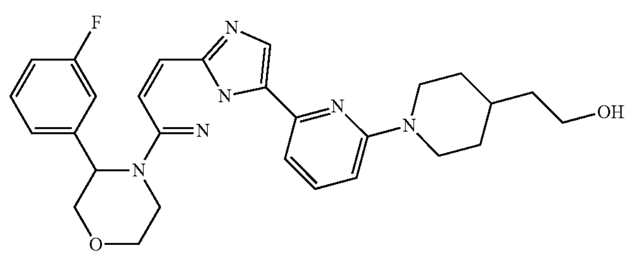 [SMILES: N=C(/C=C\c1ncc(-c2cccc(N3CCC(CCO)CC3)n2)[nH]1)N1CCOCC1c1cccc(F)c1] | MS (m/z): 502.58 |
| 29 | 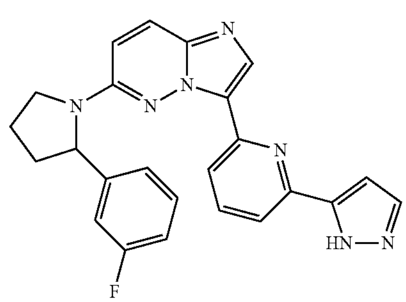 [SMILES: Fc1cccc(C2CCCN2c2ccc3ncc(-c4cccc(-c5ccn[nH]5)n4)n3n2)c1] | ¹H NMR (400 MHz, MeOH-d4) d 8.33 (s, 1H), 8.03 (s br, 1H), 7.75 (d, 1H, J = 9.6 Hz), 7.60 (m, 2H), 7.46 (d, 1H, J = 7.6 Hz), 7.26 (m, 1H), 7.09 (d, 1H, J = 7.6 Hz), 6.91 (m, 2H), 6.73 (d, 1H, J = 2.0 Hz), 6.55 (d, 1H, J = 10.0 Hz), 5.03 (dd, 1H, J = 8.0, 2.4 Hz), 3.91 (m, 1H), 3.68 (q, 1H, J = 8.8 Hz), 2.44 (m, 1H), 2.06 (m, 2H), 1.97 (m, 2H)<br>MS (m/z): 425.46 |

TABLE 7-continued
| Compound Number | Structure | Physical Data <sup>1</sup>H NMR 400 MHz (DMSO-d$_6$) and/or MS (m/z) |
|---|---|---|
| 30 | 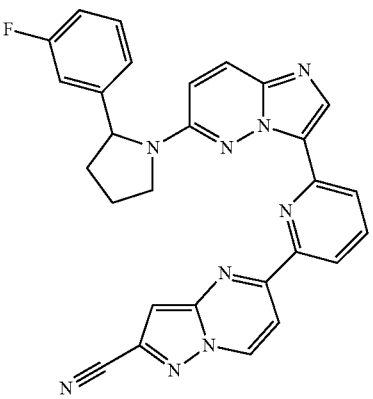 [SMILES: N#Cc1cc2nc(-c3cccc(-c4cnc5ccc(N6CCCC6c6cccc(F)c6)nn45)n3)ccn2n1] | <sup>1</sup>H NMR (400 MHz, DMSO-d6) d 9.01 (d, 1H, J = 4.8 Hz), 8.99 (s, 1H), 8.82 (d, 1H, J = 8.0 Hz), 8.52 (s br, 1H), 8.23 (d, 1H, J = 8.4 Hz), 8.07 (m, 3H), 7.43 (m, 1H), 7.22 (m, 2H), 7.07 (m, 2H), 5.25 (dd, 1H, J = 8.0, 2.4 Hz), 4.07 (m, 1H), 3.74 (q, 1H, J = 8.0 Hz), 2.47 (m, 1H), 2.08 (m, 2H), 1.92 (m, 1H) MS (m/z): 501.52 |
| 31 | 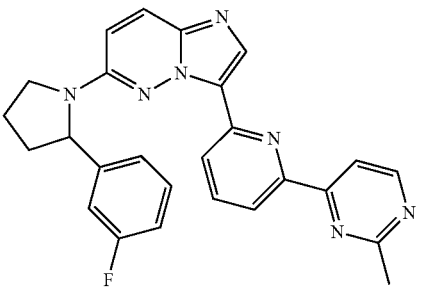 [SMILES: Cc1nccc(-c2cccc(-c3cnc4ccc(N5CCCC5c5cccc(F)c5)nn34)n2)n1] | MS (m/z): 451.50 |
| 32 | 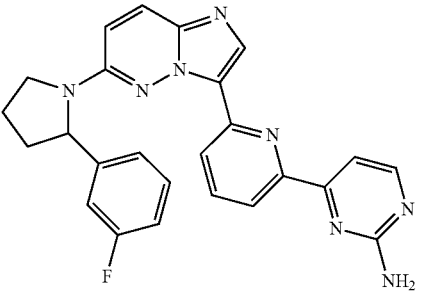 [SMILES: Nc1nccc(-c2cccc(-c3cnc4ccc(N5CCCC5c5cccc(F)c5)nn34)n2)n1] | <sup>1</sup>H NMR (400 MHz, DMSO-d6) d 8.42 (d, 1H, J = 4.8 Hz), 8.26 (s br, 1H), 8.31 (s, 1H), 8.15 (d, 1H, J = 8.0 Hz), 7.95 (d, 1H, J = 8.0 Hz), 7.89 (m, 1H), 7.64 (d, 1H, J = 4.8 Hz), 7.41 (ddd, 1H, J = 8.0, 6.4, 6.4 Hz), 7.20 (m, 2H), 7.05 (ddd, 1H, J = 8.4, 8.4, 2.4 Hz), 6.90 (s br, 1H), 6.76 (s, 2H), 5.22 (dd, 1H, J = 8.4, 2.8 Hz), 4.03 (m, 1H), 3.70 (q, 1H, J = 8.4 Hz), 2.47 (m, 1H), 2.06 (m, 2H), 1.89 (m, 1H) MS (m/z): 452.49 |
| 33 | 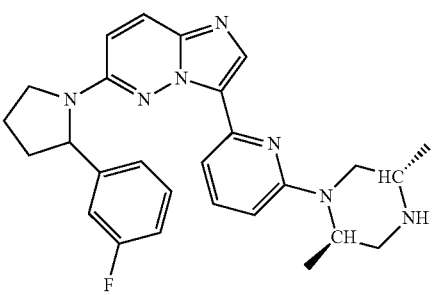 [SMILES: C[C@@H]1CN[C@@H](C)CN1c1cccc(-c2cnc3ccc(N4CCCC4c4cccc(F)c4)nn23)n1] | MS (m/z): 471.57 |

TABLE 7-continued
| Compound Number | Structure | Physical Data ¹H NMR 400 MHz (DMSO-$d_6$) and/or MS (m/z) |
|---|---|---|
| 34 | 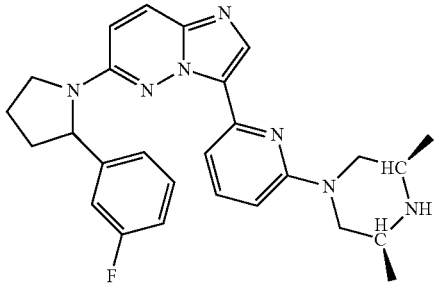 | MS (m/z): 471.57 |
| 35 | 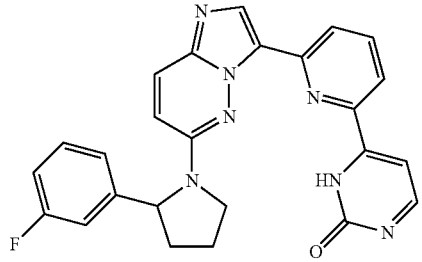 [SMILES: O=c1nccc(-c2cccc(-c3cnc4ccc(N5CCCC5c5cccc(F)c5)nn34)n2)[nH]1] | MS (m/z): 453.47 |
| 36 | 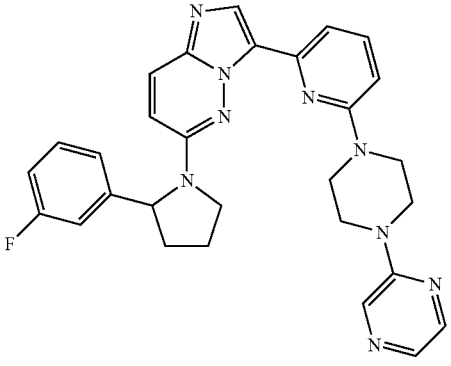 [SMILES: Fc1cccc(C2CCCN2c2ccc3ncc(-c4cccc(N5CCN(c6cnccn6)CC5)n4)n3n2)c1] | MS (m/z): 521.59 |
| 37 | 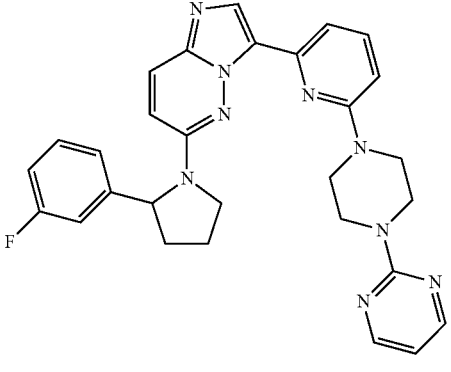 [SMILES: Fc1cccc(C2CCCN2c2ccc3ncc(-c4cccc(N5CCN(c6ncccn6)CC5)n4)n3n2)c1] | MS (m/z): 521.59 |

TABLE 7-continued

| Compound Number | Structure | Physical Data<br>¹H NMR 400 MHz (DMSO-d₆) and/or MS (m/z) |
|---|---|---|
| 38 | 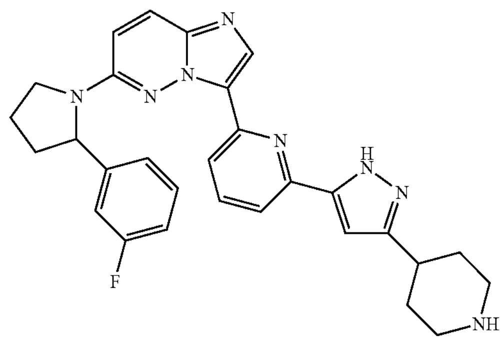 [SMILES: Fc1cccc(C2CCCN2c2ccc3ncc(-c4cccc(-c5cc(C6CCNCC6)n[nH]5)n4)n3n2)c1] | MS (m/z): 508.59 |
| 39 | 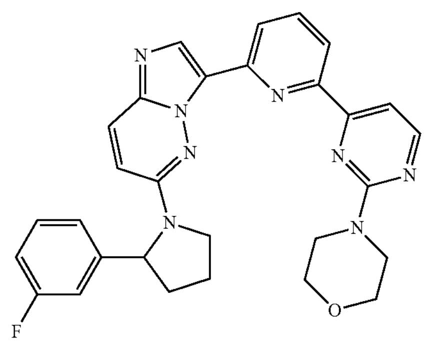 [SMILES: Fc1cccc(C2CCCN2c2ccc3ncc(-c4cccc(-c5ccnc(N6CCOCC6)n5)n4)n3n2)c1] | ¹H NMR (400 MHz, DMSO-d6) 8.64 (d, 1H, J = 4.8 Hz), 8.40 (s, 1H), 8.35 (s br, 1H), 8.34 (d, 1H, J = 8.0 Hz), 8.01 (d, 1H, J = 10.0 Hz), 7.96 (m, 1H), 7.81 (d, 1H, J = 4.8 Hz), 7.46 (m, 1H), 7.26 (d, 1H, J = 7.6 Hz), 7.10 (m, 1H), 6.96 (s br, 1H), 5.27 (dd, 1H, J = 8.0, 2.8 Hz), 4.09 (m, 1H), 3.89 (t, 4H, J = 4.8 Hz), 3.78 (m, 5H), 2.53 (m, 1H), 2.12 (m, 2H), 1.95 (m, 1H)<br>MS (m/z): 522.58 |
| 40 | 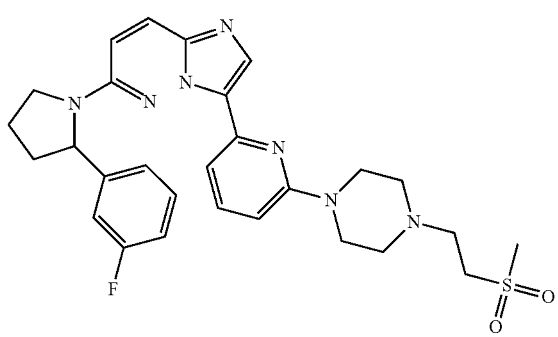 [SMILES: CS(=O)(=O)CCN1CCN(c2cccc(-c3cnc(/C=C\C(=N)N4CCCC4c4cccc(F)c4)[nH]3)n2)CC1] | MS (m/z): 549.66 |
| 41 | 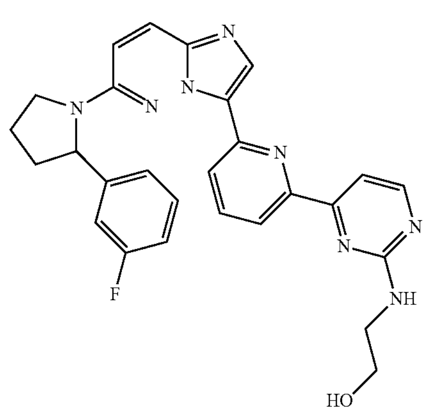 [SMILES: N=C(/C=C\c1ncc(-c2cccc(-c3ccnc(NCCO)n3)n2)[nH]1)N1CCCC1c1cccc(F)c1] | MS (m/z): 496.54 |

TABLE 7-continued

| Compound Number | Structure | Physical Data<br>¹H NMR 400 MHz (DMSO-d₆)<br>and/or MS (m/z) |
|---|---|---|
| 42 | 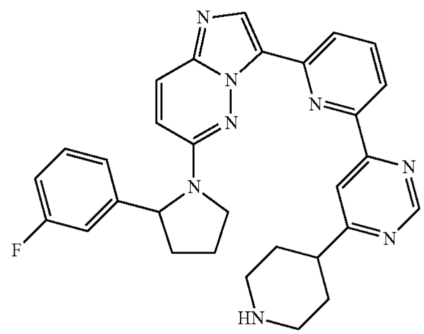 [SMILES: Fc1cccc(C2CCCN2c2ccc3ncc(-c4cccc(-c5cc(C6CCNCC6)ncn5)n4)n3n2)c1] | MS (m/z): 520.60 |
| 43 | 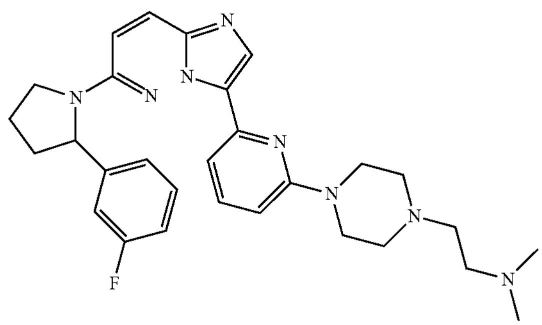 [SMILES: CN(C)CCN1CCN(c2cccc(-c3cnc(/C=C\C(=N)N4CCCC4c4cccc(F)c4)[nH]3)n2)CC1] | MS (m/z): 514.64 |
| 44 | 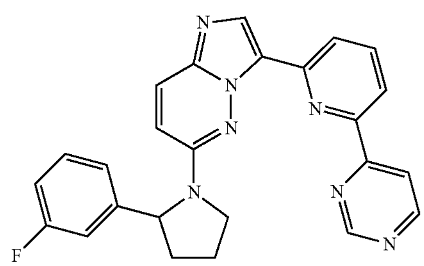 [SMILES: Fc1cccc(C2CCCN2c2ccc3ncc(-c4cccc(-c5ccncn5)n4)n3n2)c1] | ¹H NMR (400 MHz, DMSO-d6) 9.38 (d, 1H, J = 1.2 Hz), 9.05 (d, 1H, J = 5.2 Hz), 8.64 (dd, 1H, J = 9.2, 1.2 Hz), 8.46 (s, 1H), 8.36 (d, 1H, J = 8.0 Hz), 8.01 (d, 1H, J = 10.0 Hz), 7.96 (m, 1H), 7.47 (ddd, 1H, J = 8.0, 6.4, 6.4 Hz), 7.26 (m, 3H), 7.11 (ddd, 1H, J = 8.4, 8.4, 2.4 Hz), 6.98 (s br, 1H), 5.27 (dd, 1H, J = 8.0, 2.4 Hz), 4.09 (m, 1H), 3.76 (t, 4H, J = 9.2 Hz), 2.53 (m, 1H), 2.12 (m, 2H), 1.95 (m, 1H)<br>MS (m/z): 437.47 |
| 45 | 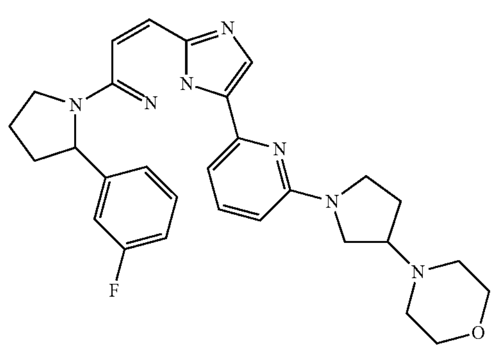 [SMILES: N=C(/C=C\c1ncc(-c2cccc(N3CCC(N4CCOCC4)C3)n2)[nH]1)N1CCCC1c1cccc(F)c1] | MS (m/z): 513.61 |

TABLE 7-continued

| Compound Number | Structure | Physical Data $^1$H NMR 400 MHz (DMSO-d$_6$) and/or MS (m/z) |
|---|---|---|
| 46 | 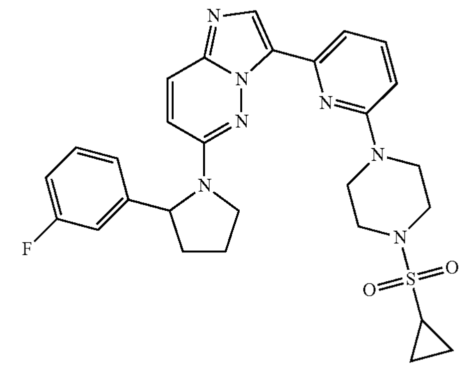 [SMILES: O=S(=O)(C1CC1)N1CCN(c2cccc(-c3cnc4ccc(N5CCCC5c5cccc(F)c5)nn34)n2)CC1] | MS (m/z): 547.65 |
| 47 | 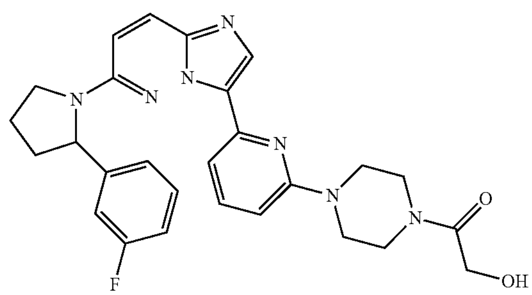 [SMILES: N=C(/C=C\c1ncc(-c2cccc(N3CCN(C(=O)CO)CC3)n2)[nH]1)N1CCCC1c1cccc(F)c1] | MS (m/z): 501.55 |
| 48 | 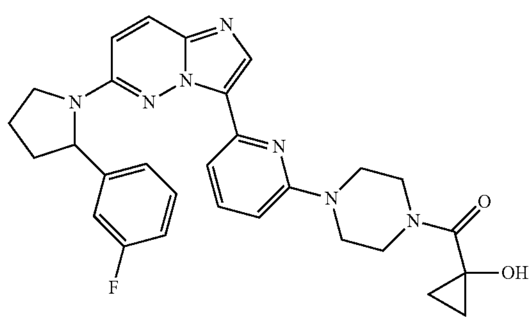 [SMILES: O=C(N1CCN(c2cccc(-c3cnc4ccc(N5CCCC5c5cccc(F)c5)nn34)n2)CC1)C1(O)CC1] | $^1$H NMR (400 MHz, DMSO-d6) d 8.10 (s, 1H), 7.89 (d, 1H, J = 6.0 Hz), 7.54 (m, 2H), 7.39 (m, 1H), 7.17 (m, 2H), 7.04 (m, 1H), 6.81 (m, 2H), 6.40 (s, 1H), 5.18 (dd, 1H, J = 8.0, 2.4 Hz), 4.00 (m, 1H), 3.69 (m, 9H), 2.45 (m, 2H), 1.87 (m, 1H), 0.96 (m, 2H), 0.80 (m, 2H) MS (m/z): 527.59 |
| 49 | 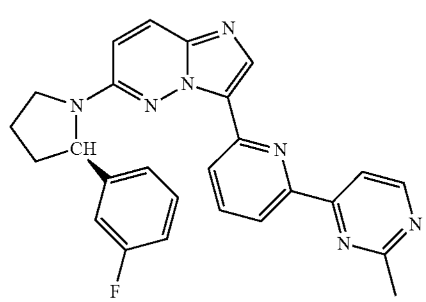 [SMILES: Cc1nccc(-c2cccc(-c3cnc4ccc(N5CCC[C@@H]5c5cccc(F)c5)nn34)n2)n1] | MS (m/z): 451.50 |

TABLE 7-continued

| Compound Number | Structure | Physical Data<br>¹H NMR 400 MHz (DMSO-d₆) and/or MS (m/z) |
|---|---|---|
| 50 | 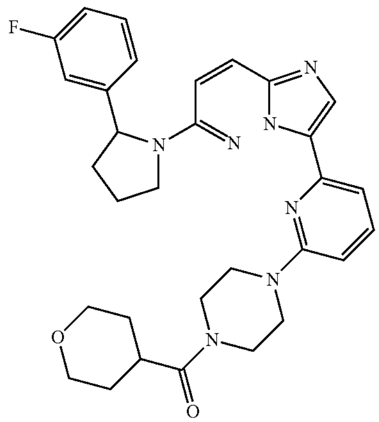 [SMILES: N=C(/C=C\c1ncc(-c2cccc(N3CCN(C(=O)C4CCOCC4)CC3)n2)[nH]1)N1CCCC1c1cccc(F)c1] | ¹H NMR (400 MHz, DMSO-d6) d 8.09 (s, 1H), 7.90 (d, 1H, J = 10.0 Hz), 7.53 (m, 2H), 7.38 (m, 1H), 7.16 (m, 2H), 7.03 (m, 1h), 6.82 (s br, 1H), 6.77 (d, 1H, J = 8.4 Hz), 5.17 (dd, 1H, J = 8.4, 2.8 Hz), 4.00 (m, 1H), 3.86 (m, 2H), 3.59 (m, 8H), 3.40 (m, 3H), 2.94 (m, 1H), 2.45 (m, 1H), 2.04 (m, 2H), 1.87 (m, 1H), 1.58 (m, 4H)<br>MS (m/z): 555.65 |
| 51 | 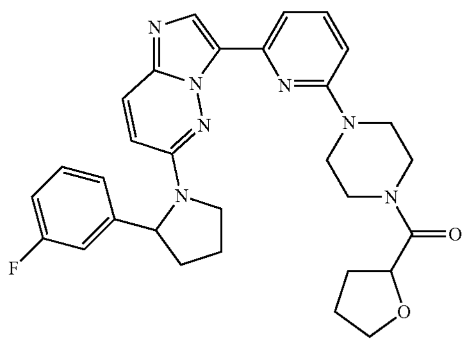 [SMILES: O=C(C1CCCO1)N1CCN(c2cccc(-c3cnc4ccc(N5CCCC5c5cccc(F)c5)nn34)n2)CC1] | ¹H NMR (400 MHz, DMSO-d6) d 8.15 9s, 1H), 7.95 (d, 1H, J = 9.6 Hz), 7.65 (d, 2H), 7.44 (d, 1H), 7.22 (m, 2H), 7.09 (m, 1H), 6.84 (m, 2H), 5.23 (dd, 1H, J = 8.0, 2.4 Hz), 4.78 (dd, 1H, J = 8.0, 5.6 Hz), 4.05 (m, 1H), 3.70 (m, 11H), 2.50 (m, 1H), 2.09 (m, 4H), 1.91 (m, 3H)<br>MS (m/z): 541.62 |
| 52 | 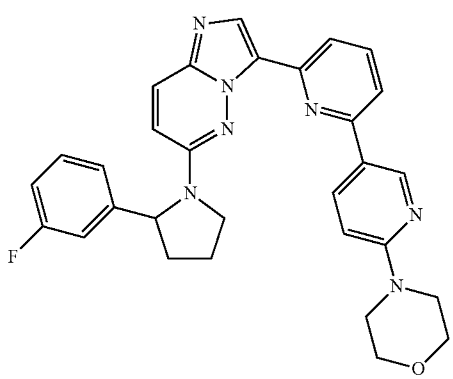 [SMILES: Fc1cccc(C2CCCN2c2ccc3ncc(-c4cccc(-c5ccc(N6CCOCC6)nc5)n4)n3n2)c1] | MS (m/z): 521.59 |
| 53 | 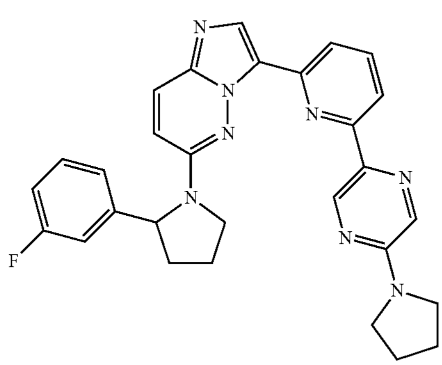 [SMILES: Fc1cccc(C2CCCN2c2ccc3ncc(-c4cccc(-c5cnc(N6CCCC6)cn5)n4)n3n2)c1] | MS (m/z): 506.58 |

TABLE 7-continued

| Compound Number | Structure | Physical Data $^1$H NMR 400 MHz (DMSO-$d_6$) and/or MS (m/z) |
|---|---|---|
| 54 | 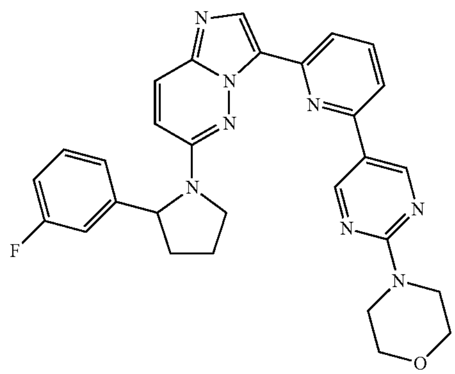 [SMILES: Fc1cccc(C2CCCN2c2ccc3ncc(-c4cccc(-c5cnc(N6CCOCC6)nc5)n4)n3n2)c1] | $^1$H NMR (400 MHz, DMSO-d6) d 9.17 (s, 1H), 8.31 (s, 1H), 8.11 (s br, 1H), 7.94 9d, 1H, J = 10.0 Hz), 7.78 (m, 2H), 7.41 (m, 2H), 7.20 (m, 2H), 7.05 (m, 1H), 6.88 (m, 1H), 5.21 (dd, 1H, J = 8.0, 2.4 Hz), 4.00 (m, 1H), 3.80 (m, 4H), 3.69 (m, 5H), 2.57 (m, 1H), 2.06 (m, 2H), 1.89 (m, 1H) MS (m/z): 522.58 |
| 55 | 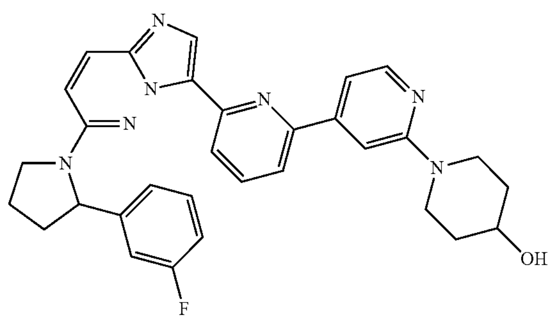 [SMILES: N=C(/C=C\c1ncc(-c2cccc(-c3ccnc(N4CCC(O)CC4)c3)n2)[nH]1)N1CCCC1c1cccc(F)c1] | MS (m/z): 536.61 |
| 56 | 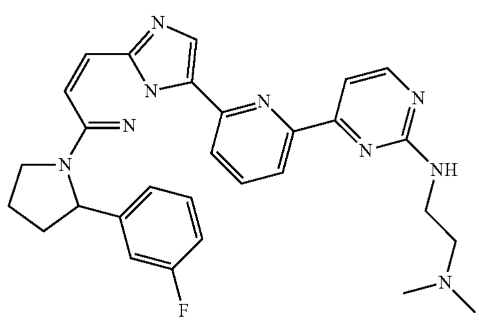 [SMILES: CN(C)CCNc1nccc(-c2cccc(-c3cnc(/C=C\C(=N)N4CCCC4c4cccc(F)c4)[nH]3)n2)n1] | MS (m/z): 523.61 |
| 57 | 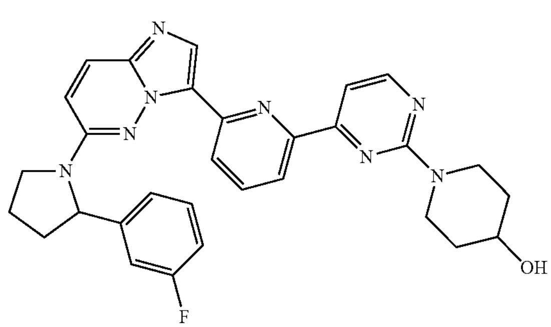 [SMILES: OC1CCN(c2nccc(-c3cccc(-c4cnc5ccc(N6CCCC6c6cccc(F)c6)nn45)n3)n2)CC1] | MS (m/z): 536.60 |

TABLE 7-continued
| Compound Number | Structure | Physical Data $^1$H NMR 400 MHz (DMSO-$d_6$) and/or MS (m/z) |
|---|---|---|
| 58 | 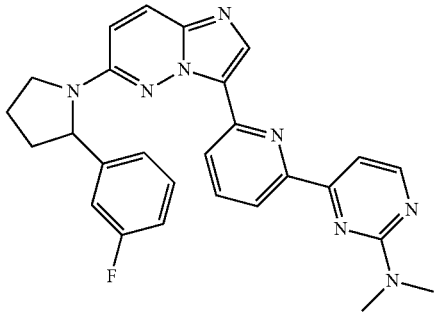 [SMILES: CN(C)c1nccc(-c2cccc(-c3cnc4ccc(N5CCCC5c5cccc(F)c5)nn34)n2)n1] | MS (m/z): 480.54 |
| 59 | 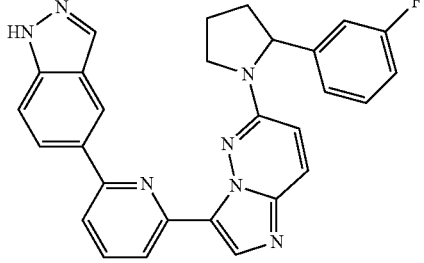 | MS (m/z): 475.52 |
| 60 | 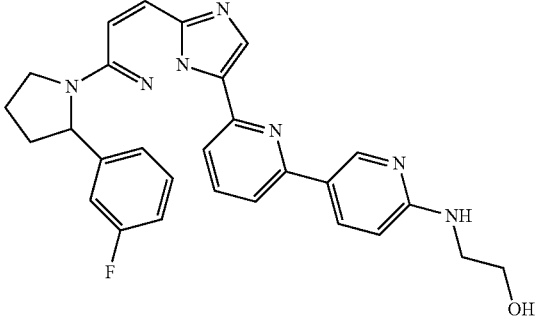 [SMILES: N=C(/C=C\c1ncc(-c2cccc(-c3ccc(NCCO)nc3)n2)[nH]1)N1CCCC1c1cccc(F)c1] | MS (m/z): 495.55 |
| 61 | 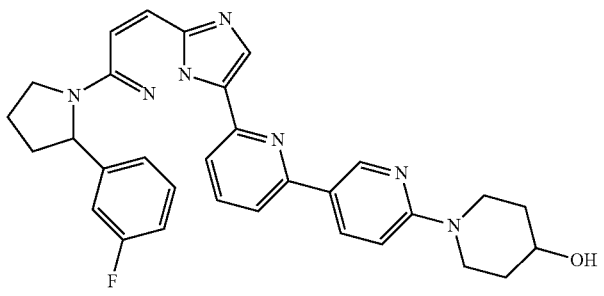 [SMILES: N=C(/C=C\c1ncc(-c2cccc(-c3ccc(N4CCC(O)CC4)nc3)n2)[nH]1)N1CCCC1c1cccc(F)c1] | MS (m/z): 535.61 |

TABLE 7-continued
| Compound Number | Structure | Physical Data<br>$^1$H NMR 400 MHz (DMSO-$d_6$)<br>and/or MS (m/z) |
|---|---|---|
| 62 | 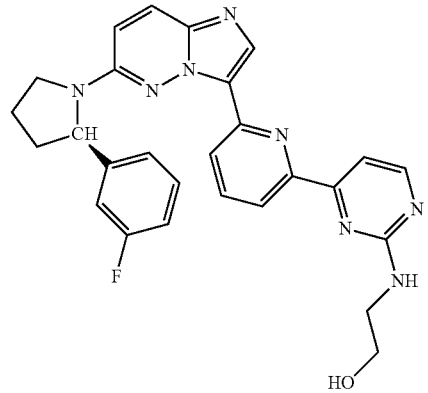 [SMILES: OCCNc1nccc(-c2cccc(-c3cnc4ccc(N5CCC[C@@H]5c5cccc(F)c5)nn34)n2)n1] | $^1$H NMR (400 MHz, DMSO-d6) d 8.46 (d, 1H, J = 4.8 Hz), 8.32 (s, 1H), 8.22 (s br, 1H), 7.95 (d, 1H, J = 6.0 Hz), 7.89 (m, 1H), 7.65 (d, 1H, J = 4.2 Hz), 7.42 (m, 1H), 7.19 (m, 3H), 7.05 (ddd, 1H, J = 8.0, 8.0, 2.0 Hz), 6.90 (m, 1H), 5.20 (m, 1H), 4.74 (t, 1H, J = 5.6 Hz), 4.03 (m, 1H), 3.70 (q, 1H, J = 8.4 Hz), 3.60 (m, 2H), 3.47 (s br, 2H), 3.34 (s, 1H), 2.49 (m, 1H), 2.06 (m, 2H), 1.95 (m, 1H)<br>MS (m/z): 496.54 |
| 63 | 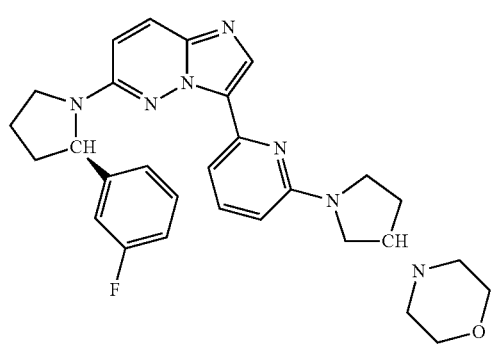 | MS (m/z): 513.61 |
| 64 | 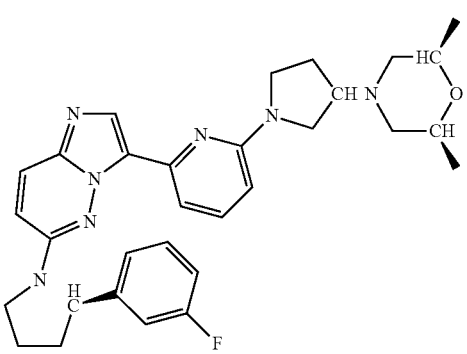 | MS (m/z): 541.66 |
| 65 | 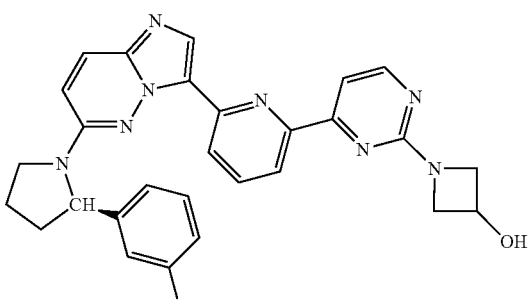 | MS (m/z): 508.55 |

TABLE 7-continued

| Compound Number | Structure | Physical Data<br>$^1$H NMR 400 MHz (DMSO-$d_6$)<br>and/or MS (m/z) |
|---|---|---|
| 66 | 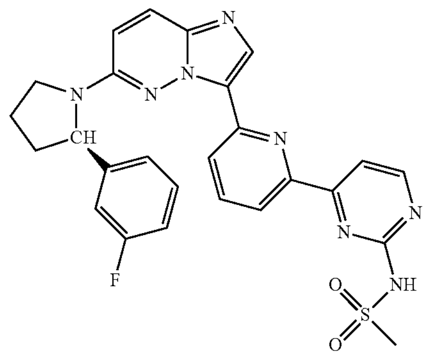 [SMILES: CS(=O)(=O)Nc1nccc(-c2cccc(-c3cnc4ccc(N5CCC[C@@H]5c5cccc(F)c5)nn34)n2)n1] | $^1$H NMR (400 MHz, DMSO-d6) d 8.53 (d, 1H, J = 4.4 Hz), 8.22 (s, 1H), 8.16 (s br, 1H), 8.07 (d, 1H, J = 7.6 Hz), 7.82 (m, 3H), 7.29 (m, 1H), 7.07 (m, 2H), 6.91 (ddd, 1H, J = 8.4, 8.4, 2.4 Hz), 6.77 (s br, 1H), 5.08 (d, 1H, J = 8.0, Hz), 3.90 (m, 1H), 3.57 (q, 1H, J = 8.0 Hz), 3.15 (s, 3H), 3.10 (m, 1H), 2.33 (m, 1H), 1.92 (m, 2H), 1.76 (m, 1H)<br>MS (m/z): 530.58 |
| 67 | 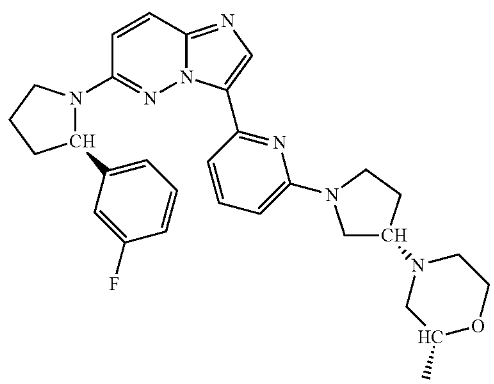 [SMILES: C[C@@H]1CN([C@H]2CCN(c3cccc(-c4cnc5ccc(N6CCC[C@@H]6c6cccc(F)c6)nn45)n3)C2)CCO1] | MS (m/z): 527.64 |
| 68 | 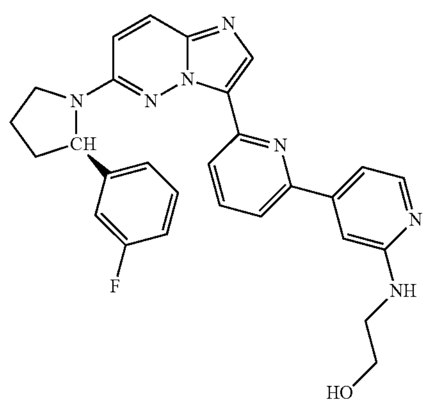 [SMILES: OCCNc1cc(-c2cccc(-c3cnc4ccc(N5CCC[C@@H]5c5cccc(F)c5)nn34)n2)ccn1] | $^1$H NMR (400 MHz, DMSO-d6) d 8.31 (s, 1H), 8.18 (s br, 1H), 8.08 (d, 1H, J = 5.2 Hz), 7.95 (d, 1H, J = 9.6 Hz), 7.79 (m, 2H), 7.40 (m, 2H), 7.19 (m, 3H), 7.05 (m, 1H), 6.90 (m, 1H), 6.68 (t, 1H, J = 5.6 Hz), 5.21 (dd, 1H, J = 8.4, 2.4 Hz), 4.78 (t, 1H, J = 5.2 Hz), 4.03 (m, 1H), 3.69 (q, 1H, J = 8.4 Hz), 3.58 (m, 2H), 3.39 (q, 1H, J = 6.0 Hz), 3.34 (s, 1H), 2.46 (m, 1H), 2.05 (m, 2H), 1.89 (m, 1H)<br>MS (m/z): 495.55 |
| 69 | 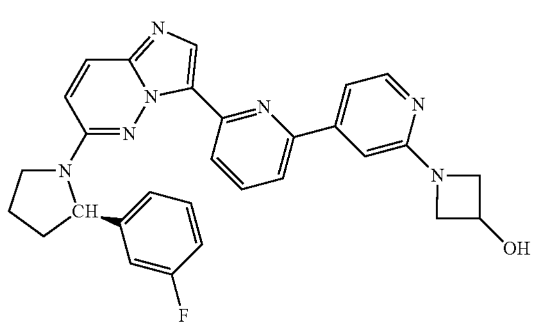 [SMILES: OC1CN(c2cc(-c3cccc(-c4cnc5ccc(N6CCC[C@@H]6c6cccc(F)c6)nn45)n3)ccn2)C1] | $^1$H NMR (400 MHz, DMSO-d6) d 8.29 (s, 1H), 8.19 (d, 1H, J = 5.2 Hz), 7.96 (d, 1H, J = 9.6 Hz), 7.91 (d, 1H, J = 8.0 Hz), 7.83 (m, 1H), 7.40 (m, 2H), 7.20 (d, 2H, J = 7.6 Hz), 7.09 (s, 1H), 7.05 (m, 1H), 6.90 (s br, 1H), 5.67 (d, 1H, J = 6.8 Hz), 5.20 (dd, 1H, J = 8.0, 2.4 Hz), 4.61 (m, 1H), 4.25 (t, 1H, J = 8.0 Hz), 4.03 (m, 1H), 3.76 (q, 1H, J = 4.0 Hz), 3.70 (m, 1H), 3.34 (s, 4H), 2.49 (m, 1H), 2.06 (m, 2H), 1.89 (m, 1H)<br>MS (m/z): 507.56 |

TABLE 7-continued

| Compound Number | Structure | Physical Data $^1$H NMR 400 MHz (DMSO-d$_6$) and/or MS (m/z) |
|---|---|---|
| 70 | 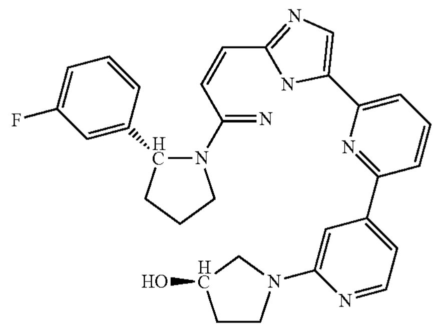 | $^1$H NMR (400 MHz, DMSO-d6) d 8.28 (s, 1H), 8.24 (s br, 1H), 8.18 (d, 1H, J = 5.2 Hz), 7.95 (d, 1H, J = 9.6 Hz), 7.90 (d, 1H, J = 8.0 Hz), 7.82 (m, 1H), 7.40 (q, 1H, J = 8.4 Hz), 7.27 (m, 1 Hz), 7.19 (d, 1H, J = 7.6 Hz) 7.14 (s, 1H), 7.05 (m, 1H), 6.89 (s br, 1H), 5.19 (dd, 1H, J = 8.0, 2.4 Hz), 4.99 (d, 1H, J = 3.2 Hz), 4.43 (s, 1H), 4.02 (m, 1H), 3.90 (q, 1H, J = 9.2 Hz), 3.58 (m, 1H), 3.42 (d, 1H, J = 10.8 Hz), 2.46 (m, 1H), 2.05 (m, 3H), 1.91 (m, 2H) MS (m/z): 521.59 |
| 71 | 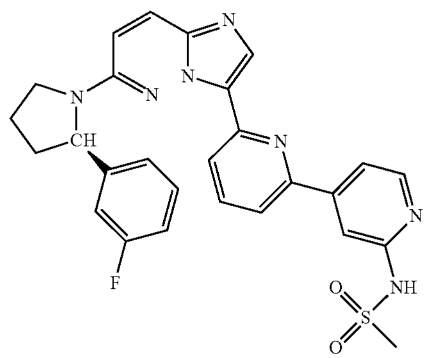 [SMILES: CS(=O)(=O)Nc1cc(-c2cccc(-c3cnc(/C=C\C(=N)N4CCC[C@@H]4c4cccc(F)c4)[nH]3)n2)ccn1] | $^1$H NMR (400 MHz, DMSO-d6) d 8.31 (d, 1H, J = 5.6 Hz), 8.29 (s, 1H), 8.25 (s br, 1H), 7.96 (d, 1H, J = 10.0 Hz), 7.87 (m, 2H), 7.73 (s, 1H), 7.60 (dd, 1H, J = 5.6, 1.2 Hz), 7.41 (m, 1H), 7.20 (d, 1H, J = 8.4 Hz), 7.05 (m, 1H), 6.91 (s br, 1H), 5.21 (dd, 1H, J = 8.4, 2.4 Hz), 4.03 (m, 1H), 3.71 (q, 1H, J = 8.0 Hz), 3.23 (s, 3H), 3.20 (m, 1H), 2.47 (m, 1H), 2.06 (m, 2H), 1.89 (m, 1H) MS (m/z): 529.59 |
| 72 | 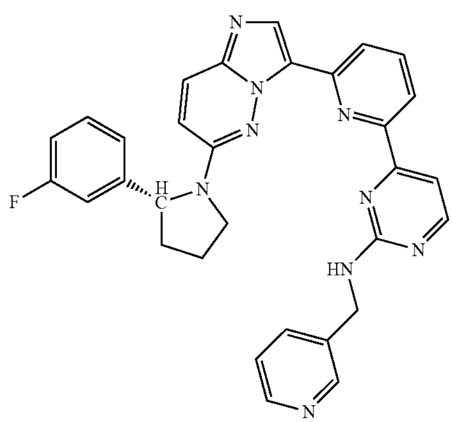 | $^1$H NMR (400 MHz, DMSO-d6) d 8.65 (s br, 1H), 8.48 (d, 1H, J = 5.2 Hz), 8.44 (dd, 1H, J = 4.8, 1.6 Hz), 8.31 (s, 1H), 8.18 (d, 1H, J = 8.0 Hz), 7.95 (d, 2H, 9.6 Hz), 7.88 (m, 1H), 7.81 (m, 1H), 7.68 (d, 1H, J = 6.8 Hz), 7.39 (m, 2H), 7.19 (m, 2H), 7.05 (ddd, 1H, J = 8.0, 8.0, 2.0 Hz), 6.90 (s br, 1H), 5.21 (dd, 1H, J = 6.0, 1.6 Hz), 4.63 (d, 2H, J = 5.6 Hz), 4.03 (m 1H), 3.70 (q, 1H, J = 8.4 Hz), 3.34 (s, 1H), 2.46 (m, 1H), 2.05 (m, 2H), 1.88 (m, 1H) MS (m/z): 543.60 |
| 73 | 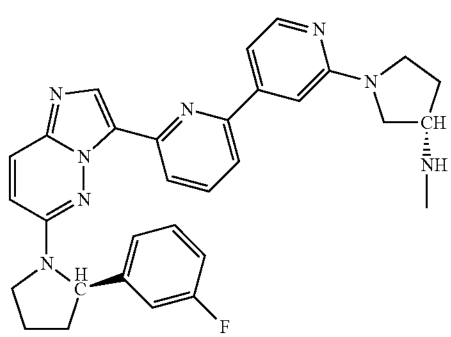 | MS (m/z): 534.63 |

TABLE 7-continued

| Compound Number | Structure | Physical Data ¹H NMR 400 MHz (DMSO-d₆) and/or MS (m/z) |
|---|---|---|
| 74 | 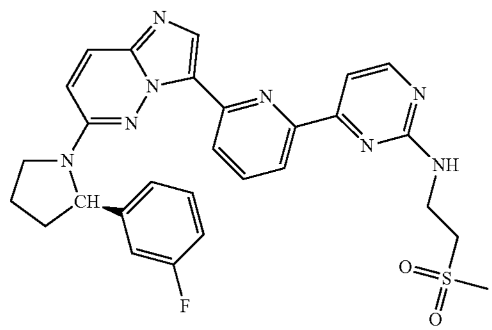 [SMILES: CS(=O)(=O)CCNc1nccc(-c2cccc(-c3cnc4ccc(N5CCC[C@@H]5c5cccc(F)c5)nn34)n2)n1] | ¹H NMR (400 MHz, DMSO-d6) d 8.51 (d, 1H, J = 4.8 Hz), 8.33 (s, 1H), 8.26 (s br, 1H), 7.96 (d, 1H, J = 9.6 Hz), 7.90 (m, 1H), 7.73 (d, 1H, J = 4.8 Hz), 7.45 (m, 2H), 7.20 (m, 2H), 7.05 (ddd, 1H, J = 8.4, 8.4, 2.0 Hz), 6.91 (s br, 1H), 5.21 (dd, 1H, J = 8.0, 2.8 Hz), 4.04 (m, 1H), 3.81 (m, 2H), 3.71 (q, 1H, J = 8.0 Hz), 3.45 (t, 2H, J = 6.8 Hz), 3.34 (s, 1H), 3.07 (s, 3H), 2.46 (m, 1H), 2.06 (m, 2H), 1.89 (m, 1H) MS (m/z): 558.63 |
| 75 | 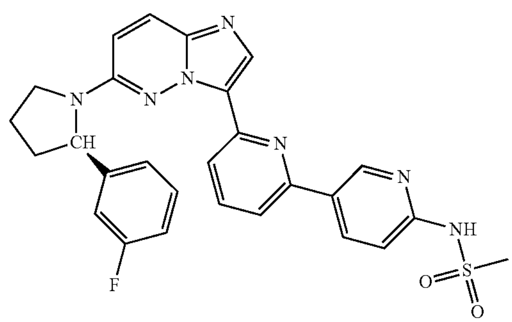 [SMILES: CS(=O)(=O)Nc1ccc(-c2cccc(-c3cnc4ccc(N5CCC[C@@H]5c5cccc(F)c5)nn34)n2)cn1] | ¹H NMR (400 MHz, DMSO-d6) d 8.98 (d, 1H, J = 6.0 Hz), 8.45 (dd, 1H, J = 8.8, 2.0 Hz), 8.31 (s, 1H), 8.10 (s br, 1H), 7.95 (d, 1H, J = 10.0 Hz), 7.80 (m, 2H), 7.41 (m, 1H), 7.07 (m, 2H), 6.91 (ddd, 1H, J = 8.4, 8.4, 2.4 Hz), 6.77 (s br, 1H), 5.08 (dd, 1H, J = 8.0, 2.4 Hz), 3.90 (m, 1H), 3.57 (q, 1H, J = 8.0 Hz), 3.15 (s, 3H), 3.10 (m, 1H), 2.33 (m, 1H), 1.92 (m, 2H), 1.76 (m, 1H) MS (m/z): 529.59 |
| 76 | 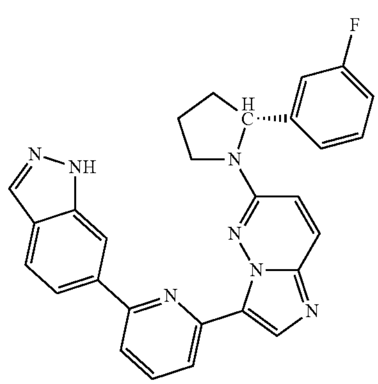 | MS (m/z): 475.52 |
| 77 | 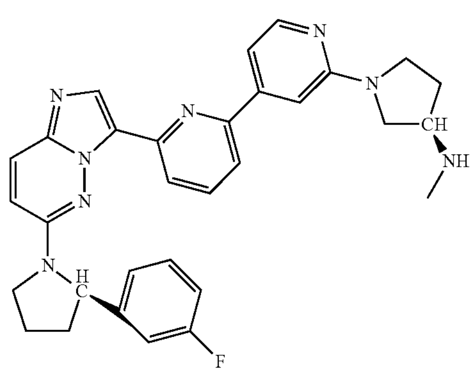 | ¹H NMR (400 MHz, DMSO-d6) d 8.30 (s, 1H), 8.23 (d, 1H, J = 5.6 Hz), 8.1 (s br, 1H), 7.95 (t, 2H, J = 8.8 Hz), 7.85 (s br, 1H), 7.39 (m, 2H), 7.21 (m, 3H), 7.05 (m, 1H), 6.90 (s br, 1H), 5.21 (dd, 1H, J = 8.0, 2.8 Hz), 4.03 (m, 1H), 3.80 (m, 2H), 3.67 (m, 3H), 2.61 (s, 3H), 2.47 (m, 1H), 2.35 (m, 1H), 2.20 (m, 1H), 2.06 (m, 2H), 1.89 (m, 1H), 1.18 (d, 1H, J = 6.8 Hz) MS (m/z): 534.63 |

TABLE 7-continued

| Compound Number | Structure | Physical Data<br>¹H NMR 400 MHz (DMSO-d₆) and/or MS (m/z) |
|---|---|---|
| 78 | 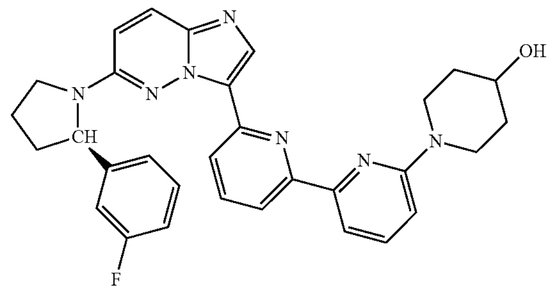 [SMILES: OC1CCN(c2cccc(-c3cccc(-c4cnc5ccc(N6CCC[C@@H]6c6cccc(F)c6)nn45)n3)n2)CC1] | ¹H NMR (400 MHz, DMSO-d6) δ 8.29 (s, 1H), 8.19 (d, 1H, J = 8.0 Hz), 7.94 (d, 1H, J = 9.6 Hz), 7.84 (m, 3H), 7.68 (t, 2H, J = 8.4 Hz), 7.41 (m, 1H), 7.19 (m, 2H), 7.05 (m, 1H), 6.93 (d, 1H, J = 8.4 Hz), 6.90 (s br), 5.21 (dd, 1H, J = 8.0, 2.8 Hz), 4.73 9d, 1H, J = 4.4 Hz), 4.16 (m, 2H), 4.03 (m, 1H), 3.73 (m, 2H), 3.17 (m, 2H), 2.47 (m, 1H), 2.06 (m, 2H), 1.87 (m, 3H), 1.44 (m, 2H)<br>MS (m/z): 535.61 |
| 79 | 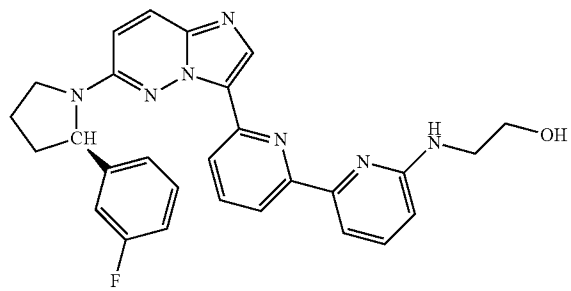 [SMILES: OCCNc1cccc(-c2cccc(-c3cnc4ccc(N5CCC[C@@H]5c5cccc(F)c5)nn34)n2)n1] | ¹H NMR (400 MHz, DMSO-d6) δ 8.28 (s, 1H), 8.14 (d, 1H, J = 8.0 Hz), 7.94 (d, 1H, 9.6 Hz), 7.82 (m, 1H), 7.68 (d, 1H, J = 7.2 Hz), 7.53 (t, 1H, J = 7.2 Hz), 7.41 (ddd, 1H, J = 8.0, 8.0, 6.4 Hz)), 7.19 (m, 2H), 7.05 (ddd, 1H, J = 8.4, 8.4, 2.0 Hz), 6.88 (s br, 1H), 6.665 (t, 1H, J = 5.6 Hz), 6.58 (d, 1H, J = 8.0 Hz), 5.21 (dd, 1H, J = 8.0, 2.4 Hz), 4.79 (t, 1H, J = 5.6 Hz), 4.03 (m, 1H), 3.66 (m, 3H), 3.46 (m, 2H), 2.45 (m, 1H), 2.06 (m, 2H), 1.89 (m, 1H)<br>MS (m/z): 495.55 |
| 80 | 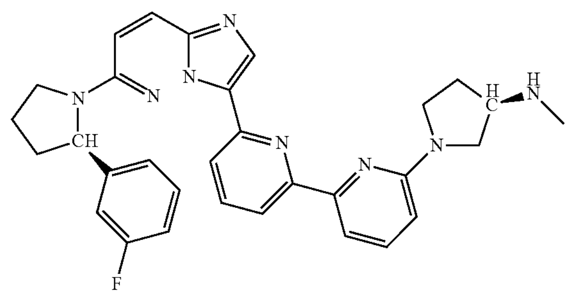 | MS (m/z): 534.63 |
| 81 | 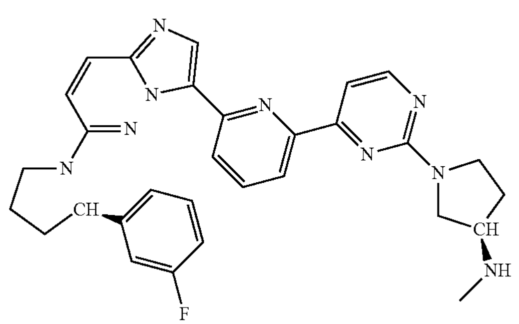 | ¹H NMR (400 MHz, DMSO-d6) δ 8.57 (s, 1H, J = 5.2 Hz), 8.39 (s, 1H), 8.36 (s br, 1H), 8.34 (d, 1H, J = 7.6 Hz), 7.99 (m, 2H), 7.72 (d, 1H, J = 4.2 Hz), 7.47 (m, 1H), 7.26 (m, 2H), 7.11 (m, 1H), 6.96 (s br, 1H), 5.27 (dd, 1H, J = 8.0, 2.0 Hz), 4.09 (m, 1H), 3.58 (m, 4H), 3.49 (s br, 1H), 3.46 (m, 2H), 2.53 (m, 1H), 2.40 (s, 3H), 2.15 (m, 3H), 1.93 (m, 2H)<br>MS (m/z): 535.62 |
| 82 | 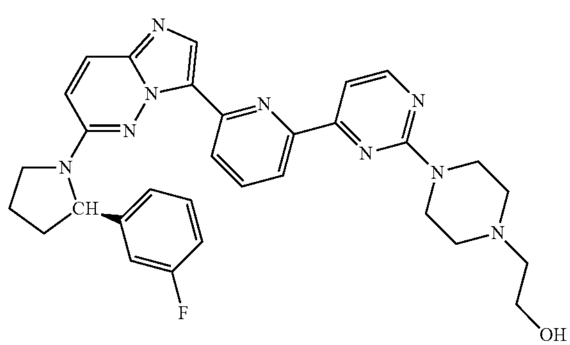 [SMILES: OCCN1CCN(c2nccc(-c3cccc(-c4cnc5ccc(N6CCC[C@@H]6c6cccc(F)c6)nn45)n3)n2)CC1] | ¹H NMR (400 MHz, DMSO-d6) δ 8.54 (d, 1H, J = 4.2 Hz), 8.33 (s, 1H), 8.25 (d, 1H, J = 7.6 Hz), 8.28 (br s, 1H), 7.94 (d, 1H, J = 10.0 Hz), 7.89 (m, 1H), 7.68 (d, 1H, J = 4.8 Hz), 7.40 (m, 1H), 7.19 (m, 2H), 7.04 (m, 1H), 6.88 (br s, 1H), 5.20 (dd, 1H, J = 8.0, 2.8 Hz), 4.48 (br s, 1H), 4.02 (m, 1H), 3.85 (m, 4H), 3.69 (1, 1H, J = 9.2 Hz), 3.57 (t, 2H, J = 6.0 Hz), 2.50 (m, 7H), 2.05 (m, 2H), 1.89 (m, 1H)<br>MS (m/z): 565.64 |

TABLE 7-continued

| Compound Number | Structure | Physical Data<br>¹H NMR 400 MHz (DMSO-d₆)<br>and/or MS (m/z) |
|---|---|---|
| 83 | 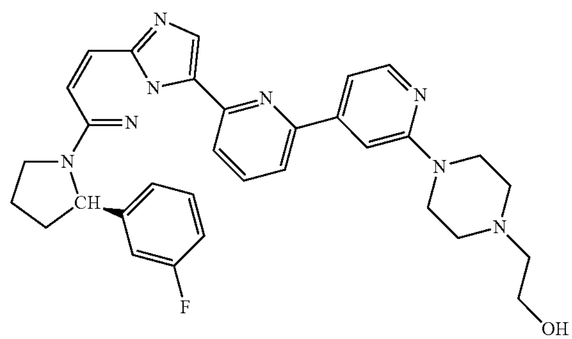 [SMILES: N=C(/C=C\c1ncc(-c2cccc(-c3ccnc(N4CCN(CCO)CC4)c3)n2)[nH]1)N1CCC[C@@H]1c1cccc(F)c1] | ¹H NMR (400 MHz, DMSO-d6) δ 8.38 (s, 1H), 8.30 (d, 1H, J = 4.2 Hz), 8.01 (m, 2H), 7.98 (br s, 1H), 7.89 (m, 1H), 7.59 (s, 1H), 7.46 (m, 2H), 7.26 (d, 2H, J = 7.6 Hz), 7.11 (m, 1H), 6.69 (br s, 1H), 5.27 (dd, 1H, J = 8.4, 2.4 Hz), 4.53 (m, 1H), 4.021 (m, 1H), 3.76 (m, 1H), 3.64 (m, 6H), 2.61 (t, 4H, 4.8 Hz), 2.53 (m, 3H), 2.11 (m, 2H), 1.96 (m, 1H)<br>MS (m/z): 564.66 |
| 84 | 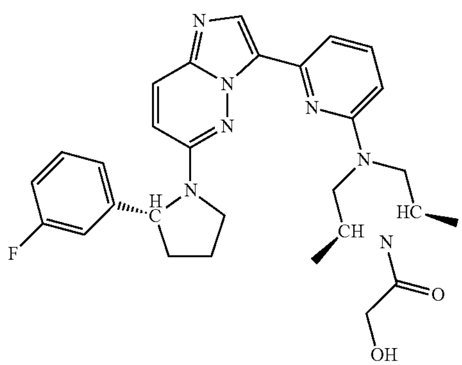 | MS (m/z): 529.61 |
| 85 | 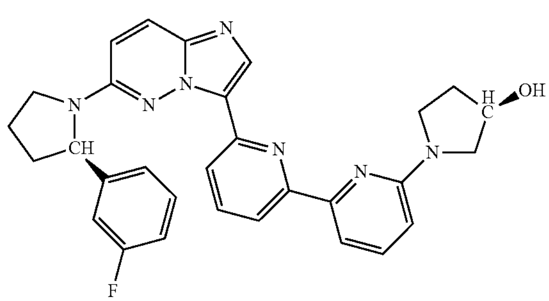 | ¹H NMR (400 MHz, DMSO-d6) δ 8.29 (s, 1H), 8.23 (d, 1H, J = 7.6 Hz), 8.15 (br s, 1H), 7.93 (d, 1H, J = 10.0 Hz), 7.82 (m, 1H), ), 7.76 (d, 1H, J = 7.2 Hz), 7.65 (t, 1H, J = 8.0 Hz), 7.40 (ddd, 1H, J = 8.0, 8.0, 6.4 Hz), 7.18 (m, 2H), 7.04 (ddd, 1H, J = 8.8, 8.0, 2.4 Hz), 6.86 (br s, 1H), 6.52 (d, 1H, J = 8.0 Hz), 5.19 (dd, 1H, J = 8.4, 2.4 Hz), 5.00 (s br, 1H), 4.44 (m, 1H), 4.02 (m, 1H), 3.69 (q, 1H, J = 7.6 Hz), 3.58 (m, 3H), 3.37 (m, 1H), 2.48 (m, 3H), 1.96 (m, 2H)<br>MS (m/z): 521.56 |
| 86 | 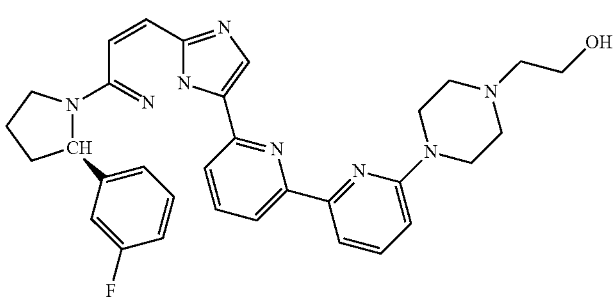 [SMILES: N=C(/C=C\c1ncc(-c2cccc(-c3cccc(N4CCN(CCO)CC4)n3)n2)[nH]1)N1CCC[C@@H]1c1cccc(F)c1] | ¹H NMR (400 MHz, DMSO-d6) δ 8.35 (s, 1H), 8.25 (d, 1H, J = 48.0 Hz), 8.20 (s br, 1H), 7.90 (d, 1H, J = 8.0 Hz), 7.81 (br s, 1H), 7.76 (t, 1H, J = 8.0 Hz), 7.46 (q, 1H, J = 8.0 Hz), 7.25 (m, 2H), 7.11 (m, 1H), 6.97 (d, 1H, J = 8.4 Hz), 6.92 (br s, 1H), 5.26 (d, 1H, J = 8.0 Hz), 4.54 (m, 1H), 4.08 (m, 1H), 3.67 (m, 7H), 2.63 (t, 4H, J = 4.2 Hz), 2.52 (t, 3H, J = 6.4 Hz), 2.11 (m, 2H), 1.96 (m, 1H)<br>MS (m/z): 564.66 |

TABLE 7-continued
| Compound Number | Structure | Physical Data ¹H NMR 400 MHz (DMSO-d₆) and/or MS (m/z) |
|---|---|---|
| 87 | 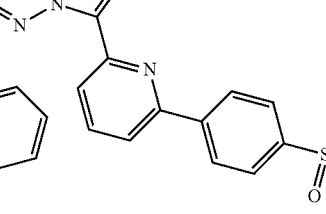 | ¹H NMR (400 MHz, DMSO-d6) δ 8.44 (d, 1H, 8.0 Hz), 8.40 (s, 1H), 8.00 (m, 3H), 7.91 (s br, 1H), 7.76 (m, 1H), 7.52 (s, 2H), 7.46 (m, 1H), 7.27 (d, 2H, J = 7.6 Hz), 7.11 (m, 1H), 6.97 (s br, 1H), 5.28 (dd, 1H, J = 8.4, 2.4 Hz), 4.20 (dd, 1H, J = 6.0, 3.2 Hz), 4.10 (m, 1H), 3.77 (1, 1H, J = 8.0 Hz), 2.60 (s, 1H), 2.53 (m, 1H), 2.12 (m, 2H), 1.95 (m, 1H) MS (m/z): 514.57 |
| 88 | 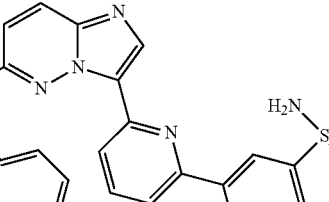 | MS (m/z): 514.57 |
| 89 | 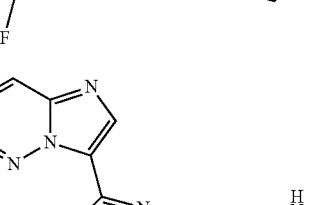 | ¹H NMR (400 MHz, DMSO-d6) δ 8.40 (s, 1H), 8.23 (d, 1H, υ = 7.6 Hz), 8.19 (d, 1H, J = 7.6 Hz), 8.10 (d, 1H, J = 8.0 Hz), 7.95 (m, 2H), 7.48 (ddd, 1H, J = 8.0, 6.4, 6.4 Hz), 7.25 (m, 3H), 7.10 (ddd, 1H, J = 8.8, 8.8, 2.4 Hz), 7.03 (d, 1H, J = 8.0 Hz), 6.95 (s br, 1H), 5.26 (dd, 1H, J = 8.4, 2.4 Hz), 4.09 (m, 1H), 3.75 (q, 1H, J = 8.4 z), 3.51 (s, 3H), 2.55 (m, 1H), 2.11 (m, 2H), 1.91 (m, 1H) MS (m/z): 529.59 |
| 90 | 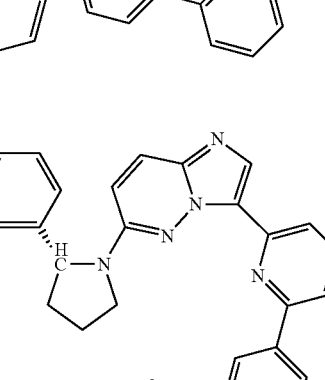 | MS (m/z): 520.60 |
| 91 | 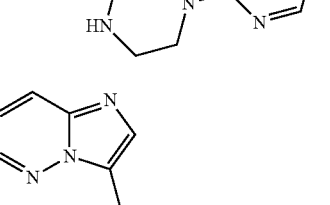 | MS (m/z): 513.59 |

TABLE 7-continued

| Compound Number | Structure | Physical Data<br>¹H NMR 400 MHz (DMSO-d₆)<br>and/or MS (m/z) |
|---|---|---|
| 92 | 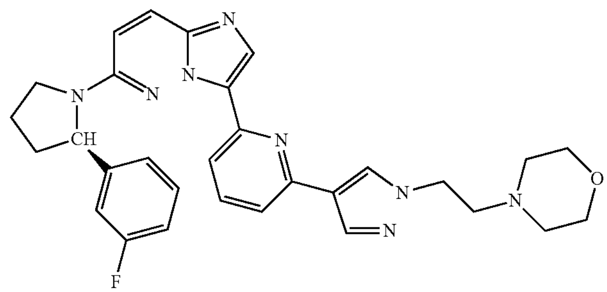 [SMILES: N=C/C(=C\NCCN1CCOCC1)c1cccc(-c2cnc(/C=C\C(=N)N3CCC[C@@H]3c3cccc(F)c3)[nH]2)n1] | ¹H NMR (400 MHz, DMSO-d6) δ 8.49 (s, 1H), 8.33 (s, 1H), 8.14 (s, 1H), 8.05 (s br, 1H), 7.99 (d, 1H, J = 9.6 Hz), 7.77 (m, 1H), 7.56 (d, 1H, J = 7.6 Hz), 7.45 (m, 1H), 7.24 (m, 2H), 7.10 (m, 1H), 6.95 (s br, 1H), 5.26 (dd, 1H, J = 8.0, 2.8 Hz), 4.34 (t, 2H, J = 7.2 Hz), 4.08 (m, 1H), 3.75 (q, 1H, J = 8.4 z), 3.62 (t, 4H, J = 4.2 Hz), 2.83 (t, 2H, J = 6.8 Hz), 2.55 (m, 4H), 2.11 (m, 2H), 1.91 (m, 1H)<br>MS (m/z): 538.62 |
| 93 | 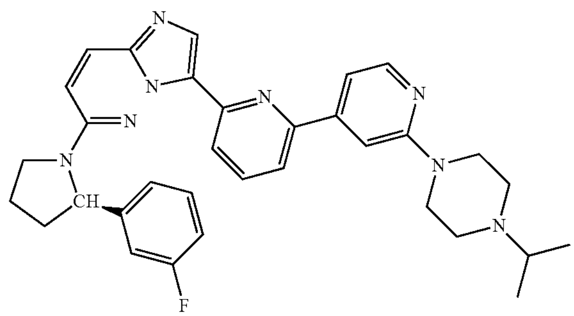 [SMILES: CC(C)N1CCN(c2cc(-c3cccc(-c4cnc(/C=C\C(=N)N5CCC[C@@H]5c5cccc(F)c5)[nH]4)n3)ccn2)CC1] | ¹H NMR (400 MHz, DMSO-d6) δ 8.38 (s, 1H), 8.29 (d, 1H, J = 4.2 Hz), 8.20 (s br, 1H), 8.01 (m, 2H), 7.90 (m, 1H), 7.59 (s, 1H), 7.46 (m, 2H), 7.26 (d, 2H, J = 7.6 Hz), 7.11 (m, 1H), 6.96 (s br, 1H), 5.27 (dd, 1H, J = 8.0, 2.8 Hz), 4.09 (m, 1H), 3.76 (m, 1H), 3.64 (m, 3H), 3.40 (s, 2H), 2.76 (m, 1H), 2.64 (m, 3H), 2.53 (m, 1H), 2.12 (m, 2H), 1.95 (m, 1H), 1.08 (d, 6H, J = 6.4 Hz)<br>MS (m/z): 562.68 |
| 94 | 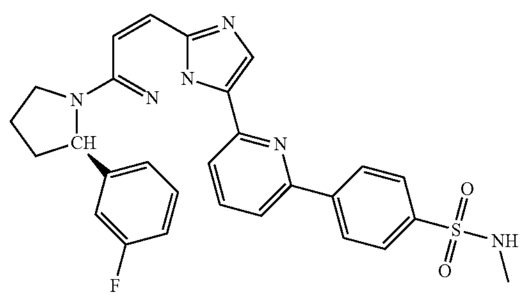 [SMILES: CNS(=O)(=O)c1ccc(-c2cccc(-c3cnc(/C=C\C(=N)N4CCC[C@@H]4c4cccc(F)c4)[nH]3)n2)cc1] | MS (m/z): 528.60 |
| 95 | 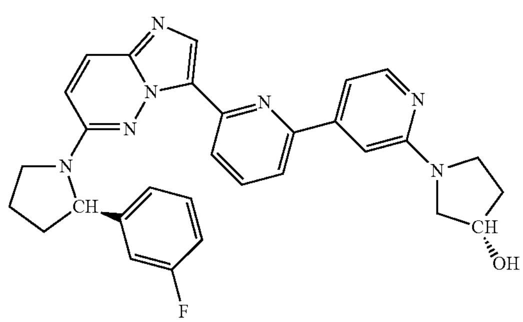 [SMILES: O[C@H]1CCN(c2cc(-c3cccc(-c4cnc5ccc(N6CCC[C@@H]6c6cccc(F)c6)nn45)n3)ccn2)C1] | MS (m/z): 521.59 |
| 96 | 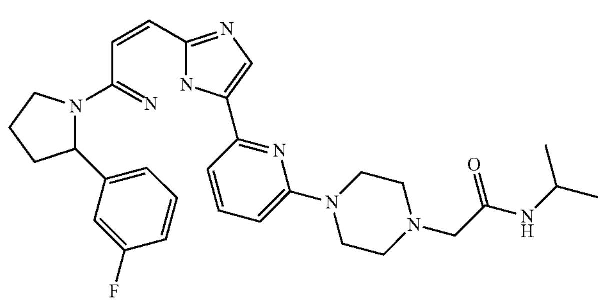 [SMILES: CC(C)NC(=O)CN1CCN(c2cccc(-c3cnc(/C=C\C(=N)N4CCCC4c4cccc(F)c4)[nH]3)n2)CC1] | 1H NMR (DMSO-d6) 8.07 (s, 1H), 7.88 (d, 1H), 7.50-7.58 (bs, 1H), 7.42-7.48 (bs, 1H), 7.35-7.40 (m, 1H), 7.13-7.17 (m, 2H), 7.01-7.05 (m, 1H), 6.78-6.85 (bs, 1H), 6.73 (d, 1H), 5.15-5.18 (q, 1H), 3.96-4.01 (m, 1H), 3.87-3.94 (m, 1H), 3.64-3.70 (m, 1H), 3.54-360 (bs, 4H), 2.91-2.96 (bs, 2H), 2.50-2.60 (bs, 4H), 2.45-2.50 (m, 1H), 2.00-2.06 (m, 2H), 1.84-1.90 (m, 1H), 1.08 (d, 6H).<br>MS (m/z): 543.7 |

TABLE 7-continued

| Compound Number | Structure | Physical Data<br>¹H NMR 400 MHz (DMSO-d₆) and/or MS (m/z) |
|---|---|---|
| 97 | 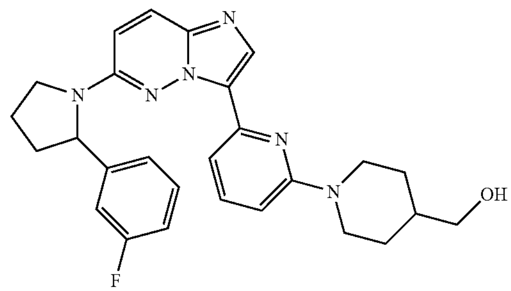 [SMILES: OCC1CCN(c2cccc(-c3cnc4ccc(N5CCCC5c5cccc(F)c5)nn34)n2)CC1] | 1H NMR (DMSO-d6) 8.04 (s, 1H), 7.87 (d, 1H), 7.40-7.50 (m, 2H), 7.35-7.40 (m, 1H), 7.13-7.17 (m, 2H), 7.01-7.05 (m, 1H), 6.76-6.85 (bs, 1H), 6.72 (d, 1H), 5.14-5.17 (q, 1H), 4.46 (t, 1H), 4.37 (d, 2H), 3.96-4.01 (m, 1H), 3.64-3.69 (q, 1H), 3.27 (t, 2H), 2.74-2.81 (m, 2H), 2.45-2.50 (m, 1H), 2.00-2.06 (m, 2H), 1.84-1.89 (m, 1H), 1.58-1.64 (m, 1H), 1.08-1.17 (m, 2H).<br>MS (m/z): 473.6 |
| 98 | 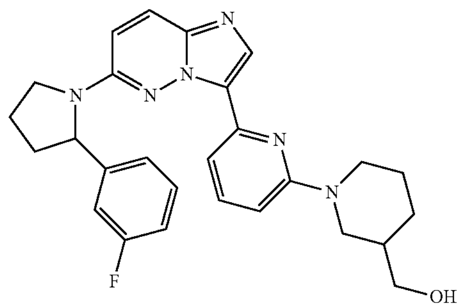 [SMILES: OCC1CCCN(c2cccc(-c3cnc4ccc(N5CCCC5c5cccc(F)c5)nn34)n2)C1] | 1H NMR (DMSO-d6) 8.05 (s, 1H), 7.88 (d, 1H), 7.40-7.50 (m, 2H), 7.34-7.40 (m, 1H), 7.13-7.17 (m, 2H), 7.00-7.05 (m, 1H), 6.76-6.85 (bs, 1H), 6.69 (t, 1H), 5.15-5.18 (q, 1H), 4.54-4.57 (m, 1H), 4.34 (d, 1H), 4.22 (d, 1H), 3.96-4.02 (m, 1H), 3.64-3.70 (q, 1H), 3.28-3.37 (m, 2H), 2.81-2.88 (m, 1H), 2.59 (t, 1H), 2.45-2.50 (m, 1H), 2.00-2.08 (m, 2H), 1.84-1.90 (m, 1H), 1.72-1.77 (m, 1H), 1.66-1.72 (m, 1H), 1.58-1.65 (m, 1H), 1.40-1.59 (m, 1H), 1.14-1.22 (m, 1H).<br>MS (m/z): 473.6 |
| 99 | 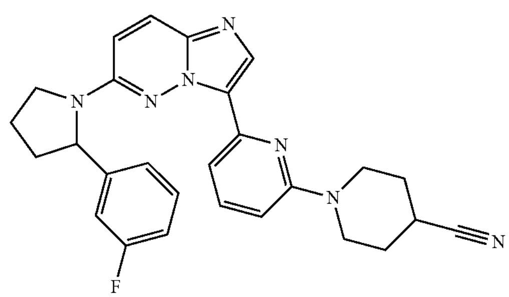 [SMILES: N#CC1CCN(c2cccc(-c3cnc4ccc(N5CCCC5c5cccc(F)c5)nn34)n2)CC1] | 1H NMR (DMSO-d6) 8.07 (s, 1H), 7.88 (d, 1H), 7.41-7.60 (m, 2H), 7.34-7.40 (m, 1H), 7.12-7.18 (m, 2H), 7.00-7.15 (m, 1H), 6.78-6.85 (bs, 1H), 6.77 (d, 1H), 5.15-5.18 (q, 1H), 3.96-4.01 (m, 1H), 3.83-3.89 (m, 2H), 3.64-3.70 (q, 1H), 3.09-3.14 (m, 1H), 2.45-2.50 (m, 1H), 2.00-2.06 (m, 2H), 1.94-1.97 (m, 2H), 1.84-1.89 (m, 1H), 1.71-1.77 (m, 2H).<br>MS (m/z): 468.5 |
| 100 | 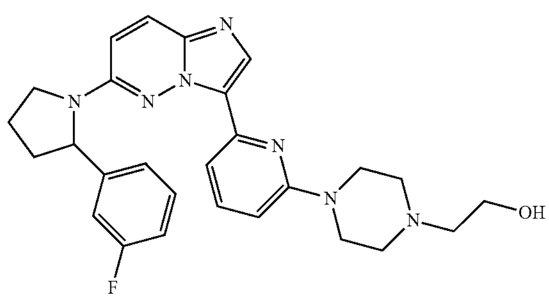 [SMILES: OCCN1CCN(c2cccc(-c3cnc4ccc(N5CCCC5c5cccc(F)c5)nn34)n2)CC1] | 1H NMR (DMSO-d6) 8.05 (s, 1H), 7.88 (d, 1H), 7.42-7.60 (m, 2H), 7.35-7.40 (m, 1H), 7.13-7.17 (m, 2H), 7.00-7.05 (m, 1H), 6.75-6.85 (bs, 1H), 6.72 (d, 1H), 5.14-5.18 (q, 1H), 4.43 (t, 1H), 3.96-4.01 (m, 1H), 3.63-3.70 (q, 1H), 3.47-3.57 (m, 6H), 2.50-2.55 (m, 4H), 2.40-2.50 (m, 3H), 2.00-2.06 (m, 2H), 1.84-1.89 (m, 1H).<br>MS (m/z): 488.6 |
| 101 | 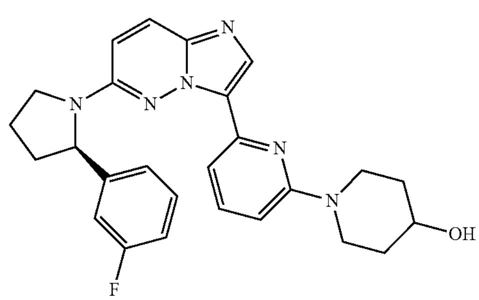 [SMILES: OC1CCN(c2cccc(-c3cnc4ccc(N5CCC[C@@H]5c5cccc(F)c5)nn34)n2)CC1] | 1H NMR (CDCl3-d6) d 8.24 (s, 1H), 7.69 (d, 1H, J = 9.6 Hz), 7.55-7.63 (m, 1H), 7.43 (t, 1H), 7.25-7.33 (m, 1H), 7.05 (d, 1H, J = 7.6 Hz), 6.90-7.00 (m, 2H), 6..59 (d, 1H, J = 8.4 Hz), 6.51 (d, 1H, j = 9.6 Hz), 5.04-5.11 (m, 1H), 4.13-4.22 (m, 2H), 3.90-4.00 (m, 2H), 3.69-3.78 (m, 1H), 3.13-3.22 (m, 2H), 2.42-2.54 (m, 1H), 2.06-2.20 (m, 2H), 1.96-2.05 (m, 3H), 1.55-1.62 (m, 2H)<br>MS (m/z): 459.5 |

TABLE 7-continued
| Compound Number | Structure | Physical Data<br>¹H NMR 400 MHz (DMSO-d₆)<br>and/or MS (m/z) |
|---|---|---|
| 102 | 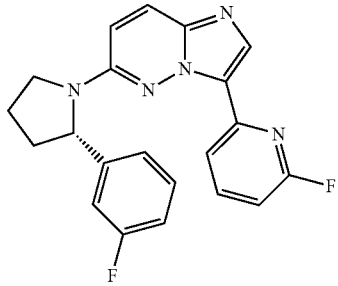 [SMILES: Fc1cccc([C@@H]2CCCN2c2ccc3ncc(-c4cccc(F)n4)n3n2)c1] | MS (m/z): 378.4 |
| 103 | 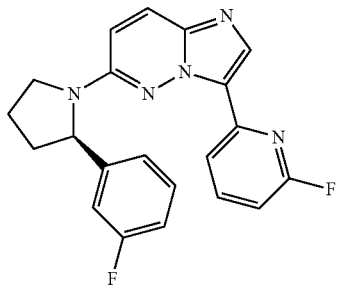 [SMILES: Fc1cccc([C@H]2CCCN2c2ccc3ncc(-c4cccc(F)n4)n3n2)c1] | MS (m/z): 378.4 |
| 104 | 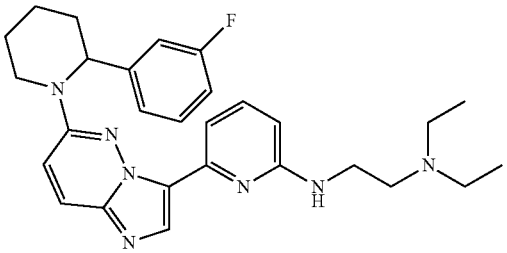 [SMILES: CCN(CC)CCNc1cccc(-c2cnc3ccc(N4CCCCC4c4cccc(F)c4)nn23)n1] | MS (m/z): 488.6 |
| 105 | 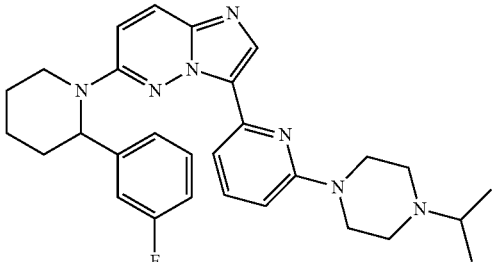 | MS (m/z): 500.6 |
| 106 | 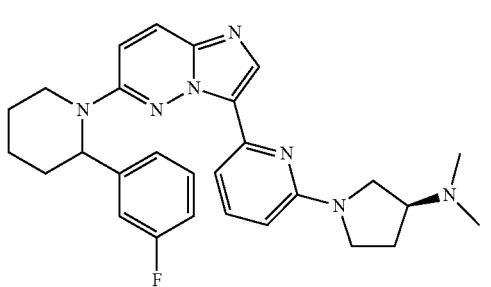 [SMILES: CN(C)[C@H]1CCN(c2cccc(-c3cnc4ccc(N5CCCCC5c5cccc(F)c5)nn34)n2)C1] | MS (m/z): 486.6 |

TABLE 7-continued

| Compound Number | Structure | Physical Data<br>¹H NMR 400 MHz (DMSO-d₆)<br>and/or MS (m/z) |
|---|---|---|
| 107 | 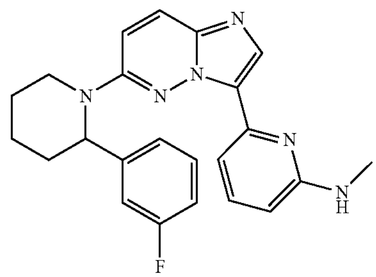 [SMILES: CNc1cccc(-c2cnc3ccc(N4CCCCC4c4cccc(F)c4)nn23)n1] | 1H NMR (DMSO-d6): d 8.06 (s, 1H), 7.75 (s, 1H), 7.51 (d, 1H), 7.32-7.40 (m, 2H), 7.22 (d, 1H), 7.14 (d, 2H), 6.99-7.05 (m, 1H), 6.45-6.50 (m, 1H), 6.35 9d, 1H), 4.14-4.21 (m, 1H), 3.30-3.39 (m, 2H), 2.82 (d, 3H), 2.17-2.26 (m, 1H), 2.00-2.10 (m, 1H), 1.56-1.83 (m, 3H), 1.35-1.50 (m, 1H).<br>MS (m/z): 403.5 |
| 108 | 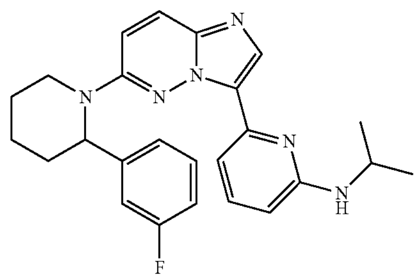 [SMILES: CC(C)Nc1cccc(-c2cnc3ccc(N4CCCCC4c4cccc(F)c4)nn23)n1] | 1H NMR (DMSO-d6): d 8.02 (s, 1H), 7.90 (d, 1H), 7.46 (d, 1H), 7.30-7.40 (m, 2H), 7.21 (d, 1H), 7.13 (d, 2H), 6.98-7.06 (m, 1H), 6.30-6.36 (m, 2H), 4.12-4.20 (m, 1H), 4.02-4.10 (m, 1H), 3.30-3.38 (m, 2H), 2.18-2.26 (m, 1H), 2.00-2.10 (m, 1H), 1.56-1.84 (m, 3H), 1.36-1.48 (m, 1H), 1.17 (d, 6H).<br>MS (m/z): 431.5 |
| 109 | 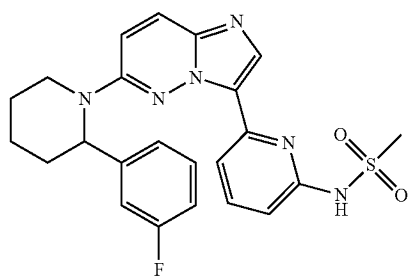 [SMILES: CS(=O)(=O)Nc1cccc(-c2cnc3ccc(N4CCCCC4c4cccc(F)c4)nn23)n1] | 1H NMR (DMSO-d6): d 10.63 (s, 1H), 8.06 (s, 1H), 7.97 (s, 1H), 7.94 (d, 1H), 7.72 (t, 1H), 7.33-7.40 (m, 1H), 7.25 (d, 1H), 7.12-7.18 (m, 2H), 6.99-7.05 (m, 1H), 6.80 (d, 1H), 4.15-4.22 (m, 1H), 3.42 (s, 3H), 3.35-3.42 (m, 2H), 2.17-2.26 (m, 1H), 2.01-2.14 (m, 1H), 1.57-1.85 (m, 3H), 1.36-1.49 (m, 1H).<br>MS (m/z): 467.5 |
| 110 | 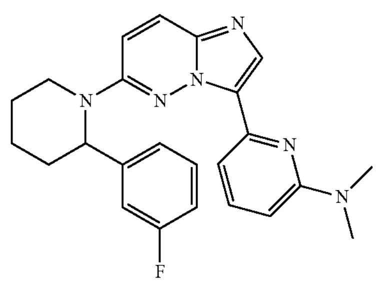 [SMILES: CN(C)c1cccc(-c2cnc3ccc(N4CCCCC4c4cccc(F)c4)nn23)n1] | MS (m/z): 417.5 |
| 111 | 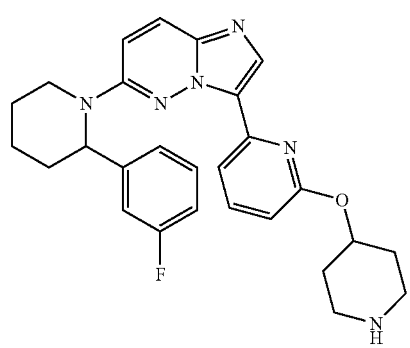 [SMILES: Fc1cccc(C2CCCCN2c2ccc3ncc(-c4cccc(OC5CCNCC5)n4)n3n2)c1] | MS (m/z): 473.6 |

TABLE 7-continued

| Compound Number | Structure | Physical Data<br>¹H NMR 400 MHz (DMSO-d₆)<br>and/or MS (m/z) |
|---|---|---|
| 112 | 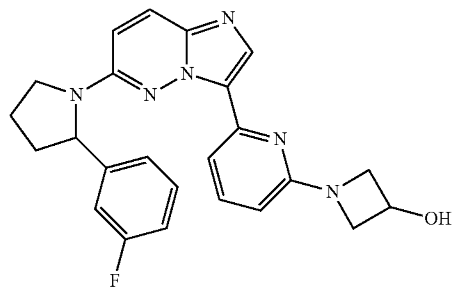 [SMILES: OC1CN(c2cccc(-c3cnc4ccc(N5CCCC5c5cccc(F)c5)nn34)n2)C1] | MS (m/z): 431.5 |
| 113 | 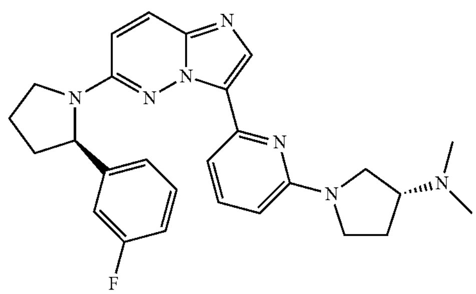 [SMILES: CN(C)[C@@H]1CCN(c2cccc(-c3cnc4ccc(N5CCC[C@@H]5c5cccc(F)c5)nn34)n2)C1] | MS (m/z): 472.6 |
| 114 | 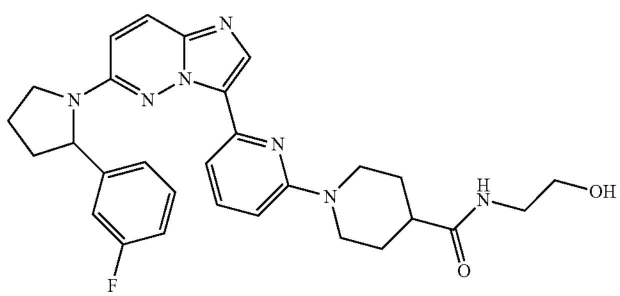 [SMILES: O=C(NCCO)C1CCN(c2cccc(-c3cnc4ccc(N5CCCC5c5cccc(F)c5)nn34)n2)CC1] | 1H NMR (DMSO-d6) 8.05 (s, 1H), 7.88 (d, 1H, J = 9.6 Hz), 7.81 (t, 1H, J = 5.6 Hz), 7.34-7.58 (m, 3H), 7.10-7.18 (m, 2H), 7.00-7.06 (m, 1H), 6.76-6.86 (bs, 1H), 6.74 (d, 1H, J = 8.8 Hz), 5.14-5.19 (m, 1H), 4.64 (t, 1H, J = 5.6 Hz), 4.33-4.42 (m, 2H), 3.95-4.02 (m, 1H), 3.62-3.71 (m, 1H), 3.34-3.42 (m, 2H), 3.07-3.13 (m, 2H), 2.76-2.86 (m, 2H), 2.44-2.50 (m, 1H), 2.32-2.44 (m, 1H), 2.00-2.10 (m, 2H), 1.84-1.91 (m, 1H), 1.67-1.78 (m, 2H), 1.46-1.60 (m, 2H). MS (m/z): 530.6 |
| 115 | 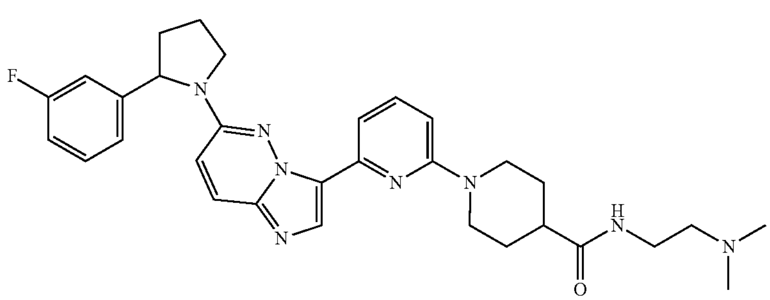 [SMILES: CN(C)CCNC(=O)C1CCN(c2cccc(-c3cnc4ccc(N5CCCC5c5cccc(F)c5)nn34)n2)CC1] | MS (m/z): 557.7 |
| 116 | 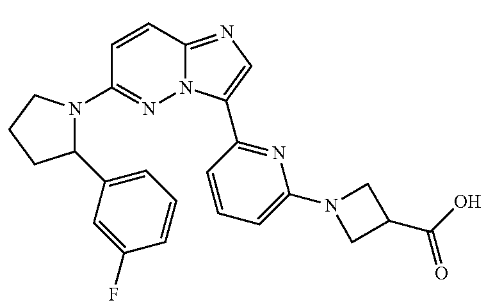 [SMILES: O=C(O)C1CN(c2cccc(-c3cnc4ccc(N5CCCC5c5cccc(F)c5)nn34)n2)C1] | MS (m/z): 459.5 |

TABLE 7-continued

| Compound Number | Structure | Physical Data<br>¹H NMR 400 MHz (DMSO-d₆)<br>and/or MS (m/z) |
|---|---|---|
| 117 | 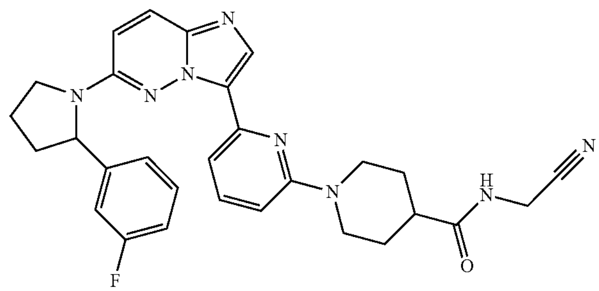 [SMILES: N#CCNC(=O)C1CCN(c2cccc(-c3cnc4ccc(N5CCCC5c5cccc(F)c5)nn34)n2)CC1] | MS (m/z): 525.6 |
| 118 | 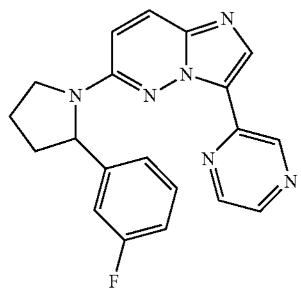 [SMILES: Fc1cccc(C2CCCN2c2ccc3ncc(-c4cnccn4)n3n2)c1] | 1H NMR (DMSO-d6) 9.30-9.60 (bs, 1H), 8.63-8.66 (m, 1H), 8.52 (d, 1H, J = 12.4 Hz), 8.16 (s, 1H), 7.95 (d, 1H, J = 10 Hz), 7.32-7.40 (m, 1H), 7.11-7.17 (m, 2H), 6.98-7.06 (m, 1H), 6.78-6.92 (bs, 1H), 5.19-5.24 (m, 1H), 3.98-4.05 (m, 1H), 3.64-3.74 (m, 1H), 2.44-2.50 (m, 1H), 2.00-2.10 (m, 2H), 1.85-1.93 (m, 1H).<br>MS (m/z): 361.4 |
| 119 | 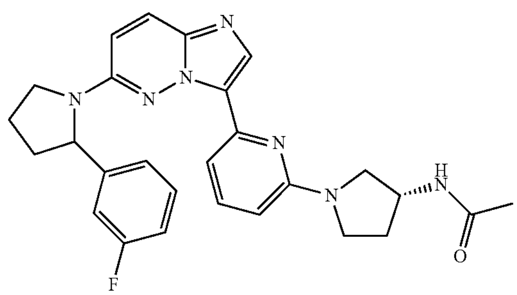 [SMILES: CC(=O)N[C@@H]1CCN(c2cccc(-c3cnc4ccc(N5CCCC5c5cccc(F)c5)nn34)n2)C1] | 1H NMR (DMSO-d6) 8.16 (d, 1H, J = 6.8 Hz), 8.04 (s, 1H), 7.87 (d, 1H, J = 9.6 Hz), 7.44-7.60 (bs, 1H), 7.34-7.44 (m, 2H), 7.12-7.20 (m, 2H), 7.00-7.06 (m, 1H), 6.72-6.90 (bs, 1H), 6.36 (d, 1H, J = 8.4 Hz), 5.14-5.20 (m, 1H), 4.30-4.40 (m, 1H), 3.96-4.02 (m, 1H), 3.61-3.72 (m, 2H), 3.42-3.60 (m, 2H), 3.24-3.30 (m, 1H), 2.42-2.50 (m, 1H), 2.10-2.20 (m, 1H), 2.00-2.10 (m, 2H), 1.82-1.90 (m, 2H), 1.81 (s, 3H).<br>MS (m/z): 486.6 |
| 120 | 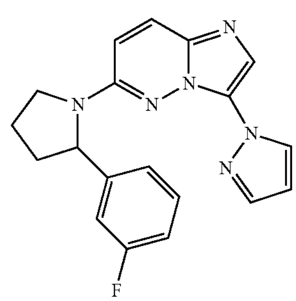 [SMILES: Fc1cccc(C2CCCN2c2ccc3ncc(-n4cccn4)n3n2)c1] | MS (m/z): 349.4 |
| 121 | 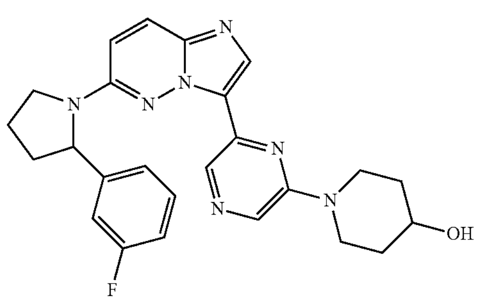 [SMILES: OC1CCN(c2cncc(-c3cnc4ccc(N5CCCC5c5cccc(F)c5)nn34)n2)CC1] | MS (m/z): 460.5 |

TABLE 7-continued

| Compound Number | Structure | Physical Data $^1$H NMR 400 MHz (DMSO-$d_6$) and/or MS (m/z) |
|---|---|---|
| 122 | 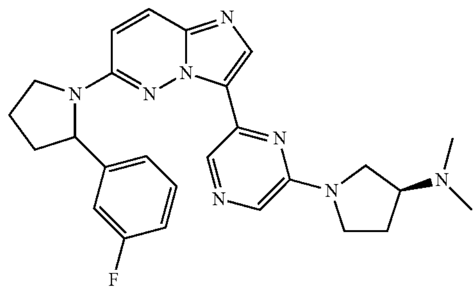 [SMILES: CN(C)[C@H]1CCN(c2cncc(-c3cnc4ccc(N5CCCC5c5cccc(F)c5)nn34)n2)C1] | MS (m/z): 473.6 |
| 123 | 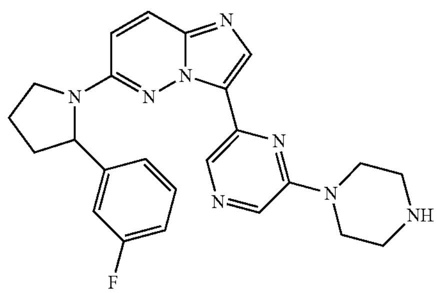 [SMILES: Fc1cccc(C2CCCN2c2ccc3ncc(-c4cncc(N5CCNCC5)n4)n3n2)c1] | MS (m/z): 445.5 |
| 124 | 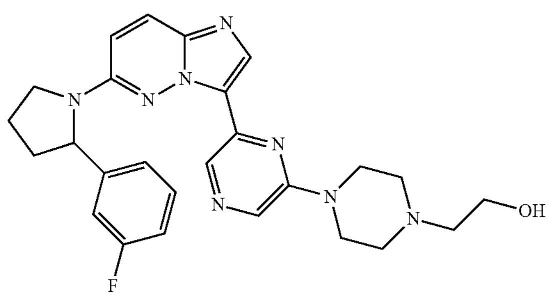 [SMILES: OCCN1CCN(c2cncc(-c3cnc4ccc(N5CCCC5c5cccc(F)c5)nn34)n2)CC1] | MS (m/z): 489.6 |
| 125 | 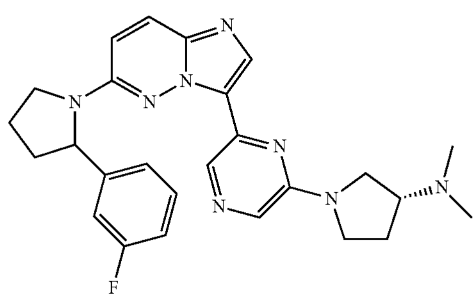 [SMILES: CN(C)[C@@H]1CCN(c2cncc(-c3cnc4ccc(N5CCCC5c5cccc(F)c5)nn34)n2)C1] | 1H NMR (DMSO-d6) 8.70-8.88 (bs, 1H), 8.12 (s, 1H), 7.86-7.90 (m, 2H), 7.34-7.39 (m, 1H), 7.04-7.15 (m, 2H), 7.00-7.06 (m, 1H), 6.65-6.82 (m, 1H), 5.17-5.23 (m, 1H), 3.95-4.05 (m, 1H), 3.75-3.83 (m, 1H), 3.64-3.74 (m, 2H), 3.36-3.45 (m, 1H), 3.15-3.23 (m, 1H), 2.75-2.85 (m, 1H), 2.42-2.50 (m, 1H), 2.24 (s, 6H), 2.13-2.22 (m, 1H), 1.95-2.08 (m, 2H), 1.75-1.92 (m, 2H). MS (m/z): 473.6 |
| 126 | 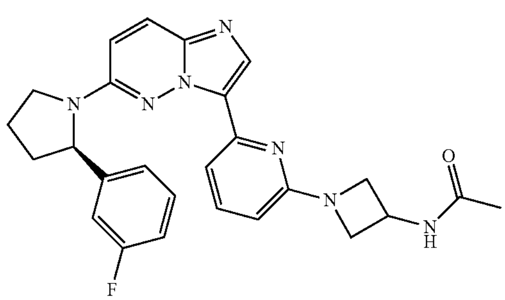 [SMILES: CC(=O)NC1CN(c2cccc(-c3cnc4ccc(N5CCC[C@@H]5c5cccc(F)c5)nn34)n2)C1] | MS (m/z): 472.5 |

TABLE 7-continued

| Compound Number | Structure | Physical Data<br>¹H NMR 400 MHz (DMSO-$d_6$)<br>and/or MS (m/z) |
|---|---|---|
| 127 | 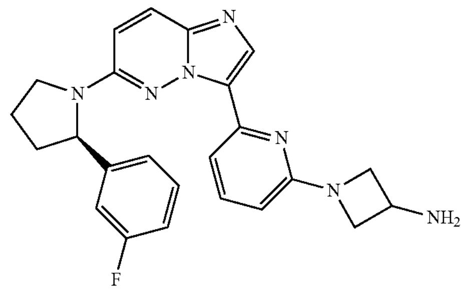 [SMILES: NC1CN(c2cccc(-c3cnc4ccc(N5CCC[C@@H]5c5cccc(F)c5)nn34)n2)C1] | 1H NMR (DMSO-d6) 8.01 (s, 1H), 7.88 (d, 1H, J = 10 Hz), 7.46-7.62 (bs, 1H), 7.32-7.44 (m, 2H), 7.12-7.18 (m, 2H), 7.00-7.06 (m, 1H), 6.72-6.90 (bs, 1H), 6.27 (d, 1H, J = 8 Hz), 5.13-5.20 (m, 1H), 4.09-4.16 (m, 2H), 3.95-4.03 (m, 1H), 3.76-3.85 (m, 1H), 3.62-3.71 (m, 1H), 3.51-3.57 (m, 2H), 2.41-2.50 (m, 1H), 2.00-2.10 (m, 2H), 1.83-1.90 (m, 1H).<br>MS (m/z): 430.5 |
| 128 | 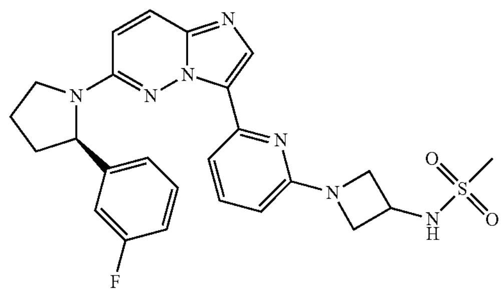 [SMILES: CS(=O)(=O)NC1CN(c2cccc(-c3cnc4ccc(N5CCC[C@@H]5c5cccc(F)c5)nn34)n2)C1] | 1H NMR (DMSO-d6) 8.03 (s, 1H), 7.89 (d, 1H, J = 10 Hz), 7.83 (d, 1H, J = 8 Hz), 7.50-7.62 (bs, 1H), 7.41-7.50 (m, 1H), 7.34-7.42 (m, 1H), 7.12-7.18 (m, 2H), 7.00-7.06 (m, 1H), 6.78-6.90 (bs, 1H), 6.32 (d, 1H, J = 8.4 Hz), 5.04-5.20 (m, 1H), 4.24-4.36 (m, 3H), 3.95-4.02 (m, 1H), 3.77-3.85 (m, 2H), 3.60-3.71 (m, 1H), 2.95 (s, 3H), 2.42-2.50 (m, 1H), 2.00-2.07 (m, 2H), 1.82-1.90 (m, 1H).<br>MS (m/z): 508.6 |
| 129 | 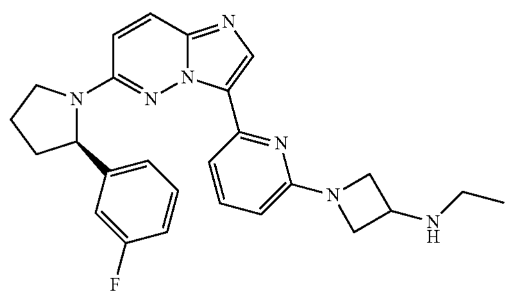 [SMILES: CCNC1CN(c2cccc(-c3cnc4ccc(N5CCC[C@@H]5c5cccc(F)c5)nn34)n2)C1] | MS (m/z): 458.5 |
| 130 | 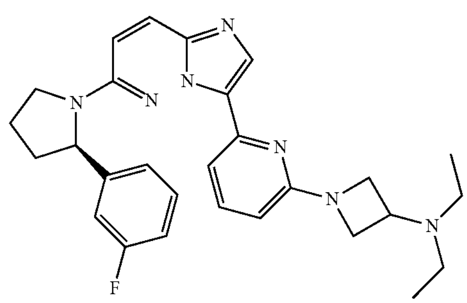 | MS (m/z): 458.6 |
| 131 | 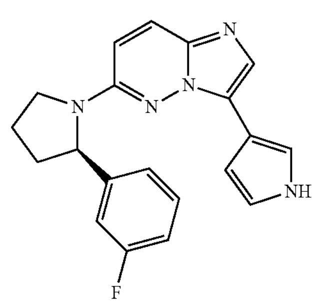 [SMILES: Fc1cccc([C@H]2CCCN2c2ccc3ncc(-c4cc[nH]c4)n3n2)c1] | MS (m/z): 348.4 |

TABLE 7-continued

| Compound Number | Structure | Physical Data $^1$H NMR 400 MHz (DMSO-$d_6$) and/or MS (m/z) |
|---|---|---|
| 132 | 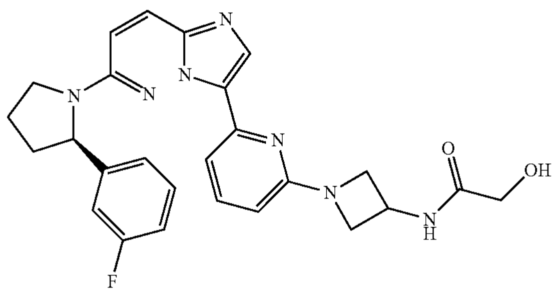 [SMILES: N=C(/C=C\c1ncc(-c2cccc(N3CC(NC(=O)CO)C3)n2)[nH]1)N1CCC[C@@H]1c1cccc(F)c1] | MS (m/z): 488.5 |
| 133 | 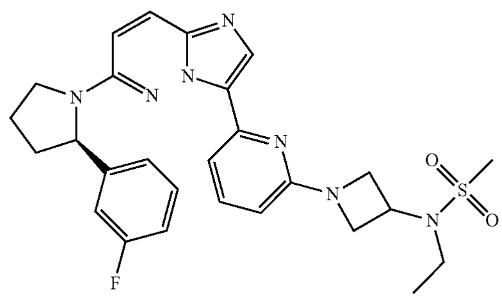 [SMILES: CCN(C1CN(c2cccc(-c3cnc(/C=C\C(=N)N4CCC[C@@H]4c4cccc(F)c4)[nH]3)n2)C1)S(C)(=O)=O] | 1H NMR (DMSO-d6) 8.03 (s, 1H), 7.88 (d, 1H, J = 10 Hz), 7.52-7.64 (bs, 1H), 7.42-7.50 (m, 1H), 7.32-7.42 (m, 1H), 7.12-7.18 (m, 2H), 7.00-7.06 (m, 1H), 6.74-6.90 (bs, 1H), 6.34 (d, 1H, J = 8 Hz), 5.12-5.2 (m, 1H), 4.62-4.70 (m, 1H), 4.22-4.32 (m, 2H), 3.94-4.02 (m, 3H), 3.62-3.70 (m, 1H), 3.30-3.38 (m, 2H), 2.95 (s, 3H), 2.42-2.50 (m, 1H), 1.98-2.08 (m, 2H), 1.82-1.90 (m, 1H), 1.20 (t, 3H). MS (m/z): 536.6 |
| 134 | 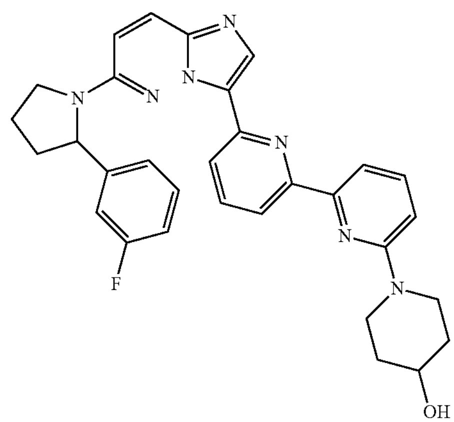 [SMILES: N=C(/C=C\c1ncc(-c2cccc(-c3cccc(N4CCC(O)CC4)n3)n2)[nH]1)N1CCCC1c1cccc(F)c1] | MS (m/z): 536.6 |
| 135 | 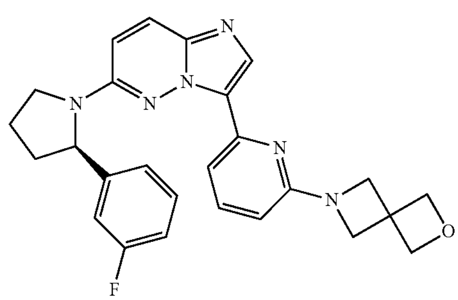 [SMILES: Fc1cccc([C@H]2CCCN2c2ccc3ncc(-c4cccc(N5CC6(COC6)C5)n4)n3n2)c1] | 1H NMR (DMSO-d6) 8.02 (s, 1H), 7.88 (d, 1H, J = 10 Hz), 7.48-7.62 (bs, 1H), 7.40-7.47 (m, 1H), 7.33-7.40 (m, 1H), 7.12-7.17 (m, 2H), 6.99-7.06 (m, 1H), 6.75-6.87 (bs, 1H), 6.29 (d, 1H, J = 8.4 Hz), 5.13-5.18 (q, 1H), 4.72 (s, 4H), 4.12 (s, 4H), 3.94-4.03 (m, 1H), 3.60-3.70 (m, 1H), 2.40-2.48 (m, 1H), 1.98-2.06 (m, 2H), 1.82-1.90 (m, 1H). MS (m/z): 457.5 |

TABLE 7-continued

| Compound Number | Structure | Physical Data<br>¹H NMR 400 MHz (DMSO-d₆)<br>and/or MS (m/z) |
|---|---|---|
| 136 | 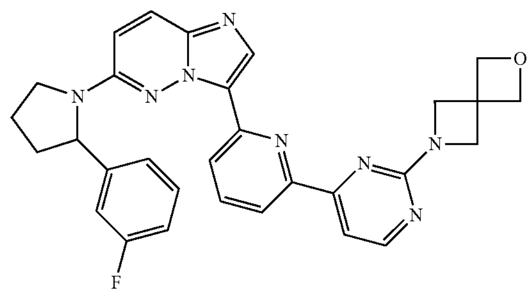 [SMILES: Fc1cccc(C2CCCN2c2ccc3ncc(-c4cccc(-c5ccnc(N6CC7(COC7)C6)n5)n4)n3n2)c1] | 1H NMR (DMSO-d6) 8.52 (d, 1H, J = 5.2 Hz), 8.32 (s, 1H), 8.21 (d, 1H, J = 7.6 Hz), 7.94 (d, 1H, J = 10 Hz), 7.86-7.92 (m, 1H), 7.74 (d, 1H, J = 4.8 Hz), 7.36-7.44 (m, 1H), 7.14-7.22 (m, 2H), 7.00-7.08 (m, 1H), 6.82-6.96 (bs, 1H), 5.17-5.23 (q, 1H), 4.76 (s, 4H), 4.29 (s, 4H), 3.98-4.06 (m, 1H), 3.64-3.74 (m, 1H), 2.43-2.50 (m, 1H), 2.00-2.10 (m, 2H), 1.84-1.92 (m, 1H).<br>MS (m/z): 535.6 |
| 137 | 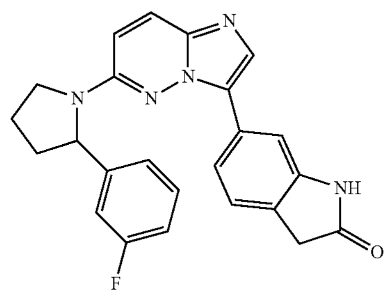 [SMILES: O=C1Cc2ccc(-c3cnc4ccc(N5CCCC5c5cccc(F)c5)nn34)cc2N1] | MS (m/z): 414.4 |
| 138 | 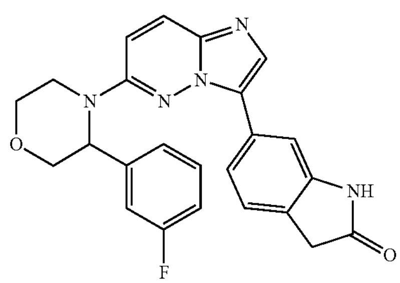 [SMILES: O=C1Cc2ccc(-c3cnc4ccc(N5CCOCC5c5cccc(F)c5)nn34)cc2N1] | 1H NMR methanol-d4, d (ppm) 8.05 (b, 2H), 7.65 (b, 1H), 7.46 (s, 1H), 7.38 (m, 1H), 7.28 (m, 1H), 7.18 (m, 1H), 7.10 (m, 2H), 6.87 (td, 1H), 5.20 (s, 1H), 4.18 (dd, 1H), 4.02 (m, 3H), 3.76 (td, 1H), 3.60 (m, 1H), 3.53 (s, 2H).<br>MS (m/z): 430.4 |
| 139 | 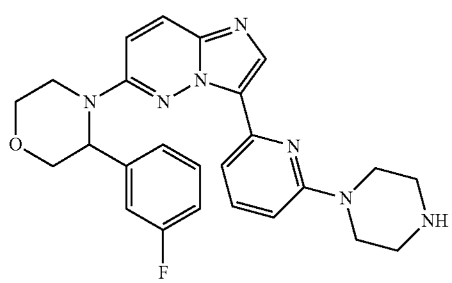 [SMILES: Fc1cccc(C2COCCN2c2ccc3ncc(-c4cccc(N5CCNCC5)n4)n3n2)c1] | MS (m/z): 460.5 |
| 140 | 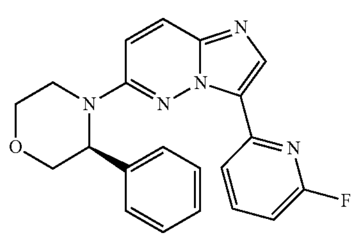 [SMILES: Fc1cccc(-c2cnc3ccc(N4CCOC[C@@H]4c4ccccc4)nn23)n1] | MS (m/z): 376.4 |

TABLE 7-continued

| Compound Number | Structure | Physical Data<br>¹H NMR 400 MHz (DMSO-d₆)<br>and/or MS (m/z) |
|---|---|---|
| 141 | 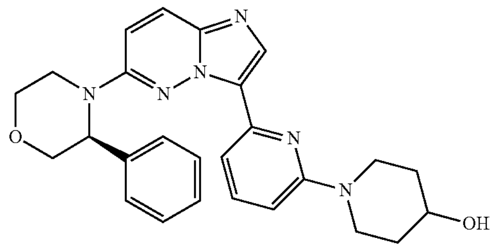 [SMILES: OC1CCN(c2cccc(-c3cnc4ccc(N5CCOC[C@@H]5c5ccccc5)nn34)n2)CC1] | 1H NMR methanol-d4, d (ppm) 7.98 (s, 1H), 7.68 (d, 1H), 7.52 (d, 1H), 7.44 (t, 1H), 7.31 (m, 2H), 7.19 (t, 2H), 7.09 (m, 2H), 6.64 (d, 1H), 5.09 (t, 1H), 4.11 (m, 3H), 4.01 (m, 2H), 3.74 (m, 3H), 3.63 (m, 1H), 3.03 (m, 2H), 1.83 (m, 2H), 1.41 (m, 2H)<br>MS (m/z): 457.5 |
| 142 | 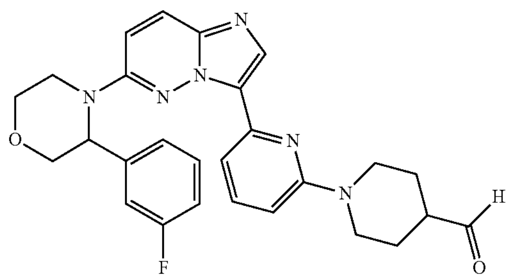 [SMILES: O=CC1CCN(c2cccc(-c3cnc4ccc(N5CCOCC5c5cccc(F)c5)nn34)n2)CC1] | 1H NMR methanol-d4, d (ppm) 8.12 (s, 1H), 7.85 (m, 1H), 7.60 (m, 2H), 7.27 (m, 4H), 6.97 (m, 1H), 6.75 (m, 1H), 5.25 (t, 1H), 4.28 (m, 4H), 4.14 (m, 3H), 3.93 (m, 2H), 3.73 (m, 1H), 2.83 (m, 1H), 1.92 (m, 2H), 1.82 (m, 1H), 1.41 (m, 1H).<br>MS (m/z): 487.5 |
| 143 | 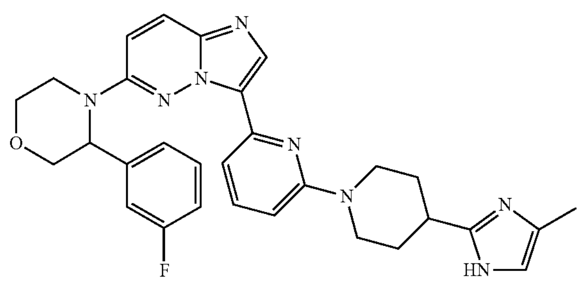 [SMILES: Cc1c[nH]c(C2CCN(c3cccc(-c4cnc5ccc(N6CCOCC6c6cccc(F)c6)nn45)n3)CC2)n1] | 1H NMR methanol-d4, d (ppm) 8.45 (s, 1H), 8.17 (d, 1H), 7.79 (d, 1H), 7.67 (m, 2H), 7.36 (m, 1H), 7.26 (m, 2H), 7.13 (d, 1H), 6.98 (m, 2H), 5.40 (m, 1H), 4.63 (m, 2H), 4.34 (m, 1H), 4.15 (m, 3H), 3.88 (m, 1H), 3.79 (m, 1H), 3.06 (td, 2H), 2.31 (s, 3H), 2.12 (m, 2H), 1.85 (m, 2H).<br>MS (m/z): 539.6 |
| 144 | 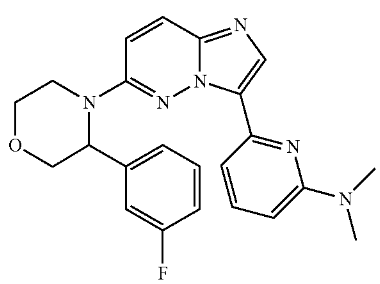 [SMILES: CN(C)c1cccc(-c2cnc3ccc(N4CCOCC4c4cccc(F)c4)nn23)n1] | MS (m/z): 419.5 |
| 145 | 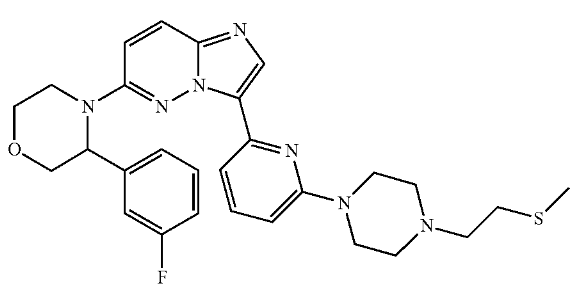 [SMILES: CSCCN1CCN(c2cccc(-c3cnc4ccc(N5CCOCC5c5cccc(F)c5)nn34)n2)CC1] | MS (m/z): 534.7 |

TABLE 7-continued

| Compound Number | Structure | Physical Data<br>¹H NMR 400 MHz (DMSO-$d_6$)<br>and/or MS (m/z) |
|---|---|---|
| 146 | 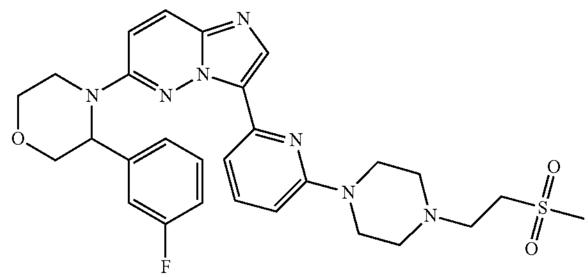 [SMILES: CS(=O)(=O)CCN1CCN(c2cccc(-c3cnc4ccc(N5CCOCC5c5cccc(F)c5)nn34)n2)CC1] | 1H NMR methanol-d4, d (ppm) 8.52 (s, 1H), 8.15 (d, 1H), 7.81 (m, 3H), 7.36 (m, 1H), 7.25 (m, 2H), 7.00 (m, 2H), 5.40 (m, 1H), 4.34 (dd, 1H), 4.15 (m, 4H), 3.89 (td, 2H), 3.74 (m, 5H), 3.51 (m, 4H), 3.33 (m, 2H), 3.13 (s, 3H). MS (m/z): 566.7 |
| 147 | 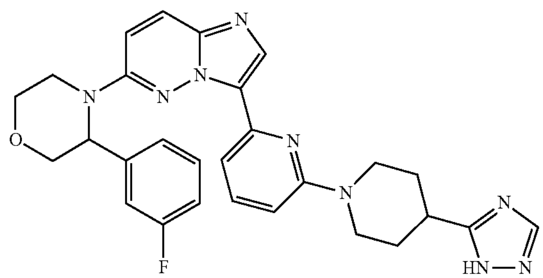 [SMILES: Fc1cccc(C2COCCN2c2ccc3ncc(-c4cccc(N5CCC(c6ncn[nH]6)CC5)n4)n3n2)c1] | 1H NMR methanol-d4, d (ppm) 8.33 (s, 1H), 8.27 (s, 1H), 8.03 (d, 1H), 7.65 (d, 1H), 7.54 (m, 2H), 7.25 (m, 1H), 7.15 (m, 2H), 6.87 (m, 2H), 5.29 (m, 1H), 4.45 (m, 2H), 4.24 (dd, 1H), 4.04 (m, 3H), 3.77 (td, 1H), 3.66 (m, 1H), 3.20 (m, 1H), 3.00 (m, 2H), 1.99 (m, 2H), 1.75 (m, 2H). MS (m/z): 526.6 |
| 148 | 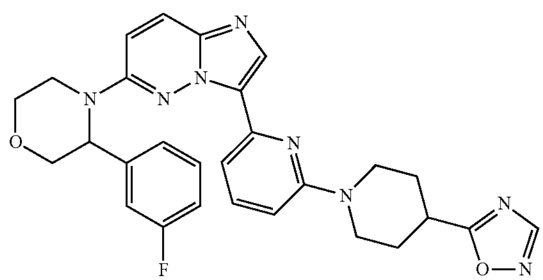 [SMILES: Fc1cccc(C2COCCN2c2ccc3ncc(-c4cccc(N5CCC(c6ncno6)CC5)n4)n3n2)c1] | 1H NMR methanol-d4, d (ppm) 8.50 (s, 1H), 8.31 (s, 1H), 8.00 (d, 1H), 7.61 (d, 1H), 7.54 (m, 2H), 7.25 (m, 1H), 7.15 (m, 2H), 6.84 (m, 2H), 5.28 (m, 1H), 4.36 (m, 2H), 4.21 (dd, 1H), 4.04 (m, 3H), 3.77 (td, 1H), 3.66 (m, 1H), 3.03 (m, 3H), 2.08 (m, 2H), 1.81 (m, 2H). MS (m/z): 527.6 |
| 149 | 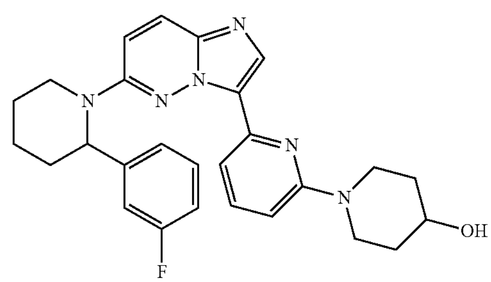 [SMILES: OC1CCN(c2cccc(-c3cnc4ccc(N5CCCCC5c5cccc(F)c5)nn34)n2)CC1] | 1H NMR (400 MHz, D6 acetone) ppm: 8.40 (br s 1H), 8.35 (d, J = 8.1 Hz, 1H), 7.85 (d, J = 7.0 Hz, 1H), 7.62 (d, J = 6.2 Hz, 1H), 7.52-7.40 (m, 1H), 7.38-7.28 (m, 1H), 7.14 (d, J = 6.0 Hz, 1H), 7.04 (app d, J = 8.0 Hz, 1H), 6.85 (app dt, J = 8.4, 3.5 Hz, 1H), 6.77 (d, J = 8.0 Hz, 1H), 5.58 (d, J = 6.7 Hz, 1H), 4.31 (app dt, J = 6.8, 2.5 Hz, 2H), 4.22-4.04 (m, 2H), 3.52-3.48 (m, 1H), 3.28-3.07 (m, 3H), 2.39-2.31 (m, 1H), 2.22-2.10 (m, 1H), 1.97-1.77 (m, 4H), 1.67-1.42 (m, 4H). MS (m/z): 473.6 |
| 150 | 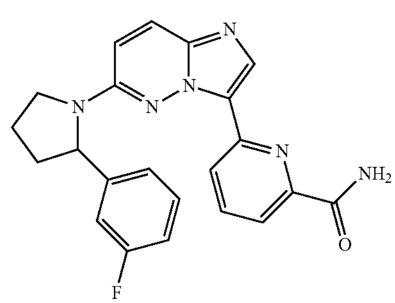 | 1H NMR (400 MHz, D3 acetonitrile) ppm: 8.45 (br s 1H), 8.06 (d, J = 8.4 Hz, 1H), 7.92 (d, J = 7.4 Hz, 1H), 7.81-7.77 (m, 2H), 7.42-7.36 (m, 2H), 7.14 (app d, J = 8.0 Hz, 1H), 6.95 (d, J = 8.2 Hz, 1H), 6.81 (app t, J = 7.2 Hz, 1H), 6.18 (br s, 2H), 5.21 (d, J = 7.7 Hz, 1H), 3.95 (app q, J = 5.5 Hz, 1H), 3.67 (app q, J = 7.5 Hz, 1H), 2.62-2.45 (m, 2H), 2.22-2.02 (m, 1H), 1.95 (app t, J = 2.5 Hz, 1H). MS (m/z): 403.4 |

TABLE 7-continued

| Compound Number | Structure | Physical Data<br>¹H NMR 400 MHz (DMSO-d₆) and/or MS (m/z) |
|---|---|---|
| 151 | 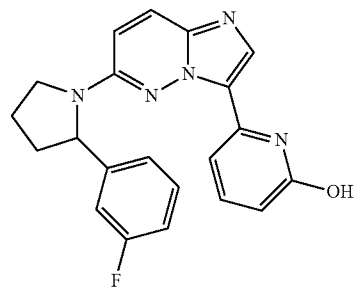 [SMILES: Oc1cccc(-c2cnc3ccc(N4CCCC4c4cccc(F)c4)nn23)n1] | 1H NMR (400 MHz, D3 acetonitrile) ppm: 8.15 (br s 1H), 7.90-7.83 (m, 1H), 7.58-7.52 (m, 1H), 7.34 (app q, J = 8.0 Hz, 1H), 7.10 (d, J = 7.2 Hz, 1H), 7.02 (d, J = 8.2 Hz, 1H), 6.89 (app t, J = 6.2 Hz, 2H), 6.82 (br s, 1H), 6.52 (app d, J = 4.6 Hz, 1.0 H), 5.19 (d, J = 7.7 Hz, 1H), 4.05 (app q, J = 6.2 Hz, 1H), 3.74 (app q, J = 8.5 Hz, 1H), 2.64-2.40 (m, 2H), 2.20-2.00 (m, 1H), 1.95 (app t, J = 2.5 Hz, 1H).<br>MS (m/z): 376.4 |
| 152 | 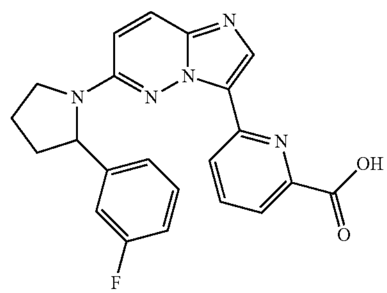 [SMILES: O=C(O)c1cccc(-c2cnc3ccc(N4CCCC4c4cccc(F)c4)nn23)n1] | MS (m/z): 404.4 |
| 153 | 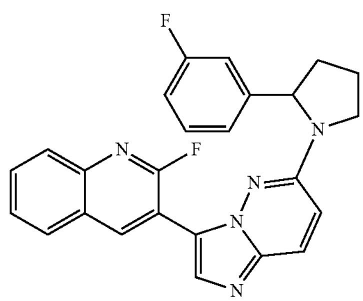 [SMILES: Fc1cccc(C2CCCN2c2ccc3ncc(-c4cc5ccccc5nc4F)n3n2)c1] | MS (m/z): 428.4 |
| 154 | 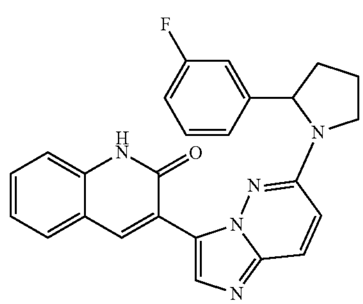 [SMILES: O=c1[nH]c2ccccc2cc1-c1cnc2ccc(N3CCCC3c3cccc(F)c3)nn12] | MS (m/z): 426.5 |
| 155 | 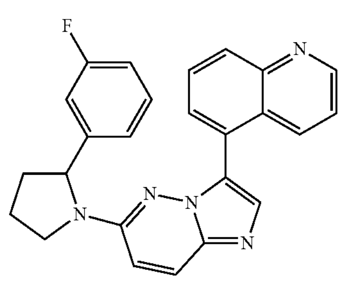 [SMILES: Fc1cccc(C2CCCN2c2ccc3ncc(-c4cccc5ncccc45)n3n2)c1] | MS (m/z): 410.5 |

TABLE 7-continued

| Compound Number | Structure | Physical Data $^1$H NMR 400 MHz (DMSO-$d_6$) and/or MS (m/z) |
|---|---|---|
| 156 | 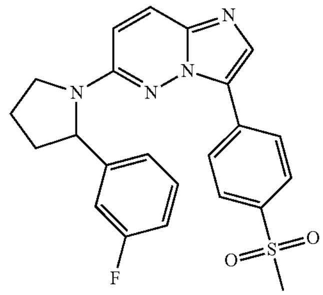 [SMILES: CS(=O)(=O)c1ccc(-c2cnc3ccc(N4CCCC4c4cccc(F)c4)nn23)cc1] | 1H NMR (400 MHz, D3 acetonitrile) ppm: 8.05-7.98 (m, 2H), 7.83 (app d, J = 6.8 Hz, 2H), 7.28 (app q, J = 6.2 Hz, 2H), 7.14 (br s, 1H), 6.98 (d, J = 7.0 Hz, 1H), 6.90 (d, J = 8.2 Hz, 1H), 6.85 (app t, J = 6.2 Hz, 2H), 5.02 (dd, J = 7.4, 2.2 Hz, 1H), 3.87 (app q, J = 5.5 Hz, 1H), 3.61 (app q, J = 8.5 Hz, 1H), 2.99 (s, 3H), 2.44-2.38 (m, 2H), 2.06-1.95 (m, 2H). MS (m/z): 437.5 |
| 157 | 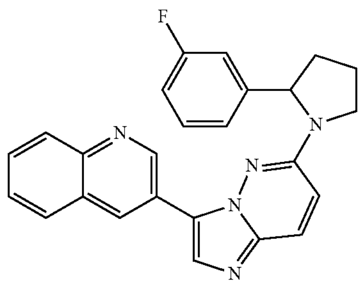 [SMILES: Fc1cccc(C2CCCN2c2ccc3ncc(-c4cnc5ccccc5c4)n3n2)c1] | 1H NMR (400 MHz, D3 acetonitrile) ppm: 8.14 (app t, J = 5.6 Hz, 2H), 8.12 (br s, 1H), 8.02 (br s, 1H), 7.98 (app dt, J = 6.8, 1.2 Hz, 2H), 7.78 (app dt, J = 6.8, 1.2 Hz, 2H), 7.30-7.25 (m, 2H), 7.15 (app d, J = 6.1 Hz, 1H), 7.04 (dd, J = 8.2, 1.9 Hz, 1H), 6.96 (t, J = 7.0 Hz, 1H), 5.22 (d, J = 7.94 Hz, 1H), 4.05 (m, 1H), 3.78 (app q, J = 7.5 Hz, 1H), 2.57-2.54 (m, 1H), 2.14-1.99 (m, 3H). MS (m/z): 410.5 |
| 158 | 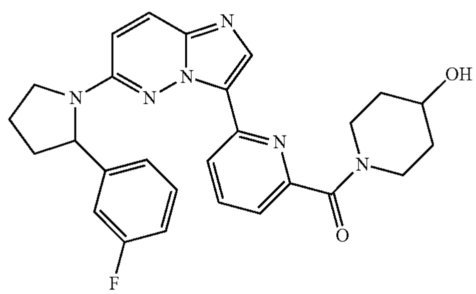 [SMILES: O=C(c1cccc(-c2cnc3ccc(N4CCCC4c4cccc(F)c4)nn23)n1)N1CCC(O)CC1] | 1H NMR (400 MHz, D3 acetonitrile) ppm: 8.30 (br s, 1H), 8.14 (app d, J = 2.6 Hz, 2H), 7.89 (br s, 1H), 7.54 (d, J = 6.8 Hz, 1H), 7.35 (q, J = 7.2 Hz, 1H), 7.25 (br s, 1H), 7.16 (d, J = 6.9 Hz, 1H), 7.08 (d, J = 8.2 Hz, 1H), 6.96 (t, J = 7.4 Hz, 1H), 5.23 (dd, J = 7.94, 1.9 Hz, 1H), 4.15 (br d, J = 7.8 Hz, 1H), 4.05 (app q, J = 6.8 Hz, 1H), 3.87 (app q, J = 6.7 Hz, 1H), 3.72 (q, J = 7.5 Hz, 1H), 3.67-3.63 (m, 1H), 3.33-3.12 (m, 4H), 2.57-2.54 (m, 1H), 2.14-1.99 (m, 2H), 1.65-1.59 (m 2H). MS (m/z): 487.5 |
| 159 | 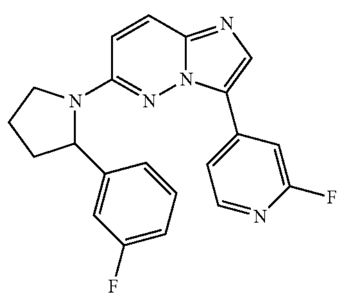 [SMILES: Fc1cccc(C2CCCN2c2ccc3ncc(-c4ccnc(F)c4)n3n2)c1] | 1H NMR (400 MHz, D3 acetonitrile) ppm: 8.28 (d, J = 6.2 Hz, 1H), 8.20 (br s, 1H), 8.04 (app d, J = 6.6 Hz, 1H), 7.74 (s, 1H), 7.67 (s, 1H), 7.34 (q, J = 6.8 Hz, 1H), 7.22-7.14 (m, 2H), 7.03 (dd, J = 6.9, 1.2 Hz, 1H), 6.97 (dt, J = 6.4, 1.2 Hz, 1H), 5.18 (dd, J = 6.7, 1.9 Hz, 1H), 4.00 (app q, J = 5.8 Hz, 1H), 3.72 (app q, J = 6.4 Hz, 1H), 2.54-2.47 (m, 1H), 2.13-2.03 (m, 2H), 1.97-1.87 (m, 1H). MS (m/z): 378.4 |
| 160 | 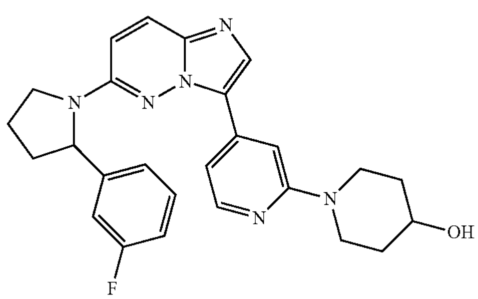 [SMILES: OC1CCN(c2cc(-c3cnc4ccc(N5CCCC5c5cccc(F)c5)nn34)ccn2)CC1] | 1H NMR (400 MHz, D3 acetonitrile) ppm: 8.18 (s, 1H), 8.04 (d, J = 6.9 Hz, 1H), 7.78 (s, 1H), 7.38 (q, J = 7.2 Hz, 1H), 7.28-7.19 (m, 1H), 7.10 (dd, J = 6.2, 1.2 Hz, 1H), 6.94 (app d, J = 6.8 Hz, 2H), 6.82-6.74 (m, 2H), 5.32 (app t, J = 2.9 Hz, 1H), 5.12 (dd, J = 7.4, 1.6 Hz, 1H), 4.01-3.86 (m, 4H), 3.74 (app q, J = 6.8 Hz, 1H), 3.52 (app t, J = 6.0 Hz, 1H), 2.58-2.50 (m, 1H), 2.20-2.18 (m, 1H), 2.15-1.98 (m, 6H), 1.67-1.61 (m, 1H). MS (m/z): 459.5 |

TABLE 7-continued

| Compound Number | Structure | Physical Data ¹H NMR 400 MHz (DMSO-d$_6$) and/or MS (m/z) |
|---|---|---|
| 161 | 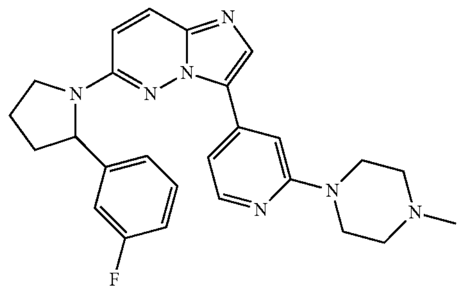 [SMILES: CN1CCN(c2cc(-c3cnc4ccc(N5CCCC5c5cccc(F)c5)nn34)ccn2)CC1] | 1H NMR (400 MHz, D3 acetonitrile) ppm: 8.08 (d, J = 7.1 Hz, 1H), 7.92 (s, 1H), 7.67 (d, J = 7.9 Hz, 1H), 7.62 (s, 1H), 7.41 (q, J = 8.2 Hz, 1H), 7.18 (app t, J = 8.9 Hz, 2H), 7.08 (d, J = 6.8 Hz, 1H), 6.95 (t, J = 5.8 Hz, 1H), 6.68 (dd, J = 7.4, 1.8 Hz, 1H), 5.17 (d, J = 6.9 Hz, 1H), 3.98 (dd, J = 7.6, 2.6 Hz, 1H), 3.72 (app q, J = 7.8 Hz, 1H), 3.58-3.51 (m, 4H), 2.46-2.40 (m, 4H), 2.20 (s, 3H), 2.08-2.03 (m, 1H). MS (m/z): 458.5 |
| 162 | 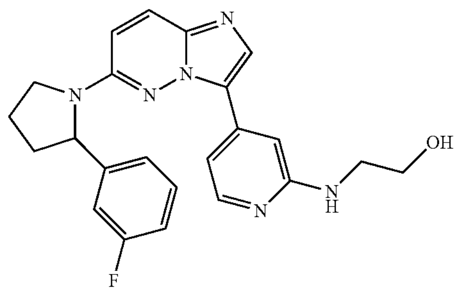 [SMILES: OCCNc1cc(-c2cnc3ccc(N4CCCC4c4cccc(F)c4)nn23)ccn1] | MS (m/z): 419.5 |
| 163 | 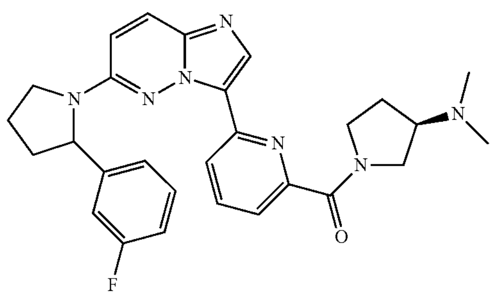 [SMILES: CN(C)[C@@H]1CCN(C(=O)c2cccc(-c3cnc4ccc(N5CCCC5c5cccc(F)c5)nn34)n2)C1] | MS (m/z): 500.6 |
| 164 | 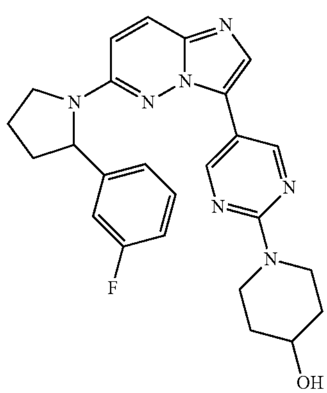 [SMILES: OC1CCN(c2ncc(-c3cnc4ccc(N5CCCC5c5cccc(F)c5)nn34)cn2)CC1] | 1H NMR (400 MHz, D3 acetonitrile) ppm: 8.82 (s, 1H), 7.73 (s, 1H), 7.72-7.70 (m, 2H), 7.35 (q, J = 6.9 Hz, 1H), 7.09 (d, J = 6.9 Hz, 1H), 7.02 (d, J = 5.6 Hz, 1H), 6.89 (t, J = 5.8 Hz, 1H), 6.69 (dd, J = 6.9, 1.3 Hz, 1H), 5.07 (d, J = 7.9 Hz, 1H), 4.48-4.42 (m, 2H), 3.92-3.89 (m, 1H), 3.85-3.80 (m, 1H), 3.66 (q, J = 7.1 Hz, 1H), 3.38-3.32 (m, 2H), 2.48-2.42 (m, 1H), 2.13-2.03 (m, 4H), 1.50-1.45 (m, 2H). MS (m/z): 460.5 |

TABLE 7-continued

| Compound Number | Structure | Physical Data<br>¹H NMR 400 MHz (DMSO-d₆)<br>and/or MS (m/z) |
|---|---|---|
| 165 | 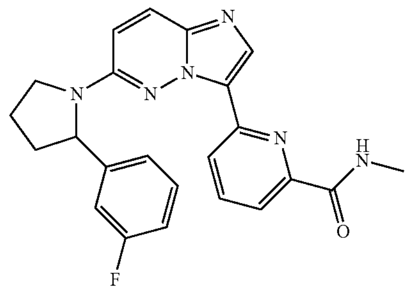 [SMILES: CNC(=O)c1cccc(-c2cnc3ccc(N4CCCC4c4cccc(F)c4)nn23)n1] | 1H NMR (400 MHz, D3 acetonitrile) ppm: 8.58 (s, 1H), 8.30-8.16 (m, 2H), 8.08 (app d, J = 6.9 Hz, 1H), 7.91 (br s, 1H), 7.42 (q, J = 5.9 Hz, 1H), 7.22 (br s, 1H), 7.19 (dd, J = 6.9, 1.2 Hz, 1H), 7.02 (d, J = 7.2 Hz, 1H), 6.99 (dt, J = 6.8, 1.0 Hz, 1H), 5.24 (dd, J = 6.8, 1.9 Hz, 1H), 4.04 (app q, J = 6.4 Hz, 1H), 3.72 (app q, J = 5.4 Hz, 1H), 2.92 (d, J = 4.2 Hz, 3H), 2.54-2.47 (m, 1H), 2.19-2.10 (m, 2H), 2.03-1.95 (m, 1H). MS (m/z): 417.5 |
| 166 | 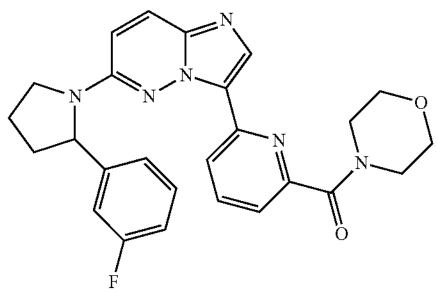 [SMILES: O=C(c1cccc(-c2cnc3ccc(N4CCCC4c4cccc(F)c4)nn23)n1)N1CCOCC1] | MS (m/z): 473.5 |
| 167 | 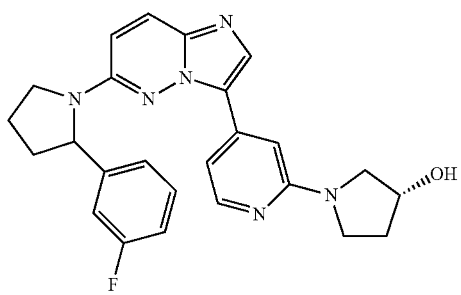 [SMILES: O[C@@H]1CCN(c2cc(-c3cnc4ccc(N5CCCC5c5cccc(F)c5)nn34)ccn2)C1] | 1H NMR (600 MHz, D3 acetonitrile) ppm: 8.08 (s, 1H), 8.04 (s, 1H), 7.72 (d, J = 7.2 Hz, 1H), 7.52-7.45 (m, 2H), 7.41 (app d, J = 3.2 Hz, 1H), 7.18 (br s, 2H), 7.01 (t, J = 6.1 Hz, 1H), 6.72 (d, J = 5.8 Hz, 1H), 5.27 (d, J = 6.9 Hz, 1H), 4.58 (br s, 1H), 4.11 (app t, J = 6.8 Hz, 1H), 4.04 (d, J = 4.5 Hz, 1H), 3.82 (q, J = 4.9 Hz, 1H), 3.77-3.54 (m, 3H), 3.52-3.48 (m, 1H), 2.66-2.60 (m, 1H), 2.20-2.01 (m, 4H). MS (m/z): 445.5 |
| 168 | 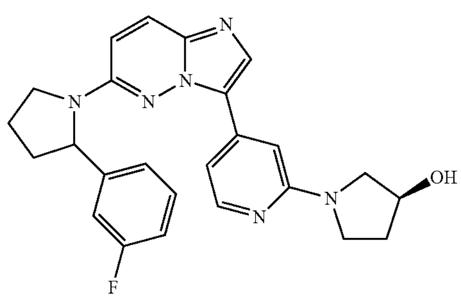 [SMILES: O[C@H]1CCN(c2cc(-c3cnc4ccc(N5CCCC5c5cccc(F)c5)nn34)ccn2)C1] | MS (m/z): 445.5 |
| 169 | 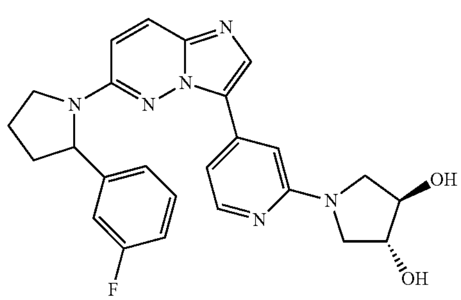 [SMILES: O[C@@H]1CN(c2cc(-c3cnc4ccc(N5CCCC5c5cccc(F)c5)nn34)ccn2)C[C@H]1O] | 1H NMR (600 MHz, D3 acetonitrile) ppm: 8.06 (br s, 2H), 7.74 (d, J = 7.2 Hz, 1H), 7.48-7.42 (m, 2H), 7.28 (d, J = 7.2 Hz, 1H), 7.18 (br s, 2H), 7.01 (t, J = 6.8 Hz, 1H), 6.72 (d, J = 6.8 Hz, 1H), 5.23 (d, J = 6.4 Hz, 1H), 4.58 (br s, 1H), 4.31 (br s, 2H), 4.11 (app t, J = 6.8 Hz, 1H), 3.88 (d, J = 4.5 Hz, 1H), 3.82 (t, J = 5.9 Hz, 1H), 3.61-3.59 (m, 2H), 3.21 (app d, J = 5.5 Hz, 1H), 2.63-2.58 (m, 1H), 2.16-2.00 (m, 4H). MS (m/z): 461.5 |

TABLE 7-continued

| Compound Number | Structure | Physical Data<br>¹H NMR 400 MHz (DMSO-d₆) and/or MS (m/z) |
|---|---|---|
| 170 | 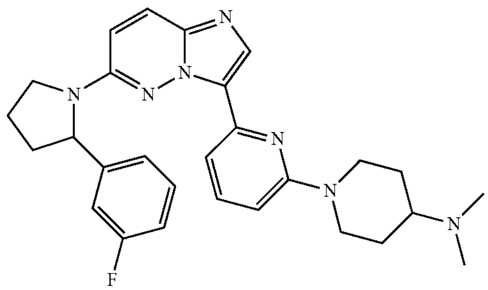 [SMILES: CN(C)C1CCN(c2cccc(-c3cnc4ccc(N5CCCC5c5cccc(F)c5)nn34)n2)CC1] | 1H NMR (400 MHz, D3 acetonitrile) ppm: 8.26 (s, 1H), 8.04 (br d, J = 6.2 Hz, 1H), 7.48 (br s, 1H), 7.39 (q, J = 7.5 Hz, 1H), 7.20 (s, 1H), 7.10-7.04 (m, 2H), 7.03 (d, J = 7.0 Hz, 1H), 6.99 (dt, J = 6.9, 1.2 Hz, 1H), 6.82 (d, J = 6.8 Hz, 1H), 5.13 (dd, J = 6.4, 1.2 Hz, 1H), 4.58 (br s, 2H), 4.02-4.00 (m, 1H), 3.62 (app q, J = 6.9 Hz, 1H), 3.22 (app t, 1H), 2.82 (app t, J = 6.5 Hz, 1H), 2.75 (br s, 6H), 2.62-2.52 (m, 2H), 2.48-2.38 (m, 3H), 2.11-2.00 (m, 3H), 1.84-1.80 (m, 1H).<br>MS (m/z): 486.6 |
| 171 | 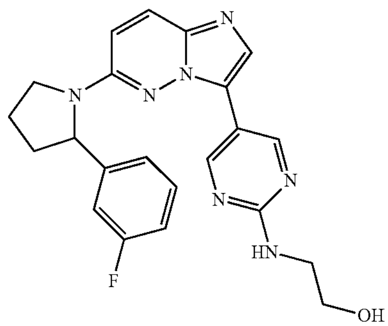 [SMILES: OCCNc1ncc(-c2cnc3ccc(N4CCCC4c4cccc(F)c4)nn23)cn1] | MS (m/z): 420.5 |
| 172 | 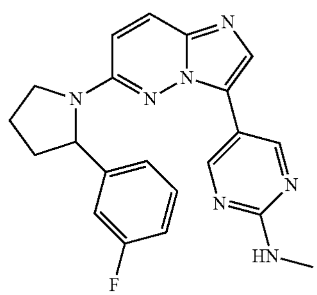 [SMILES: CNc1ncc(-c2cnc3ccc(N4CCCC4c4cccc(F)c4)nn23)cn1] | 1H NMR (400 MHz, D3 acetonitrile) ppm: 8.82 (s, 2H), 8.33 (d, 7.8 Hz, 1H), 8.18 (br s, 1H), 7.43-7.32 (m, 2H), 7.15 (d, J = 6.9 Hz, 1H), 7.04 (dd, J = 6.9, 1.5 Hz, 1H), 6.92 (t, J = 7.0 Hz, 1H), 5.27 (dd, J = 7.4, 2.2 Hz, 1H), 4.28-4.22 (m, 1H), 3.89 (app q, J = 6.7 Hz, 1H), 3.05 (s, 3H), 2.71-2.62 (m, 1H), 2.23-2.03 (m, 2H), 2.01-1.99 (m, 1H).<br>MS (m/z): 390.4 |
| 173 | 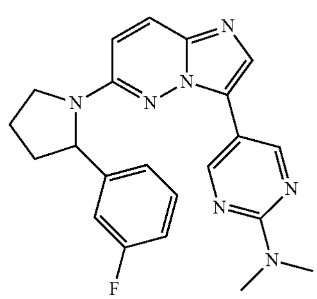 [SMILES: CN(C)c1ncc(-c2cnc3ccc(N4CCCC4c4cccc(F)c4)nn23)cn1] | 1H NMR (400 MHz, D3 acetonitrile) ppm: 8.62 (s, 2H), 8.06 (d, 7.9 Hz, 1H), 7.94 (br s, 1H), 7.23 (q, J = 6.4 Hz, 1H), 7.04 (app t, J = 6.5 Hz, 1H), 6.94 (d, J = 7.2 Hz, 1H), 6.82 (t, J = 6.1 Hz, 1H), 5.21 (dd, J = 7.0, 2.2 Hz, 1H), 3.92 (ddd, J = 6.6 Hz, 4.3 Hz, 1.9 Hz, 1H), 3.71-3.65 (m, 1H), 3.10 (s, 6H), 2.51-2.43 (m, 1H), 2.23-2.03 (m, 2H), 2.01-1.99 (m, 1H).<br>MS (m/z): 404.5 |
| 174 | 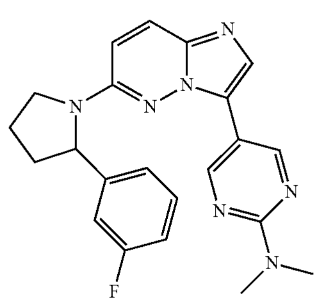 | MS (m/z): 486.6 |

TABLE 7-continued

| Compound Number | Structure | Physical Data $^1$H NMR 400 MHz (DMSO-$d_6$) and/or MS (m/z) |
|---|---|---|
| 175 | 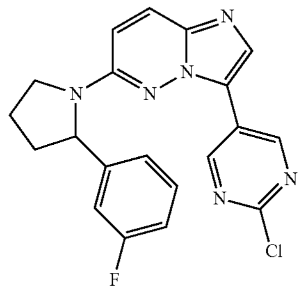 [SMILES: Fc1cccc(C2CCCN2c2ccc3ncc(-c4cnc(Cl)nc4)n3n2)c1] | MS (m/z): 395.8 |
| 176 | 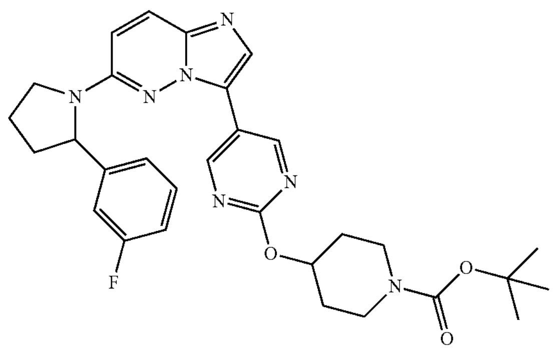 [SMILES: CC(C)(C)OC(=O)N1CCC(Oc2ncc(-c3cnc4ccc(N5CCCC5c5cccc(F)c5)nn34)cn2)CC1] | 1H NMR (400 MHz, D6 acetone) ppm: 8.91 (s, 2H), 7.80 (s, 1H), 7.62 (d, J = 8.1 Hz, 1H), 7.22 (q, J = 6.8 Hz, 1H), 6.98 (d, J = 7.5 Hz, 1H), 6.92 (d, J = 7.4 Hz, 1H), 6.82 (t, J = 7.1 Hz, 1H), 6.67 (d, J = 7.2 Hz, 1H), 5.11 (t, J = 5.4 Hz, 1H), 5.02 (dd, J = 7.0, 2.2 Hz, 1H), 3.96-3.87 (m, 1H), 3.74-3.63 (m, 2H), 3.01 (app q, J = 5.2 hz, 1H), 2.72 (s, 9H), 2.43-2.38 (m, 1H), 2.13-1.99 (m, 4H), 1.67-1.58 (m, 3H), 1.54-1.48 (m, 2H). MS (m/z): 560.6 |
| 177 | 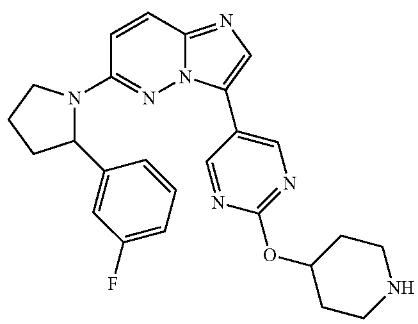 [SMILES: Fc1cccc(C2CCCN2c2ccc3ncc(-c4cnc(OC5CCNCC5)nc4)n3n2)c1] | MS (m/z): 460.5 |
| 178 | 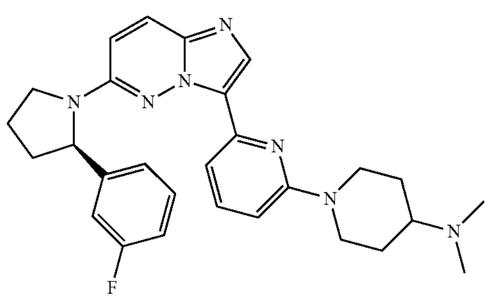 [SMILES: CN(C)C1CCN(c2cccc(-c3cnc4ccc(N5CCC[C@@H]5c5cccc(F)c5)nn34)n2)CC1] | MS (m/z): 486.6 |
| 179 | 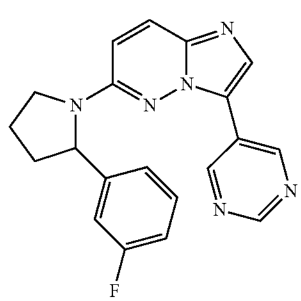 [SMILES: Fc1cccc(C2CCCN2c2ccc3ncc(-c4cncnc4)n3n2)c1] | 1H NMR (400 MHz, D6 DMSO) ppm: 9.30 (s, 2H), 9.06 (s, 1H), 8.20 (s, 1H), 7.93 (d, J = 7.9 Hz, 1H), 7.35 (q, J = 6.4 Hz, 1H), 7.15-7.05 (m, 2H), 7.03 (app t, J = 6.9 Hz, 1H), 6.88 (d, J = 7.2 Hz, 1H), 5.19 (dd, J = 7.0, 2.2 Hz, 1H), 3.99 (app d, J = 6.9 Hz, 1H), 3.66 (m, 1H), 3.10 (s, 6H), 2.51-2.43 (m, 1H), 2.23-2.03 (m, 2H), 2.01-1.99 (m, 1H). MS (m/z); 361.4 |

TABLE 7-continued

| Compound Number | Structure | Physical Data<br>¹H NMR 400 MHz (DMSO-d₆) and/or MS (m/z) |
|---|---|---|
| 180 | 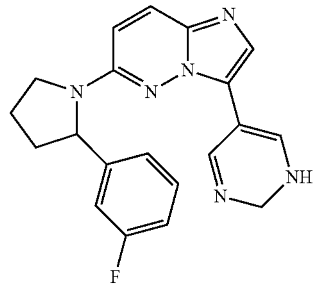 [SMILES: Fc1cccc(C2CCCN2c2ccc3ncc(C4=CNCN=C4)n3n2)c1] | MS (m/z): 363.4 |
| 181 | 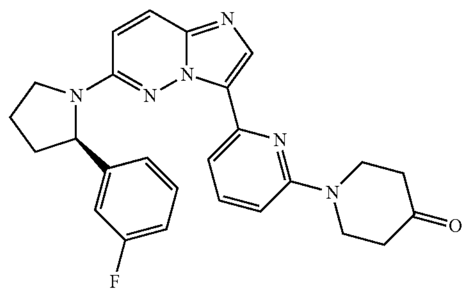 [SMILES: O=C1CCN(c2cccc(-c3cnc4ccc(N5CCC[C@@H]5c5cccc(F)c5)nn34)n2)CC1] | 1H NMR (400 MHz, D6 acetone) ppm: 8.45 (s, 1H), 8.28 (d, J = 6.7 Hz, 1H), 7.64-7.58 (m, 2H), 7.38 (app q, J = 6.9 Hz, 1H), 7.29 (br s, 1H), 7.21 (d, J = 7.3 Hz, 1H), 7.19 (d, J = 6.9 Hz, 1H), 7.02-6.97 (m, 2H), 5.34 (dd, J = 6.8, 2.49 Hz, 1H), 4.22-4.17 (m, 1H), 4.08 (app t, J = 8.4 Hz, 4H), 3.82 (app q, J = 6.4 Hz, 1H), 2.62-2.57 (m, 1H), 2.48 (app t, J = 8.4 Hz, 4H), 2.21-2.10 (m, 2H), 2.03-1.99 (m, 1H).<br>MS (m/z): 457.5 |
| 182 | 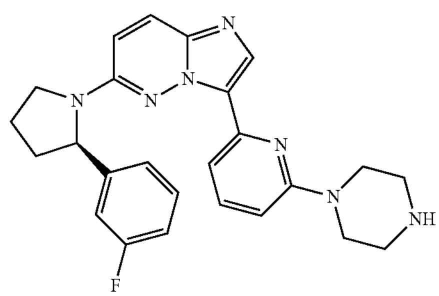 [SMILES: Fc1cccc([C@H]2CCCN2c2ccc3ncc(-c4cccc(N5CCNCC5)n4)n3n2)c1] | MS (m/z): 444.5 |
| 183 | 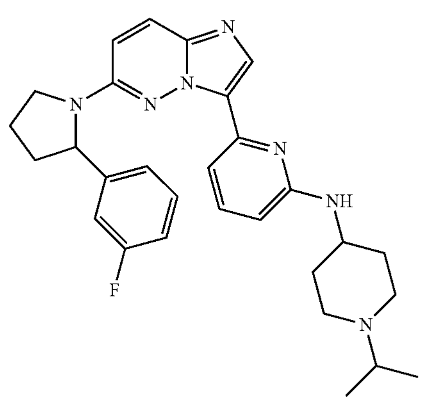 [SMILES: CC(C)N1CCC(Nc2cccc(-c3cnc4ccc(N5CCCC5c5cccc(F)c5)nn34)n2)CC1] | MS (m/z): 500.6 |

TABLE 7-continued

| Compound Number | Structure | Physical Data $^1$H NMR 400 MHz (DMSO-$d_6$) and/or MS (m/z) |
|---|---|---|
| 184 | 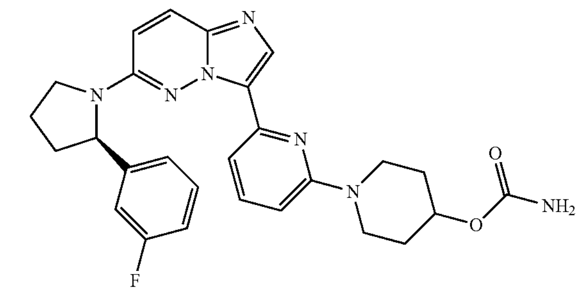 [SMILES: NC(=O)OC1CCN(c2cccc(-c3cnc4ccc(N5CCC[C@@H]5c5cccc(F)c5)nn34)n2)CC1] | 1H NMR (400 MHz, D6 acetone) ppm: 8.51 (s, 1H), 8.38 (d, J = 6.4 Hz, 1H), 7.54 (br s, 1H), 7.42 (app q, J = 6.3 Hz, 1H), 7.28 (d, J = 6.9 Hz, 1H), 7.02 (dt, J = 6.7, 1.6 Hz, 1H), 6.92 (d, J = 6.9 Hz, 1H), 5.82 (br s, 2H), 5.37 (dd, J = 6.0, 1.5 Hz, 1H), 4.88-4.77 (m, 1H), 4.32-4.26 (m, 2H), 3.92 (app q, J = 7.4 Hz, 4H), 3.42 (app dt, J = 6.8, 1.9 Hz, 1H), 2.68-2.63 (m, 1H), 2.38-2.22 (m, 2H), 2.06-2.02 (m, 1H), 2.00-1.97 (m, 1H), 1.64-1.55 (m, 2H). MS (m/z): 502.6 |
| 185 | 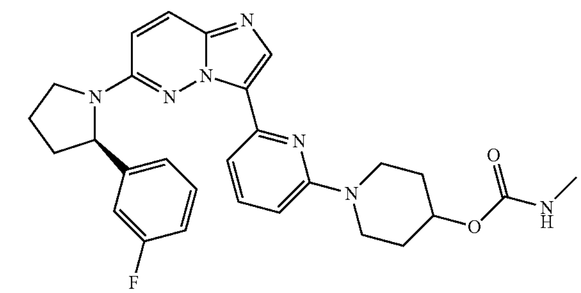 [SMILES: CNC(=O)OC1CCN(c2cccc(-c3cnc4ccc(N5CCC[C@@H]5c5cccc(F)c5)nn34)n2)CC1] | MS (m/z): 516.6 |
| 186 | 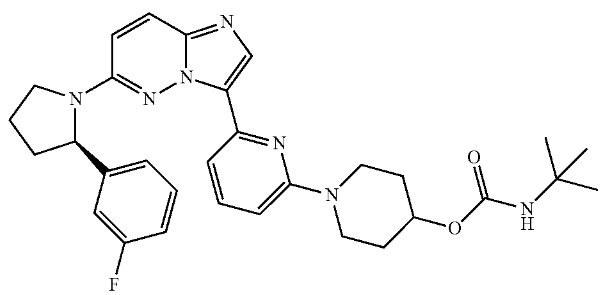 [SMILES: CC(C)(C)NC(=O)OC1CCN(c2cccc(-c3cnc4ccc(N5CCC[C@@H]5c5cccc(F)c5)nn34)n2)CC1] | MS (m/z): 558.7 |
| 187 | 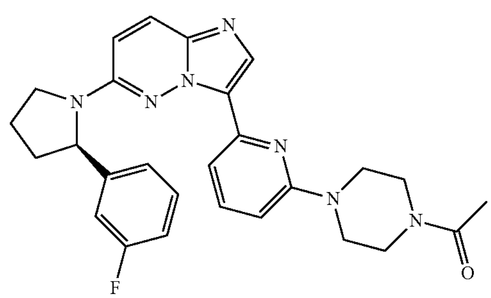 [SMILES: CC(=O)N1CCN(c2cccc(-c3cnc4ccc(N5CCC[C@@H]5c5cccc(F)c5)nn34)n2)CC1] | 1H NMR (400 MHz, D3 acetonitrile) ppm: 8.28 (s, 1H), 8.08 (s, 1H), 7.54 (br s, 1H), 7.38 (app q, J = 6.8 Hz, 1H), 7.35-7.26 (m, 2H), 7.18 (d, J = 6.9 Hz, 1H), 7.10 (d, J = 6.9 Hz, 1H), 7.00 (dt, J = 7.2, 1.9 Hz, 1H), 6.82 (d, J = 6.9 Hz, 1H), 5.22 (dd, J = 6.4, 1.7 Hz, 1H), 4.08-4.02 (m, 1H), 3.76 (app q, J = 7.0 Hz, 1H), 3.68-3.62 (m, 4H), 3.59-3.54 (m, 4H), 2.60-2.48 (m, 1H), 2.38-2.22 (m, 2H), 2.14-2.02 (m, 1H), 1.97 (s, 3H). MS (m/z): 486.6 |
| 188 | 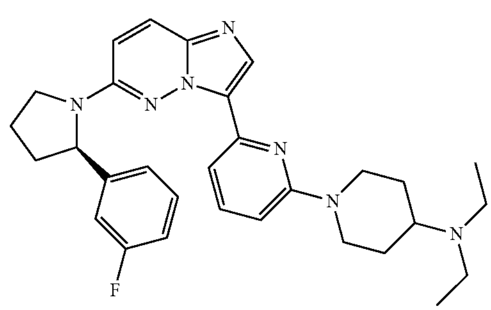 [SMILES: CCN(CC)C1CCN(c2cccc(-c3cnc4ccc(N5CCC[C@@H]5c5cccc(F)c5)nn34)n2)CC1] | MS (m/z): 514.7 |

US 8,507,488 B2

309                                                                                                310

TABLE 7-continued

| Compound Number | Structure | Physical Data<br>¹H NMR 400 MHz (DMSO-d₆) and/or MS (m/z) |
|---|---|---|
| 189 | 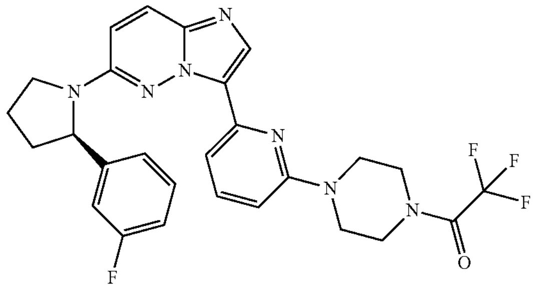 [SMILES: O=C(N1CCN(c2cccc(-c3cnc4ccc(N5CCC[C@@H]5c5cccc(F)c5)nn34)n2)CC1)C(F)(F)F] | MS (m/z): 540.5 |
| 190 | 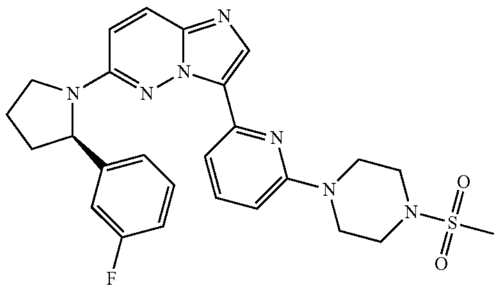 [SMILES: CS(=O)(=O)N1CCN(c2cccc(-c3cnc4ccc(N5CCC[C@@H]5c5cccc(F)c5)nn34)n2)CC1] | 1H NMR (400 MHz, D6 DMSO) ppm: 8.38 (s, 1H), 8.04 (d, J = 7.5 Hz, 1H), 7.56 (br s, 1H), 7.39 (app q, J = 7.2 Hz, 1H), 7.23 (d, J = 7.7 Hz, 1H), 7.17-7.11 (m, 2H), 7.05 (t, J = 7.9 Hz, 1H), 6.98 (d, J = 7.9 Hz, 1H), 6.90 (br d, J = 8.2 Hz, 1H), 5.22 (dd, J = 7.4, 2.2 Hz, 1H), 4.03-4.01 (m, 1H), 3.71 (br s, 2H), 3.21 (app t, J = 5.6 Hz, 1H), 2.90 (s, 3H), 2.56-2.42 (s, 6H), 2.28-2.12 (m, 2H), 2.04-1.90 (m, 2H).<br>MS (m/z): 522.6 |
| 191 | 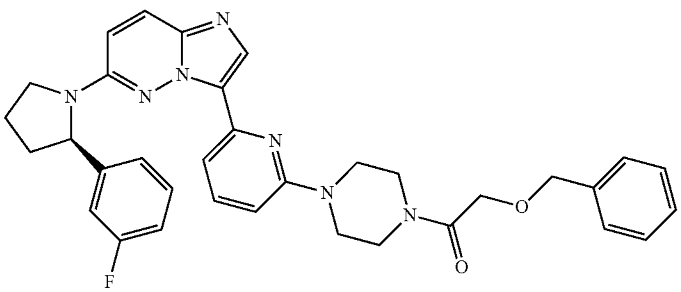 [SMILES: O=C(COCc1ccccc1)N1CCN(c2cccc(-c3cnc4ccc(N5CCC[C@@H]5c5cccc(F)c5)nn34)n2)CC1] | MS (m/z): 592.7 |
| 192 | 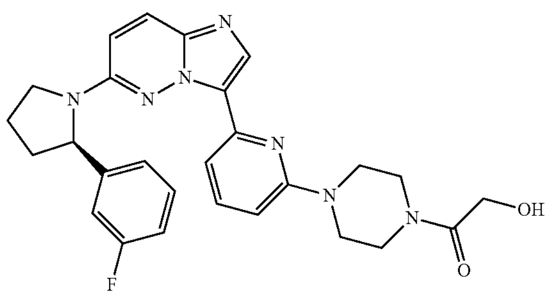 [SMILES: O=C(CO)N1CCN(c2cccc(-c3cnc4ccc(N5CCC[C@@H]5c5cccc(F)c5)nn34)n2)CC1] | 1H NMR (400 MHz, D3 acetonitrile) ppm: 8.12 (s, 1H), 7.75 (d, J = 7.5 Hz, 1H), 7.60 (br s, 1H), 7.49 (t, J = 7.0 hz, 1H), 7.36 (app q, J = 7.4 Hz, 1H), 7.18 (d, J = 7.2 Hz, 1H), 7.11 (d, J = 7.8 Hz, 1H), 6.98 (t, J = 7.7 Hz, 1H), 6.76 (dt, J = 7.2, 1.1 Hz, 1H), 6.67 (d, J = 6.9 Hz, 1H), 5.16 (dd, J = 7.8, 2.2 Hz, 1H), 4.18 (br s, 2H), 3.93 (p, J = 3.8 Hz, 1H), 3.67-3.57 (m, 8H), 3.42-3.38 (m, 1H), 2.52-2.45 (m, 1H), 2.18-2.06 (m, 2H), 1.92-1.88 (m, 1H).<br>MS (m/z): 502.6 |
| 193 | 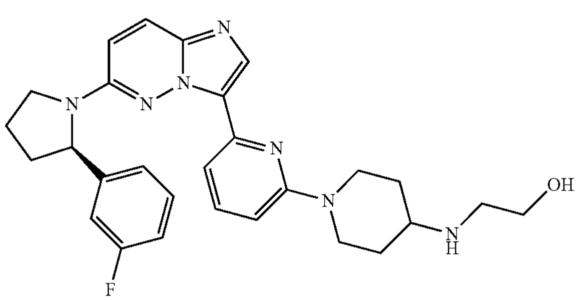 [SMILES: OCCNC1CCN(c2cccc(-c3cnc4ccc(N5CCC[C@@H]5c5cccc(F)c5)nn34)n2)CC1] | MS (m/z): 502.6 |

TABLE 7-continued
| Compound Number | Structure | Physical Data<br>¹H NMR 400 MHz (DMSO-d₆)<br>and/or MS (m/z) |
|---|---|---|
| 194 | 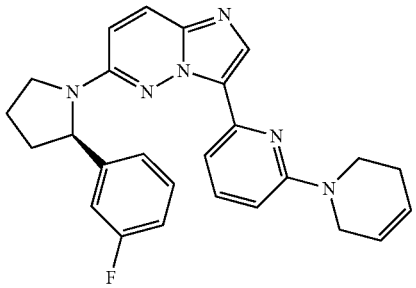 [SMILES: Fc1cccc([C@H]2CCCN2c2ccc3ncc(-c4cccc(N5CC=CCC5)n4)n3n2)c1] | MS (m/z): 441.5 |
| 195 | 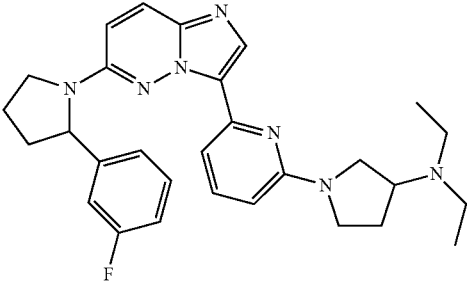 [SMILES: CCN(CC)C1CCN(c2cccc(-c3cnc4ccc(N5CCCC5c5cccc(F)c5)nn34)n2)C1] | 1H NMR (400 MHz, D6 acetone) ppm: 8.32 (s, 1H), 8.14 (d, J = 7.6 Hz, 1H), 7.55-7.46 (m, 1H), 7.41 (app q, J = 7.4 Hz, 1H), 7.41 (app q, J = 5.4 Hz, 1H), 7.21-7.11 (m, 2H), 7.03 (d, J = 7.6 Hz, 1H), 6.88 (t, J = 7.7 Hz, 1H), 6.42 (d, J = 7.2 Hz, 1H), 5.18 (d, J = 5.6 Hz, 1H), 4.10-4.00 (m, 2H), 3.70-3.59 (m, 3H), 3.38-3.04 (m, 8H), 2.50-2.40 (m, 2H), 2.06-1.99 (m, 2H), 2.18-2.06 (m, 2H), 1.42 (t, J = 6.0 Hz, 4H).<br>MS (m/z): 500.6 |
| 196 | 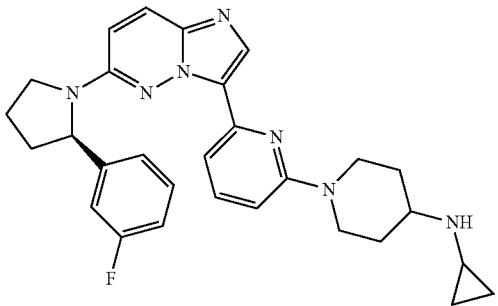 [SMILES: Fc1cccc([C@H]2CCCN2c2ccc3ncc(-c4cccc(N5CCC(NC6CC6)CC5)n4)n3n2)c1] | MS (m/z): 498.6 |
| 197 | 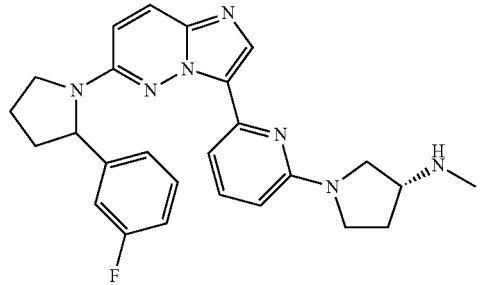 [SMILES: CN[C@@H]1CCN(c2cccc(-c3cnc4ccc(N5CCCC5c5cccc(F)c5)nn34)n2)C1] | MS (m/z): 458.5 |
| 198 | 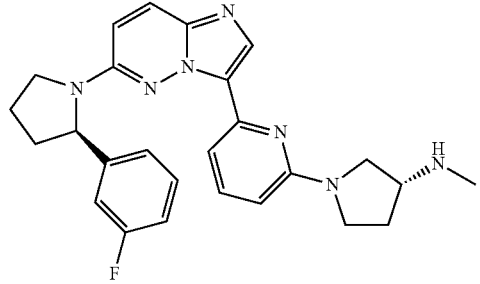 [SMILES: CN[C@@H]1CCN(c2cccc(-c3cnc4ccc(N5CCC[C@@H]5c5cccc(F)c5)nn34)n2)C1] | 1H NMR (400 MHz, D6 acetone) ppm: 8.28 (d, J = 7.1 Hz, 1H), 8.04 (s, 1H), 7.42 (app q, J = 7.8 Hz, 1H), 7.38 (br s, 1H), 7.28 (d, J = 7.4 Hz, 1H), 7.18 (d, J = 8.4 Hz, 1H), 6.94 (t, J = 7.7 Hz, 1H), 6.42 (d, J = 6.4 Hz, 1H), 5.28 (d, J = 6.6 Hz, 1H), 4.18-4.04 (m, 2H), 3.98 (app d, J = 6.8 Hz, 1H), 3.88-3.62 (m, 4H), 3.48-3.42 (m, 1H), 2.92 (s, 3H), 2.77-2.70 (m, 1H), 2.67-2.56 (m, 1H), 2.32-2.26 (m, 2H), 2.18-2.09 (m, 1H).<br>MS (m/z): 458.5 |

TABLE 7-continued

| Compound Number | Structure | Physical Data $^1$H NMR 400 MHz (DMSO-$d_6$) and/or MS (m/z) |
|---|---|---|
| 199 | 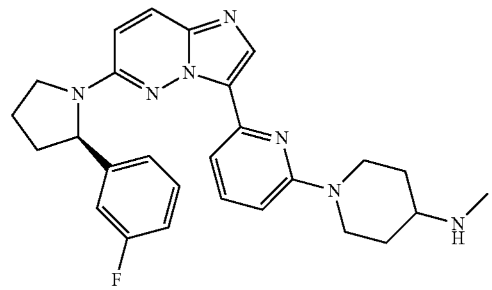 [SMILES: CNC1CCN(c2cccc(-c3cnc4ccc(N5CCC[C@@H]5c5cccc(F)c5)nn34)n2)CC1] | 1H NMR (400 MHz, D6 acetone) ppm: 9.43-9.02 (br s, 2H), 8.48 (br s, 1H), 8.35 (s, 1H), 8.56 (s, 1H), 7.42 (app q, J = 7.8 Hz, 1H), 7.31 (d, J = 5.6 Hz, 1H), 7.20 (d, J = 7.4 Hz, 1H), 7.02 (dt, J = 8.4, 1.9 Hz, 1H), 6.92 (br d, J = 4.5 Hz, 1H), 5.35 (d, J = 4.6 Hz, 1H), 4.20 (app d, J = 4.9 Hz, 1H), 3.98 (app t, J = 6.8 Hz, 1H), 3.58-3.52 (m, 1H), 3.08-2.98 (m, 3H), 2.82 (s, 3H), 2.71-2.60 (m, 1H), 2.38 (app d, J = 6.8 Hz, 2H), 2.27-2.18 (m, 2H), 2.32-2.26 (m, 2H), 1.88-1.69 (m, 2H). MS (m/z): 472.6 |
| 200 | 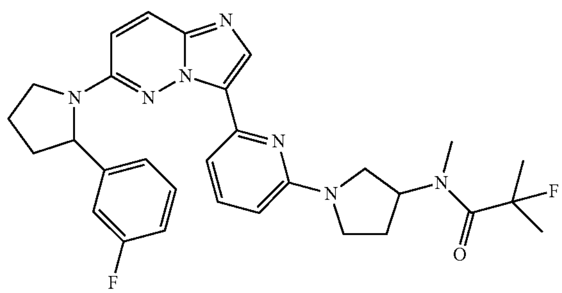 [SMILES: CN(C(=O)C(C)(C)F)C1CCN(c2cccc(-c3cnc4ccc(N5CCCC5c5cccc(F)c5)nn34)n2)C1] | MS (m/z): 546.6 |
| 201 | 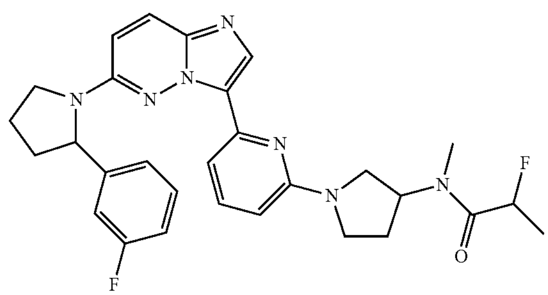 [SMILES: CC(F)C(=O)N(C)C1CCN(c2cccc(-c3cnc4ccc(N5CCCC5c5cccc(F)c5)nn34)n2)C1] | MS (m/z): 532.6 |
| 202 | 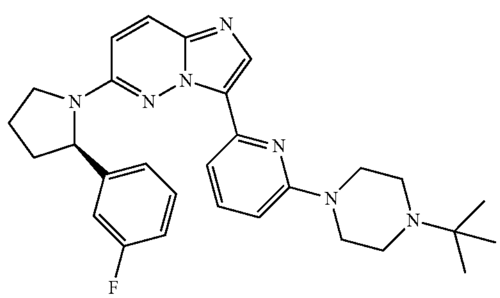 [SMILES: CC(C)(C)N1CCN(c2cccc(-c3cnc4ccc(N5CCC[C@@H]5c5cccc(F)c5)nn34)n2)CC1] | MS (m/z): 500.6 |
| 203 | 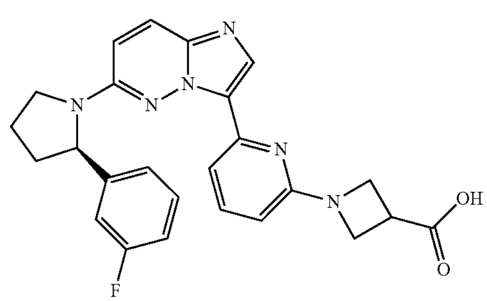 [SMILES: O=C(O)C1CN(c2cccc(-c3cnc4ccc(N5CCC[C@@H]5c5cccc(F)c5)nn34)n2)C1] | 1H NMR (400 MHz, D6 acetone) ppm: 8.28 (br s, 1H), 8.15 (d, J = 7.8 Hz, 1H), 7.56 (br s, 2H), 7.46 (app q, J = 7.8 Hz, 1H), 7.36 (d, J = 7.6 Hz, 1H), 7.30 (br s, 1H), 7.18 (d, J = 7.6 Hz, 1H), 7.04 (dt, J = 7.4, 1.9 Hz, 1H), 6.42 (br d, J = 6.5 Hz, 1H), 5.25 (d, J = 6.6 Hz, 1H), 4.20 (app d, J = 5.9 Hz, 2H), 4.12-4.06 (m, 2H), 3.98 (p, J = 6.8 Hz, 1H), 3.78 (app q, J = 8.2 Hz, 1H), 3.52-3.48 (m, 1H), 2.77-2.68 (m, 1H), 2.28-2.18 (m, 2H), 2.02-1.97 (m, 1H). MS (m/z): 459.5 |

TABLE 7-continued

| Compound Number | Structure | Physical Data $^1$H NMR 400 MHz (DMSO-$d_6$) and/or MS (m/z) |
|---|---|---|
| 204 | 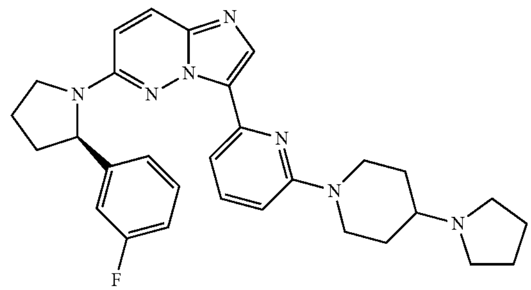 [SMILES: Fc1cccc([C@H]2CCCN2c2ccc3ncc(-c4cccc(N5CCC(N6CCCC6)CC5)n4)n3n2)c1] | 1H NMR (400 MHz, D3 acetonitrile) ppm: 8.29 (br s, 1H), 8.19 (d, J = 6.7 Hz, 1H), 7.52 (br s, 2H), 7.38 (app q, J = 7.3 Hz, 1H), 7.24 (br s, 1H), 7.19 (d, J = 7.2 Hz, 1H), 7.08 (d, J = 7.9 Hz, 1H), 6.94 (dt, J = 7.6, 1.9 Hz, 1H), 6.82 (d, J = 5.5 Hz, 1H), 5.23 (d, J = 6.9 Hz, 1H), 4.52 (app br d, J = 7.9 Hz, 2H), 4.04-3.99 (m, 1H), 3.78 (q, J = 6.9 Hz, 1H), 3.69-3.62 (m, 1H), 3.33-3.21 (m, 2H), 3.09-3.02 (m, 2H), 2.83 (app t, J = 8.0 Hz, 2H), 2.77-2.50 (m, 6H), 2.28-2.08 (m, 4H), 1.84-1.74 (m, 2H). MS (m/z): 512.6 |
| 205 | 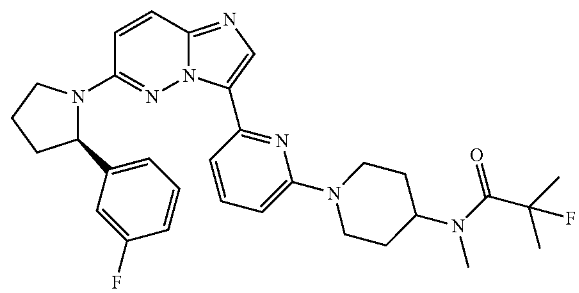 [SMILES: CN(C(=O)C(C)(C)F)C1CCN(c2cccc(-c3cnc4ccc(N5CCC[C@@H]5c5cccc(F)c5)nn34)n2)CC1] | MS (m/z): 560.7 |
| 206 | 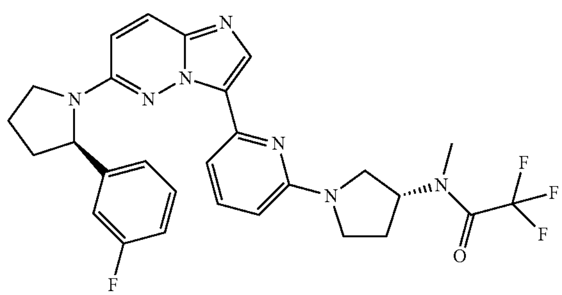 [SMILES: CN(C(=O)C(F)(F)F)[C@@H]1CCN(c2cccc(-c3cnc4ccc(N5CCC[C@@H]5c5cccc(F)c5)nn34)n2)C1] | MS (m/z): 554.6 |
| 207 | 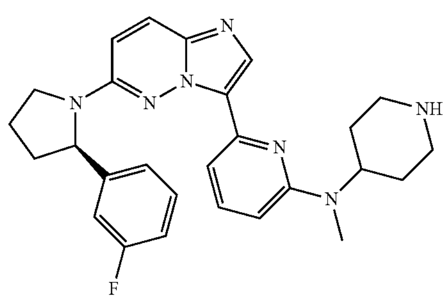 [SMILES: CN(c1cccc(-c2cnc3ccc(N4CCC[C@@H]4c4cccc(F)c4)nn23)n1)C1CCNCC1] | 1H NMR (400 MHz, D3 acetonitrile) ppm: 8.32 (br s, 1H), 8.21 (s, 1H), 8.02 (d, J = 7.4 Hz, 1H), 7.76 (br s, 1H), 7.38 (app t, J = 2.3 Hz, 1H), 7.26 (app q, J = 7.2 Hz, 1H), 7.04-6.97 (m, 2H), 6.92 (d, J = 7.6 Hz, 1H), 6.52 (d, J = 6.5 Hz, 1H), 5.15 (d, J = 6.6 Hz, 1H), 4.78 (dt, J = 6.9, 1.9 Hz, 1H), 3.91-3.79 (m, 1H), 3.58 (q, J = 6.8 Hz, 1H), 3.34 (app d, J = 8.2 Hz, 1H), 3.03 (br q, J = 4.5 Hz, 1H), 2.78 (s, 3H), 2.67-2.48 (m, 4H), 2.28-2.08 (m, 4H), 1.82-1.73 (m, 2H). MS (m/z): 472.6 |

TABLE 7-continued

| Compound Number | Structure | Physical Data $^1$H NMR 400 MHz (DMSO-d$_6$) and/or MS (m/z) |
|---|---|---|
| 208 | 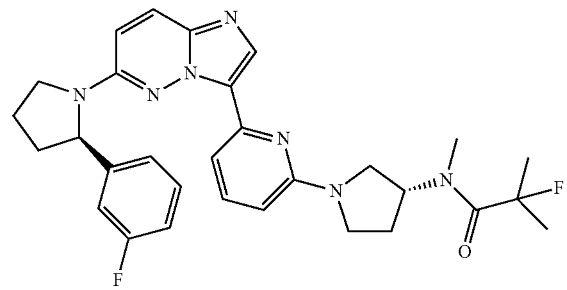 [SMILES: CN(C(=O)C(C)(C)F)[C@@H]1CCN(c2cccc(-c3cnc4ccc(N5CCC[C@@H]5c5cccc(F)c5)nn34)n2)C1] | MS (m/z): 546.6 |
| 209 | 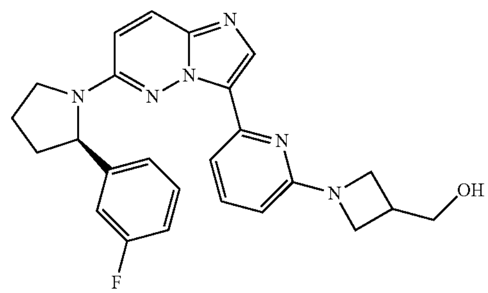 [SMILES: OCC1CN(c2cccc(-c3cnc4ccc(N5CCC[C@@H]5c5cccc(F)c5)nn34)n2)C1] | MS (m/z): 445.5 |
| 210 | 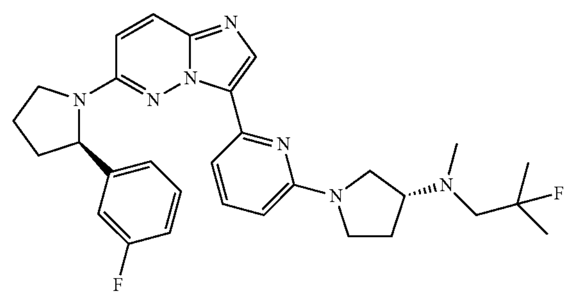 [SMILES: CN(CC(C)(C)F)[C@@H]1CCN(c2cccc(-c3cnc4ccc(N5CCC[C@@H]5c5cccc(F)c5)nn34)n2)C1] | MS (m/z): 532.6 |
| 211 | 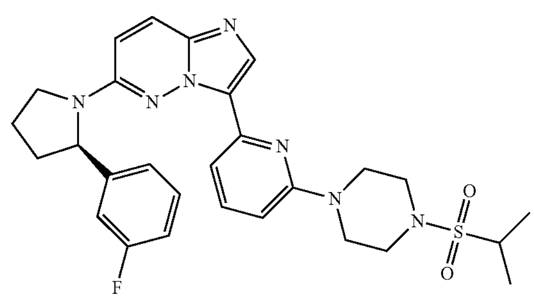 [SMILES: CC(C)S(=O)(=O)N1CCN(c2cccc(-c3cnc4ccc(N5CCC[C@@H]5c5cccc(F)c5)nn34)n2)CC1] | MS (m/z): 550.7 |
| 212 | 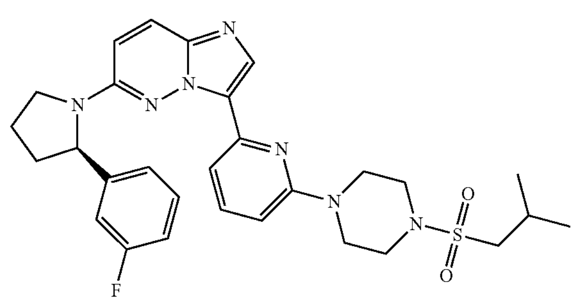 [SMILES: CC(C)CS(=O)(=O)N1CCN(c2cccc(-c3cnc4ccc(N5CCC[C@@H]5c5cccc(F)c5)nn34)n2)CC1] | MS (m/z): 564.7 |

TABLE 7-continued

| Compound Number | Structure | Physical Data ¹H NMR 400 MHz (DMSO-$d_6$) and/or MS (m/z) |
|---|---|---|
| 213 | 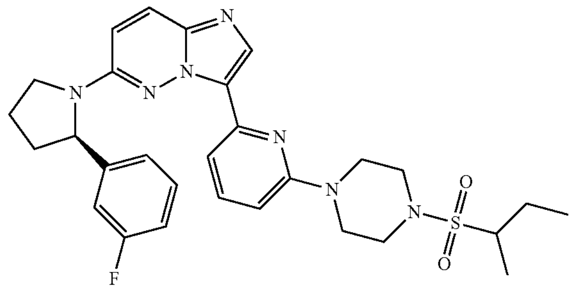 [SMILES: CCC(C)S(=O)(=O)N1CCN(c2cccc(-c3cnc4ccc(N5CCC[C@@H]5c5cccc(F)c5)nn34)n2)CC1] | MS (m/z): 564.7 |
| 214 | 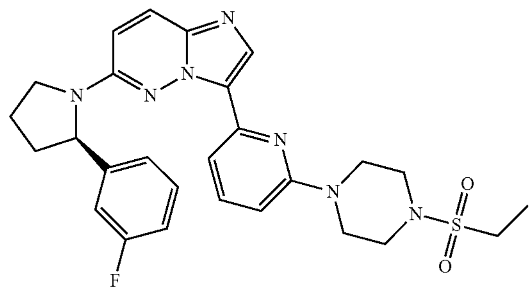 [SMILES: CCS(=O)(=O)N1CCN(c2cccc(-c3cnc4ccc(N5CCC[C@@H]5c5cccc(F)c5)nn34)n2)CC1] | 1H NMR (400 MHz, D6 DMSO) ppm: 8.35 (s, 1H), 8.03 (d, J = 8.5 Hz, 1H), 7.54 (br s, 2H), 7.39 (q, J = 7.0 hz, 1H), 7.21-7.14 (m, 2H), 7.06 (d, J = 7.0 Hz, 1H), 7.00 (br s, 1H), 6.87 (d, J = 7.8 Hz, 1H), 5.20 (d, J = 6.8 Hz, 1H), 4.08-4.00 (m, 1H), 3.78-3.67 (m, 2H), 3.30-3.26 (m, 1H), 2.67 (q, J = 7.0 Hz, 2H), 2.62-2.54 (m, 6H), 2.42-2.35 (m, 1H), 2.08-2.00 (m, 2H), 1.92-1.88 (m, 1H), 1.25 (t, J = 7.4 Hz, 3H). MS (m/z): 536.6 |
| 215 | 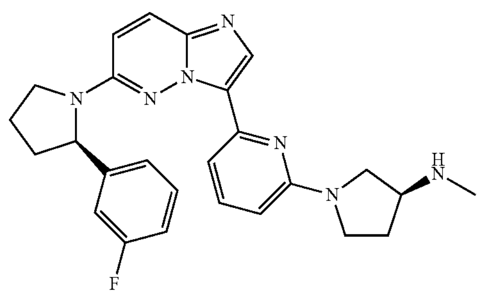 [SMILES: CN[C@H]1CCN(c2cccc(-c3cnc4ccc(N5CCC[C@@H]5c5cccc(F)c5)nn34)n2)C1] | MS (m/z): 458.5 |
| 216 | 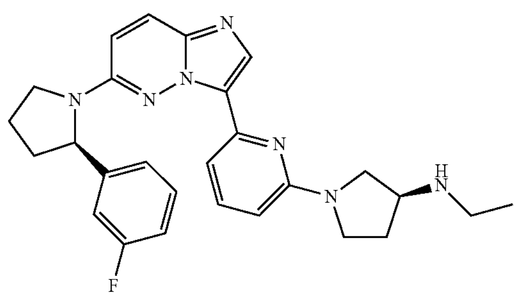 [SMILES: CCN[C@H]1CCN(c2cccc(-c3cnc4ccc(N5CCC[C@@H]5c5cccc(F)c5)nn34)n2)C1] | MS (m/z): 472.6 |
| 217 | 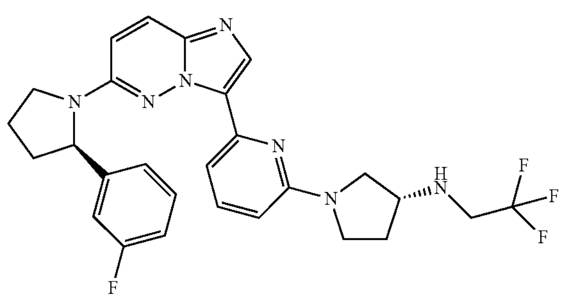 [SMILES: Fc1cccc([C@H]2CCCN2c2ccc3ncc(-c4cccc(N5CC[C@@H](NCC(F)(F)F)C5)n4)n3n2)c1] | 1H NMR (400 MHz, D6 DMSO) ppm: 8.20 (br s, 1H), 8.04 (d, J = 7.8 Hz, 1H), 7.48 (br s, 1H), 7.38 (app q, J = 6.3 Hz, 1H), 7.22 (d, J = 7.2 Hz, 1H), 7.13 (d, J = 8.2 Hz, 1H), 7.04 (d, J = 6.7 Hz, 1H), 6.92 (dt, J = 7.6, 1.9 Hz, 1H), 6.42 (d, J = 7.5 Hz, 1H), 5.25 (d, J = 6.1 Hz, 1H), 4.18-4.04 (m, 3H), 3.92 (dd, 10.1, 6.7 Hz, 1H), 3.78 (q, J = 6.8 Hz, 1H), 3.72 (q, J = 5.8 Hz, 1H), 3.48 (app d, J = 7.2 Hz, 1H), 2.92 (s, 2H), 2.72-2.64 (m, 1H), 2.58-2.53 (m, 2H), 2.21-2.17 (m, 2H), 2.05-1.98 (m, 1H). MS (m/z): 526.5 |

TABLE 7-continued

| Compound Number | Structure | Physical Data<br>¹H NMR 400 MHz (DMSO-d$_6$)<br>and/or MS (m/z) |
| --- | --- | --- |
| 218 | 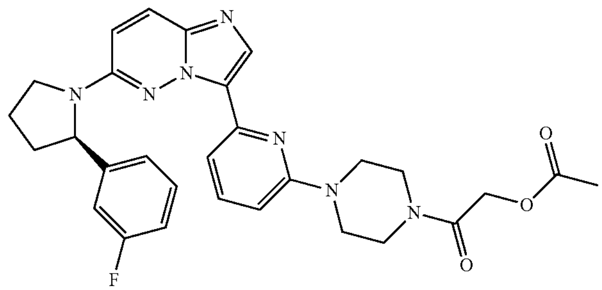 [SMILES: CC(=O)OCC(=O)N1CCN(c2cccc(-c3cnc4ccc(N5CCC[C@@H]5c5cccc(F)c5)nn34)n2)CC1] | MS (m/z): 544.6 |
| 219 | 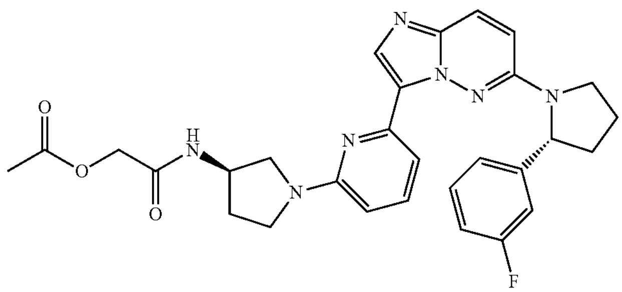 [SMILES: CC(=O)OCC(=O)N[C@@H]1CCN(c2cccc(-c3cnc4ccc(N5CCC[C@@H]5c5cccc(F)c5)nn34)n2)C1] | MS (m/z): 544.6 |
| 220 | 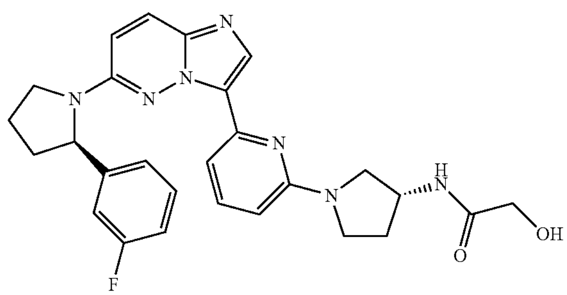 [SMILES: O=C(CO)N[C@@H]1CCN(c2cccc(-c3cnc4ccc(N5CCC[C@@H]5c5cccc(F)c5)nn34)n2)C1] | MS (m/z): 502.6 |
| 221 | 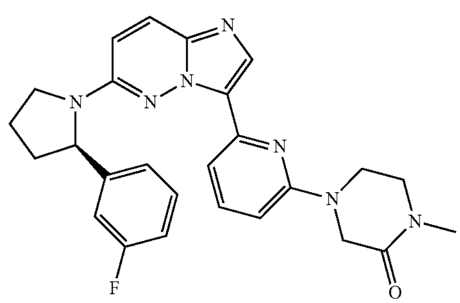 [SMILES: CN1CCN(c2cccc(-c3cnc4ccc(N5CCC[C@@H]5c5cccc(F)c5)nn34)n2)CC1=O] | MS (m/z): 472.5 |
| 222 | | MS (m/z): 502.6 | ns
TABLE 7-continued

| Compound Number | Structure | Physical Data<br>¹H NMR 400 MHz (DMSO-d₆)<br>and/or MS (m/z) |
| --- | --- | --- |
| 223 | 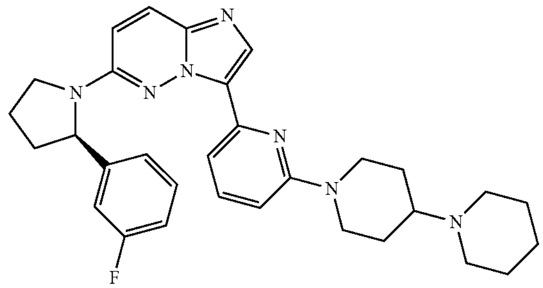 [SMILES: Fc1cccc([C@H]2CCCN2c2ccc3ncc(-c4cccc(N5CCC(N6CCCCC6)CC5)n4)n3n2)c1] | MS (m/z): 526.7 |
| 224 | 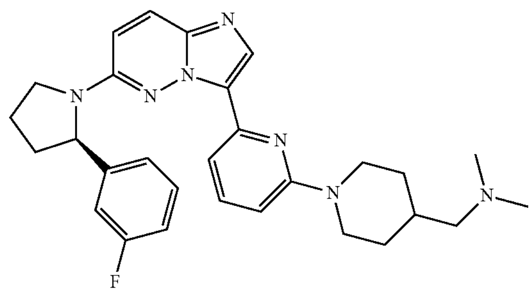 [SMILES: CN(C)CC1CCN(c2cccc(-c3cnc4ccc(N5CCC[C@@H]5c5cccc(F)c5)nn34)n2)CC1] | MS (m/z): 500.6 |
| 225 | 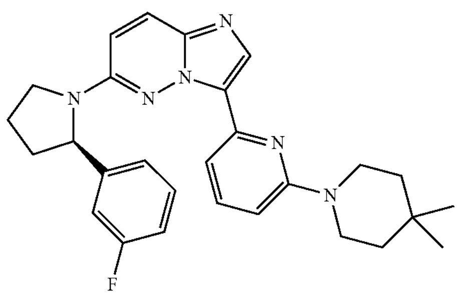 [SMILES: CC1(C)CCN(c2cccc(-c3cnc4ccc(N5CCC[C@@H]5c5cccc(F)c5)nn34)n2)CC1] | 1H NMR (400 MHz, D6 DMSO) ppm: 8.34 (s, 1H), 8.04 (br d, J = 6.4 Hz, 1H), 7.46 (br s, 2H), 7.38 (q, J = 7.6 Hz, 1H), 7.24 (s, 1H), 7.18-7.10 (m, 2H), 7.05 (t, J = 6.7 Hz, 1H), 6.82 (d, J = 6.8 Hz, 1H), 5.21 (d, J = 6.5 Hz, 1H), 4.05-4.02 (m, 2H), 3.70 (q, J = 5.6 Hz, 1H), 3.56 (app q, J = 6.2 Hz, 1H), 2.82-2.72 (m, 2H), 2.54-2.44 (m, 1H), 2.08-2.04 (m, 2H), 1.90-1.82 (m, 1H), 1.38-1.35 (m, 4H), 0.95 (s, 6H).<br>MS (m/z): 471.6 |
| 226 | 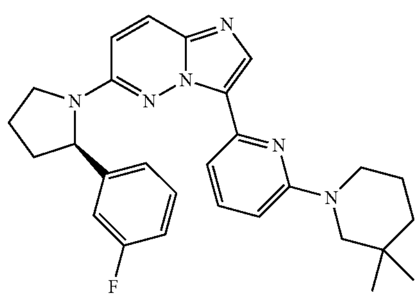 [SMILES: CC1(C)CCCN(c2cccc(-c3cnc4ccc(N5CCC[C@@H]5c5cccc(F)c5)nn34)n2)C1] | MS (m/z): 471.6 |
| 227 | 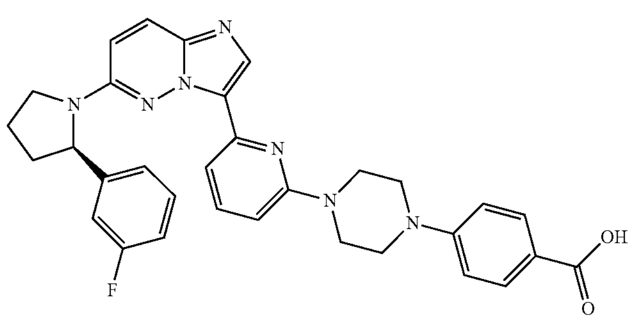 [SMILES: O=C(O)c1ccc(N2CCN(c3cccc(-c4cnc5ccc(N6CCC[C@@H]6c6cccc(F)c6)nn45)n3)CC2)cc1] | MS (m/z): 564.6 |

TABLE 7-continued

| Compound Number | Structure | Physical Data<br>¹H NMR 400 MHz (DMSO-d₆)<br>and/or MS (m/z) |
|---|---|---|
| 228 | 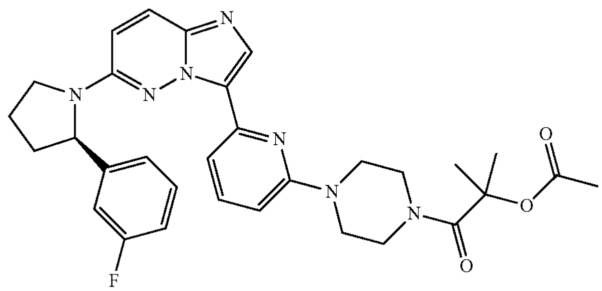 [SMILES: CC(=O)OC(C)(C)C(=O)N1CCN(c2cccc(-c3cnc4ccc(N5CCC[C@@H]5c5cccc(F)c5)nn34)n2)CC1] | MS (m/z): 572.6 |
| 229 | 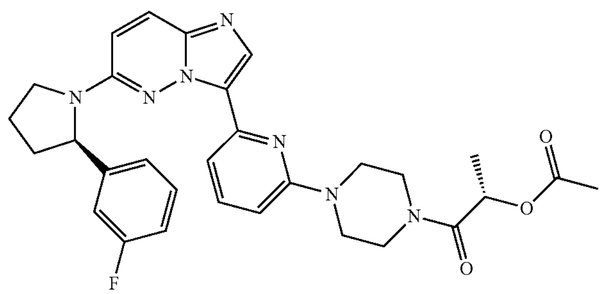 [SMILES: CC(=O)O[C@@H](C)C(=O)N1CCN(c2cccc(-c3cnc4ccc(N5CCC[C@@H]5c5cccc(F)c5)nn34)n2)CC1] | MS (m/z): 558.6 |
| 230 | 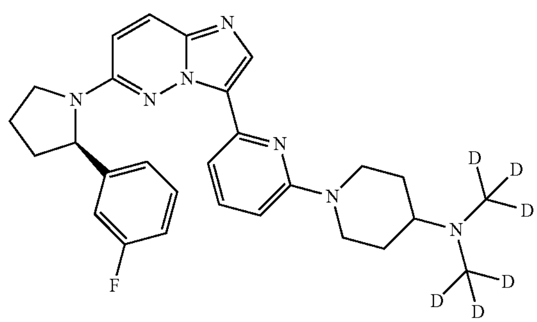 [SMILES: [2H]C([2H])([2H])N(C1CCN(c2cccc(-c3cnc4ccc(N5CCC[C@@H]5c5cccc(F)c5)nn34)n2)CC1)C([2H])([2H])[2H]] | 1H NMR (400 MHz, D3 acetonitrile) ppm: 8.20 (s, 1H), 8.00 (br d, J = 6.4 Hz, 1H), 7.40 (br s, 2H), 7.30 (q, J = 7.6 Hz, 1H), 7.04 (d, J = 6.9 Hz, 1H), 6.95 (app d, J = 7.7 Hz, 2H), 6.92 (dt, J = 6.9, 1.2 Hz, 1H), 6.62 (d, J = 6.2 Hz, 1H), 5.03 (dd, J = 6.5, 1.2 Hz, 1H), 4.45-4.40 (m, 2H), 3.98-3.90 (m, 1H), 3.62 (app q, J = 6.9 Hz, 1H), 3.22 (app t, 1H), 2.80 (app t, J = 6.0 Hz, 1H), 2.62-2.52 (m, 2H), 2.48-2.38 (m, 3H), 2.05-1.99 (m, 3H), 1.69-1.67 (m, 1H). MS (m/z): 492.6 |
| 231 | 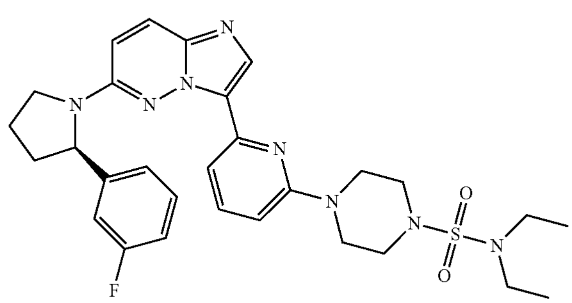 [SMILES: CCN(CC)S(=O)(=O)N1CCN(c2cccc(-c3cnc4ccc(N5CCC[C@@H]5c5cccc(F)c5)nn34)n2)CC1] | MS (m/z): 579.7 |
| 232 | 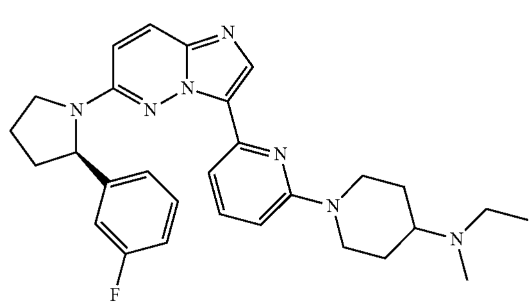 [SMILES: CCN(C)C1CCN(c2cccc(-c3cnc4ccc(N5CCC[C@@H]5c5cccc(F)c5)nn34)n2)CC1] | MS (m/z): 500.6 |

TABLE 7-continued

| Compound Number | Structure | Physical Data<br>¹H NMR 400 MHz (DMSO-d₆)<br>and/or MS (m/z) |
|---|---|---|
| 233 | 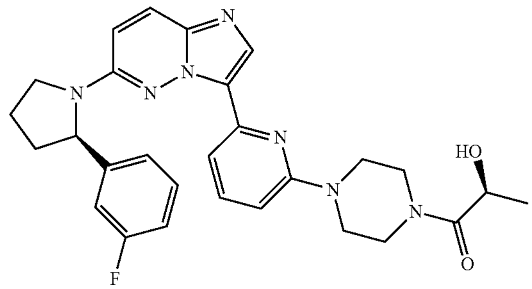 [SMILES: C[C@H](O)C(=O)N1CCN(c2cccc(-c3cnc4ccc(N5CCC[C@@H]5c5cccc(F)c5)nn34)n2)CC1] | MS (m/z): 516.6 |
| 234 | 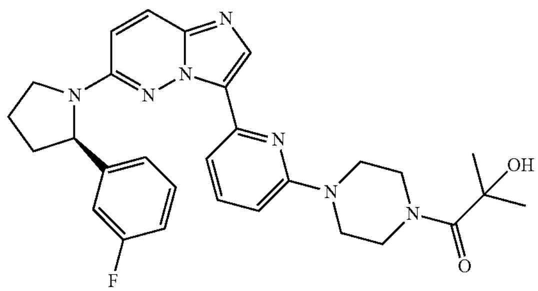 [SMILES: CC(C)(O)C(=O)N1CCN(c2cccc(-c3cnc4ccc(N5CCC[C@@H]5c5cccc(F)c5)nn34)n2)CC1] | MS (m/z): 530.6 |
| 235 | 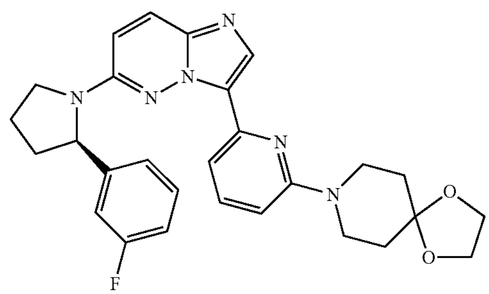 [SMILES: Fc1cccc([C@H]2CCCN2c2ccc3ncc(-c4cccc(N5CCC6(CC5)OCCO6)n4)n3n2)c1] | MS (m/z): 501.6 |
| 236 | 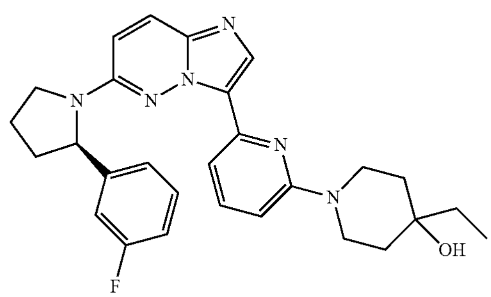 [SMILES: CCC1(O)CCN(c2cccc(-c3cnc4ccc(N5CCC[C@@H]5c5cccc(F)c5)nn34)n2)CC1] | 1H NMR (400 MHz, D3 acetonitrile) ppm: 8.18 (s, 1H), 7.92 (br s, 2H), 7.38 (br s, 2H), 7.28 (app q, J = 7.0 Hz, 1H), 7.08 (s, 1H), 7.02 (d, J = 7.3 Hz, 1H), 6.83 (app t, J = 7.2 Hz, 1H), 6.72 (d, J = 7.6 Hz, 1H), 5.08 (d, J = 6.9 Hz, 1H), 3.95-3.81 (m, 3H), 3.62 (app q, J = 6.2 Hz, 1H), 3.52 (t, J = 4.8 Hz, 1H), 3.22 (app t, J = 5.0 Hz, 2H), 2.55-2.43 (m, 1H), 2.09-1.99 (m, 2H), 1.88-1.80 (m, 1H), 1.67 (br s, 1H), 1.50-1.45 (m, 2H), 1.38 (q, J = 5.9 Hz, 2H), 0.80 (t, J = 5.0 Hz, 3H).<br>MS (m/z): 487.6 |
| 237 | 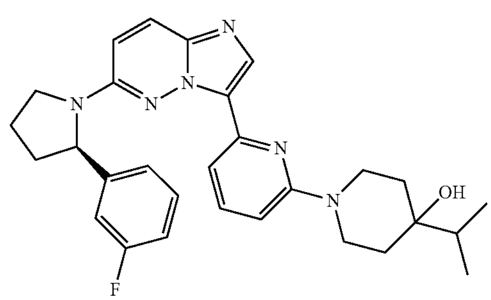 [SMILES: CC(C)C1(O)CCN(c2cccc(-c3cnc4ccc(N5CCC[C@@H]5c5cccc(F)c5)nn34)n2)CC1] | MS (m/z): 501.6 |

TABLE 7-continued

| Compound Number | Structure | Physical Data<br>¹H NMR 400 MHz (DMSO-d₆) and/or MS (m/z) |
|---|---|---|
| 238 | 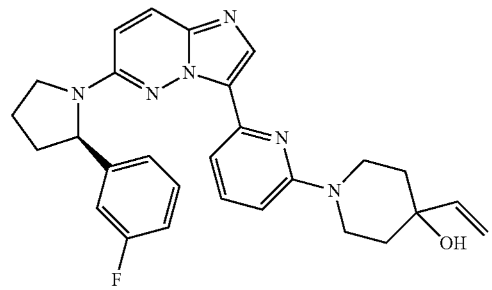 [SMILES: C=CC1(O)CCN(c2cccc(-c3cnc4ccc(N5CCC[C@@H]5c5cccc(F)c5)nn34)n2)CC1] | MS (m/z): 485.6 |
| 239 | 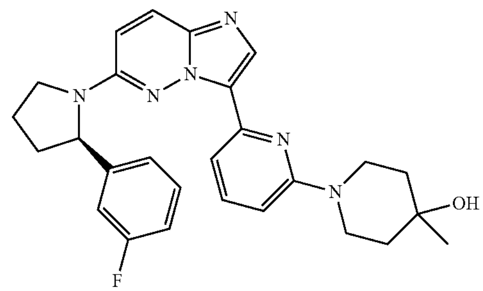 [SMILES: CC1(O)CCN(c2cccc(-c3cnc4ccc(N5CCC[C@@H]5c5cccc(F)c5)nn34)n2)CC1] | MS (m/z): 473.6 |
| 240 | 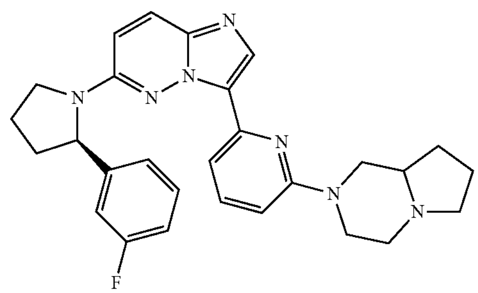 [SMILES: Fc1cccc([C@H]2CCCN2c2ccc3ncc(-c4cccc(N5CCN6CCCC6C5)n4)n3n2)c1] | 1H NMR (400 MHz, D6 acetone) ppm: 8.51 (br s, 1H), 8.41 (d, J = 8.8 Hz, 1H), 7.68-7.52 (m, 2H), 7.48 (br s, 1H), 7.38 (app q, J = 7.5 Hz, 1H), 7.20 (d, J = 7.2 Hz, 1H), 7.14 (d, J = 7.8 Hz, 1H), 6.94 (app dt, J = 7.8, 1.9 Hz, 1H), 6.90 (d, J = 5.6 Hz, 1H), 5.38 (d, J = 6.4 Hz, 1H), 5.05 (dd, J = 5.4 Hz, 1.7 Hz, 1H), 4.72 (app t, J = 7.2 Hz, 1H), 4.22 (d, J = 4.2 Hz, 2H), 4.18 (app q, J = 6.0 Hz, 1H), 4.05 (br s, 1H), 3.98-3.62 (m, 3H), 3.48-3.40 (m, 2H), 3.28-3.22 (m, 1H), 3.18-3.00 (m, 1H), 2.65-2.59 (m, 1H), 2.39-1.99 (m, 5H).<br>MS (m/z): 484.6 |
| 241 | 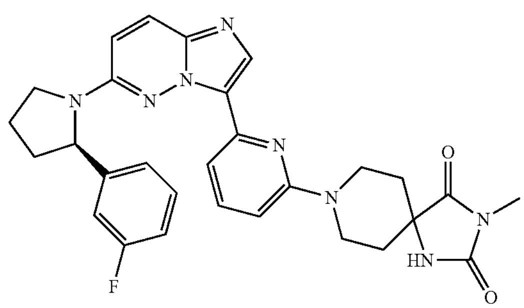 [SMILES: CN1C(=O)NC2(CCN(c3cccc(-c4cnc5ccc(N6CCC[C@@H]6c6cccc(F)c6)nn45)n3)CC2)C1=O] | MS (m/z): 541.6 |
| 242 | 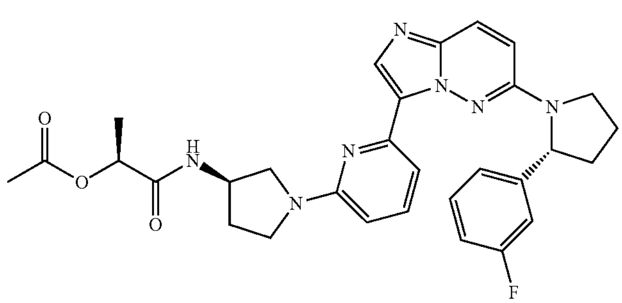 [SMILES: CC(=O)O[C@@H](C)C(=O)N[C@@H]1CCN(c2cccc(-c3cnc4ccc(N5CCC[C@@H]5c5cccc(F)c5)nn34)n2)C1] | MS (m/z): 558.6 |

TABLE 7-continued

| Compound Number | Structure | Physical Data<br>¹H NMR 400 MHz (DMSO-d₆) and/or MS (m/z) |
|---|---|---|
| 243 | 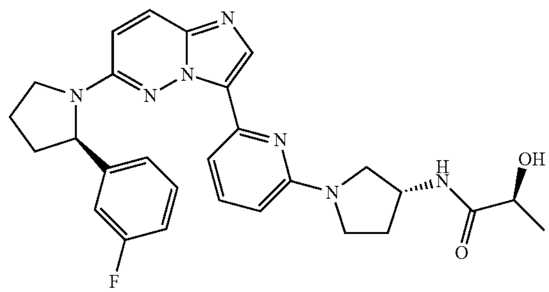 [SMILES: C[C@H](O)C(=O)N[C@@H]1CCN(c2cccc(-c3cnc4ccc(N5CCC[C@@H]5c5cccc(F)c5)nn34)n2)C1] | 1H NMR (400 MHz, D6 acetone) ppm: 8.21 (br s, 1H), 7.98-7.82 (m, 2H), 7.45 (app q, J = 6.5 Hz, 2H), 7.40 (app q, J = 6.2 Hz, 1H), 7.22 (d, J = 6.8 Hz, 1H), 7.15 (app d, J = 7.8 Hz, 1H), 6.94 (dt, J = 8.6, 1.9 Hz, 1H), 6.90 (br s, 1H), 6.42 (d, J = 6.2 Hz, 1H), 5.22 (d, J = 6.4 Hz, 1H), 4.54 (app p, J = 6.2 Hz, 1H), 4.22 (app q, J = 5.6 Hz, 2H), 3.78 (q, J = 6.8 Hz, 1H), 3.68-3.62 (m, 1H), 3.58-3.53 (m, 1H), 3.42 (dd, J = 4.8, 1.6 Hz, 1H), 3.21 (app t, J = 7.2 Hz, 2H), 2.62-2.56 (m, 1H), 2.31-2.25 (m, 1H), 2.18-1.99 (m, 3H), 1.42 (d, J = 5.4 Hz, 3H).<br>MS (m/z): 516.6 |
| 244 | 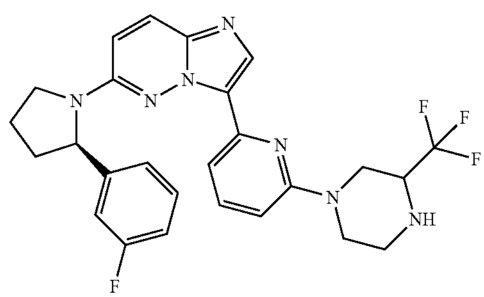 [SMILES: Fc1cccc([C@H]2CCCN2c2ccc3ncc(-c4cccc(N5CCNC(C(F)(F)F)C5)n4)n3n2)c1] | MS (m/z): 512.5 |
| 245 | 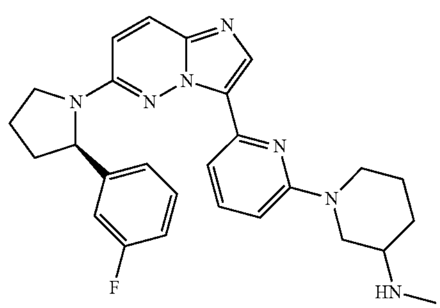 [SMILES: CNC1CCCN(c2cccc(-c3cnc4ccc(N5CCC[C@@H]5c5cccc(F)c5)nn34)n2)C1] | MS (m/z): 472.6 |
| 246 | 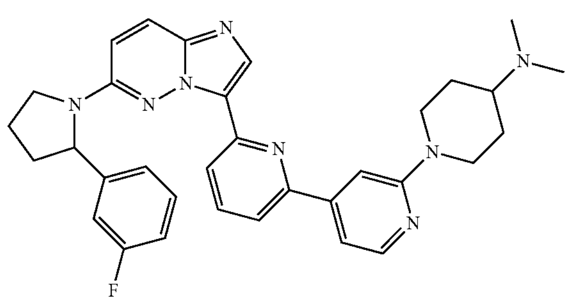 [SMILES: CN(C)C1CCN(c2cc(-c3cccc(-c4cnc5ccc(N6CCCC6c6cccc(F)c6)nn45)n3)ccn2)CC1] | 1H NMR (400 MHz, D3 acetonitrile) ppm: 8.56 (br s, 1H), 8.24 (d, J = 7.2 Hz, 1H), 8.18 (app d, J = 6.5 Hz, 2H), 7.95 (d, J = 6.2 Hz, 1H), 7.88 (br s, 1H), 7.78 (s, 1H), 7.52 (d, J = 6.4 Hz, 1H), 7.38 (app q, J = 6.8 Hz, 1H), 7.28 (br s, 1H), 7.22 (d, J = 7.2 Hz, 1H), 7.09 (d, J = 8.2 Hz, 1H), 6.92 (dt, J = 8.6, 1.9 Hz, 1H), 5.22 (dd, J = 6.9, 1.9 Hz, 1H), 4.51 (app d, J = 10 Hz, 2H), 4.02 (app q, J = 3.6 Hz, 1H), 3.78 (q, J = 6.8 Hz, 1H), 3.48 (t, J = 5.8 Hz, 1H), 3.21 (app t, J = 7.2 Hz, 2H), 2.82 (s, 6H), 2.37-2.25 (m, 2H), 2.18-2.03 (m, 2H), 1.97-1.86 (m, 4H)<br>MS (m/z): 563.7 |

TABLE 7-continued
| Compound Number | Structure | Physical Data $^1$H NMR 400 MHz (DMSO-$d_6$) and/or MS (m/z) |
|---|---|---|
| 247 | 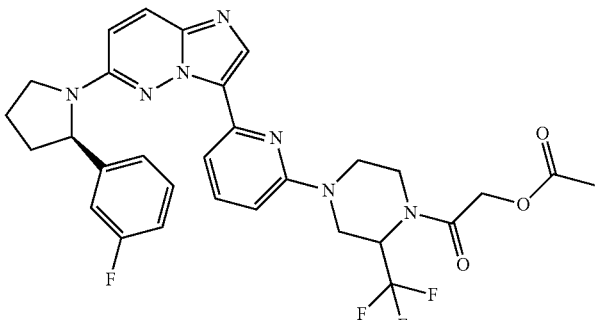 | MS (m/z): 612.6 |
| 248 | 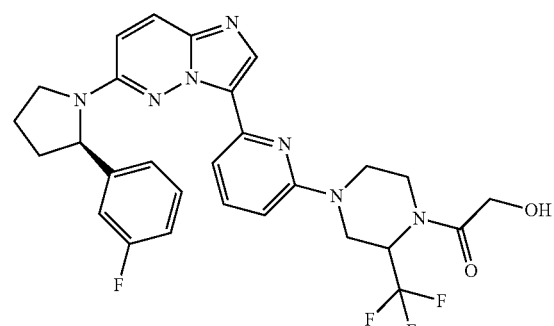 | MS (m/z): 570.6 |
| 249 | 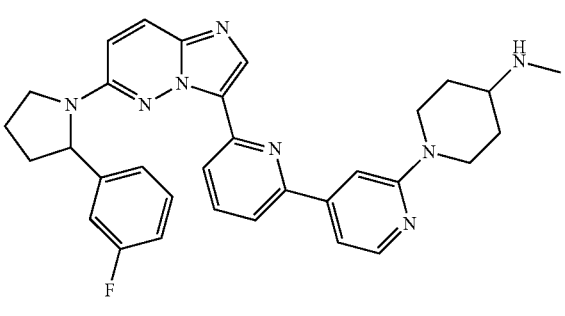 [SMILES: CNC1CCN(c2cc(-c3cccc(-c4cnc5ccc(N6CCCC6c6cccc(F)c6)nn45)n3)ccn2)CC1] | MS (m/z): 549.7 |
| 250 | 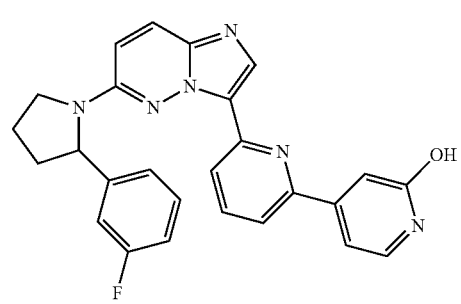 [SMILES: Oc1cc(-c2cccc(-c3cnc4ccc(N5CCCC5c5cccc(F)c5)nn34)n2)ccn1] | MS (m/z): 453.5 |

TABLE 7-continued

| Compound Number | Structure | Physical Data $^1$H NMR 400 MHz (DMSO-d$_6$) and/or MS (m/z) |
|---|---|---|
| 251 | 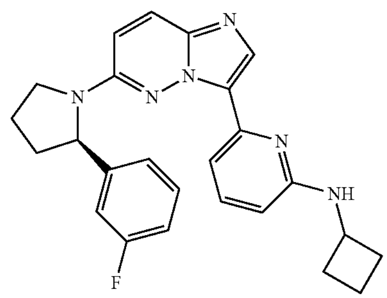 [SMILES: Fc1cccc([C@H]2CCCN2c2ccc3ncc(-c4cccc(NC5CCC5)n4)n3n2)c1] | 1H NMR (400 MHz, D3 acetonitrile) ppm: 8.61 (br s, 1H), 8.14 (d, J = 7.7 Hz, 1H), 7.62 (br s, 1H), 7.58 (s, 1H), 7.42 (app q, J = 7.8 Hz, 1H), 7.34-7.29 (m, 1H), 7.26 (d, J = 7.4 Hz, 1H), 7.17 (d, J = 7.2 Hz, 1H), 7.02 (t, J = 8.2 Hz, 1H), 6.72 (d, J = 7.6 Hz, 1H), 5.27 (dd, J = 7.9, 1.9 Hz, 1H), 4.54 (p, J = 7.6 Hz, 1H), 4.17 (app q, J = 6.6 Hz, 1H), 3.82 (q, J = 6.8 Hz, 1H), 2.77-2.67 (m, 1H), 2.48-2.35 (m, 2H), 2.38-2.06 (m, 5H), 1.97-1.82 (m, 2H) MS (m/z): 429.5 |
| 252 | 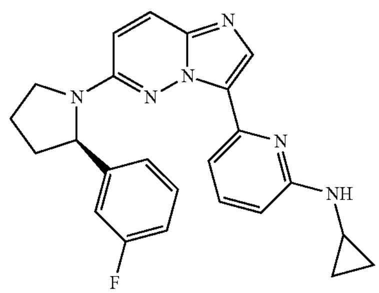 [SMILES: Fc1cccc([C@H]2CCCN2c2ccc3ncc(-c4cccc(NC5CC5)n4)n3n2)c1] | MS (m/z): 415.5 |
| 253 | 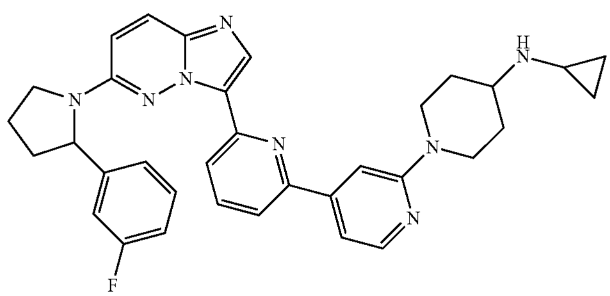 [SMILES: Fc1cccc(C2CCCN2c2ccc3ncc(-c4cccc(-c5ccnc(N6CCC(NC7CC7)CC6)c5)n4)n3n2)c1] | MS (m/z): 575.7 |
| 254 | 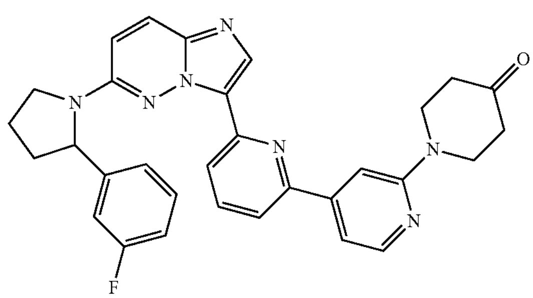 [SMILES: O=C1CCN(c2cc(-c3cccc(-c4cnc5ccc(N6CCCC6c6cccc(F)c6)nn45)n3)ccn2)CC1] | MS (m/z): 534.6 |
| 255 | 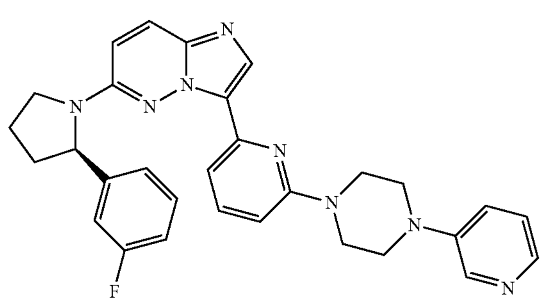 [SMILES: Fc1cccc([C@H]2CCCN2c2ccc3ncc(-c4cccc(N5CCN(c6cccnc6)CC5)n4)n3n2)c1] | MS (m/z): 521.6 |

TABLE 7-continued
| Compound Number | Structure | Physical Data <br> ¹H NMR 400 MHz (DMSO-d₆) and/or MS (m/z) |
|---|---|---|
| 256 | 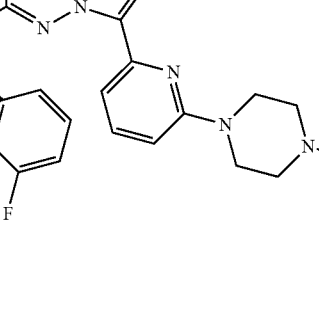 | 1H NMR (400 MHz, D3 acetonitrile) ppm: 8.38 (br s, 2H), 7.58 (s, 1H), 7.42 (q, J = 7.7 Hz, 1H), 7.39 (d, J = 6.7 Hz, 1H), 7.39-7.31 (m, 4H), 7.28 (br s, 1H), 7.22 (d, J = 6.2 Hz, 1H), 7.12 (d, J = 7.6 Hz, 1H), 6.98 (t, J = 7.2 Hz, 1H), 6.88 (d, J = 7.2 Hz, 1H), 5.27 (d, J = 7.2 Hz, 1H), 4.22-4.15 (m, 1H), 4.12-4.00 (m, 4H), 3.82 (app q, J = 6.7 Hz, 1H), 3.71-3.59 (m, 4H), 2.67-2.59 (m, 1H), 2.28-2.19 (m, 2H), 2.08-2.00 (m, 1H). <br> MS (m/z): 521.6 |
| 257 | 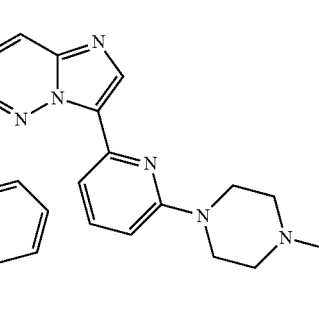 | MS (m/z): 538.6 |
| 258 | 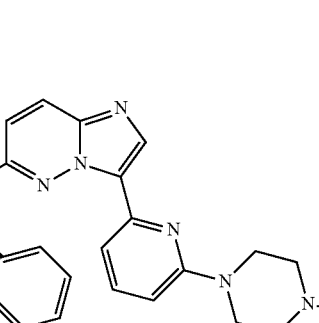 | MS (m/z): 535.6 |
| 259 | 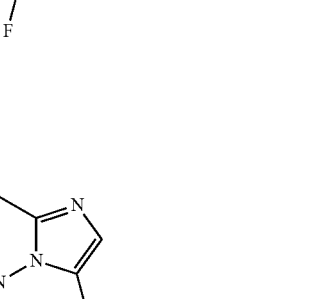 | MS (m/z): 589.6 |

TABLE 7-continued

| Compound Number | Structure | Physical Data ¹H NMR 400 MHz (DMSO-d₆) and/or MS (m/z) |
|---|---|---|
| 260 | 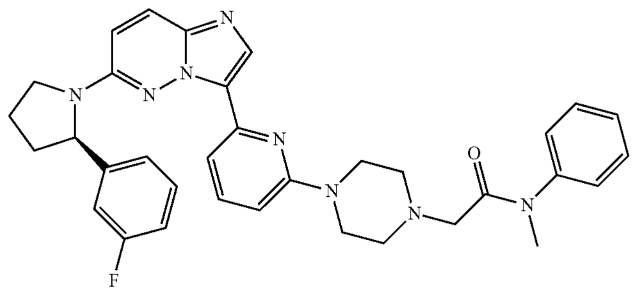 [SMILES: CN(C(=O)CN1CCN(c2cccc(-c3cnc4ccc(N5CCC[C@@H]5c5cccc(F)c5)nn34)n2)CC1)c1ccccc1] | 1H NMR (400 MHz, D3 acetonitrile) ppm: 8.35 (br s, 1H), 8.18 (app t, J = 4.5 Hz, 1H), 7.80-7.67 (m, 1H), 7.62 (app t, J = 6.7 Hz, 2H), 7.55 (q, J = 6.2 Hz, 1H), 7.35 (br s, 1H), 7.28 (d, J = 7.6 Hz, 1H), 7.22 (d, J = 7.5 Hz, 1H), 7.15 (app t, J = 8.2 Hz, 2H), 7.08 (dt, J = 7.2, 1.9 Hz, 1H), 6.95 (d, J = 6.9 Hz, 1H), 6.85-6.78 (m, 1H), 5.37 (d, J = 6.2 Hz, 1H), 4.32 (br s, 2H), 4.25-4.11 (m, 4H), 3.82 (s, 3H), 3.62-3.43 (m, 4H), 2.62-2.54 (m, 1H), 2.25-2.14 (m, 2H), 2.08-2.00 (m, 1H). MS (m/z): 591.7 |
| 261 | 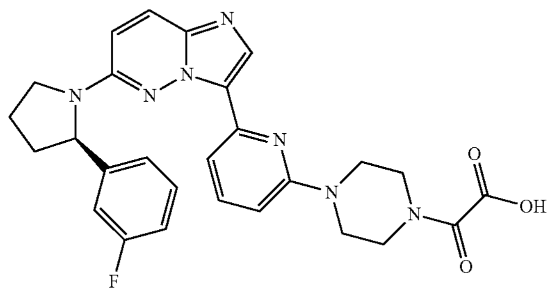 [SMILES: O=C(O)C(=O)N1CCN(c2cccc(-c3cnc4ccc(N5CCC[C@@H]5c5cccc(F)c5)nn34)n2)CC1] | MS (m/z): 516.5 |
| 262 | 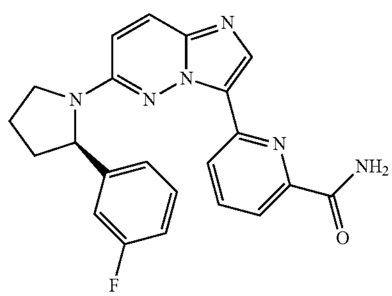 [SMILES: NC(=O)c1cccc(-c2cnc3ccc(N4CCC[C@@H]4c4cccc(F)c4)nn23)n1] | MS (m/z): 403.4 |
| 263 | 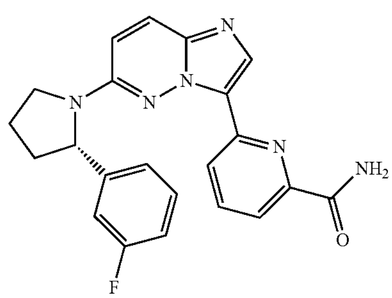 [SMILES: NC(=O)c1cccc(-c2cnc3ccc(N4CCC[C@H]4c4cccc(F)c4)nn23)n1] | MS (m/z): 403.4 |
| 264 | 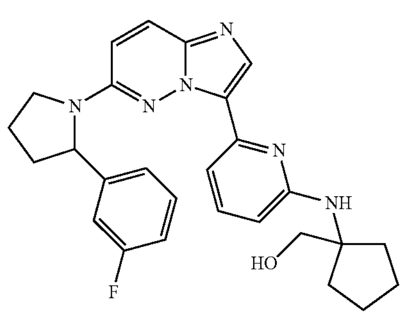 [SMILES: OCC1(Nc2cccc(-c3cnc4ccc(N5CCCC5c5cccc(F)c5)nn34)n2)CCCC1] | MS (m/z): 473.6 |

TABLE 7-continued

| Compound Number | Structure | Physical Data<br>¹H NMR 400 MHz (DMSO-d₆)<br>and/or MS (m/z) |
|---|---|---|
| 265 | 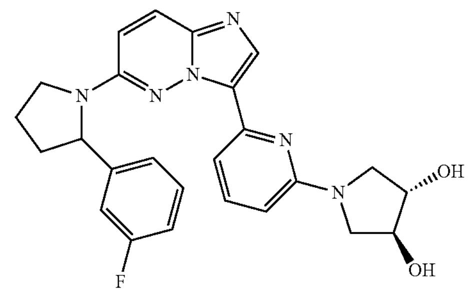 [SMILES: O[C@H]1CN(c2cccc(-c3cnc4ccc(N5CCCC5c5cccc(F)c5)nn34)n2)C[C@@H]1O] | MS (m/z): 461.5 |
| 266 | 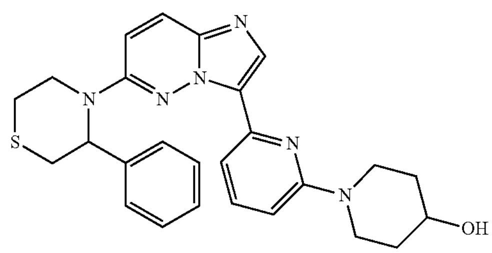 [SMILES: OC1CCN(c2cccc(-c3cnc4ccc(N5CCSCC5c5ccccc5)nn34)n2)CC1] | MS (m/z): 473.6 |
| 267 | 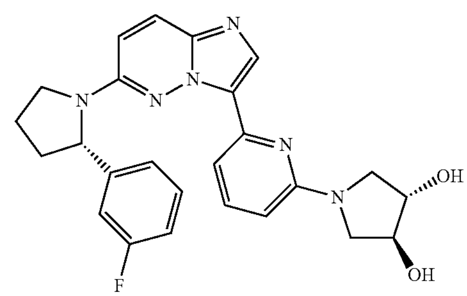 [SMILES: O[C@H]1CN(c2cccc(-c3cnc4ccc(N5CCC[C@H]5c5cccc(F)c5)nn34)n2)C[C@@H]1O] | 1H NMR 400 MHz (DMSO-d6) 7.983 (s, 1H) 7.822 (d, J = 0.024, 1H) 7.459-7.281 (m, 3H) 7.101-7.081 (m, 2H), 6.966 (dt, J = 0.021, 0.005, 1H), 6.726 (brs, 1H) 6.272 (d, J = 0.021, 1H) 5.118-5.098 (m, 2H), 3.976-3.901 (m, 2H) 3.591 (q, J = 0.021, 1H), 3.522 (dd, J = 0.027, 0.009, 2H), 2.380 (m, 1H) 1.969-1.921 (m, 3H), 1.818-1.787 (m, 2H), 1.166 (m, 2H)<br>MS (m/z): 461.5 |
| 268 | 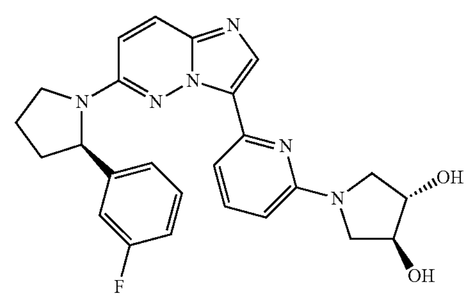 [SMILES: O[C@H]1CN(c2cccc(-c3cnc4ccc(N5CCC[C@@H]5c5cccc(F)c5)nn34)n2)C[C@@H]1O] | 1H NMR 400 MHz (DMSO-d6) 7.981 (s, 1H), 7.823 (d, J = 0.025, 1H), 7.461-7.282 (m, 3H) 7.101 (m, 2H), 6.991 (dt, J = 0.022, 0.005, 1H), 6.725 (brs, 1H) 6.272 (d, J = 0.021, 1H), 5.119 (m, 2H), 3.977-3.901 (m, 2H), 3.614 (q, J = 0.021, 1H), 3.516 (dd, J = 0.028, 0.009, 2H), 2.380 (m, 1H), 2.001-1.921 (m, 3H), 1.831-1.792 (m, 2H), 1.167 (m, 2H)<br>MS (m/z): 461.5 |
| 269 | 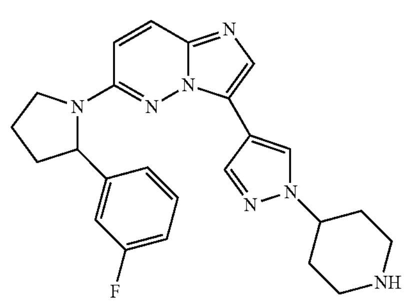 [SMILES: Fc1cccc(C2CCCN2c2ccc3ncc(-c4cnn(C5CCNCC5)c4)n3n2)c1] | MS (m/z): 432.5 |

TABLE 7-continued

| Compound Number | Structure | Physical Data $^1$H NMR 400 MHz (DMSO-d$_6$) and/or MS (m/z) |
|---|---|---|
| 270 | 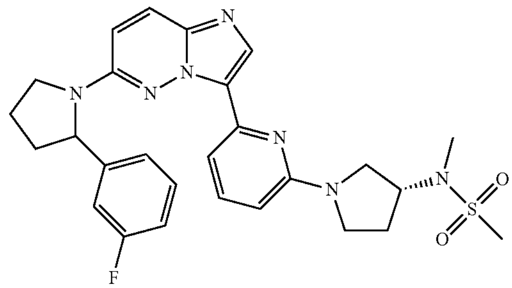 [SMILES: CN([C@@H]1CCN(c2cccc(-c3cnc4ccc(N5CCCC5c5cccc(F)c5)nn34)n2)C1)S(C)(=O)=O] | 1H NMR 400 MHz (DMSO-d6) 8.019 (s, 1H), 7.828 (d, J = 0.025, 1H), 7.507-7.282 (m, 3H), 7.105-7.081 (m, 2H), 6.988-6.943 (m, 1H) 6.725 (brs, 1H) 6.356 (d, J = 0.021, 1H), 5.111-5.091 (m, 1H), 4.483 (p, J = 0.019, 1H), 3.952-3.900 (m, 1H), 3.649-3.572 (m, 1H), 3.441-3.400 (m, 1H), 3.359-3.305 (m, 2H), 2.921 (s, 3H), 2.714 (s, 3H), 2.170-2.041 (m, 2H) 2.002, 1.929 (m, 2H), 1.832-1.771 (m, 1H) MS (m/z): 536.6 |
| 271 | 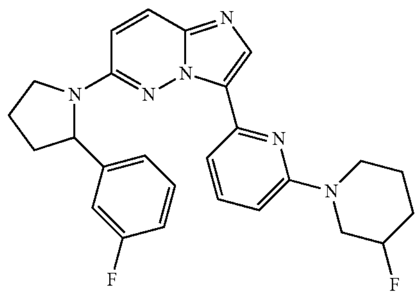 [SMILES: Fc1cccc(C2CCCN2c2ccc3ncc(-c4cccc(N5CCCC(F)C5)n4)n3n2)c1] | MS (m/z): 461.5 |
| 272 | 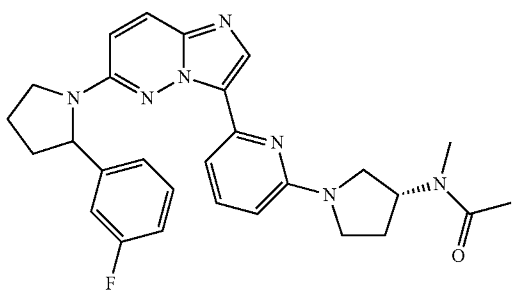 [SMILES: CC(=O)N(C)[C@@H]1CCN(c2cccc(-c3cnc4ccc(N5CCCC5c5cccc(F)c5)nn34)n2)C1] | MS (m/z): 500.6 |
| 273 | 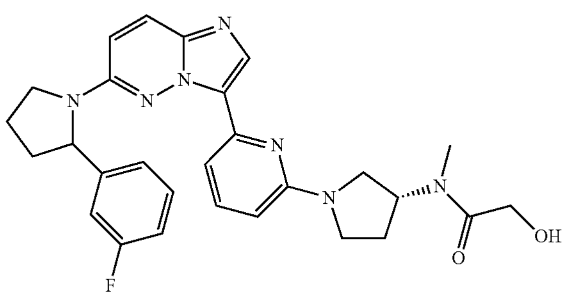 [SMILES: CN(C(=O)CO)[C@@H]1CCN(c2cccc(-c3cnc4ccc(N5CCCC5c5cccc(F)c5)nn34)n2)C1] | MS (m/z): 516.6 |
| 274 | 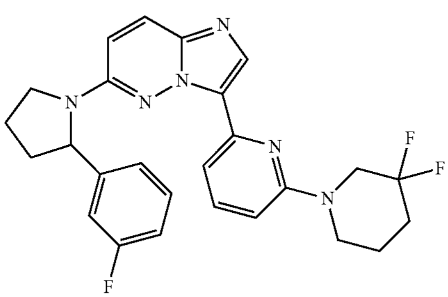 [SMILES: Fc1cccc(C2CCCN2c2ccc3ncc(-c4cccc(N5CCCC(F)(F)C5)n4)n3n2)c1] | MS (m/z): 479.5 |

TABLE 7-continued

| Compound Number | Structure | Physical Data<br>¹H NMR 400 MHz (DMSO-d₆)<br>and/or MS (m/z) |
|---|---|---|
| 275 | 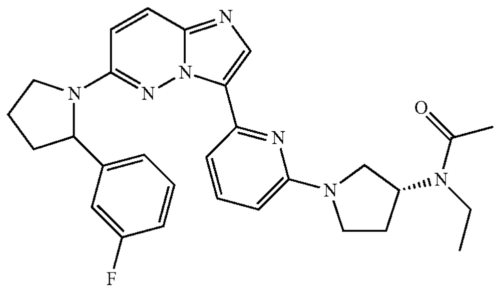 [SMILES: CCN(C(C)=O)[C@@H]1CCN(c2cccc(-c3cnc4ccc(N5CCCC5c5cccc(F)c5)nn34)n2)C1] | MS (m/z): 514.6 |
| 276 | 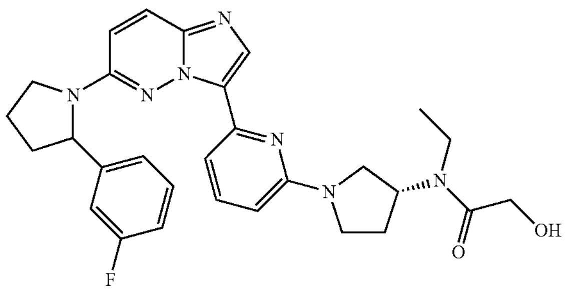 [SMILES: CCN(C(=O)CO)[C@@H]1CCN(c2cccc(-c3cnc4ccc(N5CCCC5c5cccc(F)c5)nn34)n2)C1] | MS (m/z): 530.6 |
| 277 | 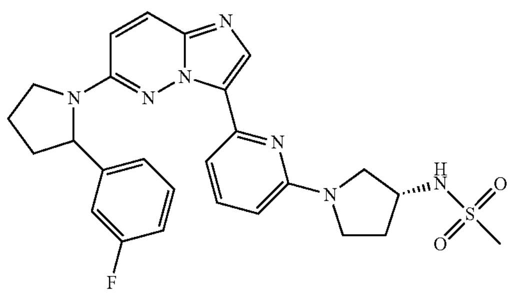 [SMILES: CS(=O)(=O)N[C@@H]1CCN(c2cccc(-c3cnc4ccc(N5CCCC5c5cccc(F)c5)nn34)n2)C1] | MS (m/z): 522.6 |
| 278 | 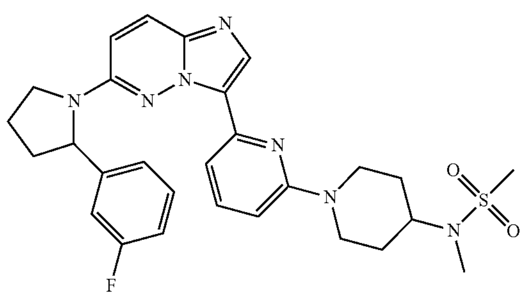 [SMILES: CN(C1CCN(c2cccc(-c3cnc4ccc(N5CCCC5c5cccc(F)c5)nn34)n2)CC1)S(C)(=O)=O] | MS (m/z): 550.7 |
| 279 | 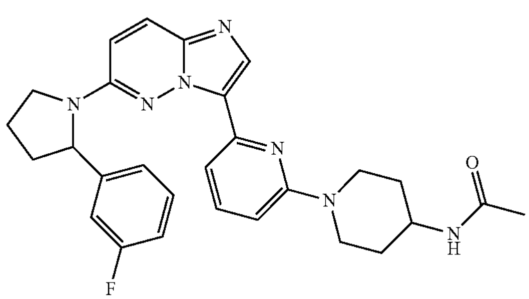 [SMILES: CC(=O)NC1CCN(c2cccc(-c3cnc4ccc(N5CCCC5c5cccc(F)c5)nn34)n2)CC1] | 1H NMR 400 MHz (DMSO-d6) 7.981 (s, 1H), 7.829 (d, J = 0.024, 1H), 7.741 (d, J = 0.02, 1H), 7.475-7.217 (m, 3H), 7.098-7.078 (m, 2H), 6.990 (dt, J = 0.022, 0.005, 1H), MS (m/z): 500.6 |

TABLE 7-continued

| Compound Number | Structure | Physical Data <br> ¹H NMR 400 MHz (DMSO-d₆) and/or MS (m/z) |
|---|---|---|
| 280 | 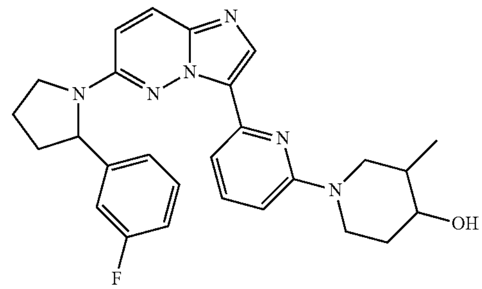 [SMILES: CC1CN(c2cccc(-c3cnc4ccc(N5CCCC5c5cccc(F)c5)nn34)n2)CCC1O] | 1H NMR 400 MHz (DMSO-d6) 8.041 (s, 1H), 7.902 (d, J = 0.025, 1H), 7.476-7.265 (m, 3H), 7.169 (d, J = 0.02, 2H), 7.055, (t, J = 0.02, 1H), 6.824 (brs, 1H), 6.763 (d, J = 0.022, 1H), 5.177 (d, J = 0.20, 1H), 4.341 (d, J = 0.033, 1H), 4.248 (d, J = 0.031, 1H), 4.018-3.967 (m, 1H), 3.701 (q, J = 0.021, 1H), 3.207-3.133 (m, 1H), 2.878 (t, J = 0.021, 1H), 2.070-1.998 (m, 3H), 1.888-1.830 (m, 2H), 1.477-1.292 (m, 3H), 0.988 (d, J = 0.016, 3H) <br> MS (m/z): 473.6 |
| 281 | 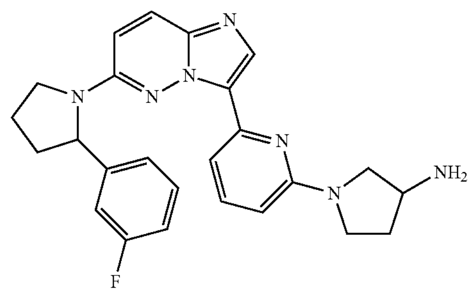 [SMILES: NC1CCN(c2cccc(-c3cnc4ccc(N5CCCC5c5cccc(F)c5)nn34)n2)C1] | MS (m/z): 444.5 |
| 282 | 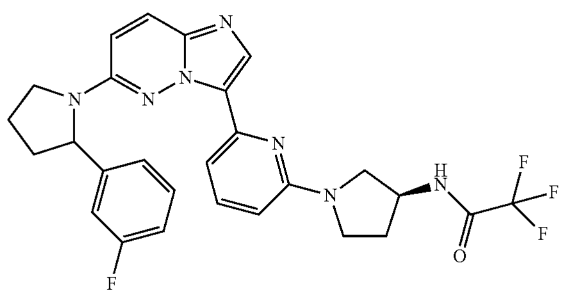 [SMILES: O=C(N[C@H]1CCN(c2cccc(-c3cnc4ccc(N5CCCC5c5cccc(F)c5)nn34)n2)C1)C(F)(F)F] | MS (m/z): 540.5 |
| 283 | 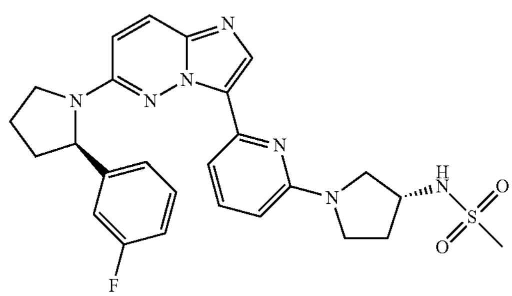 [SMILES: CS(=O)(=O)N[C@@H]1CCN(c2cccc(-c3cnc4ccc(N5CCC[C@@H]5c5cccc(F)c5)nn34)n2)C1] | 1H NMR 400 MHz (DMSO-d6) 8.061 (s, 1H), 7.871 d, J = 0.019, 1H), 7.386-7.287 (m, 3H), 7.102-7.081 (m, 2H), 6.992 (dt, J = 0.019, 0.004, 1H), 6.831 (brs, 1H), 6.343 (d, J = 0.023, 1H), 5.122 (dd, J = 0.02, 0.006, 1H), 4.108-3.908 (m, 2H), 3.713 (dd, J = 0.026, 0.010, 1H), 3.638 (q, J = 0.020, 1H), 3.536-3.478 (m, 1H), 3.375 (q, J = 0.018, 1H), 3.313 (dd, J = 0.027, 0.014, 1H), 2.409-2.359 (m, 1H), 2.223 (sextet, J = 0.015, 1H), 2.009-1.776 (m, 4H) <br> MS (m/z): 522.6 |
| 284 | 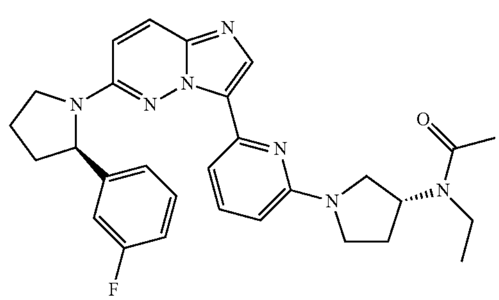 [SMILES: CCN(C(C)=O)[C@@H]1CCN(c2cccc(-c3cnc4ccc(N5CCC[C@@H]5c5cccc(F)c5)nn34)n2)C1] | 1H NMR 400 MHz (DMSO-d6) 8.047 (d, J = 0.038, 1H), 7.893 (d, J = 0.025, 1H), 7.571-7.355 (m, 3H), 7.170-7.149 (m, 2H), 7.059 (dt, J = 0.019, 0.004, 1H), 6.802 (brs, 1H), 6.413 (t, J = 0.022, 1H), 5.182 (dd, J = 0.02, 0.006, 1H), 4.879 (p, J = 0.020, 1H), 4.622 (p, J = 0.020, 1H), 4.059-3.967 (m, 1H), 3.699-3.636 (m, 3H), 3.392-3.23 (m, 2H), 2.209-1.994 (m, 7H), 1.90-1.818 (m, 1H), 1.196-1.135 (m, 2H), 1.079 (t, J = 0.017, 2H) <br> MS (m/z): 514.6 |

TABLE 7-continued

| Compound Number | Structure | Physical Data<br>¹H NMR 400 MHz (DMSO-d₆)<br>and/or MS (m/z) |
|---|---|---|
| 285 | 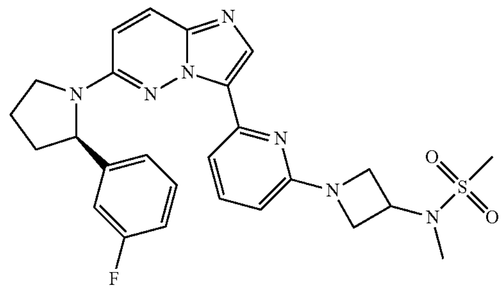 [SMILES: CN(C1CN(c2cccc(-c3cnc4ccc(N5CCC[C@@H]5c5cccc(F)c5)nn34)n2)C1)S(C)(=O)=O] | MS (m/z): 522.6 |
| 286 | 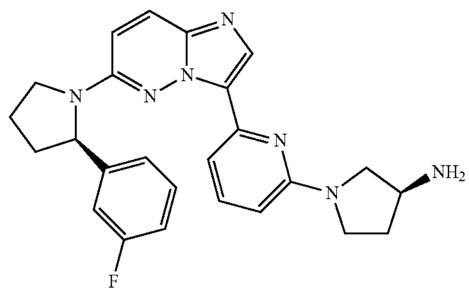 [SMILES: N[C@H]1CCN(c2cccc(-c3cnc4ccc(N5CCC[C@@H]5c5cccc(F)c5)nn34)n2)C1] | 1H NMR 400 MHz (DMSO-d6) 7.969 (s, 1H), 7.815 (d, J = 0.024, 1H), 7.397-7.279 (m, 3H), 7.096-7.069 (m, 2H), 6.984 (dt, J = 0.022, 0.006, 1H), 6.738 (brs, 1H), 6.256 (d, J = 0.022, 1H), 5.111 (dd, J = 0.020, 0.006, 1H), 3.946-3.895 (m, 1H), 3.628 (q, J = 0.021, 1H), 3.515-3.439 (m, 3H), 3.374-3.314 (m, 1H), 3.047 (q, J = 0.017, 1H), 2.405-2.355 (m, 1H), 2.018-1.922 (m, 3H), 1.827-1.766 (m, 3H), 1.666 (sextet, J = 0.016, 1H)<br>MS (m/z): 444.5 |
| 287 | 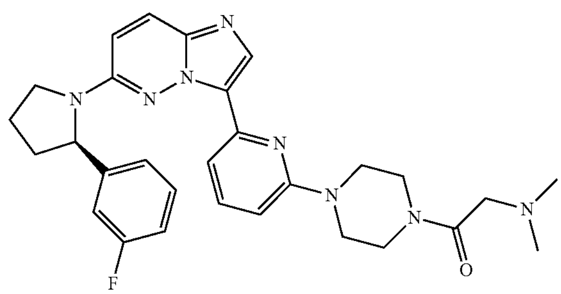 [SMILES: CN(C)CC(=O)N1CCN(c2cccc(-c3cnc4ccc(N5CCC[C@@H]5c5cccc(F)c5)nn34)n2)CC1] | MS (m/z): 529.6 |
| 288 | 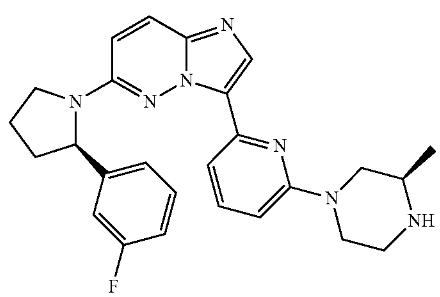 [SMILES: C[C@@H]1CN(c2cccc(-c3cnc4ccc(N5CCC[C@@H]5c5cccc(F)c5)nn34)n2)CCN1] | MS (m/z): 458.5 |
| 289 | 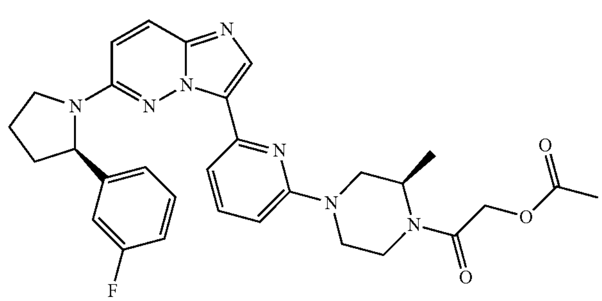 [SMILES: CC(=O)OCC(=O)N1CCN(c2cccc(-c3cnc4ccc(N5CCC[C@@H]5c5cccc(F)c5)nn34)n2)C[C@H]1C] | MS (m/z): 558.6 |

TABLE 7-continued

| Compound Number | Structure | Physical Data ¹H NMR 400 MHz (DMSO-d₆) and/or MS (m/z) |
|---|---|---|
| 290 | 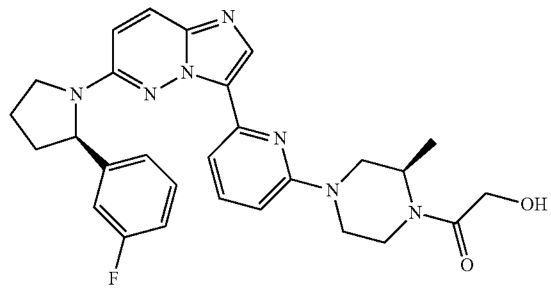 [SMILES: C[C@@H]1CN(c2cccc(-c3cnc4ccc(N5CCC[C@@H]5c5cccc(F)c5)nn34)n2)CCN1C(=O)CO] | MS (m/z): 516.6 |
| 291 | 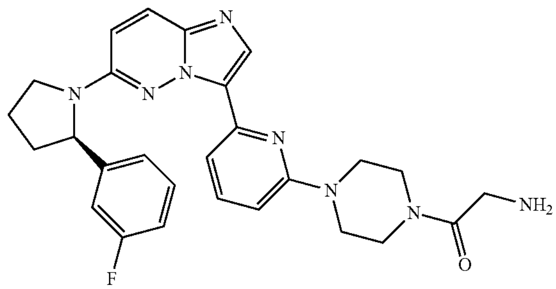 [SMILES: NCC(=O)N1CCN(c2cccc(-c3cnc4ccc(N5CCC[C@@H]5c5cccc(F)c5)nn34)n2)CC1] | MS (m/z): 501.6 |
| 292 | 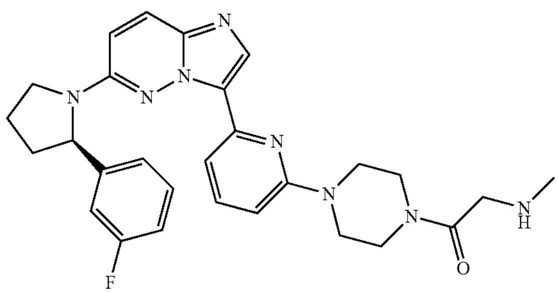 | MS (m/z): 515.6 |
| 293 | 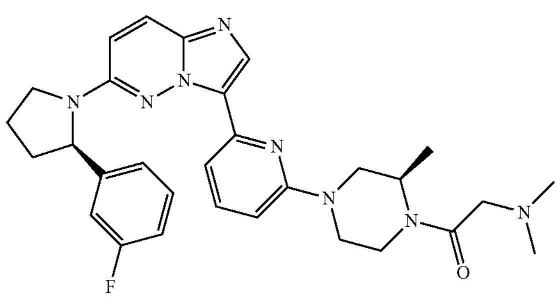 [SMILES: C[C@@H]1CN(c2cccc(-c3cnc4ccc(N5CCC[C@@H]5c5cccc(F)c5)nn34)n2)CCN1C(=O)CN(C)C] | MS (m/z): 543.7 |
| 294 | 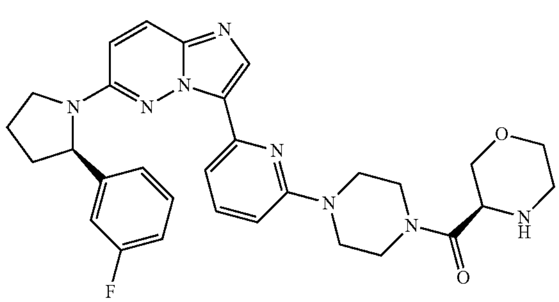 [SMILES: O=C([C@H]1COCCN1)N1CCN(c2cccc(-c3cnc4ccc(N5CCC[C@@H]5c5cccc(F)c5)nn34)n2)CC1] | MS (m/z): 557.6 |

TABLE 7-continued

| Compound Number | Structure | Physical Data<br>¹H NMR 400 MHz (DMSO-d₆)<br>and/or MS (m/z) |
|---|---|---|
| 295 | 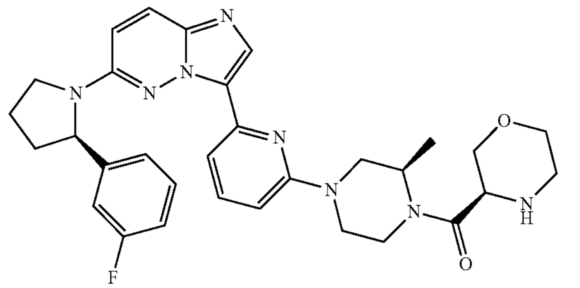 [SMILES: C[C@@H]1CN(c2cccc(-c3cnc4ccc(N5CCC[C@@H]5c5cccc(F)c5)nn34)n2)CCN1C(=O)[C@H]1COCCN1] | MS (m/z): 571.7 |
| 296 | 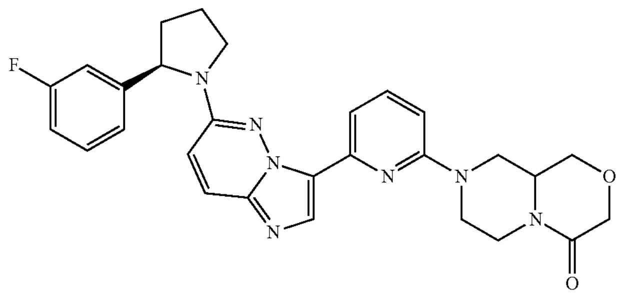 [SMILES: O=C1COCC2CN(c3cccc(-c4cnc5ccc(N6CCC[C@@H]6c6cccc(F)c6)nn45)n3)CCN12] | MS (m/z): 514.6 |
| 297 | 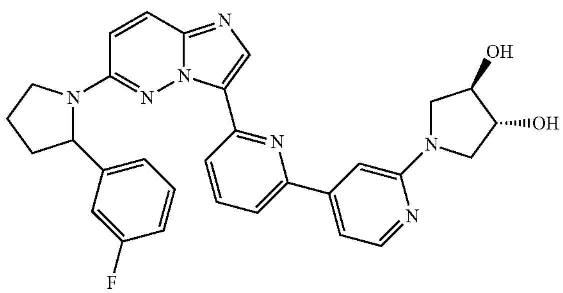 [SMILES: O[C@@H]1CN(c2cc(-c3cccc(-c4cnc5ccc(N6CCCC6c6cccc(F)c6)nn45)n3)ccn2)C[C@H]1O] | 1H NMR 400 MHz (DMSO-d6) 8.472 (s, 1H), 8.165 (d, J = 0.019, 1H), 8.003-7.976 (m, 2H), 7.888 (brs, 1H), 7.630-7.600 (m, 2H), 7.376 (q, J = 0.019, 1H), 7.148 (d, J = 0.019, 2H), 7.010 (t, J = 0.019, 2H), 5.496 (brs, 2H), 5.160 (d, J = 0.017, 1H), 4.148 (d, J = 0.007, 2H), 7.007-3.953 (m, 1H), 3.806 (d, J = 0.022, 3H), 3.674-3.582 (m, 4H), 2.031-1.958 (m, 2H), 1.854-1.819 (m, 1H)<br>MS (m/z): 538.6 |

Assays

Preparation of Compound Dilutions

Test compounds were dissolved in DMSO (10 mM) and transferred into 1.4 mL flat bottom or V-shaped Matrix tubes carrying a unique 2D matrix chip by individual compound hubs. The numbers of these chips were distinctively linked to the individual compound identification numbers. The stock solutions were stored at −20° C. if not used immediately. For the test procedure the vials were defrosted and identified by a scanner whereby a working sheet is generated that guides the subsequent working steps.

Compound dilutions were made in 384 well plates. This format enabled the assay of maximally 28 individual test compounds at 12 concentrations (single points) including 2 reference compounds. The dilution protocol included the production of pre-dilution plates, master plates and assay plates:

Compound plates: 30 µL of individual compound (10 mM) DMSO solution including standard compound were transferred into columns 1 and 13 of a 384 well plate. 20 µL of DMSO were added to the rest of the wells and the compounds were serially diluted (1:3) by transferring 10 µL from a well in column 1 or 13 to the next well in column 2 or 14 respectively and successively with the help of a Minitrack robot.

Assay plates: Identical assay plates were then prepared by adding 50 mL each of compound dilutions of the compound plates into 384-well "assay plates". In the following the compounds were mixed with 50 µL of assays components (cells or enzyme) and tested for their inhibitory activity.

Compounds of Formula (I) were assayed to measure their capacity to inhibit TrkA, TrkB, and/or TrkC protein kinases. Other compounds of Formula (I) were assayed to measure their capacity to inhibit a kinase panel, including but not limited to Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK protein kinases.

Effect on Proliferation of Various Kinases Dependent Cells

Compounds of Formula (I) were tested for their antiproliferative effect on Ba/F3 cells expressing either Tel-TrkA, Tel-TrkB or Tel-TrkC and an additional panel of 34 selected diverse kinases activated by fusion to the dimerizing partners Bcr or Tel (Abl, A1K, BMX, EphA3, EphB2, FGFR2, FGFR3, FGFR4, FGR, FLT1, FLT3, FLT4, FMS, IGF1R, InsR, JAK1, JAK2, JAK3, KDR, Kit, Lck, Lyn, MER, MET, PDGFRb, RET, RON, Ros-1, Src, Aurora, TIE2, TYK2, Tie1, ZAP70). The antiproliferative effect of these compounds on the different cell lines and on the non transformed cells were tested at 12 different concentrations of 3-fold serially diluted compounds in 384 well plates as described above (in media lacking IL3). The $IC_{50}$ values of the compounds the different cell lines were determined from dose response curves.

Upstate KinaseProfiler™—Radio-Enzymatic Filter Binding Assay

Compounds of Formula (I) were assessed for their ability to inhibit individual members of a panel of kinases (a partial, non-limiting list of kinases includes: Abl, Aurora, cSrc, TPR-Met, Tie2, MET, FGFR3, Ax1, Bmx, BTK, c-kit, CHK2, FLT3, MST2, p70S6K, PDGFR, PKB, PKCα, Raf, ROCK-II, Rsk1, SGK, TrkA, TrkB and TrkC, Ros, KDR, FMS, c-FMS, JAK2, JAK3, Lck, IGF-1R, ALK4, ALK5 and ALK kinases). The compounds were tested in duplicates at a final concentration of 10 µM following this generic protocol. Note that the kinase buffer composition and the substrates vary for the different kinases included in the "Upstate KinaseProfiler™" panel. Kinase buffer (2.5 µL, 10×—containing $MnCl_2$ when required), active kinase (0.001-0.01 Units; 2.5 µL), specific or Poly(Glu4-Tyr) peptide (5-500 µM or 0.01 mg/ml) in kinase buffer and kinase buffer (50 µM; 5 µL) were mixed in an eppendorf on ice. A Mg/ATP mix (10 µL; 67.5 (or 33.75) mM $MgCl_2$, 450 (or 225) µM ATP and 1 µCi/µl [$\gamma$-$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu4-Tyr) peptide substrate) paper square. The assay squares were washed 4 times, for 5 minutes each, with 0.75% phosphoric acid and washed once with acetone for 5 minutes. The assay squares were transferred to a scintillation vial, 5 ml scintillation cocktail were added and $^{32}$P incorporation (cpm) to the peptide substrate is quantified with a Beckman scintillation counter. Percentage inhibition is calculated for each reaction.

Inhibition of Cellular TrkA, TrkB and TrkC Dependent Proliferation

Compounds of Formula (I) were assayed to measure their capacity to selectively inhibit cell proliferation of Ba/F3 cells expressing activated TrkA, TrkB or TrkC through fusion to the dimerization domain of Tel (ETV6) transcription factor as well as Ba/F3 cells co-expressing full length rTrkA and mNGF compared with parental BaF3 cells.

The cell line used is the luciferase expressing Ba/F3 murine hematopoietic progenitor cell line transformed with human Tel-TrkA, Tel-TrkB or Tel-TrkC cDNAs (Ba/F3 EN A/B/C). These cells maintained in RPMI/10% fetal bovine serum (RPMI/FCS) supplemented with penicillin 50 mg/mL, streptomycin 50 mg/mL and L-glutamine 200 mM. Untransformed Ba/F3 cells were similarly maintained with the addition 5 ng/ml of murine recombinant IL3. 50 µl of a Ba/F3 or Ba/F3 EN A/B/C cell suspension were plated in Greiner 384 well microplates (white)) at a density of 2000 cells per well. 50 nl of serially diluted test compound (10-0.0001 mM in DMSO solution) is added to each well. The cells were incubated for 48 hours at 37° C., 5% $CO_2$. 25 µl of Bright Glo® (Promega) luciferase substrate is added to each well. The emited luminiscence is quantified using the ACQUEST™ luminescence system (Molecular Devices). $IC_{50}$ values were calculated by linear regression analysis of the percentage inhibition of each compound at 12 concentrations.

Inhibition of Cellular Anaplastic Lymphoma Kinase (ALK) Kinase Activity

The inhibition of ALK tyrosine kinase activity is demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase were performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [$\gamma$-$^{33}$P]-ATP, 2 µM ATP, 3 µg/mL poly (Glu, Tyr 4:1) Poly-EY (Sigma P-0275), 1% DMSO, 25 ng ALK enzyme. Assays were incubated for 10 mM at ambient temperature. Reactions were terminated by adding 50 µl of 125 mM EDTA, and the reaction mixture is transferred onto a MAIP Multiscreen plate (Millipore, Bedford, Mass., USA), previously wet with methanol, and rehydrated for 5 minutes with $H_2O$. Following washing (0.5% $H_3PO_4$), plates were counted in a liquid scintillation counter. $IC_{50}$ values were calculated by linear regression analysis of the percentage inhibition.

Compounds of Formula (I) potently inhibit the growth of human NPM-ALK overexpressing murine BaF3 cells. The expression of NPM-ALK is achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and results in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of Formula (I) is determined as follows. In general, BaF3-NPM-ALK cells (15,000/microtitre plate well) were transferred to 96-well microtitre plates. Test compounds dissolved in dimethyl sulfoxide (DMSO) were added in a series of concentrations (dilution series) in such a manner that the final concentration of DMSO is not greater than 1% (v/v). After the addition, the plates were incubated for two days during which the control cultures without test compound were able to undergo two cell-division cycles. The growth of the BaF3-NPM-ALK cells is measured by means of YOPRO™ staining [T Idziorek et al. J. Immunol. Methods; 185: 249-258 (1995)]: 25 µl of lysis buffer comprising 20 mM sodium citrate, pH 4.0, 26.8 mM sodium chloride, 0.4% NP40, 20 mM EDTA and 20 mM is added to each well. Cell lysis is completed within 60 minutes at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

$IC_{50}$ values were determined by a computer-aided system using the formula: $IC_{50}=[(ABS_{test}-ABS_{start})/(ABS_{control}-ABS_{start})]\times 100$. (ABS=absorption). The $IC_{50}$ value is given as the concentration of the test compound in question that results in a cell count that is 50% lower than that obtained using the control without inhibitor.

The antiproliferative action of compounds of Formula (I) were also determined in the human KARPAS-299 lymphoma cell line (DSMZ Deutsche Sammiung von Mikroorganismen and Zellkulturen GmbH, Braunschweig, Germany, described in W G Dirks et al. Int. J. Cancer 100, 49-56 (2002)) using the same methodology described above for the BaF3-NPM-ALK cell line. In some embodiments, compounds of Formula (I) exhibit inhibitory activity with an $IC_{50}$ in the range from approximately 0.01 to 1 µM. The action of compounds of Formula (I) on autophosphorylation of the ALK is determined in the human KARPAS-299 lymphoma cell line by means of an immunoblot as described in W G Dirks et al. Int. J. Cancer 100, 49-56 (2002).

Inhibition of Cellular KDR Dependent Proliferation

Compounds of Formula (I) were assayed to measure their capacity to selectively inhibit cell proliferation of Ba/F3 cells expressing activated KDR through fusion to the dimerization domain of Tel (ETV6) transcription factor compared with parental BaF3 cells.

Luciferase expressing Ba/F3 murine pro-B cells were transformed with Tel-KDR. Cells were maintained in RPMI/10% fetal calf serum (RPMI/FCS) supplemented with penicillin 50 µg/mL, streptomycin 50 µg/mL and L-glutamine 200 mM. Untransformed Ba/F3 cells were similarly maintained with the addition of murine recombinant IL3. Cells were dispensed into 384-well format plate at 5000 cell/well in 50 µL of culture medium. Compounds of Formula (I) were dissolved and diluted in dimethylsufoxide (DMSO). Twelve points 1:3 serial dilutions were made into DMSO to create concentrations gradient ranging from 10 mM to 0.05 µM. Cells were added with 50 nL of diluted compounds and incubated for 48 hours in cell culture incubator. Luminescent signal is measured following the addition of Bright Glo® (Promega) luciferase substrate. $IC_{50}$ values were calculated by linear regression analysis of the percentage inhibition of each compound at 12 concentrations.

FLT-3 (Enzymatic Assay)

Kinase activity assay with purified FLT-3 (Upstate) is carried out in a final volume of 10 µL containing 0.25 µg/mL of enzyme in kinase buffer (30 mM Tris-HCl pH7.5, 15 mM $MgCl_2$, 4.5 mM $MnCl_2$, 15 µM $Na_3VO_4$ and 50 µg/mL BSA), and substrates (5 µg/mL biotin-poly-EY(Glu, Tyr) (CIS-US, Inc.) and 3 µM ATP). Two solutions were made: the first solution of 5 µl contains the FLT-3 enzyme in kinase buffer is first dispensed into 384-well format ProxiPlate® (Perkin-Elmer) followed by adding 50 nL of compounds dissolved in DMSO, then 5 µl of second solution contains the substrate (poly-EY) and ATP in kinase buffer is added to each wells. The reactions were incubated at room temperature for one hour, stopped by adding 10 µL of HTRF detection mixture, which contains 30 mM Tris-HCl pH 7.5, 0.5 M KF, 50 mM ETDA, 0.2 mg/mL BSA, 15 µg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals were read on Analyst GT (Molecular Devices Corp.). $IC_{50}$ values were calculated by linear regression analysis of the percentage inhibition of each compound at 12 concentrations (1:3 dilution from 50 µM to 0.28 nM). In this assay, compounds of Formula (I) have an $IC_{50}$ in the range of 10 nM to 2 µM.

FLT-3 (Cellular Assay)

Compounds of Formula (I) were tested for their ability to inhibit transformed Ba/F3-FLT3-ITD cell proliferation, which is depended on FLT-3 cellular kinase activity. Ba/F3-FLT3-ITD were cultured up to 800,000 cells/mL in suspension, with RPMI 1640 supplemented with 10% fetal bovine serum as the culture medium. Cells were dispensed into 384-well format plate at 5000 cell/well in 50 µL culture medium. Compounds of Formula (I) were dissolved and diluted in dimethylsulfoxide (DMSO). Twelve points 1:3 serial dilutions were made into DMSO to create concentrations gradient ranging typically from 10 mM to 0.05 µM. Cells were added with 50 nL of diluted compounds and incubated for 48 hours in cell culture incubator. AlamarBlue® (TREK Diagnostic Systems), which can be used to monitor the reducing environment created by proliferating cells, were added to cells at final concentration of 10%. After additional four hours of incubation in a 37° C. cell culture incubator, fluorescence signals from reduced AlamarBlue® (Excitation at 530 nm, Emission at 580 nm) were quantified on Analyst GT (Molecular Devices Corp.). $IC_{50}$ values were calculated by linear regression analysis of the percentage inhibition of each compound at 12 concentrations cKit—Proliferation Assay Compounds were tested for their ability to inhibit the proliferation of wt Ba/F3 cells and Ba/F3 cells transformed with Tel c-kit fused tyrosine kinases. Untransformed Ba/F3 cells were maintained in media containing recombinant IL3. Cells were plated into 384 well TC plates at 5,000 cells in 50 ul media per well and test compound at 0.06 nM to 10 µM is added. The cells were then incubated for 48 hours at 37° C., 5% CO2. After incubating the cells, 25 µL of BRIGHT GLO® (Promega) is added to each well following manufacturer's instructions and the plates were read using Analyst GT—Luminescence mode—50000 integration time in RLU. IC50 values, the concentration of compound required for 50% inhibition, were determined from a dose response curve.

cKit—Mo7e Assay

The compounds described herein were tested for inhibition of SCF dependent proliferation using Mo7e cells which endogenously express c-kit in a 96 well format. Briefly, two-fold serially diluted test compounds (Cmax=10 µM) were evaluated for their antiproliferative activity of Mo7e cells stimulated with human recombinant SCF. After 48 hours of incubation at 37° C., cell viability is measured by using a MTT colorimetric assay from Promega.

Description of Biochemical Assay for DNA-PK:

The assay is conducted using the kit V7870 from Promega (SignaTECT® DNA-Dependent Protein Kinase Syste, comprises DNA-PK, biotinylated peptide substrate end further ingredients, Promega, Madison, Wis., USA), that quantitates DNA-dependent protein kinase activity, both in purified enzyme preparations and in cell nuclear extracts. DNA-PK is a nuclear serine/threonine protein kinase that requires double-stranded DNA (dsDNA) for activity. The binding of dsDNA to the enzyme results in the formation of the active enzyme and also brings the substrate closer to the enzyme, allowing the phosphorylation reaction to proceed.

DNA-PK X5 reaction buffer (250 mM HEPES, 500 mM KCl, 50 mM $MgCl_2$, 1 mM EGTA, 0.5 mM EDTA, 5 mM DTT, pH to 7.5 with KOH) is diluted ⅕ in deionised water and BSA (stock=10 mg/ml) is added to a final concentration of 0.1 mg/ml.

The activation buffer is made from 100 µg/ml of calf thymus DNA in control buffer (10 mM Tris-HCl (pH 7.4), 1 mM EDTA (pH 8.0)). Per tube, the reaction mix is composed of: 2.5 µl of activation or control buffers, 5 µl of X5 reaction buffer, 2.5 µl of p53-derived biotinylated peptide substrate (stock=4 mM), 0.2 µl of BSA (stock at 10 mg/ml) and 5 µl of [γ-$^{32}$P] ATP (5 µl of 0.5 mM cold ATP+0.05 µl of Redivue [γ-$^{32}$P] ATP=Amersham AA0068-250 µCi, 3000 Ci/mmol, 10 µCi/µl (now GE Gealthcare Biosciences AB, Uppsala, Sweden).

The DNA-PK enzyme (Promega V5811, concentration=100 U/µL) is diluted 1/10 in X1 reaction buffer and kept on ice until imminent use. 10.8 µl of the diluted enzyme is incubated with 1.2 µl of 100 µM compounds (diluted 1/100 in water from 10 mM stock in neat DMSO) for 10 minutes, at room temperature. During that time, 15.2 µl of the reaction mix is added to screw-capped tubes, behind Perspex glass. 9.8 µl of the enzyme is then transferred to the tubes containing the reaction mix and after 5 minutes incubation, at 30° C., the reaction is stopped by adding 12.5 µl of termination buffer (7.5 M guanidine hydrochloride).

After mixing well, a 10 µl aliquot of each tube is spotted onto a SAM2® biotin capture membrane (Promega, Madison, Wis., USA), which is left to dry for a few minutes. The membrane is then washed extensively to remove the excess free [γ-$^{32}$P] ATP and nonbiotiny-ated proteins: once for 30 seconds in 200 ml of 2M NaCl, 3 times for 2 minutes each in 200 ml of 2M NaCl, 4 times for 2 minutes each in 2M NaCl 1% $H_3PO_4$ and twice for 30 seconds each in 100 ml of deionised water. The membrane is subsequently left to air-dry at room temperature for 30-60 minutes.

Each membrane square is separated using forceps and scissors and placed into a scintillation vial, after which 8 ml of scintillation liquid (Flo-Scint 6013547 from Perkin-Elmer) is added. The amount of $^{32}$P incorporated into the DNA-PK biotinylated peptide substrate is then determined by liquid scintillation counting.

Protocol for the Detection of phospho-PKB in U87MG Cells by Elisa:

The efficacy of the compounds of Formula (I) in blocking the activation of the PI3K/PKB pathway can be demonstrated in cellular settings as follows: U87MG cells (human glioblastoma, ATCC No. HTB-14) were trypsinized, counted in a CASY cell counter (Schärffe systems, Göttingen, Germany), diluted in fresh complete DMEM high glucose medium to load, per well, 150 µL cell suspension containing $4 \times 10^4$ cells, and test plates incubated for 18 hours. In parallel, 50 µL of coating antibody, at the desired concentration in PBS/O is loaded in each well of the ELISA plates, and plates were kept for 2 hours at room temperature. This ELISA assays is performed in black flat-bottom 96-well plates (Microtest™, Falcon Becton-Dickinson, Ref: 353941) sealed with Plate Sealers (Costar-Corning, Ref: 3095). Medium in plates is discarded and replaced by complete DMEM high glucose medium containing either 0.1% DMSO or 0.1% inhibitor at titers (7) between 10 mM and 0.156 mM in DMSO. After 30 minutes of contact, the medium is quickly removed by aspiration, plates were then placed on ice and immediately cells lyzed with 70 µL of Lysis buffer. In parallel, the 96 wells plates prepared with the coating antibody (1/250 diluted (in PBS/O) Anti-Akt1 C-20, goat, Santa-Cruz-1618, Santa Cruz Biotechnology, Inc., Santa Cruz, Calif., USA) were washed 3 times for 1 minute with PBS/0 containing 0.05% Tween 20 and 0.1% Top-Block® (derivative of gelatine that blocks unspecific binding sites on surfaces; Sigma-Aldrich, Fluka, Buchs, Switzerland, Ref.: 37766), and remaining protein binding sites blocked to prevent non-specific interactions with 200 µL of PBS containing 3% Top Block®, for 2 hours at room temperature. Well content is replaced with 50 µL of samples from treated cells, and plates were incubated for 3 hours at 4° C. The ELISA assays were always done in parallel with the following controls, in 6 replicates: U87MG (untreated control) or Lysis buffer alone (LB). After 3×15 minutes washes, all wells received 50 µL of the secondary antibody (1/250 diluted (in 3% top block) Anti-S473P-PKB, rabbit, Cell Signaling-9271, Cell Signaling Technologies, Inc., Danvers, Mass., USA)), and were incubated for 16 hours at 4° C. After three washes, plates were incubated with the third and conjugated antibody (1/1000 diluted (in 3% top block) anti rabbit (HRP) Jackson Immuno Research 111-035-144) for 2 hours at room temperature. Finally, the immune-complexes were washed 2 times 15 seconds with PBS/O/tween20/top block, 1 time with 200 µL of water and finally 200 µL of water were left in each test well before a 45 minute incubation in darkness. The plates were then assayed with (SuperSignal® ELISA pico Chemiluminescent substrate, Pierce, Ref: 27070, Pierce Biotechnology, Inc., Rockford, Ill., USA). 100 µL of substrate were added, and plates shacked for 1 minute. The luminescence is read immediately on a Top-Count NXT (Packard Bioscience) luminometer.

There were also experiments that demonstrated the antitumor activity of compounds of the Formula (I) in vivo. For example, female Harlan (Indianapolis, Ind., USA) athymic nu/nu mice with s.c. transplanted human glioblastoms U87MG tumors can be used to determine the anti-tumor activity of PI3 kinase inhibitors. On day 0, with the animals under peroral Forene® (1-chloro-2,2,2-trifluoroethyldifluormethylether, Abbot, Wiesbaden, Germany) narcosis, a tumor fragment of approximately 25 mg is placed under the skin on the animals' left flank and the small incised wound is closed by means of suture clips. When tumors reach a volume of 100 mm$^3$, the mice were divided at random into groups of 6-8 animals and treatment commences. The treatment is carried out for a 2-3 weeks period with peroral, intravenous or intraperitoneal administration once daily (or less frequently) of a compound of formula (I) in a suitable vehicle at defined doses. The tumors were measured twice a week with a slide gauge and the volume of the tumors is calculated.

As an alternative to cell line U87MG, other cell lines may also be used in the same manner, for example, the MDA-MB 468 breast adenocarcinoma cell line (ATCC No. HTB 132; see also In Vitro 14, 911-15 [1978]); the MDA-MB 231 breast carcinoma cell line (ATCC No. HTB-26; see also In Vitro 12, 331 [1976]); the MDA-MB 453 breast carcinoma cell line (ATCC No. HTB-131); the Colo 205 colon carcinoma cell line (ATCC No. CCL 222; see also Cancer Res. 38, 1345-55 [1978]); the DU145 prostate carcinoma cell line DU 145 (ATCC No. HTB 81; see also Cancer Res. 37, 4049-58 [1978]); the PC-3 prostate carcinoma cell line PC-3 (especially preferred; ATCC No. CRL 1435; see also Cancer Res. 40, 524-34 [1980]) and the PC-3M prostate carcinoma cell line; the A549 human lung adenocarcinoma (ATCC No. CCL 185; see also Int. J. Cancer 17, 62-70 [1976]); the NCI-H596 cell line (ATCC No. HTB 178; see also Science 246, 491-4 [1989]), and the pancreatic cancer cell line SUIT-2 (see Tomioka et al., Cancer Res. 61, 7518-24 [2001]).

Kinase Activity of ALK5

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5 T204D is dissolved to 2.5 µg/ml in assay buffer (Assay buffer: 20 mM Tris-HCl pH 7.4, 10 mM $MgCl_2$, 2 mM $MnCl_2$) on the day of use.

Test compounds and reference compounds were dissolved in assay buffer without DTT containing 5% (v/v) DMSO. Stock solutions of test and reference compounds were diluted in assay buffer with DTT (1.25 mM) containing 4.5% (v/v) DMSO. 10 µl of test or reference compound were added to the appropriate wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 µl of dephosphorylated casein stock solution (dephosphorylated casein is dissolved in ddH$_2$O at 20 mg/ml) is added per well (200 µg/well final assay concentration). 20 µl of ALK5 T204D (2.5 µg/ml solution) is added per well (50 ng/well final assay concentration). The plates were left to incubate at room temperature for 10 minutes. 10 µl of ATP mix is added to the well to initiate the reaction (0.66 nM [$^{33}$P]ATP/1 µM unlabelled ATP/well final assay concentration). The ATP mix is prepared as follows, unlabelled ATP (3 mM) is dissolved in ddH$_2$O and pH adjusted to 7.4. The stock concentration of [$^{33}$P]ATP is 10 µCi/µl. The appropriate volume of [$^{33}$P]ATP is added to unlabelled ATP solution such that the final assay concentration per well is 0.1 µCi. Following addition of the ATP mix, the plates were incubated at room temperature for 50 minutes. The kinase reaction is terminated by the addition of 50 µL Stop Buffer (20 mM Tris-HCl pH 7.4, 10 mM EDTA). 75 µl/well from the reaction plate is transferred to a Multiscreen-IP plate (MultiScreen-IP plates were prepared by added 50 µL of 70% (v/v) ethanol per well and incubated for 5 minutes at room temperature. The ethanol is removed by aspiration via a MultiScreen HTS Vacuum Manifold unit (Millipore, Cat no: MSVMHT500). The plates were washed twice by adding 200 µl/well ddH$_2$O). The MultiScreen-IP plate is incubated at room temperature for 30 minutes to allowing binding of casein to the plate. The MultiScreen-IP plates were washed three times by adding 200 µl/well 100 mM phosphoric acid solution and the gasket is carefully removed from the back of the MultiScreen-IP plate and the plate dried in the oven for 30 minutes. The MultiScreen-IP plate is backsealed, 50 µL of Microscint™20 is added, then the plates were topsealed and radiolabelled casein detected and quantified on a TopCount™ plate-reader using the $^{33}$P scintillation protocol.

JAK/TYK-Kinase Family Profiling Assays

The efficacy of the compounds of Formula (I) as inhibitors of JAK/TYK kinase activity can be demonstrated as follows: All four kinases of the JAK/TYK-kinase family were used as purified recombinant GST-fusion proteins, containing the active kinase domains. GST-JAK1(866-1154), GST-JAK3 (811-1124), and GST-TYK2(888-1187) were expressed and purified by affinity chromatography. GST-JAK2(808-1132) is purchased from Invitrogen (Carlsbad, USA, #4288). The kinase assays were based on the Caliper mobility shift assay using the LabChip 3000 systems. This technology is similar to capillary electrophoresis and uses charge driven separation of substrate and product in a microfluidic chip. All kinase reactions were performed in 384 well microtiter plates in a total reaction volume of 18 µl. The assay plates were prepared with 0.1 µl per well of test compound in the appropriate test concentration, as described under the section "preparation of compound dilutions". The reactions were started by combining 9 µl of substrate mix (consisting of peptide and ATP) with 9 µl of kinase dilution. The reactions were incubated for 60 minutes at 30° C. and stopped by adding 70 µl of stop buffer (100 mM Hepes, 5% DMSO, 0.1% Coating reagent, 10 mM EDTA, 0.015% Brij 35). Fluorescently labeled synthetic peptides were used as substrates in all reactions. A peptide derived from the sequence of IRS-1 (IRS-1 peptide, FITC-Ahx-KKSRGDYMTMQIG-NH2) is used for JAK1 and TYK2 and a peptide named JAK3tide (FITC-GGEEEEY-FELVKKKK-NH2) for JAK2 and JAK3. Specific assay conditions are described in TableA:

TABLE A

Assay conditions of individual kinase assays

| Kinase | JAK1 | JAK2 | JAK3 | TYK2 |
|---|---|---|---|---|
| Buffer | 50 mM Hepes pH 7.5, 0.02% Tween 20, 1 mM DTT, 0.02% BSA, 12 mM MgCl2 | 50 mM Hepes pH 7.5, 0.02% Tween 20, 1 mM DTT, 0.02% BSA, 9 mM MgCl2 | 50 mM Hepes pH 7.5, 0.02% Tween 20, 1 mM DTT, 0.02% BSA, 1.5 mM MgCl2 | 50 mM Hepes pH 7.5, 0.02% Tween 20, 1 mM DTT, 0.02% BSA, 9 mM MgCl2 |
| DMSO | 0.6% | 0.6% | 0.6% | 0.6% |
| Kinase conc. | 50 nM | 1.8 nM | 6 nM | 40 nM |
| Substrate peptide conc. | 5 µM | 2 µM | 2 µM | 5 µM |
| ATP conc. | 40 µM | 20 µM | 80 µM | 30 µM |

The terminated reactions were transferred to the Caliper LabChip 3000 reader and the turnover of each reaction is measured by determining the substrate/product ratio.

PI3-Kinase Profiling Assays

The efficacy of the compounds of Formula (I) as PI3 kinase inhibitors is demonstrated as follows: The kinase reaction is performed in a final volume of 50 µL per well of a half area COSTAR, 96 well plate. The final concentrations of ATP and phosphatidyl inositol in the assay were 5 µM and 6 µg/mL respectively. The reaction is started by the addition of PI3 kinase p110β. The components of the assay were added per well as follows:

10 µL test compound in 5% DMSO per well in columns 2-1.

Total activity is determined by addition 10 µL of 5% vol/vol DMSO in the first 4 wells of column 1 and the last 4 wells of column 12.

The background is determined by addition of 10 µM control compound to the last 4 wells of column 1 and the first 4 wells of column 12.

2 mL 'Assay mix' were prepared per plate:
  1.912 mL of HEPES assay buffer
  8.33 µL of 3 mM stock of ATP giving a final concentration of 5 µM per well
  1 µL of [$^{33}$P]ATP on the activity date giving 0.05 µCi per well
  30 µL of 1 mg/mL PI stock giving a final concentration of 6 µg/mL per well
  5 µL of 1 M stock MgCl$_2$ giving a final concentration of 1 mM per well 20 µL of the assay mix were added per well.

2 mL 'Enzyme mix' were prepared per plate (X*µL PI3 kinase p110β in 2 mL of kinase buffer). The 'Enzyme mix' is kept on ice during addition to the assay plates.

20 µL 'Enzyme mix' were added/well to start the reaction. The plate is then incubated at room temperature for 90 minutes.

The reaction is terminated by the addition of 50 µL WGA-SPA bead (wheat germ agglutinin-coated Scintillation Proximity Assay beads) suspension per well.

The assay plate is sealed using TopSeal-S heat seal for polystyrene microplates, PerkinElmer LAS (Deutschland) GmbH, Rodgau, Germany) and incubated at room temperature for at least 60 minutes.

The assay plate is then centrifuged at 1500 rpm for 2 minutes using the Jouan bench top centrifuge (Jouan Inc., Nantes, France).

The assay plate is counted using a Packard TopCount, each well being counted for 20 seconds.

The volume of enzyme is dependent on the enzymatic activity of the batch in use.

Some of the compounds show a certain level of selectivity against the different paralogs PI3K alpha, beta, gamma and delta.

Certain Assay Results

Various compounds of Formula (I) in free form or in pharmaceutically acceptable salt form, exhibit pharmacological properties, for example, as indicated by the in vitro and in vivo tests described in this application. The $IC_{50}$ value in those experiments is given as that concentration of the test compound in question that results in a cell count that is 50% lower than that obtained using the control without inhibitor. In certain examples compounds of Formula (I) have $IC_{50}$ values from 1 nM to 200 µM. In some examples, compounds of Formula (I) have $IC_{50}$ values from 0.001 µM to 100 µM. In other examples, compounds of Formula (I) have $IC_{50}$ values from 0.001 µM to 50 µM. In other examples, compounds of Formula (I) have $IC_{50}$ values from 0.001 µM to 25 µM. In other examples, compounds of Formula (I) have $IC_{50}$ values from 0.001 µM to 20 µM. In other examples, compounds of Formula (I) have $IC_{50}$ values from 0.001 µM to 15 µM. In other examples, compounds of Formula (I) have $IC_{50}$ values from 0.001 µM to 10 µM. In other examples, compounds of Formula (I) have $IC_{50}$ values from 0.001 µM to 5 µM. In other examples, compounds of Formula (I) have $IC_{50}$ values from 0.001 µM to 2 µM. In other examples, compounds of Formula (I) have $IC_{50}$ values from 0.001 µM to 1 µM. In other examples, compounds of Formula (I) have $IC_{50}$ values from 0.001 µM to 0.8 µM. In other examples, compounds of Formula (I) have $IC_{50}$ values from 0.001 µM to 0.6 µM. In other examples, compounds of Formula (I) have $IC_{50}$ values from 0.001 µM to 0.4 µM. In other examples, compounds of Formula (I) have $IC_{50}$ values from 0.001 µM to 0.2 µM. In other examples, compounds of Formula (I) have $IC_{50}$ values from 0.001 µM to 0.1 µM. In other examples, compounds of Formula (I) have $IC_{50}$ values from 0.001 µM to 0.08 µM. In other examples, compounds of Formula (I) have $IC_{50}$ values from 0.001 µM to 0.06 µM. In other examples, compounds of Formula (I) have $IC_{50}$ values from 0.001 µM to 0.04 µM. In other examples, compounds of Formula (I) have $IC_{50}$ values from 0.001 µM to 0.02 µM. In other examples, compounds of Formula (I) have $IC_{50}$ values from 0.001 µM to 0.01 µM.

In some examples, compounds of Formula (I) have $IC_{50}$ values from 0.01 µM to 5 nM. In other examples, compounds of Formula (I) have $IC_{50}$ values from 0.01 µM to 1 nM. In yet other examples, compounds of Formula (I) have $IC_{50}$ values of less than 1 nM. In certain embodiments, compounds of Formula (I) exhibit a percentage inhibition of greater than 50%, or in other embodiments compounds of Formula (I) exhibit a percentage inhibition greater than about 70%, against one or more of the following kinases at 10 nM: Ros, KDR, FMS, c-FMS, FLT3, c-Kit, JAK2, JAK3, Aurora, PDGFR, Lck, TrkA, TrkB, TrkC, IGF-1R, ALK4, ALK5 and/or ALK kinases.

By way of example only, the compound (R)-1-(6-(6-(2-(3-fluorophenyl)pyrrolidin-1-yl)imidazo[1,2-b]pyridazin-3-yl)-2,4'-bipyridin-2'-yl)piperidin-4-ol (see Example 16-4) has an $IC_{50}$ of 4.41 µM, 0.0052 µM, 0.012 µM, 0.013 µM, in $BaF_3$, $BaF_3$/Tel-TrkA, $BaF_3$/Tel-TrkB and $BaF_3$/TrkA-NFG CTG cellular assays, respectively.

By way of example only, the compound (R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol (see Example 14-4) has an $IC_{50}$ of 4.07 µM, 0.0022 µM, 0.0033 µM, 0.0042 µM, in $BaF_3$, $BaF_3$/Tel-TrkA, $BaF_3$/Tel-TrkB and $BaF_3$/TrkA-NFG CTG cellular assays, respectively.

By way of example only, the $IC_{50}$ for TrkA, TrkB, TrkC inhibition by certain compounds of Formula (I) are listed in Table 8 below. The identification of each compound in Table 8 corresponds to the Table Number where the compound is listed above and the respective compound number.

TABLE 8

| Table No./Compound Number | Ba/F3 IC 50 (µM) | Ba/F3 Tel-TrkA IC 50 (µM) | Ba/F3 Tel-TrkB IC 50 (µM) | Ba/F3 Tel-TrkC IC 50 (µM) | BaF3 TRKA-NGF CTG IC 50 (µM) | KM12 luc IC 50 (µM) |
|---|---|---|---|---|---|---|
| Table 1-Compound 1 | 15.95 | 0.21 | 0.15 | 0.069 | 0.68 | 0.23 |
| Table 1-Compound 3 | >10 | 0.028 | 0.022 | 0.018 | 0.45 | 0.037 |
| Table 1-Compound 4 | — | 1.60 | 0.79 | — | — | — |
| Table 1-Compound 5 | >10 | 5.67 | 4.17 | 2.61 | 3.58 | 2.29 |
| Table 2-Compound 1 | >9.69 | 0.013 | 0.0055 | — | 0.029 | 0.0070 |
| Table 2-Compound 4 | >10 | 0.0086 | 0.0058 | — | 0.017 | 0.0083 |
| Table 2-Compound 6 | >10 | 0.058 | 0.044 | — | 0.078 | 0.056 |
| Table 2-Compound 7 | >10 | 0.083 | 0.23 | — | 0.55 | 0.14 |
| Table 2-Compound 8 | >10 | 0.0016 | 0.0022 | — | 0.029 | 0.0052 |
| Table 2-Compound 10 | >10 | 0.0069 | 0.0062 | — | 0.0088 | — |
| Table 2-Compound 16 | >7.67 | 0.10 | 0.12 | — | 0.14 | — |

TABLE 8-continued

| Table No./Compound Number | Ba/F3 IC 50 (μM) | Ba/F3 Tel-TrkA IC 50 (μM) | Ba/F3 Tel-TrkB IC 50 (μM) | Ba/F3 Tel-TrkC IC 50 (μM) | BaF3 TRKA-NGF CTG IC 50 (μM) | KM12 luc IC 50 (μM) |
|---|---|---|---|---|---|---|
| Table 2-Compound 18 | >10 | 0.036 | 0.036 | — | 0.056 | 0.022 |
| Table 2-Compound 19 | 5.05 | 2.17 | 1.70 | — | 1.42 | — |
| Table 2-Compound 20 | >10 | 0.39 | 0.39 | — | 0.28 | — |
| Table 2-Compound 23 | >10 | 0.01 | 0.024 | — | 0.012 | — |
| Table 3-Compound 1 | >10 | 2.31 | 0.47 | 0.24 | 1.73 | 0.19 |
| Table 3-Compound | >10 | 1.33 | 0.95 | 0.21 | 0.62 | 0.90 |
| Table 3-Compound 6 | >10 | 0.36 | 0.76 | 0.18 | 0.54 | 0.38 |
| Table 3-Compound 7 | 5.03 | 0.035 | 0.052 | 0.020 | 0.027 | 0.023 |
| Table 3-Compound 10 | >10 | 0.20 | 0.10 | 0.040 | 0.18 | 0.094 |
| Table 3-Compound 11 | >10 | 0.087 | 0.056 | 0.017 | 0.074 | 0.036 |
| Table 3-Compound 18 | 7.23 | 0.013 | 0.010 | 0.0014 | 0.020 | 0.024 |
| Table 3-Compound 19 | >10 | 1.02 | 0.54 | — | 0.37 | — |
| Table 3-Compound 26 | >10 | 1.02 | 0.54 | — | 0.37 | — |
| Table 3-Compound 27 | >10 | 0.14 | 0.093 | — | 0.32 | — |
| Table 3-Compound 30 | >10 | 1.10 | 1.06 | — | 1.34 | — |
| Table 3-Compound 34 | >10 | 1.20 | 0.40 | 0.13 | 0.50 | 0.010 |
| Table 3-Compound 41 | 0.2 | 0.20 | 0.21 | — | 0.11 | — |
| Table 3-Compound 44 | >10 | 1.12 | 1.14 | — | 1.20 | — |
| Table 3-Compound 45 | 8.059 | 1.02 | 0.79 | — | 1.02 | — |
| Table 3-Compound 52 | >10 | 0.012 | 0.0077 | 0.004 | 0.022 | 0.0065 |
| Table 3-Compound 54 | >10 | 0.086 | 0.041 | 0.017 | 0.111 | 0.094 |
| Table 3-Compound 58 | 7.65 | 0.044 | 0.049 | 0.014 | 0.108 | 0.034 |
| Table 3-Compound 91 | 8.409 | 0.298 | 0.129 | 0.033 | 0.72 | 0.084 |
| Table 4-Compound 5 | >10 | 0.0007 | 0.0004 | — | 0.0022 | 0.0012 |
| Table 4-Compound 14 | 5.716 | 0.021 | 0.0149 | — | 0.0452 | 0.0308 |
| Table 4-Compound 16 | >10 | 0.0068 | 0.0015 | — | 0.0052 | 0.0022 |
| Table 4-Compound 25 | 7.502 | 0.010 | 0.0071 | — | 0.028 | — |
| Table 4-Compound 32 | 4.989 | 0.0014 | 0.0015 | — | 0.0026 | — |
| Table 5-Compound 1 | 7.658 | 0.051 | 0.038 | 0.021 | 0.043 | 0.0092 |
| Table 5-Compound 2 | 6.174 | 0.026 | 0.015 | 0.0084 | 0.049 | 0.029 |
| Table 5-Compound 4 | 5.36 | 0.166 | 0.060 | 0.032 | 0.203 | 0.089 |
| Table 5-Compound 13 | 4.837 | 0.0035 | 0.035 | 0.0017 | 0.0053 | 0.0075 |
| Table 5-Compound 17 | >10 | 0.0064 | 0.015 | 0.0031 | 0.034 | 0.0088 |
| Table 5-Compound 22 | 2.249 | 0.132 | 0.088 | 0.027 | 0.316 | 0.099 |
| Table 5-Compound 23 | 3.713 | 0.136 | 0.074 | 0.016 | 0.111 | 0.109 |
| Table 6-Compound 1 | 4.129 | 1.63 | 1.175 | 0.334 | 1.496 | 1.377 |
| Table 6-Compound 3 | >10 | 0.0015 | 0.0018 | — | 0.018 | 0.0072 |

TABLE 8-continued

| Table No./Compound Number | Ba/F3 IC 50 (μM) | Ba/F3 Tel-TrkA IC 50 (μM) | Ba/F3 Tel-TrkB IC 50 (μM) | Ba/F3 Tel-TrkC IC 50 (μM) | BaF3 TRKA-NGF CTG IC 50 (μM) | KM12 luc IC 50 (μM) |
|---|---|---|---|---|---|---|
| Table 7-Compound 1 | >10 | 0.017 | 0.017 | — | 0.030 | 0.0076 |
| Table 7-Compound 2 | >10 | 0.018 | 0.013 | — | 0.031 | 0.026 |
| Table 7-Compound 3 | 3.866 | 0.0069 | 0.0066 | — | 0.019 | 0.017 |
| Table 7-Compound 5 | 4.82 | 0.0038 | 0.0062 | — | 0.0064 | — |
| Table 7-Compound 6 | >10 | 0.023 | 0.039 | — | 0.062 | — |
| Table 7-Compound 8 | 1.57 | 0.0082 | 0.0088 | — | 0.0061 | — |
| Table 7-Compound 9 | >10 | 0.059 | 0.063 | — | 0.053 | 0.014 |
| Table 7-Compound 10 | >10 | 0.061 | 0.071 | — | 0.077 | — |
| Table 7-Compound 12 | >10 | 0.0061 | 0.0067 | — | 0.0081 | 0.0012 |
| Table 7-Compound 17 | >10 | 0.081 | 0.044 | — | 0.093 | — |
| Table 7-Compound 18 | >10 | 0.047 | 0.0048 | — | 0.064 | — |
| Table 7-Compound 20 | >10 | 0.0018 | 0.0016 | — | 0.0036 | — |
| Table 7-Compound 21 | >10 | 0.090 | 0.067 | — | 0.121 | — |
| Table 7-Compound 22 | >10 | 0.043 | 0.023 | — | 0.035 | — |
| Table 7-Compound 26 | >10 | 0.0077 | 0.0075 | — | 0.012 | — |
| Table 7-Compound 54 | >10 | 0.028 | 0.037 | — | 0.041 | — |
| Table 7-Compound 57 | 6.895 | 0.020 | 0.020 | — | 0.020 | — |
| Table 7-Compound 58 | >10 | 0.115 | 0.15 | — | 0.21 | — |
| Table 7-Compound 61 | >10 | 0.0081 | 0.0079 | — | 0.0098 | 0.0040 |
| Table 7-Compound 82 | 0.397 | 0.0089 | 0.010 | — | 0.00512 | — |
| Table 7-Compound 96 | 5.989 | 0.001 | 0.002 | | 0.003 | |
| Table 7-Compound 98 | >11 | 0.006 | 0.009 | | 0.013 | |
| Table 7-Compound 100 | 4.378 | 0.002 | 0.002 | | 0.003 | |
| Table 7-Compound 115 | 4.842 | 0.014 | 0.014 | | 0.016 | |
| Table 7-Compound 116 | >9.10 | 0.003 | 0.003 | | 0.008 | 0.003 |
| Table 7-Compound 119 | >11 | 0.003 | 0.003 | | 0.004 | 0.002 |
| Table 7-Compound 121 | >10 | 0.00334 | 0.00302 | — | 0.00488 | — |
| Table 7-Compound 132 | >11 | 0.002 | 0.002 | | 0.004 | |
| Table 7-Compound 136 | 4.324 | 0.013 | 0.024 | | 0.039 | |
| Table 7-Compound 143 | >11 | 0.034 | 0.053 | | 0.031 | |
| Table 7-Compound 153 | >11 | 0.346 | 0.244 | | 0.698 | |
| Table 7-Compound 158 | >11 | 0.065 | 0.052 | | 0.087 | 0.019 |
| Table 7-Compound 171 | >11 | 0.224 | 0.129 | | 0.238 | |
| Table 7-Compound 176 | 2.753 | 1.119 | 0.971 | | 0.886 | |
| Table 7-Compound 181 | >11 | 0.007 | 0.008 | | 0.014 | |
| Table 7-Compound 185 | >11 | 0.064 | 0.07 | | 0.119 | |
| Table 7-Compound 191 | >9.56 | 0.014 | 0.012 | | 0.016 | |

TABLE 8-continued

| Table No./Compound Number | Ba/F3 IC 50 (μM) | Ba/F3 Tel-TrkA IC 50 (μM) | Ba/F3 Tel-TrkB IC 50 (μM) | Ba/F3 Tel-TrkC IC 50 (μM) | BaF3 TRKA-NGF CTG IC 50 (μM) | KM12 luc IC 50 (μM) |
|---|---|---|---|---|---|---|
| Table 7-Compound 201 | >11 | 0.013 | 0.015 | | 0.02 | 0.01 |
| Table 7-Compound 217 | >11 | 0.027 | 0.03 | | 0.06 | |
| Table 7-Compound 230 | 2.687 | 0.006 | 0.009 | | 0.029 | |
| Table 7-Compound 231 | >11 | 0.023 | 0.028 | | 0.054 | |
| Table 7-Compound 238 | >11 | 0.017 | 0.025 | | 0.035 | |
| Table 7-Compound 249 | 6.385 | 0.144 | 0.147 | | 0.13 | |
| Table 7-Compound 255 | >11 | 0.009 | 0.017 | 0.003 | 0.009 | 0.006 |
| Table 7-Compound 257 | >11 | 0.13 | 0.289 | | 0.101 | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I), or a pharmaceutically acceptable salt thereof:

Formula (I)

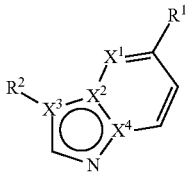

wherein:

$X^1$ and $X^2$ are N, and $X^3$ and $X^4$ are C;

$R^1$ is

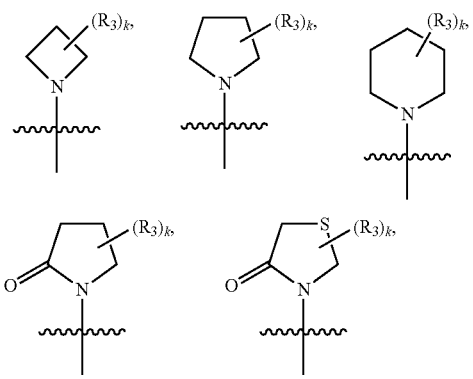

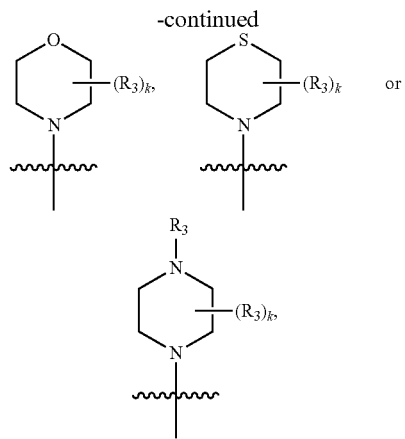

wherein k is 1, 2 or 3;
each $R^3$ is independently selected from halogen, $C_1$-$C_8$alkyl, $C_6$-$C_{14}$aryl, and $C_2$-$C_{13}$heteroaryl,
wherein the $C_1$-$C_8$alkyl, $C_6$-$C_{14}$aryl, and $C_2$-$C_{13}$heteroaryl of $R^3$ are optionally substituted with 1 to 3 substituents independently selected from halogen, hydroxyl, cyano, —$OR^9$, $C_1$-$C_8$alkyl, hydroxyl-$C_1$-$C_8$alkyl, halo-substituted-$C_1$-$C_8$alkyl and $C_3$-$C_8$cycloalkyl;
$R^2$ is $C_6$-$C_{14}$aryl, $C_2$-$C_{13}$heteroaryl or $C_2$-$C_{14}$heterocycloalkyl,
wherein the $C_6$-$C_{14}$aryl, $C_2$-$C_{13}$heteroaryl or $C_2$-$C_{14}$heterocycloalkyl of $R^2$ are substituted with 1 substituents independently selected from —$R^6$ and —$Y^1R^6$;
and the $C_6$-$C_{14}$aryl, $C_2$-$C_{13}$heteroaryl or $C_2$-$C_{14}$heterocycloalkyl of $R^2$ are optionally further substituted with a CN group;
each $R^4$ is independently selected from H, $C_1$-$C_8$ alkyl, -$L^1R^5$, -$L^1R^8$, $C_2$-$C_{13}$heteroaryl, $C_6$-$C_{14}$aryl, and $C_3$-$C_8$cycloalkyl, wherein the $C_1$-$C_8$alkyl, $C_2$-$C_{13}$heteroaryl and $C_3$-$C_8$cycloalkyl are optionally substituted with 1 to 3 substituents independently selected from halogen, deuterium, —$CD_3$, —$S(O)_2R^9$, —CN, $C_1$-$C_8$alkyl, —$OR^9$, —$N(R^9)_2$ and —$(CH_2)_p$$OR^9$;

L¹ is a bond, $C_1$-$C_8$alkylene, $-O(CH_2)_p-$, $-C(O)-$, $-N(R^9)-$, $(CH_2)_pC(O)-$, or $-C(O)(CH_2)_pO(CH_2)_p-$;

Y¹ is $C_6$-$C_{14}$arylene, $C_2$-$C_{13}$heteroarylene or $C_2$-$C_{14}$heterocycloalkylene each of which is optionally substituted with 1 to 3 substituents independently selected from halogen, $C_1$-$C_8$alkyl, $-CN$, $-C(O)N(R^4)_2$, $-C(O)R^9$, $-OR^9$, $-C(O)OR^9$, $-N(R^4)_2$, $-S(O)_2R^9$, $-S(O)_2N(R^4)_2$, $-NR^4S(O)_2R^4$, hydroxyl-$C_1$-$C_8$alkyl, and halo-substituted $C_1$-$C_8$alkyl;

R⁵ is $C_6$-$C_{14}$aryl, $C_2$-$C_{13}$heteroaryl, $-N(R^9)_2$, $-(CH_2)_pOR^9$ or $-OR^9$;

R⁶ is $C_6$-$C_{14}$aryl, $C_2$-$C_{13}$heteroaryl or $C_3$-$C_8$cycloalkyl, wherein the $C_3$-$C_8$cycloalkyl, $C_6$-$C_{14}$aryl and $C_2$-$C_{13}$heteroaryl of R⁶ are optionally substituted with 1 to 3 substituents independently selected from halogen, $-CN$, $-OR^9$, $-(CH_2)_pOR^9$, $-L^1R^8$, $-L^1R^5$, $C(O)R^9$, $-C(O)OR^9$, $-C(O)R^8$, $OC(O)N(R^4)_2$, $-N(R^9)_2$, $-C(O)C(O)OR^9$, $-(CH_2)_pN(R^9)_2$, $-N(R^4)_2$, $-C(O)N(R^4)_2$, $-N(R^4)C(O)R^4$, $-N(R^4)C(O)OR^4$, $-(CH_2)_pS(O)_2R^9$, $-S(O)_2R^9$, $-S(O)_2N(R^4)_2$, $-NR^4S(O)_2R^4$, $-NR^4S(O)_2R^9$, $C_1$-$C_8$alkyl, $C_2$-$C_8$alkene, hydroxyl-substituted $C_1$-$C_8$alkyl, and halo-substituted $C_1$-$C_8$alkyl;

or R⁶ is a $C_2$-$C_{14}$heterocycloalkyl substituted with 1 to 3 substituents independently selected from halogen, =O, $-CN$, $-OR^9$, $-(CH_2)_pOR^9$, $-L^1R^8$, $-L^1R^5$, $-C(O)R^9$, $-C(O)OR^9$, $-C(O)R^8$, $OC(O)N(R^4)_2$, $-N(R^9)_2$, $-C(O)C(O)OR^9$, $-(CH_2)_pN(R^9)_2$, $-N(R^4)_2$, $-C(O)N(R^4)_2$, $-N(R^4)C(O)R^4$, $-N(R^4)C(O)OR^4$, $-(CH_2)_pS(O)_2R^9$, $-S(O)_2R^9$, $-S(O)_2N(R^4)_2$, $-NR^4S(O)_2R^4$, $-NR^4S(O)_2R^9$, $C_1$-$C_8$alkyl, $C_2$-$C_8$alkene, hydroxyl-substituted $C_1$-$C_8$alkyl, and halo-substituted $C_1$-$C_8$alkyl;

R⁸ is H, $-N(R^9)_2$, $-N(R^4)_2$, $-SR^9$, $-CN$, $C_1$-$C_8$alkyl, $C_3$-$C_8$cycloalkyl and $C_2$-$C_{14}$heterocycloalkyl, wherein the $C_1$-$C_8$alkyl, $C_3$-$C_8$cycloalkyl and $C_2$-$C_{14}$heterocycloalkyl of R⁸ are optionally substituted with 1 to 3 substituents independently selected from halogen, $C_1$-$C_6$alkyl, $-CN$, $-OR^9$, $-(CH_2)_pOR^9$, $-C(O)R^9$, $-OC(O)R^9$, $-C(O)OR^9$, $-N(R^9)_2$, $-N(R^4)_2$, $-C(O)N(R^4)_2$, $-N(R^4)C(O)R^4$, $-N(R^4)C(O)OR^4$, $-S(O)_2R^9$, $-S(O)_2N(R^4)_2$, and $-NR^4S(O)_2$;

each R⁹ is independently selected from H, $C_3$-$C_8$cycloalkyl and $C_1$-$C_8$alkyl, and each p is independently 1, 2, 3, 4, 5 or 6.

2. The compound of claim 1, wherein each R³ is independently selected from halogen or phenyl, wherein the phenyl is optionally substituted with 1 to 3 substituents independently selected from halogen, hydroxyl, $-OR^9$, $C_1$-$C_8$alkyl, hydroxyl-$C_1$-$C_8$alkyl, halo-substituted-$C_1$-$C_8$alkyl and $C_3$-$C_8$cycloalkyl.

3. The compound of claim 2, wherein k is 1, and

R³ is phenyl substituted with a fluoro.

4. The compound of claim 3, wherein R² is $C_6$-$C_{14}$aryl or $C_2$-$C_{13}$heteroaryl, wherein the $C_6$-$C_{14}$aryl and $C_2$-$C_{13}$heteroaryl of R² are substituted with $-R$ or $-Y1R^6$.

5. The compound of claim 4, wherein R² is selected from

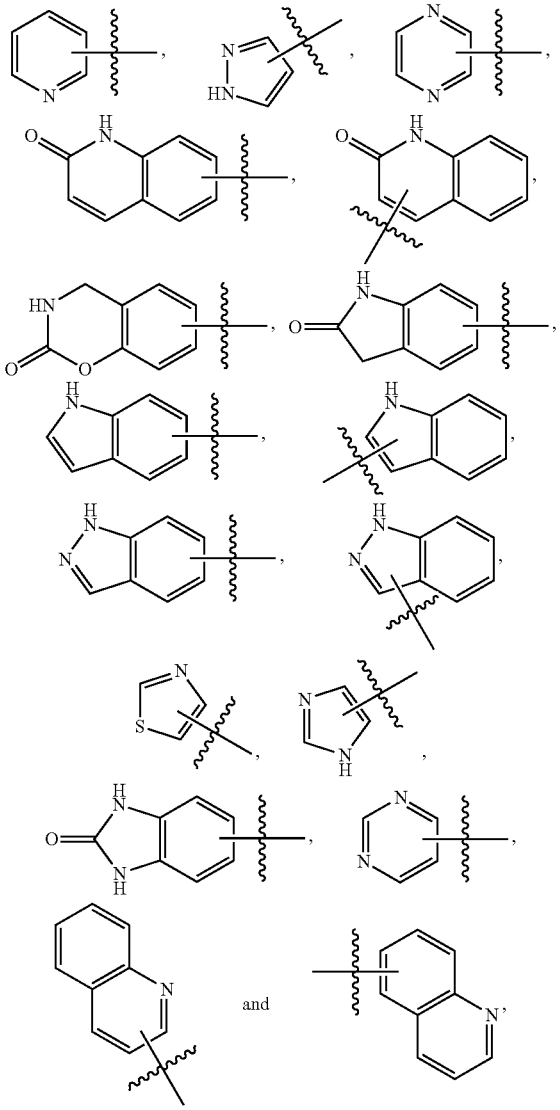

wherein each is substituted with $-R^6$ or $-Y^1R^6$.

6. The compound of claim 5, wherein R² is selected from

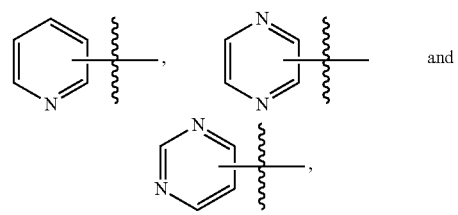

wherein each is substituted with $-Y^1R^6$.

7. The compound of claim 6, wherein

Y¹ is $C_6$-$C_{14}$arylene or $C_2$-$C_{13}$heteroarylene, and

R⁶ is $C_2$-$C_{13}$heteroaryl, or $C_2$-$C_{14}$heterocycloalkyl, wherein the $C_2$-$C_{13}$heteroaryl, and $C_2$-$C_{14}$heterocycloalkyl of R⁶ are optionally substituted with 1 to 3 substituents independently selected from halogen, $-CN$, $-OR^9$, $-(CH_2)_pOR^9$, $-L^1R^8$, $-L^1R^5$, $-C(O)OR^9$, $-C(O)R^9$, $-N(R^9)_2$, $-C(O)N(R^4)_2$, —N(R⁴)C(O)OR⁴, —N(R⁴)C(O)R⁴, —N(R⁴)₂, —S(O)₂R⁹, C₁-C₈alkyl, C₂-C₈alkene, and hydroxyl-substituted C₁-C₈alkyl.

8. The compound of claim 7, wherein Y¹ is C₆arylene or C₂-C₁₃heteroarylene, and R⁶ is selected from

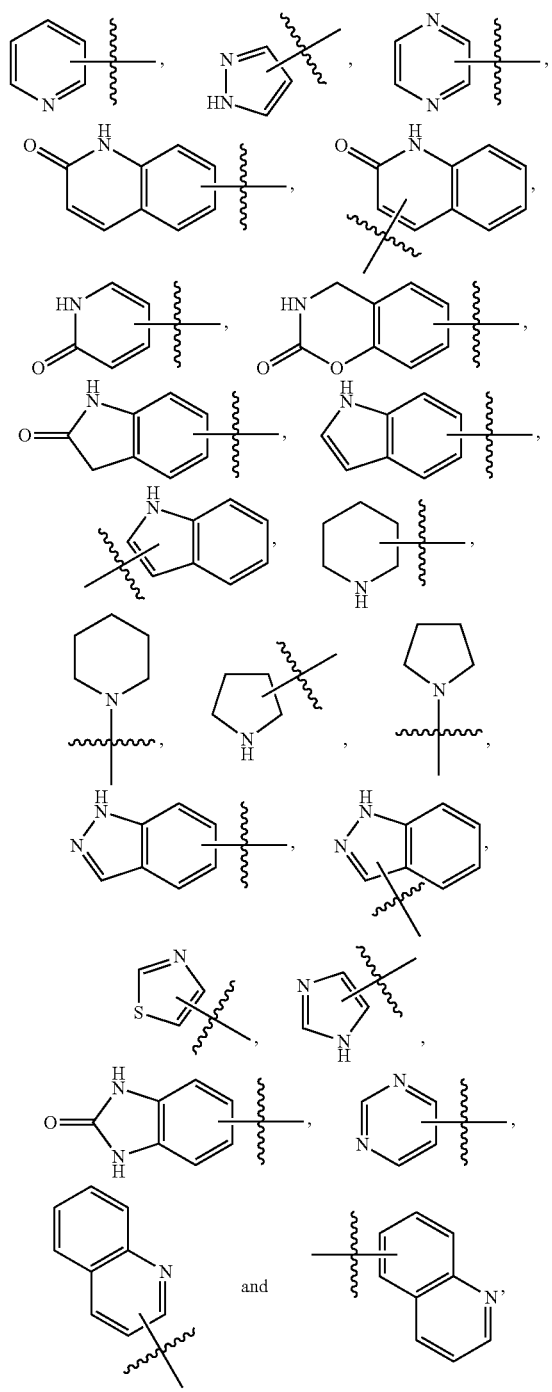

wherein each is optionally substituted with 1 to 3 substituents independently selected from halogen, —CN, —OR⁹, —(CH₂)ₚOR⁹, -L¹R⁸, -L¹R⁵, —C(O)OR⁹, —C(O)R⁹, —N(R⁵)₂, —C(O)N(R⁴)₂, —N(R⁴)C(O)OR⁴, —N(R⁴)C(O) R⁴, —N(R⁴)₂, —S(O)₂R⁹, C₁-C₈alkyl, C₂-C₈alkene, and hydroxyl-substituted C₁-C₈alkyl.

9. The compound of claim 8, wherein Y¹ is selected from

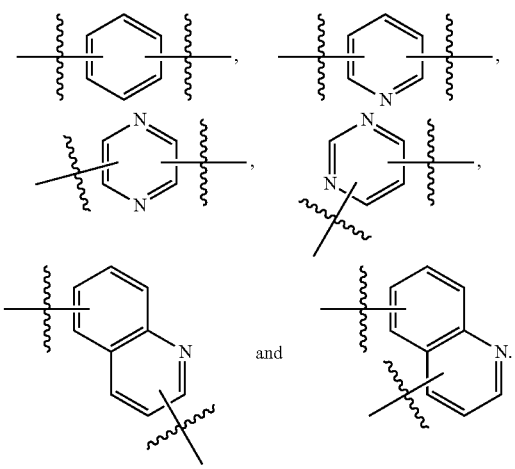

10. The compound of claim 9, wherein R⁶ is

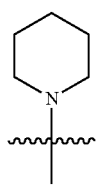 [SMILES: *N1CCCCC1]

substituted with 1 to 3 substituents independently selected from halogen, —OR⁹ and —(CH₂)ₚOR⁹.

11. The compound of claim 1 selected from:
(R)-1-(4-(6-(6-((R)-2-(3-fluorophenyl)pyrrolidin-1-yl) imidazo[1,2-b]pyridazin-3-yl)pyridin-2-yl)pyrimidin-2-yl)pyrrolidin-3-ol;
(R)-1-(6-(6-(2-(3-fluorophenyl)pyrrolidin-1-yl)imidazo [1,2-b]pyridazin-3-yl)-2,4'-bipyridin-2'-yl)piperidin-4-ol;
5-(6-(2-(2,5-difluorophenyl)pyrrolidin-1-yl)imidazo[1,2-b]pyridazin-3-yl)-2-(4-methylpiperazin-1-yl)benzonitrile;
5-(6-(2-(2,5-difluorophenyl)pyrrolidin-1-yl)imidazo[1,2-b]pyridazin-3-yl)-2-(4-(2-methoxyethyl)piperazin-1-yl)benzonitrile;
4-(6-(2-(2,5-difluorophenyl)pyrrolidin-1-yl)imidazo[1,2-b]pyridazin-3-yl)-2-(dimethylamino)benzonitrile;
4-(6-(2-(2,5-difluorophenyl)pyrrolidin-1-yl)imidazo[1,2-b]pyridazin-3-yl)-2-(4-methylpiperazin-1-yl)benzonitrile;
4-(6-(2-(2,5-difluorophenyl)pyrrolidin-1-yl)imidazo[1,2-b]pyridazin-3-yl)-2-(4-(2-methoxyethyl)piperazin-1-yl)benzonitrile;
4-(6-(2-(2,5-difluorophenyl)pyrrolidin-1-yl)imidazo[1,2-b]pyridazin-3-yl)-2-morpholinobenzonitrile;
4-(6-(2-(2,5-difluorophenyl)pyrrolidin-1-yl)imidazo[1,2-b]pyridazin-3-yl)-2-(4-morpholinopiperidin-1-yl)benzonitrile;
4-(6-(2-(2,5-difluorophenyl)pyrrolidin-1-yl)imidazo[1,2-b]pyridazin-3-yl)-2-(3-(dimethylamino)pyrrolidin-1-yl)benzonitrile;
4-(6-(2-(2,5-difluorophenyl)pyrrolidin-1-yl)imidazo[1,2-b]pyridazin-3-yl)-2-(2,6-dimethylmorpholino)benzonitrile;

4-(6-(2-(2,5-difluorophenyl)pyrrolidin-1-yl)imidazo[1,2-b]pyridazin-3-yl)-2-(3-morpholinopyrrolidin-1-yl)benzonitrile;

4-(6-(2-(2,5-difluorophenyl)pyrrolidin-1-yl)imidazo[1,2-b]pyridazin-3-yl)-2-((2-(dimethylamino)ethyl)(methyl)amino)benzonitrile;

5-(6-(3-(3-fluorophenyl)morpholino)imidazo[1,2-b]pyridazin-3-yl)-2-(4-hydroxypiperidin-1-yl)benzonitrile;

5-(6-(2-(3-fluorophenyl)pyrrolidin-1-yl)imidazo[1,2-b]pyridazin-3-yl)-2-morpholinobenzonitrile;

5-(6-(2-(3-fluorophenyl)pyrrolidin-1-yl)imidazo[1,2-b]pyridazin-3-yl)-2-(4-methylpiperazin-1-yl)benzonitrile;

5-(6-(2-(3-fluorophenyl)pyrrolidin-1-yl)imidazo[1,2-b]pyridazin-3-yl)-2-(4-(2-methoxyethyl)piperazin-1-yl)benzonitrile;

5-(6-(2-(3-fluorophenyl)pyrrolidin-1-yl)imidazo[1,2-b]pyridazin-3-yl)-2-(4-morpholinopiperidin-1-yl)benzonitrile;

4-(6-(2-(3-fluorophenyl)pyrrolidin-1-yl)imidazo[1,2-b]pyridazin-3-yl)-2-(4-methylpiperazin-1-yl)benzonitrile, 5-(6-(2-(3-fluorophenyl)pyrrolidin-1-yl)imidazo[1,2-b]pyridazin-3-yl)-2-(4-(2-morpholino-2-oxoethyl)piperazin-1-yl)benzonitrile;

2-(4-(2-cyano-4-(6-(2-(3-fluorophenyl)pyrrolidin-1-yl)imidazo[1,2-b]pyridazin-3-yl)phenyl)piperazin-1-yl)-N,N-dimethylacetamide;

5-(6-(2-(3-fluorophenyl)pyrrolidin-1-yl)imidazo[1,2-b]pyridazin-3-yl)-2-(4-hydroxypiperidin-1-yl)benzonitrile;

6-(2-(3-fluorophenyl)pyrrolidin-1-yl)-3-(5-(4-methylpiperazin-1-yl)pyrazin-2-yl)imidazo[1,2-b]pyridazine;

tert-butyl 4-(6-(6-(2-(3-fluorophenyl)pyrrolidin-1-yl)imidazo[1,2-b]pyridazin-3-yl)pyridin-2-yl)piperazine-1-carboxylate;

3-(6-(1H-imidazol-1-yl)pyrazin-2-yl)-6-(2-(3-fluorophenyl)pyrrolidin-1-yl)imidazo[1,2-b]pyridazine;

2-(4-(2-cyano-4-(6-(3-(3-fluorophenyl)morpholino)imidazo[1,2-b]pyridazin-3-yl)phenyl)piperazin-1-yl)-N,N-dimethylacetamide;

1-(6-(6-(2-(3-fluorophenyl)pyrrolidin-1-yl)imidazo[1,2-b]pyridazin-3-yl)pyridin-2-yl)piperidin-4-ol;

4-(6-(6-(2-(3-fluorophenyl)pyrrolidin-1-yl)imidazo[1,2-b]pyridazin-3-yl)pyridin-2-yl)piperazin-2-one;

6-(2-(3-fluorophenyl)pyrrolidin-1-yl)-3-(6-(4-methylpiperazin-1-yl)pyridin-2-yl)imidazo[1,2-b]pyridazine;

6-(2-(2,5-difluorophenyl)pyrrolidin-1-yl)-3-(6-(4-methylpiperazin-1-yl)pyridin-2-yl)imidazo[1,2-b]pyridazine;

4-(6-(6-(2-(2,5-difluorophenyl)pyrrolidin-1-yl)imidazo[1,2-b]pyridazin-3-yl)pyridin-2-yl)piperazin-2-one;

(3S)-1-(6-(6-(2-(3-fluorophenyl)pyrrolidin-1-yl)imidazo[1,2-b]pyridazin-3-yl)pyridin-2-yl)pyrrolidin-3-ol;

(3R)-1-(6-(6-(2-(3-fluorophenyl)pyrrolidin-1-yl)imidazo[1,2-b]pyridazin-3-yl)pyridin-2-yl)pyrrolidin-3-ol;

(3S,4S)-1-(6-(6-(2-(3-fluorophenyl)pyrrolidin-1-yl)imidazo[1,2-b]pyridazin-3-yl)pyridin-2-yl)pyrrolidine-3,4-diol;

1-(6-(6-(2-(2,5-difluorophenyl)pyrrolidin-1-yl)imidazo[1,2-b]pyridazin-3-yl)pyridin-2-yl)piperidin-4-ol;

5-(6-(3-(3-fluorophenyl)morpholino)imidazo[1,2-b]pyridazin-3-yl)-2-(4-methylpiperazin-1-yl)benzonitrile;

2-(4-acetylpiperazin-1-yl)-5-(6-(3-(3-fluorophenyl)morpholino)imidazo[1,2-b]pyridazin-3-yl)benzonitrile;

5-(6-(2-(2-fluorophenyl)pyrrolidin-1-yl)imidazo[1,2-b]pyridazin-3-yl)-2-(4-hydroxypiperidin-1-yl)benzonitrile;

1-(6-(6-(3-(3-fluorophenyl)morpholino)imidazo[1,2-b]pyridazin-3-yl)pyridin-2-yl)piperidin-4-ol;

(2S)-4-(6-(6-(2-(3-fluorophenyl)pyrrolidin-1-yl)imidazo[1,2-b]pyridazin-3-yl)pyridin-2-yl)-2-methylmorpholine;

1-(6-(6-(2-(3-fluorophenyl)pyrrolidin-1-yl)imidazo[1,2-b]pyridazin-3-yl)pyridin-2-yl)piperidine-4-carboxylic acid;

1-(6-(6-(2-(3-fluorophenyl)pyrrolidin-1-yl)imidazo[1,2-b]pyridazin-3-yl)pyridin-2-yl)piperidin-3-ol;

(3R)-1-(6-(6-(2-(3-fluorophenyl)pyrrolidin-1-yl)imidazo[1,2-b]pyridazin-3-yl)pyridin-2-yl)-N,N-dimethylpyrrolidin-3-amine;

5-(6-(3-(3-fluorophenyl)morpholino)imidazo[1,2-b]pyridazin-3-yl)-2-(piperazin-1-yl)benzonitrile;

tert-butyl 4-(6-(6-(3-(3-fluorophenyl)morpholino)imidazo[1,2-b]pyridazin-3-yl)pyridin-2-yl)piperazine-1-carboxylate;

3-(3-fluorophenyl)-4-(3-(6-(4-methylpiperazin-1-yl)pyridin-2-yl)imidazo[1,2-b]pyridazin-6-yl)morpholine;

4-(6-(3-(3-fluorophenyl)morpholino)imidazo[1,2-b]pyridazin-3-ethyl 4-(5-(6-(3-(3-fluorophenyl)morpholino)imidazo[1,2-b]pyridazin-3-yl)-2-oxo-2,3-dihydro-1H-benzo[d]imidazol-1-yl)piperidine-1-carboxylate;

2-(4-(6-(6-(2-(3-fluorophenyl)pyrrolidin-1-yl)imidazo[1,2-b]pyridazin-3-yl)pyridin-2-yl)piperazin-1-yl)-N,N-dimethylacetamide;

6-(2-(3-fluorophenyl)pyrrolidin-1-yl)-3-(6-(4-isopropylpiperazin-1-yl)pyridin-2-yl)imidazo[1,2-b]pyridazine;

2-(1-(6-(6-(2-(3-fluorophenyl)pyrrolidin-1-yl)imidazo[1,2-b]pyridazin-3-yl)pyridin-2-yl)piperidin-4-yl)propan-2-ol;

4-(1-(6-(6-(2-(3-fluorophenyl)pyrrolidin-1-yl)imidazo[1,2-b]pyridazin-3-yl)pyridin-2-yl)piperidin-4-yl)morpholine;

3-(4-(6-(6-(2-(3-fluorophenyl)pyrrolidin-1-yl)imidazo[1,2-b]pyridazin-3-yl)pyridin-2-yl)piperazin-1-yl)propanenitrile;

1-(6-(6-(2-(3-fluorophenyl)piperidin-1-yl)imidazo[1,2-b]pyridazin-3-yl)pyridin-2-yl)piperidin-4-ol;

2-(4-(6-(6-(2-(3-fluorophenyl)pyrrolidin-1-yl)imidazo[1,2-b]pyridazin-3-yl)pyridin-2-yl)piperazin-1-yl)-N-isopropylacetamide;

(1-(6-(6-(2-(3-fluorophenyl)pyrrolidin-1-yl)imidazo[1,2-b]pyridazin-3-yl)pyridin-2-yl)piperidin-4-yl)methanol;

(1-(6-(6-(2-(3-fluorophenyl)pyrrolidin-1-yl)imidazo[1,2-b]pyridazin-3-yl)pyridin-2-yl)piperidin-3-yl)methanol;

1-(6-(6-(2-(3-fluorophenyl)pyrrolidin-1-yl)imidazo[1,2-b]pyridazin-3-yl)pyridin-2-yl)piperidine-4-carbonitrile;

2-(4-(6-(6-(2-(3-fluorophenyl)pyrrolidin-1-yl)imidazo[1,2-b]pyridazin-3-yl)pyridin-2-yl)piperazin-1-yl)ethanol;

6-(2-(3-fluorophenyl)pyrrolidin-1-yl)-3-(6-(5-methyl-1H-imidazol-2-yl)pyridin-2-yl)imidazo[1,2-b]pyridazine;

(R)-1-(6-(6-(2-(3-fluorophenyl)pyrrolidin-1-yl)imidazo[1,2-b]pyridazin-3-yl)pyridin-2-yl)piperidin-4-ol;

(1-(6-(6-(3-(3-fluorophenyl)morpholino)imidazo[1,2-b]pyridazin-3-yl)pyridin-2-yl)piperidin-4-yl)methanol;

2-(1-(6-(6-(3-(3-fluorophenyl)morpholino)imidazo[1,2-b]pyridazin-3-yl)pyridin-2-1-(6-(6-(3-(3-fluorophenyl)

morpholino)imidazo[1,2-b]pyridazin-3-yl)pyridin-2-yl)piperidine-3-carboxamide;
1-(6-(6-(3-(3-fluorophenyl)morpholino)imidazo[1,2-b]pyridazin-3-yl)pyridin-2-yl)piperidine-4-carboxamide;
3-(3-fluorophenyl)-4-(3-(6-(4-(1-methylpiperidin-4-yl)piperazin-1-yl)pyridin-2-yl)imidazo[1,2-b]pyridazin-6-yl)morpholine;
1-(4-(6-(2-(3-fluorophenyl)pyrrolidin-1-yl)imidazo[1,2-b]pyridazin-3-yl)pyridin-2-yl)piperidin-4-ol;
6-(2-(3-fluorophenyl)piperidin-1-yl)-3-(6-(4-isopropylpiperazin-1-yl)pyridin-2-yl)imidazo[1,2-b]pyridazine;
(3S)-1-(6-(6-(2-(3-fluorophenyl)piperidin-1-yl)imidazo[1,2-b]pyridazin-3-yl)pyridin-2-yl)-N,N-dimethylpyrrolidin-3-amine;
(2S,6R)-4-(6-(6-(2-(3-fluorophenyl)pyrrolidin-1-yl)imidazo[1,2-b]pyridazin-3-yl)pyridin-2-yl)-2,6-dimethylmorpholine;
1-(6-(6-(2-(pyridin-2-yl)pyrrolidin-1-yl)imidazo[1,2-b]pyridazin-3-yl)pyridin-2-yl)piperidin-4-ol;
1-(6-(6-(2-(pyridin-3-yl)pyrrolidin-1-yl)imidazo[1,2-b]pyridazin-3-yl)pyridin-2-yl)piperidin-4-ol;
N-(6-(6-(2-(3-fluorophenyl)piperidin-1-yl)imidazo[1,2-b]pyridazin-3-yl)pyridin-2-yl)methanesulfonamide;
1-(6-(6-(2-(3-fluorophenyl)pyrrolidin-1-yl)imidazo[1,2-b]pyridazin-3-yl)pyridin-2-yl)azetidine-3-carboxylic acid;
1-(6-(6-(2-(3-fluorophenyl)pyrrolidin-1-yl)imidazo[1,2-b]pyridazin-3-yl)pyridin-2-yl)azetidin-3-ol;
1-(6-(6-(3-(3-fluorophenyl)morpholino)imidazo[1,2-b]pyridazin-3-yl)pyridin-2-yl)piperidin-4-ol;
(1-(6-(6-(3-(3-fluorophenyl)morpholino)imidazo[1,2-b]pyridazin-3-yl)pyridin-2-yl)piperidin-4-yl)methanol;
2-(4-(6-(6-(3-(3-fluorophenyl)morpholino)imidazo[1,2-b]pyridazin-3-yl)pyridin-2-yl)piperazin-1-yl)ethanol;
3-(3-fluorophenyl)-4-(3-(6-(4-(1-methylpiperidin-4-yl)piperazin-1-yl)pyridin-2-yl)imidazo[1,2-b]pyridazin-6-yl)morpholine;
4-(3-(6-(2,5-diazabicyclo[2.2.1]heptan-2-yl)pyridin-2-yl)imidazo[1,2-b]pyridazin-6-yl)-3-(3-fluorophenyl)morpholine;
1-(6-(6-(3-(3-fluorophenyl)morpholino)imidazo[1,2-b]pyridazin-3-yl)pyridin-2-yl)-N-methylpiperidine-4-carboxamide;
1-(6-(6-(3-(3-fluorophenyl)morpholino)imidazo[1,2-b]pyridazin-3-yl)pyridin-2-yl)-N-(2-hydroxyethyl)piperidine-4-carboxamide;
(S)-1-(6-(6-(3-(3-fluorophenyl)morpholino)imidazo[1,2-b]pyridazin-3-yl)pyridin-2-yl)piperidin-4-ol;
(R)-1-(6-(6-(3-(3-fluorophenyl)morpholino)imidazo[1,2-b]pyridazin-3-yl)pyridin-2-yl)piperidin-4-ol;
ethyl 1-(6-(6-(3-(3-fluorophenyl)morpholino)imidazo[1,2-b]pyridazin-3-yl)pyridin-2-yl)piperidine-4-carboxylate;
1-(6-(6-(3-(3-fluorophenyl)morpholino)imidazo[1,2-b]pyridazin-3-yl)pyridin-2-yl)piperidine-4-carboxylic acid;
5-(6-(6-(2-(3-fluorophenyl)pyrrolidin-1-yl)imidazo[1,2-b]pyridazin-3-yl)pyridin-2-yl)oxazole;
3-(3-fluorophenyl)-4-(3-(6-(4-(3-isopropyl-1,2,4-oxadiazol-5-yl)piperidin-1-yl)pyridin-2-yl)imidazo[1,2-b]pyridazin-6-yl)morpholine;
N-(cyclopropylmethoxy)-1-(6-(6-(3-(3-fluorophenyl)morpholino)imidazo[1,2-b]pyridazin-3-yl)pyridin-2-yl)piperidine-4-carboxamide;
1-(6-(6-(3-(3-fluorophenyl)morpholino)imidazo[1,2-b]pyridazin-3-yl)pyridin-2-yl)-N-isopropylpiperidine-4-carboxamide;
N-cyclopropyl-1-(6-(6-(3-(3-fluorophenyl)morpholino)imidazo[1,2-b]pyridazin-3-yl)pyridin-2-yl)piperidine-4-carboxamide;
1-(6-(6-(3-(3-fluorophenyl)morpholino)imidazo[1,2-b]pyridazin-3-yl)pyridin-2-yl)-N-(isoxazol-3-yl)piperidine-4-carboxamide;
(1-(6-(6-(3-(3-fluorophenyl)morpholino)imidazo[1,2-b]pyridazin-3-yl)pyridin-2-yl)piperidin-4-yl)(3-hydroxypyrrolidin-1-yl)methanone;
N-(cyanomethyl)-1-(6-(6-(3-(3-fluorophenyl)morpholino)imidazo[1,2-b]pyridazin3-yl)pyridin-2-yl)piperidine-4-carboxamide;
3-(6-(1H-pyrazol-5-yl)pyridin-2-yl)-6-(2-(3-fluorophenyl)pyrrolidin-1-yl)imidazo[1,2-b]pyridazine;
5-(6-(6-(2-(3-fluorophenyl)pyrrolidin-1-yl)imidazo[1,2-b]pyridazin-3-yl)pyridin-2-yl)pyrazolo[1,5-a]pyrimidine-2-carbonitrile;
6-(2-(3-fluorophenyl)pyrrolidin-1-yl)-3-(6-(2-methylpyrimidin-4-yl)pyridin-2-yl)imidazo[1,2-b]pyridazine;
4-(6-(6-(2-(3-fluorophenyl)pyrrolidin-1-yl)imidazo[1,2-b]pyridazin-3-yl)pyridin-2-yl)pyrimidin-2-amine;
3-(6-((2R,5S)-2,5-dimethylpiperazin-1-yl)pyridin-2-yl)-6-(2-(3-fluorophenyl)pyrrolidin-1-yl)imidazo[1,2-b]pyridazine;
3-(6-((3S,5R)-3,5-dimethylpiperazin-1-yl)pyridin-2-yl)-6-(2-(3-fluorophenyl)pyrrolidin-1-yl)imidazo[1,2-b]pyridazine;
6-(2-(3-fluorophenyl)pyrrolidin-1-yl)-3-(6-(4-(pyrazin-2-yl)piperazin-1-yl)pyridin-2-yl)imidazo[1,2-b]pyridazine;
6-(2-(3-fluorophenyl)pyrrolidin-1-yl)-3-(6-(4-(pyrimidin-2-yl)piperazin-1-yl)pyridin-2-yl)imidazo[1,2-b]pyridazine;
6-(2-(3-fluorophenyl)pyrrolidin-1-yl)-3-(6-(3-(piperidin-4-yl)-1H-pyrazol-5-yl)pyridin-2-yl)imidazo[1,2-b]pyridazine;
4-(4-(6-(6-(2-(3-fluorophenyl)pyrrolidin-1-yl)imidazo[1,2-b]pyridazin-3-yl)pyridin-2-yl)pyrimidin-2-yl)morpholine;
6-(2-(3-fluorophenyl)pyrrolidin-1-yl)-3-(6-(4-(2-(methylsulfonyl)ethyl)piperazin-1-yl)pyridin-2-yl)imidazo[1,2-b]pyridazine;
6-(2-(3-fluorophenyl)pyrrolidin-1-yl)-3-(6-(6-(piperidin-4-yl)pyrimidin-2-yl)pyridin-2-yl)imidazo[1,2-b]pyridazine;
2-(4-(6-(6-(2-(3-fluorophenyl)pyrrolidin-1-yl)imidazo[1,2-b]pyridazin-3-yl)pyridin-2-yl)piperazin-1-yl)-N,N-dimethylethanamine;
6-(2-(3-fluorophenyl)pyrrolidin-1-yl)-3-(6-(pyrimidin-4-yl)pyridin-2-yl)imidazo[1,2-b]pyridazine;
4-(1-(6-(6-(2-(3-fluorophenyl)pyrrolidin-1-yl)imidazo[1,2-b]pyridazin-3-yl)pyridin-2-yl)pyrrolidin-3-yl)morpholine;
3-(6-(4-(cyclopropylsulfonyl)piperazin-1-yl)pyridin-2-yl)-6-(2-(3-fluorophenyl)pyrrolidin-1-yl)imidazo[1,2-b]pyridazine;
1-(4-(6-(6-(2-(3-fluorophenyl)pyrrolidin-1-yl)imidazo[1,2-b]pyridazin-3-yl)pyridin-2-yl)piperazin-1-yl)-2-hydroxyethanone;
(4-(6-(6-(2-(3-fluorophenyl)pyrrolidin-1-yl)imidazo[1,2-b]pyridazin-3-yl)pyridin-2-yl)piperazin-1-yl)(1-hydroxycyclopropyl)methanone;
(R)-6-(2-(3-fluorophenyl)pyrrolidin-1-yl)-3-(6-(2-methylpyrimidin-4-yl)pyridin-2-yl)imidazo[1,2-b]pyridazine;

(4-(6-(6-(2-(3-fluorophenyl)pyrrolidin-1-yl)imidazo[1,2-b]pyridazin-3-yl)pyridin-2-yl)piperazin-1-yl)(tetrahydro-2H-pyran-4-yl)methanone;
(4-(6-(6-(2-(3-fluorophenyl)pyrrolidin-1-yl)imidazo[1,2-b]pyridazin-3-yl)pyridin-2-yl)piperazin-1-yl)(tetrahydrofuran-2-yl)methanone;
4-(6-(6-(2-(3-fluorophenyl)pyrrolidin-1-yl)imidazo[1,2-b]pyridazin-3-yl)-2,3'-bipyridin-6'-yl)morpholine;
6-(2-(3-fluorophenyl)pyrrolidin-1-yl)-3-(6-(5-(pyrrolidin-1-yl)pyrazin-2-yl)pyridin-2-yl)imidazo[1,2-b]pyridazine;
4-(5-(6-(6-(2-(3-fluorophenyl)pyrrolidin-1-yl)imidazo[1,2-b]pyridazin-3-yl)pyridin-2-yl)pyrimidin-2-yl)morpholine;
1-(6-(6-(2-(3-fluorophenyl)pyrrolidin-1-yl)imidazo[1,2-b]pyridazin-3-yl)-2,4'-bipyridin-2'-yl)piperidin-4-ol;
N1-(4-(6-(6-(2-(3-fluorophenyl)pyrrolidin-1-yl)imidazo[1,2-b]pyridazin-3-yl)pyridin-2-yl)pyrimidin-2-yl)-N2,N2-dimethylethane-1,2-diamine;
1-(4-(6-(6-(2-(3-fluorophenyl)pyrrolidin-1-yl)imidazo[1,2-b]pyridazin-3-yl)pyridin-2-yl)pyrimidin-2-yl)piperidin-4-ol;
4-(6-(6-(2-(3-fluorophenyl)pyrrolidin-1-yl)imidazo[1,2-b]pyridazin-3-yl)pyridin-2-yl)-N,N-dimethylpyrimidin-2-amine;
3-(6-(1H-indazol-5-yl)pyridin-2-yl)-6-(2-(3-fluorophenyl)pyrrolidin-1-yl)imidazo[1,2-b]pyridazine;
2-(6-(6-(2-(3-fluorophenyl)pyrrolidin-1-yl)imidazo[1,2-b]pyridazin-3-yl)-2,3'-bipyridin-6'-ylamino)ethanol;
1-(6-(6-(2-(3-fluorophenyl)pyrrolidin-1-yl)imidazo[1,2-b]pyridazin-3-yl)-2,3'-bipyridin-6'-yl)piperidin-4-ol;
(R)-2-(4-(6-(6-(2-(3-fluorophenyl)pyrrolidin-1-yl)imidazo[1,2-b]pyridazin-3-yl)pyridin-2-yl)pyrimidin-2-ylamino)ethanol;
4-((S)-1-(6-(6-((R)-2-(3-fluorophenyl)pyrrolidin-1-yl)imidazo[1,2-b]pyridazin-3-yl)pyridin-2-yl)pyrrolidin-3-yl)morpholine;
(2S,6R)-4-((S)-1-(6-(6-((R)-2-(3-fluorophenyl)pyrrolidin-1-yl)imidazo[1,2-b]pyridazin-3-yl)pyridin-2-yl)pyrrolidin-3-yl)-2,6-dimethylmorpholine;
(R)-1-(4-(6-(6-(2-(3-fluorophenyl)pyrrolidin-1-yl)imidazo[1,2-b]pyridazin-3-yl)pyridin-2-yl)pyrimidin-2-yl)azetidin-3-ol;
(R)—N-(4-(6-(6-(2-(3-fluorophenyl)pyrrolidin-1-yl)imidazo[1,2-b]pyridazin-3-yl)pyridin-2-yl)pyrimidin-2-yl)methanesulfonamide;
(R)-4-((S)-1-(6-(6-((R)-2-(3-fluorophenyl)pyrrolidin-1-yl)imidazo[1,2-b]pyridazin-3-yl)pyridin-2-yl)pyrrolidin-3-yl)-2-methylmorpholine;
(R)-2-(6-(6-(2-(3-fluorophenyl)pyrrolidin-1-yl)imidazo[1,2-b]pyridazin-3-yl)-2,4'-bipyridin-2'-ylamino)ethanol;
(R)-1-(6-(6-(2-(3-fluorophenyl)pyrrolidin-1-yl)imidazo[1,2-b]pyridazin-3-yl)-2,4'-bipyridin-2'-yl)azetidin-3-ol;
(R)-1-(6-(6-((R)-2-(3-fluorophenyl)pyrrolidin-1-yl)imidazo[1,2-b]pyridazin-3-yl)-2,4'-bipyridin-2'-yl)pyrrolidin-3-ol;
(R)—N-(6-(6-(2-(3-fluorophenyl)pyrrolidin-1-yl)imidazo[1,2-b]pyridazin-3-yl)-2,4'-bipyridin-2'-yl)methanesulfonamide;
(R)-4-(6-(6-(2-(3-fluorophenyl)pyrrolidin-1-yl)imidazo[1,2-b]pyridazin-3-yl)pyridin-2-yl)-N-(pyridin-3-ylmethyl)pyrimidin-2-amine;
(S)-1-(6-(6-((R)-2-(3-fluorophenyl)pyrrolidin-1-yl)imidazo[1,2-b]pyridazin-3-yl)-2,4'-bipyridin-2'-yl)-N-methylpyrrolidin-3-amine;

(R)-4-(6-(6-(2-(3-fluorophenyl)pyrrolidin-1-yl)imidazo[1,2-b]pyridazin-3-yl)pyridin-2-yl)-N-(2-(methylsulfonyl)ethyl)pyrimidin-2-amine;
(R)—N-(6-(6-(2-(3-fluorophenyl)pyrrolidin-1-yl)imidazo[1,2-b]pyridazin-3-yl)-2,3'-bipyridin-6'-yl)methanesulfonamide;
(R)-3-(6-(1H-indazol-6-yl)pyridin-2-yl)-6-(2-(3-fluorophenyl)pyrrolidin-1-yl)imidazo[1,2-b]pyridazine;
(R)-1-(6-(6-((R)-2-(3-fluorophenyl)pyrrolidin-1-yl)imidazo[1,2-b]pyridazin-3-yl)-2,4'-bipyridin-2'-yl)-N-methylpyrrolidin-3-amine;
(R)-1-(6'-(6-(2-(3-fluorophenyl)pyrrolidin-1-yl)imidazo[1,2-b]pyridazin-3-yl)-2,2'-bipyridin-6-yl)piperidin-4-ol;
(R)-2-(6'-(6-(2-(3-fluorophenyl)pyrrolidin-1-yl)imidazo[1,2-b]pyridazin-3-yl)-2,2'-bipyridin-6-ylamino)ethanol;
(R)-1-(6'-(6-((R)-2-(3-fluorophenyl)pyrrolidin-1-yl)imidazo[1,2-b]pyridazin-3-yl)-2,2'-bipyridin-6-yl)-N-methylpyrrolidin-3-amine;
(R)-1-(4-(6-(6-((R)-2-(3-fluorophenyl)pyrrolidin-1-yl)imidazo[1,2-b]pyridazin-3-yl)pyridin-2-yl)pyrimidin-2-yl)-N-methylpyrrolidin-3-amine;
(R)-2-(4-(4-(6-(6-(2-(3-fluorophenyl)pyrrolidin-1-yl)imidazo[1,2-b]pyridazin-3-yl)pyridin-2-yl)pyrimidin-2-yl)piperazin-1-yl)ethanol;
(R)-2-(4-(6-(6-(2-(3-fluorophenyl)pyrrolidin-1-yl)imidazo[1,2-b]pyridazin-3-yl)-2,4'-bipyridin-2'-yl)piperazin-1-yl)ethanol;
1-((2S,6R)-4-(6-(6-((R)-2-(3-fluorophenyl)pyrrolidin-1-yl)imidazo[1,2-b]pyridazin-3-yl)pyridin-2-yl)-2,6-dimethylpiperazin-1-yl)-2-hydroxyethanone;
(R)-1-(6'-(6-((R)-2-(3-fluorophenyl)pyrrolidin-1-yl)imidazo[1,2-b]pyridazin-3-yl)-2,2'-bipyridin-6-yl)pyrrolidin-3-ol;
(R)-2-(4-(6'-(6-(2-(3-fluorophenyl)pyrrolidin-1-yl)imidazo[1,2-b]pyridazin-3-yl)-2,2'-bipyridin-6-yl)piperazin-1-yl)ethanol;
(R)-4-(6-(6-(2-(3-fluorophenyl)pyrrolidin-1-yl)imidazo[1,2-b]pyridazin-3-yl)pyridin-2-yl)benzenesulfonamide;
(R)-3-(6-(6-(2-(3-fluorophenyl)pyrrolidin-1-yl)imidazo[1,2-b]pyridazin-3-yl)pyridin-2-yl)benzenesulfonamide;
(R)—N-(6'-(6-(2-(3-fluorophenyl)pyrrolidin-1-yl)imidazo[1,2-b]pyridazin-3-yl)-2,2'-bipyridin-6-yl)methanesulfonamide;
(R)-6-(2-(3-fluorophenyl)pyrrolidin-1-yl)-3-(2'-(piperazin-1-yl)-2,4'-bipyridin-6-yl)imidazo[1,2-b]pyridazine;
(R)-6-(2-(3-fluorophenyl)pyrrolidin-1-yl)-3-(6-(4-(methylsulfonyl)phenyl)pyridin-2-yl)imidazo[1,2-b]pyridazine;
(R)-4-(2-(4-(6-(6-(2-(3-fluorophenyl)pyrrolidin-1-yl)imidazo[1,2-b]pyridazin-3-yl)pyridin-2-yl)-1H-pyrazol-1-yl)ethyl)morpholine;
(R)-6-(2-(3-fluorophenyl)pyrrolidin-1-yl)-3-(2'-(4-isopropylpiperazin-1-yl)-2,4'-bipyridin-6-yl)imidazo[1,2-b]pyridazine;
(R)-4-(6-(6-(2-(3-fluorophenyl)pyrrolidin-1-yl)imidazo[1,2-b]pyridazin-3-yl)pyridin-2-yl)-N-methylbenzenesulfonamide;
(S)-1-(6-(6-((R)-2-(3-fluorophenyl)pyrrolidin-1-yl)imidazo[1,2-b]pyridazin-3-yl)-2,4'-bipyridin-2'-yl)pyrrolidin-3-ol;

{1-[(6-{6-[2-(3-fluorophenyl)pyrrolidin-1-yl]imidazo[1, 2-b]pyridazin-3-yl}pyridin-2-yl)amino] cyclopentyl}methanol;

(3S,4S)-1-(6-{6-[2-(3-fluorophenyl)pyrrolidin-1-yl]imidazo[1,2-b]pyridazin-3-yl}pyridin-2-yl)pyrrolidine-3, 4-diol;

1-{6-[6-(3-phenylthiomorpholin-4-yl)imidazo[1,2-b]pyridazin-3-yl]pyridin-2-yl}piperidin-4-ol;

2-{6-[2-(3-fluorophenyl)pyrrolidin-1-yl]imidazo[1,2-b] pyridazin-3-yl}-6-[(1-methanesulfonylpiperidin-4-yl) oxy]pyridine;

(3S,4S)-1-(6-{6-[(2S)-2-(3-fluorophenyl)pyrrolidin-1-yl] imidazo[1,2-b]pyridazin-3-yl}pyridin-2-yl)pyrrolidine-3,4-diol;

(3S,4S)-1-(6-{6-[(2R)-2-(3-fluorophenyl)pyrrolidin-1-yl] imidazo[1,2-b]pyridazin-3-yl}pyridin-2-yl)pyrrolidine-3,4-diol;

N-[(3R)-1-(6-{6-[2-(3-fluorophenyl)pyrrolidin-1-yl]imidazo[1,2-b]pyridazin-3-yl}pyridin-2-yl)pyrrolidin-3-yl]-N-methylmethanesulfonamide;

2-{6-[2-(3-fluorophenyl)pyrrolidin-1-yl]imidazo[1,2-b] pyridazin-3-yl}-6-(3-fluoropiperidin-1-yl)pyridine;

N-[(3R)-1-(6-{6-[2-(3-fluorophenyl)pyrrolidin-1-yl]imidazo[1,2-b]pyridazin-3-yl}pyridin-2-yl)pyrrolidin-3-yl]-N-methylacetamide;

N-[(3R)-1-(6-{6-[2-(3-fluorophenyl)pyrrolidin-1-yl]imidazo[1,2-b]pyridazin-3-yl}pyridin-2-yl)pyrrolidin-3-yl]-2-hydroxy-N-methylacetamide;

2-(3,3-difluoropiperidin-1-yl)-6-{6-[2-(3-fluorophenyl) pyrrolidin-1-yl]imidazo[1,2-b]pyridazin-3-yl}pyridine;

N-ethyl-N-[(3R)-1-(6-{6-[2-(3-fluorophenyl)pyrrolidin-1-yl]imidazo[1,2-b]pyridazin-3-yl}pyridin-2-yl)pyrrolidin-3-yl]acetamide;

N-ethyl-N-[(3R)-1-(6-{6-[2-(3-fluorophenyl)pyrrolidin-1-yl]imidazo[1,2-b]pyridazin-3-yl}pyridin-2-yl)pyrrolidin-3-yl]-2-hydroxyacetamide;

N-[(3R)-1-(6-{6-[2-(3-fluorophenyl)pyrrolidin-1-yl]imidazo[1,2-b]pyridazin-3-yl}pyridin-2-yl)pyrrolidin-3-yl]methanesulfonamide;

N-[1-(6-{6-[2-(3-fluorophenyl)pyrrolidin-1-yl]imidazo [1,2-b]pyridazin-3-yl}pyridin-2-yl)piperidin-4-yl]-N-methylmethanesulfonamide;

N-[1-(6-{6-[2-(3-fluorophenyl)pyrrolidin-1-yl]imidazo [1,2-b]pyridazin-3-yl}pyridin-2-yl)piperidin-4-yl]acetamide;

1-(6-{6-[2-(3-fluorophenyl)pyrrolidin-1-yl]imidazo[1,2-b]pyridazin-3-yl}pyridin-2-yl)-3-methylpiperidin-4-ol;

1-(6-{6-[2-(3-fluorophenyl)pyrrolidin-1-yl]imidazo[1,2-b]pyridazin-3-yl}pyridin-2-yl)pyrrolidin-3-amine;

2,2,2-trifluoro-N-[(3S)-1-(6-{6-[2-(3-fluorophenyl)pyrrolidin-1-yl]imidazo[1,2-b]pyridazin-3-yl}pyridin-2-yl)pyrrolidin-3-yl]acetamide;

N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]methanesulfonamide;

N-ethyl-N-[(3R)-1-(6-{6-[(2R)-2-(3-fluorophenyl)pyrrolidin-1-yl]imidazo[1,2-b]pyridazin-3-yl}pyridin-2-yl) pyrrolidin-3-yl]acetamide;

N-[1-(6-{6-[(2R)-2-(3-fluorophenyl)pyrrolidin-1-yl]imidazo[1,2-b]pyridazin-3-yl}pyridin-2-yl)azetidin-3-yl]-N-methylmethanesulfonamide;

(3S)-1-(6-{6-[(2R)-2-(3-fluorophenyl)pyrrolidin-1-yl] imidazo[1,2-b]pyridazin-3-yl}pyridin-2-yl)pyrrolidin-3-amine;

2-(dimethylamino)-1-[4-(6-{6-[(2R)-2-(3-fluorophenyl) pyrrolidin-1-yl]imidazo[1,2-b]pyridazin-3-yl}pyridin-2-yl)piperazin-1-yl]ethan-1-one;

(3R)-1-(6-{6-[(2R)-2-(3-fluorophenyl)pyrrolidin-1-yl] imidazo[1,2-b]pyridazin-3-yl}pyridin-2-yl)-3-methylpiperazine;

2-[(2R)-4-(6-{6-[(2R)-2-(3-fluorophenyl)pyrrolidin-1-yl] imidazo[1,2-b]pyridazin-3-yl}pyridin-2-yl)-2-methylpiperazin-1-yl]-2-oxoethyl acetate;

1-[(2R)-4-(6-{6-[(2R)-2-(3-fluorophenyl)pyrrolidin-1-yl] imidazo[1,2-b]pyridazin-3-yl}pyridin-2-yl)-2-methylpiperazin-1-yl]-2-hydroxyethan-1-one;

2-amino-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one;

1-[4-(6-{6-[(2R)-2-(3-fluorophenyl)pyrrolidin-1-yl]imidazo[1,2-b]pyridazin-3-yl}pyridin-2-yl)piperazin-1-yl]-2-(methylamino)ethan-1-one;

2-(dimethylamino)-1-[(2R)-4-(6-{6-[(2R)-2-(3-fluorophenyl)pyrrolidin-1-yl]imidazo[1,2-b]pyridazin-3-yl}pyridin-2-yl)-2-methylpiperazin-1-yl]ethan-1-one;

(3R)-3-{[4-(6-{6-[(2R)-2-(3-fluorophenyl)pyrrolidin-1-yl]imidazo[1,2-b]pyridazin-3-yl}pyridin-2-yl)piperazin-1-yl]carbonyl}morpholine;

(3R)-3-{[(2R)-4-(6-{6-[(2R)-2-(3-fluorophenyl)pyrrolidin-1-yl]imidazo[1,2-b]pyridazin-3-yl}pyridin-2-yl)-2-methylpiperazin-1-yl]carbonyl}morpholine;

(3R,4R)-1-[4-(6-{6-[(2R)-2-(3-fluorophenyl)pyrrolidin-1-yl]imidazo[1,2-b]pyridazin-3-yl}pyridin-2-yl)pyridin-2-yl]pyrrolidine-3,4-diol;

1-(6-{6-[2-(3-fluorophenyl)piperidin-1-yl]imidazo[1,2-b] pyridazin-3-yl}pyridin-2-yl)piperidin-4-ol;

1-(4-{6-[2-(3-fluorophenyl)pyrrolidin-1-yl]imidazo[1,2-b]pyridazin-3-yl}pyridin-2-yl)piperidin-4-ol;

1-(4-{6-[2-(3-fluorophenyl)pyrrolidin-1-yl]imidazo[1,2-b]pyridazin-3-yl}pyridin-2-yl)-4-methylpiperazine;

2-[(4-{6-[2-(3-fluorophenyl)pyrrolidin-1-yl]imidazo[1,2-b]pyridazin-3-yl}pyridin-2-yl)amino]ethan-1-ol;

1-(5-{6-[2-(3-fluorophenyl)pyrrolidin-1-yl]imidazo[1,2-b]pyridazin-3-yl}pyrimidin-2-yl)piperidin-4-ol;

(3R)-1-(4-{6-[2-(3-fluorophenyl)pyrrolidin-1-yl]imidazo [1,2-b]pyridazin-3-yl}pyridin-2-yl)pyrrolidin-3-ol;

(3S)-1-(4-{6-[2-(3-fluorophenyl)pyrrolidin-1-yl]imidazo [1,2-b]pyridazin-3-yl}pyridin-2-yl)pyrrolidin-3-ol;

(3R,4R)-1-(4-{6-[2-(3-fluorophenyl)pyrrolidin-1-yl]imidazo[1,2-b]pyridazin-3-yl}pyridin-2-yl)pyrrolidine-3, 4-diol;

1-(6-{6-[2-(3-fluorophenyl)pyrrolidin-1-yl]imidazo[1,2-b]pyridazin-3-yl}pyridin-2-yl)-N,N-dimethylpiperidin-4-amine;

1-(4-{6-[2-(3-fluorophenyl)pyrrolidin-1-yl]imidazo[1,2-b]pyridazin-3-yl}pyridin-2-yl)-N,N-dimethylpiperidin-4-amine;

1-(6-{6-[(2R)-2-(3-fluorophenyl)pyrrolidin-1-yl]imidazo [1,2-b]pyridazin-3-yl}pyridin-2-yl)-N,N-dimethylpiperidin-4-amine;

1-(6-{6-[(2R)-2-(3-fluorophenyl)pyrrolidin-1-yl]imidazo [1,2-b]pyridazin-3-yl}pyridin-2-yl)piperidin-4-one;

[1-(6-{6-[(2R)-2-(3-fluorophenyl)pyrrolidin-1-yl]imidazo[1,2-b]pyridazin-3-yl}pyridin-2-yl)piperidin-4-yl] carbamate;

1-(6-{6-[(2R)-2-(3-fluorophenyl)pyrrolidin-1-yl]imidazo [1,2-b]pyridazin-3-yl}pyridin-2-yl)piperidin-4-yl N-methylcarbamate;

1-(6-{6-[(2R)-2-(3-fluorophenyl)pyrrolidin-1-yl]imidazo [1,2-b]pyridazin-3-yl}pyridin-2-yl)piperidin-4-yl N-tert-butylcarbamate;

1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one;

N,N-diethyl-1-(6-{6-[(2R)-2-(3-fluorophenyl)pyrrolidin-1-yl]imidazo[1,2-b]pyridazin-3-yl}pyridin-2-yl)piperidin-4-amine;

2,2,2-trifluoro-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one;

1-(6-{6-[(2R)-2-(3-fluorophenyl)pyrrolidin-1-yl]imidazo[1,2-b]pyridazin-3-yl}pyridin-2-yl)-4-methanesulfonylpiperazine;

2-(benzyloxy)-1-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-one;

1-[4-(6-{6-[(2R)-2-(3-fluorophenyl)pyrrolidin-1-yl]imidazo[1,2-b]pyridazin-3-yl}pyridin-2-yl)piperazin-1-yl]-2-hydroxyethan-1-one;

2-{[1-(6-{6-[(2R)-2-(3-fluorophenyl)pyrrolidin-1-yl]imidazo[1,2-b]pyridazin-3-yl}pyridin-2-yl)piperidin-4-yl]amino}ethan-1-ol;

2-{6-[(2R)-2-(3-fluorophenyl)pyrrolidin-1-yl]imidazo[1,2-b]pyridazin-3-yl}-6-(1,2,3,6-tetrahydropyridin-1-yl)pyridine;

N,N-diethyl-1-(6-{6-[2-(3-fluorophenyl)pyrrolidin-1-yl]imidazo[1,2-b]pyridazin-3-yl}pyridin-2-yl)pyrrolidin-3-amine;

N-cyclopropyl-1-(6-{6-[(2R)-2-(3-fluorophenyl)pyrrolidin-1-yl]imidazo[1,2-b]pyridazin-3-yl}pyridin-2-yl)piperidin-4-amine;

(3R)-1-(6-{6-[2-(3-fluorophenyl)pyrrolidin-1-yl]imidazo[1,2-b]pyridazin-3-yl}pyridin-2-yl)-N-methylpyrrolidin-3-amine;

(3R)-1-(6-{6-[(2R)-2-(3-fluorophenyl)pyrrolidin-1-yl]imidazo[1,2-b]pyridazin-3-yl}pyridin-2-yl)-N-methylpyrrolidin-3-amine;

1-(6-{6-[(2R)-2-(3-fluorophenyl)pyrrolidin-1-yl]imidazo[1,2-b]pyridazin-3-yl}pyridin-2-yl)-N-methylpiperidin-4-amine;

2-fluoro-N-[1-(6-{6-[2-(3-fluorophenyl)pyrrolidin-1-yl]imidazo[1,2-b]pyridazin-3-yl}pyridin-2-yl)pyrrolidin-3-yl]-N,2-dimethylpropanamide;

2-fluoro-N-[1-(6-{6-[2-(3-fluorophenyl)pyrrolidin-1-yl]imidazo[1,2-b]pyridazin-3-yl}pyridin-2-yl)pyrrolidin-3-yl]-N-methylpropanamide;

1-tert-butyl-4-(6-{6-[(2R)-2-(3-fluorophenyl)pyrrolidin-1-yl]imidazo[1,2-b]pyridazin-3-yl}pyridin-2-yl)piperazine;

1-(6-{6-[(2R)-2-(3-fluorophenyl)pyrrolidin-1-yl]imidazo[1,2-b]pyridazin-3-yl}pyridin-2-yl)azetidine-3-carboxylic acid;

2-{6-[(2R)-2-(3-fluorophenyl)pyrrolidin-1-yl]imidazo[1,2-b]pyridazin-3-yl}-6-[4-(pyrrolidin-1-yl)piperidin-1-yl]pyridine;

2-fluoro-N-[1-(6-{6-[(2R)-2-(3-fluorophenyl)pyrrolidin-1-yl]imidazo[1,2-b]pyridazin-3-yl}pyridin-2-yl)piperidin-4-yl]-N,2-dimethylpropanamide;

2,2,2-trifluoro-N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-N-methylacetamide;

2-fluoro-N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-N,2-dimethylpropanamide;

[1-(6-{6-[(2R)-2-(3-fluorophenyl)pyrrolidin-1-yl]imidazo[1,2-b]pyridazin-3-yl}pyridin-2-yl)azetidin-3-yl]methanol; (3R)—N-(2-fluoro-2-methylpropyl)-1-(6-{6-[(2R)-2-(3-fluorophenyl)pyrrolidin-1-yl]imidazo[1,2-b]pyridazin-3-yl}pyridin-2-yl)-N-methylpyrrolidin-3-amine;

1-(6-{6-[(2R)-2-(3-fluorophenyl)pyrrolidin-1-yl]imidazo[1,2-b]pyridazin-3-yl}pyridin-2-yl)-4-(propane-2-sulfonyl)piperazine;

1-(6-{6-[(2R)-2-(3-fluorophenyl)pyrrolidin-1-yl]imidazo[1,2-b]pyridazin-3-yl}pyridin-2-yl)-4-[(2-methylpropane)sulfonyl]piperazine;

1-(butane-2-sulfonyl)-4-(6-{6-[(2R)-2-(3-fluorophenyl)pyrrolidin-1-yl]imidazo[1,2-b]pyridazin-3-yl}pyridin-2-yl)piperazine;

1-(ethanesulfonyl)-4-(6-{6-[(2R)-2-(3-fluorophenyl)pyrrolidin-1-yl]imidazo[1,2-b]pyridazin-3-yl}pyridin-2-yl)piperazine;

(3S)-1-(6-{6-[(2R)-2-(3-fluorophenyl)pyrrolidin-1-yl]imidazo[1,2-b]pyridazin-3-yl}pyridin-2-yl)-N-methylpyrrolidin-3-amine; —(3S)—N-ethyl-1-(6-{6-[(2R)-2-(3-fluorophenyl)pyrrolidin-1-yl]imidazo[1,2-b]pyridazin-3-yl}pyridin-2-yl)pyrrolidin-3-amine;

(3R)-1-(6-{6-[(2R)-2-(3-fluorophenyl)pyrrolidin-1-yl]imidazo[1,2-b]pyridazin-3-yl}pyridin-2-yl)-N-(2,2,2-trifluoroethyl)pyrrolidin-3-amine;

2-[4-(6-{6-[(2R)-2-(3-fluorophenyl)pyrrolidin-1-yl]imidazo[1,2-b]pyridazin-3-yl}pyridin-2-yl)piperazin-1-yl]-2-oxoethyl acetate;

{[(3R)-1-(6-{6-[(R2R)-2-(3-fluorophenyl)pyrrolidin-1-yl]imidazo[1,2-b]pyridazin-3-yl}pyridin-2-yl)pyrrolidin-3-yl]carbamoyl}methyl acetate;

N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-2-hydroxyacetamide;

4-(6-{6-[(2R)-2-(3-fluorophenyl)pyrrolidin-1-yl]imidazo[1,2-b]pyridazin-3-yl}pyridin-2-yl)-1-methylpiperazin-2-one;

4-(6-{6-[(2R)-2-(3-fluorophenyl)pyrrolidin-1-yl]imidazo[1,2-b]pyridazin-3-yl}pyridin-2-yl)-1-(2-hydroxyethyl)piperazin-2-one;

2-{6-[(2R)-2-(3-fluorophenyl)pyrrolidin-1-yl]imidazo[1,2-b]pyridazin-3-yl}-6-[4-(piperidin-1-yl)piperidin-1-yl]pyridine;

{[1-(6-{6-[(2R)-2-(3-fluorophenyl)pyrrolidin-1-yl]imidazo[1,2-b]pyridazin-3-yl}pyridin-2-yl)piperidin-4-yl]methyl}dimethylamine;

2-(4,4-dimethylpiperidin-1-yl)-6-{6-[(2R)-2-(3-fluorophenyl)pyrrolidin-1-yl]imidazo[1,2-b]pyridazin-3-yl}pyridine;

2-(3,3-dimethylpiperidin-1-yl)-6-{6-[(2R)-2-(3-fluorophenyl)pyrrolidin-1-yl]imidazo[1,2-b]pyridazin-3-yl}pyridine;

4-[4-(6-{6-[(2R)-2-(3-fluorophenyl)pyrrolidin-1-yl]imidazo[1,2-b]pyridazin-3-yl}pyridin-2-yl)piperazin-1-yl]benzoic acid;

1-[4-(6-{6-[(2R)-2-(3-fluorophenyl)pyrrolidin-1-yl]imidazo[1,2-b]pyridazin-3-yl}pyridin-2-yl)piperazin-1-yl]-2-methyl-1-oxopropan-2-yl acetate;

(2S)-1-[4-(6-{6-[(2R)-2-(3-fluorophenyl)pyrrolidin-1-yl]imidazo[1,2-b]pyridazin-3-yl}pyridin-2-yl)piperazin-1-yl]-1-oxopropan-2-yl acetate;

1-(6-{6-[(2R)-2-(3-fluorophenyl)pyrrolidin-1-yl]imidazo[1,2-b]pyridazin-3-yl}pyridin-2-yl)-N,N-dimethylpiperidin-4-amine;

N,N-diethyl-4-(6-{6-[(2R)-2-(3-fluorophenyl)pyrrolidin-1-yl]imidazo[1,2-b]pyridazin-3-yl}pyridin-2-yl)piperazine-1-sulfonamide;

N-ethyl-1-(6-{6-[(2R)-2-(3-fluorophenyl)pyrrolidin-1-yl]imidazo[1,2-b]pyridazin-3-yl}pyridin-2-yl)-N-methylpiperidin-4-amine;

(2)-1-[4-(6-{6-[(2R)-2-(3-fluorophenyl)pyrrolidin-1-yl]imidazo[1,2-b]pyridazin-3-yl}pyridin-2-yl)piperazin-1-yl]-2-hydroxypropan-1-one;

1-[4-(6-{6-[(2R)-2-(3-fluorophenyl)pyrrolidin-1-yl]imidazo[1,2-b]pyridazin-3-yl}pyridin-2-yl)piperazin-1-yl]-2-hydroxy-2-methylpropan-1-one;

8-(6-{6-[(2R)-2-(3-fluorophenyl)pyrrolidin-1-yl]imidazo[1,2-b]pyridazin-3-yl}pyridin-2-yl)-1,4-dioxa-8-azaspiro[4.5]decane;

4-ethyl-1-(6-{6-[(2R)-2-(3-fluorophenyl)pyrrolidin-1-yl]imidazo[1,2-b]pyridazin-3-yl}pyridin-2-yl)piperidin-4-ol;

1-(6-{6-[(2R)-2-(3-fluorophenyl)pyrrolidin-1-yl]imidazo[1,2-b]pyridazin-3-yl}pyridin-2-yl)-4-(propan-2-yl)piperidin-4-ol;

4-ethenyl-1-(6-{6-[(2R)-2-(3-fluorophenyl)pyrrolidin-1-yl]imidazo[1,2-b]pyridazin-3-yl}pyridin-2-yl)piperidin-4-ol;

1-(6-{6-[(2R)-2-(3-fluorophenyl)pyrrolidin-1-yl]imidazo[1,2-b]pyridazin-3-yl}pyridin-2-yl)-4-methylpiperidin-4-ol;

8-(6-{6-[(2R)-2-(3-fluorophenyl)pyrrolidin-1-yl]imidazo[1,2-b]pyridazin-3-yl}pyridin-2-yl)-3-methyl-1,3,8-triazaspiro[4.5]decane-2,4-dione;

(1S)-1-{[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]carbamoyl}ethyl acetate;

(2S)—N-[(3R)-1-(6-{6-[(2R)-2-(3-fluorophenyl)pyrrolidin-1-yl]imidazo[1,2-b]pyridazin-3-yl}pyridin-2-yl)pyrrolidin-3-yl]-2-hydroxypropanamide;

1-(6-{6-[(2R)-2-(3-fluorophenyl)pyrrolidin-1-yl]imidazo[1,2-b]pyridazin-3-yl}pyridin-2-yl)-3-(trifluoromethyl)piperazine;

1-(6-{6-[(2R)-2-(3-fluorophenyl)pyrrolidin-1-yl]imidazo[1,2-b]pyridazin-3-yl}pyridin-2-yl)-N-methylpiperidin-3-amine;

1-[4-(6-{6-[(2R)-2-(3-fluorophenyl)pyrrolidin-1-yl]imidazo[1,2-b]pyridazin-3-yl}pyridin-2-yl)pyridin-2-yl]-N,N-dimethylpiperidin-4-amine;

2-[4-(6-{6-[(2R)-2-(3-fluorophenyl)pyrrolidin-1-yl]imidazo[1,2-b]pyridazin-3-yl}pyridin-2-yl)-2-(trifluoromethyl)piperazin-1-yl]-2-oxoethyl acetate;

1-[4-(6-{6-[(2R)-2-(3-fluorophenyl)pyrrolidin-1-yl]imidazo[1,2-b]pyridazin-3-yl}pyridin-2-yl)-2-(trifluoromethyl)piperazin-1-yl]-2-hydroxyethan-1-one;

1-[4-(6-{6-[(2R)-2-(3-fluorophenyl)pyrrolidin-1-yl]imidazo[1,2-b]pyridazin-3-yl}pyridin-2-yl)pyridin-2-yl]-N-methylpiperidin-4-amine;

4-(6-{6-[(2R)-2-(3-fluorophenyl)pyrrolidin-1-yl]imidazo[1,2-b]pyridazin-3-yl}pyridin-2-yl)pyridin-2-ol;

N-cyclopropyl-1-[4-(6-{6-[(2R)-2-(3-fluorophenyl)pyrrolidin-1-yl]imidazo[1,2-b]pyridazin-3-yl}pyridin-2-yl)pyridin-2-yl]piperidin-4-amine;

1-[4-(6-{6-[(2R)-2-(3-fluorophenyl)pyrrolidin-1-yl]imidazo[1,2-b]pyridazin-3-yl}pyridin-2-yl)pyridin-2-yl]piperidin-4-one;

1-(6-{6-[(2R)-2-(3-fluorophenyl)pyrrolidin-1-yl]imidazo[1,2-b]pyridazin-3-yl}pyridin-2-yl)-4-(pyridin-3-yl)piperazine;

1-(6-{6-[(2R)-2-(3-fluorophenyl)pyrrolidin-1-yl]imidazo[1,2-b]pyridazin-3-yl}pyridin-2-yl)-4-(pyridin-2-yl)piperazine;

1-(4-fluorophenyl)-4-(6-{6-[(2R)-2-(3-fluorophenyl)pyrrolidin-1-yl]imidazo[1,2-b]pyridazin-3-yl}pyridin-2-yl)piperazine;

1-(6-{6-[(2R)-2-(3-fluorophenyl)pyrrolidin-1-yl]imidazo[1,2-b]pyridazin-3-yl}pyridin-2-yl)-4-(6-methylpyridin-2-yl)piperazine;

1-(6-{6-[(2R)-2-(3-fluorophenyl)pyrrolidin-1-yl]imidazo[1,2-b]pyridazin-3-yl}pyridin-2-yl)-4-[5-(trifluoromethyl)pyridin-2-yl]piperazine;

2-[4-(6-{6-[(2R)-2-(3-fluorophenyl)pyrrolidin-1-yl]imidazo[1,2-b]pyridazin-3-yl}pyridin-2-yl)piperazin-1-yl]-N-methyl-N-phenylacetamide;

2-[4-(6-{6-[(2R)-2-(3-fluorophenyl)pyrrolidin-1-yl]imidazo[1,2-b]pyridazin-3-yl}pyridin-2-yl)piperazin-1-yl]-2-oxoacetic acid;

2-[4-(6-{6-[(2R)-2-(3-fluorophenyl)pyrrolidin-1-yl]imidazo[1,2-b]pyridazin-3-yl}pyridin-2-yl)piperazin-1-yl]ethan-1-ol;

2-[4-(6-{6-[2-(3-fluorophenyl)pyrrolidin-1-yl]imidazo[1,2-b]pyridazin-3-yl}pyridin-2-yl)piperazin-1-yl]-N-(propan-2-yl)acetamide;

[1-(6-{6-[2-(3-fluorophenyl)pyrrolidin-1-yl]imidazo[1,2-b]pyridazin-3-yl}pyridin-2-yl)piperidin-4-yl]methanol;

[1-(6-{6-[2-(3-fluorophenyl)pyrrolidin-1-yl]imidazo[1,2-b]pyridazin-3-yl}pyridin-2-yl)piperidin-3-yl]methanol;

1-(6-{6-[2-(3-fluorophenyl)pyrrolidin-1-yl]imidazo[1,2-b]pyridazin-3-yl}pyridin-2-yl)piperidine-4-carbonitrile;

2-[4-(6-{6-[2-(3-fluorophenyl)pyrrolidin-1-yl]imidazo[1,2-b]pyridazin-3-yl}pyridin-2-yl)piperazin-1-yl]ethan-1-ol;

1-(6-{6-[(2R)-2-(3-fluorophenyl)pyrrolidin-1-yl]imidazo[1,2-b]pyridazin-3-yl}pyridin-2-yl)piperidin-4-ol;

1-(6-{6-[2-(3-fluorophenyl)piperidin-1-yl]imidazo[1,2-b]pyridazin-3-yl}pyridin-2-yl)-4-(propan-2-yl)piperazine;

(3)-1-(6-{6-[2-(3-fluorophenyl)piperidin-1-yl]imidazo[1,2-b]pyridazin-3-yl}pyridin-2-yl)-N,N-dimethylpyrrolidin-3-amine;

1-(6-{6-[2-(3-fluorophenyl)pyrrolidin-1-yl]imidazo[1,2-b]pyridazin-3-yl}pyridin-2-yl)azetidin-3-ol;

(3R)-1-(6-{6-[(2R)-2-(3-fluorophenyl)pyrrolidin-1-yl]imidazo[1,2-b]pyridazin-3-yl}pyridin-2-yl)-N,N-dimethylpyrrolidin-3-amine;

1-(6-{6-[2-(3-fluorophenyl)pyrrolidin-1-yl]imidazo[1,2-b]pyridazin-3-yl}pyridin-2-yl)-N-(2-hydroxyethyl)piperidine-4-carboxamide;

N-[2-(dimethylamino)ethyl]-1-(6-{6-[2-(3-fluorophenyl)pyrrolidin-1-yl]imidazo[1,2-b]pyridazin-3-yl}pyridin-2-yl)piperidine-4-carboxamide;

1-(6-{6-[2-(3-fluorophenyl)pyrrolidin-1-yl]imidazo[1,2-b]pyridazin-3-yl}pyridin-2-yl)azetidine-3-carboxylic acid;

N-(cyanomethyl)-1-(6-{6-[2-(3-fluorophenyl)pyrrolidin-1-yl]imidazo[1,2-b]pyridazin-3-yl}pyridin-2-yl)piperidine-4-carboxamide;

2-{6-[2-(3-fluorophenyl)pyrrolidin-1-yl]imidazo[1,2-b]pyridazin-3-yl}pyrazine;

N-[(3R)-1-(6-{6-[2-(3-fluorophenyl)pyrrolidin-1-yl]imidazo[1,2-b]pyridazin-3-yl}pyridin-2-yl)pyrrolidin-3-yl]acetamide;

1-(6-{6-[2-(3-fluorophenyl)pyrrolidin-1-yl]imidazo[1,2-b]pyridazin-3-yl}pyrazin-2-yl)piperidin-4-ol;

(3S)-1-(6-{6-[2-(3-fluorophenyl)pyrrolidin-1-yl]imidazo[1,2-b]pyridazin-3-yl}pyrazin-2-yl)-N,N-dimethylpyrrolidin-3-amine;
2-[4-(6-{6-[2-(3-fluorophenyl)pyrrolidin-1-yl]imidazo[1,2-b]pyridazin-3-yl}pyrazin-2-yl)piperazin-1-yl]ethan-1-ol;
(3R)-1-(6-{6-[2-(3-fluorophenyl)pyrrolidin-1-yl]imidazo[1,2-b]pyridazin-3-yl}pyrazin-2-yl)-N,N-dimethylpyrrolidin-3-amine;
N-[1-(6-{6-[(2R)-2-(3-fluorophenyl)pyrrolidin-1-yl]imidazo[1,2-b]pyridazin-3-yl}pyridin-2-yl)azetidin-3-yl]acetamide;
1-(6-{6-[(2R)-2-(3-fluorophenyl)pyrrolidin-1-yl]imidazo[1,2-b]pyridazin-3-yl}pyridin-2-yl)azetidin-3-amine;
N-[1-(6-{6-[(2R)-2-(3-fluorophenyl)pyrrolidin-1-yl]imidazo[1,2-b]pyridazin-3-yl}pyridin-2-yl)azetidin-3-yl]methanesulfonamide;
N-ethyl-1-(6-{6-[(2R)-2-(3-fluorophenyl)pyrrolidin-1-yl]imidazo[1,2-b]pyridazin-3-yl}pyridin-2-yl)azetidin-3-amine;
N,N-diethyl-1-(6-{6-[(2R)-2-(3-fluorophenyl)pyrrolidin-1-yl]imidazo[1,2-b]pyridazin-3-yl}pyridin-2-yl)azetidin-3-amine;
N-[1-(6-{6-[(2R)-2-(3-fluorophenyl)pyrrolidin-1-yl]imidazo[1,2-b]pyridazin-3-yl}pyridin-2-yl)azetidin-3-yl]-2-hydroxyacetamide;
N-ethyl-N-[1-(6-{6-[(2R)-2-(3-fluorophenyl)pyrrolidin-1-yl]imidazo[1,2-b]pyridazin-3-yl}pyridin-2-yl)azetidin-3-yl]methanesulfonamide;
1-[6-(6-{6-[(2R)-2-(3-fluorophenyl)pyrrolidin-1-yl]imidazo[1,2-b]pyridazin-3-yl}pyridin-2-yl)pyridin-2-yl]piperidin-4-ol;
6-(6-{6-[(2R)-2-(3-fluorophenyl)pyrrolidin-1-yl]imidazo[1,2-b]pyridazin-3-yl}pyridin-2-yl)-2-oxa-6-azaspiro[3.3]heptane;
6-[4-(6-{6-[(2R)-2-(3-fluorophenyl)pyrrolidin-1-yl]imidazo[1,2-b]pyridazin-3-yl}pyridin-2-yl)pyrimidin-2-yl]-2-oxa-6-azaspiro[3.3]heptane;
1-(6-{6-[(3S)-3-phenylmorpholin-4-yl]imidazo[1,2-b]pyridazin-3-yl}pyridin-2-yl)piperidin-4-ol;
1-(6-{6-[3-(3-fluorophenyl)morpholin-4-yl]imidazo[1,2-b]pyridazin-3-yl}pyridin-2-yl)piperidine-4-carbaldehyde;
3-(3-fluorophenyl)-4-(3-{6-[4-(4-methyl-1H-imidazol-2-yl)piperidin-1-yl]pyridin-2-yl}imidazo[1,2-b]pyridazin-6-yl)morpholine;
3-(3-fluorophenyl)-4-[3-(6-{4-[2-(methylsulfanyl)ethyl]piperazin-1-yl}pyridin-2-yl)imidazo[1,2-b]pyridazin-6-yl]morpholine;
3-(3-fluorophenyl)-4-(3-{6-[4-(2-methanesulfonylethyl)piperazin-1-yl]pyridin-2-yl}imidazo[1,2-b]pyridazin-6-yl)morpholine;
(N-cyclopropyl-1-(6-(6-(2-(3-fluorophenyl)pyrrolidin-1-yl)imidazo[1,2-b]pyridazin-3-yl)-2,4'-bipyridin-2'-yl)piperidin-4-amine);
3-(3-fluorophenyl)-4-(3-{6-[4-(1H-1,2,4-triazol-5-yl)piperidin-1-yl]pyridin-2-yl}imidazo[1,2-b]pyridazin-6-yl)morpholine, and
3-(3-fluorophenyl)-4-(3-{6-[4-(1,2,4-oxadiazol-5-yl)piperidin-1-yl]pyridin-2-yl}imidazo[1,2-b]pyridazin-6-yl)morpholine.

12. The compound of claim 1, wherein the compound is (R)-1-(4-(6-(6-((R)-2-(3-fluorophenyl)pyrrolidin-1-yl)imidazo[1,2-b]pyridazin-3-yl)pyridin-2-yl)pyrimidin-2-yl)pyrrolidin-3-ol.

13. The compound of claim 1, wherein the compound is (R)-1-(6-(6-(2-(3-fluorophenyl)pyrrolidin-1-yl)imidazo[1,2-b]pyridazin-3-yl)-2,4'-bipyridin-2'-yl)piperidin-4-ol.

14. A pharmaceutical composition comprising a therapeutically effective amount of a compound of Formula (I) of claim 1 and a pharmaceutically acceptable carrier.

15. A compound selected from:
6-(6-(3-(3-fluorophenyl)morpholino)imidazo[1,2-b]pyridazin-3-yl)indolin-2-one;
3-(6-((3S)-2-(3-fluorophenyl)-3-hydroxypyrrolidin-1-yl)imidazo[1,2-b]pyridazin-3-yl)benzonitrile;
5-(6-(2-(2,5-dimethylphenyl)pyrrolidin-1-yl)imidazo[1,2-b]pyridazin-3-yl)-2-fluorobenzonitrile;
(R)-4-(6-(2-(2,5-difluorophenyl)pyrrolidin-1-yl)imidazo[1,2-b]pyridazin-3-yl)benzonitrile;
4-(5-(6-(2-(3-fluorophenyl)piperidin-1-yl)imidazo[1,2-b]pyridazin-3-yl)pyridin-2-yl)morpholine;
4-(5-(6-(2-(3-fluorophenyl)pyrrolidin-1-yl)imidazo[1,2-b]pyridazin-3-yl)pyridin-2-yl)morpholine;
5-(6-(2-(3-fluorophenyl)pyrrolidin-1-yl)imidazo[1,2-b]pyridazin-3-yl)-N-methylpicolinamide;
4-(6-(2-(3-fluorophenyl)pyrrolidin-1-yl)imidazo[1,2-b]pyridazin-3-yl)benzonitrile;
5-(6-(2-(3-fluorophenyl)piperidin-1-yl)imidazo[1,2-b]pyridazin-3-yl)-N-methylpicolinamide;
(S)-4-(6-(2-(3-fluorophenyl)pyrrolidin-1-yl)imidazo[1,2-b]pyridazin-3-yl)benzonitrile;
(R)-4-(6-(2-(3-fluorophenyl)pyrrolidin-1-yl)imidazo[1,2-b]pyridazin-3-yl)benzonitrile;
4-(6-(2-(2,5-difluorophenyl)pyrrolidin-1-yl)imidazo[1,2-b]pyridazin-3-yl)benzonitrile;
4-(5-(6-(2-(2,5-difluorophenyl)pyrrolidin-1-yl)imidazo[1,2-b]pyridazin-3-yl)pyridin-2-yl)morpholine;
4-(6-(2-phenylazetidin-1-yl)imidazo[1,2-b]pyridazin-3-yl)benzonitrile;
(R)-4-(6-(2-(2,5-difluorophenyl)pyrrolidin-1-yl)imidazo[1,2-b]pyridazin-3-yl)benzonitrile;
(S)-4-(6-(2-(2,5-difluorophenyl)pyrrolidin-1-yl)imidazo[1,2-b]pyridazin-3-yl)benzonitrile;
4-(6-(2-(3-fluorophenyl)-2-methylpyrrolidin-1-yl)imidazo[1,2-b]pyridazin-3-yl)benzonitrile;
6-(6-(2-(3-fluorophenyl)pyrrolidin-1-yl)imidazo[1,2-b]pyridazin-3-yl)-3,4-dihydro-2H-benzo[e][1,3]oxazin-2-one;
6-(6-(2-(2,5-difluorophenyl)pyrrolidin-1-yl)imidazo[1,2-b]pyridazin-3-yl)-3,4-dihydro-2H-benzo[e][1,3]oxazin-2-one;
5-(6-(2-(3-fluorophenyl)pyrrolidin-1-yl)imidazo[1,2-b]pyridazin-3-yl)indolin-2-one;
6-(6-(2-(3-fluorophenyl)pyrrolidin-1-yl)imidazo[1,2-b]pyridazin-3-yl)indolin-2-one;
4-(6-(2-(2,5-difluorophenyl)-5-methylpyrrolidin-1-yl)imidazo[1,2-b]pyridazin-3-yl)benzonitrile;
4-(2-(4-(6-(2-(2,5-difluorophenyl)pyrrolidin-1-yl)imidazo[1,2-b]pyridazin-3-yl)-1H-pyrazol-1-yl)ethyl)morpholine;
N-(2-(4-(6-(2-(2,5-difluorophenyl)pyrrolidin-1-yl)imidazo[1,2-b]pyridazin-3-yl)-1H-pyrazol-1-yl)ethyl)acetamide;
(Z)-3-((1H-pyrrol-2-yl)methylene)-6-(6-(2-(3-fluorophenyl)pyrrolidin-1-yl)imidazo[1,2-b]pyridazin-3-yl)indolin-2-one;
5-(6-(2-(2,5-difluorophenyl)pyrrolidin-1-yl)imidazo[1,2-b]pyridazin-3-yl)-2-fluorobenzonitrile;
5-(6-(2-(2,5-difluorophenyl)pyrrolidin-1-yl)imidazo[1,2-b]pyridazin-3-yl)-2-morpholinobenzonitrile;

4-(6-(2-(2,5-difluorophenyl)pyrrolidin-1-yl)imidazo[1,2-b]pyridazin-3-yl)-2-fluorobenzonitrile;
5-(6-(2-(2,5-difluorophenyl)pyrrolidin-1-yl)imidazo[1,2-b]pyridazin-3-yl)-2-(dimethylamino)benzonitrile;
5-(6-(2-(2,5-difluorophenyl)pyrrolidin-1-yl)imidazo[1,2-b]pyridazin-3-yl)-2-(2-morpholinoethylamino)benzonitrile;
4-(6-(2-(2,5-difluorophenyl)pyrrolidin-1-yl)imidazo[1,2-b]pyridazin-3-yl)-2-(2-morpholinoethylamino)benzonitrile;
3-(6-(2-(2,5-difluorophenyl)pyrrolidin-1-yl)imidazo[1,2-b]pyridazin-3-yl)benzonitrile;
4-(6-(2-(2,5-difluorophenyl)pyrrolidin-1-yl)imidazo[1,2-b]pyridazin-3-yl)-2-(pyrrolidin-1-yl)benzonitrile;
4-(6-(2-(2,5-difluorophenyl)pyrrolidin-1-yl)imidazo[1,2-b]pyridazin-3-yl)-2-(2-(pyrrolidin-1-yl)ethoxy)benzonitrile;
5-(6-(2-(2,5-difluorophenyl)pyrrolidin-1-yl)imidazo[1,2-b]pyridazin-3-yl)nicotinonitrile;
6-(6-(2-(2,5-difluorophenyl)pyrrolidin-1-yl)imidazo[1,2-b]pyridazin-3-yl)picolinonitrile;
4-(4-(6-(2-(2,5-difluorophenyl)pyrrolidin-1-yl)imidazo[1,2-b]pyridazin-3-yl)thiazol-2-yl)morpholine;
4-(6-(2-(2,5-difluorophenyl)pyrrolidin-1-yl)imidazo[1,2-b]pyridazin-3-yl)-2-(3-morpholinopropylamino)benzonitrile;
4-(6-(2-(2,5-difluorophenyl)pyrrolidin-1-yl)imidazo[1,2-b]pyridazin-3-yl)-2-(1-methylpyrrolidin-3-yloxy)benzonitrile;
4-(6-(2-(2,5-difluorophenyl)pyrrolidin-1-yl)imidazo[1,2-b]pyridazin-3-yl)-2-((1-methylpyrrolidin-3-yl)methoxy)benzonitrile;
4-(6-(2-(2,5-difluorophenyl)pyrrolidin-1-yl)imidazo[1,2-b]pyridazin-3-yl)-2-(3-morpholinopropoxy)benzonitrile;
3-(5-(2-(3-fluorophenyl)pyrrolidin-1-yl)-3H-imidazo[4,5-b]pyridin-3-yl)benzonitrile;
4-(5-(2-(3-fluorophenyl)pyrrolidin-1-yl)-3H-imidazo[4,5-b]pyridin-3-yl)benzonitrile;
3-(5-(2-(2,5-difluorophenyl)thiazolidin-3-yl)-3H-imidazo[4,5-b]pyridin-3-yl)benzonitrile;
3-(5-(2-(2,5-difluorophenyl)thiazolidin-3-yl)-3H-imidazo[4,5-b]pyridin-3-yl)benzonitrile;
3-(3-(1H-imidazol-2-yl)phenyl)-5-(2-(2,5-difluorophenyl)pyrrolidin-1-yl)-3H-imidazo[4,5-b]pyridine;
3-(5-(2-(2,5-difluorophenyl)-4-oxothiazolidin-3-yl)-3H-imidazo[4,5-b]pyridin-3-yl)benzonitrile;
3-(5-(2-(2,5-difluorophenyl)pyrrolidin-1-yl)-3H-imidazo[4,5-b]pyridin-3-yl)benzonitrile;
4-(5-(2-(2,5-difluorophenyl)pyrrolidin-1-yl)-3H-imidazo[4,5-b]pyridin-3-yl)benzonitrile;
3-(6-(2-(3-fluorophenyl)-3-oxopyrazolidin-1-yl)imidazo[1,2-b]pyridazin-3-yl)benzonitrile;
2-(1,3-bis(dimethylamino)propan-2-yloxy)-4-(6-(2-(2,5-difluorophenyl)pyrrolidin-1-yl)imidazo[1,2-b]pyridazin-3-yl)benzonitrile;
4-(6-(2-(2,5-difluorophenyl)pyrrolidin-1-yl)imidazo[1,2-b]pyridazin-3-yl)-2-(1-(dimethylamino)propan-2-yloxy)benzonitrile;
4-(6-(2-(2,5-difluorophenyl)pyrrolidin-1-yl)imidazo[1,2-b]pyridazin-3-yl)-2-(2-(1-methylpyrrolidin-2-yl)ethoxy)benzonitrile;
4-(6-(2-(2,5-difluorophenyl)pyrrolidin-1-yl)imidazo[1,2-b]pyridazin-3-yl)-2-(3-(dimethylamino)-2-hydroxypropoxy)benzonitrile;
4-(6-(2-(2,5-difluorophenyl)pyrrolidin-1-yl)imidazo[1,2-b]pyridazin-3-yl)-2-((1-methylpyrrolidin-2-yl)methoxy)benzonitrile;
4-(6-(2-(3-fluorophenyl)piperidin-1-yl)imidazo[1,2-b]pyridazin-3-yl)benzonitrile;
3-(6-(2-(3-fluorophenyl)piperidin-1-yl)imidazo[1,2-b]pyridazin-3-yl)benzonitrile;
2-(2-(diethylamino)ethylamino)-4-(6-(2-(2,5-difluorophenyl)pyrrolidin-1-yl)imidazo[1,2-b]pyridazin-3-yl)benzonitrile;
7-(6-(2-(2,5-difluorophenyl)pyrrolidin-1-yl)imidazo[1,2-b]pyridazin-3-yl)-2-oxo-1,2-dihydroquinoline-3-carbonitrile;
5-(6-(2-(3-fluorophenyl)pyrrolidin-1-yl)imidazo[1,2-b]pyridazin-3-yl)-2-(2-morpholinoethylamino)benzonitrile;
5-(6-(2-(3-fluorophenyl)pyrrolidin-1-yl)imidazo[1,2-b]pyridazin-3-yl)-2-(2-(pyrrolidin-1-yl)ethoxy)benzonitrile;
5-(6-(2-(3-fluorophenyl)pyrrolidin-1-yl)imidazo[1,2-b]pyridazin-3-yl)-2-(2-(1-methylpyrrolidin-2-yl)ethoxy)benzonitrile;
4-(6-(2-(3-fluorophenyl)pyrrolidin-1-yl)imidazo[1,2-b]pyridazin-3-yl)-2-(2-(pyrrolidin-1-yl)ethoxy)benzonitrile;
4-(6-(2-(3-fluorophenyl)pyrrolidin-1-yl)imidazo[1,2-b]pyridazin-3-yl)-2-(2-morpholinoethoxy)benzonitrile;
(R)-3-(6-(2-(3-fluorophenyl)piperidin-1-yl)imidazo[1,2-b]pyridazin-3-yl)benzonitrile;
(S)-3-(6-(2-(3-fluorophenyl)piperidin-1-yl)imidazo[1,2-b]pyridazin-3-yl)benzonitrile;
4-(6-(3-(3-fluorophenyl)morpholino)imidazo[1,2-b]pyridazin-3-yl)benzonitrile;
(R)-4-(6-(2-(3-fluorophenyl)piperidin-1-yl)imidazo[1,2-b]pyridazin-3-yl)benzonitrile;
(S)-4-(6-(2-(3-fluorophenyl)piperidin-1-yl)imidazo[1,2-b]pyridazin-3-yl)benzonitrile;
6-(6-(2-(2,5-dimethylphenyl)pyrrolidin-1-yl)imidazo[1,2-b]pyridazin-3-yl)picolinic acid;
3-(6-((2R,4S)-3,3-difluoro-4-methyl-2-phenylpyrrolidin-1-yl)imidazo[1,2-b]pyridazin-3-yl)benzonitrile;
3-(6-(2-phenylpyrrolidin-1-yl)imidazo[1,2-b]pyridazin-3-yl)benzonitrile;
6-(6-(2-phenylpyrrolidin-1-yl)imidazo[1,2-b]pyridazin-3-yl)-3,4-dihydro-2H-benzo[e][1,3]oxazin-2-one;
4-(6-(2-(2,5-difluorophenyl)pyrrolidin-1-yl)imidazo[1,2-b]pyridazin-3-yl)-2-((R)-pyrrolidin-2-ylmethoxy)benzonitrile;
4-(6-(2-(2,5-difluorophenyl)pyrrolidin-1-yl)imidazo[1,2-b]pyridazin-3-yl)-2-((S)-pyrrolidin-2-ylmethoxy)benzonitrile
2-(4-(3-(dimethylamino)propyl)piperazin-1-yl)-5-(6-(2-(3-fluorophenyl)pyrrolidin-1-yl)imidazo[1,2-b]pyridazin-3-yl)benzonitrile;
5-(6-(2-(3-fluorophenyl)pyrrolidin-1-yl)imidazo[1,2-b]pyridazin-3-yl)-2-(2-(4-isopropylpiperazin-1-yl)ethoxy)benzonitrile;
5-(6-(2-(3-fluorophenyl)pyrrolidin-1-yl)imidazo[1,2-b]pyridazin-3-yl)-2-(2-(4-(2-hydroxyethyl)piperazin-1-yl)ethoxy)benzonitrile;
5-(6-(2-(3-fluorophenyl)pyrrolidin-1-yl)imidazo[1,2-b]pyridazin-3-yl)-2-(((R)-5-oxopyrrolidin-2-yl)methoxy)benzonitrile;
3-(6-((2R,4S)-3,3-difluoro-2-(3-fluorophenyl)-4-methylpyrrolidin-1-yl)imidazo[1,2-b]pyridazin-3-yl)benzonitrile;

6-(2-(3-fluorophenyl)pyrrolidin-1-yl)-3-(1H-indol-4-yl)imidazo[1,2-b]pyridazine;
6-(2-(3-fluorophenyl)pyrrolidin-1-yl)-3-(1-methyl-1H-indol-2-yl)imidazo[1,2-b]pyridazine;
6-(2-(3-fluorophenyl)pyrrolidin-1-yl)-3-(1H-indol-5-yl)imidazo[1,2-b]pyridazine;
4-(6-(2-(3-fluorophenyl)pyrrolidin-1-yl)imidazo[1,2-b]pyridazin-3-yl)-2-(piperidin-1-yl)thiazole;
6-(2-(3-fluorophenyl)pyrrolidin-1-yl)-3-(5-(pyrrolidin-1-yl)pyrazin-2-yl)imidazo[1,2-b]pyridazine;
3-(6-(2-(3-fluorophenyl)pyrrolidin-1-yl)imidazo[1,2-b]pyridazin-3-yl)benzonitrile;
tert-butyl 5-(6-(2-(3-fluorophenyl)pyrrolidin-1-yl)imidazo[1,2-b]pyridazin-3-yl)-2-methylphenylcarbamate;
6-(2-(3-fluorophenyl)pyrrolidin-1-yl)-3-(pyridin-2-yl)imidazo[1,2-b]pyridazine;
3-(6-chloropyrazin-2-yl)-6-(2-(3-fluorophenyl)pyrrolidin-1-yl)imidazo[1,2-b]pyridazine;
2-chloro-5-(6-(2-(3-fluorophenyl)pyrrolidin-1-yl)imidazo[1,2-b]pyridazin-3-yl)thiazole;
5-(6-(2-(3-fluorophenyl)pyrrolidin-1-yl)imidazo[1,2-b]pyridazin-3-yl)-N,N-dimethylpyrazin-2-amine;
6-(2-(3-fluorophenyl)pyrrolidin-1-yl)-3-(6-(piperazin-1-yl)pyridin-2-yl)imidazo[1,2-b]pyridazine;
4-(6-(6-(2-(3-fluorophenyl)pyrrolidin-1-yl)imidazo[1,2-b]pyridazin-3-yl)pyridin-2-yl)morpholine;
(S)-6-(6-(2-(2,5-difluorophenyl)pyrrolidin-1-yl)imidazo[1,2-b]pyridazin-3-yl)picolinonitrile;
(R)-6-(6-(2-(2,5-difluorophenyl)pyrrolidin-1-yl)imidazo[1,2-b]pyridazin-3-yl)picolinonitrile;
3-(6-(3-(3-fluorophenyl)morpholino)imidazo[1,2-b]pyridazin-3-yl)benzonitrile;
6-(2-(2,5-difluorophenyl)pyrrolidin-1-yl)-3-(1H-indol-4-yl)imidazo[1,2-b]pyridazine;
4-(6-(6-(2-(2,5-difluorophenyl)pyrrolidin-1-yl)imidazo[1,2-b]pyridazin-3-yl)pyridin-2-yl)morpholine;
6-(2-(2,5-difluorophenyl)pyrrolidin-1-yl)-3-(1H-indol-5-yl)imidazo[1,2-b]pyridazine;
(R)-4-(6-(3-(3-fluorophenyl)morpholino)imidazo[1,2-b]pyridazin-3-yl)benzonitrile;
(S)-4-(6-(3-(3-fluorophenyl)morpholino)imidazo[1,2-b]pyridazin-3-yl)benzonitrile;
6-(2-(3-fluorophenyl)pyrrolidin-1-yl)-3-(1H-indazol-5-yl)imidazo[1,2-b]pyridazine;
3-(5-fluoro-6-methylpyridin-2-yl)-6-(2-(3-fluorophenyl)pyrrolidin-1-yl)imidazo[1,2-b]pyridazine;
3-(3-fluorophenyl)-4-(3-(pyridin-2-yl)imidazo[1,2-b]pyridazin-6-yl)morpholine;
6-(6-(3-(3-fluorophenyl)morpholino)imidazo[1,2-b]pyridazin-3-yl)nicotinonitrile;
2-fluoro-5-(6-(3-(3-fluorophenyl)morpholino)imidazo[1,2-b]pyridazin-3-yl)benzonitrile;
6-(2-(3-fluorophenyl)pyrrolidin-1-yl)-3-(6-methoxypyridin-2-yl)imidazo[1,2-b]pyridazine;
6-(2-(3-fluorophenyl)pyrrolidin-1-yl)-3-(6-fluoropyridin-2-yl)imidazo[1,2-b]pyridazine;
5-(6-(2-(3-fluorophenyl)pyrrolidin-1-yl)imidazo[1,2-b]pyridazin-3-yl)-N-(2-hydroxyethyl)picolinamide;
5-(6-(2-(3-fluorophenyl)pyrrolidin-1-yl)imidazo[1,2-b]pyridazin-3-yl)picolinamide;
6-(2-(3-fluorophenyl)pyrrolidin-1-yl)-3-(1H-indazol-6-yl)imidazo[1,2-b]pyridazine;
6-(2-(2,5-difluorophenyl)pyrrolidin-1-yl)-3-(1H-indazol-6-yl)imidazo[1,2-b]pyridazine;
6-(2-(3-fluorophenyl)pyrrolidin-1-yl)-3-(6-(piperazin-1-yl)pyridin-3-yl)imidazo[1,2-b]pyridazine;
2-(6-(6-(2-(3-fluorophenyl)pyrrolidin-1-yl)imidazo[1,2-b]pyridazin-3-yl)pyridin-2-ylamino)ethanol;
6-(2-(2,5-difluorophenyl)pyrrolidin-1-yl)-3-(6-fluoropyridin-2-yl)imidazo[1,2-b]pyridazine;
7-(6-(2-(3-fluorophenyl)pyrrolidin-1-yl)imidazo[1,2-b]pyridazin-3-yl)-2-oxo-1,2-dihydroquinoline-3-carbonitrile;
4-(6-(2-(3-fluorophenyl)pyrrolidin-1-yl)imidazo[1,2-b]pyridazin-3-yl)-2-(piperazin-1-ylmethyl)benzonitrile;
N1,N1-diethyl-N2-(6-(6-(2-(3-fluorophenyl)pyrrolidin-1-yl)imidazo[1,2-b]pyridazin-3-yl)pyridin-2-yl)ethane-1,2-diamine;
(2S)-3-(6-(6-(2-(3-fluorophenyl)pyrrolidin-1-yl)imidazo[1,2-b]pyridazin-3-yl)pyridin-2-ylamino)propane-1,2-diol;
6-(2-(2,5-difluorophenyl)pyrrolidin-1-yl)-3-(6-(piperazin-1-yl)pyridin-3-yl)imidazo[1,2-b]pyridazine;
6-(2-(2,5-difluorophenyl)pyrrolidin-1-yl)-3-(6-(piperazin-1-yl)pyridin-2-yl)imidazo[1,2-b]pyridazine;
3-(3-fluorophenyl)-4-(3-(5-(morpholinomethyl)pyridin-2-yl)imidazo[1,2-b]pyridazin-6-yl)morpholine;
4-((6-(6-(2-(3-fluorophenyl)pyrrolidin-1-yl)imidazo[1,2-b]pyridazin-3-yl)pyridin-3-yl)methyl)morpholine;
4-(6-(3-(3-fluorophenyl)morpholino)imidazo[1,2-b]pyridazin-3-yl)-2-((4-methylpiperazin-1-yl)methyl)benzonitrile;
3-(3-fluorophenyl)-4-(3-(6-fluoropyridin-2-yl)imidazo[1,2-b]pyridazin-6-yl)morpholine;
(5-(6-(2-(3-fluorophenyl)pyrrolidin-1-yl)imidazo[1,2-b]pyridazin-3-yl)pyridin-2-yl)(4-hydroxypiperidin-1-yl)methanone;
3-(3-fluorophenyl)-4-(3-(6-morpholinopyridin-2-yl)imidazo[1,2-b]pyridazin-6-yl)morpholine;
3-(3-fluorophenyl)-4-(3-(6-(piperazin-1-yl)pyridin-2-yl)imidazo[1,2-b]pyridazin-6-yl)morpholine;
4-(6-(2-(2-fluorophenyl)pyrrolidin-1-yl)imidazo[1,2-b]pyridazin-3-yl)benzonitrile;
3-(6-(2-(2-fluorophenyl)pyrrolidin-1-yl)imidazo[1,2-b]pyridazin-3-yl)benzonitrile;
4-(4-(6-(2-(2-fluorophenyl)pyrrolidin-1-yl)imidazo[1,2-b]pyridazin-3-yl)thiazol-2-yl)morpholine;
N-(5-(6-(2-(3-fluorophenyl)pyrrolidin-1-yl)imidazo[1,2-b]pyridazin-3-yl)pyrazin-2-yl)cyclopropanecarboxamide;
4-(6-(2-(3-fluorophenyl)pyrrolidin-1-yl)imidazo[1,2-b]pyridazin-3-yl)-2-((4-methylpiperazin-1-yl)methyl)benzonitrile;
5-(6-(2-(3-fluorophenyl)pyrrolidin-1-yl)imidazo[1,2-b]pyridazin-3-yl)-2-methoxythiazole;
4-(6-(2-(3-fluorophenyl)pyrrolidin-1-yl)imidazo[1,2-b]pyridazin-3-yl)thiazole-2-carboxylic acid;
(4-(6-(2-(3-fluorophenyl)pyrrolidin-1-yl)imidazo[1,2-b]pyridazin-3-yl)thiazol-2-yl)methanol;
6-(2-(3-fluorophenyl)pyrrolidin-1-yl)-3-(1-methyl-1H-imidazol-2-yl)imidazo[1,2-b]pyridazine;
4-(6-(2-(3-fluorophenyl)pyrrolidin-1-yl)imidazo[1,2-b]pyridazin-3-yl)-2-(piperazin-1-ylmethyl)thiazole;
2,2'-(6-(6-(2-(3-fluorophenyl)pyrrolidin-1-yl)imidazo[1,2-b]pyridazin-3-yl)pyridin-2-ylazanediyl)diethanol;
4-(2-(6-(6-(2-(3-fluorophenyl)pyrrolidin-1-yl)imidazo[1,2-b]pyridazin-3-yl)pyridin-2-yloxy)ethyl)morpholine;
6-(2-(3-fluorophenyl)pyrrolidin-1-yl)-3-(6-(2-(pyrrolidin-1-yl)ethoxy)pyridin-2-yl)imidazo[1,2-b]pyridazine;
4-((6-(6-(2-(3-fluorophenyl)pyrrolidin-1-yl)imidazo[1,2-b]pyridazin-3-yl)pyridin-2-yl)methyl)morpholine;

4-((6-(6-(2-(3-fluorophenyl)pyrrolidin-1-yl)imidazo[1,2-b]pyridazin-3-yl)pyridin-2-yl)methyl)-2,6-dimethylmorpholine;
1-((6-(6-(2-(3-fluorophenyl)pyrrolidin-1-yl)imidazo[1,2-b]pyridazin-3-yl)pyridin-2-yl)methyl)pyrrolidin-3-ol;
4-(6-(2-(3-fluorophenyl)pyrrolidin-1-yl)imidazol[1,2-b]pyridazin-3-yl)-2-methoxythiazole;
6-(6-(2-(2,5-difluorophenyl)pyrrolidin-1-yl)imidazo[1,2-b]pyridazin-3-yl)nicotinonitrile;
5-(6-(3-(3-fluorophenyl)morpholino)imidazo[1,2-b]pyridazin-3-yl)-1-(piperidin-4-yl)-1H-benzo[d]imidazol-2(3H)-one;
(6-(6-(2-(3-fluorophenyl)pyrrolidin-1-yl)imidazo[1,2-b]pyridazin-3-yl)pyridin-2-yl)methanol;
6-(6-(2-(3-fluorophenyl)pyrrolidin-1-yl)imidazo[1,2-b]pyridazin-3-yl)picolinamide;
(R)-6-(2-(3-fluorophenyl)pyrrolidin-1-yl)-3-(6-fluoropyridin-2-yl)imidazo[1,2-b]pyridazine;
6-(6-(2-(3-fluorophenyl)pyrrolidin-1-yl)imidazo[1,2-b]pyridazin-3-yl)pyridin-2-ol;
6-(6-(2-(3-fluorophenyl)pyrrolidin-1-yl)imidazo[1,2-b]pyridazin-3-yl)picolinic acid;
2-fluoro-3-(6-(2-(3-fluorophenyl)pyrrolidin-1-yl)imidazo[1,2-b]pyridazin-3-yl)quinoline;
3-(6-(2-(3-fluorophenyl)pyrrolidin-1-yl)imidazo[1,2-b]pyridazin-3-yl)quinolin-2(1H)-one ;
5-(6-(2-(3-fluorophenyl)pyrrolidin-1-yl)imidazo[1,2-b]pyridazin-3-yl)quinoline;
6-(2-(3-fluorophenyl)pyrrolidin-1-yl)-3-(4-(methylsulfonyl)phenyl)imidazo[1,2-b]pyridazine;
(1-(6-(6-(2-(3-fluorophenyl)pyrrolidin-1-yl)imidazo[1,2-b]pyridazin-3-yl)pyridin-2-ylamino)cyclopentyl)methanol;
3-(6-(2-(3-fluorophenyl)pyrrolidin-1-yl)imidazo[1,2-b]pyridazin-3-yl)quinoline;
(6-(6-(2-(3-fluorophenyl)pyrrolidin-1-yl)imidazo[1,2-b]pyridazin-3-yl)pyridin-2-yl)(4-hydroxypiperidin-1-yl)methanone;
6-(2-(3-fluorophenyl)pyrrolidin-1-yl)-3-(2-fluoropyridin-4-yl)imidazo[1,2-b]pyridazine;
N1,N1-diethyl-N2-(6-(6-(2-(3-fluorophenyl)piperidin-1-yl)imidazo[1,2-b]pyridazin-3-yl)pyridin-2-yl)ethane-1,2-diamine;
4-(3-(6-(2,5-diazabicyclo [2.2.1]heptan-2-yl)pyridin-2-yl)imidazo[1,2-b]pyridazin-6-yl)-3-(3-fluorophenyl)morpholine;
6-(6-(3-(3-fluorophenyl)morpholino)imidazo[1,2-b]pyridazin-3-yl)-N-(2-(piperazin-1-yl)ethyl)pyridin-2-amine;
6-(2-(3-fluorophenyl)pyrrolidin-1-yl)-3-(6-(1-(methylsulfonyl)piperidin-4-yloxy)pyridin-2-yl)imidazo[1,2-b]pyridazine;
4-(6-(2-(2,5-difluorophenyl)pyrrolidin-1-yl)imidazo[1,2-a]pyridin-3-yl)-2-fluorobenzonitrile;
2-ethoxy-4-(6-(2-(3-fluorophenyl)pyrrolidin-1-yl)imidazo[1,2-a]pyridin-3-yl)thiazole;
5-(6-(2-(2,5-difluorophenyl)pyrrolidin-1-yl)imidazo[1,2-a]pyridin-3-yl)-2-fluorobenzonitrile;
4-(6-(2-(3-fluorophenyl)pyrrolidin-1-yl)imidazo[1,2-b]pyridazin-3-yl)picolinic acid;
5-(6-(2-(3-fluorophenyl)pyrrolidin-1-yl)imidazo[1,2-b]pyridazin-3-yl)picolinic acid;
4-(6-(6-(2-(pyridin-2-yl)pyrrolidin-1-yl)imidazo[1,2-b]pyridazin-3-yl)pyridin-2-yl)morpholine;
6-(6-(2-(3-fluorophenyl)piperidin-1-yl)imidazo[1,2-b]pyridazin-3-yl)-N-methylpyridin-2-amine;
6-(6-(2-(3-fluorophenyl)piperidin-1-yl)imidazo[1,2-b]pyridazin-3-yl)-N-isopropylpyridin-2-amine;
N-(6-(6-(2-(3-fluorophenyl)piperidin-1-yl)imidazo[1,2-b]pyridazin-3-yl)pyridin-2-yl)methanesulfonamide;
6-(6-(2-(3-fluorophenyl)piperidin-1-yl)imidazo[1,2-b]pyridazin-3-yl)-N,N-dimethylpyridin-2-amine;
6-(2-(3-fluorophenyl)piperidin-1-yl)-3-(6-(piperidin-4-yloxy)pyridin-2-yl)imidazo[1,2-b]pyridazine,
4-(6-(2-(2,5-difluorophenyl)pyrrolidin-1-yl)imidazo[1,2-a]pyridin-3-yl)-2-ethoxythiazole;
6-(6-(3-(3-fluorophenyl)morpholino)imidazo[1,2-b]pyridazin-3-yl)-N-(2-(piperazin-1-yl)ethyl)pyridin-2-amine;
(S)-6-(6-(3-(3-fluorophenyl)morpholino)imidazo[1,2-b]pyridazin-3-yl)indolin-2-one;
(R)-6-(6-(3-(3-fluorophenyl)morpholino)imidazo[1,2-b]pyridazin-3-yl)indolin-2-one;
3-(6-(1,3-dioxolan-2-yl)pyridin-2-yl)-6-(2-(3-fluorophenyl)pyrrolidin-1-yl)imidazo[1,2-b]pyridazine;
6-(6-(6-(2-(3-fluorophenyl)pyrrolidin-1-yl)imidazo[1,2-b]pyridazin-3-yl)pyridin-2-yl)pyrimidin-2(1H)-one;
2-(4-(6-(6-(2-(3-fluorophenyl)pyrrolidin-1-yl)imidazo[1,2-b]pyridazin-3-yl)pyridin-2-yl)pyrimidin-2-ylamino)ethanol;
3-{6-[2-(3-fluorophenyl)pyrrolidin-1-yl]imidazo[1,2-b]pyridazin-3-yl}-1,2-dihydroquinolin-2-one;
5-{6-[2-(3-fluorophenyl)pyrrolidin-1-yl]imidazo[1,2-b]pyridazin-3-yl}quinoline;
3-{6-[2-(3-fluorophenyl)pyrrolidin-1-yl]imidazo[1,2-b]pyridazin-3-yl}quinoline;
2-[(5-{6-[2-(3-fluorophenyl)pyrrolidin-1-yl]imidazo[1,2-b]pyridazin-3-yl}pyrimidin-2-yl)amino]ethan-1-ol;
5-{6-[2-(3-fluorophenyl)pyrrolidin-1-yl]imidazo[1,2-b]pyridazin-3-yl}-N-methylpyrimidin-2-amine;
5-{6-[2-(3-fluorophenyl)pyrrolidin-1-yl]imidazo[1,2-b]pyridazin-3-yl}-N,N-dimethylpyrimidin-2-amine;
2-chloro-5-{6-[2-(3-fluorophenyl)pyrrolidin-1-yl]imidazo[1,2-b]pyridazin-3-yl}pyrimidine;
tert-butyl 4-[(5-{6-[2-(3-fluorophenyl)pyrrolidin-1-yl]imidazo[1,2-b]pyridazin-3-yl}pyrimidin-2-yl)oxy]piperidine-1-carboxylate;
5-{6-[2-(3-fluorophenyl)pyrrolidin-1-yl]imidazo[1,2-b]pyridazin-3-yl}-2-(piperidin-4-yloxy)pyrimidine;
5-{6-[2-(3-fluorophenyl)pyrrolidin-1-yl]imidazo[1,2-b]pyridazin-3-yl}pyrimidine;
5-{6-[2-(3-fluorophenyl)pyrrolidin-1-yl]imidazo[1,2-b]pyridazin-3-yl}-1,2-dihydropyrimidine;
6-{6-[(2R)-2-(3-fluorophenyl)pyrrolidin-1-yl]imidazo[1,2-b]pyridazin-3-yl}-N-methyl-N-(piperidin-4-yl)pyridin-2-amine;
N-cyclobutyl-6-{6-[(2R)-2-(3-fluorophenyl)pyrrolidin-1-yl]imidazo[1,2-b]pyridazin-3-yl}pyridin-2-amine;
N-cyclopropyl-6-{6-[(2R)-2-(3-fluorophenyl)pyrrolidin-1-yl]imidazo[1,2-b]pyridazin-3-yl}pyridin-2-amine;
6-{6-[2-(3-fluorophenyl)piperidin-1-yl]imidazo[1,2-b]pyridazin-3-yl}-N,N-dimethylpyridin-2-amine;
3-{6-[(2R)-2-(3-fluorophenyl)pyrrolidin-1-yl]imidazo[1,2-b]pyridazin-3-yl}-1H-pyrrole;
6-{6-[3-(3-fluorophenyl)morpholin-4-yl]imidazo[1,2-b]pyridazin-3-yl}-N,N-dimethylpyridin-2-amine;
3-(3-fluorophenyl)-4-(3-(6-(piperidin-4-yloxy)pyridin-2-yl)imidazo[1,2-b]pyridazin-6-yl)morpholine;
2-{6-[2-(3-fluorophenyl)pyrrolidin-1-yl]imidazo[1,2-b]pyridazin-3-yl}-6-(piperidin-4-yloxy)pyridine;
6-(2-(3-fluorophenyl)pyrrolidin-1-yl)-3-(6-(piperidin-4-yloxy)pyridin-2-yl)imidazo[1,2-b]pyridazine;

4-(4-{6-[2-(3-fluorophenyl)pyrrolidin-1-yl]imidazo[1,2-b]pyridazin-3-yl}-1H-pyrazol-1-yl)piperidine;
2-fluoro-4-{6-[2-(3-fluorophenyl)pyrrolidin-1-yl]imidazo[1,2-b]pyridazin-3-yl}pyridine;
2-(3-fluorophenyl)-1-[3-(4-methanesulfonylphenyl)imidazo[1,2-b]pyridazin-6-yl]pyrrolidine;
6-{6-[2-(3-fluorophenyl)pyrrolidin-1-yl]imidazo[1,2-b]pyridazin-3-yl}pyridine-2-carboxylic acid;
6-{6-[2-(3-fluorophenyl)pyrrolidin-1-yl]imidazo[1,2-b]pyridazin-3-yl}pyridin-2-ol;
6-{6-[2-(3-fluorophenyl)pyrrolidin-1-yl]imidazo[1,2-b]pyridazin-3-yl}pyridine-2-carboxamide;
6-{6-[(2R)-2-(3-fluorophenyl)pyrrolidin-1-yl]imidazo[1,2-b]pyridazin-3-yl}pyridine-2-carboxamide;
6-{6-[(2S)-2-(3-fluorophenyl)pyrrolidin-1-yl]imidazo[1,2-b]pyridazin-3-yl}pyridine-2-carboxamide;
6-{6-[2-(3-fluorophenyl)pyrrolidin-1-yl]imidazo[1,2-b]pyridazin-3-yl}-N-methylpyridine-2-carboxamide;
(3R)-1-[(6-{6-[2-(3-fluorophenyl)pyrrolidin-1-yl]imidazo[1,2-b]pyridazin-3-yl}pyridin-2-yl)carbonyl]-N,N-dimethylpyrrolidin-3-amine;
1-[(6-{6-[2-(3-fluorophenyl)pyrrolidin-1-yl]imidazo[1,2-b]pyridazin-3-yl}pyridin-2-yl)carbonyl]piperidin-4-ol;
4-[(6-{6-[2-(3-fluorophenyl)pyrrolidin-1-yl]imidazo[1,2-b]pyridazin-3-yl}pyridin-2-yl)carbonyl]morpholine;
1-(6-{6-[(2R)-2-(3-fluorophenyl)pyrrolidin-1-yl]imidazo[1,2-b]pyridazin-3-yl}pyridin-2-yl)piperazine;
6-{6-[2-(3-fluorophenyl)pyrrolidin-1-yl]imidazo[1,2-b]pyridazin-3-yl}-N-[1-(propan-2-yl)piperidin-4-yl]pyridin-2-amine;
2-fluoro-6-{6-[(2S)-2-(3-fluorophenyl)pyrrolidin-1-yl]imidazo[1,2-b]pyridazin-3-yl}pyridine;
2-fluoro-6-{6-[(2R)-2-(3-fluorophenyl)pyrrolidin-1-yl]imidazo[1,2-b]pyridazin-3-yl}pyridine;
diethyl({2-[(6-{6-[2-(3-fluorophenyl)piperidin-1-yl]imidazo[1,2-b]pyridazin-3-yl}pyridin-2-yl)amino]ethyl})amine;
6-{6-[2-(3-fluorophenyl)piperidin-1-yl]imidazo[1,2-b]pyridazin-3-yl}-N-methylpyridin-2-amine;
6-{6-[2-(3-fluorophenyl)piperidin-1-yl]imidazo[1,2-b]pyridazin-3-yl}-N-(propan-2-yl)pyridin-2-amine;
N-(6-{6-[2-(3-fluorophenyl)piperidin-1-yl]imidazo[1,2-b]pyridazin-3-yl}pyridin-2-yl)methanesulfonamide;
2-{6-[2-(3-fluorophenyl)piperidin-1-yl]imidazo[1,2-b]pyridazin-3-yl}-6-(piperidin-4-yloxy)pyridine;
1-{6-[2-(3-fluorophenyl)pyrrolidin-1-yl]imidazo[1,2-b]pyridazin-3-yl}-1H-pyrazole;
2-{6-[2-(3-fluorophenyl)pyrrolidin-1-yl]imidazo[1,2-b]pyridazin-3-yl}-6-(piperazin-1-yl)pyrazine;
6-{6-[2-(3-fluorophenyl)pyrrolidin-1-yl]imidazo[1,2-b]pyridazin-3-yl}-2,3-dihydro-1H-indol-2-one;
6-{6-[3-(3-fluorophenyl)morpholin-4-yl]imidazo[1,2-b]pyridazin-3-yl}-2,3-dihydro-1H-indol-2-one;
3-(3-fluorophenyl)-4-{3-[6-(piperazin-1-yl)pyridin-2-yl]imidazo[1,2-b]pyridazin-6-yl}morpholine, and
(3S)-4-[3-(6-fluoropyridin-2-yl)imidazo[1,2-b]pyridazin-6-yl]-3-phenylmorpholine.

* * * * *

UNITED STATES PATENT AND TRADEMARK OFFICE
CERTIFICATE OF CORRECTION

PATENT NO.        : 8,507,488 B2
APPLICATION NO.   : 12/992027
DATED             : August 13, 2013
INVENTOR(S)       : Albaugh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 68 days.

Signed and Sealed this
Twenty-sixth Day of November, 2013

Margaret A. Focarino
*Commissioner for Patents of the United States Patent and Trademark Office*